United States Patent
Brown et al.

(10) Patent No.: US 9,944,626 B2
(45) Date of Patent: Apr. 17, 2018

(54) 6-(5-HYDROXY-1H-PYRAZOL-1-YL) NICOTINAMIDE INHIBITORS OF PHD

(71) Applicant: Takeda Pharmaceutical Company Limited, Osaka (JP)

(72) Inventors: Jason W. Brown, San Diego, CA (US); Melinda Davis, San Diego, CA (US); Anthony Ivetac, San Diego, CA (US); Benjamin Jones, Cardiff-by-the-Sea, CA (US); Andre A. Kiryanov, San Diego, CA (US); Jon Kuehler, San Diego, CA (US); Marion Lanier, San Diego, CA (US); Joanne Miura, San Diego, CA (US); Sean Murphy, San Diego, CA (US); Xiaolun Wang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/620,620

(22) Filed: Jun. 12, 2017

(65) Prior Publication Data

US 2017/0275271 A1    Sep. 28, 2017

Related U.S. Application Data

(62) Division of application No. 15/150,976, filed on May 10, 2016, now Pat. No. 9,708,296, which is a division of application No. 14/693,110, filed on Apr. 22, 2015, now Pat. No. 9,345,713, which is a division of application No. 14/226,722, filed on Mar. 26, 2014, now Pat. No. 9,040,522.

(60) Provisional application No. 61/916,715, filed on Dec. 16, 2013, provisional application No. 61/806,806, filed on Mar. 29, 2013.

(51) Int. Cl.

| | |
|---|---|
| C07D 413/14 | (2006.01) |
| A61K 31/5377 | (2006.01) |
| C07D 401/14 | (2006.01) |
| C07D 487/06 | (2006.01) |
| C07D 417/14 | (2006.01) |
| C07D 491/10 | (2006.01) |
| A61K 31/551 | (2006.01) |
| A61K 31/444 | (2006.01) |
| C07D 487/10 | (2006.01) |
| A61K 31/4545 | (2006.01) |
| C07D 401/04 | (2006.01) |
| C07D 471/08 | (2006.01) |
| C07D 405/14 | (2006.01) |
| C07D 491/107 | (2006.01) |
| A61K 31/5513 | (2006.01) |
| A61K 31/4985 | (2006.01) |
| C07D 487/04 | (2006.01) |
| A61K 31/496 | (2006.01) |

(52) U.S. Cl.
CPC .......... *C07D 401/14* (2013.01); *A61K 31/444* (2013.01); *A61K 31/4545* (2013.01); *A61K 31/496* (2013.01); *A61K 31/4985* (2013.01); *A61K 31/5377* (2013.01); *A61K 31/551* (2013.01); *A61K 31/5513* (2013.01); *C07D 401/04* (2013.01); *C07D 405/14* (2013.01); *C07D 413/14* (2013.01); *C07D 417/14* (2013.01); *C07D 471/08* (2013.01); *C07D 487/04* (2013.01); *C07D 487/06* (2013.01); *C07D 487/10* (2013.01); *C07D 491/10* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 4,663,327 A | 5/1987 | Sasse et al. | |
| 4,698,344 A | 10/1987 | Sasse et al. | |
| 9,040,522 B2 | 5/2015 | Brown et al. | |
| 9,345,713 B2 * | 5/2016 | Brown ................. | A61K 31/496 |
| 9,708,296 B2 * | 7/2017 | Brown ................. | C07D 491/10 |
| 2010/0035906 A1 | 2/2010 | Flamme et al. | |
| 2010/0093803 A1 | 4/2010 | Thede et al. | |
| 2010/0305085 A1 | 12/2010 | Thede et al. | |
| 2011/0294788 A1 | 12/2011 | Altenburger et al. | |
| 2011/0301148 A1 | 12/2011 | Altenburger et al. | |

FOREIGN PATENT DOCUMENTS

| | | |
|---|---|---|
| DE | 102007044032 | 3/2009 |
| EP | 0165448 A2 | 5/1985 |
| EP | 0165448 B1 | 5/1985 |
| EP | 0183159 A2 | 11/1985 |
| WO | WO/2007/020426 A1 | 2/2007 |
| WO | WO/2008/080969 A1 | 7/2008 |

OTHER PUBLICATIONS

Rabinowtz et al. "Chapter 8—Inhibitors of HIF Prolyl Hydroxylases" Annual Reports in Medicinal Chemistry, 2010, vol. 45, pp. 123-139.

* cited by examiner

*Primary Examiner* — Emily Bernhardt
(74) *Attorney, Agent, or Firm* — Matthew J. Russo; David M. Stemerick

(57) ABSTRACT

The present invention provides compounds of the formula:

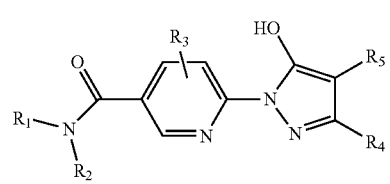

which are useful as inhibitors of PHD, pharmaceutical compositions thereof, methods for treatment of conditions associated with HIF, processes for making the compounds and intermediates thereof.

7 Claims, No Drawings

6-(5-HYDROXY-1H-PYRAZOL-1-YL) NICOTINAMIDE INHIBITORS OF PHD

RELATED APPLICATIONS

This application claims the benefit of U.S. Provisional Application No. 61/806,806, filed Mar. 29, 2013, and U.S. Provisional Application No. 61/916,715, filed Dec. 16, 2013 which are both incorporated herein by reference.

FIELD OF THE INVENTION

The present invention relates to medicinal chemistry, pharmacology, and medicine.

BACKGROUND OF THE INVENTION

The present invention relates to novel compounds, methods, and compositions capable of decreasing HIF prolyl hydroxylase (PHD) enzyme activity, thereby increasing the stability and/or activity and/or levels of hypoxia inducible factor (HIF).

HIF mediates changes in gene expression in response to changes in cellular oxygen concentration. HIF is a heterodimer having an oxygen-regulated subunit (HIF-α) and a constitutively expressed subunit (HIF-β). In cells with adequate oxygen HIF-α is hydroxylated at conserved proline residues by propyl-hydroxylases (PHD) resulting in its rapid degradation. Prolyl hydroxylases, PHDs, exist in a number of isoforms and function as oxygen sensors and in the regulation of cell metabolism in response to oxygen content in cells. Due to PHD's central role in oxygen sensing, PHD inhibitors are useful in treating cardiovascular disorders, such as ischemic events, hematological disorders, such as anemia, pulmonary disorders, brain disorders, and kidney disorders. There is a need for treatment of such conditions and others described herein with compounds that are PHD inhibitors. The present invention provides inhibitors of PHD.

Certain inhibitors of calpain are described in WO2008/080969, lipoxygenase inhibitors are disclosed in U.S. Pat. No. 4,698,344 and microicidal activity is disclosed in U.S. Pat. No. 4,663,327, MtSK inhibitors are disclosed in WO2007/020426, and inhibitors of PHD are described in US2010/035906 and US2010/0093803.

SUMMARY OF THE INVENTION

The present invention provides a compound of formula I

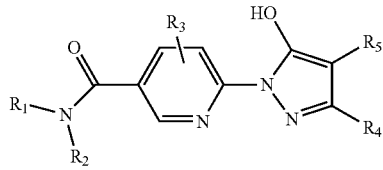

wherein
R$_1$ is selected from the group consisting of optionally substituted C$_{1-6}$ alkyl, optionally substituted C$_{3-8}$ cycloalkyl, and optionally substituted C$_{3-6}$ heterocyclyl;
R$_2$ is selected from the group consisting of hydrogen, C$_{3-8}$ cycloalkyl, and optionally substituted C$_{1-4}$ alkyl;
or
R$_1$ and R$_2$ together with the nitrogen to which they are attached form a 4 to 12 membered, saturated, ring optionally having 1 or 2 additional ring heteroatoms independently selected from the group N, O, and S and optionally substituted on any of the ring carbon atoms with 1 to 5 substituents independently selected from the group consisting of cyano, halo, hydroxy, amino, C$_{1-12}$ substituted amino, optionally substituted C$_{3-6}$ heterocyclyl, C$_{1-9}$ amide, optionally substituted C$_{1-6}$ alkyl, and C$_{1-4}$ alkoxy and substituted on any additional ring nitrogen by a substituent independently selected from the group consisting of hydrogen, optionally substituted C$_{3-8}$ cycloalkyl, and optionally substituted C$_{1-6}$ alkyl;
R$_3$, each time taken, is independently selected from the group consisting of hydrogen, hydroxyl, amino, C$_{1-8}$ alkylamino, cyano, halo, optionally substituted C$_{1-6}$ alkyl, and C$_{1-4}$ alkoxy;
R$_4$ is selected from the group consisting of hydrogen, cyano, halo, methyl, ethyl, methoxy, and trifluoromethyl;
R$_5$ is selected from the group consisting of

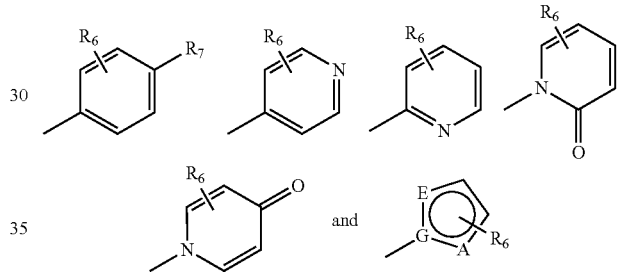

G is carbon;
A is selected from the group consisting of N, O, S, CR$_6$ and NR$_6$;
E is selected from the group consisting of N, O, S, and CR$_6$;
provided that only one of A and E can be O or S;
or G is N and A and E are CR$_6$;
or G and A are N and E is CR$_6$;
or G, A, and E are N;
R$_6$, each time taken, is independently selected from the group consisting of hydrogen, cyano, halo, C$_{3-8}$ cycloalkyl, optionally substituted C$_{1-6}$ alkyl, C$_{1-4}$ alkoxy, and trifluoromethyl;
R$_7$ is selected from the group consisting of cyano and cyanomethyl;
or a pharmaceutically acceptable salt thereof.

The present invention also provides pharmaceutical compositions, comprising: a compound of formula I or a pharmaceutically acceptable salt thereof and a pharmaceutically acceptable excipient.

The compounds of the invention are inhibitors of PHD they are useful for the treatment of conditions associated with HIF, including cardiovascular disorders. Thus, the present invention provides for the use of the compounds of the invention as a medicament, including for the manufacture of a medicament. The present invention also provides methods of treating the conditions associated with HIF, comprising: administering to a patient in need thereof an effective amount of the compounds of the invention.

The present invention also provides processes from making PHD inhibitors and intermediates thereof.

DETAILED DESCRIPTION OF THE INVENTION

The term "$C_{1-3}$ alkyl" refers to a straight or branched alkyl chain of one to three carbon atoms.

The term "$C_{1-4}$ alkyl" refers to a straight or branched alkyl chain of one to four carbon atoms.

The term "optionally substituted $C_{1-4}$ alkyl" refers to a $C_{1-4}$ alkyl optionally substituted with 1 to 6 substituents independently selected from the group consisting of optionally substituted $C_{1-4}$ alkoxy, $C_{1-4}$ thioalkoxy, $C_{1-9}$ amide, $C_{1-7}$ amido, amino, $C_{1-8}$ alkylamino, $C_{1-5}$ oxycarbonyl, $C_{1-5}$ carbonyloxy, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocyclyl, optionally substituted $C_{1-10}$ heteroaryl, and optionally substituted $C_{5-10}$ aryl.

More particularly "optionally substituted $C_{1-4}$ alkyl" refers to a $C_{1-4}$ alkyl optionally substituted with 1 to 6 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-4}$ alkyl" refers to a $C_{1-4}$ alkyl optionally substituted with 1 to 6 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ alkyl" refers to a straight or branched alkyl chain of one to six carbon atoms.

The term "optionally substituted $C_{1-6}$ alkyl" refers to a $C_{1-6}$ alkyl optionally substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-7}$ amido, $C_{1-5}$ oxycarbonyl, $C_{1-5}$ carbonyloxy, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{5-10}$ aryl.

More particularly "optionally substituted $C_{1-6}$ alkyl" refers to a $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-6}$ alkyl" refers to a $C_{1-6}$ alkyl optionally substituted with 1 to 7 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-2}$ alkoxy" refers to a $C_{1-2}$ alkyl, that is methyl and ethyl, attached through an oxygen atom.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally substituted with 1 to 6 substituents independently selected from the group consisting of $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted $C_{5-10}$ aryl. While it is understood that where the optional substituent is $C_{1-4}$ alkoxy or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally substituted with 1 to 6 substituents independently selected from the group consisting of $C_{1-4}$ alkoxy, cyano, $C_{3-8}$ cycloalkyl, halo, hydroxy, and optionally substituted phenyl. Even more particularly "optionally substituted $C_{1-4}$ alkoxy" refers to trifluoromethoxy, difluoromethoxy, and fluoromethoxy.

The term "$C_{1-9}$ amide" refers to a —C(O)NR$_a$R$_b$ group in which R$_a$ is selected from the group consisting of hydrogen and $C_{1-4}$ alkyl, and R$_b$ is selected from the group consisting of hydrogen, $C_{1-3}$ alkyl, and optionally substituted phenyl.

The term "$C_{1-7}$ amido" refers to a —NHC(O)R$_c$ group in which R$_c$ is selected from the group consisting of hydrogen, $C_{1-6}$ alkyl, and optionally substituted phenyl.

The term "$C_{1-5}$ carbamoyl" refers to an O- or N-linked carbamate substituted with a terminal $C_{1-4}$ alkyl.

The term "$C_{1-5}$ ureido" refers to a urea optionally substituted with a $C_{1-4}$ alkyl.

The term "$C_{1-8}$ alkylamino" refers to a —NR$_d$R$_e$ group in which R$_d$ is a $C_{1-4}$ alkyl and R$_e$ is selected from the group consisting of hydrogen and $C_{1-4}$ alkyl.

The term "$C_{5-10}$ aryl" refers to a monocyclic and polycyclic unsaturated, conjugated hydrocarbon having five to ten carbon atoms, and includes cyclopentyldienyl, phenyl, and naphthyl.

More particularly "$C_{5-10}$ aryl" refers to phenyl.

The term "optionally substituted $C_{5-10}$ aryl" refers to a $C_{5-10}$ aryl optionally substituted with 1 to 5 substituents independently selected from the group consisting of optionally substituted $C_{1-4}$ alkyl, optionally substituted $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, cyano, halo, and hydroxyl.

More particularly "optionally substituted $C_{5-10}$ aryl" refers to a $C_{5-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy.

Even more particularly "optionally substituted $C_{5-10}$ aryl" refers to phenyl optionally substituted with 1 to 5 substituents independently selected from the group consisting of $C_{1-4}$ alkyl, $C_{1-4}$ alkoxy, cyano, halo, trifluoromethyl, and trifluoromethoxy.

The term "$C_{1-5}$ oxycarbonyl" refers to an oxycarbonyl group (—CO$_2$H) and $C_{1-4}$ alkyl ester thereof.

The term "$C_{1-5}$ carbonyloxy" refers to a carbonyloxy group (—O$_2$CR$_f$), in which R$_f$ is selected from the group consisting of hydrogen and $C_{1-4}$ alkyl, for example, acetoxy.

The term "$C_{3-8}$ cycloalkyl" refers to monocyclic or bicyclic, saturated or partially (but not fully) unsaturated alkyl ring of three to eight carbon atoms, and includes cyclopropyl, cyclobutyl, cyclopentyl, cyclohexyl, and the like. It is understood that the term includes benzofused cyclopentyl and cyclohexyl.

The term "optionally substituted $C_{3-8}$ cycloalkyl" refers to a $C_{3-8}$ cycloalkyl optionally substituted with 1 to 6 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally substituted with 1 to 3 substituents independently selected from the group consisting of $C_{1-4}$ alkoxy, halo, hydroxy, and $C_{1-4}$ alkyl optionally substituted with $C_{1-4}$ alkoxy, halo, and hydroxy.

The term "$C_{3-8}$ cycloalkoxy" refers to a $C_{3-8}$ cycloalkyl attached through and oxygen.

The terms "halogen" and "halo" refers to a chloro, fluoro, bromo or iodo atom.

The term "$C_{3-6}$ heterocyclyl" refers to a 4 to 8 membered monocyclic or bicyclic, saturated or partially (but not fully) unsaturated ring having three to six carbons and one or two heteroatoms selected from the group consisting of nitrogen, oxygen, and sulfur and the ring optionally includes a carbonyl to form a lactam or lactone. It is understood that where sulfur is included that the sulfur may be either —S—, —SO—, and —SO$_2$—. It is also under that the term includes spirofused bicyclic systems. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like. It is understood that a $C_{3-6}$ heterocyclyl can be attached as a substituent through a ring carbon or a ring nitrogen atom.

More particularly "$C_{3-6}$ heterocyclyl" is selected from the group consisting of azetidinyl, pyrrolidinyl, piperidinyl, piperazinyl, morpholinyl, oxetanyl, tetrahydropyranyl, tetrahydrothiopyranyl, and tetrahydrofuryl.

The term "optionally substituted $C_{3-6}$ heterocyclyl" refers to a $C_{3-6}$ heterocyclyl optionally substituted on the ring carbons with 1 to 4 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally substituted on any ring nitrogen with a substituent independently selected from the group consisting of optionally substituted $C_{1-4}$ alkyl, $C_{3-8}$ cycloalkyl, optionally substituted $C_{3-6}$ heterocyclyl, optionally substituted $C_{1-10}$ heteroaryl, and optionally substituted phenyl.

More particularly "optionally substituted $C_{3-6}$ heterocyclyl" refers to a $C_{3-6}$ heterocyclyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to thirteen membered, monocyclic or polycyclic fully unsaturated, ring or ring system with one to ten carbon atoms and one or more, typically one to four, heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like. It is understood that a $C_{1-10}$ heteroaryl can be attached as a substituent through a ring carbon or a ring nitrogen atom where such an attachment mode is available, for example for a pyrrolyl, indolyl, imidazolyl, pyrazolyl, azepinyl, triazolyl, pyrazinyl, etc.

More particularly "$C_{1-10}$ heteroaryl" is selected from the group consisting of furyl, thienyl, pyrrolyl, imidazolyl, oxazolyl, thiazolyl, pyrazolyl, triazolyl, pyridyl, and pyrimidyl.

The term "optionally substituted $C_{1-10}$ heteroaryl" refers to a $C_{1-10}$ heteroaryl optionally substituted with 1 to 5 substituents on carbon independently selected from the group consisting of amino, $C_{1-8}$ alkylamino, $C_{1-6}$ amide, $C_{1-7}$ amido, $C_{1-5}$ carbamoyl, $C_{1-6}$ sulfonylamido, aminosulfonyl, $C_{1-10}$ aminosulfonyl, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ carbonyloxy, $C_{1-5}$ oxycarbonyl, and $C_{1-8}$ sulfonyl and optionally substituted with a substituent on each nitrogen independently selected from the group consisting of optionally substituted $C_{1-4}$ alkyl, $C_{1-8}$ sulfonyl, optionally substituted $C_{3-6}$ heterocyclyl, and optionally substituted phenyl.

More particularly "optionally substituted $C_{1-10}$ heteroaryl" refers to a $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxyl, oxo, trifluoromethyl, and trifluoromethoxy and optionally substituted on a ring nitrogen with a $C_{1-4}$ alkyl.

Even more particularly "optionally substituted $C_{1-10}$ heteroaryl" refers to a $C_{1-10}$ heteroaryl selected from the group consisting of furyl, thienyl, pyrrolyl, imidazolyl, oxazolyl, thiazolyl, pyrazolyl, diazolyl, pyridyl, pyrimidyl, and triazolyl each optionally substituted with 1 to 3 substituents independently selected from the group consisting of $C_{1-4}$ alkyl, $C_{1-4}$ alkoxy, cyano, halo, trifluoromethyl, and trifluoromethoxy and optionally substituted on a ring nitrogen with a methyl.

The term "oxo" refers to an oxygen atom doubly bonded to the carbon to which it is attached to form the carbonyl of a ketone or aldehyde. For example, a pryidone radical is contemplated as an oxo substituted $C_{1-10}$ heteroaryl.

The term "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amide, amino, $C_{1-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxyl, nitro, and trifluoromethyl.

The term "$C_{1-6}$ sulfonylamido" refers to a —NHS(O)$_2$—R$_g$ group wherein R$_g$ is selected from the group consisting of $C_{1-6}$ alkyl and optionally substituted phenyl.

The term "aminosulfonyl" refers to a —S(O)$_2$NH$_2$.

The term "$C_{1-10}$ aminosulfonyl" refers to a —S(O)$_2$NR$_h$R$_i$ group wherein R$_h$ is selected from the group consisting of hydrogen and $C_{1-4}$ alkyl and R$_i$ is selected from the group consisting of $C_{1-4}$ alkyl, and optionally substituted phenyl.

The term "$C_{1-12}$ substituted amino" refers to a NR$_j$R$_k$ group in which R$_j$ is selected from the group consisting of hydrogen and optionally substituted $C_{1-4}$ alkyl and R$_k$ is selected from the group consisting of optionally substituted $C_{1-4}$ alkyl, and $C_{3-8}$ cycloalkyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group are replaced with non-hydrogen radicals (substituent(s)). It is understood that the substituents may be either the same or different at every substituted position. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, the mentioned number refers to the mentioned group and does not include any carbons that may be present in any optional substituent(s) thereon.

The skilled artisan will appreciate that certain of the compounds of the present invention exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the present invention exist as tautomers. All tautomeric forms of the compounds of the invention are contemplated to be within the scope of the present invention. In particular it is understood that compounds of formula I and embodiments related thereto can exist in either the hydroxy form depicted in formula I, 1, 2, 3, 4, and 5 or the keto forms depicted below:

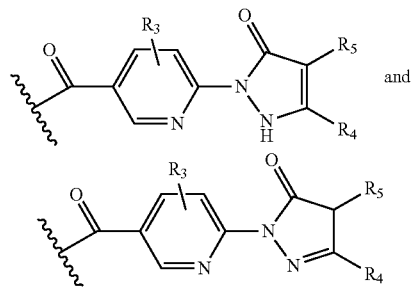

Compounds of the invention also include all pharmaceutically acceptable isotopic variations, in which at least one atom is replaced by an atom having the same atomic number, but an atomic mass different from the predominant atomic mass. Isotopes suitable for inclusion in compounds of formula I include, for example, isotopes of hydrogen, such as $^2H$ and $^3H$; isotopes of carbon, such as $^{11}C$, $^{13}C$, and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; and isotopes of iodine, such as $^{123}I$ and $^{125}I$. Use of isotopic variations (e.g., deuterium, $^2H$) may afford greater metabolic stability. Additionally, certain isotopic variations of the compounds of the invention may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The terms "compounds of the invention" and "a compound of the invention" and the like include the embodiment of formulae I, 1, 2, 3, 4, or 5 and the other more particular embodiments encompassed by formula I, 1, 2, 3, 4, or 5 described herein and exemplified compounds described herein and a pharmaceutically acceptable salt of each of these embodiments.

It is understood that a variable $R_6$ is at every open valency in the formulae:

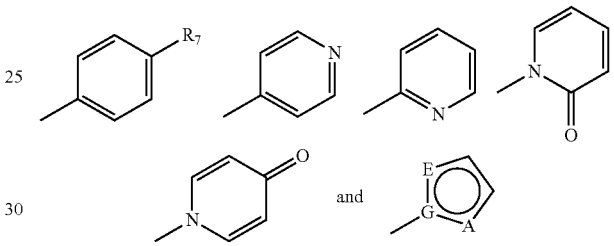

That is, from left to right, the first, second, third, fourth and fifth formula above have 4 $R_6$ groups; the last formula has 2 to 4 $R_6$ groups depending on A and E.

Likewise, for the variable $R_3$, it occurs at every open valency of the pyridinyl moiety depicted in the formulae I, 1, 2, and 3.

In the same manner, for the variable $R_8$, it occurs at every open valency of the ring moiety depicted in the formulae 3 and 5 and for the variable $R_{10}$, it occurs at every open valency of the ring moiety depicted in the formula 4.

One embodiment of the present invention provides a compound of formula 1

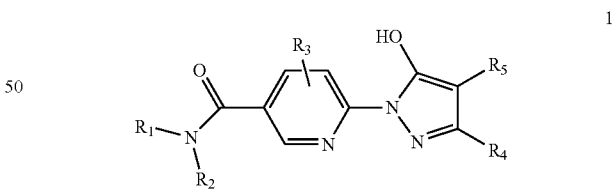

wherein
$R_1$ is selected from the group consisting of optionally substituted $C_{1-6}$ alkyl, optionally substituted $C_{3-8}$ cycloalkyl, and optionally substituted $C_{3-6}$ heterocyclyl;
$R_2$ is selected from the group consisting of hydrogen and $C_{1-4}$ alkyl;
or
$R_1$ and $R_2$ together with the nitrogen to which they are attached form a 4 to 8 membered, saturated, ring optionally having an additional ring heteroatom selected from the group N, O, and S and optionally substituted on any of the ring carbon atoms with 1 to 5 substituents independently selected from the group consisting of cyano, halo, hydroxy, amino, $C_{1-9}$ amide, $C_{1-4}$ alkyl, $C_{1-4}$ alkoxy, hydroxymethyl, and trifluoromethyl and optionally substituted on any optional additional ring nitrogen by optionally substituted $C_{1-4}$ alkyl;

$R_3$, each time taken, is independently selected from the group consisting of hydrogen, hydroxyl, amino, $C_{1-8}$ alkylamino, cyano, halo, optionally substituted $C_{1-6}$ alkyl, and $C_{1-4}$ alkoxy;

$R_4$ is selected from the group consisting of hydrogen, cyano, halo, methyl, ethyl, methoxy, and trifluoromethyl;

$R_5$ is selected from the group consisting of

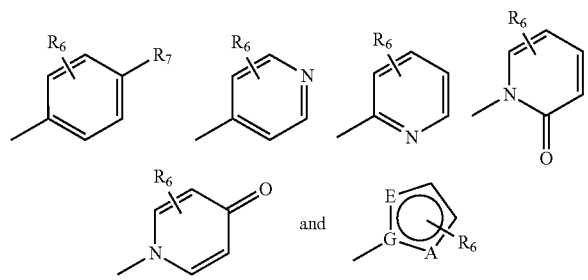

G is carbon;
A is selected from the group consisting of N, O, S, $CR_6$ and $NR_6$;
E is selected from the group consisting of N, O, S, and $CR_6$; provided that only one of A and E can be O or S;
or G is N and A and E are $CR_6$;
or G and A are N and E is $CR_6$;
or G, A, and E are N;
$R_6$, each time taken, is independently selected from the group consisting of hydrogen, cyano, halo, optionally substituted $C_{1-6}$ alkyl, $C_{1-4}$ alkoxy, and trifluoromethyl;
$R_7$ is selected from the group consisting of cyano and cyanomethyl;
or a pharmaceutically acceptable salt thereof.

One embodiment of the present invention provides a compound of formula 2

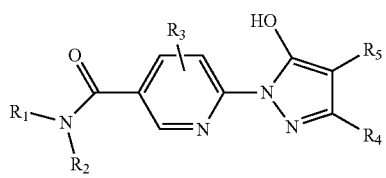

wherein
$R_1$ and $R_2$ together with the nitrogen to which they are attached form a 4 to 12 membered, saturated, ring optionally having 1 or 2 additional ring heteroatoms independently selected from the group N, O, and S and optionally substituted on any of the ring carbon atoms with 1 to 5 substituents independently selected from the group consisting of cyano, halo, hydroxy, amino, $C_{1-12}$ substituted amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent independently selected from the group consisting of hydrogen, optionally substituted $C_{3-8}$ cycloalkyl, and optionally substituted $C_{1-6}$ alkyl;

$R_3$, each time taken, is independently selected from the group consisting of hydrogen, hydroxyl, amino, $C_{1-8}$ alkylamino, cyano, halo, optionally substituted $C_{1-6}$ alkyl, and $C_{1-4}$ alkoxy;

$R_4$ is selected from the group consisting of hydrogen, cyano, halo, methyl, ethyl, methoxy, and trifluoromethyl;

$R_5$ is selected from the group consisting of

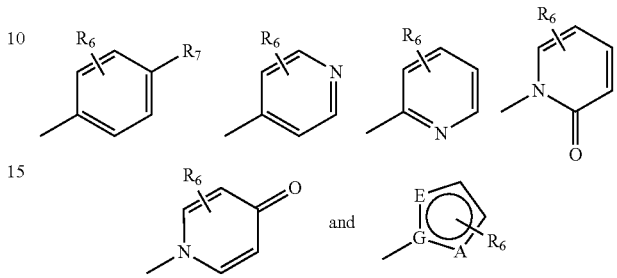

G is carbon;
A is selected from the group consisting of N, O, S, $CR_6$ and $NR_6$;
E is selected from the group consisting of N, O, S, and $CR_6$; provided that only one of A and E can be O or S;
or G is N and A and E are $CR_6$;
or G and A are N and E is $CR_6$;
or G, A, and E are N;
$R_6$, each time taken, is independently selected from the group consisting of hydrogen, cyano, halo, $C_{3-8}$ cycloalkyl, optionally substituted $C_{1-6}$ alkyl, $C_{1-4}$ alkoxy, and trifluoromethyl;
$R_7$ is selected from the group consisting of cyano and cyanomethyl;
or a pharmaceutically acceptable salt thereof.

One embodiment of the present invention provides a compound of formula 3

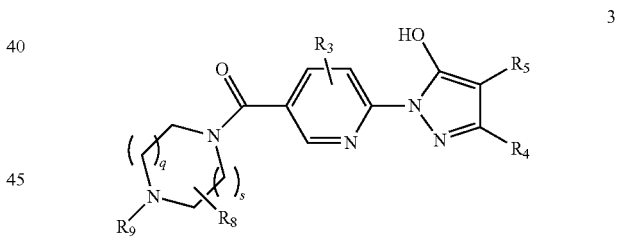

wherein
q is 0, 1, or 2;
s is 0, 1, or 2;
$R_3$, each time taken, is independently selected from the group consisting of hydrogen, hydroxyl, amino, $C_{1-8}$ alkylamino, cyano, halo, optionally substituted $C_{1-6}$ alkyl, and $C_{1-4}$ alkoxy;
$R_4$ is selected from the group consisting of hydrogen, cyano, halo, methyl, ethyl, methoxy, and trifluoromethyl;
$R_5$ is selected from the group consisting of

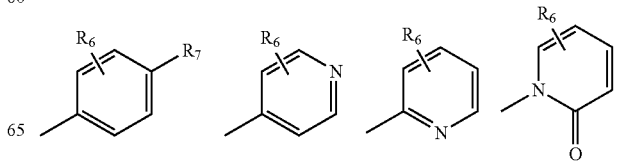

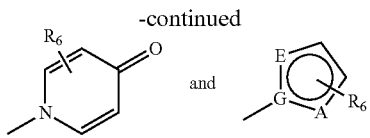

G is carbon;
A is selected from the group consisting of N, O, S, $CR_6$ and $NR_6$;
E is selected from the group consisting of N, O, S, and $CR_6$; provided that only one of A and E can be O or S;
or G is N and A and E are $CR_6$;
or G and A are N and E is $CR_6$;
or G, A, and E are N;
$R_6$, each time taken, is independently selected from the group consisting of hydrogen, cyano, halo, $C_{3-8}$ cycloalkyl, optionally substituted $C_{1-6}$ alkyl, $C_{1-4}$ alkoxy, and trifluoromethyl;
$R_7$ is selected from the group consisting of cyano and cyanomethyl;
$R_8$, each time taken, is independently selected from the group consisting of hydrogen, cyano, halo, $C_{1-4}$ alkyl, $C_{1-4}$ alkoxy, and trifluoromethyl;
$R_9$ is selected from the group consisting of hydrogen, $C_{1-6}$ alkyl optionally substituted with 1 to 3 fluoro, and $C_{3-8}$ cycloalkyl;
or a pharmaceutically acceptable salt thereof.

One embodiment of the present invention provides a compound of formula 4

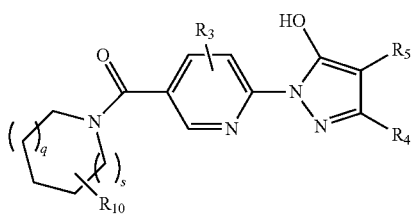

4 wherein
q is 0, 1, or 2;
s is 0, 1, or 2;
$R_3$, each time taken, is independently selected from the group consisting of hydrogen, hydroxyl, amino, $C_{1-8}$ alkylamino, cyano, halo, optionally substituted $C_{1-6}$ alkyl, and $C_{1-4}$ alkoxy;
$R_4$ is selected from the group consisting of hydrogen, cyano, halo, methyl, ethyl, methoxy, and trifluoromethyl;
$R_5$ is selected from the group consisting of

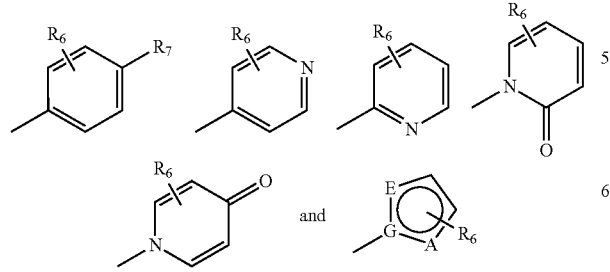

G is carbon;
A is selected from the group consisting of N, O, S, $CR_6$ and $NR_6$;
E is selected from the group consisting of N, O, S, and $CR_6$; provided that only one of A and E can be O or S;
or G is N and A and E are $CR_6$;
or G and A are N and E is $CR_6$;
or G, A, and E are N;
$R_6$, each time taken, is independently selected from the group consisting of hydrogen, cyano, halo, $C_{3-8}$ cycloalkyl, optionally substituted $C_{1-6}$ alkyl, $C_{1-4}$ alkoxy, and trifluoromethyl;
$R_7$ is selected from the group consisting of cyano and cyanomethyl;
$R_{10}$, each time taken, is independently selected from the group consisting of hydrogen, cyano, halo, hydroxy, amino, $C_{1-12}$ substituted amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent independently selected from the group consisting of hydrogen, optionally substituted $C_{3-8}$ cycloalkyl, and optionally substituted $C_{1-6}$ alkyl; or a pharmaceutically acceptable salt thereof.

One embodiment of the present invention provides a compound of formula 5

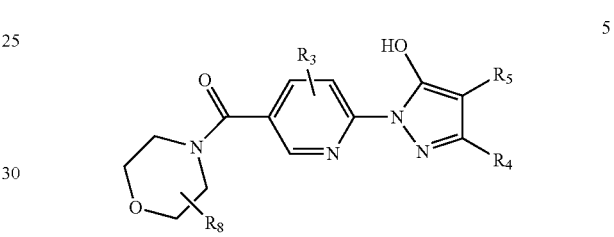

5 wherein
$R_3$, each time taken, is independently selected from the group consisting of hydrogen, hydroxyl, amino, $C_{1-8}$ alkylamino, cyano, halo, optionally substituted $C_{1-6}$ alkyl, and $C_{1-4}$ alkoxy;
$R_4$ is selected from the group consisting of hydrogen, cyano, halo, methyl, ethyl, methoxy, and trifluoromethyl;
$R_5$ is selected from the group consisting of

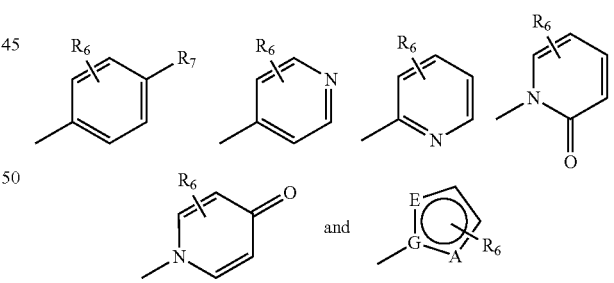

G is carbon;
A is selected from the group consisting of N, O, S, $CR_6$ and $NR_6$;
E is selected from the group consisting of N, O, S, and $CR_6$; provided that only one of A and E can be O or S;
or G is N and A and E are $CR_6$;
or G and A are N and E is $CR_6$;
or G, A, and E are N;
$R_6$, each time taken, is independently selected from the group consisting of hydrogen, cyano, halo, $C_{3-8}$ cycloalkyl, optionally substituted $C_{1-6}$ alkyl, $C_{1-4}$ alkoxy, and trifluoromethyl;

$R_7$ is selected from the group consisting of cyano and cyanomethyl;
$R_8$, each time taken, is independently selected from the group consisting of hydrogen, cyano, halo, $C_{1-4}$ alkyl, $C_{1-4}$ alkoxy, and trifluoromethyl;
or a pharmaceutically acceptable salt thereof.

(a) One embodiment relates to compounds of formula I, 1, 2, 3, 4, or 5 wherein $R_5$ is

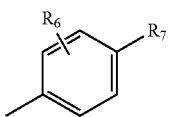

(b) One embodiment relates to compounds of embodiment (a) wherein $R_7$ is cyano.

(ba) One embodiment relates to compounds of embodiment (b) wherein one of $R_6$ is 3-methyl and each other $R_6$ is independently selected from the group consisting of hydrogen, fluoro, and methyl, depicted below:

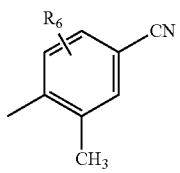

(bb) One embodiment relates to compounds of embodiment (b) wherein one of $R_6$ is 3-methyl, one of $R_6$ is fluoro, and each other $R_6$ is hydrogen depicted below:

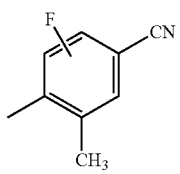

(bc) One embodiment relates to compounds of embodiment (b) wherein one of $R_6$ is 3-methyl and each other $R_6$ is hydrogen depicted below:

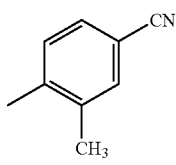

(c) One embodiment relates to compounds of embodiment (a) wherein $R_7$ is cyanomethyl.

(ca) One embodiment relates to compounds of embodiment (c) wherein $R_6$, each time taken, is independently selected from the group consisting of hydrogen, cyano, halo, and $C_{1-6}$ alkyl.

(cb) One embodiment relates to compounds of embodiment (c) wherein $R_6$, each time taken, is independently selected from the group consisting of hydrogen, cyano, fluoro, and methyl.

(d) One embodiment relates to compounds of formula I, 1, 2, 3, 4, or 5 wherein $R_5$ is selected from the group consisting of

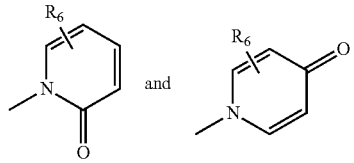

(da) One embodiment relates to compounds of embodiment (d) wherein $R_6$, each time taken, is independently selected from the group consisting of hydrogen, cyano, halo, and $C_{1-6}$ alkyl.

(db) One embodiment relates to compounds of embodiment (d) wherein $R_6$, each time taken, is independently selected from the group consisting of hydrogen, cyano, fluoro, and methyl.

(e) One embodiment relates to compounds of formula I, 1, 2, 3, 4, or 5 wherein $R_5$ is

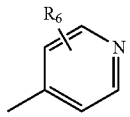

(ea) One embodiment relates to compounds of embodiment (e) wherein $R_6$, each time taken, is independently selected from the group consisting of hydrogen, cyano, halo, and $C_{1-6}$ alkyl.

(eb) One embodiment relates to compounds of embodiment (e) wherein $R_6$, each time taken, is independently selected from the group consisting of hydrogen, cyano, fluoro, and methyl.

(f) One embodiment relates to compounds of embodiment (e) wherein at least one of $R_6$ is methoxy.

(fa) One embodiment relates to compounds of embodiment (0 wherein $R_6$, each time taken, is independently selected from the group consisting of hydrogen, cyano, halo, and $C_{1-6}$ alkyl.

(fb) One embodiment relates to compounds of embodiment (e) wherein $R_6$, each time taken, is independently selected from the group consisting of hydrogen, cyano, fluoro, and methyl.

(g) One embodiment relates to compounds of formula I, 1, 2, 3, 4, or 5 wherein $R_5$ is

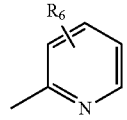

(ga) One embodiment relates to compounds of embodiment (g) wherein $R_6$, each time taken, is independently selected from the group consisting of hydrogen, cyano, halo, and $C_{1-6}$ alkyl.

(gb) One embodiment relates to compounds of embodiment (e) wherein $R_6$, each time taken, is independently selected from the group consisting of hydrogen, cyano, fluoro, and methyl.

(h) One embodiment relates to compounds of formula I, 1, 2, 3, 4, or 5 wherein $R_5$ is

(i) One embodiment relates to compounds of embodiment (h) wherein G and A are N and E is $CR_6$.

(j) One embodiment relates to compounds of embodiment (h) wherein G, A, and E are N.

(ja) One embodiment relates to compounds of embodiments (h), (i), or (j) wherein $R_6$, each time taken, is independently selected from the group consisting of hydrogen, cyano, halo, and $C_{1-6}$ alkyl.

(jb) One embodiment relates to compounds of embodiments (h), (i), or (j) wherein $R_6$, each time taken, is independently selected from the group consisting of hydrogen, cyano, fluoro, and methyl.

(k) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is optionally substituted $C_{1-6}$ alkyl.

(l) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, optionally substituted $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

(n) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is $C_{1-6}$ alkyl optionally substituted with 1 to 7 substituents independently selected from the group consisting of $C_{1-4}$ alkoxy, amino, $C_{1-8}$ alkylamino, cyano, $C_{3-8}$ cycloalkyl, halo, hydroxy, $C_{3-6}$ heterocyclyl optionally substituted on any ring nitrogen by $C_{1-4}$ alkyl.

(m) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is $C_{1-6}$ alkyl optionally substituted with 1 to 3 substituents independently selected from the group consisting of $C_{1-4}$ alkoxy, amino, cyano, $C_{3-8}$ cycloalkyl, hydroxy, $C_{3-6}$ heterocyclyl optionally substituted on any ring nitrogen by $C_{1-4}$ alkyl.

(o) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is $C_{1-6}$ alkyl substituted with $C_{3-6}$ heterocyclyl optionally substituted on any ring nitrogen by $C_{1-4}$ alkyl.

(p) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is $C_{1-6}$ alkyl substituted with optionally substituted $C_{3-8}$ cycloalkyl.

(q) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is $C_{1-6}$ alkyl substituted with 1 to 3 hydroxy.

(r) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is optionally substituted $C_{3-8}$ cycloalkyl.

(s) One embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), and (k) wherein $R_1$ is optionally substituted $C_{3-6}$ heterocyclyl.

(t) Another embodiment relates to compounds of formula I or 1 and embodiments (a), (b), (ba), (bb), (bc), (c), (ca), (cb), (d), (da), (db), (e), (ea), (eb), (f), (fa), (fb), (g), (h), (i), (j), (ja), (jb), (k), (l), (m), (n), (o), (p), (q), (r), and (s) wherein $R_2$ is hydrogen.

(u) Another embodiment relates to compounds of formula I, 1, 2, 3, 4, or 5 and embodiments (a), (b), (ba), (bb), (bc), (c), (ca), (cb), (d), (da), (db), (e), (ea), (eb), (f), (fa), (fb), (g), (h), (i), (j), (ja), (jb), (k), (l), (m), (n), (o), (p), (q), (r), (s), and (t) wherein each $R_3$ is hydrogen.

(v) Another embodiment relates to compounds of formula I, 1, 2, 3, 4, or 5 and embodiments (a), (b), (ba), (bb), (bc), (c), (ca), (cb), (d), (da), (db), (e), (ea), (eb), (f), (fa), (fb), (g), (h), (i), (j), (ja), (jb), (k), (l), (m), (n), (o), (p), (q), (r), (s), (t), and (u) wherein $R_4$ is hydrogen.

(w) Another embodiment relates to compounds of formula I, 1, or 2 and embodiments (a), (b), (ba), (bb), (bc), (c), (ca), (cb), (d), (da), (db), (e), (ea), (eb), (f), (fa), (fb), (g), (h), (i), (j), (ja), (jb), (u), and (v) wherein $R_1$ and $R_2$ together with the nitrogen to which they are attached form a 4 to 12 membered, saturated, ring optionally having 1 or 2 additional ring heteroatoms independently selected from the group N, O, and S and optionally substituted on any of the ring carbon atoms with 1 to 5 substituents independently selected from the group consisting of cyano, halo, hydroxy, $C_{1-12}$ substituted amino, optionally substituted $C_{3-6}$ heterocyclyl, and optionally substituted $C_{1-6}$ alkyl, and substituted on any additional ring nitrogen by a substituent independently selected from the group consisting of hydrogen, optionally substituted $C_{3-8}$ cycloalkyl, and optionally substituted $C_{1-6}$ alkyl.

(x) Another embodiment relates to compounds of formula I, 1, or 2 and embodiments (a), (b), (ba), (bb), (bc), (c), (ca), (cb), (d), (da), (db), (e), (ea), (eb), (f), (fa), (fb), (g), (h), (i), (j), (ja), (jb), (u), and (v) wherein $R_1$ and $R_2$ together with the nitrogen to which they are attached form a 4 to 12 membered, saturated, ring having 1 additional ring heteroatom independently selected from the group N, O, and S and optionally substituted on any of the ring carbon atoms with 1 to 5 substituents independently selected from the group consisting of cyano, halo, hydroxy, amino, $C_{1-12}$ substituted amino, optionally substituted $C_{3-6}$ heterocyclyl, $C_{1-9}$ amide, optionally substituted $C_{1-6}$ alkyl, and $C_{1-4}$ alkoxy and optionally substituted on any additional ring nitrogen by a substituent selected from the group consisting of hydrogen, optionally substituted $C_{3-8}$ cycloalkyl, and optionally substituted $C_{1-6}$ alkyl.

(y) Another embodiment relates to compounds of formula I, 1, or 2 and embodiments (a), (b), (ba), (bb), (bc), (c), (ca), (cb), (d), (da), (db), (e), (ea), (eb), (f), (fa), (fb), (g), (h), (i), (j), (ja), (jb), (u), and (v) wherein $R_1$ and $R_2$ together with the nitrogen to which they are attached form a monocyclic 4 to 8 membered, saturated, ring having 1 additional ring heteroatom independently selected from the group N, O, and S and optionally substituted o on any of the ring carbon atoms with 1 to 5 substituents independently selected from the group consisting of cyano, halo, hydroxy, amino, $C_{1-12}$ substituted amino, optionally substituted $C_{3-6}$ heterocyclyl, $C_{1-9}$ amide, optionally substituted $C_{1-6}$ alkyl, and $C_{1-4}$ alkoxy and optionally substituted on any additional ring nitrogen by a substituent selected from the group consisting of hydrogen, optionally substituted $C_{3-8}$ cycloalkyl, and optionally substituted $C_{1-6}$ alkyl.

(z) Another embodiment relates to compounds of formula I, 1, or 2 and embodiments (a), (b), (ba), (bb), (bc), (c), (ca), (cb), (d), (da), (db), (e), (ea), (eb), (f), (fa), (fb), (g), (h), (i), (j), (ja), (jb), (u), and (v) wherein $R_1$ and $R_2$ together with the nitrogen to which they are attached form a monocyclic 4 to 8 membered, saturated, ring having 1 additional ring N and optionally substituted on any of the ring carbon atoms with 1 to 5 substituents independently selected from the group consisting of cyano, halo, hydroxy, amino, $C_{1-12}$ substituted amino, optionally substituted $C_{3-6}$ heterocyclyl, $C_{1-9}$ amide, optionally substituted $C_{1-6}$ alkyl, and $C_{1-4}$ alkoxy and substituted on the additional ring nitrogen by a substituent selected from the group consisting of hydrogen, optionally substituted $C_{3-8}$ cycloalkyl, and optionally substituted $C_{1-6}$ alkyl.

(aa) Another embodiment relates to compounds of formula I, 1, or 2 and embodiments (a), (b), (ba), (bb), (bc), (c), (ca), (cb), (d), (da), (db), (e), (ea), (eb), (f), (fa), (fb), (g), (h), (i), (j), (ja), (jb), (u), and (v) wherein $R_1$ and $R_2$ together with the nitrogen to which they are attached form a monocyclic 4 to 8 membered, saturated, ring having 1 additional ring N and substituted on the additional ring nitrogen by a $C_{1-6}$ alkyl.

(ab) Another embodiment relates to compounds of formula 3 and embodiments (a), (b), (ba), (bb), (bc), (c), (ca), (cb), (d), (da), (db), (e), (ea), (eb), (f), (fa), (fb), (g), (h), (i), (j), (ja), (jb), (u), and (v) wherein $R_9$ is $C_{1-6}$ alkyl.

(ac) Another embodiment relates to compounds of formulae 3, 4, and 5 and embodiments (a), (b), (ba), (bb), (bc), (c), (ca), (cb), (d), (da), (db), (e), (ea), (eb), (f), (fa), (fb), (g), (h), (i), (j), (ja), (jb), (u), (v), and (ab) wherein s is 1 and q is 1.

(ad) Another embodiment relates to compounds of formulae 3 and 5 and embodiments (a), (b), (ba), (bb), (bc), (c), (ca), (cb), (d), (da), (db), (e), (ea), (eb), (f), (fa), (fb), (g), (h), (i), (j), (ja), (jb), (u), (v), (ab), and (ac) wherein one of $R_8$ is $C_{1-6}$ alkyl and each other $R_8$ is hydrogen.

(ae) Another embodiment relates to compounds of formulae 3 and 5 and embodiments (a), (b), (ba), (bb), (bc), (c), (ca), (cb), (d), (da), (db), (e), (ea), (eb), (f), (fa), (fb), (g), (h), (i), (j), (ja), (jb), (u), (v), (ab), and (ac) wherein each $R_8$ is hydrogen.

(af) Another embodiment relates to compounds of formula 4 and embodiments (a), (b), (ba), (bb), (bc), (c), (ca), (cb), (d), (da), (db), (e), (ea), (eb), (f), (fa), (fb), (g), (h), (i), (j), (ja), (jb), (u), (v), (ab), and (ac) wherein each $R_{10}$ is hydrogen.

(ay) Another embodiment relates to a pharmaceutically acceptable salt of each of the above embodiments.

(az) Another embodiment relates to a pharmaceutically acceptable salt of each of the exemplified compounds.

It is understood that when $R_1$ and $R_2$ together with the nitrogen to which they are attached form a 4 to 12 membered, saturated, ring optionally having 1 or 2 additional ring heteroatoms independently selected from the group N, O, and S and optionally substituted on any of the ring carbon atoms with 1 to 5 substituents independently selected from the group consisting of cyano, halo, hydroxy, amin, $C_{1-12}$ substituted amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent independently selected from the group consisting of hydrogen, optionally substituted $C_{3-8}$ cycloalkyl, and optionally substituted $C_{1-6}$ alkyl that the ring formed by $R_1$ and $R_2$ together with the nitrogen to which they are attached can be monocyclic or bicyclic, including spiro, fused, and bridged systems.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991). It is understood that formula I encompasses formulae 1, 2, 3, 4, and 5 and that the procedures below are also amenable to preparing compounds of formulae 1, 2, 3, 4, and 5.

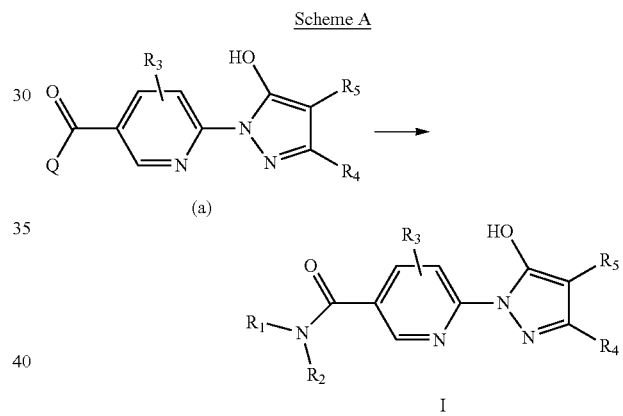

Scheme A

Scheme A depicts the amidation of an appropriate compound of formula (a) to give a compound of formula I. An appropriate compound of formula (a) is one in which $R_3$, $R_4$, and $R_5$ are defined in formula I or give rise to $R_3$, $R_4$, and $R_5$ as defined in formula I and Q gives rise to —$NR_aR_2$ to a desired final product of formula I. Typical groups Q are hydroxyl or a leaving group, such as chloro, bromo, or imidazolyl, an activating moiety, a mixed anhydride of another carboxylic acid, such as formic acid, acetic acid, or represents the other part of a symmetrical anhydride formed from two compounds of formula (a). The preparation of compounds of formula (a) is readily appreciated in the art. A compound of formula (a) is reacted in an amide forming reaction with an amine of formula $HN(R_1)(R_2)$ in which $R_1$ and $R_2$ are defined in formula I or give rise to $R_1$ and $R_2$ as defined in formula I.

For example, standard amide forming conditions can be used, such as those using coupling agents, including those used in peptide couplings, such as 2-(1H-7-azabenzotriazol-1-yl)-1,1,3,3-tetramethyl uronium hexafluorophosphate methanaminium (HATU), dicyclohexylcarbodiimide (DCC), and 1-(3-dimethylaminopropyl)-3-ethylcarbodiimide hydrochloride. If necessary or desired, an additive such as 4-(dimethylamino)pyridine, 1-hydroxybenzotriazole, and the like may be used to facilitate the reaction. Such reactions are generally carried out using a base, such as N-methylmorpholine or triethylamine, in a wide variety of suitable solvents such as dichloromethane, dimethylformamide (DMF), N-methylpyrrolidone (NMP), dimethylacetamide (DMA), tetrahydrofuran (THF), and the like. Such amide forming reactions are well understood and appreciated in the art.

Scheme B

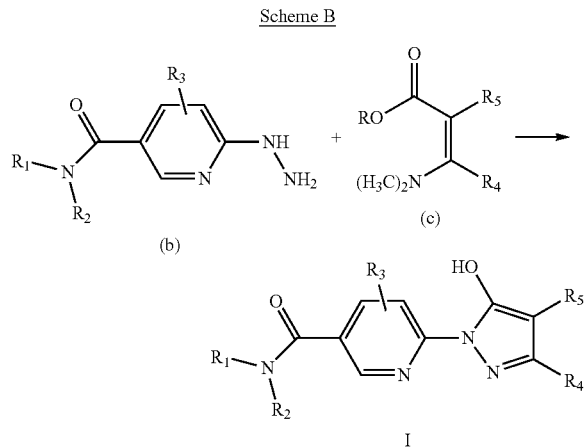

Scheme B the coupling of an appropriate compound of formula (b) and an appropriate compound of formula (c) to give a compound of formula I. An appropriate compound of formula (b) is one in which $R_1$, $R_2$, and $R_3$ are defined in formula I or give rise to $R_1$, $R_2$, and $R_3$ as defined in formula I. An appropriate compound of formula (c) is one in which R is H or preferably a $C_{1-4}$ alkyl and $R_4$ and $R_5$ are defined in formula I or gives rise to $R_5$ as defined in formula I. For convenience the N,N-dimethylamino-acrylate is depicted but any suitable leaving group on the acrylate can be used. The preparation of compounds of formula (b) and (c) is readily appreciated in the art.

For example, a compound of formula (b) and (c) are combined in a solvent, such as a lower alcohol, e.g., methanol, ethanol, or isopropanol, optionally in the presence of an acid, such as hydrochloric acid. Typically, a base is later added and the reaction continued to give a compound of formula I. Suitable bases include organic amines, such as Hunig's base, triethylamine, and the like. The reaction can optionally be heated if necessary under either the acidic or basic conditions.

Scheme C

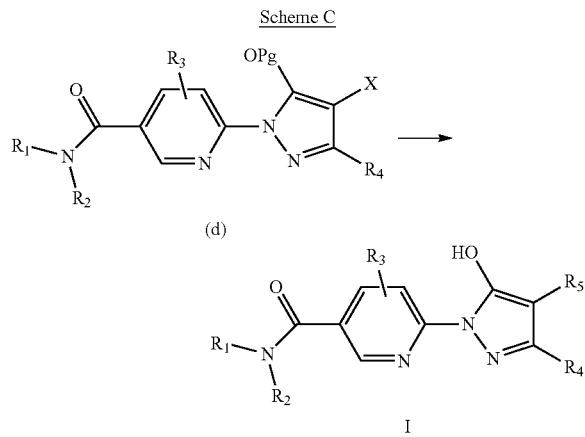

Scheme C depicts coupling of an appropriate compound of formula (d) and an appropriate $R_5$-boronic acid or boronic ester to give a compound of formula I. An appropriate compound of formula (d) is one in which $R_1$, $R_2$, $R_3$, and $R_4$ are defined in formula I or give rise to $R_1$, $R_2$, $R_3$, and $R_4$ as defined in formula I, X is a leaving group, such as halo, in particular chloro and bromo, and Pg is an appropriate protecting group, such a methyl. The selection and removal of suitable protecting groups is well known in the art. An appropriate $R_5$-boronic acid or boronic ester is one in which $R_5$ is as defined in formula I or give rise to $R_5$ as defined in formula I. Such reactions are generally known as a Suzuki reaction and are well known in the art. While a Suzuki reaction is depicted in Scheme C it is understood that other carbon-carbon bond forming coupling reactions can be used to produce compounds of formula I. In a step, not shown, the product of compound (d) from the carbon-carbon bond forming reaction depicted in Scheme C is deprotected to tive a compound of formula I.

It will be recognized by one of ordinary skill in the art that a compound of formula I can be elaborated in a variety of ways to further give compounds of formula I. Such reactions include hydrolysis, oxidation, reduction, alkylation, esterification, amidation, sulfonation, and the like.

Also, in an optional step, not shown, the compounds of formula I can be converted to a pharmaceutically acceptable salt by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (chloroform-d), DMSO-d6 (deuterodimethylsulfoxide), $CD_3OD$ (methanol-d4)), and THF-d8 (deuterotetrahydrofuran). Other abbreviations have their usual meaning unless otherwise indicated, for example, HOBT is 1-hydroxybenzotriazole, EDC is 1-(3-dimethylaminopropyl)-3-ethylcarbodiimide, generally used as its hydrochloride salt, DMSO is dimethylsulfoxide, etc. The mass spectra, unless otherwise indicated, were recorded using either electrospray ionization (ESI) or atmospheric pressure chemical ionization.

The examples below were carried out in appropriate vessels and were typically stirred. Where indicated, products of certain preparations and examples are purified by mass-triggered HPLC (e.g., Pump: Waters™ 2525; MS: ZQ™; Software: MassLynx™), flash chromatography, or preparative thin layer chromatography (TLC). Reverse phase chromatography can be carried out using a variety of systems, including on a column (Gemini™ 5µ C18 110A, Axia™, ID30×75 mm, 5µ) under acidic conditions, eluting with acetonitrile (ACN) and water mobile phases containing 0.035% and 0.05% trifluoroacetic acid (TFA), respectively, or 0.1% formic acid (FA) in 20/80(v/v) water/methanol or under basic conditions, eluting with water and 20/80 (v/v) water/acetonitrile mobile phases, both containing 10 mM $NH_4HCO_3$; or (XSelect™ C18, 5µ, ID30×75 mm) under acidic conditions, eluting with ACN and water mobile phases containing 0.1% FA or under basic conditions, eluting with 0.1% ammonium hydroxide in water (pH=9.5-10) and 0.1% ammonium hydroxide in ACN (pH=9.5-10). After isolation by chromatography, the solvent is removed and the product is obtained by evaporating product containing fractions (e.g., GeneVac™), rotary evaporator, evacuated flask, lyophilization, etc.

Preparation 1 (2-ethoxy-2-oxoethyl)zinc(II) bromide

Combined THF (60.0 mL), zinc (19.61 g, 300 mmol), and copper(I) chloride (2.97 g, 30.0 mmol) under nitrogen. The stirred suspension was heated to reflux for 40 minutes, cooled to ambient temperature, and ethyl 2-bromoacetate (6.64 mL, 60 mmol) was added slowly. The reaction was stirred for an additional 1 h at ambient temperature and was left overnight without stirring. The top clear layer was cannulated into a separate flask under nitrogen to give the title compound (approximately 1M concentration) which used in the next step without further purification.

Preparation 2 ethyl 2-(2-methoxypyridin-4-yl)acetate

Combined 4-bromo-2-methoxypyridine (654 µl, 5.32 mmol), (2-ethoxy-2-oxoethyl)zinc(II) bromide (5850 µl, 5.85 mmol), and Pd(PPh$_3$)$_4$ catalyst (615 mg, 0.532 mmol) in THF (15.2 mL) and heated to 120° C. in a microwave for 5 minutes. The reaction was filtered through a course glass frit, concentrated to an oil and purified via flash chromatography (100 g silica gel using a 5% to 50% EtOAc in heptane gradient). The appropriate fractions were combined and concentrated to acquire ethyl 2-(2-methoxypyridin-4-yl)acetate (400 mg, 38.5% yield) as a colorless oil. MS m/z [M+H]$^+$ 196.1.

Preparation 3 ethyl 3-(dimethylamino)-2-(2-methoxypyridin-4-yl)acrylate

Combined ethyl 2-(2-methoxypyridin-4-yl)acetate (320 mg, 1.639 mmol) and 1,1-diethoxy-N,N-dimethylmethanamine (2079 µl, 12.13 mmol) and heated to 100° C. for 1 h then cooled to ambient temperature with stirring overnight. The reaction was concentrated in vacuo to afford a brown oil. The oil was partitioned between EtOAc and water (200 mL). The aqueous phase was back-extracted with EtOAc (2×20 mL) and the organic layers were combined, washed with brine (100 mL), dried over sodium sulfate, and concentrated to an oil in vacuo. The oil was purified by flash chromatography (100 g basic silica using a 5% to 50% EtOAc in heptanes gradient) to give the title compound as a light yellow oil. MS m/z [M+H]$^+$ 251.1.

Preparation 4 6-(5-hydroxy-4-(2-methoxypyridin-4-yl)-1H-pyrazol-1-yl)nicotinic acid Combined 6-hydrazinylnicotinic acid (167 mg, 1.090 mmol), ethyl 3-(dimethylamino)-2-(2-methoxypyridin-4-yl)acrylate (300 mg, 1.199 mmol), 2-propanol (3632 µl), and hydrochloric acid (1.85% aqueous, 2.15 mL, 1.090 mmol). The reaction was stirred at room temperature. After 1 hour Hunig's base (949 µl, 5.45 mmol) was added to the suspension which became a yellow solution. The reaction was washed with EtOAc (2×15 mL) and the aqueous phase was concentrated in vacuo, yielding a yellow solid. The solid was triturated with 1N HCl (50 mL), collected by filtration, and washed with water. The solid was then slurried in methanol (2×60 mL) and diethyl ether (2×60 mL), the dried under vacuum to give the title compound. MS m/z [M+H]$^+$ 313.0.

Preparation 5 methyl 3-(dimethylamino)-2-(4-methoxyphenyl)acrylate

Combined methyl 2-(4-methoxyphenyl)acetate (3.58 mL, 22.20 mmol) and 1,1-dimethoxy-N,N-dimethylmethanamine (11.89 mL, 89 mmol) and heated to 100° C. for 14 h. The reaction was concentrated in vacuo to afford a light yellow oil which was purified by flash chromatography (100 g basic silica using a 5% to 50% EtOAc in heptanes gradient to give the title compound (361 mg, 6.91%) as a colorless oil. MS m/z [M+H]$^+$ 236.1.

Preparation 6 6-hydrazinylnicotinic acid

A suspension of 6-chloronicotinic acid (30.0 g, 189 mmol) in 1,4-dioxane (29.0 mL) was treated with hydrazine hydrate (134 mL, 1.51 mol) and heated to 90° C. overnight. The mixture was cooled to ambient temperature and then in ice for 30 min. Precipitate formation was induced by etching the side of the flask and the precipitate was filtered and re-suspended in EtOH (500 mL) with vigorous stirring. The resulting suspension was filtered. The precipitate was dissolved in water (300 mL) and HCl (6N) was added until pH=1. The pH was then adjusted to 5 with NaOH (50%, aq.) and the resulting suspension was stirred for 1 h. The solids were collected by filtration and dried in vacuum to give the title compound (16.65 g, 57.7% yield) as an off-white solid. $^1$H NMR (400 MHz, DMSO-d$_6$) δ ppm 6.70 (d, 1H) 7.86 (dd, J=8.97, 2.15 Hz, 1H) 8.32 (br. s., 1H) 8.52 (d, J=1.77 Hz, 1H). MS m/z [M+H]$^+$ 154.

Preparation 7 6-(4-(4-cyanophenyl)-5-hydroxy-1H-pyrazol-1-yl)nicotinic acid

Combined 6-hydrazinylnicotinic acid (6.00 g, 39.2 mmol) and ethyl 2-(4-cyanophenyl)-3-(dimethylamino)acrylate (10.05 g, 41.1 mmol) and 2-propanol (80 mL) and treated with 1.85% hydrochloric acid (77 mL, 39.2 mmol). The reaction was stirred at room temperature for 16 h, then Hunig's base (34.1 mL, 196 mmol) was add to the suspension which became homogeneous. The mixture was stirred for 3 h. The reaction mixture was washed with isopropyl acetate (2×150 mL). The combined organic layers were extracted with water (40 mL) and the combined aqueous layers were concentrated in vacuo to give a solid. The solid was triturated with 1N HCl (300 mL), filtered and washed with water (20 mL), then slurried in ethanol (350 mL) and granulated overnight. The solid was collected by filtration and dried in vacuum to give the title compound (9.20 g, 77% yield) as a tan solid. $^1$H NMR (400 MHz, DMSO-d$_6$) δ ppm 7.79 (d, J=8.34 Hz, 2H) 8.14 (br. s., 2H) 8.47 (d, J=7.07 Hz, 1H) 8.71 (br. s., 2H) 8.97 (s, 1H) 13.44 (br. s., 1H) 13.60 (br. s., 1H). MS [M+H] 307.

Preparation 8 ethyl 2-(4-cyano-1H-pyrazol-1-yl)acetate

Combined 1H-pyrazole-4-carbonitrile (0.432 g, 4.64 mmol) in acetone (9.28 mL), potassium carbonate (1.924 g, 13.92 mmol) and ethyl 2-bromoacetate (1.027 mL, 9.28 mmol). The reaction mixture was stirred at room temperature overnight, then concentrated in vacuo, diluted with EtOAc (10 mL), washed with water (10 mL), dried (MgSO$_4$) and concentrated in vacuo to give a residue. The residue was purified using flash column chromatography on silica gel (EtOAc in heptane, 10-50% gradient) to give a white solid. The solid was suspended in heptane and then filtered and dried to give the title compound (0.4314 g, 51.9% yield) as a white solid. $^1$H NMR (400 MHz, DMSO-d$_6$) δ ppm 1.21 (t, J=7.20 Hz, 3H) 4.17 (q, J=7.07 Hz, 2H) 5.19 (s, 2H) 8.11 (s, 1H) 8.57 (s, 1H). MS m/z [M+H]$^+$ 180.

Preparation 9 ethyl 2-(4-cyano-1H-pyrazol-1-yl)-3-(dimethylamino)acrylate

Combined ethyl 2-(4-cyano-1H-pyrazol-1-yl)acetate (0.427 g, 2.383 mmol) with 1,1-diethoxy-N,N-dimethylmethanamine (1.403 g, 9.53 mmol) and heated in a closed vial at 100° C. for 2.5 h. The mixture was concentrated in vacuo and purified using flash column chromatography on NH silica gel (30 g SiO2, EtOAc in heptane, 10-50% gradient) to give the title compound (0.4942 g, 89% yield) as a yellow solid. $^1$H NMR (400 MHz, DMSO-$d_6$) δ ppm 1.12 (t, 3H) 1.91-2.43 (m, 3H) 2.70-3.29 (m, 3H) 4.03 (q, J=7.07 Hz, 2H) 7.59 (s, 1H) 8.14 (s, 1H) 8.56 (s, 1H). MS m/z [M+H]+ 235

Preparation 10 ethyl 3-(dimethylamino)-2-(4-fluorophenyl)acrylate

Combined ethyl 2-(4-fluorophenyl)acetate (500 mg, 2.74 mmol) in 1,1-dimethoxy-N,N-dimethylmethanamine (1.837 mL, 13.72 mmol) and DMF (2 mL) and heated at 100° C. for 5 h. The reaction was then diluted with EtOAc (50 mL), washed with saturated aqueous ammonium chloride (50 mL) and brine, dried over magnesium sulfate and concentrated in vacuo to give a yellow oil. The oil was purified on a 30 g NH silica column (Moritex) eluted with 0 to 60% EtOAc in hexanes to give the title compound (223 mg, 34.2% yield) as a clear, colorless oil. $^1$H NMR (400 MHz, DMSO-$d_6$) δ ppm 1.10 (t, J=7.1 Hz, 3H) 2.64 (s, 6H) 3.98 (q, J=7.1 Hz, 2H) 7.06-7.15 (m, 4H) 7.49 (s, 1H).

Preparation 11 methyl 2-(4-cyano-3-fluorophenyl)-3-(dimethylamino)acrylate

The title compound was prepared in a manner similar to Example Preparation 10 using methyl 2-(4-cyano-3-fluorophenyl)acetate to give the title compound. $^1$H NMR (400 MHz, DMSO-$d_6$) δ ppm 2.73 (br. s., 6H) 3.54 (s, 3H) 7.11 (dd, J=8.1, 1.5 Hz, 1H) 7.25 (dd, J=11.1, 1.5 Hz, 1H) 7.63 (s, 1H) 7.77 (t, J=7.7 Hz, 1H).

Preparation 12 ethyl 3-(dimethylamino)-2-(4-(trifluoromethyl)phenyl)acrylate The title compound was prepared in a manner similar to Example Preparation 10 using ethyl 2-(4-(trifluoromethyl)phenyl)acetate and 1,1-diethoxy-N,N-dimethylmethanamine to give the title compound. $^1$H NMR (400 MHz, chloroform-d) δ ppm 1.21 (t, J=7.1 Hz, 3H) 2.71 (s, 6H) 4.14 (q, J=7.2 Hz, 2H) 7.31 (d, J=7.8 Hz, 2H) 7.53 (d, J=7.8 Hz, 2H) 7.61 (s, 1H).

Preparation 13 ethyl 3-(dimethylamino)-2-(4-oxopyridin-1(4H)-yl)acrylate

The title compound was prepared in a manner similar to Example Preparation 10 using ethyl 2-(4-oxopyridin-1(4H)-yl)acetate and 1,1-diethoxy-N,N-dimethylmethanamine to give the title compound. MS m/z 237 [M+H]+. $^1$H NMR (400 MHz, DMSO-$d_6$) δ ppm 1.16 (t, J=7.1 Hz, 3H) 2.86 (br. s, 6H) 4.06 (q, J=7.1 Hz, 2H) 6.01-6.11 (m, 2H) 7.43-7.47 (m, 2H) 7.48 (s, 1H).

Preparation 14 tert-butyl 2-(3-cyanophenyl)acetate

Combined 3-bromobenzonitrile (1500 mg, 8.24 mmol), 0.5 M (2-(tert-butoxy)-2-oxoethyl)zinc(II) chloride (24.72 mL, 12.36 mmol), 2'-(dicyclohexylphosphino)-N,N-dimethyl-[1,1'-biphenyl]-2-amine (324 mg, 0.824 mmol) and Pd(dba)2 (237 mg, 0.412 mmol) in THF (25 mL) and heated at 100° in an oil bath for 14 h. The reaction solution was concentrated onto Celite® and chromatographed on a 120 g silica gel column eluted with 0 to 50% EtOAc in hexanes to give the title compound (1.537 g, 86% yield) as a yellow oil. MS m/z 218 [M+H]+. $^1$H NMR (400 MHz, chloroform-d) δ ppm 1.45 (s, 9H) 3.56 (s, 2H) 7.40-7.46 (m, 1H) 7.49-7.54 (m, 1H) 7.54-7.59 (m, 2H).

Preparation 15 ethyl 2-(3-cyanophenyl)acetate

Combined tert-butyl 2-(3-cyanophenyl)acetate (500 mg, 2.301 mmol), ethanol (10 mL) and 4 N HCl in dioxane (0.288 mL, 1.151 mmol) and the solution heated at 60° C. for 22 h. The solution was concentrated in vacuo to give the title compound a yellow oil which was used without further purification. MS m/z 190 [M+H]+. $^1$H NMR (400 MHz, chloroform-d) δ ppm 1.23-1.31 (m, 3H) 3.65 (s, 2H) 4.17 (q, J=7.1 Hz, 2H) 7.40-7.47 (m, 1H) 7.51-7.56 (m, 1H) 7.56-7.62 (m, 2H).

Preparation 16 ethyl 2-(3-cyanophenyl)-3-(dimethylamino)acrylate

The title compound was prepared in a manner similar to Example Preparation 10 using ethyl 2-(3-cyanophenyl)acetate and 1,1-diethoxy-N,N-dimethylmethanamine to give the title compound. $^1$H NMR (400 MHz, DMSO-d6) δ ppm 1.12 (t, J=7.1 Hz, 3H) 2.67 (s, 6H) 4.00 (q, J=7.1 Hz, 2H) 7.42-7.45 (m, 1H) 7.45-7.50 (m, 1H) 7.53-7.55 (m, 1H) 7.57 (s, 1H) 7.64 (dt, J=7.1, 1.7 Hz, 1H).

Preparation 17 methyl 2-(4-(methylsulfonyl)phenyl)acetate

Combined 2-(4-(methylsulfonyl)phenyl)acetic acid (1 g, 4.67 mmol) in DCM (15 mL) and MeOH (5 mL) and slowly added TMS-diazomethane (2 M in hexanes) (3.50 mL, 7.00 mmol) and the solution was stirred at 20° C. for 3 h. The reaction was quenched with acetic acid (0.134 mL, 2.334 mmol), let stir for 15 min, then concentrated in vacuo to give the title compound which was used without further purification. MS m/z 229 [M+H]+.

Preparation 18 methyl 3-(dimethylamino)-2-(4-(methylsulfonyl)phenyl)acrylate The title compound was prepared in a manner similar to Example Preparation 10 using methyl 2-(4-(methylsulfonyl)phenyl)acetate to give the title compound. $^1$H NMR (400 MHz, DMSO-$d_6$) δ ppm 2.68 (br. s., 6H) 3.22 (s, 3H) 3.53 (s, 3H) 7.36 (d, J=8.6 Hz, 2H) 7.61 (s, 1H) 7.80 (d, J=8.6 Hz, 2H).

Preparation 19 ethyl 3-(dimethylamino)-2-(2-oxopyridin-1(2H)-yl)acrylate

Combined ethyl 2-(2-oxopyridin-1(2H)-yl)acetate (500 mg, 2.76 mmol), 1,1-diethoxy-N,N-dimethylmethanamine (2031 mg, 13.80 mmol) and DMF (2 mL) and heated at 100° C. for 15 h. The reaction mixture was diluted with xylenes and concentrated onto Celite® then purified on a 30 g NH silica column (Moritex) eluted with 0 to 100% EtOAc in hexanes to give the title compound (551 mg, 85% yield) as a light yellow solid. MS m/z 237 [M+H]+. $^1$H NMR (400

MHz, DMSO-d$_6$) δ ppm 1.13 (br. s., 3H) 2.77 (br. s., 6H) 3.94-4.08 (m, 2H) 6.17 (td, J=6.7, 1.3 Hz, 1H) 6.36 (dt, J=9.0, 1.1 Hz, 1H) 7.35-7.45 (m, 2H) 7.47 (s, 1H).

Preparation 20
1-(2-methoxyethyl)cyclopropanamine

Combined 3-methoxypropanenitrile (2.00 g, 23.50 mmol) and THF (75 mL) at 0° C. then added titanium(IV) isopropoxide (7.57 mL, 25.9 mmol) followed by dropwise addition of ethylmagnesium bromide (49.4 mL, 49.4 mmol). The solution stirred for 30 min at 20° C. and then boron trifluoride etherate (5.96 mL, 47.0 mmol) was added at 20° C. (solution warmed up and turned black). The mixture stirred 40 min and was then quenched at 0° C. with 12 mL 15% aqueous sodium hydroxide solution. The reaction was concentrated in vacuo to give a residue which was diluted with water to about 100 mL and extracted 6×100 mL with chloroform. Extracts 3-6 were dried over magnesium sulfate and concentrated in vacuo to give the title compound (1.2 g, 44% yield) as a brown oil. $^1$H NMR (400 MHz, chloroform-d) δ ppm 0.39-0.45 (m, 2H) 0.53-0.60 (m, 2H) 1.68 (t, J=6.4 Hz, 2H) 3.36 (s, 3H) 3.59 (t, J=6.4 Hz, 2H).

Preparation 21
6-chloro-N-(3-methoxypropyl)nicotinamide

Combined 6-chloronicotinic acid (6.0 g, 38.1 mmol), HOBT (2.57 g, 19.04 mmol) and EDC (10.95 g, 57.1 mmol) in CH$_2$Cl$_2$ (100 mL) the Hunig's base (9.98 mL, 57.1 mmol) and 3-methoxypropan-1-amine (5.85 mL, 57.1 mmol) were added and stirred at 20° C. for 22 h. The reaction mixture was concentrated in vacuo to give a residue which was taken up in EtOAc (250 mL) and washed with saturated aqueous ammonium chloride (250 mL) and brine, dried over magnesium sulfate and concentrated in vacuo to give a residue which was purified on an 330 g silica gel column eluted with 10 to 80% EtOAc in hexanes to give the title compound (6.6 g, 76% yield) as a white solid. MS m/z 229, 231 [M+H]$^+$. $^1$H NMR (400 MHz, DMSO-d$_6$) δ ppm 1.76 (quin, J=6.7 Hz, 2H) 3.24 (s, 3H) 3.27-3.35 (m, 2H) 3.38 (t, J=6.3 Hz, 2H) 7.65 (dd, J=8.3, 0.8 Hz, 1H) 8.23 (dd, J=8.3, 2.5 Hz, 1H) 8.73 (t, J=5.3 Hz, 1H) 8.82 (dd, J=2.5, 0.8 Hz, 1H).

Preparation 22
6-hydrazinyl-N-(3-methoxypropyl)nicotinamide

A solution of 6-chloro-N-(3-methoxypropyl)nicotinamide (6.6 g, 28.9 mmol) and hydrazine (4.53 mL, 144 mmol) in isopropanol (100 mL) was heated at 80° C. for 21 h. More hydrazine (3 mL) was added and heating continued at 80° C. for 24 h. The reaction was then concentrated in vacuo to give a tan oil which was reconcentrated from toluene to give the title compound as its hydrochloride salt as a white solid in quantitative yield. MS m/z 225 [M+H]$^+$. $^1$H NMR (400 MHz, DMSO-d$_6$) δ ppm 1.66-1.78 (m, 2H) 3.18-3.30 (m, 5H) 3.35 (t, J=6.3 Hz, 2H) 6.68 (d, J=8.8 Hz, 1H) 7.87 (dd, J=8.8, 2.3 Hz, 1H) 7.99 (br. s., 1H) 8.20 (t, J=5.6 Hz, 1H) 8.49 (dd, J=2.4, 0.6 Hz, 1H).

Preparation 23 potassium 4-(ethoxycarbonyl)-1-(5-((3-methoxypropyl)carbamoyl)pyridin-2-yl)-1H-pyrazol-5-olate A mixture of 6-hydrazinyl-N-(3-methoxypropyl)nicotinamide hydrochloride (7.5 g, 28.8 mmol), diethyl 2-(ethoxymethylene)malonate (14 mL, 69 mmol), and potassium carbonate (9.94 g, 71.9 mmol) in water (150 mL) and ethanol (25 mL) and stirred at 25° C. for 3 h and then at 60° C. for 18 h. The mixture was cooled to 20° C. to give a precipitate which was collected by filtration and washed with water to give the title compound (8.14 g, 73.2% yield) as a yellow solid. MS m/z 349 [M+H]$^+$. $^1$H NMR (400 MHz, DMSO-d$_6$) δ ppm 1.19 (t, J=7.1 Hz, 3H) 1.77 (quin, J=6.7 Hz, 2H) 3.25 (s, 3H) 3.27-3.34 (m, 2H) 3.38 (t, J=6.3 Hz, 2H) 4.02 (q, J=7.1 Hz, 2H) 7.52 (s, 1H) 8.10 (dd, J=8.8, 2.5 Hz, 1H) 8.42 (dd, J=8.8, 0.5 Hz, 1H) 8.48 (t, J=5.6 Hz, 1H) 8.78 (dd, J=2.4, 0.6 Hz, 1H).

Preparation 24 5-hydroxy-1-(5-((3-methoxypropyl)carbamoyl)pyridin-2-yl)-1H-pyrazole-4-carboxylate A mixture of potassium 4-(ethoxycarbonyl)-1-(5-((3-methoxypropyl)carbamoyl)pyridin-2-yl)-1H-pyrazol-5-olate (3.0 g, 7.76 mmol), saturated aqueous ammonium chloride (100 mL), and 4 N aqueous HCl (1.941 mL, 7.76 mmol) was stirred for 2 h to give a yellow solid. The solid was collected by filtration, rinsed with water and dried in a lyophilizer to give the title compound (2.228 g, 82% yield) as a yellow solid. MS m/z 349 [M+H]$^+$.

Preparation 25 ethyl 5-methoxy-1-(5-((3-methoxypropyl)carbamoyl)pyridin-2-yl)-1H-pyrazole-4-carboxylate Combined ethyl 5-hydroxy-1-(5-((3-methoxypropyl)carbamoyl)pyridin-2-yl)-1H-pyrazole-4-carboxylate (2.2 g, 6.32 mmol), MeOH (5 mL), and DCM (50 mL) and added 2.0 M TMS-diazomethane in hexanes (4.42 mL, 8.84 mmol) (over about 10 minutes) and stirred at 20° C. for 20 min. The reaction was then quenched with acetic acid (0.145 mL, 2.53 mmol) and concentrated in vacuo to give a residue which was purified on an 80 g silica gel column eluted with 10 to 100% EtOAc in hexanes to give the title compound (2.0 g, 87% yield) as a white solid. MS m/z 363 [M+H]$^+$. $^1$H NMR (400 MHz, DMSO-d$_6$) δ ppm 1.30 (t, J=7.1 Hz, 3H) 1.78 (quin, J=6.6 Hz, 2H) 3.25 (s, 3H) 3.30-3.37 (m, 2H) 3.39 (t, J=6.3 Hz, 2H) 4.14 (s, 3H) 4.27 (q, J=7.1 Hz, 2H) 7.79 (dd, J=8.5, 0.6 Hz, 1H) 8.03 (s, 1H) 8.39 (dd, 2.4 Hz, 1H) 8.76 (t, J=5.6 Hz, 1H) 8.98 (dd, J=2.4, 0.6 Hz, 1H).

Preparation 26 5-methoxy-1-(5-((3-methoxypropyl)carbamoyl)pyridin-2-yl)-1H-pyrazole-4-carboxylic acid Combined ethyl 5-methoxy-1-(5-((3-methoxypropyl)carbamoyl)pyridin-2-yl)-1H-pyrazole-4-carboxylate (2.4 g, 6.62 mmol) and dioxane (50 mL) and added 1.0 M aq. lithium hydroxide (29.8 mL, 29.8 mmol) and the mixture was stirred at 20° C. for 2 days. The reaction was acidified with 1 N aq. HCl (30 mL) and extracted with chloroform (100 mL then 2×50 mL). The combined organics were dried over magnesium sulfate and concentrated in vacuo to give the title compound (2.195 g, 99% yield) as an off-white solid. MS m/z 335 [M+H]$^+$. $^1$H NMR (400 MHz, DMSO-d$_6$) δ ppm 1.74 (quin, J=6.6 Hz, 2H) 3.21 (s, 3H) 3.30 (q, J=6.7 Hz, 2H) 3.36 (t, J=6.3 Hz, 2H) 4.10 (s, 3H) 7.74 (dd, J=8.5, 0.6 Hz, 1H) 7.94 (s, 1H) 8.35 (dd, J=8.5, 2.4 Hz, 1H) 8.72 (t, J=5.6 Hz, 1H) 8.94 (dd, J=2.4, 0.6 Hz, 1H) 12.64 (br. s., 1H).

Preparation 27 6-(4-bromo-5-methoxy-1H-pyrazol-1-yl)-N-(3-methoxypropyl)nicotinamide Combined 5-methoxy-1-(5-((3-methoxypropyl)carbamoyl)pyridin-2-yl)-1H-pyrazole-4-carboxylic acid (2.19 g, 6.55 mmol), NBS (1.749 g, 9.83 mmol), and sodium bicarbonate (1.651 g, 19.65 mmol) in DMF (20 mL) and stirred at 20° C. for 1 h. The reaction was diluted with water (100 mL) and extracted with EtOAc (100 mL, then 2×50 mL). The combined organics were washed with brine, dried over magnesium sulfate and concentrated in vacuo to give a residue which was purified on a 120 g silica gel column eluted with 10 to 100% EtOAc in hexanes to give the title compound (2.348 g, 97% yield) as a white solid. MS m/z 369, 371 [M+H]$^+$. $^1$H NMR (400 MHz, DMSO-d$_6$) δ ppm 1.78 (quin, J=6.6 Hz, 2H) 3.25 (s, 3H) 3.30-3.37 (m, 2H) 3.40 (t, J=6.3 Hz, 2H) 4.05 (s, 3H) 7.79 (dd, J=8.6, 0.5 Hz, 1H) 7.85 (s, 1H) 8.38 (dd, J=8.6, 2.3 Hz, 1H) 8.74 (t, J=5.6 Hz, 1H) 8.96 (dd, J=2.4, 0.6 Hz, 1H).

Preparation 28
6-chloro-N-(4-cyanobenzyl)nicotinamide

Combined 6-chloronicotinic acid (1.0 g, 6.35 mmol), 4-(aminomethyl)benzonitrile (1.007 g, 7.62 mmol), and EDC (1.825 g, 9.52 mmol) in methylene chloride (50 mL) then added Hunig's base (2.328 mL, 13.33 mmol) and the mixture stirred at 20° C. for 2 h. More 4-(aminomethyl)benzonitrile (250 mg), EDC (750 mg) and Hunig's base (1 mL) was added and stirring continued for 2 days. The reaction was concentrated in vacuo to give a residue which was taken up in EtOAc (100 mL) and washed with saturated aqueous ammonium chloride (100 mL) and brine, dried over magnesium sulfate and concentrated in vacuo to give a residue which was purified on an 80 g silica gel column eluted with 0 to 80% EtOAc in hexanes to give the title compound (1.1 g, 63.8% yield) as a white solid. MS m/z 272, 274 [M+H]$^+$. $^1$H NMR (400 MHz, DMSO-d$_6$) δ ppm 4.58 (d, J=6.1 Hz, 2H) 7.53 (d, J=8.6 Hz, 2H) 7.68 (dd, J=8.3, 0.8 Hz, 1H) 7.77-7.85 (m, 2H) 8.28 (dd, J=8.3, 2.5 Hz, 1H) 8.89 (dd, J=2.5, 0.5 Hz, 1H) 9.40 (t, J=5.7 Hz, 1H).

Preparation 29
N-(4-cyanobenzyl)-6-hydrazinylnicotinamide

Combined 6-chloro-N-(4-cyanobenzyl)nicotinamide (500 mg, 1.840 mmol) and hydrazine (0.578 mL, 18.40 mmol) in isopropanol (5 mL) and heated at 90° C. for 5 h. The supernatant was decanted and concentrated in vacuo to give a white solid which was stirred vigorously with water (ca. 10 mL) for 2 hours, then was filtered and the solid dried to give the title compound (batch 1, 101 mg) as a pink solid. The fine solids from the reaction (after supernatant was removed) was stirred vigorously with water (ca. 10 mL) for 2 hours, then filtered and dried in the lyophilizer to give the title compound (batch 2, 179 mg) as a tan solid. Large solids from the reaction (after supernatant was removed) were crushed and stirred vigorously with water (10 mL) for 1 hour, then filtered and dried in the lyophilizer to give the title (batch 3, 135 mg) as a beige solid. The combined yield was 415 mg (84% yield). MS m/z 268 [M+H]$^+$.

Preparation 30 6-chloro-N-((tetrahydro-2H-pyran-4-yl)methyl)nicotinamide

Combined 6-chloronicotinic acid (2.0 g, 12.69 mmol), (tetrahydro-2H-pyran-4-yl)methanamine (2.193 g, 19.04 mmol) and EDC (4.87 g, 25.4 mmol) in CH$_2$Cl$_2$ (100 mL) then added Hunig's base (6.65 mL, 38.1 mmol) and the mixture stirred at 20° C. for 24 h. More (tetrahydro-2H-pyran-4-yl)methanamine (1 g, 0.7 equiv), Hunig's base (2.2 mL, 1 equiv.) and DMAP (ca. 10 mg) were added and the reaction was heated at 45° C. for 18 h. More Hunig's base (3 mL) and DMAP (80 mg) was added and heating continued at 50° C. for 5 h. The reaction was then concentrated in vacuo to give a residue which was taken up in EtOAc (100 mL) and washed with saturated aqueous ammonium chloride (100 mL) and brine, dried over magnesium sulfate and concentrated in vacuo to give a residue which was purified on an 80 g silica gel column eluted with 0 to 100% EtOAc in hexanes, then filtered and dried in the lyophilizer to give the title compound (0.985 g, 30.5% yield) as a white solid. MS m/z 255, 257 [M+H]$^+$. $^1$H NMR (400 MHz, DMSO-d$_6$) δ ppm 1.12-1.28 (m, 2H) 1.60 (dd, J=12.9, 1.8 Hz, 2H) 1.78 (td, J=7.4, 3.7 Hz, 1H) 3.13-3.20 (m, 2H) 3.26 (td, J=11.7, 2.1 Hz, 2H) 3.84 (dd, J=11.4, 2.5 Hz, 2H) 7.64 (dd, J=8.3, 0.5 Hz, 1H) 8.23 (dd, J=8.3, 2.5 Hz, 1H) 8.74 (t, J=5.6 Hz, 1H) 8.82 (dd, J=2.5, 0.8 Hz, 1H).

Preparation 31 6-hydrazinyl-N-((tetrahydro-2H-pyran-4-yl)methyl)nicotinamide

Combined 6-chloro-N-((tetrahydro-2H-pyran-4-yl)methyl)nicotinamide (828 mg, 3.25 mmol) and hydrazine (0.510 mL, 16.25 mmol) in isopropanol (10 mL) and heated at 80° C. for 22 h. Cool to 20° C. and after 2 days a white precipitate formed and was collected by filtration, rinsed with isopropanol, and dried under vacuum to give the title compound as its HCl salt (322 mg) as a white solid. A second crop was collected from the filtrate (500 mg). The combined yield was 822 mg (88%). MS m/z 251 [M+H]$^+$. $^1$H NMR (400 MHz, DMSO-d$_6$) δ ppm 1.09-1.26 (m, 2H) 1.57 (dd, J=12.9, 1.8 Hz, 2H) 1.75 (dtt, J=14.9, 7.5, 7.5, 3.4, 3.4 Hz, 1H) 3.11 (t, J=6.3 Hz, 2H) 3.19-3.31 (m, 2H) 3.83 (dd, J=11.4, 2.5 Hz, 2H) 4.26 (br. s., 2H) 6.68 (d, J=8.8 Hz, 1H) 7.87 (dd, J=8.8, 2.3 Hz, 1H) 7.97 (s, 1H) 8.18 (t, J=5.7 Hz, 1H) 8.49 (d, J=1.8 Hz, 1H).

Preparation 32 methyl 6-(4-(4-cyano-2-fluorophenyl)-5-methoxy-1H-pyrazol-1-yl)nicotinate Combined methyl 6-(4-bromo-5-methoxy-1H-pyrazol-1-yl)nicotinate (1.0 g, 3.20 mmol), 3-fluoro-4-(4,4,5,5-tetramethyl-1,3,2-dioxaborolan-2-yl)benzonitrile (1.583 g, 6.41 mmol), dichloro[1,1'-bis(di-t-butylphosphino)ferrocene]palladium(II) (0.209 g, 0.320 mmol) and sodium bicarbonate (1.346 g, 16.02 mmol) in dioxane (10 mL) and water (2.5 mL) and heated at 110° C. for 30 min in the microwave. The reaction was diluted with EtOAc, concentrated on Celite® and purified on a 100 g NH column (Moritex) eluted with 10 to 80% EtOAc in hexanes to give the title compound (1.0 g) which was used without further purification. MS m/z 353 [M+H]$^+$. $^1$H NMR (400 MHz, DMSO-d6) δ ppm 3.90 (s, 3H) 3.92 (s, 3H) 7.81 (dd, J=8.1, 1.8 Hz, 1H) 7.89-7.98 (m, 2H) 8.00 (dd, J=10.7, 1.6 Hz, 1H) 8.09 (d, J=3.0 Hz, 1H) 8.51 (dd, J=8.6, 2.3 Hz, 1H) 9.08 (dd, J=2.3, 0.5 Hz, 1H).

Preparation 33 6-(4-(4-cyano-2-fluorophenyl)-5-hydroxy-1H-pyrazol-1-yl)nicotinic acid Combined the product of the preparation above, methyl 6-(4-(4-cyano-2-fluorophenyl)-5-methoxy-1H-pyrazol-1-yl)nicotinate (300 mg, 0.638 mmol) and lithium chloride (135 mg, 3.19 mmol) in anhydrous N-methyl-2-pyrrolidinone (5 mL) and heated at 60° C. for 16 h. Then 1.0 M aqueous lithium hydroxide (3 mL, 3.00 mmol) was added and stirred at 20° C. for 4 h. The reaction mixture was then acidified with 1 N aqueous HCl (5 mL) to form a yellow precipitate. The precipitate was collected by filtration, rinsed with water and dried under high vacuum (ca.10 Pa) to give the title compound containing 0.9 equiv. N-methyl-2-pyrrolidinone (230 mg, quantitative yield) as a brown solid. MS m/z 325 [M+H]$^+$. $^1$H NMR (400 MHz, DMSO-d$_6$) δ ppm 7.65 (dd, J=8.2, 1.6 Hz, 1H) 7.80 (dd, J=11.7, 1.6 Hz, 1H) 8.24 (br. s., 1H) 8.38-8.44 (m, 1H) 8.52 (br. s., 2H) 8.87-8.94 (m, 1H) 13.40 (br. s., 1H).

Preparation 34 tert-butyl 2-(4-cyano-2-fluorophenyl)acetate

Combined 4-bromo-3-fluorobenzonitrile (2.0 g, 10.00 mmol), Pd(dba)$_2$ (0.287 g, 0.500 mmol), and 2'-(dicyclohexylphosphino)-N,N-dimethyl-[1,1'-biphenyl]-2-amine (0.394 g, 1.000 mmol) in THF (60 mL) with nitrogen purge. Then (2-(tert-butoxy)-2-oxoethyl)zinc(II) chloride (0.5M, 30 mL, 15.0 mmol) was added via syringe. The reaction mixture was heated in an oil bath at 50° C. for 18 hours and then was adsorbed onto silica gel (11 g) and purified by flash chromatography using an eluent of 1:1 heptane/EtOAc on an 80 g silica gel column (Single Step™) to give a residue. The residue was dissolved in toluene (0.5 mL) and purified by flash chromatography using a gradient eluent of heptane/EtOAc (0-25% EtOAc) on an 80 g silica gel column (Single Step™) to give the title compound (1.752 g, 74.5% yield) as a yellow solid. $^1$H NMR (400 MHz, chloroform-d) δ ppm 1.45 (s, 9H) 3.64 (d, J=1.26 Hz, 2H) 7.36 (dd, J=8.97, 1.39 Hz, 1H) 7.40 (d, J=7.07 Hz, 1H) 7.42-7.45 (m, 1H). MS m/z [M+H]$^+$ 236.1.

Preparation 35 ethyl 2-(4-cyano-2-fluorophenyl)acetate

Combined tert-butyl 2-(4-cyano-2-fluorophenyl)acetate (227.3 mg, 0.966 mmol) with EtOH (5 mL) and added a 4M hydrogen chloride solution in dioxane (0.121 mL, 0.483 mmol) and stirred in a heating block at 60° C. for 16 h. Then the reaction mixture was concentrated via rotary evaporation and re-constituted in EtOH (5 mL). An additional portion of a 4M hydrogen chloride solution in dioxane (17.61 mg, 0.483 mmol) was added to the vial and the mixture was stirred at 60° C. for an additional 1 h. The reaction mixture was then concentrated via rotary evaporation and dried in vacuo to give the title compound (198 mg, 99% yield) as a yellow oil. $^1$H NMR (400 MHz, chloroform-d) δ ppm 1.27 (t, J=7.07 Hz, 3H) 3.72 (d, J=1.26 Hz, 2H) 4.19 (q, J=7.24 Hz, 2H) 7.36-7.40 (m, 1H) 7.40-7.43 (m, 1H) 7.43-7.46 (m, 1H). MS m/z [M+H]$^+$ 208.0.

Preparation 36 ethyl 2-(4-cyano-2-fluorophenyl)-3-(dimethylamino)acrylate

The title compound was prepared in a manner similar to Example Preparation 10 using ethyl 2-(4-cyano-2-fluorophenyl)acetate and 1,1-diethoxy-N,N-dimethylmethanamine to give the title compound. $^1$H NMR (400 MHz, DMSO-d$_6$) δ ppm 1.10 (t, J=7.07 Hz, 3H) 2.71 (br. s., 6H) 4.00 (quin, J=6.76 Hz, 2H) 7.37 (t, J=7.71 Hz, 1H) 7.60 (dd, J=7.96, 1.64 Hz, 1H) 7.64 (s, 1H) 7.75 (dd, J=9.47, 1.64 Hz, 1H). MS m/z [M+H]$^+$ 236.2, 263.2.

Preparation 37 ethyl 5-hydroxy-1-(5-(((tetrahydro-2H-pyran-4-yl)methyl)carbamoyl)pyridin-2-yl)-1H-pyrazole-4-carboxylate Combined 6-hydrazinyl-N-((tetrahydro-2H-pyran-4-yl)methyl)nicotinamide (1.0 g, 4.00 mmol) and potassium carbonate (2.209 g, 15.98 mmol) in water (25 mL) and added diethyl 2-(ethoxymethylene)malonate (0.807 mL, 4.00 mmol) at 23° C. The reaction mixture was stirred at 100° C. for 14 hours, then 3N HCl (10 mL, 7.5 eq) was added to give a tan suspension. The solid was filtered, rinsed with water (3×5 mL), and dried in vacuo to give the title compound (1.114 g, 74.5% yield) as a yellow solid. $^1$H NMR (400 MHz, DMSO-d$_6$) δ ppm 1.15-1.24 (m, 2H) 1.26 (t, J=7.07 Hz, 3H) 1.56-1.68 (m, 2H) 1.81 (qdd, J=11.16, 11.16, 11.16, 6.95, 3.79 Hz, 1H) 3.19 (t, J=6.32 Hz, 2H) 3.27 (td, J=11.75, 2.02 Hz, 2H) 3.82-3.90 (m, 2H) 4.18 (q, J=7.24 Hz, 2H) 8.12 (br. s., 1H) 8.13-8.24 (m, 1H) 8.46 (dd, J=8.84, 2.27 Hz, 1H) 8.76 (t, J=5.68 Hz, 1H) 8.89 (dd, J=2.27, 0.76 Hz, 1H) 13.73 (br. s., 1H). MS m/z [M+H]$^+$ 329.3, 375.4.

Preparation 38 ethyl 5-methoxy-1-(5-(((tetrahydro-2H-pyran-4-yl)methyl)carbamoyl)pyridin-2-yl)-1H-pyrazole-4-carboxylate Combined ethyl 5-hydroxy-1-(5-(((tetrahydro-2H-pyran-4-yl)methyl)carbamoyl)pyridin-2-yl)-1H-pyrazole-4-carboxylate (0.6 g, 1.603 mmol), EtOAc (30 mL), and MeOH (10 mL) then added (diazomethyl)trimethylsilane, 2.0 M solution in hexanes (2.60 mL, 5.21 mmol) at 23° C. over 20 minutes. The reaction mixture was stirred at 23° C. for 1 hour, quenched with acetic acid (0.206 mL, 3.61 mmol), and the mixture was stirred for 2 hours at 23° C. The reaction mixture was concentrated to give an orange-brown oil which was purified by medium pressure chromatography using an eluent of 100% EtOAc on a 25 g silica gel column (Single Step™) to give the title compound (408 mg, 65.5% yield) as an off-white solid. $^1$H NMR (400 MHz, DMSO-d$_6$) δ ppm 1.16-1.27 (m, 2H) 1.31 (t, J=7.07 Hz, 3H) 1.62 (dd, J=12.88, 2.02 Hz, 2H) 1.81 (ttd, J=11.13, 11.13, 7.31, 7.31, 3.79 Hz, 1H) 3.20 (t, J=6.44 Hz, 2H) 3.27 (td, J=11.68, 2.15 Hz, 2H) 3.85 (dt, J=9.35, 2.27 Hz, 2H) 4.14 (s, 3H) 4.27 (q, J=7.07 Hz, 2H) 7.79 (dd, J=8.34, 0.76 Hz, 1H) 8.03 (s, 1H) 8.38-8.43 (m, 1H) 8.78 (t, J=5.81 Hz, 1H) 8.98 (dd, J=2.53, 0.76 Hz, 1H). MS m/z [M+H]$^+$ 389.4.

Preparation 39 5-methoxy-1-(5-(((tetrahydro-2H-pyran-4-yl)methyl)carbamoyl)pyridin-2-yl)-1H-pyrazole-4-carboxylic acid Combined ethyl 5-methoxy-1-(5-(((tetrahydro-2H-pyran-4-yl)methyl)carbamoyl)pyridin-2-yl)-1H-pyrazole-4-carboxylate (401 mg, 1.032 mmol), dioxane (7 mL) and 1M aqueous LiOH (5.16 mL, 5.16 mmol) at 23° C. The reaction mixture was stirred at 23° C. for 3 hours, and then quenched with 1N HCl (aq.) (5.16 mL, 5.16 mmol), and concentrated via rotary evaporation to furnish an off-white suspension. The suspension was filtered, rinsed with water (5×3 mL), and dried in vacuo to give the title compound (339.8 mg, 91% yield) as a white solid. $^1$H NMR (400 MHz, DMSO-d$_6$) δ ppm 1.16-1.28 (m, 2H) 1.58-1.67 (m, 2H) 1.75-1.88 (m, 1H) 3.20 (t, J=6.32 Hz, 2H) 3.27 (td, J=11.62, 2.02 Hz, 2H) 3.82-3.90 (m, 2H) 4.14 (s, 3H) 7.78 (dd, J=8.59, 0.76 Hz, 1H) 7.98 (s, 1H) 8.40 (dd, J=8.46, 2.40 Hz, 1H) 8.78 (t, J=5.81 Hz, 1H) 8.98 (dd, J=2.40, 0.63 Hz, 1H) 12.68 (s, 1H). MS m/z [M+H]$^+$ 361.4.

Preparation 40 6-(4-bromo-5-methoxy-1H-pyrazol-1-yl)-N-((tetrahydro-2H-pyran-4-yl)methyl)nicotinamide Combined 5-methoxy-1-(5-(((tetrahydro-2H-pyran-4-yl)methyl)carbamoyl)pyridin-2-yl)-1H-pyrazole-4-carboxylic acid (329.5 mg, 0.914 mmol) and sodium bicarbonate (307 mg, 3.66 mmol) in DMF (3 mL) then added 1-bromopyrrolidine-2,5-dione (163 mg, 0.914 mmol) at 23° C. The reaction mixture was stirred at 23° C. for 30 minutes and then diluted with water (15 mL) to give a suspension. The suspension was filtered, rinsed with water (3×5 mL), and dried in vacuo to give the title compound (302 mg, 84% yield) as a white solid. $^1$H NMR (400 MHz, DMSO-$d_6$) δ ppm 1.15-1.28 (m, 2H) 1.62 (dd, J=12.88, 1.77 Hz, 2H) 1.80 (dddt, J=14.78, 11.12, 7.39, 3.44, 3.44 Hz, 1H) 3.16-3.23 (m, 2H) 3.23-3.31 (m, 2H) 3.81-3.89 (m, 2H) 4.05 (s, 3H) 7.79 (dd, J=8.59, 0.76 Hz, 1H) 7.84 (s, 1H) 8.38 (dd, J=8.46, 2.40 Hz, 1H) 8.75 (t, J=5.81 Hz, 1H) 8.96 (dd, J=2.53, 0.76 Hz, 1H). MS m/z [M+H]$^+$ 395.3, 397.3.

Preparation 41 ethyl 3-(dimethylamino)-2-(pyridin-4-yl)acrylate

Combined ethyl 2-(pyridin-4-yl)acetate (0.927 mL, 6.05 mmol) and 1,1-diethoxy-N,N-dimethylmethanamine (5.19 mL, 30.3 mmol) in DMF (3.03 mL) and heated to 100° C. for 6 hours. The reaction mixture was concentrated, diluted with 50 mL dichloromethane, and washed twice with 50 mL water. The organic layer was collected, dried over magnesium sulfate, filtered and concentrated to give a residue which was purified on a 60 g NH silica gel column eluted with hexanes and EtOAc to give the title compound (1.333 g, 76%) as a yellow oil. $^1$H NMR (400 MHz, chloroform-d) δ ppm 1.13 (t, J=7.1 Hz, 3H) 2.67 (s, 6H) 4.06 (q, J=7.1 Hz, 2H) 6.98-7.12 (m, 2H) 7.56 (s, 1H) 8.29-8.53 (m, 2H).

Preparation 42 tert-butyl 2-(4-cyano-2 methoxyphenyl)acetate

Combined (2-(tert-butoxy)-2-oxoethyl)zinc(II) chloride (4.24 mL, 2.122 mmol) and 4-bromo-3-methoxybenzonitrile (0.30 g, 1.42 mmol) in THF (4.29 mL), then 2'-(dicyclohexylphosphino)-N,N-dimethyl-[1,1'-biphenyl]-2-amine (0.056 g, 0.141 mmol) and Pd(dba)$_2$ (0.041 g, 0.071 mmol) were added and the reaction was refluxed at 100° C. overnight. The reaction mixture was concentrated down by rotary evaporation and purified on a silica gel column eluting with hexanes and EtOAc to give the title compound as a yellow oil (102 mg, 29%). MS m/z [M+H]$^+$ 248.

Preparation 43 ethyl 2-(4-cyano-2-methoxyphenyl)-3-(dimethylamino)acrylate

Combined tert-butyl 2-(4-cyano-2-methoxyphenyl)acetate (549 mg, 2.218 mmol) and 4N HCl in dioxane (0.277 mL, 1.109 mmol) in ethanol (7.4 mL) and stirred for 16 hours at 60° C. The reaction was concentrated by rotary evaporation and then combined with ethyl 2-(4-cyano-2-methoxyphenyl)acetate (0.486 g, 2.217 mmol) and 1,1-diethoxy-N,N-dimethylmethanamine (1.9 mL, 11.08 mmol) in DMF (4.43 mL) and stirred for 16 hours at 100° C. The reaction mixture was diluted with 200 mL EtOAc and washed twice with 200 mL water. Organic layer was dried with sodium sulfate and concentrated to give a residue which was purified on a 60 g NH silica gel column eluting with hexanes and EtOAc to give the title compound (405 mg, 74%).

Preparation 44 tert-butyl 2-(2-chloro-4-cyanophenyl)acetate

Combined 4-bromo-3-chlorobenzonitrile (0.600 g, 2.77 mmol) and (2-(tert-butoxy)-2-oxoethyl)zinc(II) chloride (8.32 mL, 4.16 mmol) in THF (5.54 mL), then Pd(dba)2 (0.080 g, 0.139 mmol) and 2'-(dicyclohexylphosphino)-N,N-dimethyl-[1,1'-biphenyl]-2-amine (0.109 g, 0.277 mmol) were added and the reaction was refluxed overnight at 65° C. The reaction was concentrated by rotary evaporation and purified on a silica gel column eluting with hexanes and EtOAc to give the title compound (274 mg, 39%) as a yellow oil. MS m/z [M+H]$^+$ 252.

Preparation 45 ethyl 2-(2-chloro-4-cyanophenyl)-3-(dimethylamino)acrylate

Combined tert-butyl 2-(2-chloro-4-cyanophenyl)acetate (274 mg, 1.089 mmol) and 4N HCl in dioxane (0.136 mL, 0.544 mmol) in ethanol (2.51 mL). The mixture was stirred for 16 hours at 60° C., then concentrated by rotary evaporation and combined with ethyl 2-(2-chloro-4-cyanophenyl) acetate (0.243 g, 1.086 mmol) and 1,1-diethoxy-N,N-dimethylmethanamine (0.931 mL, 5.43 mmol) in DMF (2.173 mL) and stirred for 16 hours at 100° C. The reaction was concentrated in rotary evaporation and purified on a NH silica gel column eluting with hexanes and EtOAc to give the title compound (164 mg, 54%) as a yellow oil. $^1$H NMR (400 MHz, chloroform-d) δ ppm 1.04-1.29 (m, 1H) 3.96-4.31 (m, 1H) 7.38 (d, J=7.8 Hz, 1H) 7.49 (dd, J=7.8, 1.8 Hz, 1H) 7.63-7.71 (m, 1H).

Preparation 46 1-(tetrahydro-2H-pyran-4-yl)cyclopropanamine

Combined tetrahydro-2H-pyran-4-carbonitrile (1.000 g, 9.00 mmol) and titanium (IV)isopropoxide (2.90 mL, 9.90 mmol) in ether (45.0 mL), then ethylmagnesium bromide (6.60 mL, 19.79 mmol) was added and the reaction was allowed to warm to room temperature for 1 hour. The reaction was stirred for an additional 30 minutes and boron trifluoride etherate (2.280 mL, 18.0 mmol) was added and the reaction was stirred for 2 hours. The reaction was then diluted with 10 mL water and 20 mL 1N HCl and extracted twice with 200 mL EtOAc. The organic layers were combined and concentrated to afford the title compound (850 mg, 53.5%) as a yellow oil.

Preparation 47 6-(4-(4-cyano-2-methoxyphenyl)-5-hydroxy-1H-pyrazol-1-yl)nicotinic acid Combined ethyl 2-(4-cyano-2-methoxyphenyl)-3-(dimethylamino)acrylate (1.427 g, 5.20 mmol), 6-hydrazinylnicotinic acid (0.664 g, 4.34 mmol), and HCl (4.34 mL, 4.34 mmol) in 2-propanol (21.7 mL) and stirred at room temperature for 8 hours to give a solid. The solid was collected by filtration and combined with Hunig's base (1.50 mL, 8.61 mmol) in 2-propanol (10 mL) and water (1 mL) and stirred for 32 hours at 50° C., then 10 mL of 1 N HCl was added and the reaction was filtered to give a solid. The solid was washed with 30 mL MeOH and 30 mL of ether and dried in vacuo to give the title compound (708 mg, 73.3%) as a beige solid. MS m/z [M+H]$^+$ 337.3.

Preparation 48 N-benzyl-6-chloronicotinamide

Combined 6-chloronicotinic acid (20 g, 12.74 mmol) and HATU (72.6 g, 19.1 mmol) in DMF (200 mL) and added triethylamine (38.6 g, 38.2 mmol) drop wise, followed by benzylamine (16.36 g, 15.28 mmol) and stirred at room temperature overnight. Then the reaction mixture was poured into ice-water and stirred for 20 minutes to give a solid. The solid was collected by filtration, washed with water (30 mL×2), and dried under reduced pressure to give the title compound (20 g, 64%) as a yellow solid.

Preparation 49 N-benzyl-6-hydrazinylnicotinamide

Combined N-benzyl-6-chloronicotinamide (13 g, 52.8 mmol) and ethanol (60 mL) then added hydrazine hydrate (85%, 30 mL) drop wise at room temperature. After the addition, the solution was heated to reflux overnight. The reaction mixture was then concentrated to remove ethanol and a solid was obtained. The solid was collected by filtration, washed with EtOAc (3×20 mL), and dried under reduced pressure to give the title compound (10 g, 78%) as an off-yellow solid.

Preparation 50 ethyl 2-(4-cyanophenyl)-3-(dimethylamino)acrylate

Combined ethyl 2-(4-cyanophenyl)acetate (25 g, 0.132 mol) with DMF-DEA (60 mL) and heated to 70° C. for 3 hours. The reaction mixture was cooled to room temperature and concentrated and then purified by flash chromatography to give the title compound (20 g, 62%) as a solid. $^1$H NMR (400 MHz, DMSO-$d_6$) δ ppm 7.71 (d, J=8.4 Hz, 2H), 7.59 (s, 1H), 7.29 (d, J=8.4 Hz, 2H), 4.03 (q, J=6.8 Hz, 2H), 2.67 (s, 6H), 1.13 (t, J=6.8 Hz, 3H).

Preparation 51 5-bromo-2-hydrazinyl-4-methylpyridine

Combined 5-bromo-2-chloro-4-methylpyridine (15.0 g, 72.46 mmol) and EtOH (60 mL) and added hydrazine hydrate (85%, 45 mL) and stirred at 120° C. overnight. The reaction mixture was concentrated to give a residue which was extracted with EtOAc (50 mL×2) and water (50 mL×2). Then combined organic layers were extracted with brine, dried over $Na_2SO_4$ to and concentrated to give a residue which was purified by flash chromatography (petroleum ether: EtOAc=10:1 to 1:5) to give the title compound (7.8 g, 53%).

Preparation 52 4-(1-(5-bromo-4-methylpyridin-2-yl)-5-hydroxy-1H-pyrazol-4-yl)benzonitrile Combined 5-bromo-2-hydrazinyl-4-methylpyridine (6.0 g, 29.85 mmol) and isopropanol (100 mL) and added ethyl 2-(4-cyanophenyl)-3-(dimethylamino)acrylate (8.02 g, 32.84 mmol) and HCl solution (aqueous, 1.85%, 49.75 mL) and stirred at room temperature for 2 h, then DIEA (19.40 g, 149.25 mmol) was added. After about 30 minutes the reaction was evaporated to give a residue which was extracted with EtOAc (50 mL×2) and water (50 mL×2), the EtOAc layers were combined and washed with brine, dried over $Na_2SO_4$ to give a residue which was purified by flash chromatography (petroleum ether: EtOAc 5:1-1:8) to give the title compound (8.67 g, 82.04%).

Preparation 53 4-(1-(5-bromo-4-methylpyridin-2-yl)-5-((2-(trimethylsilyl)ethoxy)methoxy)-1H-pyrazol-4-yl)benzonitrile Combined 4-(1-(5-bromo-4-methylpyridin-2-yl)-5-hydroxy-1H-pyrazol-4-yl)benzonitrile (8.67 g, 24.49 mmol), THF (100 mL), (trimethylsilyl)ethoxy)methyl chloride (8.91 g, 48.98 mmol), and triethylamine (7.42 g, 73.47 mmol) and stir at room temperature for 3 h. The reaction mixture was then evaporated in vacuum to give a residue which was extracted with EtOAc (100 mL×2) and water (100 mL×2), the EtOAc layers were washed with brine, dried over $Na_2SO_4$, evaporated to give a residue whish was purified by flash chromatography on silica gel (petroleum ether: EtOAc 10:1-1:3) to give the title compound (10.5 g, 88.2%).

Preparation 54 methyl 6-(4-(4-cyanophenyl)-5-((2-(trimethylsilyl)ethoxy)methoxy)-1H-pyrazol-1-yl)-4-methylnicotinate Combined 4-(1-(5-bromo-4-methylpyridin-2-yl)-5-((2-(trimethylsilyl)ethoxy)methoxy)-1H-pyrazol-4-yl)benzonitrile (10.0 g, 20.66 mmol), DMF (60 mL) and MeOH (60 mL) then added triethylamine (6.26 g, 61.98 mmol) and Pd(dppf)Cl$_2$ (756.2 mg, 1.033 mmol). The mixture was stirred at 120° C. under 1 MPa of CO overnight. Then the reaction mixture was evaporated in vacuum to give a residue which was combined with water, filtered, and the aqueous was extracted with EtOAc (100 mL×2). The combined EtOAc layers were washed with brine and dried ($Na_2SO_4$), and concentrated to give the title compound (8.67 g).

Preparation 55 6-(4-(4-cyanophenyl)-5-hydroxy-1H-pyrazol-1-yl)-4-methylnicotinic acid Combined methyl 6-(4-(4-cyanophenyl)-5-((2-(trimethylsilyl)ethoxy)methoxy)-1H-pyrazol-1-yl)-4-methylnicotinate (8.67 g, 25.96 mmol), methanol (50 mL), water (50 mL) and LiOH (3.27 g, 77.87 mmol). The reaction mixture was stirred at room temperature for 6 h and at 50° C. overnight. The reaction mixture was concentrated to remove most of the methanol and then the pH was adjusted to 3 by addition of 3N HCl to give a solid. The solid was collected by filtration and dried in vacuum to give the title compound (4.3 g, 51.76%).

Preparation 56 ethyl 2-(4-cyanophenyl)acetate

Combined ethyl 2-(4-bromophenyl)acetate (30 g, 0.123 mol) and NMP (200 mL). Then CuCN (33 g, 0.370 mol) was added in portions and then degassed and refilled with nitrogen three times. Then CuI (4.7 g, 0.0247 mol) was added in one portion. The reaction was degassed and refilled with nitrogen three times and then heated to 160° C. for 4 hours. Then the reaction was heated to 180° C. for another 3 hours. The solution was then cooled to room temperature and diluted with EtOAc (500 mL) and water (500 mL). After stirring for 10 mins, the reaction was filtered and the aqueous layer was extracted with EtOAc (500 mL×2). The combined organic layers were washed with brine, dried over $Na_2SO_4$ and concentrated to dryness to give the title compound (31 g, 66.5%) as a brown solid.

Preparation 57 N-benzyl-6-chloronicotinamide

Combined 6-chloronicotinoyl chloride (1.76 g, 10.00 mmol) and DCM (20 mL) and cooled in an ice-bath then triethylamine (2.09 mL, 15.0 mmol) and phenylmethanamine (1.072 g, 10.00 mmol) were added. The reaction was then stirred at room temperature for 3 hours before being diluted in DCM (30 ml), washed with 1N aqueous HCl (50 ml), saturated aqueous sodium bicarbonate (50 ml), brine (50 ml), dried over $Na_2SO_4$, and concentrated to give the title compound (2.19 g, 89%) as a light beige solid which was used without further purification. MS m/z [M+H]$^+$ 247.1.

Preparation 58 N-benzyl-6-hydrazinylnicotinamide

Combined hydrazine (1.67 mL, 53.3 mmol) and a solution of N-benzyl-6-chloronicotinamide (2.19 g, 8.88 mmol) in ethanol (70 mL) and heated overnight at 100° C. The reaction mixture was then cooled and evaporated to give a solid. The solid was collected by filtration, washed with 70 mL water, and recrystallized from hot ethanol to give the title compound (1.32 g, 61%) as an off-white solid. MS m/z [M+H]$^+$ 243.2.

Preparation 59 methyl 3-(dimethylamino)-2-(pyridin-2-yl)acrylate

Combined of N1,N1,N2,N2-tetramethylethane-1,2-diamine (0.15 mL, 1.000 mmol), methyl 2-(pyridin-2-yl)acetate (1 g, 6.62 mmol), and N,N-dimethylformamide dimethyl acetal (3.9 mL, 29.1 mmol) and heated at 115° C. overnight. The reaction mixture was then cooled and partitioned between 12 mL of saturated aqueous ammonium chloride and 12 mL of EtOAc. The organic layer was separated, dried over Na$_2$SO$_4$, and concentrated to give the title compound as a dark oil which was used as is in the next step without further purification. $^1$H NMR (400 MHz, DMSO-d$_6$) δ ppm 2.73 (s, 1H), 2.64 (brs, 6H), 3.50 (s, 6H), 7.16 (dd, J=6.95, 5.43 Hz, 1H), 7.26 (dt, J=7.83, 1.01 Hz, 1H), 7.54 (s, 1H), 7.65 (td, J=7.71, 1.77 Hz, 1H), 8.49 (d, J=4.04 Hz, 1H). MS m/z [M+H]$^+$ 207.1

Preparation 60 Ethyl 2-(5-cyanopyridin-2-yl)-3-(dimethylamino)acrylate

Combined ethyl 2(4-cyanophenyl)acetate (513 mg) and N,N-dimethylformamide dimethyl acetal (323 mg) and heated at 80° C. overnight. The reaction mixture was evaporated to give a residue which was dissolved in diethyl ether (20 ml) and extracted with water (10 ml), brine (10 ml), the dried with Na$_2$SO$_4$, and evaporated to give the title compound (537 mg) as a beige solid. $^1$H NMR (400 MHz, chloroform-d) δ ppm 1.20 (t, J=7.07 Hz, 3H), 2.62-2.77 (m, 6H), 4.13 (q, J=7.07 Hz, 2H), 7.29 (d, J=8.59 Hz, 2H), 7.56 (d, J=8.59 Hz, 2H).

Preparation 61 ethyl 3-(2-(4-(benzylcarbamoyl)phenyl)hydrazinyl)-2-(4-cyanophenyl)acrylate Combined N-benzyl-6-hydrazinylnicotinamide (126 mg, 0.520 mmol) and ethyl 2-(4-cyanophenyl)-3-(dimethylamino)acrylate (127 mg, 0.520 mmol) in ethanol (10 mL) and stirred at room temperature overnight. The reaction mixture was evaporated to give a residue which was dissolved in DCM (100 ml), extracted with saturated aqueous sodium bicarbonate (50 ml), dried with Na$_2$SO$_4$, and concentrated to a residue which was purified by chromatography (12 g SiO$_2$, DCM-MeOH 0 to 10%) to give the title compound (90 mg, 39%) as an oil. MS m/z [M+H]$^+$ 442.4.

Preparation 62 methyl 3-(2-(4-(benzylcarbamoyl)phenyl)hydrazinyl)-2-(pyridin-2-yl)acrylate Combined N-benzyl-6-hydrazinylnicotinamide (200 mg, 0.826 mmol), methyl 3-(dimethylamino)-2-(pyridin-2-yl)acrylate (170 mg, 0.826 mmol) and TFA (0.127 mL, 1.651 mmol) in ethanol (3 mL) and stirred overnight at room temperature. The reaction mixture was diluted in EtOAc (50 mL), washed with saturated aqueous sodium bicarbonate (20 ml), brine (20 ml), dried with Na$_2$SO$_4$ and concentrated to give the title compound (244 mg) as an orange solid, was used without further purification. MS m/z [M+H]$^+$ 404.4.

Preparation 63 tert-butyl 3-(cyclobutyl(methyl)amino)azetidine-1-carboxylate Combined a solution of tert-butyl 3-oxoazetidine-1-carboxylate (500 mg, 2.92 mmol) and N-methylcyclobutanamine (0.373 mL, 3.50 mmol) in methylene chloride (15 mL) and added sodium triacetoxyborohydride (929 mg, 4.38 mmol) and the solution stirred at 20° C. for 3 h. The solution was concentrated in vacuo to give a white solid. The solid was taken up in ethyl acetate (50 mL), washed with saturated sodium bicarbonate (50 mL) and brine, dried with magnesium sulfate, and concentrated in vacuo to give a residue which was purified on a 40 g silica gel column eluted with 0 to 70% ethyl acetate in hexanes to give the title compound (342 mg, 1.423 mmol, 48.7%) as a clear, colorless oil. $^1$H NMR (400 MHz, METHANOL-d4) δ ppm 1.43 (s, 9H) 1.60-1.75 (m, 2H) 1.85-2.04 (m, 4H) 2.07 (s, 3H) 2.81-2.94 (m, 1H) 3.27-3.30 (m, 1H) 3.81-3.88 (m, 2H) 3.88-3.97 (m, 2H); MS: 241 (M+H).

Preparation 64 N-cyclobutyl-N-methylazetidin-3-amine

Combined a solution of tert-butyl 3-(cyclobutyl(methyl)amino)azetidine-1-carboxylate (285 mg, 1.186 mmol) in methylene chloride (6 mL) and added 4 M HCl in dioxane (1.186 mL, 4.74 mmol) and the solution stirred at 20° C. for 30 h. The solution was concentrated in vacuo and concentrated from heptane/methylene chloride to give the title compound as a hydrochloride acid salt (191 mg, 0.896 mmol, 76%) as a light yellow solid which was used without further purification.

Preparation 65 tert-butyl 3-(cyclopropyl(methyl)amino)azetidine-1-carboxylate Combined a solution of tert-butyl 3-oxoazetidine-1-carboxylate (175 mg, 1.022 mmol) and N-methylcyclopropanamine hydrochloride (121 mg, 1.124 mmol) in methylene chloride (5 mL) and added sodium triacetoxyborohydride (325 mg, 1.533 mmol) and the solution stirred at 20° C. for 30 min. The solution was concentrated in vacuo to give white solid which was taken up in ethyl acetate (50 mL), washed with saturated sodium bicarbonate (50 mL) and brine, dried with magnesium sulfate and concentrated in vacuo, and then purified on a 40 g silica gel column eluted with 0 to 50% ethyl acetate in hexanes to give the title compound (128 mg, 0.566 mmol, 55.3%) as a clear, colorless oil. MS: 227 (M+H). $^1$H NMR (400 MHz, METHANOL-d4) δ ppm 0.41-0.47 (m, 2H) 0.48-0.56 (m, 2H) 1.43 (s, 9H) 1.64 (tt, J=6.7, 3.9 Hz, 1H) 2.28 (s, 3H) 3.50 (tt, J=7.5, 5.7 Hz, 1H) 3.84-4.01 (m, 4H).

Preparation 66 N-cyclopropyl-N-methylazetidin-3-amine

Combine a solution of tert-butyl 3-(cyclopropyl(methyl)amino)azetidine-1-carboxylate (73 mg, 0.323 mmol) in methylene chloride (3 mL) and 4 M HCl in dioxane (0.323 mL, 1.290 mmol) and the solution stirred at 20° C. for 4 hours then added 4 M HCl in dioxane (0.323 mL, 1.290 mmol) and stirred at 20° C. for 21 h. The solution was then concentrated in vacuo to give the title compound as a hydrochloride salt which was used without further purification.

Preparation 67 tert-butyl 6,6-difluoro-4-methyl-1,4-diazepane-1-carboxylate

Combined tert-butyl 6,6-difluoro-1,4-diazepane-1-carboxylate (49 mg, 0.207 mmol) and sodium cyanoborohydride (52 mg, 0.83 mmol) in THF (1.5 mL) and added 37% aqueous formaldehyde (0.077 mL, 1.037 mmol) and acetic acid (0.018 mL, 0.311 mmol) and then stirred at 20° C. for 16 h. Then methanol (300 uL) was added and the mixture was concentrated in vacuo to give a residue which was taken up in ethyl acetate (40 mL), washed with saturated aqueous sodium bicarbonate (50 mL) and brine, dried with magnesium sulfate and concentrated in vacuo to give the title compound (51 mg, 0.204 mmol, 98%) as a clear, colorless oil. MS: 251 (M+H). $^1$H NMR (400 MHz, CHLOROFORM-d) δ ppm 1.46 (s, 9H) 2.50 (s, 3H) 2.73 (d, J=4.8 Hz, 2H) 2.92 (t, J=13.5 Hz, 2H) 3.55 (d, J=4.8 Hz, 2H) 3.75-3.94 (m, 2H).

Preparation 68 6,6-difluoro-1-methyl-1,4-diazepane

Combined a solution of tert-butyl 6,6-difluoro-4-methyl-1,4-diazepane-1-carboxylate (50 mg, 0.200 mmol) in dichloromethane (2 mL) and 4 M HCl in dioxane (0.4 mL, 1.6 mmol) and the solution stirred at 20° C. for 21 h. The reaction was then concentrated in vacuo to give the title compound as a hydrochloride acid salt which was used without further purification. MS: 151 (M+H).

Preparation Methyl 2-(4-cyano-5-fluoro-2-methylphenyl)acetate

Combined 4-bromo-2-fluoro-5-methylbenzonitrile (4 g, 18.69 mmol) and dimethyl malonate (29.9 mL, 262 mmol). While purging the mixture with nitrogen, added potassium carbonate (3.87 g, 28.0 mmol), potassium hydrogencarbonate (2.81 g, 28.0 mmol), tri-tert-butylphosphonium tetrafluoroborate (0.119 g, 0.411 mmol), and bis(dibenzylidineacetone)palladium (0) (0.118 g, 0.206 mmol). The reaction mixture was heated in an oil bath at 170° C. for 3 hours, then cooled, diluted with ethyl acetate, and filtered through Celite®. The filtrate was concentrated and the residue dissolved in EtOAc, extracted with 1M aqueous sodium hydroxide (2×), twice with 10% aqueous sodium chloride, and brine. The organic phase was dried over sodium sulfate, filtered, and concentrated in vacuo, then purified by flash chromatography to give the title compound (1.67 g, 43%) as a clear colorless oil. $^1$H NMR (400 MHz, CHLOROFORM-d) δ ppm 2.30 (s, 3H) 3.67 (s, 2H) 3.72 (s, 3H) 7.10 (d, J=9.60 Hz, 1H) 7.42 (d, J=6.32 Hz, 1H).

Preparation 69 methyl 2-(4-cyano-3-fluoro-2-methylphenyl)acetate

Combine 4-bromo-2-fluoro-3-methylbenzonitrile (2 g, 9.34 mmol), dimethyl malonate (12.28 mL, 107 mmol), potassium carbonate (1.937 g, 14.02 mmol) and potassium hydrogencarbonate (1.403 g, 14.02 mmol). Nitrogen gas was bubbled through this mixture vigorously for 1 minute and then tri-tert-butylphosphonium tetrafluoroborate (0.030 g, 0.103 mmol), and bis(dibenzylidineacetone)palladium (0) (0.027 g, 0.047 mmol) were added. The reaction mixture was then heated in an oil bath (170° C.) and stirred for 1 hour, then cooled to ambient temperature and diluted with EtOAc (80 mL). The EtOAc layer was decanted and passed through a plug of Celite® (~7 cm wide and 1.5 cm thick). The chunky dark precipitate that was left in the flask was diluted with additional EtOAc portions and sonicated until a fine suspension resulted. The EtOAc triturates were also passed through the Celite® plug. The combined organics from filtration were concentrated in vacuo at ~40° C. and then at 90° C. for 45 minutes to give a residue. The residue was purified using flash column chromatography to give the title compound (1.05 g, 5.07 mmol, 54.2%) as a clear colorless oil. $^1$H NMR (400 MHz, CHLOROFORM-d) δ ppm 2.17 (d, J=2.27 Hz, 3H) 3.63 (s, 3H) 3.91 (s, 2H) 7.29 (d, J=8.08 Hz, 1H) 7.71 (t, J=7.33 Hz, 1H)

Preparation 70 methyl 2-(4-cyano-5-fluoro-2-methylphenyl)-3-(dimethylamino)acrylate Combined methyl 2-(4-cyano-5-fluoro-2-methylphenyl) acetate (5.00 g, 24.13 mmol), 1,1-dimethoxy-N,N-dimethylmethanamine (32.2 mL, 241 mmol), and lithium chloride (0.102 g, 2.413 mmol) and heated to 105° C. After 2 hours the reaction mixture was concentrated in vacuo and repeatedly diluted with EtOAc (30 mL) and concentrated to give an oil. The oil was dissolved in EtOAc (50 mL) and washed with water, 10% aqueous sodium chloride, and then brine. The organic layer was dried over sodium sulfate, filtered, and concentrated to afford a thick red oil, which was crystallized to give the title compound as a yellow solid (6.1 g, 23.26 mmol, 96%). $^1$H NMR (400 MHz, DMSO-d$_6$) δ ppm 2.10 (s, 3H) 2.34 (s, 1H) 2.54-2.81 (m, 6H) 3.50 (s, 3H) 7.20 (d, J=10.11 Hz, 1H) 7.58 (s, 1H) 7.72 (d, J=7.07 Hz, 1H). ESI-MS m/z [M+H]$^+$ 263.2.

Preparation 71 6-(4-(4-cyano-3-fluoro-2-methylphenyl)-5-hydroxy-1H-pyrazol-1-yl)nicotinic acid Combined 6-hydrazinylnicotinic acid (1.10 g, 7.18 mmol), methyl 2-(4-cyano-3-fluoro-2-methylphenyl)-3-(dimethylamino)acrylate (2.072 g, 7.90 mmol), 2-propanol (18 mL), and 0.5M aqueous hydrochloric acid (17.24 mL, 8.62 mmol). After 2 hours, N-ethyl-N-isopropylpropan-2-amine (6.26 mL, 35.9 mmol) was added. After another hour the reaction mixture was diluted with water and washed twice with IPAc. The aqueous phase was acidified to ~pH=3.5 and stirred for 30 minutes to give a solid which was collected by filtration, washed with water, ethanol, and heptanes, and dried overnight under vacuum to give the title compound (1.60 g, 66%). $^1$H NMR (400 MHz, DMSO-d$_6$) δ ppm 2.34 (d, J=2.27 Hz, 3H) 7.64 (d, J=8.08 Hz, 1H) 7.69-7.80 (m, 1H) 8.26 (br. s., 1H) 8.48 (br. s., 2H) 8.98 (t, J=1.52 Hz, 1H) 13.45 (br. s., 2H). ESI-MS m/z [M+H]$^+$ 339.2.

Preparation 72 6-(4-(4-cyano-5-fluoro-2-methylphenyl)-5-hydroxy-1H-pyrazol-1-yl)nicotinic acid Combined 6-hydrazinylnicotinic acid (0.73 g, 4.77 mmol), methyl 2-(4-cyano-5-fluoro-2-methylphenyl)-3-(dimethylamino)acrylate (1.375 g, 5.24 mmol), 2-propanol (18 mL), and 0.5M aqueous hydrochloric acid (11.44 mL, 5.72 mmol). After 2 hours, N-ethyl-N-isopropylpropan-2-amine (4.15 mL, 23.83 mmol). After an hour the reaction mixture was diluted with water and washed with IPAc twice. The aqueous phase was acidified to ~pH=3.5 and stirred for 30 minutes to give a solid which was collected by filtration, washed with water, ethanol, and heptanes, and dried overnight under vacuum to give the title compound (1.20 g, 74%). ¹H NMR (400 MHz, DMSO-d₆) δ ppm 2.41 (s, 3H) 7.74 (d, J=7.07 Hz, 1H) 7.91 (d, J=11.62 Hz, 1H) 8.26 (s, 1H) 8.37-8.47 (m, 1H) 8.47-8.56 (m, 1H) 8.96 (dd, J=2.15, 0.88 Hz, 1H). ESI-MS m/z [M+H]⁺ 339.2.

Preparation 73 methyl 2-(4-cyano-5-fluoro-2-methylphenyl)acetate

Combined 4-bromo-2-fluoro-5-methylbenzonitrile (4 g, 18.69 mmol) and dimethyl malonate (29.9 mL, 262 mmol) and purged with nitrogen. Potassium carbonate (3.87 g, 28.0 mmol), potassium hydrogencarbonate (2.81 g, 28.0 mmol), tri-tert-butylphosphonium tetrafluoroborate (0.119 g, 0.411 mmol), and bis(dibenzylidineacetone)palladium(0) (0.118 g, 0.206 mmol) were added. The reaction mixture was then heated in an oil bath at 170° C. After 3 hours, the reaction mixture was cooled, diluted with ethyl acetate, and filtered through Celite®. The filtrate was concentrated and the residue dissolved in EtOAc. The organic solution was washed with 1N aqueous sodium hydroxide (2×), twice with 10% aqueous sodium chloride, and then brine. The organic phase was dried over sodium sulfate, filtered, and concentrated in vacuo to give a residue which was purified by flash chromatography to give the title compound (1.67 g, 43%) as a clear colorless oil. ¹H NMR (400 MHz, CHLOROFORM-d) δ ppm 2.30 (s, 3H) 3.67 (s, 2H) 3.72 (s, 3H) 7.10 (d, J=9.60 Hz, 1H) 7.42 (d, J=6.32 Hz, 1H).

Preparation 74 methyl 2-(4-cyano-3-fluoro-2-methylphenyl)acetate

Combined 4-bromo-2-fluoro-3-methylbenzonitrile (2 g, 9.34 mmol), dimethyl malonate (12.28 mL, 107 mmol), potassium carbonate (1.937 g, 14.02 mmol) and potassium hydrogencarbonate (1.403 g, 14.02 mmol). Purged with nitrogen for 1 min and then tri-tert-butylphosphonium tetrafluoroborate (0.030 g, 0.103 mmol), and bis(dibenzylidineacetone)palladium (0) (0.027 g, 0.047 mmol) were added. The reaction was placed in a pre-heated oil bath (170° C.). After 1 hour the mixture was cooled to ambient temperature and diluted with EtOAc (80 mL). The EtOAc layer was decanted and passed through a plug of Celite® (~7 cm wide and 1.5 cm thick). The chunky dark precipitate that was left in the flask was diluted with additional EtOAc portions and sonicated until a fine suspension resulted. The EtOAc triturates were also passed through the Celite® plug and then concentrated in vacuo at ~40° C. and then at 90° C. for 45 minutes to give a residue which was purified using flash column chromatography to give the title compound (1.05 g, 5.07 mmol, 54.2%) as a clear colorless oil. ¹H NMR (400 MHz, CHLOROFORM-d) δ ppm 2.17 (d, J=2.27 Hz, 3H) 3.63 (s, 3H) 3.91 (s, 2H) 7.29 (d, J=8.08 Hz, 1H) 7.71 (t, J=7.33 Hz, 1H).

Preparation 75 methyl 2-(4-cyano-3-fluoro-2-methylphenyl)-3-(dimethylamino)acrylate Combined methyl 2-(4-cyano-3-fluoro-2-methylphenyl)acetate (10.0 g, 48.3 mmol), 1,1-dimethoxy-N,N-dimethylmethanamine (17.25 g, 145 mmol), and solid lithium chloride (0.205 g, 4.83 mmol) and heated to 105° C. for 1.5 h. The mixture was cooled to 10° C. and water (210 mL) was added slowly. The solid was collected by vacuum filtration, dissolved in DCM and was purified by column chromatography to afford the title compound (7.95 g, 63%) as a pale yellow solid. ¹H NMR (400 MHz, DMSO-d₆) δ ppm 2.07 (d, J=2.53 Hz, 3H) 2.54-2.86 (m, 6H) 3.50 (s, 3H) 7.10 (d, J=7.83 Hz, 1H) 7.62 (s, 1H) 7.63-7.66 (m, 1H). ESI-MS m/z [M+H]⁺ 263.2.

Preparation 76 2-methyl-4-(4,4,5,5-tetramethyl-1,3, 2-dioxaborolan-2-yl)benzonitrile In a microwave tube, combined Pd₂(dba)₃ (0.070 g, 0.077 mmol) and tricyclohexylphosphine (0.103 g, 0.367 mmol). Dioxane (15.32 ml) was added and the resulting mixture was stirred for 30 minutes at room temperature. Bis(pinacolato) diboron (1.425 g, 5.61 mmol), potassium acetate (0.751 g, 7.65 mmol) and 4-bromo-2-methylbenzonitrile (1 g, 5.10 mmol) were added successively. The tube was flushed with nitrogen. Then the reaction mixture was stirred in microwave at 100° C. for 1 hour. The mixture was treated with water (26 mL), and extracted with ether. The organic layer was washed with brine, dried over sodium sulfate, and concentrated to give the title compound (1.55 g) which was used in next step without further purification.

Example 1 6-(5-hydroxy-4-(2-methoxypyridin-4-yl)-1H-pyrazol-1-yl)-N-((tetrahydro-2H-pyran-4-yl)methyl)nicotinamide

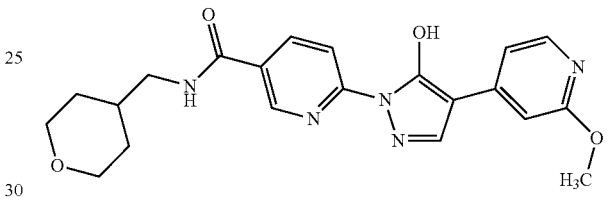

Combined 6-(5-hydroxy-4-(2-methoxypyridin-4-yl)-1H-pyrazol-1-yl)nicotinic acid (30 mg, 0.096 mmol), EDCI (27.6 mg, 0.144 mmol), HOBT (19.47 mg, 0.144 mmol), and DMF (961 µl), then added (tetrahydro-2H-pyran-4-yl)methanamine (17.66 µl, 0.144 mmol) and Hunig's base (68.3 µl, 0.384 mmol) and stirred at room temperature overnight. The reaction mixture was purified via preparative HPLC to give the title compound (32.1 mg, 82%) as a yellow solid. ¹H NMR (400 MHz, methanol-d₄) δ ppm 1.35 (qd, J=12.38, 4.55 Hz, 2H) 1.71 (d, J=12.88 Hz, 2H) 1.84-1.99 (m, 1H) 3.42 (td, J=11.68, 1.64 Hz, 2H) 3.95 (d, J=3.28 Hz, 1H) 3.98 (s, 3H) 4.19 (s, 3H) 7.76 (d, J=6.57 Hz, 1H) 7.84 (s, 1H) 8.03 (d, J=6.57 Hz, 1H) 8.28-8.47 (m, 2H) 8.55 (br. s., 1H) 8.85 (br. s., 1H). MS m/z [M+H]⁺ 410.1.

Example 2 N-benzyl-6-(5-hydroxy-4-(2-methoxypyridin-4-yl)-1H-pyrazol-1-yl)nicotinamide

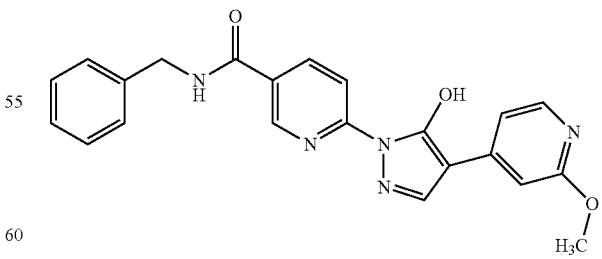

The title compound was prepared in a manner similar to Example 1 using phenylmethanamine. ¹H NMR (400 MHz, methanol-d₄) δ ppm 4.20 (s, 3H) 4.59 (s, 2H) 7.20-7.48 (m, 5H) 7.72-7.95 (m, 2H) 8.04 (d, J=6.32 Hz, 1H) 8.24-8.75 (m, 3H) 8.90 (br. s., 1H), MS m/z [M+H]⁺ 402.1.

Example 3 6-(5-hydroxy-4-(2-methoxypyridin-4-yl)-1H-pyrazol-1-yl)-N-(1-(methoxymethyl)cyclopentyl)nicotinamide

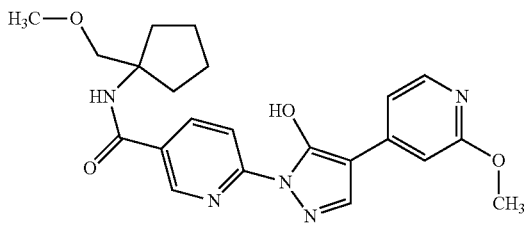

The title compound was prepared in a manner similar to Example 1 using 1-(methoxymethyl)cyclopentanamine. $^1$H NMR (400 MHz, DMSO-d$_6$) δ ppm 1.51-1.80 (m, 6H) 2.00-2.11 (m, 2H) 3.27 (s, 3H) 3.60 (s, 2H) 3.91 (s, 3H) 7.39-7.65 (m, 2H) 8.01-8.19 (m, 2H) 8.43 (br. s., 2H) 8.68 (br. s., 1H) 8.86 (t, J=1.52 Hz, 1H). MS m/z [M+H]$^+$ 424.3.

Example 4 6-(5-hydroxy-4-(2-methoxypyridin-4-yl)-1H-pyrazol-1-yl)-N-(1-methylcyclopropyl)nicotinamide

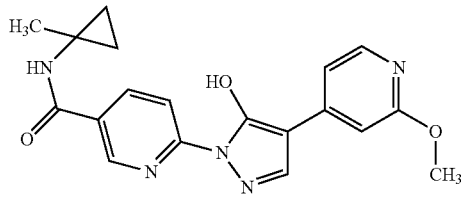 [SMILES: COc1cc(-c2cnn(-c3ccc(C(=O)NC4(C)CC4)cn3)c2O)ccn1]

The title compound was prepared in a manner similar to Example 1 using 1-methylcyclopropanamine. $^1$H NMR (400 MHz, DMSO-d$_6$) δ ppm 0.61-0.68 (m, 2H) 0.74-0.80 (m, 2H) 1.39 (s, 3H) 3.91 (s, 3H) 7.41-7.65 (m, 2H) 8.09 (d, J=5.81 Hz, 1H) 8.31-8.52 (m, 2H) 8.69 (s, 1H) 8.82-8.97 (m, 2H). MS m/z [M+H]$^+$ 366.2.

Example 5 6-(5-hydroxy-4-(2-methoxypyridin-4-yl)-1H-pyrazol-1-yl)-N-isopropylnicotinamide

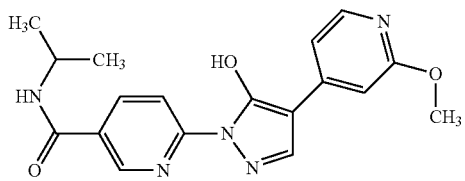 [SMILES: COc1cc(-c2cnn(-c3ccc(C(=O)NC(C)C)cn3)c2O)ccn1]

The title compound was prepared in a manner similar to Example 1 using propan-2-amine. MS m/z [M+H]$^+$ 354.2.

Example 6 6-(5-hydroxy-4-(2-methoxypyridin-4-yl)-1H-pyrazol-1-yl)-N-isobutylnicotinamide

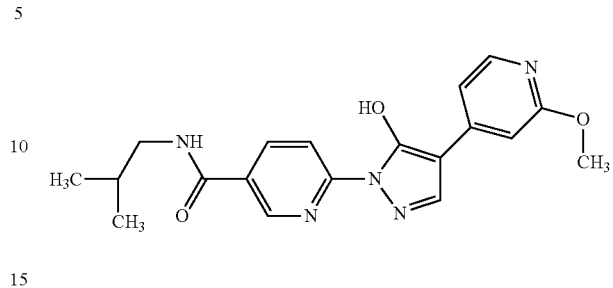

The title compound was prepared in a manner similar to Example 1 using 2-methylpropan-1-amine. MS m/z [M+H]$^+$ 368.3.

Example 7 6-(5-hydroxy-4-(2-methoxypyridin-4-yl)-1H-pyrazol-1-yl)-N-(2-isopropoxyethyl)nicotinamide

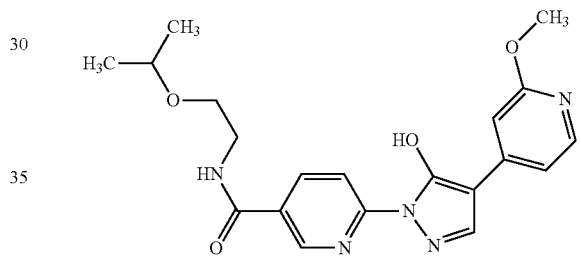

The title compound was prepared in a manner similar to Example 1 using 2-isopropoxyethanamine. MS m/z [M+H]$^+$ 398.3.

Example 8 6-(5-hydroxy-4-(2-methoxypyridin-4-yl)-1H-pyrazol-1-yl)-N-propylnicotinamide

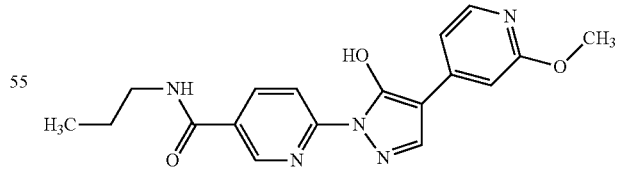

The title compound was prepared in a manner similar to Example 1 using propan-1-amine. $^1$H NMR (400 MHz, DMSO-d$_6$) δ ppm 0.92 (t, J=7.45 Hz, 3H) 1.44-1.68 (m, 2H) 3.14-3.34 (m, 2H) 3.93 (s, 3H) 7.46-7.70 (m, 2H) 8.10 (d, J=5.81 Hz, 1H) 8.35-8.59 (m, 2H) 8.61-8.80 (m, 2H) 8.82-8.99 (m, 1H). MS m/z [M+H]$^+$ 354.2.

Example 9 6-(5-hydroxy-4-(2-methoxypyridin-4-yl)-1H-pyrazol-1-yl)-N-((1 s,4 s)-4-methoxycyclohexyl)nicotinamide

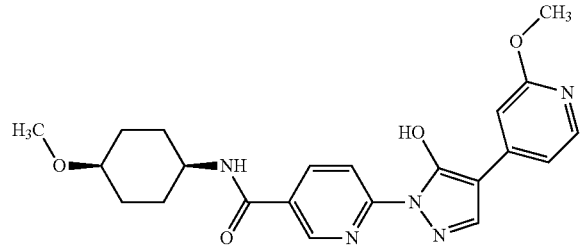 [SMILES: COc1cc(-c2cnn(-c3ccc(C(=O)N[C@H]4CC[C@@H](OC)CC4)cn3)c2O)ccn1]

The title compound was prepared in a manner similar to Example 1 using (1s,4s)-4-methoxycyclohexanamine. $^1$H NMR (400 MHz, DMSO-d$_6$) δ ppm 1.36-1.74 (m, 6H) 1.89 (dd, J=9.09, 4.04 Hz, 2H) 3.23 (s, 3H) 3.32-3.44 (m, 1H) 3.72-4.09 (m, 4H) 7.44-7.66 (m, 2H) 8.09 (d, J=5.81 Hz, 1H) 8.36-8.57 (m, 3H) 8.68 (br. s., 1H) 8.90 (s, 1H). MS m/z [M+H]$^+$ 424.2.

Example 10 (S)—N-(sec-butyl)-6-(5-hydroxy-4-(2-methoxypyridin-4-yl)-1H-pyrazol-1-yl)nicotinamide

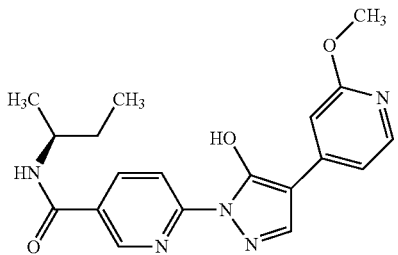 [SMILES: CC[C@H](C)NC(=O)c1ccc(-n2ncc(-c3ccnc(OC)c3)c2O)nc1]

The title compound was prepared in a manner similar to Example 1 using (S)-butan-2-amine. MS m/z [M+H]$^+$ 368.2.

Example 11 6-(5-hydroxy-4-(2-methoxypyridin-4-yl)-1H-pyrazol-1-yl)-N-(2-(tetrahydro-2H-pyran-4-yl)ethyl)nicotinamide

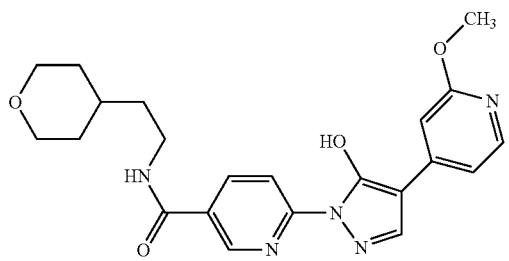 [SMILES: COc1cc(-c2cnn(-c3ccc(C(=O)NCCC4CCOCC4)cn3)c2O)ccn1]

The title compound was prepared in a manner similar to Example 1 using 2-(tetrahydro-2H-pyran-4-yl)ethanamine. MS m/z [M+H]$^+$ 424.3.

Example 12 N-(3-ethoxypropyl)-6-(5-hydroxy-4-(2-methoxypyridin-4-yl)-1H-pyrazol-1-yl)nicotinamide

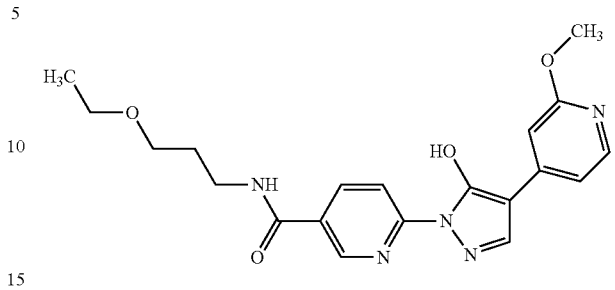

The title compound was prepared in a manner similar to Example 1 using 3-ethoxypropan-1-amine. $^1$H NMR (400 MHz, DMSO-d$_6$) δ ppm 1.11 (t, J=6.95 Hz, 3H) 1.69-1.84 (m, 2H) 3.31-3.37 (m, 3H) 3.40-3.45 (m, 3H) 3.85 (s, 3H) 7.33-7.56 (m, 2H) 8.05 (d, J=5.56 Hz, 1H) 8.27-8.80 (m, 4H) 8.84-8.98 (m, 1H) 13.54 (br. s., 1H). MS m/z [M+H]$^+$ 398.3.

Example 13 N-cyclobutyl-6-(5-hydroxy-4-(2-methoxypyridin-4-yl)-1H-pyrazol-1-yl)nicotinamide

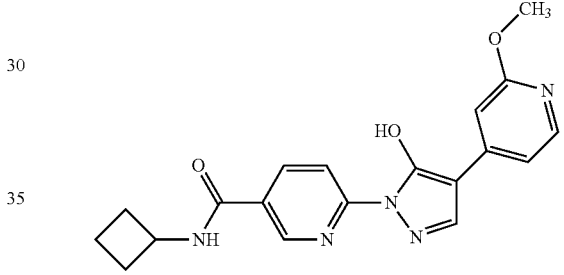

The title compound was prepared in a manner similar to Example 1 using cyclobutanamine. $^1$H NMR (400 MHz, DMSO-d$_6$) δ ppm 1.63-1.77 (m, 2H) 2.04-2.18 (m, 2H) 2.19-2.30 (m, 2H) 4.02 (s, 3H) 4.35-4.52 (m, 1H) 7.63-7.85 (m, 2H) 8.14 (d, J=6.32 Hz, 1H) 8.32-8.68 (m, 2H) 8.70-9.13 (m, 3H) MS m/z [M+H]$^+$ 366.2.

Example 14 6-(5-hydroxy-4-(2-methoxypyridin-4-yl)-1H-pyrazol-1-yl)-N-((1-(methoxymethyl)cyclopropyl)methyl)nicotinamide

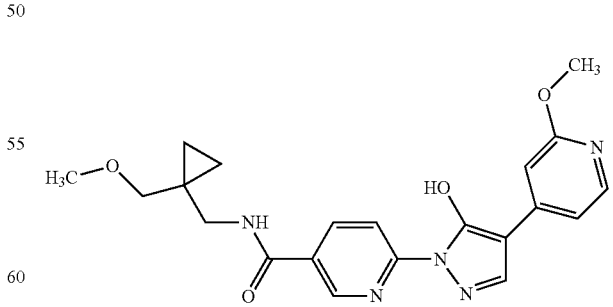

The title compound was prepared in a manner similar to Example 1 using (1-(methoxymethyl)cyclopropyl)methanamine. $^1$H NMR (400 MHz, DMSO-d$_6$) δ ppm 0.31-0.48 (m, 2H) 0.50-0.62 (m, 2H) 3.23-3.27 (m, 4H) 3.35 (d, J=6.06 Hz, 2H) 3.86 (s, 3H) 7.34-7.58 (m, 2H) 8.06 (d, J=5.56 Hz, 1H)

8.35-8.72 (m, 4H) 8.84-8.97 (m, 1H) 8.90 (s, 1H) 13.51 (br. s., 1H). MS m/z [M+H]+ 410.3.

Example 15 6-(5-hydroxy-4-(2-methoxypyridin-4-yl)-1H-pyrazol-1-yl)-N-(tetrahydro-2H-pyran-4-yl)nicotinamide

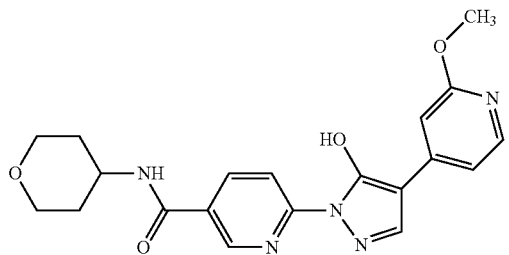 [SMILES: COc1cc(-c2cnn(-c3ccc(C(=O)NC4CCOCC4)cn3)c2O)ccn1]

The title compound was prepared in a manner similar to Example 1 using tetrahydro-2H-pyran-4-amine. ¹H NMR (400 MHz, DMSO-d$_6$) δ ppm 1.49-1.68 (m, 2H) 1.80 (dd, J=12.51, 2.40 Hz, 2H) 3.37-3.44 (m, 2H) 3.82-3.95 (m, 5H) 3.96-4.10 (m, 1H) 7.35-7.59 (m, 2H) 8.06 (d, J=5.56 Hz, 1H) 8.33-8.78 (m, 4H) 8.86-8.97 (m, 1H) 13.55 (br. s., 1H). MS m/z [M+H]+ 396.2.

Example 16 (S)-6-(5-hydroxy-4-(2-methoxypyridin-4-yl)-1H-pyrazol-1-yl)-N-(1-(tetrahydro-2H-pyran-4-yl)ethyl)nicotinamide

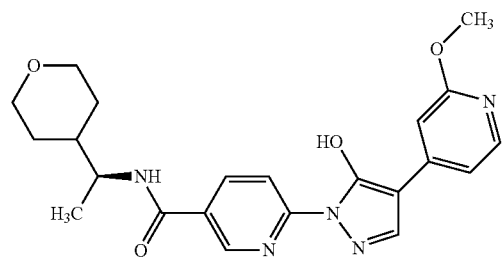 [SMILES: COc1cc(-c2cnn(-c3ccc(C(=O)N[C@@H](C)C4CCOCC4)cn3)c2O)ccn1]

The title compound was prepared in a manner similar to Example 1 using (S)-1-(tetrahydro-2H-pyran-4-yl)ethanamine. ¹H NMR (400 MHz, DMSO-d$_6$) δ ppm 1.14 (s, 3H) 1.18-1.32 (m, 2H) 1.55-1.74 (m, 3H) 3.19-3.30 (m, 2H) 3.79-3.96 (m, 6H) 7.27-7.66 (m, 2H) 8.06 (d, J=5.30 Hz, 1H) 8.22-8.82 (m, 4H) 8.84-8.97 (m, 1H) 13.53 (br. s., 1H). MS m/z [M+H]+ 424.3.

Example 17 6-(5-hydroxy-4-(2-methoxypyridin-4-yl)-1H-pyrazol-1-yl)-N-(1-methoxy-2-methylpropan-2-yl)nicotinamide

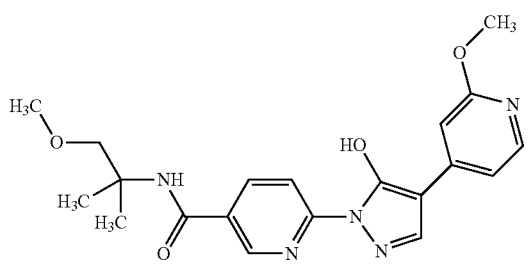 [SMILES: COCC(C)(C)NC(=O)c1ccc(-n2ncc(-c3ccnc(OC)c3)c2O)nc1]

The title compound was prepared in a manner similar to Example 1 using 1-methoxy-2-methylpropan-2-amine. ¹H NMR (400 MHz, DMSO-d$_6$) δ ppm 1.30-1.41 (m, 6H) 3.29 (s, 3H) 3.48-3.61 (m, 2H) 3.78-3.93 (m, 3H) 7.36-7.44 (m, 1H) 7.46-7.53 (m, 1H) 7.95 (s, 1H) 8.05 (d, J=5.56 Hz, 1H) 8.30-8.68 (m, 3H) 8.84 (d, J=1.52 Hz, 1H) 13.53 (br. s., 1H). MS m/z [M+H]+ 398.3.

Example 18 6-(5-hydroxy-4-(2-methoxypyridin-4-yl)-1H-pyrazol-1-yl)-N-(3-(piperidin-1-yl)propyl)nicotinamide

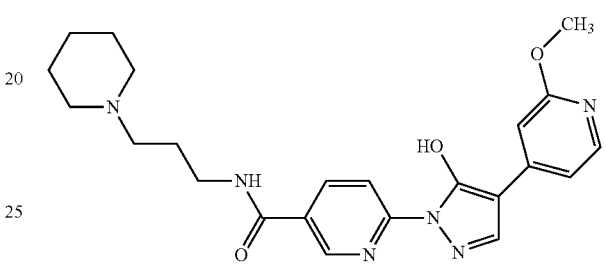

The title compound was prepared in a manner similar to Example 1 using 3-(piperidin-1-yl)propan-1-amine. ¹H NMR (400 MHz, DMSO-d$_6$) δ ppm 1.28-1.48 (m, 1H) 1.54-1.75 (m, 3H) 1.75-1.88 (m, 2H) 1.88-2.01 (m, 2H) 2.88 (br. s., 2H) 3.03-3.19 (m, 2H) 3.32-3.50 (m, 4H) 7.80 (d, J=8.59 Hz, 2H) 8.15 (d, J=8.08 Hz, 2H) 8.37-8.81 (m, 3H) 8.82-8.98 (m, 2H) 9.15 (br. s., 1H) 13.53 (br. s., 1H). MS m/z [M+H]+ 431.2.

Example 19 6-(5-hydroxy-4-(2-methoxypyridin-4-yl)-1H-pyrazol-1-yl)-N-(3-(pyrrolidin-1-yl)propyl)nicotinamide

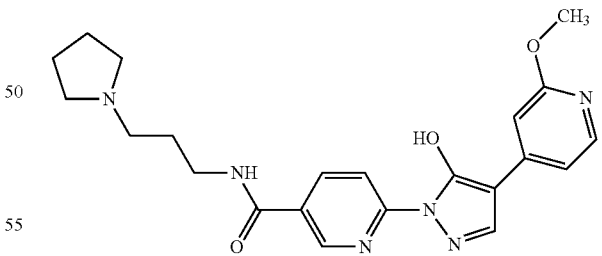

The title compound was prepared in a manner similar to Example 1 using 3-(pyrrolidin-1-yl)propan-1-amine. ¹H NMR (400 MHz, DMSO-d$_6$) δ ppm 1.71-2.21 (m, 6H) 3.01 (br. s., 2H) 3.14-3.26 (m, 2H) 3.38 (q, J=6.57 Hz, 2H) 3.56 (br. s., 2H) 7.79 (d, J=8.59 Hz, 2H) 8.15 (d, J=8.08 Hz, 2H) 8.37-8.58 (m, 2H) 8.67 (br. s., 1H) 8.86 (t, J=5.56 Hz, 1H) 8.90-8.97 (m, 1H) 9.63 (br. s., 1H) 13.53 (br. s., 1H). MS m/z [M+H]+ 417.2.

Example 20 6-(5-hydroxy-4-(2-methoxypyridin-4-yl)-1H-pyrazol-1-yl)-N-(3-(2-oxopyrrolidin-1-yl)propyl)nicotinamide

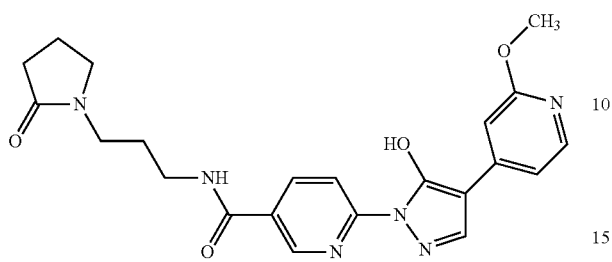

The title compound was prepared in a manner similar to Example 1 using 1-(3-aminopropyl)pyrrolidin-2-one. $^1$H NMR (400 MHz, DMSO-d$_6$) δ ppm 1.74 (quin, J=7.07 Hz, 2H) 1.87-1.99 (m, 2H) 2.17-2.28 (m, 2H) 3.20-3.31 (m, 4H) 3.33-3.41 (m, 2H) 7.80 (d, J=8.34 Hz, 2H) 8.02-8.86 (m, 6H) 8.87-8.99 (m, 1H) 13.55 (br. s., 1H). MS m/z [M+H]$^+$ 431.1.

Example 21 N-(3-(1H-imidazol-1-yl)propyl)-6-(5-hydroxy-4-(2-methoxypyridin-4-yl)-1H-pyrazol-1-yl)nicotinamide

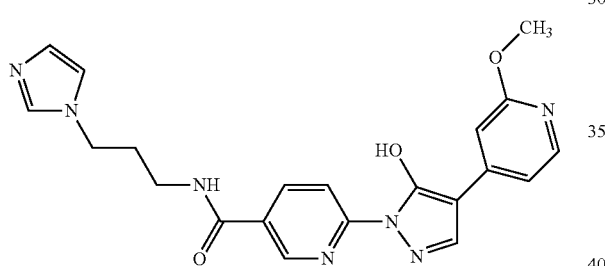

The title compound was prepared in a manner similar to Example 1 using 3-(1H-imidazol-1-yl)propan-1-amine. $^1$H NMR (400 MHz, DMSO-d$_6$) δ ppm 2.11 (quin, J=6.76 Hz, 2H) 3.32 (q, J=6.40 Hz, 2H) 4.28 (t, J=6.95 Hz, 2H) 7.69 (t, J=1.52 Hz, 1H) 7.75-7.87 (m, 3H) 8.15 (d, J=8.59 Hz, 2H) 8.41 (dd, J=8.84, 2.27 Hz, 1H) 8.50 (d, J=8.08 Hz, 1H) 8.68 (s, 1H) 8.82 (br. s., 1H) 8.88-8.96 (m, 1H) 9.11 (s, 1H) 13.95 (br. s., 1H). MS m/z [M+H]$^+$ 414.1.

Example 22 N-(1-ethylpiperidin-4-yl)-6-(5-hydroxy-4-(2-methoxypyridin-4-yl)-1H-pyrazol-1-yl)nicotinamide

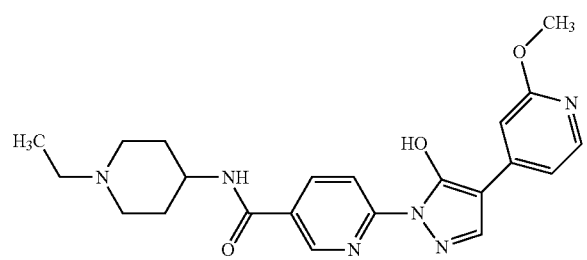 [SMILES: CCN1CCC(NC(=O)c2ccc(-n3ncc(-c4ccnc(OC)c4)c3O)nc2)CC1]

The title compound was prepared in a manner similar to Example 1 using 1-ethylpiperidin-4-amine. $^1$H NMR (400 MHz, DMSO-d$_6$) δ ppm 1.20 (t, J=7.33 Hz, 3H) 1.69-2.08 (m, 4H) 2.86-3.25 (m, 4H) 3.45 (br. s., 2H) 3.89-4.19 (m, 1H) 7.73 (d, J=8.34 Hz, 2H) 8.05-8.79 (m, 5H) 8.84-8.99 (m, 1H) 9.77-10.36 (m, 1H) 13.47 (br. s., 1H). MS m/z [M+H]$^+$ 417.

Example 23 6-(5-hydroxy-4-(2-methoxypyridin-4-yl)-1H-pyrazol-1-yl)-N-(2-(1-methylpyrrolidin-2-yl)ethyl)nicotinamide

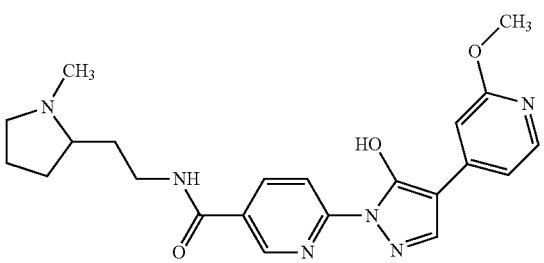 [SMILES: COc1cc(-c2cnn(-c3ccc(C(=O)NCCC4CCCN4C)cn3)c2O)ccn1]

The title compound was prepared in a manner similar to Example 1 using 2-(1-methylpyrrolidin-2-yl)ethanamine. $^1$H NMR (400 MHz, DMSO-d$_6$) δ ppm 1.59-2.06 (m, 4H) 2.10-2.25 (m, 1H) 2.28-2.42 (m, 1H) 2.65-2.94 (m, 3H) 3.00-3.13 (m, 1H) 3.22-3.46 (m, 3H) 3.52-3.63 (m, 1H) 7.80 (d, J=8.34 Hz, 2H) 8.15 (d, J=7.58 Hz, 2H) 8.30-8.77 (m, 3H) 8.78-9.00 (m, 2H) 9.63 (br. s., 1H) 13.53 (br. s., 1H). MS m/z [M+H]$^+$ 417.

Example 24 6-(5-hydroxy-4-(2-methoxypyridin-4-yl)-1H-pyrazol-1-yl)-N-(1-propylpiperidin-4-yl)nicotinamide

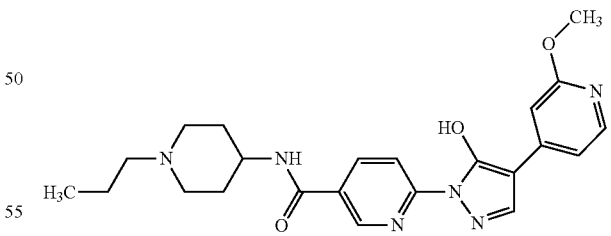

The title compound was prepared in a manner similar to Example 1 using 1-propylpiperidin-4-amine. $^1$H NMR (400 MHz, DMSO-d$_6$) δ ppm 0.91 (t, J=7.45 Hz, 3H) 1.23 (br. s., 1H) 1.54-1.84 (m, 4H) 1.95-2.08 (m, 2H) 2.75-3.03 (m, 3H) 3.34-3.48 (m, 2H) 4.02 (br. s., 1H) 7.53 (d, J=8.59 Hz, 2H) 7.99 (d, J=8.59 Hz, 3H) 8.18 (dd, J=8.84, 2.27 Hz, 1H) 8.43 (br. s., 1H) 8.58 (d, J=8.84 Hz, 1H) 8.81 (d, J=2.02 Hz, 1H). MS m/z [M+H]$^+$ 437.

Example 25 6-(5-hydroxy-4-(2-methoxypyridin-4-yl)-1H-pyrazol-1-yl)-N-(2-hydroxyethyl)nicotinamide

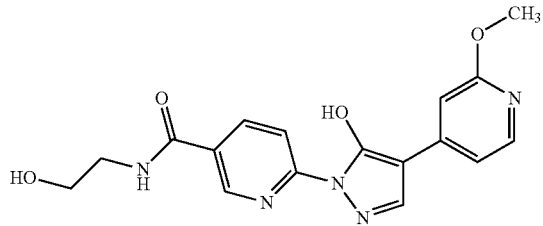 [SMILES: COc1cc(-c2cnn(-c3ccc(C(=O)NCCO)cn3)c2O)ccn1]

The title compound was prepared in a manner similar to Example 1 using 2-aminoethanol. $^1$H NMR (400 MHz, DMSO-d$_6$) δ ppm 3.30 (q, J=5.89 Hz, 2H) 3.42-3.55 (m, 2H) 3.94 (s, 3H) 7.52-7.73 (m, 2H) 8.06 (d, J=6.06 Hz, 1H) 8.35-8.52 (m, 2H) 8.67-8.83 (m, 2H) 8.85-8.93 (m, 1H). MS m/z [M+H]$^+$ 356.1.

Example 26 6-(5-hydroxy-4-(2-methoxypyridin-4-yl)-1H-pyrazol-1-yl)-N-(3-hydroxypropyl)nicotinamide

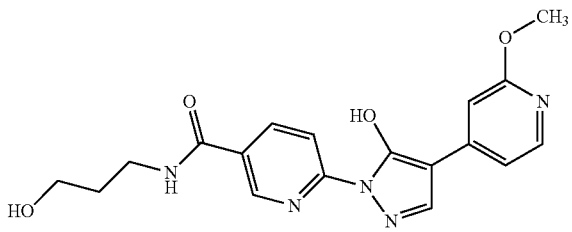 [SMILES: COc1cc(-c2cnn(-c3ccc(C(=O)NCCCO)cn3)c2O)ccn1]

The title compound was prepared in a manner similar to Example 1 using 3-aminopropan-1-ol. $^1$H NMR (400 MHz, DMSO-d$_6$) δ ppm 1.70 (quin, J=6.63 Hz, 2H) 3.35 (q, J=6.74 Hz, 2H) 3.48 (t, J=6.19 Hz, 2H) 3.92 (s, 3H) 7.39-7.69 (m, 2H) 8.09 (d, J=5.81 Hz, 1H) 8.34-8.57 (m, 2H) 8.72 (d, J=7.58 Hz, 2H) 8.90 (t, J=1.39 Hz, 1H). MS m/z [M+H]$^+$ 370.2.

Example 27 N-(2-hydroxy-1-(tetrahydrofuran-3-yl)ethyl)-6-(5-hydroxy-4-(2-methoxypyridin-4-yl)-1H-pyrazol-1-yl)nicotinamide

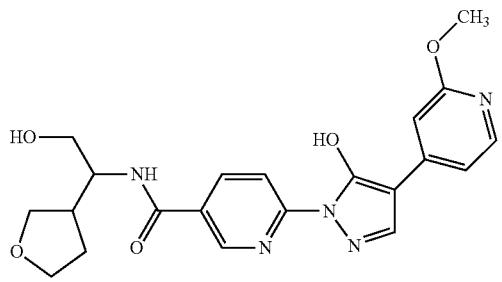 [SMILES: COc1cc(-c2cnn(-c3ccc(C(=O)NC(CO)C4CCOC4)cn3)c2O)ccn1]

The title compound was prepared in a manner similar to Example 1 using 2-amino-2-(tetrahydrofuran-3-yl)ethanol. $^1$H NMR (400 MHz, DMSO-d$_6$) δ ppm 1.52-1.73 (m, 1H) 1.85-2.06 (m, 1H) 3.37-3.82 (m, 7H) 3.86 (s, 3H) 3.93-4.03 (m, 1H) 4.78 (br. s., 1H) 7.08-7.70 (m, 2H) 8.06 (d, J=5.05 Hz, 1H) 8.18-8.85 (m, 4H) 8.91 (dt, J=5.56, 1.39 Hz, 1H) 13.53 (br. s., 1H). MS m/z [M+H]$^+$ 426.

Example 28 6-(5-hydroxy-4-(2-methoxypyridin-4-yl)-1H-pyrazol-1-yl)-N-(4-hydroxybutyl)nicotinamide

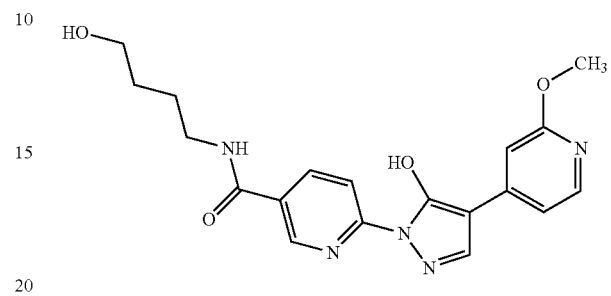

The title compound was prepared in a manner similar to Example 1 using 4-aminobutan-1-ol. $^1$H NMR (400 MHz, DMSO-d$_6$) δ ppm 1.42-1.62 (m, 4H) 3.24-3.34 (m, 2H) 3.43 (t, J=6.44 Hz, 2H) 3.85 (s, 3H) 4.43 (br. s., 1H) 7.30-7.55 (m, 2H) 8.05 (d, J=5.56 Hz, 1H) 8.23-8.82 (m, 4H) 8.84-8.96 (m, 1H) 13.53 (br. s., 1H). MS m/z [M+H]$^+$ 384.2.

Example 29 6-(5-hydroxy-4-(2-methoxypyridin-4-yl)-1H-pyrazol-1-yl)-N-(3-(2-methylpiperidin-1-yl)propyl)nicotinamide

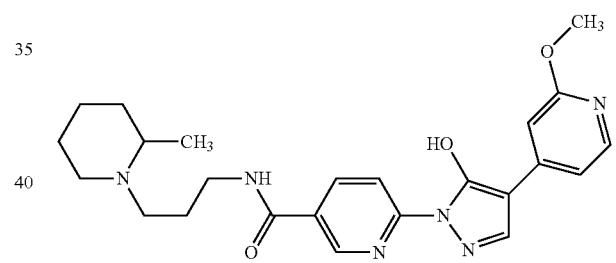

The title compound was prepared in a manner similar to Example 1 using 3-(2-methylpiperidin-1-yl)propan-1-amine. $^1$H NMR (400 MHz, DMSO-d$_6$) δ ppm 1.16-1.36 (m, 3H) 1.40-2.03 (m, 8H) 2.82-3.52 (m, 7H) 3.83-4.03 (m, 3H) 7.37-7.73 (m, 2H) 8.10 (d, J=4.80 Hz, 1H) 8.31-8.81 (m, 3H) 8.92 (br. s., 2H) 9.07-9.42 (m, 1H). MS m/z [M+H]$^+$ 451.2.

Example 30 6-(5-hydroxy-4-(2-methoxypyridin-4-yl)-1H-pyrazol-1-yl)-N-((1-methylpiperidin-4-yl)methyl)nicotinamide

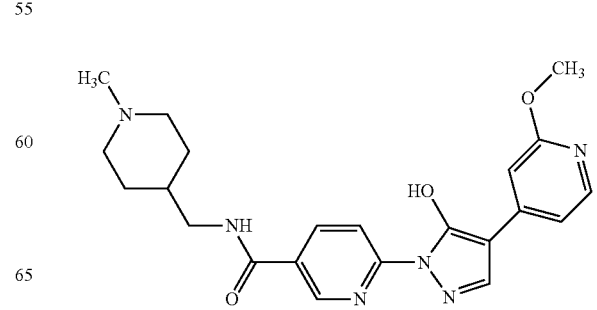

The title compound was prepared in a manner similar to Example 1 using (1-methylpiperidin-4-yl)methanamine ¹H NMR (400 MHz, DMSO-d₆) δ ppm 1.38 (d, J=12.88 Hz, 2H) 1.81 (d, J=3.54 Hz, 1H) 1.91 (d, J=13.64 Hz, 2H) 2.76 (d, J=4.55 Hz, 3H) 2.85-2.97 (m, 2H) 3.23 (t, J=6.32 Hz, 2H) 3.44 (d, J=12.63 Hz, 2H) 3.88 (s, 3H) 7.35-7.61 (m, 2H) 8.07 (d, J=5.81 Hz, 1H) 8.23-8.73 (m, 3H) 8.79 (t, J=5.68 Hz, 1H) 8.86-8.95 (m, 1H) 9.12 (br. s., 1H). MS m/z [M+H]⁺ 423.2.

Example 31 6-(5-hydroxy-4-(2-methoxypyridin-4-yl)-1H-pyrazol-1-yl)-N-(2-(1-methylpyrrolidin-2-yl)ethyl)nicotinamide

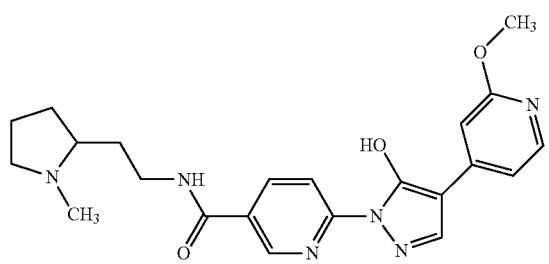 [SMILES: COc1cc(-c2cnn(-c3ccc(C(=O)NCCC4CCCN4C)cn3)c2O)ccn1]

The title compound was prepared in a manner similar to Example 1 using 3-(1-methylpyrrolidin-2-yl)propan-1-amine ¹H NMR (400 MHz, DMSO-d₆) δ ppm 1.60-1.81 (m, 2H) 1.85-2.06 (m, 2H) 2.11-2.23 (m, 1H) 2.28-2.41 (m, 1H) 2.84 (d, J=4.80 Hz, 3H) 3.00-3.13 (m, 1H) 3.22-3.35 (m, 1H) 3.40 (q, J=6.32 Hz, 2H) 3.58 (dd, J=11.49, 7.96 Hz, 1H) 3.91 (s, 3H) 7.40-7.64 (m, 2H) 8.09 (d, J=5.81 Hz, 1H) 8.35-8.56 (m, 2H) 8.68 (s, 1H) 8.78-8.99 (m, 2H) 9.61 (br. s., 1H). MS m/z [M+H]⁺ 423.2.

Example 32 6-(5-hydroxy-4-(2-methoxypyridin-4-yl)-1H-pyrazol-1-yl)-N-(3-morpholinopropyl)nicotinamide

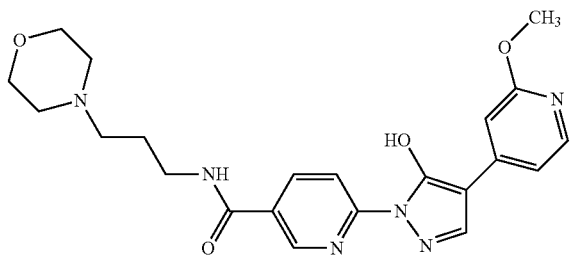 [SMILES: COc1cc(-c2cnn(-c3ccc(C(=O)NCCCN4CCOCC4)cn3)c2O)ccn1]

The title compound was prepared in a manner similar to Example 1 using 3-morpholinopropan-1-amine ¹H NMR (400 MHz, DMSO-d₆) δ ppm 1.89-2.00 (m, 2H) 3.09 (br. s., 2H) 3.16-3.24 (m, 2H) 3.33-3.51 (m, 4H) 3.65 (t, J=12.00 Hz, 2H) 3.92 (s, 3H) 3.99 (d, J=11.62 Hz, 2H) 7.44-7.68 (m, 2H) 8.10 (d, J=5.81 Hz, 1H) 8.36-8.57 (m, 2H) 8.71 (s, 1H) 8.80-9.01 (m, 2H) 9.78 (br. s., 1H). MS m/z [M+H]⁺ 439.2.

Example 33 6-(5-hydroxy-4-(2-methoxypyridin-4-yl)-1H-pyrazol-1-yl)-N-(1-methylpiperidin-4-yl)nicotinamide

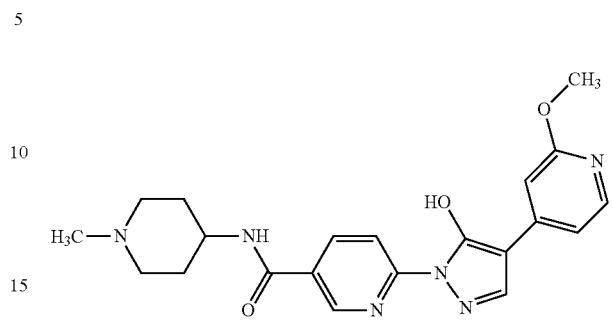

The title compound was prepared in a manner similar to Example 1 using 1-methylpiperidin-4-amine ¹H NMR (400 MHz, DMSO-d₆) δ ppm 1.68-2.00 (m, 2H) 2.08 (s, 2H) 2.70-2.88 (m, 3H) 3.01-3.24 (m, 2H) 3.50 (d, J=12.13 Hz, 2H) 3.95 (s, 3H) 3.99-4.11 (m, 1H) 7.49-7.70 (m, 2H) 8.11 (d, J=5.81 Hz, 1H) 8.40-8.53 (m, 2H) 8.67-8.83 (m, 2H) 8.84-8.98 (m, 1H) 9.64 (br. s., 1H). MS m/z [M+H]⁺ 409.2.

Example 34 N-ethyl-6-(5-hydroxy-4-(2-methoxypyridin-4-yl)-1H-pyrazol-1-yl)nicotinamide

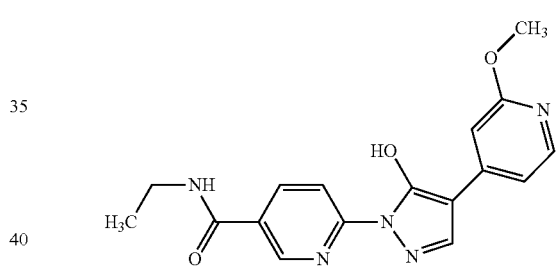

The title compound was prepared in a manner similar to Example 1 using ethanamine hydrochloride ¹H NMR (400 MHz, DMSO-d₆) δ ppm 1.16 (t, J=7.20 Hz, 3H) 3.22-3.39 (m, 2H) 3.90 (s, 3H) 7.28-7.72 (m, 2H) 8.08 (d, J=5.56 Hz, 1H) 8.31-8.84 (m, 4H) 8.91 (s, 1H). MS m/z [M+H]⁺ 340.2.

Example 35 N-(3-(1H-imidazol-1-yl)propyl)-6-(5-hydroxy-4-(2-methoxypyridin-4-yl)-1H-pyrazol-1-yl)nicotinamide

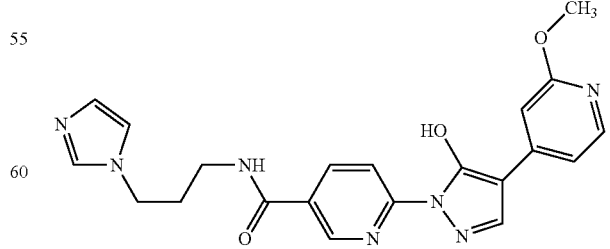

The title compound was prepared in a manner similar to Example 1 using 3-(1H-imidazol-1-yl)propan-1-amine ¹H NMR (400 MHz, DMSO-d₆) δ ppm 2.02-2.18 (m, 2H) 3.32 (q, J=6.48 Hz, 2H) 3.92 (s, 3H) 4.29 (t, J=6.95 Hz, 2H) 7.54

(s, 1H) 7.60 (d, J=5.81 Hz, 1H) 7.72 (t, J=1.64 Hz, 1H) 7.85 (t, J=1.64 Hz, 1H) 8.10 (d, J=5.81 Hz, 1H) 8.37-8.56 (m, 2H) 8.71 (s, 1H) 8.84 (t, J=5.68 Hz, 1H) 8.91 (dd, J=2.27, 0.76 Hz, 1H) 9.16 (t, J=1.26 Hz, 1H). MS m/z [M+H]$^+$ 420.2.

Example 36 6-(5-hydroxy-4-(2-methoxypyridin-4-yl)-1H-pyrazol-1-yl)-N-((1-methylpyrrolidin-3-yl)methyl)nicotinamide

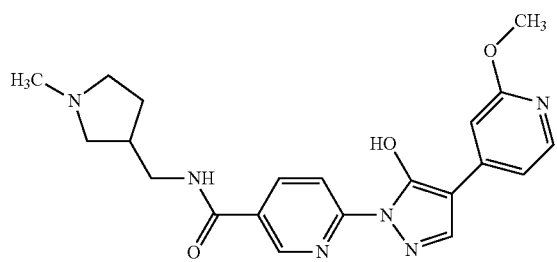 [SMILES: COc1cc(-c2cnn(-c3ccc(C(=O)NCC4CCN(C)C4)cn3)c2O)ccn1]

The title compound was prepared in a manner similar to Example 1 using (1-methylpyrrolidin-3-yl)methanamine. $^1$H NMR (400 MHz, DMSO-d$_6$) δ ppm 1.57-2.29 (m, 3H) 2.76-3.22 (m, 5H) 3.32-3.73 (m, 4H) 3.89-4.01 (m, 3H) 7.45-7.71 (m, 2H) 8.11 (d, J=6.06 Hz, 1H) 8.32-8.59 (m, 2H) 8.72 (s, 1H) 8.81-9.01 (m, 2H) 9.90 (br. s., 1H). MS m/z [M+H]$^+$ 409.2.

Example 37 N-(1-ethylpiperidin-4-yl)-6-(5-hydroxy-4-(2-methoxypyridin-4-yl)-1H-pyrazol-1-yl)nicotinamide

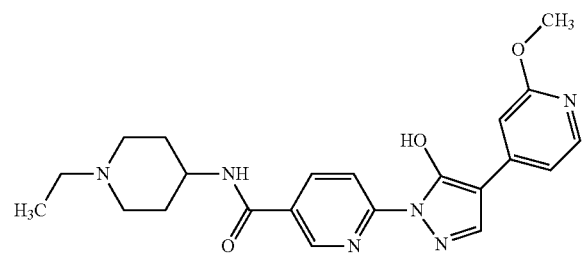 [SMILES: CCN1CCC(NC(=O)c2ccc(-n3ncc(-c4ccnc(OC)c4)c3O)nc2)CC1]

The title compound was prepared in a manner similar to Example 1 using 1-ethylpiperidin-4-amine. $^1$H NMR (400 MHz, DMSO-d$_6$) δ ppm 1.19-1.33 (m, 3H) 1.69-2.15 (m, 4H) 2.98-3.32 (m, 4H) 3.34-3.64 (m, 2H) 3.93 (s, 3H) 3.99-4.25 (m, 1H) 7.45-7.67 (m, 2H) 8.10 (d, J=5.81 Hz, 1H) 8.37-8.82 (m, 4H) 8.86-8.97 (m, 1H) 9.29 (br. s., 1H). MS m/z [M+H]$^+$ 423.2.

Example 38 6-(5-hydroxy-4-(2-methoxypyridin-4-yl)-1H-pyrazol-1-yl)-N-(3-(piperidin-1-yl)propyl)nicotinamide

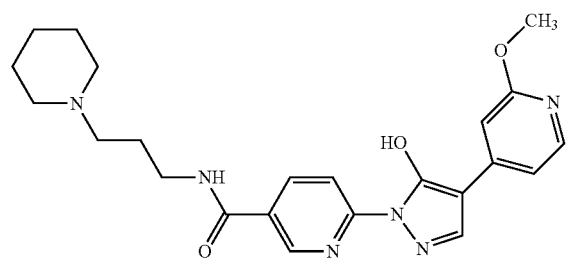 [SMILES: COc1cc(-c2cnn(-c3ccc(C(=O)NCCCN4CCCCC4)cn3)c2O)ccn1]

The title compound was prepared in a manner similar to Example 1 using 3-(piperidin-1-yl)propan-1-amine. $^1$H NMR (400 MHz, DMSO-d$_6$) δ ppm 1.38 (dd, J=12.25, 3.66 Hz, 1H) 1.55-1.74 (m, 3H) 1.82 (d, J=14.15 Hz, 2H) 1.88-1.99 (m, 2H) 2.79-2.96 (m, 2H) 3.11 (dt, J=10.67, 5.15 Hz, 2H) 3.28-3.52 (m, 4H) 3.93 (s, 3H) 7.45-7.70 (m, 2H) 8.10 (d, J=5.81 Hz, 1H) 8.35-8.57 (m, 2H) 8.71 (s, 1H) 8.82-8.99 (m, 2H) 9.14 (br. s., 1H). MS m/z [M+H]$^+$ 437.2.

Example 39 6-(5-hydroxy-4-(2-methoxypyridin-4-yl)-1H-pyrazol-1-yl)-N-(3-(pyrrolidin-1-yl)propyl)nicotinamide

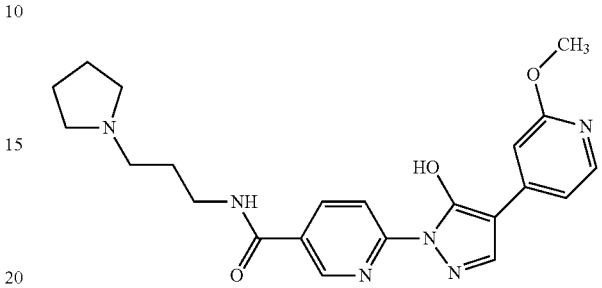

The title compound was prepared in a manner similar to Example 1 using 3-(pyrrolidin-1-yl)propan-1-amine. $^1$H NMR (400 MHz, DMSO-d$_6$) δ ppm 1.79-2.07 (m, 6H) 2.93-3.07 (m, 2H) 3.21 (dt, J=10.42, 5.53 Hz, 2H) 3.32-3.43 (m, 2H) 3.57 (dd, J=10.48, 5.18 Hz, 2H) 3.93 (s, 3H) 7.42-7.71 (m, 2H) 8.10 (d, J=5.81 Hz, 1H) 8.33-8.57 (m, 2H) 8.72 (s, 1H) 8.80-8.99 (m, 2H) 9.65 (br. s., 1H). MS m/z [M+H]$^+$ 423.2.

Example 40 6-(5-hydroxy-4-(2-methoxypyridin-4-yl)-1H-pyrazol-1-yl)-N-methylnicotinamide

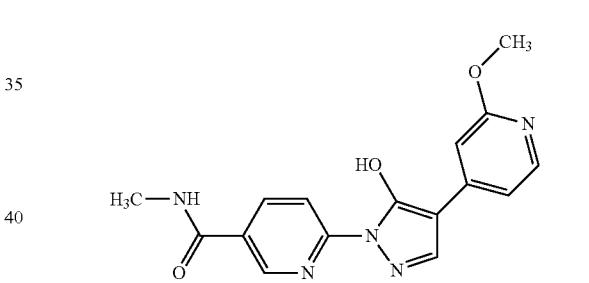

The title compound was prepared in a manner similar to Example 1 using methanamine hydrochloride. $^1$H NMR (400 MHz, DMSO-d$_6$) δ ppm 2.83 (d, J=4.55 Hz, 3H) 3.95 (s, 3H) 7.58 (s, 1H) 7.65 (d, J=5.81 Hz, 1H) 8.12 (d, J=5.81 Hz, 1H) 8.38-8.52 (m, 2H) 8.66-8.80 (m, 2H) 8.90 (d, J=1.01 Hz, 1H). MS m/z [M+H]$^+$ 326.1.

Example 41 N-(1-cyclopropylpiperidin-4-yl)-6-(5-hydroxy-4-(2-methoxypyridin-4-yl)-1H-pyrazol-1-yl)nicotinamide

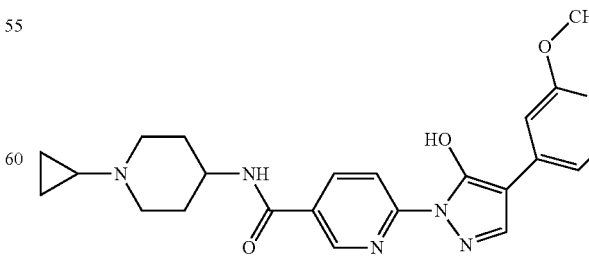

The title compound was prepared in a manner similar to Example 1 using 1-cyclopropylpiperidin-4-amine. $^1$H NMR (400 MHz, DMSO-d$_6$) δ ppm 0.74-1.02 (m, 3H) 2.08 (s, 5H)

2.72-2.99 (m, 1H) 3.58 (br. s., 4H) 3.92 (s, 3H) 4.01-4.27 (m, 1H) 7.45-7.65 (m, 2H) 8.10 (d, J=5.56 Hz, 1H) 8.37-8.81 (m, 4H) 8.90 (s, 2H). MS m/z [M+H]⁺ 435.2.

Example 42 6-(5-hydroxy-4-(2-methoxypyridin-4-yl)-1H-pyrazol-1-yl)-N-(3-(methylamino)propyl)nicotinamide

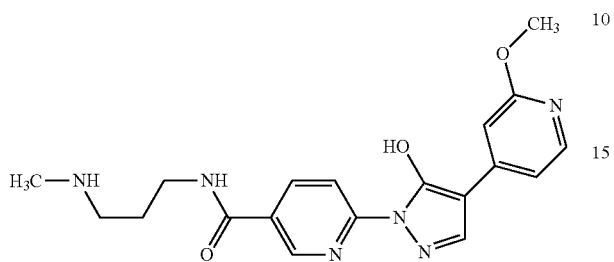

The title compound was prepared in a manner similar to Example 1 using N1-methylpropane-1,3-diamine. ¹H NMR (400 MHz, DMSO-d₆) δ ppm 1.75-1.93 (m, 2H) 2.59 (t, J=5.43 Hz, 3H) 2.90-3.01 (m, 2H) 3.37 (q, J=6.57 Hz, 2H) 3.88 (s, 3H) 7.38-7.60 (m, 2H) 8.07 (d, J=5.56 Hz, 1H) 8.21-8.79 (m, 5H) 8.85 (t, J=5.68 Hz, 1H) 8.89-8.99 (m, 1H). MS m/z [M+H]⁺ 383.2.

Example 43 N-(3-(1H-pyrazol-1-yl)propyl)-6-(5-hydroxy-4-(2-methoxypyridin-4-yl)-1H-pyrazol-1-yl)nicotinamide

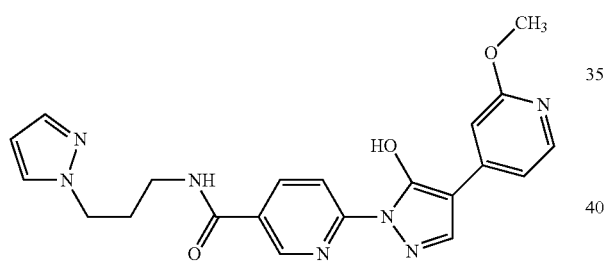

The title compound was prepared in a manner similar to Example 1 using 3-(1H-pyrazol-1-yl)propan-1-amine. ¹H NMR (400 MHz, DMSO-d₆) δ ppm 1.97-2.12 (m, 2H) 3.28 (q, J=6.74 Hz, 2H) 3.93 (s, 3H) 4.20 (t, J=6.95 Hz, 2H) 6.17-6.31 (m, 1H) 7.41-7.48 (m, 1H) 7.50-7.67 (m, 2H) 7.74-7.81 (m, 1H) 8.10 (d, J=5.81 Hz, 1H) 8.32-8.57 (m, 2H) 8.63-8.85 (m, 2H) 8.87-8.95 (m, 1H). MS m/z [M+H]⁺ 420.2.

Example 44 N-(3-(dimethylamino)propyl)-6-(5-hydroxy-4-(2-methoxypyridin-4-yl)-1H-pyrazol-1-yl)nicotinamide

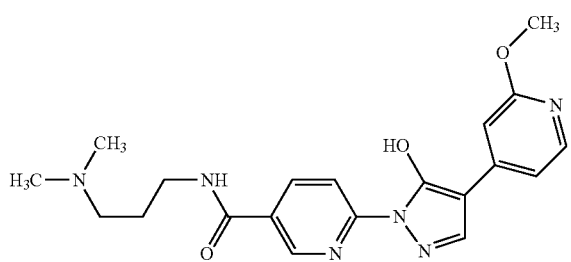 [SMILES: COc1cc(-c2cnn(-c3ccc(C(=O)NCCCN(C)C)cn3)c2O)ccn1]

The title compound was prepared in a manner similar to Example 1 using N1,N1-dimethylpropane-1,3-diamine. ¹H NMR (400 MHz, DMSO-d₆) δ ppm 1.77-1.98 (m, 2H) 2.80 (d, J=4.29 Hz, 6H) 3.13 (dt, J=10.23, 4.99 Hz, 2H) 3.37 (q, J=6.32 Hz, 2H) 3.90 (s, 3H) 7.40-7.66 (m, 2H) 8.08 (d, J=5.81 Hz, 1H) 8.33-8.57 (m, 2H) 8.68 (s, 1H) 8.77-9.01 (m, 2H) 9.54 (br. s., 1H). MS m/z [M+H]⁺ 397.3.

Example 45 6-(5-hydroxy-4-(2-methoxypyridin-4-yl)-1H-pyrazol-1-yl)-N-((1R,2S)-2-(methoxymethyl)cyclopentyl)nicotinamide

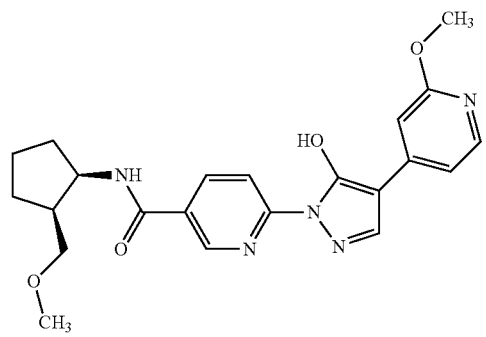 [SMILES: COC[C@H]1CCC[C@H]1NC(=O)c1ccc(-n2ncc(-c3ccnc(OC)c3)c2O)nc1]

The title compound was prepared in a manner similar to Example 1 using (1R,2S)-2-(methoxymethyl)cyclopentanamine. ¹H NMR (400 MHz, DMSO-d₆) δ ppm 1.43-1.59 (m, 2H) 1.61-1.82 (m, 3H) 1.87-1.99 (m, 1H) 2.24-2.35 (m, 1H) 3.19 (s, 3H) 3.20-3.24 (m, 1H) 3.40 (dd, J=9.35, 6.06 Hz, 1H) 3.92 (s, 3H) 4.43 (dt, J=14.78, 7.26 Hz, 2H) 7.52 (s, 1H) 7.59 (d, J=5.56 Hz, 1H) 8.10 (d, J=5.81 Hz, 1H) 8.32 (d, J=8.08 Hz, 1H) 8.38-8.55 (m, 2H) 8.69 (s, 1H) 8.80-8.98 (m, 1H). MS m/z [M+H]⁺ 424.2.

Example 46 6-(5-hydroxy-4-(2-methoxypyridin-4-yl)-1H-pyrazol-1-yl)-N-((4-methylmorpholin-2-yl)methyl)nicotinamide

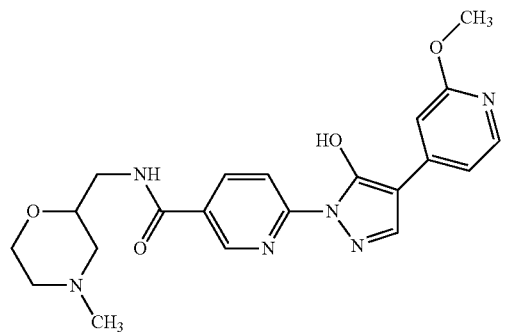 [SMILES: COc1cc(-c2cnn(-c3ccc(C(=O)NCC4CN(C)CCO4)cn3)c2O)ccn1]

The title compound was prepared in a manner similar to Example 1 using (4-methylmorpholin-2-yl)methanamine. ¹H NMR (400 MHz, DMSO-d₆) δ ppm 2.76-2.92 (m, 4H) 2.97-3.10 (m, 1H) 3.34-3.54 (m, 4H) 3.68 (t, J=11.87 Hz, 1H) 3.82-3.90 (m, 4H) 4.07 (dd, J=12.76, 2.65 Hz, 1H) 7.30-7.69 (m, 2H) 8.07 (d, J=5.56 Hz, 1H) 8.31-8.56 (m, 2H) 8.65 (s, 1H) 8.85-9.06 (m, 2H) 10.08 (br. s., 1H). MS m/z [M+H]⁺ 425.2.

Example 47 6-(5-hydroxy-4-(2-methoxypyridin-4-yl)-1H-pyrazol-1-yl)-N-((1-(methoxymethyl)cyclopentyl)methyl)nicotinamide

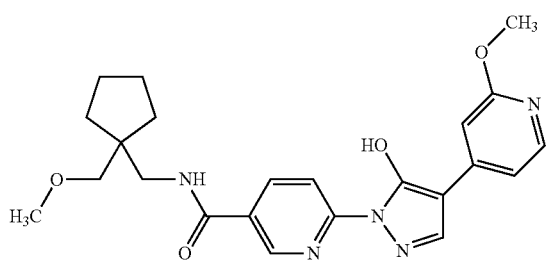 [SMILES: COCC1(CNC(=O)c2ccc(-n3ncc(-c4ccnc(OC)c4)c3O)nc2)CCCC1]

The title compound was prepared in a manner similar to Example 1 using (1-(methoxymethyl)cyclopentyl)methanamine. $^1$H NMR (400 MHz, DMSO-d$_6$) δ ppm 1.30-1.67 (m, 8H) 3.19 (s, 2H) 3.24-3.37 (m, 5H) 3.92 (s, 3H) 7.41-7.66 (m, 2H) 8.09 (d, J=5.81 Hz, 1H) 8.35-8.56 (m, 3H) 8.69 (s, 1H) 8.82-8.94 (m, 1H). MS m/z [M+H]$^+$ 438.2.

Example 48 6-(5-hydroxy-4-(2-methoxypyridin-4-yl)-1H-pyrazol-1-yl)-N-((tetrahydro-2H-pyran-2-yl)methyl)nicotinamide

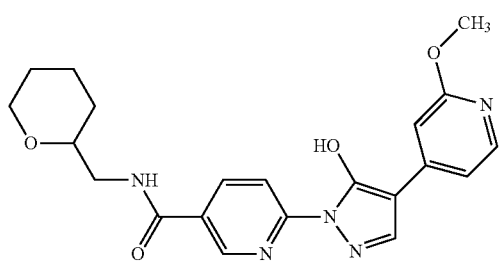 [SMILES: COc1cc(-c2cnn(-c3ccc(C(=O)NCC4CCCCO4)cn3)c2O)ccn1]

The title compound was prepared in a manner similar to Example 1 using (tetrahydro-2H-pyran-2-yl)methanamine. $^1$H NMR (400 MHz, DMSO-d$_6$) δ ppm 1.11-1.28 (m, 1H) 1.37-1.54 (m, 3H) 1.64 (d, J=12.88 Hz, 1H) 1.72-1.86 (m, 1H) 3.20-3.51 (m, 4H) 3.81-4.02 (m, 4H) 7.57 (s, 1H) 7.64 (dd, J=5.94, 0.88 Hz, 1H) 8.11 (d, J=5.81 Hz, 1H) 8.47 (s, 2H) 8.73 (s, 1H) 8.82 (t, J=5.81 Hz, 1H) 8.92 (t, J=1.52 Hz, 1H). MS m/z [M+H]$^+$ 410.2.

Example 49 6-(5-hydroxy-4-(2-methoxypyridin-4-yl)-1H-pyrazol-1-yl)-N-(3-methoxy-2-methylpropyl)nicotinamide

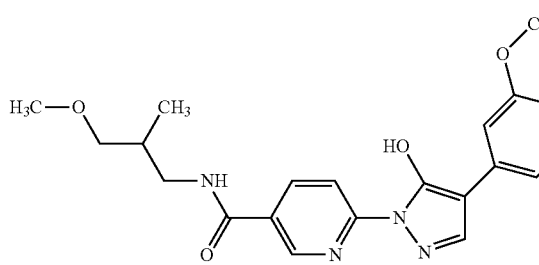

The title compound was prepared in a manner similar to Example 1 using 3-methoxy-2-methylpropan-1-amine. $^1$H NMR (400 MHz, DMSO-d$_6$) δ ppm 0.91 (d, J=6.82 Hz, 3H) 1.94-2.08 (m, 1H) 3.08-3.36 (m, 7H) 3.92 (s, 3H) 7.53 (s, 1H) 7.60 (d, J=5.81 Hz, 1H) 8.09 (d, J=5.81 Hz, 1H) 8.36-8.52 (m, 2H) 8.61-8.74 (m, 2H) 8.86-8.93 (m, 1H). MS m/z [M+H]$^+$ 398.2.

Example 50 6-(5-hydroxy-4-(2-methoxypyridin-4-yl)-1H-pyrazol-1-yl)-N-(3-methoxybutyl)nicotinamide

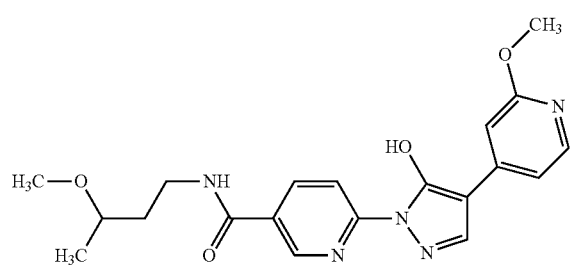 [SMILES: COc1cc(-c2cnn(-c3ccc(C(=O)NCCC(C)OC)cn3)c2O)ccn1]

The title compound was prepared in a manner similar to Example 1 using 3-methoxybutan-1-amine. $^1$H NMR (400 MHz, DMSO-d$_6$) δ ppm 1.11 (d, J=6.06 Hz, 3H) 1.55-1.80 (m, 2H) 3.24 (s, 3H) 3.30-3.43 (m, 3H) 3.92 (s, 3H) 7.42-7.65 (m, 2H) 8.09 (d, J=5.81 Hz, 1H) 8.35-8.53 (m, 2H) 8.58-8.76 (m, 2H) 8.85-8.94 (m, 1H). MS m/z [M+H]$^+$ 398.2.

Example 51 N-(1-(dimethylamino)-2-methylpropan-2-yl)-6-(5-hydroxy-4-(2-methoxypyridin-4-yl)-1H-pyrazol-1-yl)nicotinamide

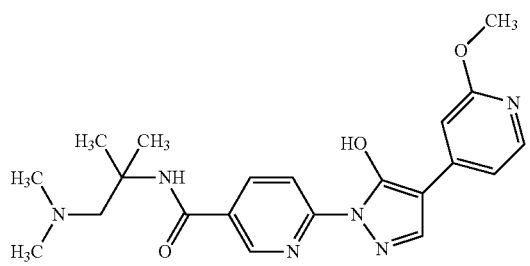 [SMILES: COc1cc(-c2cnn(-c3ccc(C(=O)NC(C)(C)CN(C)C)cn3)c2O)ccn1]

The title compound was prepared in a manner similar to Example 1 using N1,N1,2-trimethylpropane-1,2-diamine. $^1$H NMR (400 MHz, DMSO-d$_6$) δ ppm 1.47 (s, 6H) 2.86 (s, 6H) 3.65 (br. s., 2H) 3.89 (s, 3H) 7.40-7.63 (m, 2H) 8.07 (d, J=5.56 Hz, 1H) 8.32-8.52 (m, 3H) 8.66 (s, 1H) 8.84-8.95 (m, 1H) 9.24 (br. s., 1H). MS m/z [M+H]$^+$ 411.2.

Example 52 6-(5-hydroxy-4-(2-methoxypyridin-4-yl)-1H-pyrazol-1-yl)-N-((1s,4s)-4-methylcyclohexyl)nicotinamide

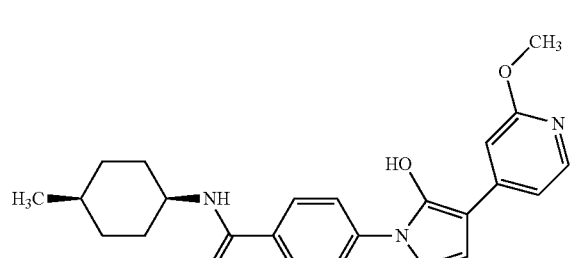

The title compound was prepared in a manner similar to Example 1 using (1s,4s)-4-methylcyclohexanamine. $^1$H NMR (400 MHz, DMSO-d$_6$) δ ppm 0.89 (d, J=6.57 Hz, 3H) 0.94-1.10 (m, 2H) 1.36 (qd, J=12.51, 3.16 Hz, 3H) 1.71 (d, J=11.87 Hz, 2H) 1.78-1.95 (m, 2H) 3.74 (dtd, J=11.68, 7.74, 7.74, 3.92 Hz, 1H) 3.92 (s, 3H) 7.45-7.65 (m, 2H) 8.09 (d, J=5.81 Hz, 1H) 8.35-8.54 (m, 3H) 8.68 (s, 1H) 8.88 (t, J=1.52 Hz, 1H). MS m/z [M+H]$^+$ 408.2.

Example 53 6-(4-(4-cyanophenyl)-5-hydroxy-1H-pyrazol-1-yl)-N-(2-cyclopropylethyl)nicotinamide

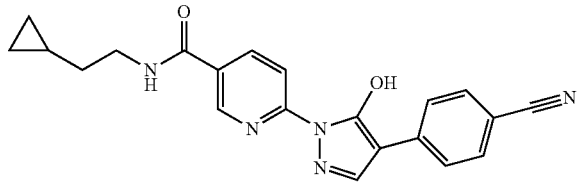 [SMILES: N#Cc1ccc(-c2cnn(-c3ccc(C(=O)NCCC4CC4)cn3)c2O)cc1]

Combined HOBT (66.2 mg, 0.490 mmol) and EDCI (94 mg, 0.490 mmol), a solution 6-(4-(4-cyanophenyl)-5-hydroxy-1H-pyrazol-1-yl)nicotinic acid (100 mg, 0.327 mmol, in DMF (1 mL)) and Hunig's base (169 mg, 1.306 mmol) in DMF (1 mL). Then 2-cyclopropylethanamine (41.7 mg, 0.490 mmol) was added and the reaction was stirred at ambient temperature for 14 h. The reaction mixture was diluted with MeOH (2 mL) and water (3 mL) and acidified to pH 4 using 1 N HCl to give a solid which were collected by filtration and recrystallized from MeOH to give the title compound as a solid. $^1$H NMR (400 MHz, DMSO-d$_6$) δ ppm 0.01-0.14 (m, 2H) 0.35-0.49 (m, 2H) 0.68-0.81 (m, 1H) 1.46 (q, J=7.07 Hz, 2H) 3.27-3.43 (m, 2H) 7.79 (d, J=8.59 Hz, 2H) 8.14 (d, J=6.32 Hz, 2H) 8.34-8.79 (m, 4H) 8.85-8.97 (m, 1H) 13.53 (br. s., 1H). MS m/z [M+H]$^+$ 374.2.

Example 54 6-(4-(4-cyanophenyl)-5-hydroxy-1H-pyrazol-1-yl)-N-(2,2-dimethylcyclopropyl)nicotinamide

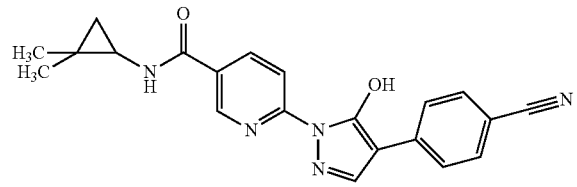 [SMILES: CC1(C)CC1NC(=O)c1ccc(-n2ncc(-c3ccc(C#N)cc3)c2O)nc1]

The title compound was prepared in a manner similar to Example example 53 using 2,2-dimethylcyclopropanamine. MS m/z [M+H]$^+$ 374.1.

Example 55 6-(4-(4-cyanophenyl)-5-hydroxy-1H-pyrazol-1-yl)-N-(2-methoxy-2-methylpropyl)nicotinamide

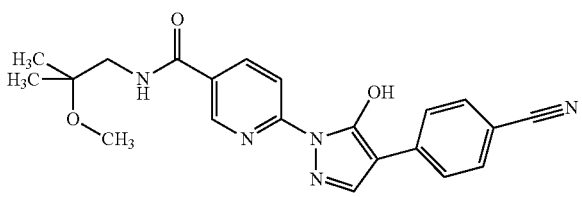 [SMILES: COC(C)(C)CNC(=O)c1ccc(-n2ncc(-c3ccc(C#N)cc3)c2O)nc1]

The title compound was prepared in a manner similar to Example example 53 using 2-methoxy-2-methylpropan-1-amine. MS m/z [M+H]$^+$ 392.1.

Example 56 6-(4-(4-cyanophenyl)-5-hydroxy-1H-pyrazol-1-yl)-N-((1-(methoxymethyl)cyclopropyl)methyl)nicotinamide

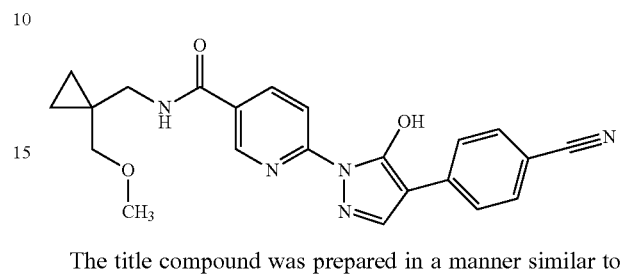

The title compound was prepared in a manner similar to Example example 53 using (1-(methoxymethyl)cyclopropyl)methanamine. $^1$H NMR (400 MHz, DMSO-d$_6$) δ ppm 0.20-0.74 (m, 4H) 3.26 (s, 2H) 3.32-3.38 (m, 2H) 7.79 (d, J=8.59 Hz, 2H) 8.14 (d, J=5.31 Hz, 2H) 8.26-8.85 (m, 4H) 8.86-8.98 (m, 1H) 13.53 (br. s., 1H). MS m/z [M+H]$^+$ 404.1.

Example 57 6-(4-(4-cyanophenyl)-5-hydroxy-1H-pyrazol-1-yl)-N-((1-methylpiperidin-4-yl)methyl)nicotinamide

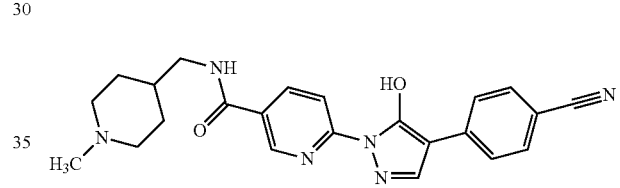

The title compound was prepared in a manner similar to Example example 53 using (1-methylpiperidin-4-yl)methanamine. $^1$H NMR (400 MHz, DMSO-d$_6$) δ ppm 1.24-1.48 (m, 2H) 1.75-1.95 (m, 3H) 2.70-2.98 (m, 5H) 3.23 (t, J=6.19 Hz, 2H) 3.44 (d, J=11.62 Hz, 2H) 7.80 (d, J=8.34 Hz, 2H) 8.14 (br. s., 2H) 8.32-8.77 (m, 3H) 8.81 (t, J=5.43 Hz, 1H) 8.88-8.97 (m, 1H) 9.20 (br. s., 1H) 13.53 (br. s., 1H). MS m/z [M+H]$^+$ 417.2.

Example 58 (R)—N-(sec-butyl)-6-(4-(4-cyano-2-methylphenyl)-5-hydroxy-1H-pyrazol-1-yl)nicotinamide

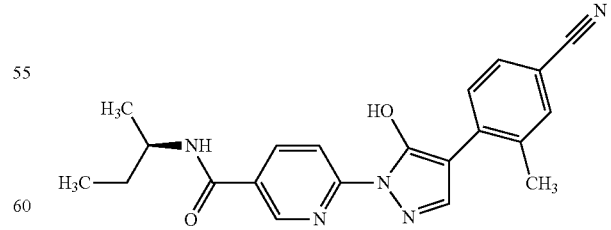

Combined (R)-butan-2-amine (22.8 mg, 0.312 mmol) and a solution consisting of 6-(4-(4-cyano-2-methylphenyl)-5-hydroxy-1H-pyrazol-1-yl)nicotinic acid (50 mg, 0.156 mmol), HOBT hydrate (35.9 mg, 0.234 mmol), EDCI (44.9 mg, 0.234 mmol), and Hunig's base (0.103 mL, 0.624 mmol) in DMA (1 mL) and stirred at 50° C. for 4 h. The reaction mixture was then purified via preparative HPLC to give the title compound as a yellow solid. $^1$H NMR (400 MHz, DMSO-d6) δ ppm 0.90 (t, J=7.45 Hz, 3H) 1.17 (d, J=6.57 Hz, 3H) 1.44-1.63 (m, 2H) 2.44 (s, 3H) 3.95 (dt, J=14.02, 7.14 Hz, 1H) 7.57-7.90 (m, 3H) 7.92-8.73 (m, 4H) 8.82-8.97 (m, 1H) 13.20 (br. s., 1H). MS m/z [M+H]$^+$ 376.

Example 59 6-(4-(4-cyano-2-methylphenyl)-5-hydroxy-1H-pyrazol-1-yl)-N-(tetrahydro-2H-pyran-4-yl)nicotinamide

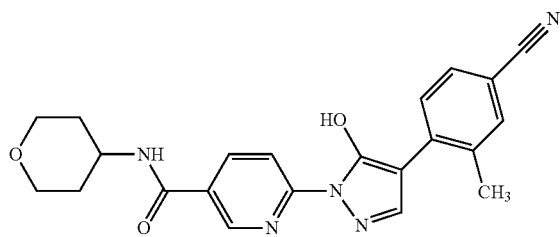 [SMILES: Cc1cc(C#N)ccc1-c1cnn(-c2ccc(C(=O)NC3CCOCC3)cn2)c1O]

The title compound was prepared in a manner similar to Example 58 using tetrahydro-2H-pyran-4-amine. $^1$H NMR (400 MHz, DMSO-d$_6$) δ ppm 1.60 (qd, J=11.96, 4.29 Hz, 2H) 1.80 (dd, J=12.51, 2.40 Hz, 2H) 2.38-2.48 (m, 3H) 3.41 (td, J=11.62, 1.77 Hz, 2H) 3.90 (dt, J=9.85, 2.02 Hz, 2H) 3.98-4.10 (m, 1H) 7.56-7.88 (m, 3H) 8.18 (br. s., 1H) 8.35-8.71 (m, 3H) 8.82-9.02 (m, 1H) 13.18 (br. s., 1H). MS m/z [M+H]$^+$ 404.2.

Example 60 6-(4-(4-cyano-2-methylphenyl)-5-hydroxy-1H-pyrazol-1-yl)-N-propylnicotinamide

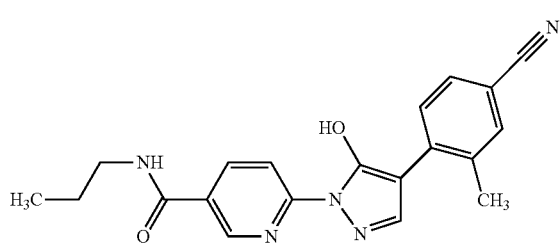 [SMILES: CCCNC(=O)c1ccc(-n2ncc(-c3ccc(C#N)cc3C)c2O)nc1]

The title compound was prepared in a manner similar to Example 58 using propan-1-amine. $^1$H NMR (400 MHz, DMSO-d$_6$) δ ppm 0.92 (t, J=7.33 Hz, 3H) 1.57 (sxt, J=7.33 Hz, 2H) 2.44 (s, 3H) 3.19-3.33 (m, 2H) 7.55-7.89 (m, 3H) 7.93-8.80 (m, 4H) 8.81-9.09 (m, 1H) 13.20 (br. s., 1H) MS m/z [M+H]$^+$ 362.2.

Example 61 6-(4-(4-cyano-2-methylphenyl)-5-hydroxy-1H-pyrazol-1-yl)-N-(1-methylcyclopropyl)nicotinamide

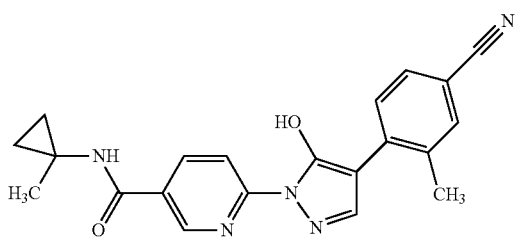 [SMILES: Cc1cc(C#N)ccc1-c1cnn(-c2ccc(C(=O)NC3(C)CC3)cn2)c1O]

The title compound was prepared in a manner similar to Example 58 using 1-methylcyclopropanamine. $^1$H NMR (400 MHz, DMSO-d$_6$) δ ppm 0.53-0.62 (m, 2H) 0.66-0.75 (m, 2H) 1.33 (s, 3H) 2.36 (s, 3H) 7.53-7.79 (m, 3H) 8.03-8.20 (m, 1H) 8.32 (d, J=7.33 Hz, 2H) 8.69-9.00 (m, 2H) 13.13 (br. s., 1H). MS m/z [M+H]$^+$ 374.2.

Example 62 (S)-6-(4-(4-cyano-2-methylphenyl)-5-hydroxy-1H-pyrazol-1-yl)-N-(1-methoxy-3-methylbutan-2-yl)nicotinamide

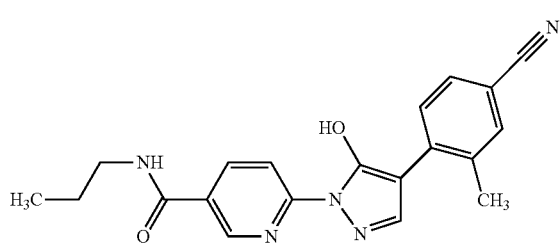 [SMILES: CCCNC(=O)c1ccc(-n2ncc(-c3ccc(C#N)cc3C)c2O)nc1]

The title compound was prepared in a manner similar to Example 58 using (S)-1-methoxy-3-methylbutan-2-amine. $^1$H NMR (400 MHz, DMSO-d$_6$) δ ppm 0.85-1.01 (m, 6H) 1.86-1.97 (m, 1H) 2.38-2.48 (m, 3H) 3.21-3.31 (m, 3H) 3.40-3.52 (m, 2H) 3.93-4.07 (m, 1H) 7.60-7.87 (m, 3H) 7.99-8.72 (m, 4H) 8.83-9.03 (m, 1H) 13.19 (br. s., 1H). MS m/z [M+H]$^+$ 420.2.

Example 63 (R)-6-(4-(4-cyano-2-methylphenyl)-5-hydroxy-1H-pyrazol-1-yl)-N-(1-(tetrahydro-2H-pyran-4-yl)ethyl)nicotinamide The title compound was prepared in a manner similar to Example 58 using (R)-1-(tetrahydro-2H-pyran-4-yl)ethanamine. $^1$H NMR (400 MHz, DMSO-d$_6$) δ ppm 1.08-1.14 (m, 1H) 1.14-1.23 (m, 2H) 1.40-1.46 (m, 2H) 1.56 (d, J=12.88 Hz, 2H) 2.31-2.40 (m, 3H) 3.14-3.33 (m, 4H) 3.77 (dd, J=11.12, 3.28 Hz, 2H) 7.55-7.79 (m, 3H) 7.99-8.72 (m, 4H) 8.80-8.90 (m, 1H) 13.14 (br. s., 1H). MS m/z [M+H]$^+$ 432.2.

Example 64 6-(4-(4-cyano-2-methylphenyl)-5-hydroxy-1H-pyrazol-1-yl)-N-(2-(tetrahydro-2H-pyran-4-yl)ethyl)nicotinamide

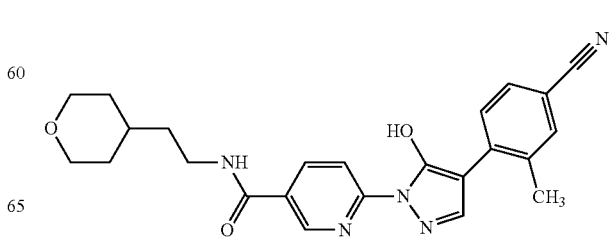

The title compound was prepared in a manner similar to Example 58 using 2-(tetrahydro-2H-pyran-4-yl)ethanamine. ¹H NMR (400 MHz, DMSO-d6) δ ppm 1.08-1.14 (m, 1H) 1.14-1.23 (m, 2H) 1.40-1.46 (m, 2H) 1.56 (d, J=12.88 Hz, 2H) 2.31-2.40 (m, 3H) 3.14-3.33 (m, 4H) 3.77 (dd, J=11.12, 3.28 Hz, 2H) 7.55-7.79 (m, 3H) 7.99-8.72 (m, 4H) 8.80-8.90 (m, 1H) 13.14 (br. s., 1H). MS m/z [M+H]⁺ 432.2.

Example 65 6-(4-(4-cyano-2-methylphenyl)-5-hydroxy-1H-pyrazol-1-yl)-N-(1-methoxy-2-methylpropan-2-yl)nicotinamide

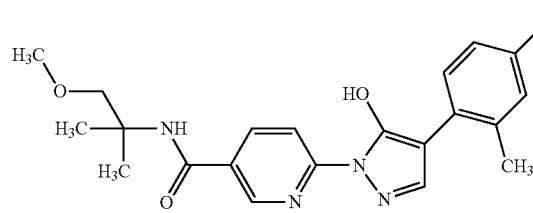

The title compound was prepared in a manner similar to Example 58 using 1-methoxy-2-methylpropan-2-amine. ¹H NMR (400 MHz, DMSO-d6) δ ppm 1.36 (s, 6H) 2.44 (s, 3H) 3.29 (s, 3H) 3.55 (s, 2H) 7.62-7.81 (m, 3H) 7.89-8.52 (m, 4H) 8.83-8.89 (m, 1H) 13.22 (br. s., 1H). MS m/z [M+H]⁺ 406.2.

Example 66 6-(4-(4-cyano-2-methylphenyl)-5-hydroxy-1H-pyrazol-1-yl)-N-(2-(tetrahydrofuran-3-yl)ethyl)nicotinamide

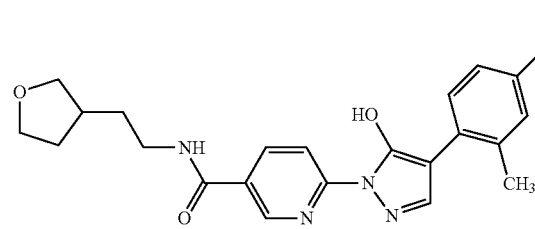

The title compound was prepared in a manner similar to Example 58 using 2-(tetrahydrofuran-3-yl)ethanamine. ¹H NMR (400 MHz, DMSO-d₆) δ ppm 1.41 (dq, J=11.94, 7.81 Hz, 1H) 1.49-1.59 (m, 2H) 1.97 (dtd, J=12.06, 7.48, 7.48, 4.80 Hz, 1H) 2.13 (dt, J=14.72, 7.42 Hz, 1H) 2.36 (s, 3H) 3.15-3.30 (m, 3H) 3.56 (q, J=7.58 Hz, 1H) 3.66 (td, J=8.21, 4.80 Hz, 1H) 3.76 (dd, J=7.83, 7.33 Hz, 1H) 7.55-7.80 (m, 3H) 7.92-8.58 (m, 3H) 8.67 (br. s., 1H) 8.80-8.89 (m, 1H) 13.14 (br. s., 1H). MS m/z [M+H]⁺ 418.2.

Example 67 6-(4-(4-cyano-2-methylphenyl)-5-hydroxy-1H-pyrazol-1-yl)-N-(4-methoxy-2-methylbutan-2-yl)nicotinamide

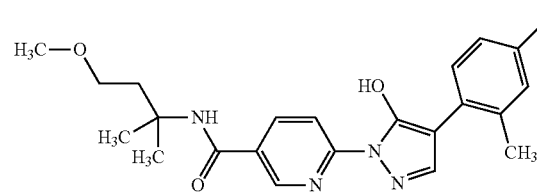

The title compound was prepared in a manner similar to Example 58 using 4-methoxy-2-methylbutan-2-amine in place. MS m/z [M+H]⁺ 420.2.

Example 68 6-(4-(4-cyano-2-methylphenyl)-5-hydroxy-1H-pyrazol-1-yl)-N-((1r,4r)-4-methoxycyclohexyl)nicotinamide

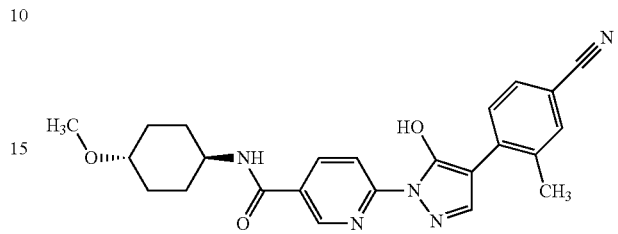

The title compound was prepared in a manner similar to Example 58 using (1r,4r)-4-methoxycyclohexanamine. ¹H NMR (400 MHz, DMSO-d₆) δ ppm 1.08-1.22 (m, 2H) 1.25-1.41 (m, 2H) 1.76-1.89 (m, 2H) 1.97 (d, J=10.36 Hz, 2H) 2.36 (s, 3H) 2.99-3.12 (m, 1H) 3.13-3.22 (m, 3H) 3.72 (dtd, J=11.27, 7.44, 7.44, 3.92 Hz, 1H) 7.54-7.76 (m, 3H) 7.85-8.61 (m, 4H) 8.83 (d, J=1.26 Hz, 1H) 13.12 (br. s., 1H). MS m/z [M+H]⁺ 432.2

Example 69 6-(4-(4-cyano-2-methylphenyl)-5-hydroxy-1H-pyrazol-1-yl)-N-(4-methoxybutan-2-yl)nicotinamide

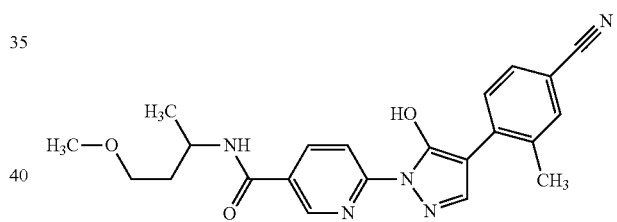

The title compound was prepared in a manner similar to Example 58 using 4-methoxybutan-2-amine. ¹H NMR (400 MHz, DMSO-d₆) δ ppm 1.11 (d, J=6.82 Hz, 3H) 1.58-1.80 (m, 2H) 2.31-2.40 (m, 3H) 3.10-3.20 (m, 3H) 3.31 (t, J=6.44 Hz, 2H) 3.97-4.13 (m, 1H) 7.52-7.78 (m, 3H) 7.88-8.68 (m, 4H) 8.78-8.88 (m, 1H) 13.13 (br. s., 1H). MS m/z [M+H]⁺ 406.2.

Example 70 6-(4-(4-cyano-2-methylphenyl)-5-hydroxy-1H-pyrazol-1-yl)-N-(3-(cyclopropylmethoxy)propyl)nicotinamide

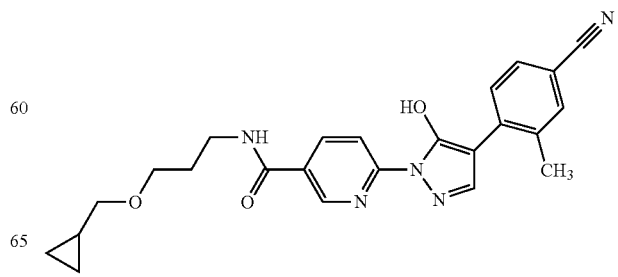

The title compound was prepared in a manner similar to Example 58 using 3-(cyclopropylmethoxy)propan-1-amine. ¹H NMR (400 MHz, DMSO-d₆) δ ppm −0.07-0.05 (m, 2H) 0.24-0.35 (m, 2H) 0.75-0.90 (m, 1H) 1.63 (quin, J=6.63 Hz, 2H) 2.28 (s, 3H) 3.07 (d, J=6.82 Hz, 2H) 3.16-3.25 (m, 2H) 3.30 (t, J=6.32 Hz, 2H) 7.46-7.70 (m, 3H) 7.81-8.64 (m, 4H) 8.72-8.81 (m, 1H) 13.04 (br. s., 1H). MS m/z [M+H]⁺ 432.2.

Example 71 6-(4-(4-cyano-2-methylphenyl)-5-hydroxy-1H-pyrazol-1-yl)-N-(2-hydroxy-1-(tetrahydrofuran-3-yl)ethyl)nicotinamide

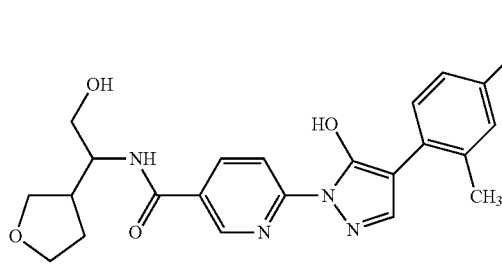

The title compound was prepared in a manner similar to Example 58 using 2-amino-2-(tetrahydrofuran-3-yl)ethanol. ¹H NMR (400 MHz, DMSO-d₆) δ ppm 1.50-1.66 (m, 1H) 1.81-1.97 (m, 1H) 2.34-2.39 (m, 3H) 3.32-3.77 (m, 7H) 3.86-3.96 (m, 1H) 4.71 (br. s., 1H) 7.52-7.82 (m, 3H) 7.93-8.64 (m, 4H) 8.86 (ddd, J=5.81, 2.15, 0.88 Hz, 1H) 13.16 (br. s., 1H). MS m/z [M+H]⁺ 434.1.

Example 72 6-(5-hydroxy-4-(2-methoxypyridin-4-yl)-1H-pyrazol-1-yl)-N-(piperidin-4-yl)nicotinamide

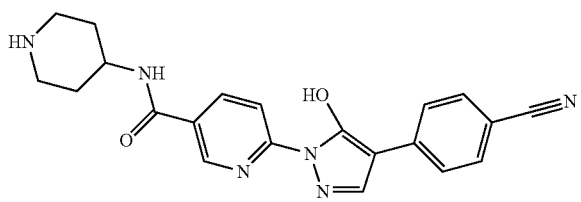 [SMILES: N#Cc1ccc(-c2cnn(-c3ccc(C(=O)NC4CCNCC4)cn3)c2O)cc1]

Combined 6-(4-(4-cyanophenyl)-5-hydroxy-1H-pyrazol-1-yl)nicotinic acid (50 mg, 0.163 mmol), EDC (46.9 mg, 0.245 mmol) and HOBT (37.5 mg, 0.245 mmol) and DMA (1 mL), and treated with Hunig's base (0.114 ml, 0.653 mmol) and stirred at ambient temperature for 5 minutes, then added to 4-amino-1-Boc-piperidine (38.5 mg, 0.327 mmol) and stirred at room temperature overnight. The reaction mixture was then diluted to a total volume of about 1.5 mL with methanol and purified via prep HPLC. The product containing fractions were collected and concentrated in vacuum to give a residue which was treated with TFA (2 mL) in DCM (2 mL). After stirring at ambient temperature overnight the reaction was concentrated in vacuo and dried under vacuum to give the title compound (39.3 mg, 62%) as a yellow solid. ¹H NMR (400 MHz, DMSO-d6) δ ppm 1.65-1.82 (m, 2H) 1.93-2.08 (m, 2H) 2.94-3.16 (m, 2H) 3.35 (d, J=12.63 Hz, 2H) 3.99-4.19 (m, 1H) 7.80 (d, J=8.59 Hz, 2H) 8.15 (d, J=7.33 Hz, 2H) 8.29-8.78 (m, 6H) 8.87-8.99 (m, 1H) 13.59 (br. s., 1H). MS m/z [M+H]⁺ 389.2.

Example 73 (S)-6-(4-(4-cyanophenyl)-5-hydroxy-1H-pyrazol-1-yl)-N-(pyrrolidin-3-yl)nicotinamide

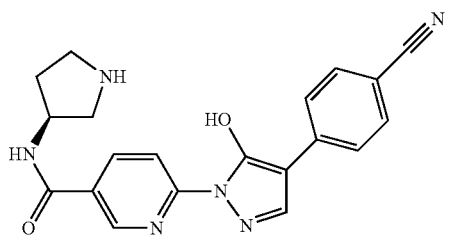 [SMILES: N#Cc1ccc(-c2cnn(-c3ccc(C(=O)N[C@H]4CCNC4)cn3)c2O)cc1]

The title compound was prepared in a manner similar to Example 72 using (S)-tert-butyl 3-aminopyrrolidine-1-carboxylate. ¹H NMR (400 MHz, DMSO-d6) δ ppm 1.93-2.12 (m, 1H) 2.16-2.30 (m, 1H) 3.11-3.53 (m, 4H) 4.53 (dq, J=11.94, 6.04 Hz, 1H) 7.80 (d, J=8.34 Hz, 2H) 8.15 (br. s., 2H) 8.27-9.07 (m, 7H) 13.53 (br. s., 1H). MS m/z [M+H]⁺ 375.2.

Example 74 (R)—N-(1-cyanobutan-2-yl)-6-(4-(4-cyanophenyl)-5-hydroxy-1H-pyrazol-1-yl)nicotinamide

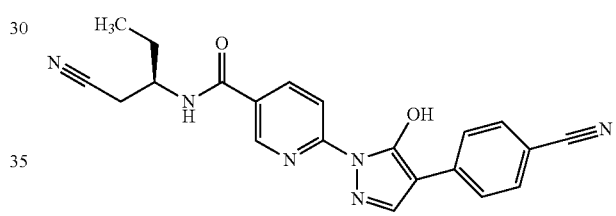

Combined 6-(4-(4-cyanophenyl)-5-hydroxy-1H-pyrazol-1-yl)nicotinic acid (29 mg, 0.095 mmol), EDCI (27.2 mg, 0.142 mmol), HOBT (19.2 mg, 0.142 mmol) in DMF (1 mL) and added N,N-diisopropyl ethylamine (66.0 pt, 0.379 mmol). Then (R)-3-aminopentanenitrile (13.9 mg, 0.142 mmol) was added and the reaction was stirred at room temperature for 16 hours. The reaction mixture was purified by preparative HPLC (SunFire™ C18, 5 μm, ID 30 mm×75 mm) using a gradient of 40-65% ACN (with 0.035% TFA) in water (with 0.05% TFA) to give the title compound (16.2 mg, 44%). ¹H NMR (400 MHz, DMSO-d6) δ ppm 0.93 (t, J=7.33 Hz, 3H) 1.67 (quin, J=7.20 Hz, 2H) 2.70-2.95 (m, 2H) 4.05-4.22 (m, 1H) 7.80 (d, J=8.34 Hz, 2H) 8.15 (br. s., 2H) 8.41-8.86 (m, 4H) 8.94 (s, 1H). MS m/z [M+H]⁺ 387.2.

Example 75 6-(4-(4-cyanophenyl)-5-hydroxy-1H-pyrazol-1-yl)-N-cyclohexylnicotinamide

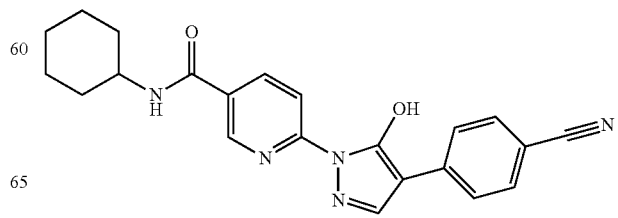

The title compound was prepared in a manner similar to Example 74 using cyclohexanamine. ¹H NMR (400 MHz, DMSO-d₆) δ ppm 1.06-1.23 (m, 1H) 1.33 (t, J=9.60 Hz, 4H) 1.52-1.66 (m, 1H) 1.76 (br. s., 2H) 1.86 (br. s., 2H) 3.66-3.92 (m, 1H) 7.79 (d, J=8.34 Hz, 2H) 8.14 (d, J=5.30 Hz, 2H) 8.45 (d, J=8.34 Hz, 3H) 8.53-8.76 (m, 1H) 8.90 (s, 1H) 13.19-13.98 (m, 1H). MS m/z [M+H]⁺ 388.2.

Example 76 6-(4-(4-cyanophenyl)-5-hydroxy-1H-pyrazol-1-yl)-N-(1-methylazetidin-3-yl)nicotinamide

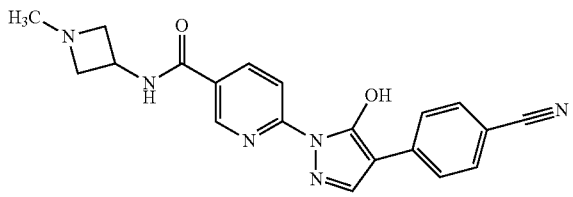 [SMILES: CN1CC(NC(=O)c2ccc(-n3ncc(-c4ccc(C#N)cc4)c3O)nc2)C1]

The title compound was prepared in a manner similar to Example 74 using 1-methylazetidin-3-amine. ¹H NMR (400 MHz, DMSO-d6) δ ppm 2.92 (s, 3H) 3.98-4.27 (m, 4H) 4.36-4.58 (m, 2H) 4.67-4.95 (m, 1H) 7.80 (d, J=8.34 Hz, 2H) 8.03-8.29 (m, 2H) 8.32-8.83 (m, 3H) 8.87-9.02 (m, 1H) 9.17-9.41 (m, 1H). MS m/z [M+H]⁺ 375.2.

Example 77 6-(4-(4-cyanophenyl)-5-hydroxy-1H-pyrazol-1-yl)-N-(2,2,2-trifluoroethyl)nicotinamide

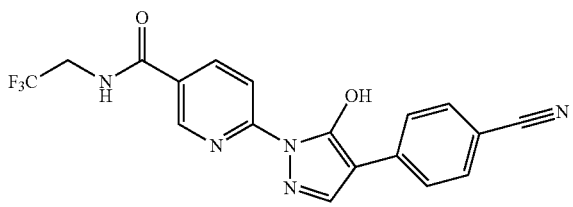 [SMILES: N#Cc1ccc(-c2cnn(-c3ccc(C(=O)NCC(F)(F)F)cn3)c2O)cc1]

The title compound was prepared in a manner similar to Example 74 using 2,2,2-trifluoroethanamine. ¹H NMR (400 MHz, DMSO-d6) δ ppm 4.06-4.25 (m, 2H) 7.79 (d, J=8.59 Hz, 2H) 8.15 (d, J=8.34 Hz, 2H) 8.41-8.59 (m, 2H) 9.35 (t, J=6.32 Hz, 1H). MS m/z [M+H]⁺ 388.0.

Example 78 6-(4-(4-cyanophenyl)-5-hydroxy-1H-pyrazol-1-yl)-N-(2-fluoroethyl)nicotinamide

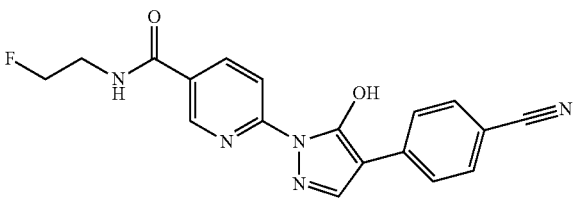 [SMILES: N#Cc1ccc(-c2cnn(-c3ccc(C(=O)NCCF)cn3)c2O)cc1]

The title compound was prepared in a manner similar to Example 74 using 2-fluoroethanamine. ¹H NMR (400 MHz, DMSO-d6) δ ppm 3.58 (q, J=5.05 Hz, 1H) 3.62-3.69 (m, 1H) 4.52 (t, J=5.05 Hz, 1H) 4.64 (t, J=4.93 Hz, 1H) 7.79 (d, J=8.59 Hz, 2H) 8.15 (d, J=8.08 Hz, 2H) 8.39-8.56 (m, 2H) 8.67 (br. s., 1H) 8.89-9.02 (m, 2H). MS m/z [M+H]⁺ 352.1.

Example 79 N-(6-chloro-2,3-dihydro-1H-inden-1-yl)-6-(4-(4-cyanophenyl)-5-hydroxy-1H-pyrazol-1-yl)nicotinamide

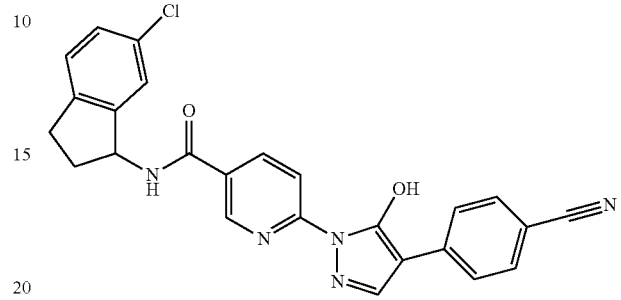

The title compound was prepared in a manner similar to Example 74 using 6-chloro-2,3-dihydro-1H-inden-1-amine. ¹H NMR (400 MHz, DMSO-d₆) δ ppm 1.92-2.13 (m, 1H) 2.80-2.92 (m, 1H) 2.94-3.08 (m, 1H) 5.57 (q, J=7.83 Hz, 1H) 7.18-7.45 (m, 3H) 7.79 (d, J=8.34 Hz, 2H) 8.02-8.27 (m, 2H) 8.35-8.58 (m, 2H) 8.66 (br. s., 1H) 8.87-9.01 (m, 1H) 9.06 (d, J=7.83 Hz, 1H) 13.56 (br. s., 1H). MS m/z [M+H]⁺ 456.1.

Example 80 N-(sec-butyl)-6-(4-(4-cyanophenyl)-5-hydroxy-1H-pyrazol-1-yl)nicotinamide

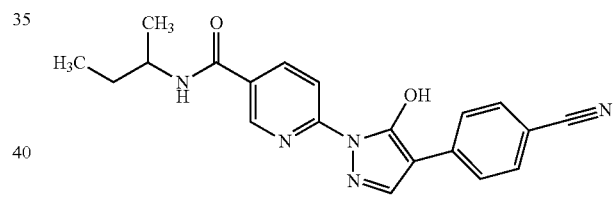

The title compound was prepared in a manner similar to Example 74 using butan-2-amine. ¹H NMR (400 MHz, DMSO-d6) δ 0.89 (t, J=7.45 Hz, 3H) 1.17 (d, J=6.57 Hz, 3H) 1.44-1.63 (m, 2H) 3.95 (dt, J=13.96, 7.04 Hz, 1H) 7.79 (d, J=8.59 Hz, 2H) 8.14 (br. s., 2H) 8.33-8.55 (m, 3H) 8.66 (br. s., 1H) 8.85-8.98 (m, 1H). MS m/z [M+H]⁺ 362.1.

Example 81 6-(4-(4-cyanophenyl)-5-hydroxy-1H-pyrazol-1-yl)-N-(tetrahydro-2H-pyran-4-yl)nicotinamide

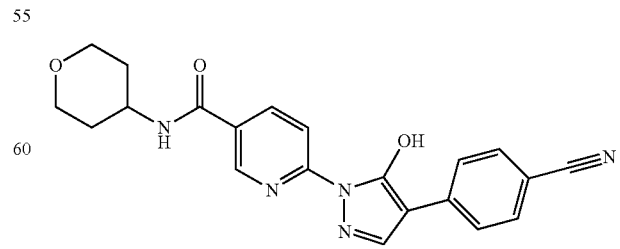

The title compound was prepared in a manner similar to Example 74 using tetrahydro-2H-pyran-4-amine. ¹H NMR (400 MHz, DMSO-d$_6$) δ ppm 1.50-1.68 (m, 2H) 1.80 (dd, J=12.63, 2.27 Hz, 2H) 3.40-3.47 (m, 2H) 3.84-3.96 (m, 2H) 3.97-4.12 (m, 1H) 7.79 (d, J=8.59 Hz, 2H) 8.09-8.19 (m, 2H) 8.33-8.48 (m, 2H) 8.52-8.60 (m, 1H) 8.64 (br. s., 1H) 8.85-8.97 (m, 1H) 13.31-13.80 (m, 1H). MS m/z [M+H]$^+$ 390.1.

Example 82 6-(4-(4-cyanophenyl)-5-hydroxy-1H-pyrazol-1-yl)-N-(1-methyl-2-oxopiperidin-4-yl)nicotinamide

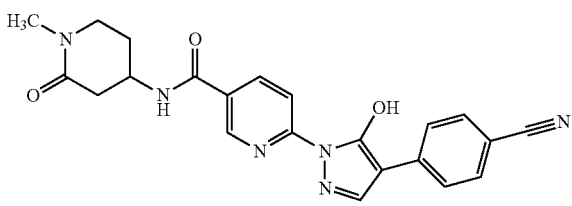 [SMILES: CN1CCC(NC(=O)c2ccc(-n3ncc(-c4ccc(C#N)cc4)c3O)nc2)CC1=O]

The title compound was prepared in a manner similar to Example 74 using 4-amino-1-methylpiperidin-2-one. $^1$H NMR (400 MHz, DMSO-d$_6$) δ ppm 1.76-1.94 (m, 1H) 1.96-2.12 (m, 1H) 2.33 (dd, J=17.05, 8.97 Hz, 1H) 2.53-2.63 (m, 1H) 2.83 (s, 3H) 3.31-3.35 (m, 2H) 4.25 (td, J=6.38, 3.41 Hz, 1H) 7.79 (d, J=8.59 Hz, 2H) 8.15 (br. s., 2H) 8.43 (d, J=7.07 Hz, 2H) 8.70 (d, J=6.57 Hz, 2H) 8.91 (s, 1H) 13.19-13.81 (m, 1H). MS m/z [M+H]$^+$ 456.1.

Example 83 6-(4-(4-cyanophenyl)-5-hydroxy-1H-pyrazol-1-yl)-N-(6-methoxy-2,3-dihydro-1H-inden-1-yl)nicotinamide

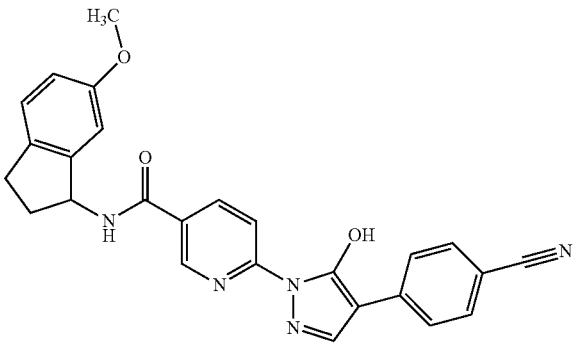 [SMILES: COc1ccc2c(c1)C(NC(=O)c1ccc(-n3ncc(-c4ccc(C#N)cc4)c3O)nc1)CC2]

The title compound was prepared in a manner similar to Example 74 using 6-methoxy-2,3-dihydro-1H-inden-1-amine. $^1$H NMR (400 MHz, DMSO-d$_6$) δ ppm 1.99 (dd, J=12.63, 8.34 Hz, 1H) 2.44-2.55 (m, 2H) 2.73-2.85 (m, 1H) 2.92 (dd, J=8.72, 2.91 Hz, 1H) 3.72 (s, 3H) 5.55 (d, J=7.83 Hz, 1H) 6.69-6.92 (m, 2H) 7.19 (d, J=8.08 Hz, 1H) 7.79 (d, J=8.59 Hz, 2H) 8.15 (d, J=7.83 Hz, 2H) 8.34-8.81 (m, 3H) 8.87-9.12 (m, 2H) 13.24-13.87 (m, 1H). MS m/z [M+H]$^+$ 452.1.

Example 84 6-(4-(4-cyanophenyl)-5-hydroxy-1H-pyrazol-1-yl)-N-(4,4-difluorocyclohexyl)nicotinamide

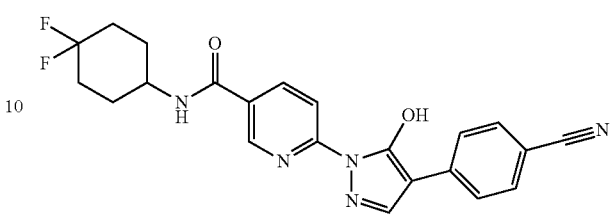

The title compound was prepared in a manner similar to Example 74 using 4,4-difluorocyclohexanamine. $^1$H NMR (400 MHz, DMSO-d$_6$) δ ppm 1.60-1.71 (m, 2H) 1.85-1.98 (m, 3H) 2.05-2.21 (m, 3H) 3.97-4.10 (m, 1H) 7.79 (d, J=8.59 Hz, 2H) 8.14 (br. s., 2H) 8.33-8.55 (m, 3H) 8.66 (br. s., 1H) 8.85-8.98 (m, 1H). MS m/z [M+H]$^+$ 424.1.

Example 85 6-(4-(4-cyanophenyl)-5-hydroxy-1H-pyrazol-1-yl)-N-(1-(2-hydroxyethyl)piperidin-4-yl)nicotinamide

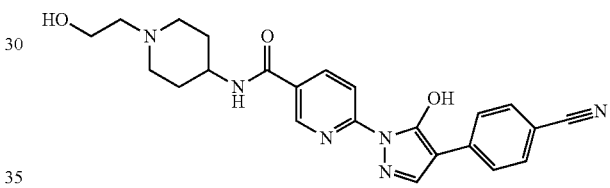

The title compound was prepared in a manner similar to Example 74 using 2-(4-aminopiperidin-1-yl)ethanol. $^1$H NMR (400 MHz, DMSO-d$_6$) δ ppm 1.79-1.96 (m, 2H) 1.98-2.18 (m, 2H) 3.07-3.25 (m, 4H) 3.37 (d, J=19.45 Hz, 1H) 3.59 (d, J=11.87 Hz, 2H) 3.76 (t, J=4.93 Hz, 2H) 3.98-4.25 (m, 1H) 7.79 (d, J=8.34 Hz, 2H) 8.14 (d, J=6.57 Hz, 2H) 8.45 (d, J=6.57 Hz, 1H) 8.52-8.71 (m, 1H) 8.75 (d, J=7.07 Hz, 1H) 8.93 (s, 1H). MS m/z [M+H]$^+$ 433.1.

Example 86 (R)—N-(sec-butyl)-6-(4-(4-cyanophenyl)-5-hydroxy-1H-pyrazol-1-yl)nicotinamide

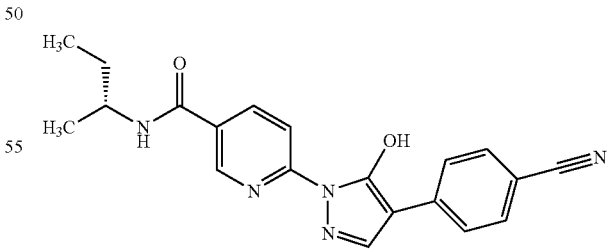

The title compound was prepared in a manner similar to Example 74 using (R)-butan-2-amine. $^1$H NMR (400 MHz, DMSO-d$_6$) δ ppm 0.89 (t, J=7.45 Hz, 3H) 1.16 (d, J=6.82 Hz, 3H) 1.42-1.65 (m, 2H) 3.95 (dt, J=13.89, 7.20 Hz, 1H) 7.79 (d, J=8.59 Hz, 2H) 8.14 (d, J=5.81 Hz, 2H) 8.41 (dd, J=13.89, 7.58 Hz, 3H) 8.65 (br. s., 1H) 8.91 (s, 1H). MS m/z [M+H]$^+$ 362.1.

Example 86 (S)-6-(4-(4-cyanophenyl)-5-hydroxy-1H-pyrazol-1-yl)-N-(tetrahydrofuran-3-yl)nicotinamide

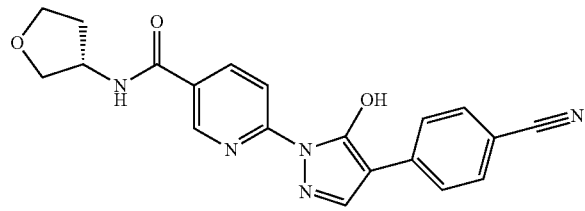 [SMILES: N#Cc1ccc(-c2cnn(-c3ccc(C(=O)N[C@H]4CCOC4)cn3)c2O)cc1]

The title compound was prepared in a manner similar to Example 74 using (S)-tetrahydrofuran-3-amine. $^1$H NMR (400 MHz, DMSO-d$_6$) δ ppm 1.83-2.01 (m, 1H) 2.18 (s, 1H) 3.63 (dd, J=8.97, 4.17 Hz, 1H) 3.66-3.79 (m, 1H) 3.80-3.95 (m, 2H) 4.41-4.59 (m, 1H) 7.79 (d, J=8.59 Hz, 2H) 8.14 (br. s., 2H) 8.45 (br. s., 2H) 8.55-8.73 (m, 1H) 8.78 (d, J=6.32 Hz, 1H) 8.92 (s, 1H). MS m/z [M+H]$^+$ 376.1.

Example 87 (S)—N-(sec-butyl)-6-(4-(4-cyanophenyl)-5-hydroxy-1H-pyrazol-1-yl)nicotinamide

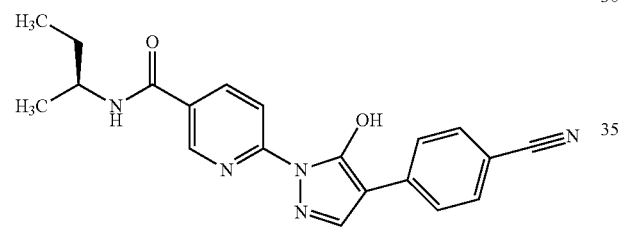

The title compound was prepared in a manner similar to Example 74 using (S)-butan-2-amine. $^1$H NMR (400 MHz, DMSO-d$_6$) δ 0.90 (t, J=7.45 Hz, 3H) 1.17 (d, J=6.57 Hz, 3H) 1.40-1.68 (m, 2H) 3.95 (dt, J=13.89, 7.20 Hz, 1H) 7.79 (d, J=8.34 Hz, 2H) 7.99-8.25 (m, 2H) 8.29-8.55 (m, 3H) 8.64 (br. s., 1H) 8.91 (s, 1H) 13.54 (br. s., 1H). MS m/z [M+H]$^+$ 362.1.

Example 88 (R)-6-(4-(4-cyanophenyl)-5-hydroxy-1H-pyrazol-1-yl)-N-(1-cyclopropylethyl)nicotinamide

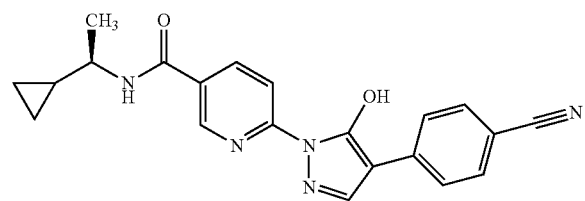 [SMILES: C[C@@H](NC(=O)c1ccc(-n2ncc(-c3ccc(C#N)cc3)c2O)nc1)C1CC1]

The title compound was prepared in a manner similar to Example 74 using (R)-1-cyclopropylethanamine. $^1$H NMR (400 MHz, DMSO-d$_6$) δ ppm 0.17-0.27 (m, 1H) 0.28-0.36 (m, 1H) 0.36-0.44 (m, 1H) 0.44-0.53 (m, 1H) 0.93-1.08 (m, 1H) 1.25 (d, J=6.82 Hz, 3H) 3.42-3.61 (m, 1H) 7.79 (d, J=8.59 Hz, 2H) 8.13 (br. s., 2H) 8.44 (d, J=6.82 Hz, 2H) 8.54-8.78 (m, 2H) 8.91 (s, 1H) 13.54 (br. s., 1H). MS m/z [M+H]$^+$ 374.1.

Example 89 6-(4-(4-cyanophenyl)-5-hydroxy-1H-pyrazol-1-yl)-N-(2-isopropoxyethyl)nicotinamide

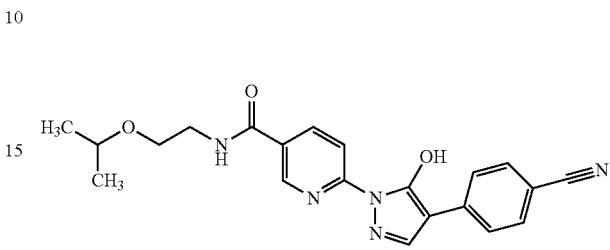

The title compound was prepared in a manner similar to Example 74 using 6-(4-(4-cyanophenyl)-5-hydroxy-1H-pyrazol-1-yl)nicotinic acid and 2-isopropoxyethanamine. $^1$H NMR (400 MHz, DMSO-d$_6$) δ 1.10 (d, J=6.06 Hz, 6H) 3.42 (q, J=5.81 Hz, 2H) 3.48-3.55 (m, 2H) 3.55-3.64 (m, 1H) 7.79 (d, J=8.34 Hz, 2H) 8.15 (br. s., 2H) 8.42 (d, J=7.58 Hz, 1H) 8.68 (br. s., 1H) 8.77 (t, J=5.05 Hz, 1H) 8.92 (s, 1H) 13.54 (br. s., 1H). MS m/z [M+H]$^+$ 392.1.

Example 90 6-(4-(4-cyanophenyl)-5-hydroxy-1H-pyrazol-1-yl)-N-(3-(2-methylpiperidin-1-yl)propyl)nicotinamide

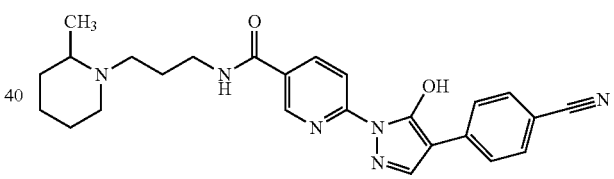

The title compound was prepared in a manner similar to Example 74 using 1-(3-aminopropyl)2-methylpiperidine as a TFA salt. $^1$H NMR (400 MHz, DMSO-d$_6$) δ ppm 1.18-1.33 (m, 3H) 1.39-1.55 (m, 2H) 1.56-1.73 (m, 2H) 1.74-2.03 (m, 4H) 2.90-3.34 (m, 5H) 3.42-3.86 (m, 2H) 7.80 (d, J=7.83 Hz, 2H) 8.06-8.29 (m, 2H) 8.34-8.62 (m, 2H) 8.68 (br. s., 1H) 8.89 (br. s., 1H) 8.93 (s, 1H) 8.98-9.33 (m, 1H) 13.54 (br. s., 1H). MS m/z [M+H]$^+$ 445.3.

Example 91 6-(4-(4-cyanophenyl)-5-hydroxy-1H-pyrazol-1-yl)-N-(3-morpholinopropyl)nicotinamide

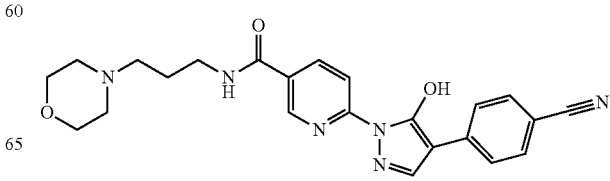

The title compound was prepared in a manner similar to Example 74 using N-(3-aminopropyl)morpholine as a TFA salt. $^1$H NMR (400 MHz, DMSO-d$_6$) δ ppm 1.85-2.02 (m, 2H) 3.10 (br. s., 2H) 3.15-3.23 (m, 2H) 3.34-3.43 (m, 3H) 3.67 (br. s., 3H) 3.96 (br. s., 2H) 7.80 (d, J=8.59 Hz, 2H) 8.15 (d, J=5.31 Hz, 2H) 8.43 (d, J=7.07 Hz, 1H) 8.47-8.61 (m, 1H) 8.68 (br. s., 1H) 8.88 (t, J=5.56 Hz, 1H) 8.91-8.96 (m, 1H) 9.47-10.02 (m, 1H) 13.21-13.71 (m, 1H) MS m/z [M+H]$^+$ 433.2.

Example 92 6-(4-(4-cyanophenyl)-5-hydroxy-1H-pyrazol-1-yl)-N-((1-methylpyrrolidin-3-yl)methyl)nicotinamide

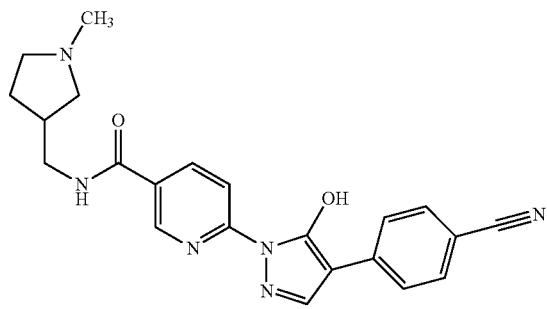 [SMILES: CN1CCC(CNC(=O)c2ccc(-n3ncc(-c4ccc(C#N)cc4)c3O)nc2)C1]

The title compound was prepared in a manner similar to Example 74 using (1-methylpyrrolidin-3-yl)methanamine as a TFA salt. $^1$H NMR (400 MHz, DMSO-d$_6$) δ ppm 1.60-1.96 (m, 1H) 1.98-2.29 (m, 1H) 2.45-2.60 (m, 1H) 2.71-2.92 (m, 4H) 2.96-3.25 (m, 2H) 3.30-3.45 (m, 1H) 3.51-3.74 (m, 1H) 7.80 (d, J=8.59 Hz, 2H) 8.15 (d, J=7.58 Hz, 1H) 8.42 (dd, J=8.59, 2.02 Hz, 1H) 8.51 (br. s., 1H) 8.67 (br. s., 1H) 8.88 (br. s., 1H) 8.90-8.98 (m, 1H) 9.79 (br. s., 1H) 13.51 (br. s., 1H). MS m/z [M+H]$^+$ 403.2.

Example 93 6-(4-(4-cyanophenyl)-5-hydroxy-1H-pyrazol-1-yl)-N-(1-cyclopropylpiperidin-4-yl)nicotinamide

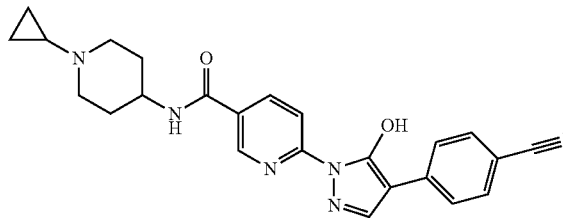

The title compound, as a TFA salt, was prepared in a manner similar to Example 74 using 1-cyclopropylpiperidin-4-amine. $^1$H NMR (400 MHz, DMSO-d$_6$) δ ppm 0.84 (d, J=6.57 Hz, 2H) 0.93-1.01 (m, 2H) 1.76 (t, J=6.06 Hz, 2H) 2.07-2.20 (m, 2H) 2.73-2.91 (m, 1H) 3.25-3.41 (m, 2H) 3.51-3.69 (m, 2H) 4.08 (br. s., 1H) 7.80 (d, J=8.34 Hz, 2H) 8.15 (br. s., 2H) 8.45 (br. s., 1H) 8.50-8.81 (m, 3H) 8.85-9.17 (m, 2H) 13.53 (br. s., 1H) MS m/z [M+H]$^+$ 429.2.

Example 94 6-(4-(4-cyano-2-methylphenyl)-5-hydroxy-1H-pyrazol-1-yl)-N-((1-methylpiperidin-4-yl)methyl)nicotinamide

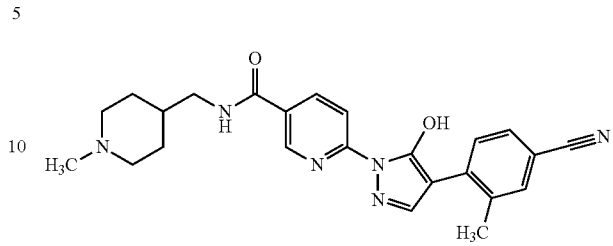

The title compound, as a TFA salt, was prepared in a manner similar to Example 74 using 6-(4-(4-cyano-2-methylphenyl)-5-hydroxy-1H-pyrazol-1-yl)nicotinic acid and (1-methlpiperidin-4-yl)methanamine. $^1$H NMR (400 MHz, DMSO-d$_6$) δ ppm 1.22-1.29 (m, 1H) 1.32-1.46 (m, 2H) 1.80 (d, J=3.54 Hz, 1H) 1.91 (d, J=13.64 Hz, 2H) 2.44 (s, 3H) 2.71-2.84 (m, 3H) 2.85-3.00 (m, 2H) 3.23 (t, J=6.19 Hz, 2H) 3.45 (br. s., 1H) 7.67 (d, J=7.83 Hz, 1H) 7.71-7.90 (m, 2H) 8.22 (d, J=13.64 Hz, 1H) 8.43 (br. s., 2H) 8.82 (br. s., 1H) 8.93 (dd, J=2.02, 0.76 Hz, 1H) 9.28 (br. s., 1H) 13.23 (br. s., 1H). MS m/z [M+H]$^+$ 431.2.

Example 95 6-(4-(4-cyano-2-methylphenyl)-5-hydroxy-1H-pyrazol-1-yl)-N-(3-(dimethylamino)propyl)nicotinamide

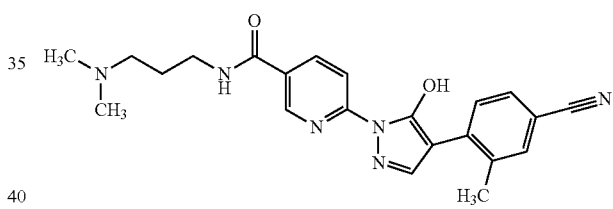

The title compound, as a TFA salt, was prepared in a manner similar to Example 74 using 6-(4-(4-cyano-2-methylphenyl)-5-hydroxy-1H-pyrazol-1-yl)nicotinic acid and N1,N1-dimethylpropane-1,3-diamine. $^1$H NMR (400 MHz, DMSO-d$_6$) δ ppm 1.81-2.01 (m, 2H) 2.44 (s, 3H) 2.80 (d, J=4.04 Hz, 6H) 3.13 (dt, J=10.36, 4.93 Hz, 2H) 3.37 (q, J=6.40 Hz, 2H) 7.67 (d, J=7.83 Hz, 1H) 7.74 (s, 1H) 7.79 (br. s., 1H) 8.22 (d, J=16.93 Hz, 1H) 8.43 (br. s., 1H) 8.86 (br. s., 1H) 8.93 (dd, J=2.15, 0.88 Hz, 1H) 9.38 (br. s., 1H) 13.25 (br. s., 1H). MS m/z [M+H]$^+$ 405.2.

Example 96 6-(4-(4-cyano-2-methylphenyl)-5-hydroxy-1H-pyrazol-1-yl)-N-((1-methylpyrrolidin-3-yl)methyl)nicotinamide

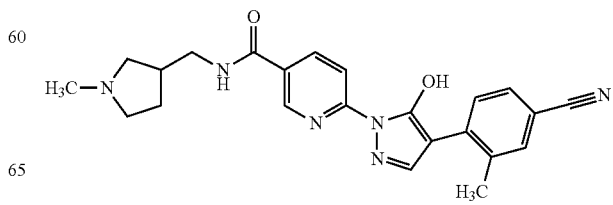

The title compound, as a TFA salt, was prepared in a manner similar to Example 74 using 6-(4-(4-cyano-2-methylphenyl)-5-hydroxy-1H-pyrazol-1-yl)nicotinic acid and (1-methylpyrrolidin-3-yl)methanamine. $^1$H NMR (400 MHz, DMSO-d$_6$) δ ppm 1.61-1.97 (m, 1H) 1.98-2.29 (m, 1H) 2.40-2.47 (m, 3H) 2.54-2.65 (m, 1H) 2.73-2.91 (m, 4H) 2.97-3.25 (m, 1H) 3.40 (dt, J=18.51, 6.28 Hz, 2H) 3.50-3.78 (m, 2H) 7.67 (d, J=7.33 Hz, 1H) 7.70-7.89 (m, 2H) 8.12-8.32 (m, 1H) 8.33-8.74 (m, 2H) 8.77-8.98 (m, 2H) 9.66-9.94 (m, 1H) 12.62-13.68 (m, 1H). MS m/z [M+H]$^+$ 417.2.

Example 97 6-(4-(4-cyano-2-methylphenyl)-5-hydroxy-1H-pyrazol-1-yl)-N-(3-(2-methylpiperidin-1-yl)propyl)nicotinamide

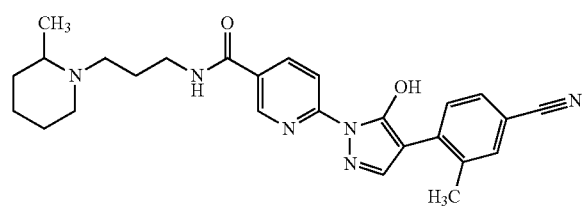 [SMILES: Cc1cc(C#N)ccc1-c1cnn(-c2ccc(C(=O)NCCCN3CCCCC3C)cn2)c1O]

The title compound, as a TFA salt, was prepared in a manner similar to Example 74 using 6-(4-(4-cyano-2-methylphenyl)-5-hydroxy-1H-pyrazol-1-yl)nicotinic acid and 3-(2-methylpiperidin-1-yl)propan-1-amine. $^1$H NMR (400 MHz, DMSO-d$_6$) δ ppm 1.20-1.32 (m, 3H) 1.38-1.55 (m, 2H) 1.56-1.74 (m, 2H) 1.74-2.06 (m, 4H) 2.40-2.47 (m, 3H) 2.91-3.16 (m, 2H) 3.16-3.34 (m, 2H) 3.35-3.69 (m, 3H) 7.63-7.70 (m, 1H) 7.72-7.86 (m, 2H) 8.20 (br. s., 1H) 8.42 (d, J=7.33 Hz, 2H) 8.85-9.00 (m, 2H) 9.03-9.38 (m, 1H) 12.63-13.81 (m, 1H). MS m/z [M+H]$^+$ 459.2.

Example 98 6-(4-(4-cyano-2-methylphenyl)-5-hydroxy-1H-pyrazol-1-yl)-N-(1-ethylpiperidin-4-yl)nicotinamide

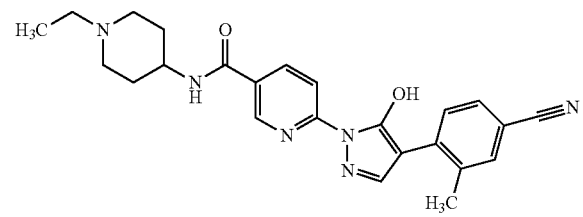 [SMILES: CCN1CCC(NC(=O)c2ccc(-n3ncc(-c4ccc(C#N)cc4C)c3O)nc2)CC1]

The title compound, as a TFA salt, was prepared in a manner similar to Example 74 using 6-(4-(4-cyano-2-methylphenyl)-5-hydroxy-1H-pyrazol-1-yl)nicotinic acid and 1-ethylpiperidin-4-amine. $^1$H NMR (400 MHz, DMSO-d$_6$) δ ppm 1.13-1.31 (m, 3H) 1.71-1.88 (m, 2H) 1.91-2.20 (m, 2H) 2.44 (s, 3H) 3.01-3.18 (m, 3H) 3.23-3.43 (m, 1H) 3.55 (d, J=12.13 Hz, 2H) 3.99-4.28 (m, 1H) 7.67 (d, J=7.83 Hz, 1H) 7.70-7.86 (m, 2H) 8.07-8.31 (m, 1H) 8.32-8.64 (m, 2H) 8.73 (d, J=6.32 Hz, 1H) 8.84-8.99 (m, 1H) 9.24 (br. s., 1H) 12.78-13.45 (m, 1H). MS m/z [M+H]$^+$ 431.2.

Example 99 6-(4-(4-cyano-2-methylphenyl)-5-hydroxy-1H-pyrazol-1-yl)-N-(3-(piperidin-1-yl)propyl)nicotinamide

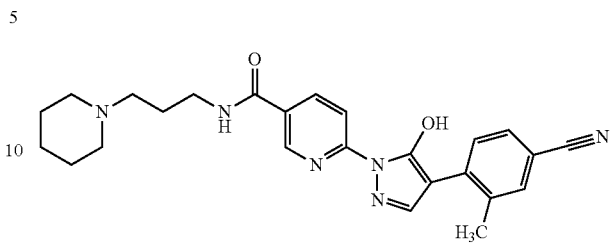

The title compound, as a TFA salt, was prepared in a manner similar to Example 74 using 6-(4-(4-cyano-2-methylphenyl)-5-hydroxy-1H-pyrazol-1-yl)nicotinic acid and 3-(piperidin-1-yl)propan-1-amine. $^1$H NMR (400 MHz, DMSO-d$_6$) δ ppm 1.20-1.47 (m, 1H) 1.52-1.75 (m, 3H) 1.82 (d, J=14.40 Hz, 2H) 1.88-2.02 (m, 2H) 2.44 (s, 3H) 2.78-2.98 (m, 2H) 3.11 (dt, J=10.55, 4.96 Hz, 2H) 3.37 (q, J=6.48 Hz, 2H) 3.46 (d, J=11.87 Hz, 2H) 7.67 (d, J=7.83 Hz, 1H) 7.74 (s, 1H) 7.78 (br. s., 1H) 8.20 (br. s., 1H) 8.42 (d, J=7.58 Hz, 1H) 8.53 (br. s., 1H) 8.89 (t, J=5.18 Hz, 1H) 8.91-8.98 (m, 1H) 9.13 (br. s., 1H) 13.25 (br. s., 1H). MS m/z [M+H]$^+$ 445.2.

Example 100 6-(4-(4-cyano-2-methylphenyl)-5-hydroxy-1H-pyrazol-1-yl)-N-(1-methylpiperidin-4-yl)nicotinamide

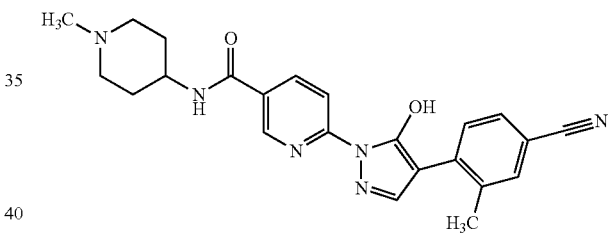

The title compound, as a TFA salt, was prepared in a manner similar to Example 74 using 6-(4-(4-cyano-2-methylphenyl)-5-hydroxy-1H-pyrazol-1-yl)nicotinic acid and 1-methylpiperidin-4-amine. $^1$H NMR (400 MHz, DMSO-d$_6$) δ ppm 1.71-1.85 (m, 2H) 1.92-2.14 (m, 2H) 2.38-2.47 (m, 3H) 2.70-2.89 (m, 3H) 3.06-3.18 (m, 2H) 3.24-3.40 (m, 1H) 3.49 (d, J=11.87 Hz, 1H) 3.98-4.24 (m, 1H) 7.67 (d, J=7.58 Hz, 1H) 7.71-7.87 (m, 2H) 8.21 (d, J=12.13 Hz, 1H) 8.35-8.59 (m, 2H) 8.72 (d, J=6.32 Hz, 1H) 8.88-8.98 (m, 1H) 9.46 (br. s., 1H) 12.72-13.42 (m, 1H). MS m/z [M+H]$^+$ 417.2.

Example 101 6-(4-(4-cyano-2-methylphenyl)-5-hydroxy-1H-pyrazol-1-yl)-N-((4-methylmorpholin-2-yl)methyl)nicotinamide

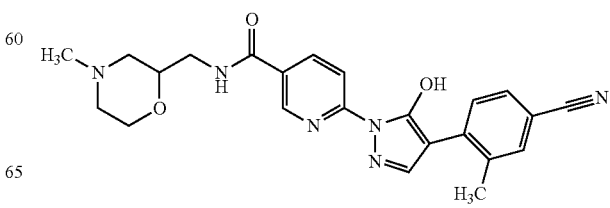

The title compound, as a TFA salt, was prepared in a manner similar to Example 74 using 6-(4-(4-cyano-2-methylphenyl)-5-hydroxy-1H-pyrazol-1-yl)nicotinic acid and (4-methylmorpholin-2-yl)methanamine. ¹H NMR (400 MHz, DMSO-d₆) δ ppm 2.44 (s, 3H) 2.78-2.94 (m, 4H) 2.98-3.15 (m, 1H) 3.31-3.58 (m, 4H) 3.68 (t, J=11.75 Hz, 1H) 3.78-3.95 (m, 1H) 4.08 (dd, J=12.88, 3.03 Hz, 1H) 7.67 (d, J=8.08 Hz, 1H) 7.74 (s, 1H) 7.78 (br. s., 1H) 8.21 (d, J=6.32 Hz, 1H) 8.44 (d, J=7.07 Hz, 2H) 8.85-9.06 (m, 2H) 9.93 (br. s., 1H) 12.57-13.73 (m, 1H). MS m/z [M+H]⁺ 433.2.

Example 102 6-(4-(4-cyano-2-methylphenyl)-5-hydroxy-1H-pyrazol-1-yl)-N-(2-(1-methylpyrrolidin-2-yl)ethyl)nicotinamide

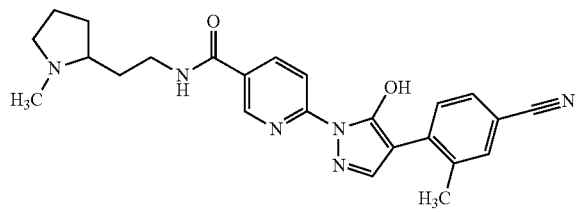 [SMILES: Cc1cc(C#N)ccc1-c1cnn(-c2ccc(C(=O)NCCC3CCCN3C)cn2)c1O]

The title compound, as a TFA salt, was prepared in a manner similar to Example 74 using 6-(4-(4-cyano-2-methylphenyl)-5-hydroxy-1H-pyrazol-1-yl)nicotinic acid and 2-(1-methylpyrrolidin-2-yl)ethanamine. ¹H NMR (400 MHz, DMSO-d₆) δ ppm 1.60-1.83 (m, 2H) 1.83-2.08 (m, 2H) 2.18 (dd, J=12.88, 4.29 Hz, 1H) 2.27-2.41 (m, 1H) 2.44 (s, 3H) 2.84 (d, J=3.54 Hz, 3H) 3.08 (br. s., 1H) 3.29 (br. s., 1H) 3.40 (q, J=6.57 Hz, 2H) 3.58 (d, J=4.29 Hz, 1H) 7.67 (d, J=7.58 Hz, 1H) 7.70-7.89 (m, 2H) 8.20 (br. s., 1H) 8.42 (br. s., 1H) 8.50-8.71 (m, 1H) 8.84 (br. s., 1H) 8.89-8.95 (m, 1H) 9.53 (br. s., 1H) 12.81-13.56 (m, 1H). MS m/z [M+H]⁺ 431.2.

Example 103 6-(4-(4-cyano-2-methylphenyl)-5-hydroxy-1H-pyrazol-1-yl)-N-((1R,2S)-2-(methoxymethyl)cyclopentyl)nicotinamide

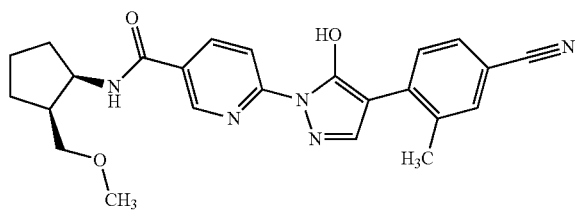 [SMILES: COC[C@H]1CCC[C@H]1NC(=O)c1ccc(-n2ncc(-c3ccc(C#N)cc3C)c2O)nc1]

The title compound was prepared in a manner similar to Example 74 using 6-(4-(4-cyano-2-methylphenyl)-5-hydroxy-1H-pyrazol-1-yl)nicotinic acid and (1R,2S)-2-(methoxymethyl)cyclopentanamine. ¹H NMR (400 MHz, DMSO-d₆) δ ppm 1.42-1.60 (m, 2H) 1.60-1.83 (m, 3H) 1.84-2.01 (m, 1H) 2.20-2.37 (m, 1H) 2.44 (s, 3H) 3.19 (s, 3H) 3.20-3.27 (m, 1H) 3.40 (dd, J=9.35, 6.06 Hz, 2H) 4.43 (t, J=7.45 Hz, 1H) 7.67 (d, J=7.58 Hz, 1H) 7.74 (br. s., 1H) 7.81 (d, J=18.69 Hz, 1H) 8.24-8.70 (m, 3H) 8.88 (d, J=1.77 Hz, 1H) 13.24 (br. s., 1H). MS m/z [M+H]⁺ 432.2.

Example 104 6-(4-(4-cyano-2-methylphenyl)-5-hydroxy-1H-pyrazol-1-yl)-N-(3-morpholinopropyl)nicotinamide

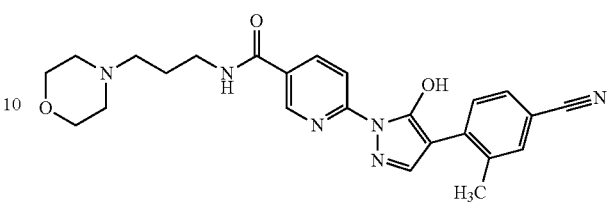

The title compound was prepared in a manner similar to Example 74 using 6-(4-(4-cyano-2-methylphenyl)-5-hydroxy-1H-pyrazol-1-yl)nicotinic acid and 3-morpholinopropan-1-amine TFA salt. ¹H NMR (400 MHz, DMSO-d₆) δ ppm 1.17-1.31 (m, 2H) 1.32-1.45 (m, 2H) 1.77-1.91 (m, 4H) 2.40-2.46 (m, 3H) 3.37-3.49 (m, 1H) 3.65-3.82 (m, 1H) 4.58 (br. s., 1H) 7.65 (dd, J=7.83, 1.52 Hz, 1H) 7.73 (s, 1H) 7.77 (d, J=7.83 Hz, 1H) 8.16 (br. s., 1H) 8.25-8.65 (m, 3H) 8.80-9.01 (m, 1H) 12.36-13.83 (m, 1H). MS m/z [M+H]⁺ 447.2

Example 105 6-(4-(4-cyano-2-methylphenyl)-5-hydroxy-1H-pyrazol-1-yl)-N-(3-(pyrrolidin-1-yl)propyl)nicotinamide

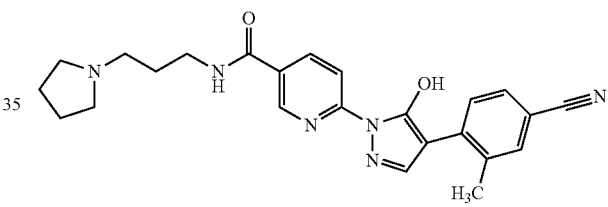

The title compound was prepared in a manner similar to Example 74 using 6-(4-(4-cyano-2-methylphenyl)-5-hydroxy-1H-pyrazol-1-yl)nicotinic acid and 3-(pyrrolidin-1-yl)propan-1-amine as a TFA salt. ¹H NMR (400 MHz, DMSO-d₆) δ ppm 1.80-1.96 (m, 4H) 1.97-2.08 (m, 2H) 2.44 (s, 3H) 2.91-3.09 (m, 2H) 3.21 (dt, J=10.36, 5.43 Hz, 2H) 3.38 (q, J=6.40 Hz, 2H) 3.49-3.64 (m, 2H) 7.67 (d, J=7.58 Hz, 1H) 7.74 (s, 2H) 8.03-8.33 (m, 1H) 8.43 (br. s., 2H) 8.85 (br. s., 1H) 8.88-8.98 (m, 1H) 9.50 (br. s., 1H) 12.61-13.62 (m, 1H). MS m/z [M+H]⁺ 431.2

Example 106 N-(3-(1H-imidazol-1-yl)propyl)-6-(4-(4-cyano-2-methylphenyl)-5-hydroxy-1H-pyrazol-1-yl)nicotinamide

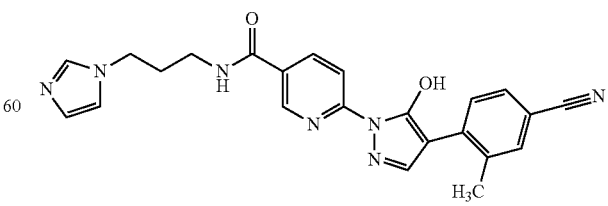

The title compound was prepared in a manner similar to Example 74 using 6-(4-(4-cyano-2-methylphenyl)-5-hydroxy-1H-pyrazol-1-yl)nicotinic acid and 3-(1H-imidazol- 1-yl)propan-1-amine. $^1$H NMR (400 MHz, DMSO-d$_6$) δ ppm 2.09-2.17 (m, 2H) 2.44 (s, 3H) 3.32 (q, J=6.40 Hz, 2H) 4.28 (t, J=6.95 Hz, 2H) 7.63-7.72 (m, 2H) 7.74 (s, 1H) 7.78 (d, J=8.08 Hz, 1H) 7.83 (t, J=1.64 Hz, 1H) 8.19 (br. s., 1H) 8.35-8.55 (m, 2H) 8.82 (t, J=5.68 Hz, 1H) 8.89-8.96 (m, 1H) 9.11 (s, 1H) 13.26-14.08 (m, 1H). MS m/z [M+H]$^+$ 428.2.

Example 107 6-(4-(4-cyano-2-methylphenyl)-5-hydroxy-1H-pyrazol-1-yl)-N-methylnicotinamide

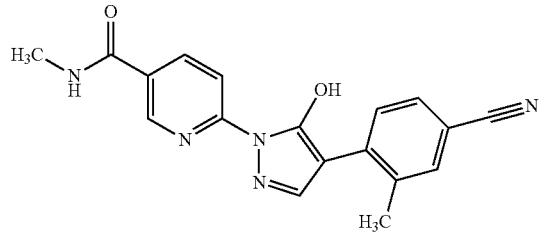 [SMILES: CNC(=O)c1ccc(-n2ncc(-c3ccc(C#N)cc3C)c2O)nc1]

The title compound was prepared in a manner similar to Example 74 using 6-(4-(4-cyano-2-methylphenyl)-5-hydroxy-1H-pyrazol-1-yl)nicotinic acid and methanamine. $^1$H NMR (400 MHz, DMSO-d$_6$) δ ppm 2.36 (s, 3H) 2.76 (d, J=4.55 Hz, 3H) 7.59 (dd, J=7.96, 1.39 Hz, 1H) 7.66 (s, 1H) 7.71 (d, J=7.83 Hz, 1H) 8.11 (br. s., 1H) 8.33 (d, J=6.32 Hz, 2H) 8.61 (d, J=4.55 Hz, 1H) 8.79-8.89 (m, 1H) 12.66-13.53 (m, 1H). MS m/z [M+H]$^+$ 334.1.

Example 108 6-(4-(4-cyano-2-methylphenyl)-5-hydroxy-1H-pyrazol-1-yl)-N-ethylnicotinamide

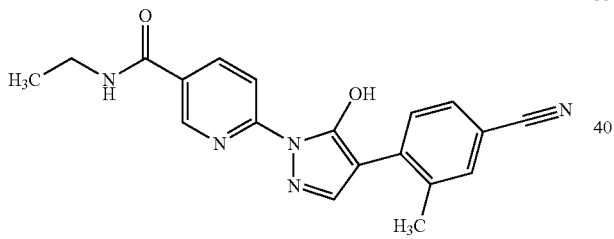

The title compound was prepared in a manner similar to Example 74 using 6-(4-(4-cyano-2-methylphenyl)-5-hydroxy-1H-pyrazol-1-yl)nicotinic acid and ethanamine. $^1$H NMR (400 MHz, DMSO-d$_6$) δ ppm 1.09 (t, J=7.33 Hz, 3H) 2.36 (s, 3H) 3.16-3.37 (m, 2H) 7.59 (d, J=8.08 Hz, 1H) 7.66 (s, 1H) 7.71 (br. s., 1H) 7.99-8.22 (m, 1H) 8.34 (d, J=7.58 Hz, 2 H) 8.65 (t, J=5.05 Hz, 1H) 8.78-8.90 (m, 1H) 12.84-13.41 (m, 1H). MS m/z [M+H]$^+$ 348.1.

Example 109 6-(4-(4-cyanophenyl)-5-hydroxy-1H-pyrazol-1-yl)-N-(1-(dimethylamino)-2-methylpropan-2-yl)nicotinamide

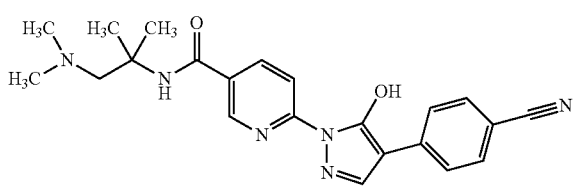 [SMILES: CN(C)CC(C)(C)NC(=O)c1ccc(-n2ncc(-c3ccc(C#N)cc3)c2O)nc1]

The title compound, as a TFA salt, was prepared in a manner similar to Example 74 using N1,N1-trimethylproan-2-diamine. $^1$H NMR (400 MHz, DMSO-d$_6$) δ ppm 1.48 (s, 6H) 2.86 (s, 6H) 3.66 (s, 2H) 7.80 (d, J=8.59 Hz, 2H) 8.15 (br. s., 2H) 8.29-8.85 (m, 4H) 8.85-9.02 (m, 1H) 9.19 (br. s., 1H) 13.07-13.83 (m, 1H). MS m/z [M+H]$^+$ 405.2.

Example 110 6-(4-(4-cyanophenyl)-5-hydroxy-1H-pyrazol-1-yl)-N-((1R,2S)-2-(methoxymethyl)cyclopentyl)nicotinamide The title compound was prepared in a manner similar to Example 74 using (1R,2S)-2-(methoxymethyl)cyclopentanamine. $^1$H NMR (400 MHz, DMSO-d$_6$) δ ppm 1.44-1.60 (m, 2H) 1.61-1.72 (m, 1H) 1.72-1.82 (m, 2H) 1.85-2.00 (m, 1H) 2.19-2.35 (m, 1H) 3.16-3.26 (m, 4H) 3.40 (dd, J=9.35, 6.06 Hz, 1H) 4.36-4.51 (m, 1H) 7.80 (d, J=8.34 Hz, 2H) 8.15 (br. s., 2H) 8.25-8.47 (m, 2H) 8.68 (br. s., 2H) 8.88 (s, 1H) 13.53 (br. s., 1H). MS m/z [M+H]$^+$ 418.2.

Example 111 6-(4-(4-cyanophenyl)-5-hydroxy-1H-pyrazol-1-yl)-N-((4-methylmorpholin-2-yl)methyl)nicotinamide The title compound, as the TFA salt, was prepared in a manner similar to Example 74 using (4-methylmorpholin-2-yl)methanamine. $^1$H NMR (400 MHz, DMSO-d$_6$) δ ppm 2.79-2.94 (m, 4H) 2.98-3.12 (m, 1H) 3.32-3.58 (m, 4H) 3.69 (t, J=11.75 Hz, 1H) 3.79-3.92 (m, 1H) 4.07 (dd, J=12.88, 3.03 Hz, 1H) 7.80 (d, J=8.34 Hz, 2H) 8.15 (br. s., 2H) 8.34-8.84 (m, 3H) 8.84-9.14 (m, 2H) 9.99 (br. s., 1H) 13.56 (br. s., 1H). MS m/z [M+H]$^+$ 419.1.

Example 112 6-(4-(4-cyanophenyl)-5-hydroxy-1H-pyrazol-1-yl)-N-(2-ethoxy ethyl)nicotinamide Combined 6-(4-(4-cyanophenyl)-5-hydroxy-1H-pyrazol-1-yl)nicotinic acid (100 mg, 0.327 mmol), EDCI (94.0 mg, 0.490 mmol), and HOBT (66.2 mg, 0.490 mmol) in DMF (2.5 mL) and added N,N-diisopropyl ethylamine (227 µL, 1.306 mmol). Then 2-ethoxyethanamine (43.7 mg, 0.490 mmol) was added and the reaction allowed to stir at room temperature for 16 hours. The reaction mixture was then diluted with water (3.5 mL) and acidified to an approximate pH=4 to give a solid which was collected by filtration, washed with water, MeOH, and diethyl ether to give the title compound. $^1$H NMR (400 MHz, DMSO-d$_6$) δ 1.04 (t, J=6.95 Hz, 3H) 3.33-3.41 (m, 4H) 3.41-3.48 (m, 2H) 7.70 (d, J=8.34 Hz, 2H) 8.06 (d, J=7.07 Hz, 2H) 8.26-8.49 (m, 2H) 8.58 (br. s., 1H) 8.71 (t, J=5.18 Hz, 1H) 8.77-8.93 (m, 1H) 12.95-13.90 (m, 1H). MS m/z [M+H]$^+$ 378.1.

Example 113 6-(4-(4-cyanophenyl)-5-hydroxy-1H-pyrazol-1-yl)-N-(1-(tetrahydrofuran-2-yl)ethyl)nicotinamide

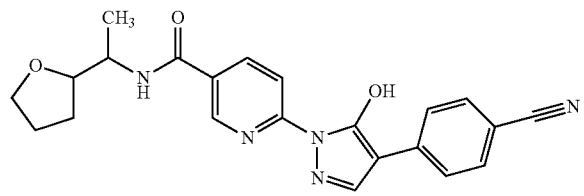 [SMILES: CC(NC(=O)c1ccc(-n2ncc(-c3ccc(C#N)cc3)c2O)nc1)C1CCCO1]

The title compound was prepared in a manner similar to Example 112 using 1-(tetrahydrofuran-2-yl)ethanamine. $^1$H NMR (400 MHz, DMSO-d$_6$) δ 1.11-1.23 (m, 3H) 1.52-1.73 (m, 1H) 1.74-1.98 (m, 3H) 3.66 (dd, J=10.61, 7.07 Hz, 1H) 3.73-3.91 (m, 2H) 3.96-4.19 (m, 1H) 7.80 (d, J=8.34 Hz, 2H) 8.14 (br. s., 2H) 8.33-8.79 (m, 4H) 8.91 (br. s., 1H) 13.55 (br. s., 1H). MS m/z [M+H]$^+$ 404.1.

Example 114 6-(5-hydroxy-4-(2-methoxypyridin-4-yl)-1H-pyrazol-1-yl)-N-(4-methoxybutan-2-yl)nicotinamide

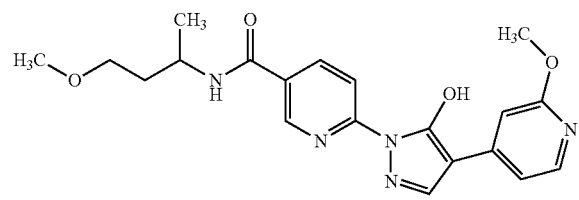 [SMILES: COCCC(C)NC(=O)c1ccc(-n2ncc(-c3ccnc(OC)c3)c2O)nc1]

The title compound was prepared in a manner similar to Example 112 using 6-(5-hydroxy-4-(2-methoxypyridin-4-yl)-1H-pyrazol-1-yl)nicotinic acid and 4-methoxybutan-2-amine. $^1$H NMR (400 MHz, methanol-d$_4$) δ ppm 1.28 (d, J=6.32 Hz, 3H) 1.86 (dd, J=6.95, 5.43 Hz, 2H) 3.33 (s, 3H) 3.44-3.57 (m, 2H) 4.18 (s, 3H) 4.22-4.34 (m, 1H) 7.77 (d, J=5.31 Hz, 1H) 7.86 (s, 1H) 8.04 (d, J=6.57 Hz, 1H) 8.44 (br. s., 3H) 8.68-9.15 (m, 1H). MS m/z [M+H]$^+$ 398.2.

Example 115 6-(4-(4-cyanophenyl)-5-hydroxy-1H-pyrazol-1-yl)-N-(1-isopropylpiperidin-4-yl)nicotinamide

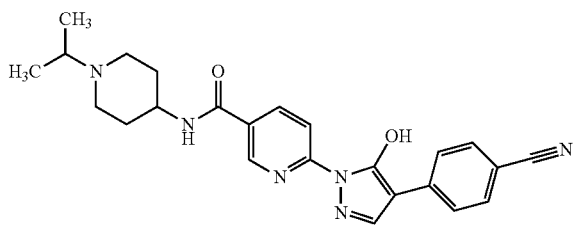 [SMILES: CC(C)N1CCC(NC(=O)c2ccc(-n3ncc(-c4ccc(C#N)cc4)c3O)nc2)CC1]

The title compound was prepared in a manner similar to Example 112 using 1-isopropyl-piperidin-4-ylamine as an HCl salt. $^1$H NMR (400 MHz, DMSO-d$_6$) δ ppm 1.16-1.27 (m, 6H) 1.86-2.01 (m, 4H) 2.96-3.11 (m, 2H) 3.31-3.41 (m, 3H) 3.96-4.20 (m, 1H) 7.73 (d, J=8.34 Hz, 2H) 8.08 (d, J=6.57 Hz, 2H) 8.40 (d, J=6.06 Hz, 2H) 8.60 (br. s., 1H) 8.77 (d, J=7.07 Hz, 1H) 8.83-8.95 (m, 1H) 9.96 (br. s., 1H) 13.07-13.88 (m, 1H). MS m/z [M+H]$^+$ 431.2.

Example 116 6-(4-(4-cyanophenyl)-5-hydroxy-1H-pyrazol-1-yl)-N-(3-(thiazol-2-yl)propyl)nicotinamide

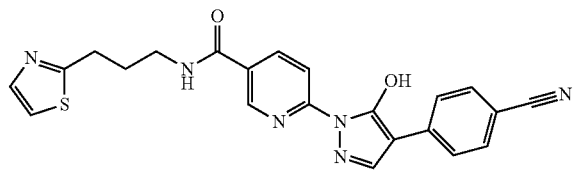 [SMILES: N#Cc1ccc(-c2cnn(-c3ccc(C(=O)NCCCc4nccs4)cn3)c2O)cc1]

The title compound was prepared in a manner similar to Example 112 using 3-(thiazol-2-yl)propan-1-amine to give the title compound. $^1$H NMR (400 MHz, DMSO-d$_6$) δ ppm 1.90-2.00 (m, 2H) 3.01 (t, J=7.58 Hz, 2H) 3.30-3.37 (m, 2H) 7.52 (d, J=3.28 Hz, 1H) 7.64 (d, J=3.28 Hz, 1H) 7.72 (d, J=8.59 Hz, 2H) 8.08 (d, J=7.58 Hz, 2H) 8.29-8.49 (m, 2H) 8.59 (br. s., 1H) 8.71 (t, J=5.43 Hz, 1H) 8.80-8.87 (m, 1H) 13.40 (br. s., 1H). MS m/z [M+H]$^+$ 431.1.

Example 117 N-(3-(1H-pyrazol-1-yl)propyl)-6-(4-(4-cyanophenyl)-5-hydroxy-1H-pyrazol-1-yl)nicotinamide

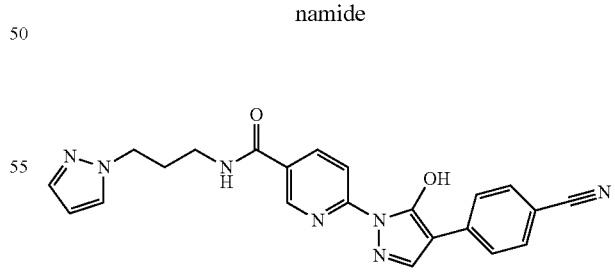

The title compound was prepared in a manner similar to Example 112 using 6-(4-(4-cyanophenyl)-5-hydroxy-1H-pyrazol-1-yl)nicotinic acid and 3-(1H-pyrazol-1-yl)propan-1-amine. $^1$H NMR (400 MHz, DMSO-d$_6$) δ ppm 2.00-2.10 (m, 2H) 3.25-3.30 (m, 2H) 4.19 (t, J=6.95 Hz, 2H) 6.23 (t, J=2.02 Hz, 1H) 7.45 (d, J=1.77 Hz, 1H) 7.77 (d, J=1.52 Hz, 1H) 7.79 (d, J=8.59 Hz, 2H) 8.14 (d, J=7.33 Hz, 2H)

8.37-8.44 (m, 1H) 8.45-8.58 (m, 1H) 8.66 (br. s., 1H) 8.74 (t, J=5.31 Hz, 1H) 8.88-8.94 (m, 1H) 13.54 (br. s., 1H). MS m/z [M+H]⁺ 414.2.

Example 118 6-(4-(4-cyanophenyl)-5-hydroxy-1H-pyrazol-1-yl)-N-(3-(cyclopropylmethoxy)propyl)nicotinamide

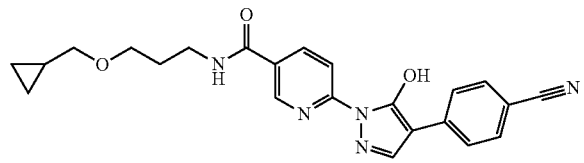 [SMILES: N#Cc1ccc(-c2cnn(-c3ccc(C(=O)NCCCOCC4CC4)cn3)c2O)cc1]

The title compound was prepared in a manner similar to Example 112 using 3-(cyclopropylmethoxy)propan-1-amine. ¹H NMR (400 MHz, DMSO-d₆) δ ppm 0.13-0.19 (m, 2H) 0.41-0.49 (m, 2H) 0.99 (tddd, J=9.84, 9.84, 4.96, 3.03, 1.89 Hz, 1H) 1.78 (quin, J=6.63 Hz, 2H) 3.22 (d, J=6.82 Hz, 2H) 3.32-3.38 (m, 2H) 3.45 (t, J=6.32 Hz, 2H) 7.79 (d, J=8.59 Hz, 2H) 8.14 (d, J=7.58 Hz, 2H) 8.38-8.43 (m, 1H) 8.47 (br. s., 1H) 8.60-8.76 (m, 2H) 8.89-8.93 (m, 1H) 13.53 (br. s., 1H). MS m/z [M+H]⁺ 418.2.

Example 118A 6-(4-(4-cyano-2-methylphenyl)-5-hydroxy-1H-pyrazol-1-yl)-N-(1-(methoxymethyl)cyclopropyl)nicotinamide

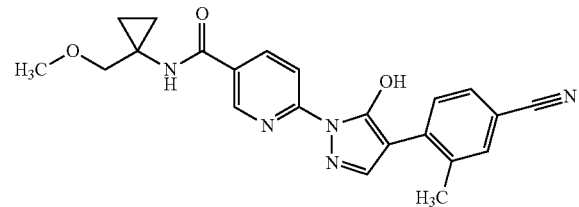 [SMILES: COCC1(NC(=O)c2ccc(-n3ncc(-c4ccc(C#N)cc4C)c3O)nc2)CC1]

The title compound was prepared in a manner similar to Example 112 using 6-(4-(4-cyano-2-methylphenyl)-5-hydroxy-1H-pyrazol-1-yl)nicotinic acid 1-(methoxymethyl)cyclopropanamine. ¹H NMR (400 MHz, DMSO-d₆) δ ppm 0.81 (s, 4H) 2.43 (s, 3H) 3.29 (s, 3H) 3.49 (s, 2H) 7.66 (d, J=7.83 Hz, 1H) 7.73 (s, 1H) 7.78 (br. s., 1 H) 8.04-8.33 (m, 1H) 8.42 (d, J=7.07 Hz, 2H) 8.91 (d, J=1.26 Hz, 1H) 8.98 (s, 1H) 12.83-13.55 (m, 1H). MS m/z [M+H]⁺ 404.1.

Example 119 6-(4-(4-cyano-2-methylphenyl)-5-hydroxy-1H-pyrazol-1-yl)-N-((1s,4s)-4-methoxycyclohexyl)nicotinamide

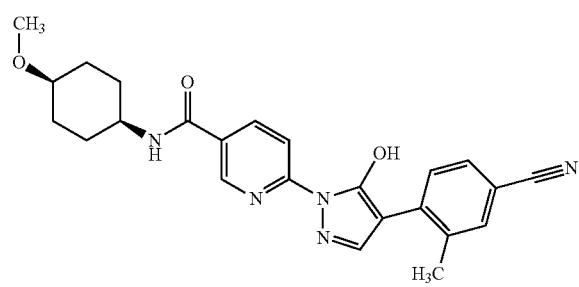 [SMILES: CO[C@H]1CC[C@@H](NC(=O)c2ccc(-n3ncc(-c4ccc(C#N)cc4C)c3O)nc2)CC1]

The title compound was prepared in a manner similar to Example 112 using 6-(4-(4-cyano-2-methylphenyl)-5-hydroxy-1H-pyrazol-1-yl)nicotinic acid and (1s,4s)-4-methoxycyclohexanamine. ¹H NMR (400 MHz, DMSO-d₆) δ ppm 1.35-1.48 (m, 2H) 1.50-1.62 (m, 4H) 1.77-1.89 (m, 2H) 2.36 (s, 3H) 3.17 (s, 3H) 3.23-3.36 (m, 1H) 3.80 (dq, J=12.66, 4.87 Hz, 1H) 7.54-7.63 (m, 1H) 7.66 (s, 1H) 7.70 (br. s., 1H) 8.10 (br. s., 1H) 8.38 (t, J=8.72 Hz, 3H) 8.74-8.92 (m, 1H) 13.12 (br. s., 1H). MS m/z [M+H]⁺ 432.2.

Example 120 (S)-6-(4-(4-cyano-2-methylphenyl)-5-hydroxy-1H-pyrazol-1-yl)-N-(tetrahydrofuran-3-yl)nicotinamide

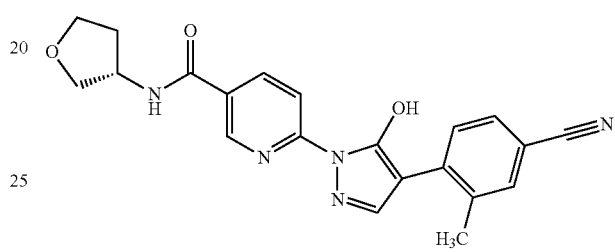

The title compound was prepared in a manner similar to Example 112 using 6-(4-(4-cyano-2-methylphenyl)-5-hydroxy-1H-pyrazol-1-yl)nicotinic acid and (S)-tetrahydrofuran-3-amine. ¹H NMR (400 MHz, DMSO-d₆) δ ppm 1.84-2.02 (m, 1H) 2.09-2.27 (m, 1H) 2.43 (s, 3H) 3.63 (dd, J=8.84, 4.04 Hz, 1H) 3.73 (td, J=8.08, 5.81 Hz, 1H) 3.83-3.95 (m, 2H) 4.42-4.58 (m, 1H) 7.66 (d, J=7.83 Hz, 1H) 7.73 (s, 1H) 7.77 (br. s., 1H) 8.18 (br. s., 1H) 8.44 (d, J=6.82 Hz, 2H) 8.78 (d, J=6.32 Hz, 1H) 8.92 (s, 1H) 13.18 (br. s., 1H). MS m/z [M+H]⁺ 390.1.

Example 121 6-(4-(4-cyano-2-methylphenyl)-5-hydroxy-1H-pyrazol-1-yl)-N-(3-methoxypropyl)nicotinamide

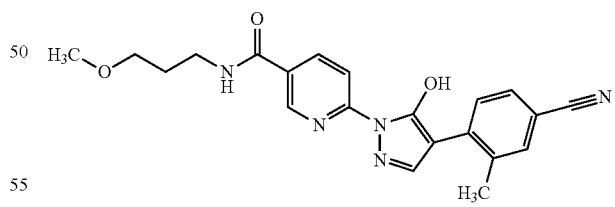

The title compound was prepared in a manner similar to Example 112 using 6-(4-(4-cyano-2-methylphenyl)-5-hydroxy-1H-pyrazol-1-yl)nicotinic acid and 3-methoxypropan-1-amine. ¹H NMR (400 MHz, DMSO-d₆) δ ppm 1.79 (quin, J=6.63 Hz, 2H) 2.44 (s, 3H) 3.25 (s, 3H) 3.34 (q, J=6.65 Hz, 2H) 3.40 (t, J=6.19 Hz, 2H) 7.67 (d, J=7.83 Hz, 1H) 7.74 (s, 1H) 7.78 (d, J=6.82 Hz, 1H) 8.18 (br. s., 1H) 8.41 (d, J=6.06 Hz, 2H) 8.71 (t, J=5.31 Hz, 1H) 8.83-9.01 (m, 1H) 13.19 (br. s., 1H). MS m/z [M+H]⁺ 392.2.

Example 122 (S)—N-(sec-butyl)-6-(4-(4-cyano-2-methylphenyl)-5-hydroxy-1H-pyrazol-1-yl)nicotinamide

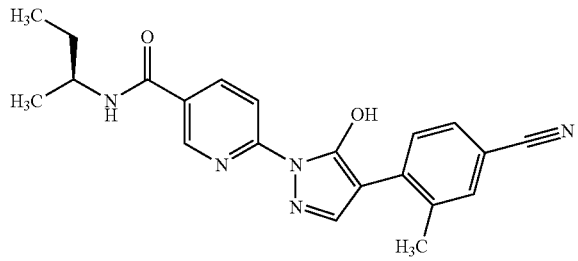 [SMILES: CC[C@H](C)NC(=O)c1ccc(-n2ncc(-c3ccc(C#N)cc3C)c2O)nc1]

The title compound was prepared in a manner similar to Example 112 using 6-(4-(4-cyano-2-methylphenyl)-5-hydroxy-1H-pyrazol-1-yl)nicotinic acid and (S)-butan-2-amine. $^1$H NMR (400 MHz, DMSO-d$_6$) δ ppm 0.90 (t, J=7.33 Hz, 3H) 1.17 (d, J=6.57 Hz, 3H) 1.46-1.63 (m, 2H) 2.44 (s, 3H) 3.95 (dt, J=13.83, 7.11 Hz, 1H) 7.67 (dd, J=8.08, 1.26 Hz, 1H) 7.74 (s, 1H) 7.78 (br. s., 1H) 8.17 (br. s., 1H) 8.32-8.58 (m, 3H) 8.87-8.95 (m, 1H) 13.18 (br. s., 1H). MS m/z [M+H]$^+$ 376.2.

Example 123 4-(5-hydroxy-1-(5-(morpholine-4-carbonyl)pyridin-2-yl)-1H-pyrazol-4-yl)benzonitrile

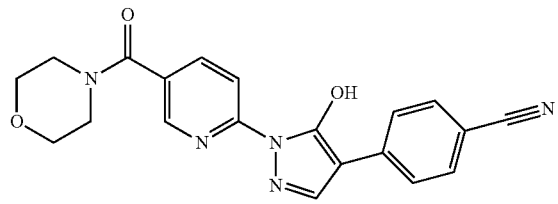 [SMILES: N#Cc1ccc(-c2cnn(-c3ccc(C(=O)N4CCOCC4)cn3)c2O)cc1]

The title compound was prepared in a manner similar to Example 112 using morpholine. $^1$H NMR (400 MHz, DMSO-d$_6$) δ ppm 3.11-4.08 (m, 8H) 7.80 (d, J=8.59 Hz, 2H) 8.10 (dd, J=8.59, 2.02 Hz, 1H) 8.15 (d, J=7.83 Hz, 2H) 8.46 (br. s., 1H) 8.54-8.59 (m, 1H) 8.65 (br. s., 1H) 13.51 (br. s., 1H). MS m/z [M+H]$^+$ 376.1

Example 124 6-(4-(4-cyano-2-methylphenyl)-5-hydroxy-1H-pyrazol-1-yl)-N-isobutylnicotinamide

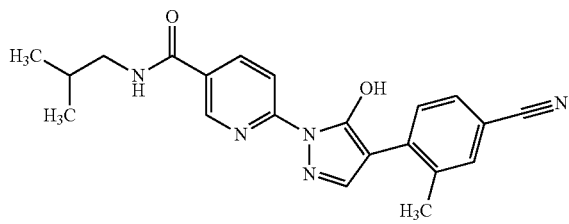 [SMILES: Cc1cc(C#N)ccc1-c1cnn(-c2ccc(C(=O)NCC(C)C)cn2)c1O]

The title compound was prepared in a manner similar to Example 112 using 6-(4-(4-cyano-2-methylphenyl)-5-hydroxy-1H-pyrazol-1-yl)nicotinic acid and isobutylamine. $^1$H NMR (400 MHz, DMSO-d$_6$) δ ppm 0.92 (d, J=6.57 Hz, 6H) 1.87 (dt, J=13.52, 6.63 Hz, 1H) 2.44 (s, 3H) 3.13 (t, J=6.32 Hz, 2H) 7.67 (d, J=8.08 Hz, 1H) 7.74 (s, 1H) 7.78 (br. s., 1H) 8.18 (br. s., 1H) 8.43 (d, J=6.82 Hz, 1H) 8.70 (t, J=5.31 Hz, 1H) 8.92 (s, 1H) 13.18 (br. s., 1H). MS m/z [M+H]$^+$ 376.2.

Example 125 6-(4-(4-cyano-2-methylphenyl)-5-hydroxy-1H-pyrazol-1-yl)-N-(3-hydroxypropyl)nicotinamide

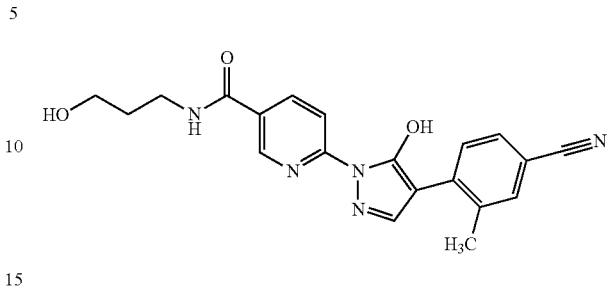

The title compound was prepared in a manner similar to Example 112 using 6-(4-(4-cyano-2-methylphenyl)-5-hydroxy-1H-pyrazol-1-yl)nicotinic acid and 3-aminopropan-1-ol. $^1$H NMR (400 MHz, DMSO-d$_6$) δ ppm 1.71 (quin, J=6.69 Hz, 2H) 2.44 (s, 3H) 3.32-3.39 (m, 2H) 3.49 (br. s., 2H) 4.51 (br. s., 1H) 7.66 (dd, J=7.83, 1.52 Hz, 1H) 7.73 (s, 1H) 7.78 (d, J=6.82 Hz, 1H) 8.17 (br. s., 1H) 8.41 (d, J=6.32 Hz, 2H) 8.69 (t, J=5.43 Hz, 1H) 8.88-8.95 (m, 1H) 12.93-13.41 (m, 1H). MS m/z [M+H]$^+$ 378.1.

Example 126 6-(4-(4-cyano-2-methylphenyl)-5-hydroxy-1H-pyrazol-1-yl)-N-(2-ethoxyethyl)nicotinamide

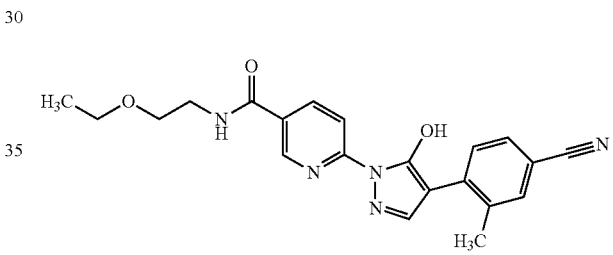

The title compound was prepared in a manner similar to Example 112 using 6-(4-(4-cyano-2-methylphenyl)-5-hydroxy-1H-pyrazol-1-yl)nicotinic acid and 2-ethoxyethylamine. $^1$H NMR (400 MHz, DMSO-d$_6$) δ ppm 1.12 (t, J=6.95 Hz, 3H) 2.43 (s, 3H) 3.42-3.49 (m, 4H) 3.49-3.55 (m, 2H) 7.66 (dd, J=8.08, 1.52 Hz, 1H) 7.73 (s, 1H) 7.75-7.85 (m, 1H) 8.06-8.27 (m, 1H) 8.42 (d, J=6.82 Hz, 2H) 8.80 (t, J=5.18 Hz, 1H) 8.88-8.96 (m, 1H) 12.86-13.47 (m, 1H). MS m/z [M+H]$^+$ 392.2.

Example 127 6-(4-(4-cyano-2-methylphenyl)-5-hydroxy-1H-pyrazol-1-yl)-N-cyclopropylnicotinamide

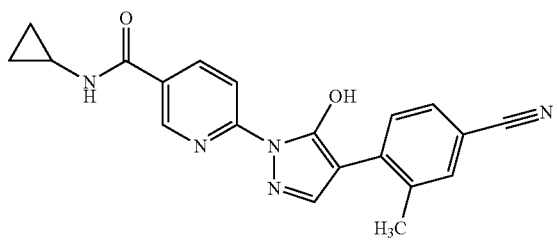 [SMILES: Cc1cc(C#N)ccc1-c1cnn(-c2ccc(C(=O)NC3CC3)cn2)c1O]

The title compound was prepared in a manner similar to Example 112 using 6-(4-(4-cyano-2-methylphenyl)-5-hydroxy-1H-pyrazol-1-yl)nicotinic acid and cyclopropylamine. ¹H NMR (400 MHz, DMSO-d₆) δ ppm 0.51-0.66 (m, 2H) 0.66-0.82 (m, 2H) 2.43 (s, 3H) 2.87 (dt, J=7.39, 3.51 Hz, 1H) 7.65 (dd, J=8.08, 1.52 Hz, 1H) 7.73 (s, 1H) 7.77 (d, J=7.83 Hz, 1H) 8.16 (br. s., 1H) 8.38 (d, J=5.81 Hz, 2H) 8.68 (d, J=4.04 Hz, 1H) 8.83-8.93 (m, 1H) 12.92-13.43 (m, 1H). MS m/z [M+H]⁺ 360.1

Example 128 6-(4-(4-cyano-2-methylphenyl)-5-hydroxy-1H-pyrazol-1-yl)-N-isopropylnicotinamide

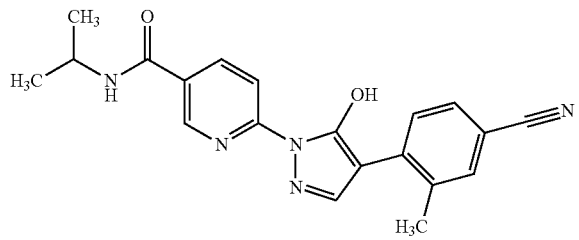 [SMILES: Cc1cc(C#N)ccc1-c1cnn(-c2ccc(C(=O)NC(C)C)cn2)c1O]

The title compound was prepared in a manner similar to Example 112 using 6-(4-(4-cyano-2-methylphenyl)-5-hydroxy-1H-pyrazol-1-yl)nicotinic acid and isopropylamine. ¹H NMR (400 MHz, DMSO-d₆) δ ppm 1.20 (d, J=6.57 Hz, 6H) 2.44 (s, 3H) 4.13 (dd, J=14.15, 6.57 Hz, 1H) 7.66 (dd, J=8.08, 1.52 Hz, 1H) 7.74 (s, 1H) 7.75-7.85 (m, 1H) 8.07-8.28 (m, 1H) 8.45 (dd, J=19.70, 6.82 Hz, 3H) 8.84-8.98 (m, 1H) 12.97-13.37 (m, 1H). MS m/z [M+H]⁺ 362.2.

Example 129 6-(4-(4-cyano-2-methylphenyl)-5-hydroxy-1H-pyrazol-1-yl)-N-(1-(methoxymethyl)cyclopentyl)nicotinamide

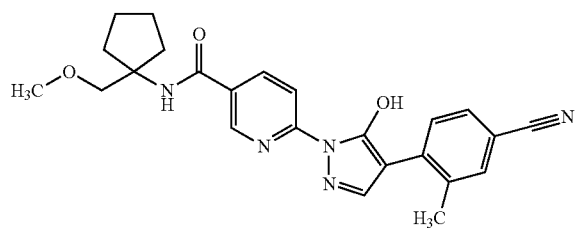 [SMILES: COCC1(NC(=O)c2ccc(-n3ncc(-c4ccc(C#N)cc4C)c3O)nc2)CCCC1]

The title compound was prepared in a manner similar to Example 112 using 6-(4-(4-cyano-2-methylphenyl)-5-hydroxy-1H-pyrazol-1-yl)nicotinic acid and 1-(methoxymethyl)cyclopentanamine. ¹H NMR (400 MHz, DMSO-d₆) δ ppm 1.45-1.74 (m, 6H) 1.94-2.08 (m, 2H) 2.37 (s, 3H) 3.20 (s, 3H) 3.54 (s, 2H) 7.59 (dd, J=7.96, 1.39 Hz, 1H) 7.66 (s, 1H) 7.70 (br. s., 1H) 8.04 (s, 1H) 8.06-8.18 (m, 1H) 8.33 (d, J=6.57 Hz, 2H) 8.75-8.86 (m, 1H) 12.59-13.45 (m, 1H). MS m/z [M+H]⁺ 432.2

Example 130 6-(4-(4-cyano-2-methylphenyl)-5-hydroxy-1H-pyrazol-1-yl)-N-(4-hydroxybutyl)nicotinamide

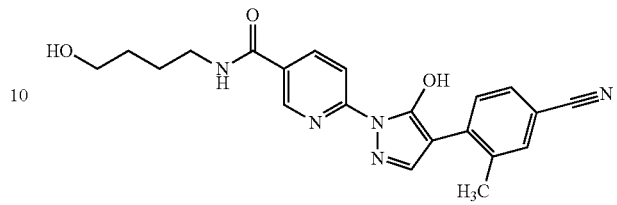

The title compound was prepared in a manner similar to Example 112 using 6-(4-(4-cyano-2-methylphenyl)-5-hydroxy-1H-pyrazol-1-yl)nicotinic acid and 4-aminobutan-1-ol. ¹H NMR (400 MHz, DMSO-d₆) δ ppm 1.43-1.53 (m, 2H) 1.53-1.64 (m, 2H) 2.44 (s, 3H) 3.27-3.33 (m, 2H) 3.44 (br. s., 2H) 4.43 (br. s., 1H) 7.67 (d, J=8.08 Hz, 1H) 7.74 (s, 1H) 7.78 (br. s., 1H) 8.07-8.27 (m, 1H) 8.41 (d, J=6.57 Hz, 2H) 8.70 (t, J=5.43 Hz, 1H) 8.85-8.97 (m, 1H) 12.82-13.57 (m, 1H). MS m/z [M+H]⁺ 392.2

Example 131 6-(4-(4-cyano-2-methylphenyl)-5-hydroxy-1H-pyrazol-1-yl)-N-((1s,4s)-4-hydroxycyclohexyl)nicotinamide

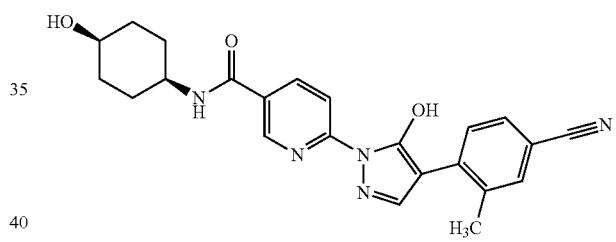

The title compound was prepared in a manner similar to Example 112 using 6-(4-(4-cyano-2-methylphenyl)-5-hydroxy-1H-pyrazol-1-yl)nicotinic acid and (1s,4s)-4-aminocyclohexanol. ¹H NMR (400 MHz, DMSO-d₆) δ ppm 1.31-1.56 (m, 4H) 1.55-1.80 (m, 4H) 2.37 (s, 3H) 3.72 (br. s., 2H) 4.34 (br. s., 1H) 7.59 (d, J=8.08 Hz, 1H) 7.66 (s, 1H) 7.68-7.78 (m, 1H) 8.01-8.18 (m, 1H) 8.39 (d, J=7.07 Hz, 3H) 8.81-8.87 (m, 1H) 12.83-13.38 (m, 1H). MS m/z [M+H]⁺ 418.2

Example 132 6-(4-(4-cyano-2-methylphenyl)-5-hydroxy-1H-pyrazol-1-yl)-N-((1r,4r)-4-hydroxycyclohexyl)nicotinamide

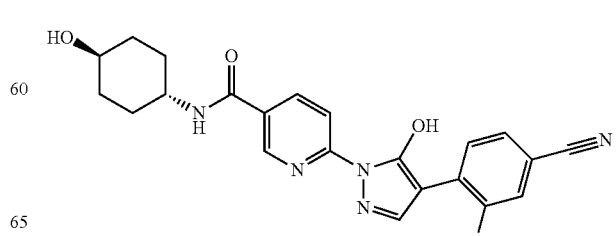

The title compound was prepared in a manner similar to Example 112 using 6-(4-(4-cyano-2-methylphenyl)-5-hydroxy-1H-pyrazol-1-yl)nicotinic acid and (1r,4r)-4-aminocyclohexanol. ¹H NMR (400 MHz, DMSO-d₆) δ ppm 1.17-1.31 (m, 2H) 1.32-1.45 (m, 2H) 1.77-1.91 (m, 4H) 2.40-2.46 (m, 3H) 3.37-3.49 (m, 1H) 3.65-3.82 (m, 1H) 4.58 (br. s., 1H) 7.65 (dd, J=7.83, 1.52 Hz, 1H) 7.73 (s, 1H) 7.77 (d, J=7.83 Hz, 1H) 8.16 (br. s., 1H) 8.25-8.65 (m, 3H) 8.80-9.01 (m, 1H) 12.36-13.83 (m, 1H). MS m/z [M+H]⁺ 418.2

Example 133 6-(4-(4-cyano-2-methylphenyl)-5-hydroxy-1H-pyrazol-1-yl)-N-((tetrahydrofuran-2-yl)methyl)nicotinamide

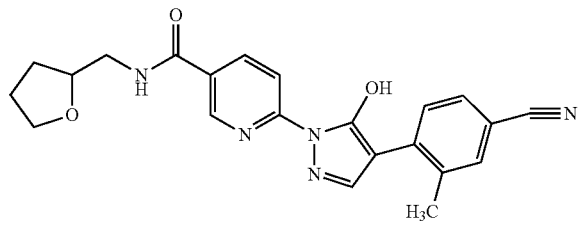 [SMILES: Cc1cc(C#N)ccc1-c1cnn(-c2ccc(C(=O)NCC3CCCO3)cn2)c1O]

The title compound was prepared in a manner similar to Example 112 using 6-(4-(4-cyano-2-methylphenyl)-5-hydroxy-1H-pyrazol-1-yl)nicotinic acid and (tetrahydrofuran-2-yl)methanamine. ¹H NMR (400 MHz, DMSO-d₆) δ ppm 1.49-1.67 (m, 1H) 1.75-1.89 (m, 2H) 1.89-2.01 (m, 1H) 2.44 (s, 3H) 3.35-3.42 (m, 2H) 3.65 (q, J=7.49 Hz, 1H) 3.80 (q, J=6.82 Hz, 1H) 4.00 (t, J=6.32 Hz, 1H) 7.67 (d, J=7.83 Hz, 1H) 7.74 (s, 1H) 7.78 (br. s., 1H) 8.18 (br. s., 1H) 8.43 (d, J=6.57 Hz, 2H) 8.82 (t, J=5.31 Hz, 1H) 8.93 (s, 1H) 13.20 (br. s., 1H). MS m/z [M+H]⁺ 404.2

Example 134 6-(4-(4-cyano-2-methylphenyl)-5-hydroxy-1H-pyrazol-1-yl)-N-cyclobutylnicotinamide

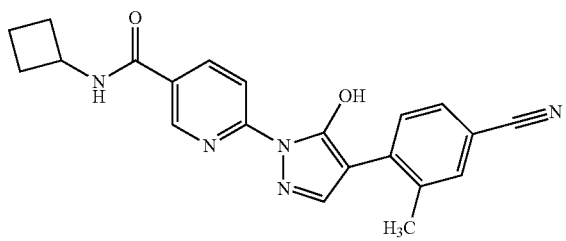 [SMILES: Cc1cc(C#N)ccc1-c1cnn(-c2ccc(C(=O)NC3CCC3)cn2)c1O]

The title compound was prepared in a manner similar to Example 112 using 6-(4-(4-cyano-2-methylphenyl)-5-hydroxy-1H-pyrazol-1-yl)nicotinic acid and cyclobutylamine. ¹H NMR (400 MHz, DMSO-d₆) δ ppm 1.55-1.71 (m, 2H) 1.95-2.09 (m, 2H) 2.11-2.24 (m, 2H) 2.36 (s, 3H) 4.28-4.48 (m, 1H) 7.59 (dd, J=8.08, 1.52 Hz, 1H) 7.66 (s, 1H) 7.70 (br. s., 1H) 8.10 (br. s., 1H) 8.35 (d, J=6.57 Hz, 2H) 8.78 (d, J=7.33 Hz, 1H) 8.81-8.91 (m, 1H) 13.12 (br. s., 1H). MS m/z [M+H]⁺ 374.2

Example 135 6-(4-(4-cyano-2-methylphenyl)-5-hydroxy-1H-pyrazol-1-yl)-N-((1-(methoxy methyl)cyclopropyl)methyl)nicotinamide

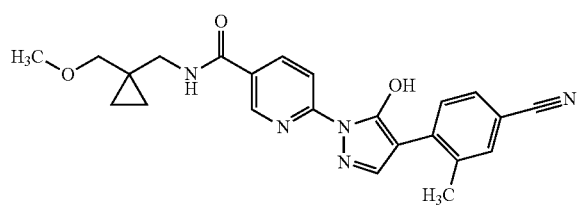 [SMILES: COCC1(CNC(=O)c2ccc(-n3ncc(-c4ccc(C#N)cc4C)c3O)nc2)CC1]

The title compound was prepared in a manner similar to Example 112 using 6-(4-(4-cyano-2-methylphenyl)-5-hydroxy-1H-pyrazol-1-yl)nicotinic acid and (1-(methoxymethyl)cyclopropyl)methanamine. ¹H NMR (400 MHz, DMSO-d₆) δ ppm 0.36-0.44 (m, 2H) 0.52-0.60 (m, 2H) 2.43 (s, 3H) 3.22-3.28 (m, 5H) 3.35 (s, 2H) 7.66 (d, J=7.83 Hz, 1H) 7.73 (s, 1H) 7.77 (br. s., 1H) 8.08-8.26 (m, 1H) 8.42 (d, J=6.57 Hz, 2H) 8.64 (t, J=5.56 Hz, 1H) 8.88-8.94 (m, 1H) 12.96-13.46 (m, 1H). MS m/z [M+H]⁺ 418.2

Example 136 6-(4-(4-cyano-2-methylphenyl)-5-hydroxy-1H-pyrazol-1-yl)-N-(1-methoxypropan-2-yl)nicotinamide

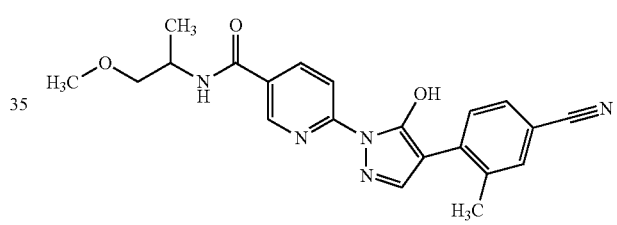

The title compound was prepared in a manner similar to Example 112 using 6-(4-(4-cyano-2-methylphenyl)-5-hydroxy-1H-pyrazol-1-yl)nicotinic acid and 1-methoxypropan-2-amine. ¹H NMR (400 MHz, DMSO-d₆) δ ppm 1.17 (d, J=6.82 Hz, 3H) 2.44 (s, 3H) 3.29 (s, 3H) 3.30-3.33 (m, 1H) 3.44 (dd, J=9.47, 6.44 Hz, 1H) 4.15-4.32 (m, 1H) 7.67 (d, J=8.08 Hz, 1H) 7.74 (s, 1H) 7.78 (br. s., 1H) 8.19 (br. s., 1H) 8.43 (d, J=6.82 Hz, 1H) 8.50 (d, J=7.83 Hz, 2H) 8.87-8.96 (m, 1H) 13.19 (br. s., 1H). MS m/z [M+H]⁺ 392.2

Example 137 (R)-6-(4-(4-cyano-2-methylphenyl)-5-hydroxy-1H-pyrazol-1-yl)-N-(tetrahydrofuran-3-yl)nicotinamide

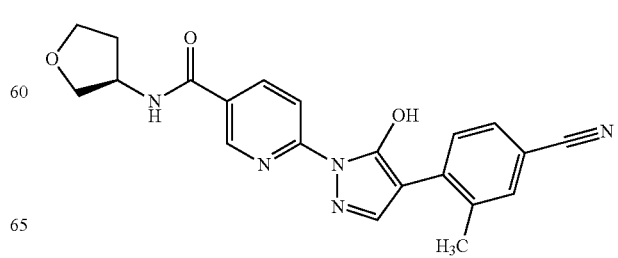

The title compound was prepared in a manner similar to Example 112 using 6-(4-(4-cyano-2-methylphenyl)-5-hydroxy-1H-pyrazol-1-yl)nicotinic acid and (R)-tetrahydrofuran-3-amine. $^1$H NMR (400 MHz, DMSO-d$_6$) δ ppm 1.79-1.94 (m, 1H) 2.03-2.19 (m, 1H) 2.36 (s, 3H) 3.56 (dd, J=9.09, 4.04 Hz, 1H) 3.66 (td, J=8.15, 5.94 Hz, 1H) 3.75-3.88 (m, 2H) 4.42 (dtt, J=8.07, 6.29, 6.29, 4.20, 4.20 Hz, 1H) 7.54-7.63 (m, 1H) 7.66 (s, 1H) 7.71 (br. s., 1H) 8.11 (br. s., 1H) 8.20-8.62 (m, 2H) 8.71 (d, J=6.32 Hz, 1H) 8.80-8.90 (m, 1H) 13.12 (br. s., 1H). MS m/z [M+H]$^+$ 390.2

Example 138A (R)-6-(4-(4-cyano-2-methylphenyl)-5-hydroxy-1H-pyrazol-1-yl)-N-(1-cyclopropylethyl)nicotinamide

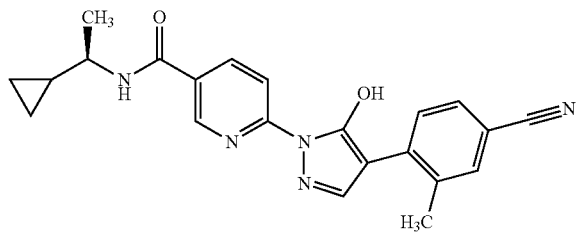 [SMILES: Cc1cc(C#N)ccc1-c1cnn(-c2ccc(C(=O)N[C@H](C)C3CC3)cn2)c1O]

The title compound was prepared in a manner similar to Example 112 using 6-(4-(4-cyano-2-methylphenyl)-5-hydroxy-1H-pyrazol-1-yl)nicotinic acid and (R)-1-cyclopropylethanamine. $^1$H NMR (400 MHz, DMSO-d$_6$) δ ppm 0.17-0.27 (m, 1H) 0.27-0.36 (m, 1H) 0.36-0.44 (m, 1H) 0.44-0.53 (m, 1H) 0.94-1.07 (m, 1H) 1.25 (d, J=6.82 Hz, 3H) 2.43 (s, 3H) 3.42-3.57 (m, 1H) 7.66 (dd, J=8.08, 1.52 Hz, 1H) 7.69-7.75 (m, 1H) 7.78 (d, J=7.58 Hz, 1H) 8.17 (br. s., 1H) 8.43 (d, J=6.32 Hz, 2H) 8.59 (d, J=8.08 Hz, 1H) 8.85-8.95 (m, 1H) 13.19 (br. s., 1H). MS m/z [M+H]$^+$ 388.2.

Example 138B (S)-6-(4-(4-cyano-2-methylphenyl)-5-hydroxy-1H-pyrazol-1-yl)-N-(1-cyclopropylethyl)nicotinamide

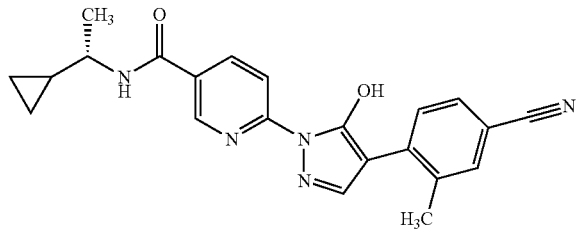 [SMILES: Cc1cc(C#N)ccc1-c1cnn(-c2ccc(C(=O)N[C@@H](C)C3CC3)cn2)c1O]

The title compound was prepared in a manner similar to Example 112 using 6-(4-(4-cyano-2-methylphenyl)-5-hydroxy-1H-pyrazol-1-yl)nicotinic acid and (S)-1-cyclopropylethanamine. $^1$H NMR (400 MHz, DMSO-d$_6$) δ ppm 0.18-0.26 (m, 1H) 0.28-0.36 (m, 1H) 0.36-0.44 (m, 1H) 0.44-0.53 (m, 1H) 0.92-1.08 (m, 1H) 1.25 (d, J=6.82 Hz, 3H) 2.43 (s, 3H) 3.39-3.60 (m, 1H) 7.66 (dd, J=8.08, 1.52 Hz, 1H) 7.73 (s, 1H) 7.78 (d, J=6.57 Hz, 1H) 8.17 (br. s., 1H) 8.43 (d, J=6.57 Hz, 2H) 8.59 (d, J=8.08 Hz, 1H) 8.79-9.05 (m, 1H) 13.19 (br. s., 1H). MS m/z [M+H]$^+$ 388.2.

Example 139 6-(4-(4-cyano-2-methylphenyl)-5-hydroxy-1H-pyrazol-1-yl)-N-((1r,4r)-4-hydroxycyclohexyl)nicotinamide

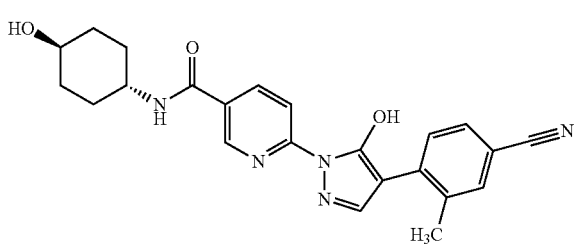 [SMILES: Cc1cc(C#N)ccc1-c1cnn(-c2ccc(C(=O)N[C@H]3CC[C@H](O)CC3)cn2)c1O]

The title compound was prepared in a manner similar to Example 112 using 6-(4-(4-cyano-2-methylphenyl)-5-hydroxy-1H-pyrazol-1-yl)nicotinic acid and (1r, 4r)-4-aminocyclohexanol. $^1$H NMR (400 MHz, DMSO-d$_6$) δ ppm 1.17-1.31 (m, 2H) 1.32-1.45 (m, 2H) 1.77-1.91 (m, 4H) 2.40-2.46 (m, 3H) 3.37-3.49 (m, 1H) 3.65-3.82 (m, 1H) 4.58 (br. s., 1H) 7.65 (dd, J=7.83, 1.52 Hz, 1H) 7.73 (s, 1H) 7.77 (d, J=7.83 Hz, 1H) 8.16 (br. s., 1H) 8.25-8.65 (m, 3H) 8.80-9.01 (m, 1H) 12.36-13.83 (m, 1H). MS m/z [M+H]$^+$ 418.2.

Example 140 6-(4-(4-cyano-2-methylphenyl)-5-hydroxy-1H-pyrazol-1-yl)-N-(1-cyclopropylpiperidin-4-yl)nicotinamide

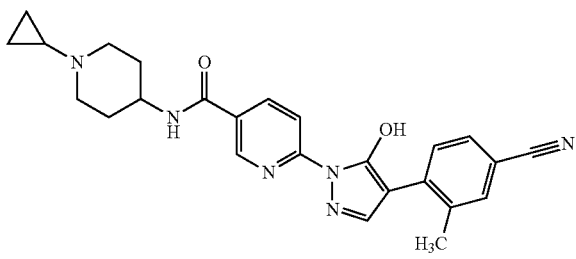 [SMILES: Cc1cc(C#N)ccc1-c1cnn(-c2ccc(C(=O)NC3CCN(C4CC4)CC3)cn2)c1O]

The title compound was prepared in a manner similar to Example 112 using 6-(4-(4-cyano-2-methylphenyl)-5-hydroxy-1H-pyrazol-1-yl)nicotinic acid and 1-cyclopropylpiperidin-4-amine. $^1$H NMR (400 MHz, DMSO-d$_6$) δ ppm 0.69 (d, J=6.06 Hz, 2H) 0.82 (br. s., 2H) 1.79 (d, J=10.86 Hz, 2H) 1.97 (d, J=10.86 Hz, 2H) 2.43 (s, 4H) 2.88-3.14 (m, 2H) 3.35-3.34 (m, 2H) 4.00 (d, J=6.57 Hz, 1H) 7.65 (dd, J=8.08, 1.52 Hz, 1H) 7.72 (s, 1H) 7.79 (d, J=8.08 Hz, 1H) 8.16 (s, 1H) 8.35-8.50 (m, 2H) 8.66 (d, J=7.07 Hz, 1H) 8.92 (t, J=1.52 Hz, 1H) 11.41-12.67 (m, 1H). MS m/z [M+H]$^+$ 443.2.

Example 141 6-(4-(4-cyano-2-methylphenyl)-5-hydroxy-1H-pyrazol-1-yl)-N-((1r,4r)-4-hydroxycyclohexyl)nicotinamide

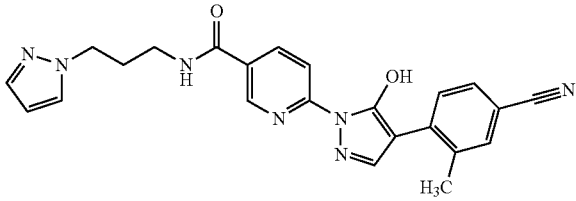 [SMILES: Cc1cc(C#N)ccc1-c1cnn(-c2ccc(C(=O)NCCCn3cccn3)cn2)c1O]

The title compound was prepared in a manner similar to Example 112 using 6-(4-(4-cyano-2-methylphenyl)-5-hydroxy-1H-pyrazol-1-yl)nicotinic acid and (1r, 4r)-4-aminocyclohexanol. $^1$H NMR (400 MHz, DMSO-d$_6$) δ ppm 2.06 (quin, J=6.88 Hz, 2H) 2.44 (s, 3H) 3.28 (q, J=6.74 Hz, 2H) 4.20 (t, J=6.82 Hz, 2H) 6.24 (t, J=2.02 Hz, 1H) 7.38-7.50 (m, 1H) 7.67 (dd, J=8.21, 1.39 Hz, 1H) 7.71-7.86 (m, 3H) 8.19 (br. s., 1H) 8.42 (d, J=7.33 Hz, 2H) 8.75 (t, J=5.18 Hz, 1H) 8.87-8.95 (m, 1H) 13.20 (br. s., 1H). MS m/z [M+H]$^+$ 428.2.

Example 142 6-(4-(4-cyano-2-methylphenyl)-5-hydroxy-1H-pyrazol-1-yl)-N-((tetrahydro-2H-pyran-2-yl)methyl)nicotinamide

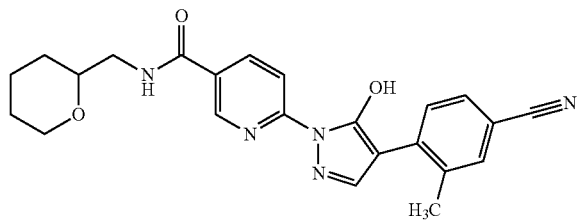 [SMILES: Cc1cc(C#N)ccc1-c1cnn(-c2ccc(C(=O)NCC3CCCCO3)cn2)c1O]

The title compound was prepared in a manner similar to Example 112 using 6-(4-(4-cyano-2-methylphenyl)-5-hydroxy-1H-pyrazol-1-yl)nicotinic acid and (tetrahydro-2H-pyran-2-yl)methanamine. $^1$H NMR (400 MHz, DMSO-d$_6$) δ ppm 1.17-1.31 (m, 2H) 1.32-1.45 (m, 2H) 1.77-1.91 (m, 4H) 2.40-2.46 (m, 3H) 3.37-3.49 (m, 1H) 3.65-3.82 (m, 1H) 4.58 (br. s., 1H) 7.65 (dd, J=7.83, 1.52 Hz, 1H) 7.73 (s, 1H) 7.77 (d, J=7.83 Hz, 1H) 8.16 (br. s., 1H) 8.25-8.65 (m, 3H) 8.80-9.01 (m, 1H) 12.36-13.83 (m, 1H). MS m/z [M+H]$^+$ 418.2.

Example 143 6-(4-(4-cyano-2-methylphenyl)-5-hydroxy-1H-pyrazol-1-yl)-N-((1-(methoxymethyl)cyclopentyl)methyl)nicotinamide

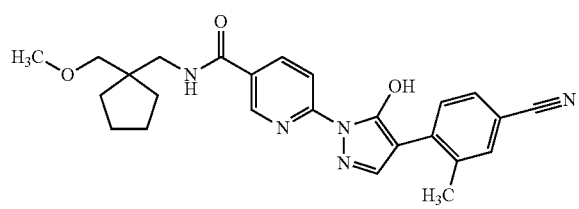 [SMILES: COCC1(CNC(=O)c2ccc(-n3ncc(-c4ccc(C#N)cc4C)c3O)nc2)CCCC1]

The title compound was prepared in a manner similar to Example 112 using 6-(4-(4-cyano-2-methylphenyl)-5-hydroxy-1H-pyrazol-1-yl)nicotinic acid and (1-(methoxymethyl)cyclopentyl)methanamine. $^1$H NMR (400 MHz, DMSO-d$_6$) δ ppm 1.26-1.38 (m, 2H) 1.38-1.59 (m, 6H) 2.37 (s, 3H) 3.13 (s, 2H) 3.21 (s, 3H) 3.26 (d, J=6.32 Hz, 2H) 7.59 (dd, J=7.83, 1.52 Hz, 1H) 7.66 (s, 1H) 7.73 (d, J=8.08 Hz, 1H) 8.09 (s, 1H) 8.33 (s, 2H) 8.42 (t, J=6.06 Hz, 1H) 8.82 (t, J=1.52 Hz, 1H) 12.56-13.49 (m, 1H). MS m/z [M+H]$^+$ 446.2.

Example 144 6-(4-(4-cyanophenyl)-5-hydroxy-1H-pyrazol-1-yl)-N-((1r,4r)-4-methylcyclohexyl)nicotinamide

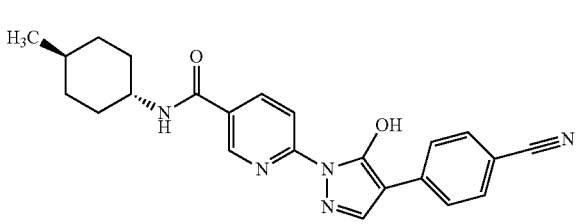 [SMILES: C[C@H]1CC[C@H](NC(=O)c2ccc(-n3ncc(-c4ccc(C#N)cc4)c3O)nc2)CC1]

The title compound was prepared in a manner similar to Example 112 using 6-(4-(4-cyanophenyl)-5-hydroxy-1H-pyrazol-1-yl)nicotinic acid and (1r,4r)-4-methylcyclohexanamine. $^1$H NMR (400 MHz, DMSO-d$_6$) δ ppm 0.82 (d, J=6.57 Hz, 3H) 0.87-1.05 (m, 2H) 1.29 (qd, J=12.34, 2.91 Hz, 3H) 1.64 (d, J=11.87 Hz, 2H) 1.72-1.85 (m, 2H) 3.67 (tdt, J=11.67, 11.67, 7.74, 3.92, 3.92 Hz, 1H) 7.72 (d, J=8.59 Hz, 2H) 8.07 (d, J=7.58 Hz, 2H) 8.23-8.48 (m, 3H) 8.57 (br. s., 1H) 8.75-8.93 (m, 1H) 13.47 (br. s., 1H). MS m/z [M+H]$^+$ 402.2.

Example 145 6-(4-(4-cyanophenyl)-5-hydroxy-1H-pyrazol-1-yl)-N-(3-methoxybutyl)nicotinamide

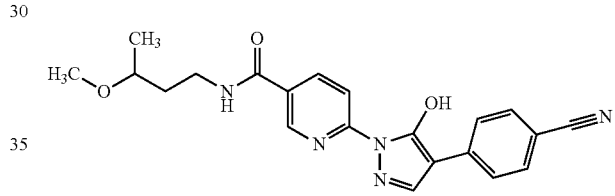

The title compound was prepared in a manner similar to Example 112 using 6-(4-(4-cyanophenyl)-5-hydroxy-1H-pyrazol-1-yl)nicotinic acid and 3-methoxybutan-1-amine. $^1$H NMR (400 MHz, DMSO-d$_6$) δ ppm 1.05 (d, J=6.32 Hz, 3H) 1.52-1.70 (m, 2H) 3.17 (s, 3H) 3.26-3.36 (m, 3H) 7.72 (d, J=8.59 Hz, 2H) 8.07 (d, J=6.57 Hz, 2H) 8.27-8.50 (m, 2H) 8.61 (t, J=5.43 Hz, 2H) 8.76-8.96 (m, 1H) 13.46 (br. s., 1H). MS m/z [M+H]$^+$ 392.1.

Example 146 6-(4-(4-cyanophenyl)-5-hydroxy-1H-pyrazol-1-yl)-N-(3-methoxy-2-methylpropyl)nicotinamide

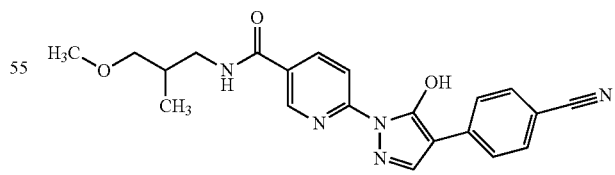

The title compound was prepared in a manner similar to Example 112 using 3-methoxy-2-methoxypropan-1-amine. $^1$H NMR (400 MHz, DMSO-d$_6$) δ ppm 0.84 (d, J=6.82 Hz, 3H) 1.85-2.02 (m, 1H) 3.03-3.31 (m, 7H) 7.72 (d, J=8.59 Hz, 2H) 8.07 (d, J=8.08 Hz, 2H) 8.26-8.50 (m, 2H) 8.53-8.69 (m, 2H) 8.77-8.91 (m, 1H) 13.47 (br. s., 1H). MS m/z [M+H]$^+$ 392.1.

Example 147 6-(4-(4-cyanophenyl)-5-hydroxy-1H-pyrazol-1-yl)-N-((1-(methoxymethyl)cyclopentyl)methyl)nicotinamide

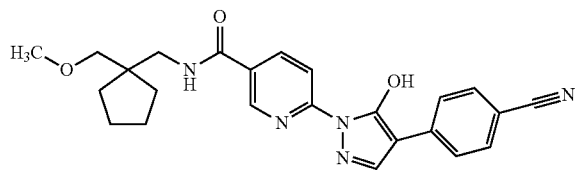 [SMILES: COCC1(CNC(=O)c2ccc(-n3ncc(-c4ccc(C#N)cc4)c3O)nc2)CCCC1]

The title compound was prepared in a manner similar to Example 112 using and (1-(methoxymethyl)cyclopentyl)methanamine. $^1$H NMR (400 MHz, DMSO-d$_6$) δ ppm 1.30-1.56 (m, 9H) 3.13 (s, 2H) 3.21 (s, 3H) 3.26 (d, J=6.32 Hz, 2H) 7.73 (d, J=8.34 Hz, 2H) 8.08 (br. s., 2H) 8.34 (d, J=7.83 Hz, 1H) 8.40-8.47 (m, 1H) 8.63 (br. s., 1H) 8.76-8.93 (m, 1H) 13.47 (br. s., 1H). MS m/z [M+H]$^+$ 432.2.

Example 148 6-(4-(4-cyanophenyl)-5-hydroxy-1H-pyrazol-1-yl)-N-(3-methoxypropyl)nicotinamide

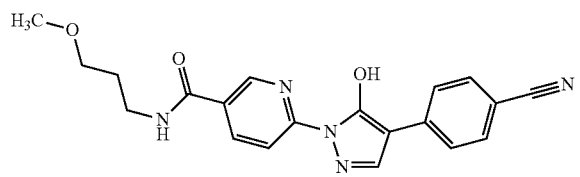 [SMILES: COCCCNC(=O)c1ccc(-n2ncc(-c3ccc(C#N)cc3)c2O)nc1]

Combined 6-(4-(4-cyanophenyl)-5-hydroxy-1H-pyrazol-1-yl)nicotinic acid (4.00 g, 13.06 mmol), EDCI (3.76 g, 19.59 mmol), and HOBT hydrate (3.00 g, 19.59 mmol) in DMF (39.6 mL) and treated with Hunig's base (6.82 mL, 39.2 mmol). Then 3-methoxypropan-1-amine (2.005 mL, 19.59 mmol) was added and the reaction mixture was stirred at ambient temperature for 24 h. The reaction mixture was then diluted with water (200 mL) and acidified with HCl (aq., 1N) until pH=5 and stirred to give a fine suspension. The solid was collected by filtration, suspended in MeOH (150 mL), and heated to reflux for 8 hours, the slowly cooled to ambient temperature. The solid was collected by filtration and dried in vacuum to give the title compound (4.25 g, 11.26 mmol, 86% yield) as a light yellow solid. $^1$H NMR (400 MHz, DMSO-d$_6$) δ ppm 1.78 (quin, J=6.63 Hz, 2H) 3.30-3.37 (m, 2H) 3.40 (t, J=6.32 Hz, 2H) 7.79 (d, J=8.34 Hz, 2H) 8.14 (d, J=6.57 Hz, 2H) 8.31-8.69 (m, 3H) 8.71 (t, J=5.31 Hz, 1H) 8.91 (s, 1H) 13.54 (br. s., 1H). MS [M+H] 378.

Example 149 6-(4-(4-cyanophenyl)-5-hydroxy-1H-pyrazol-1-yl)-N-(1-(methoxymethyl)cyclopentyl)nicotinamide

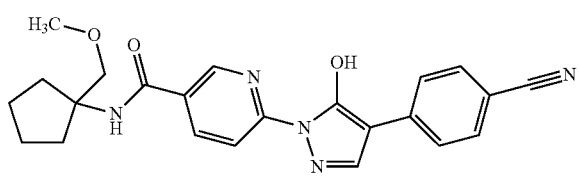 [SMILES: COCC1(NC(=O)c2ccc(-n3ncc(-c4ccc(C#N)cc4)c3O)nc2)CCCC1]

Combine 6-(4-(4-cyanophenyl)-5-hydroxy-1H-pyrazol-1-yl)nicotinic acid (30 mg, 0.098 mmol), EDCI (28.2 mg, 0.147 mmol), and HOBT hydrate (22.50 mg, 0.147 mmol) in DMF (1 mL) and added Hunig's base (50.6 mg, 0.392 mmol). Then 1-(methoxymethyl)cyclopentanamine (19.0 mg, 0.147 mmol) was added and the reaction mixture was stirred at ambient temperature for 20 h. The reaction mixture was purified using HPLC (45-70% ACN in water, TFA-buffered) to give the title compound as a solid. $^1$H NMR (400 MHz, DMSO-d6) δ ppm 1.52-1.80 (m, 6H) 2.00-2.13 (m, 2H) 3.27 (s, 3H) 3.60 (s, 2H) 7.79 (d, J=8.59 Hz, 2H) 7.96-8.78 (m, 6H) 8.79-8.99 (m, 1H) 13.53 (br. s., 1H). MS m/z [M+H]$^+$ 418.

Example 150 6-(4-(4-cyanophenyl)-5-hydroxy-1H-pyrazol-1-yl)-N-methylnicotinamide

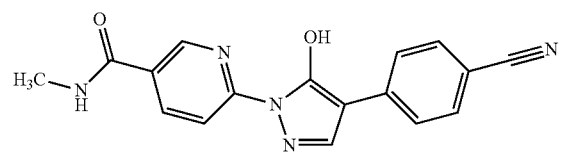 [SMILES: CNC(=O)c1ccc(-n2ncc(-c3ccc(C#N)cc3)c2O)nc1]

The title compound was prepared in a manner similar to Example 149 using methylamine. MS m/z [M+H]$^+$ 320

Example 151 6-(4-(4-cyanophenyl)-5-hydroxy-1H-pyrazol-1-yl)-N-cyclopentylnicotinamide

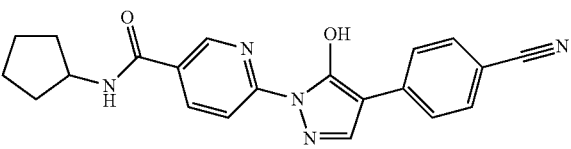 [SMILES: N#Cc1ccc(-c2cnn(-c3ccc(C(=O)NC4CCCC4)cn3)c2O)cc1]

The title compound was prepared in a manner similar to Example 149 using cyclopentanamine. $^1$H NMR (400 MHz, DMSO-d6) δ ppm 1.46-1.80 (m, 6H) 1.84-2.00 (m, 2H) 4.25 (dq, J=13.96, 7.05 Hz, 1H) 7.79 (d, J=8.34 Hz, 2H) 7.95-8.80 (m, 6H) 8.83-8.97 (m, 1H) 13.53 (br. s., 1H). MS m/z [M+H]$^+$ 374.

Example 152 6-(4-(4-cyanophenyl)-5-hydroxy-1H-pyrazol-1-yl)-N-(2-methoxyethyl)nicotinamide

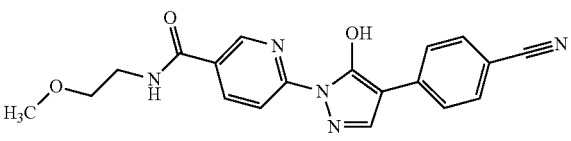 [SMILES: COCCNC(=O)c1ccc(-n2ncc(-c3ccc(C#N)cc3)c2O)nc1]

The title compound was prepared in a manner similar to Example 149 using 2-methoxyethanamine. MS m/z [M+H]$^+$ 364.

Example 153 6-(4-(4-cyanophenyl)-5-hydroxy-1H-pyrazol-1-yl)-N-((tetrahydrofuran-2-yl)methyl)nicotinamide

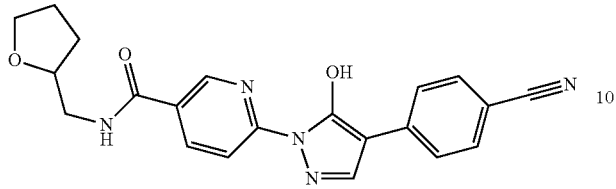

The title compound was prepared in a manner similar to Example 149 using (tetrahydrofuran-2-yl)methanamine. MS m/z [M+H]+ 390.

Example 154 (R)-6-(4-(4-cyanophenyl)-5-hydroxy-1H-pyrazol-1-yl)-N-(tetrahydrofuran-3-yl)nicotinamide

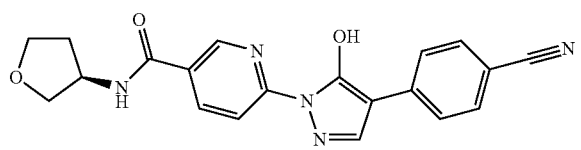 [SMILES: N#Cc1ccc(-c2cnn(-c3ccc(C(=O)N[C@@H]4CCOC4)cn3)c2O)cc1]

The title compound was prepared in a manner similar to Example 149 using (R)-tetrahydrofuran-3-amine. MS m/z [M+H]+ 376.

Example 155 6-(4-(4-cyanophenyl)-5-hydroxy-1H-pyrazol-1-yl)-N-(tetrahydro-2H-pyran-3-yl)nicotinamide

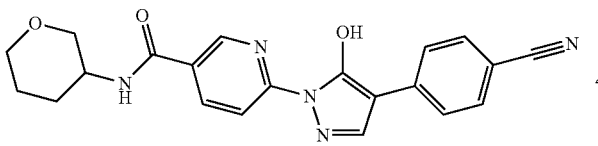

The title compound was prepared in a manner similar to Example 149 using tetrahydro-2H-pyran-3-amine. MS m/z [M+H]+ 390.

Example 156 6-(4-(4-cyanophenyl)-5-hydroxy-1H-pyrazol-1-yl)-N-(1-methoxy-3-methylbutan-2-yl)nicotinamide

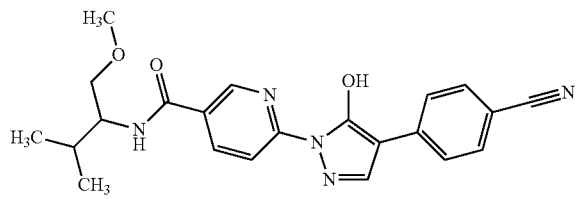 [SMILES: COCC(NC(=O)c1ccc(-n2ncc(-c3ccc(C#N)cc3)c2O)nc1)C(C)C]

The title compound was prepared in a manner similar to Example 149 using 1-methoxy-3-methylbutan-2-amine. MS m/z [M+H]+ 406.

Example 157 N-benzyl-6-(4-cyano-5'-hydroxy-1'H-[1,4'-bipyrazol]-1'-yl)nicotinamide

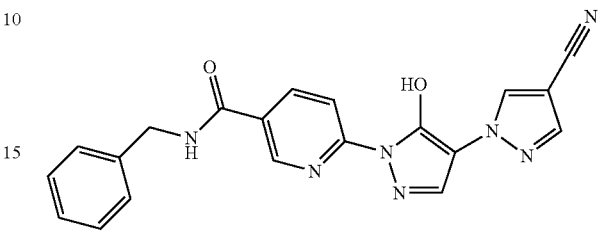

Combined N-benzyl-6-hydrazinylnicotinamide (103 mg, 0.427 mmol) and ethyl 2-(4-cyano-1H-pyrazol-1-yl)-3-(dimethylamino)acrylate (100 mg, 0.427 mmol) in 2-propanol (1.4 mL) and treated with 1.85N HCl (841 mg, 0.427 mmol). The resulting clear mixture was stirred for 2.5 h and then Hunig's base (297 µl, 1.708 mmol) was added and the resulting red solution was stirred at ambient temperature for 2.5 h. The reaction mixture was then concentrated in vacuo and purified using HPLC (20-95% ACN in water, TFA-buffered). Product-containing fractions were concentrated in vacuo to give a solid (volume ~50 mL). The solid was filtered and dried in vacuum to give the title compound (65.4 mg, 39.8% yield) as an off-white solid. $^1$H NMR (400 MHz, DMSO-$d_6$) δ ppm 4.53 (d, J=5.81 Hz, 2H) 7.27 (dq, J=8.46, 4.17 Hz, 1H) 7.31-7.44 (m, 4H) 8.29 (s, 1H) 8.33-8.58 (m, 3H) 8.93 (s, 1H) 8.98 (s, 1H) 9.30 (t, J=5.81 Hz, 1H) 12.33-14.49 (br s, 1H). MS m/z [M+H]+ 386.

Example 158 6-(4-cyano-5'-hydroxy-1'H-[1,4'-bipyrazol]-1'-yl)-N-((tetrahydro-2H-pyran-4-yl)methyl)nicotinamide

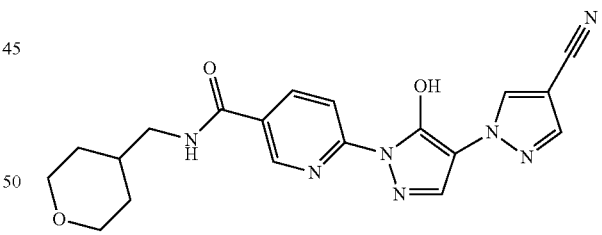

Combined 6-hydrazinyl-N-((tetrahydro-2H-pyran-4-yl)methyl)nicotinamide (107 mg, 0.427 mmol) and ethyl 2-(4-cyano-1H-pyrazol-1-yl)-3-(dimethylamino)acrylate (100 mg, 0.427 mmol) in 2-propanol (1423 µl) and treated with 1.85N HCl (841 mg, 0.427 mmol). The resulting clear mixture was stirred overnight (15 h) and then Hunig's base (297 µl, 1.708 mmol) was added and the reaction was stirred at ambient temperature for 2.5 h. The reaction mixture was then concentrated in vacuo and purified using HPLC (20-95% ACN in water, TFA-buffered). Product-containing fractions were concentrated in vacuo to give a solid (volume 20 mL). The solid was filtered and dried in vacuum to give the title compound (57.4 mg, 34.2% yield) as an off-white solid. $^1$H NMR (400 MHz, DMSO-$d_6$) δ ppm 1.22 (qd, J=12.21, 4.29 Hz, 2H) 1.62 (d, J=12.88 Hz, 2H) 1.81 (m, J=10.96, 7.29, 3.76, 3.76 Hz, 1H) 3.20 (t, 2H) 3.27 (t, J=10.86 Hz, 2H) 3.86 (dd, J=11.24, 2.65 Hz, 2H) 8.29 (s, 1H) 8.42 (br. s., 3H) 8.74 (t, J=5.68 Hz, 1H) 8.93 (s, 2H) 13.41 (br. s., 1H). MS m/z [M+H]+ 394.

Example 159 6-(4-(4-cyanophenyl)-5-hydroxy-1H-pyrazol-1-yl)-N-isopropylnicotinamide

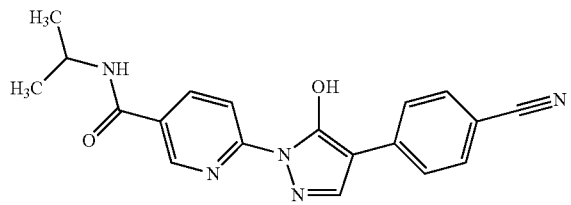 [SMILES: CC(C)NC(=O)c1ccc(-n2ncc(-c3ccc(C#N)cc3)c2O)nc1]

Combined 6-(4-(4-cyanophenyl)-5-hydroxy-1H-pyrazol-1-yl)nicotinic acid (100 mg, 0.327 mmol), EDCI (94 mg, 0.490 mmol), HOBT hydrate (75 mg, 0.490 mmol) in DMF (1 mL) and then add Hunig's base (127 mg, 0.980 mmol). Then propan-2-amine (28.9 mg, 0.490 mmol) was added and the mixture was stirred at ambient temperature for 16 h. The mixture was diluted with water (4 mL) and acidified with 1N HCl to pH=5-6 to give a solid. The solid was collected by filtration, washed with water (2 mL), and recrystallized from hot MeOH (3-6 mL) to give the title compound (62.0 mg, 54.7% yield) as an off-white solid. MS m/z [M+H]+ 348.

Example 160 6-(4-(4-cyanophenyl)-5-hydroxy-1H-pyrazol-1-yl)-N-isobutylnicotinamide

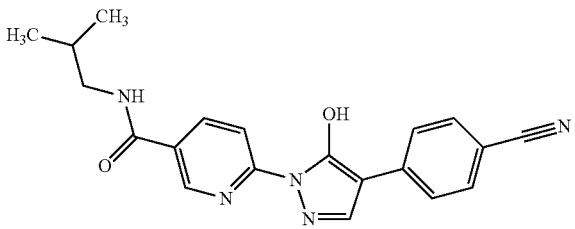 [SMILES: CC(C)CNC(=O)c1ccc(-n2ncc(-c3ccc(C#N)cc3)c2O)nc1]

The title compound was prepared in a manner similar to Example 159 using 2-methylpropan-1-amine. MS m/z [M+H]+ 362

Example 161 6-(4-(4-cyanophenyl)-5-hydroxy-1H-pyrazol-1-yl)-N-cyclopropylnicotinamide

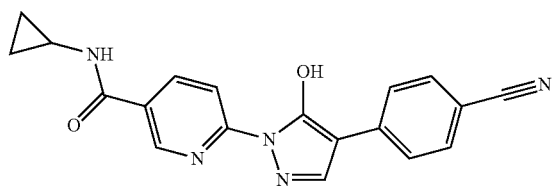 [SMILES: N#Cc1ccc(-c2cnn(-c3ccc(C(=O)NC4CC4)cn3)c2O)cc1]

The title compound was prepared in a manner similar to Example 159 using cyclopropanamine. 1H NMR (400 MHz, DMSO-d6) δ ppm 0.55-0.66 (m, 2H) 0.67-0.78 (m, 2H) 2.87 (m, J=10.99, 7.33, 3.98, 3.98 Hz, 1H) 7.79 (d, J=8.34 Hz, 2H) 8.14 (br. s., 2H) 8.40 (br. s., 1H) 8.42-8.60 (m, 1H) 8.68 (d, J=3.54 Hz, 2H) 8.85-8.90 (m, 1H) 13.53 (br. s., 2H). MS m/z [M+H]+ 346.

Example 162 6-(4-(4-cyanophenyl)-5-hydroxy-1H-pyrazol-1-yl)-N-(3-ethoxypropyl)nicotinamide

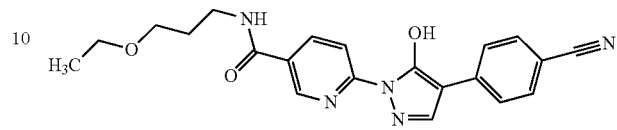

The title compound was prepared in a manner similar to Example 159 using 3-ethoxypropan-1-amine. 1H NMR (400 MHz, DMSO-d6) δ ppm 1.12 (t, J=7.07 Hz, 3H) 1.78 (quin, 2H) 3.35 (q, J=6.74 Hz, 2H) 3.42 (q, J=6.82 Hz, 4H) 7.79 (d, J=8.34 Hz, 2H) 8.14 (br. s., 2H) 8.41 (d, J=7.33 Hz, 2H) 8.69 (t, J=5.31 Hz, 1H) 8.87-8.95 (m, 1H) 13.54 (br. s., 1H). MS m/z [M+H]+ 392.

Example 163 6-(4-(4-cyanophenyl)-5-hydroxy-1H-pyrazol-1-yl)-N-(3-isopropoxypropyl)nicotinamide

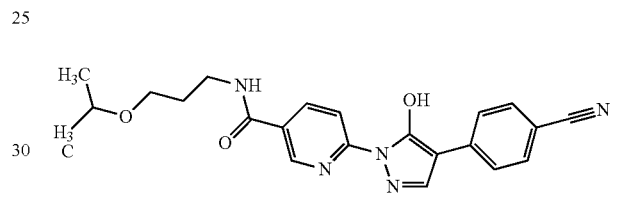

The title compound was prepared in a manner similar to Example 159 using 3-isopropoxypropan-1-amine. MS m/z [M+H]+ 406.

Example 164 6-(4-(4-cyanophenyl)-5-hydroxy-1H-pyrazol-1-yl)-N-((1s,4s)-4-hydroxycyclohexyl)nicotinamide

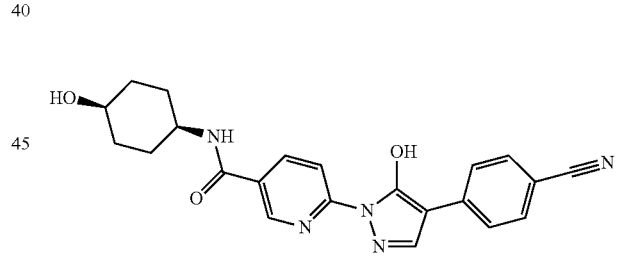

The title compound was prepared in a manner similar to Example 159 using (1s,4s)-4-aminocyclohexanol hydrochloride. MS m/z [M+H]+ 404.

Example 165 6-(4-(4-cyanophenyl)-5-hydroxy-1H-pyrazol-1-yl)-N-((1r,4r)-4-hydroxycyclohexyl)nicotinamide

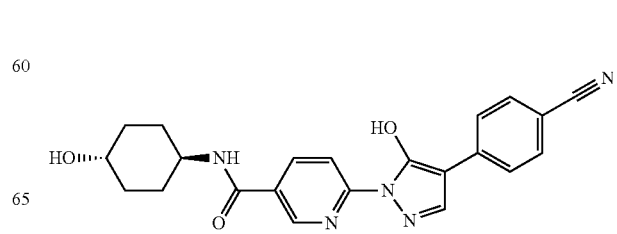

The title compound was prepared in a manner similar to Example 159 using (1r,4r)-4-aminocyclohexanol hydrochloride. $^1$H NMR (400 MHz, DMSO-d$_6$) δ ppm 1.42-1.86 (m, 8H) 3.71-3.96 (m, 5H) 4.41 (br. s., 1H) 7.21-7.68 (m, 2H) 8.06 (d, J=5.05 Hz, 1H) 8.13-8.79 (m, 4H) 8.90 (s, 1H) 13.53 (br. s., 1H). MS m/z [M+H]$^+$ 404.

Example 166 6-(5-hydroxy-4-(2-methoxypyridin-4-yl)-1H-pyrazol-1-yl)-N-((1s,4s)-4-hydroxycyclohexyl)nicotinamide

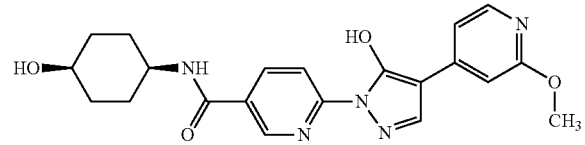 [SMILES: COc1cc(-c2cnn(-c3ccc(C(=O)N[C@H]4CC[C@@H](O)CC4)cn3)c2O)ccn1]

The title compound was prepared in a manner similar to Example 159 using 6-(5-hydroxy-4-(2-methoxypyridin-4-yl)-1H-pyrazol-1-yl)nicotinic acid and (1s,4s)-4-aminocyclohexanol hydrochloride. $^1$H NMR (400 MHz, DMSO-d$_6$) δ ppm 1.15-1.46 (m, 4H) 1.77-1.96 (m, 4H) 3.38-3.48 (m, 1H) 3.67-3.82 (m, 1H) 4.58 (br. s., 1H) 7.79 (d, J=8.34 Hz, 2H) 8.14 (d, J=6.82 Hz, 2H) 8.29-8.76 (m, 4H) 8.89 (s, 1H) 13.53 (br. s., 1H). MS m/z [M+H]$^+$ 410.

Example 167 6-(5-hydroxy-4-(2-methoxypyridin-4-yl)-1H-pyrazol-1-yl)-N-((1r,4r)-4-hydroxycyclohexyl)nicotinamide

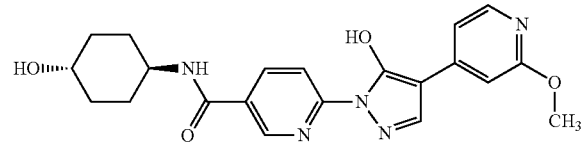 [SMILES: COc1cc(-c2cnn(-c3ccc(C(=O)N[C@H]4CC[C@H](O)CC4)cn3)c2O)ccn1]

The title compound was prepared in a manner similar to Example 159 using 6-(5-hydroxy-4-(2-methoxypyridin-4-yl)-1H-pyrazol-1-yl)nicotinic acid and (1r,4r)-4-aminocyclohexanol hydrochloride. MS m/z [M+H]$^+$ 410.

Example 168 6-(4-(4-cyano-2-methoxyphenyl)-5-hydroxy-1H-pyrazol-1-yl)-N-(1-(2-methoxyethyl)cyclopropyl)nicotinamide

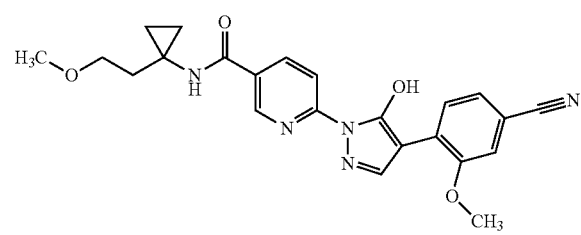 [SMILES: COCCC1(NC(=O)c2ccc(-n3ncc(-c4ccc(C#N)cc4OC)c3O)nc2)CC1]

The title compound was prepared in a manner similar to Example 159 using 6-(4-(4-cyano-2-methoxyphenyl)-5-hydroxy-1H-pyrazol-1-yl)nicotinic acid and 1-(2-methoxyethyl)cyclopropanamine. $^1$H NMR (400 MHz, DMSO-d6) δ 0.58-0.74 (m, 4H) 1.80 (t, J=6.9 Hz, 2H) 3.14 (s, 4H) 3.39 (t, J=7.1 Hz, 2H) 3.89 (s, 3H) 7.32-7.44 (m, 2H) 8.27-8.35 (m, 2H) 8.42 (d, J=8.8 Hz, 1H) 8.57 (d, J=7.6 Hz, 1H) 8.76 (s, 1H) 8.80 (d, J=1.8 Hz, 1H). MS m/z [M+H]$^+$ 434.5.

Example 169 6-(4-(4-cyanophenyl)-5-hydroxy-1H-pyrazol-1-yl)-N-((1s,2s)-2-methylcyclopropyl)nicotinamide

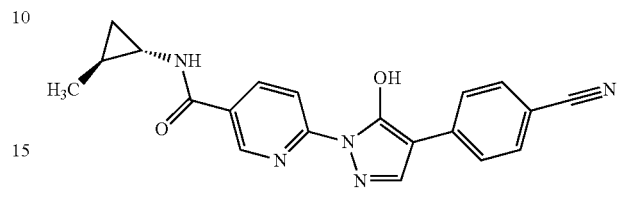

Combine 6-(4-(4-cyanophenyl)-5-hydroxy-1H-pyrazol-1-yl)nicotinic acid (100 mg, 0.327 mmol), EDCI (94 mg, 0.490 mmol), HOBT hydrate (75 mg, 0.490 mmol) in DMF (1 mL) and added Hunig's base (127 mg, 0.980 mmol). Then (1s,2s)-2-methylcyclopropanamine (34.8, 0.490 mmol) was added and the mixture was stirred at 60° C. for 3 h. The reaction mixture was diluted with water (4 mL) and acidified with 1N HCl to pH=5-6 to give a solid. The solid was collected by filtration, washed with water (2 mL), and recrystallized from hot MeOH (3-6 mL) to give the title compound (79.2 mg, 67.5% yield) as a white solid. MS m/z [M+H]$^+$ 360.

Example 170 (R)-6-(4-(4-cyanophenyl)-5-hydroxy-1H-pyrazol-1-yl)-N-(1,1,1-trifluoropropan-2-yl)nicotinamide

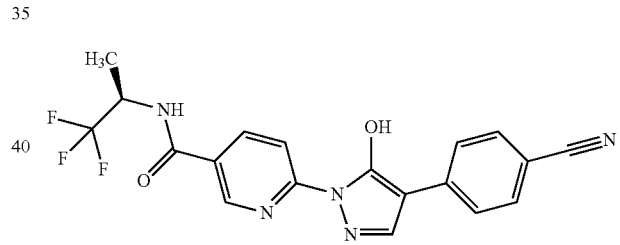

The title compound was prepared in a manner similar to Example 169 using (R)-1,1,1-trifluoropropan-2-amine. $^1$H NMR (400 MHz, DMSO-d$_6$) δ ppm 1.40 (d, J=7.07 Hz, 3H) 4.89 (m, J=15.36, 7.44, 7.44, 7.44, 7.44, 7.44 Hz, 1H) 7.79 (d, J=8.34 Hz, 2H) 8.15 (d, J=7.58 Hz, 2H) 8.35-8.77 (m, 3H) 8.95 (s, 1H) 9.08 (d, J=8.84 Hz, 1H) 13.53 (br. s., 1H). MS m/z [M+H]$^+$ 402.

Example 171 (S)-6-(4-(4-cyanophenyl)-5-hydroxy-1H-pyrazol-1-yl)-N-(1,1,1-trifluoropropan-2-yl)nicotinamide

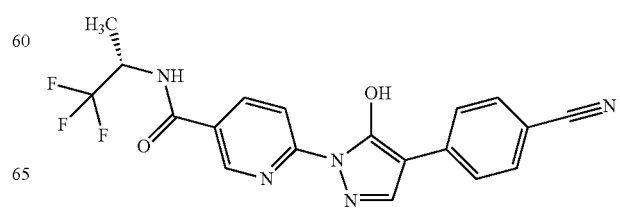

The title compound was prepared in a manner similar to Example 169 using (S)-1,1,1-trifluoropropan-2-amine. ¹H NMR (400 MHz, DMSO-d₆) δ ppm 1.40 (d, 3H) 4.89 (m, J=15.47, 7.64, 7.64, 7.64 Hz, 1H) 7.79 (d, J=8.34 Hz, 2H) 8.15 (d, J=5.30 Hz, 2H) 8.29-8.81 (m, 3H) 8.95 (s, 1H) 9.09 (d, J=8.59 Hz, 1H) 13.54 (br. s., 1H). MS m/z [M+H]⁺ 402.

Example 172 (R)-6-(4-(4-cyanophenyl)-5-hydroxy-1H-pyrazol-1-yl)-N-(1-(tetrahydro-2H-pyran-4-yl)ethyl)nicotinamide

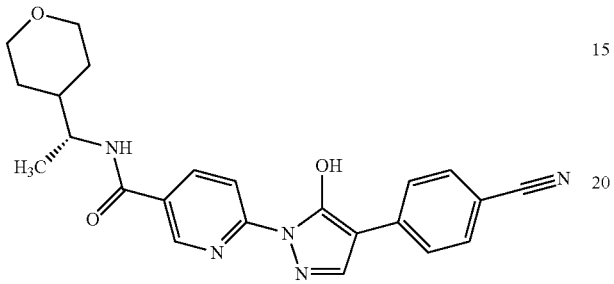

The title compound was prepared in a manner similar to Example 169 using (R)-1-(tetrahydro-2H-pyran-4-yl)ethanamine. MS m/z [M+H]⁺ 418.

Example 173 (S)-6-(4-(4-cyanophenyl)-5-hydroxy-1H-pyrazol-1-yl)-N-(1-(tetrahydro-2H-pyran-4-yl)ethyl)nicotinamide

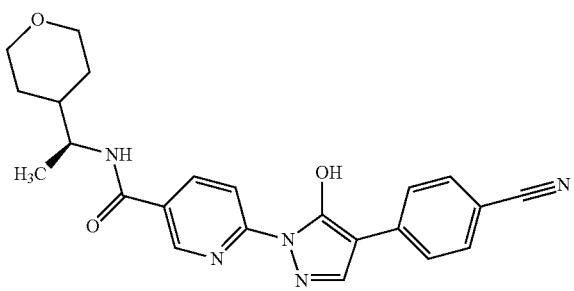 [SMILES: C[C@H](NC(=O)c1ccc(-n2ncc(-c3ccc(C#N)cc3)c2O)nc1)C1CCOCC1]

The title compound was prepared in a manner similar to Example 169 using (S)-1-(tetrahydro-2H-pyran-4-yl)ethanamine. MS m/z [M+H]⁺ 418.

Example 174 6-(4-(4-cyanophenyl)-5-hydroxy-1H-pyrazol-1-yl)-N-(2-(tetrahydro-2H-pyran-4-yl)ethyl)nicotinamide

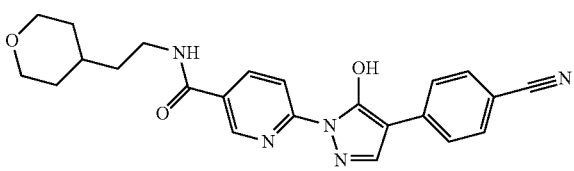 [SMILES: N#Cc1ccc(-c2cnn(-c3ccc(C(=O)NCCC4CCOCC4)cn3)c2O)cc1]

The title compound was prepared in a manner similar to Example 169 using 2-(tetrahydro-2H-pyran-4-yl)ethanamine hydrochloride. MS m/z [M+H]⁺ 418.

Example 175 6-(4-(4-cyanophenyl)-5-hydroxy-1H-pyrazol-1-yl)-N-(4-methoxy-2-methylbutan-2-yl)nicotinamide

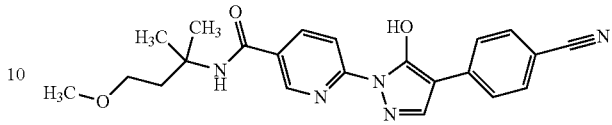

The title compound was prepared in a manner similar to Example 169 using 4-methoxy-2-methylbutan-2-amine. MS m/z [M+H]⁺ 406.

Example 176 6-(4-(4-cyanophenyl)-5-hydroxy-1H-pyrazol-1-yl)-N-(4-methoxybutan-2-yl)nicotinamide

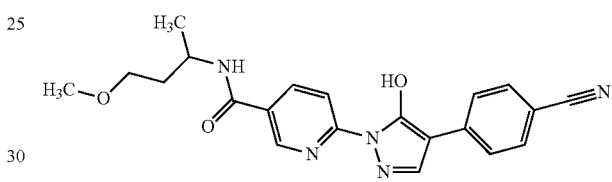

The title compound was prepared in a manner similar to Example 169 using 4-methoxybutan-2-amine. ¹H NMR (400 MHz, DMSO-d₆) δ ppm 1.18 (d, 3H) 1.64-1.88 (m, 2H) 3.22 (s, 3H) 3.38 (t, J=6.57 Hz, 2H) 4.03-4.21 (m, 1H) 7.79 (d, 2H) 8.14 (br. s., 2H) 8.27-8.79 (m, 4H) 8.90 (s, 1H) 13.53 (br. s., 1H). MS m/z [M+H]⁺ 392.

Example 177 6-(4-(4-cyanophenyl)-5-hydroxy-1H-pyrazol-1-yl)-N-(2-(tetrahydrofuran-3-yl)ethyl)nicotinamide

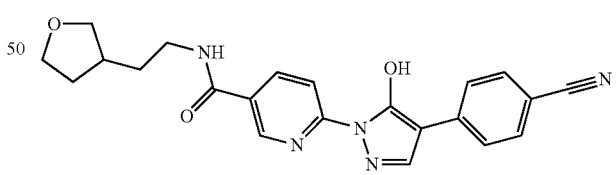

The title compound was prepared in a manner similar to Example 169 using 2-(tetrahydrofuran-3-yl)ethanamine. ¹H NMR (400 MHz, DMSO-d₆) δ ppm 1.48 (dq, J=11.97, 7.72 Hz, 1H) 1.62 (qd, J=7.16, 1.52 Hz, 2H) 2.04 (m, J=12.13, 7.58, 7.58, 4.80 Hz, 1H) 2.13-2.26 (m, 1H) 3.23-3.32 (m, 3H) 3.58-3.67 (m, 1H) 3.73 (td, J=8.21, 4.80 Hz, 1H) 3.80-3.87 (m, 1H) 7.79 (d, 2H) 8.14 (br. s., 2H) 8.31-8.78 (m, 4H) 8.87-8.94 (m, 4H) 13.54 (br. s., 1H). MS m/z [M+H]⁺ 404.

Example 178 6-(4-(4-cyanophenyl)-5-hydroxy-1H-pyrazol-1-yl)-N-(2-(tetrahydro-2H-pyran-3-yl)ethyl)nicotinamide

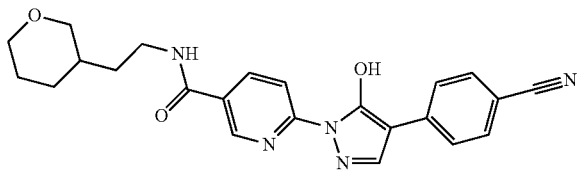 [SMILES: N#Cc1ccc(-c2cnn(-c3ccc(C(=O)NCCC4CCCOC4)cn3)c2O)cc1]

The title compound was prepared in a manner similar to Example 169 using 2-(tetrahydro-2H-pyran-3-yl)ethanamine. MS m/z [M+H]$^+$ 418.

Example 179 6-(4-(4-cyano-2-methylphenyl)-5-hydroxy-1H-pyrazol-1-yl)-N-(4-methoxybutyl)nicotinamide

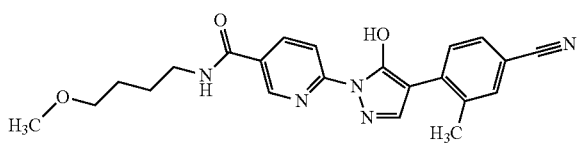 [SMILES: COCCCCNC(=O)c1ccc(-n2ncc(-c3ccc(C#N)cc3C)c2O)nc1]

Combined 6-(4-(4-cyano-2-methylphenyl)-5-hydroxy-1H-pyrazol-1-yl)nicotinic acid (50 mg, 0.156 mmol) and 4-methoxybutan-1-amine (29.0 mg, 0.281 mmol) in DMF (1 mL). Then added a solution of 1-(3-dimethylaminopropyl)-3-ethylcarbodiimide hydrochloride (50 mg, 0.261 mmol) and triethylamine (0.121 mL, 0.868 mmol) in DMF (0.5 mL), and a solution of HOBT (35 mg, 0.259 mmol) in DMF (0.5 mL). The mixture was then stirred overnight at room temperature. Into the reaction mixture was then poured 20 mL of saturated ammonium chloride solution and was rigorously stirred for 1 hour to give a solid. The solid was collected on by filtration, washed three times with saturated ammonium chloride solution, and then twice with ether, before being dried to give the title compound (49 mg, 77% yield) as an off-white solid. $^1$H NMR (400 MHz, DMSO-d$_6$) δ ppm 1.50-1.61 (m, 4H) 2.42 (s, 3H) 3.23 (s, 3H) 3.25-3.45 (m, 8H) 7.42-7.47 (m, 1H) 7.49 (s, 1H) 7.80 (s, 1H) 8.19 (dd, J=8.72, 2.40 Hz, 1H) 8.27 (d, J=8.34 Hz, 1H) 8.49-8.57 (m, 2H) 8.83 (d, J=2.02 Hz, 1H). MS m/z [M+H]$^+$ 406.2.

Example 180 6-(4-(4-cyano-2-methylphenyl)-5-hydroxy-1H-pyrazol-1-yl)-N-(cyclobutylmethyl)nicotinamide

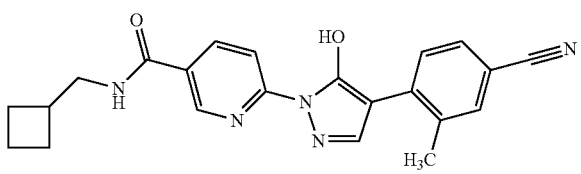 [SMILES: Cc1cc(C#N)ccc1-c1cnn(-c2ccc(C(=O)NCC3CCC3)cn2)c1O]

The title compound was prepared in a manner similar to Example 179 using cyclobutylmethanamine. $^1$H NMR (400 MHz, DMSO-d$_6$) δ ppm 1.64-1.90 (m, 4H) 1.93-2.09 (m, 2H) 2.43 (s, 3H) 7.61-7.84 (m, 3H) 8.10-8.24 (m, 1H) 8.35-8.51 (m, 2H) 8.62-8.76 (m, 1H) 8.86-8.97 (m, 1H) 12.98-13.41 (m, 1H). MS m/z [M+H]$^+$ 388.2.

Example 181 6-(4-(4-cyano-2-methylphenyl)-5-hydroxy-1H-pyrazol-1-yl)-N-(3-methoxybutyl)nicotinamide

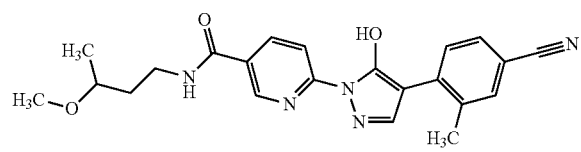 [SMILES: COC(C)CCNC(=O)c1ccc(-n2ncc(-c3ccc(C#N)cc3C)c2O)nc1]

The title compound was prepared in a manner similar to Example 179 using 3-methoxybutan-1-amine, HCl. $^1$H NMR (400 MHz, DMSO-d$_6$) δ ppm 1.11 (d, J=6.06 Hz, 3H) 1.54-1.80 (m, 2H) 2.41 (s, 3H) 3.24 (s, 3H) 7.23 (br. s., 3H) 7.36-7.50 (m, 2H) 7.72 (s, 1H) 8.14 (dd, J=8.84, 2.27 Hz, 1H) 8.34-8.40 (m, 1H) 8.46 (d, J=10.61 Hz, 1H) 8.58 (s, 1H) 8.80 (d, J=2.02 Hz, 1H). MS m/z [M+H]$^+$ 406.2.

Example 182 6-(4-(4-cyano-2-methylphenyl)-5-hydroxy-1H-pyrazol-1-yl)-N-(3-methoxy-2-methylpropyl)nicotinamide

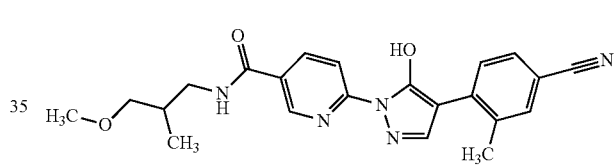

The title compound was prepared in a manner similar to Example 179 using 3-methoxy-2-methylpropan-1-amine, HCl. $^1$H NMR (400 MHz, DMSO-d$_6$) δ ppm 0.90 (d, J=6.82 Hz, 3H) 2.01 (dd, J=13.14, 6.57 Hz, 1H) 2.41 (s, 3H) 3.07-3.17 (m, 1H) 3.17-3.23 (m, 1H) 3.26 (s, 3H) 7.24 (br. s., 4H) 7.40 (dd, J=8.21, 1.64 Hz, 1H) 7.43 (s, 1H) 7.71 (s, 1H) 8.15 (dd, J=8.84, 2.53 Hz, 1H) 8.39 (d, J=8.34 Hz, 1H) 8.46 (t, J=5.68 Hz, 1H) 8.56 (d, J=8.84 Hz, 1H) 8.81 (d, J=2.02 Hz, 1H). MS m/z [M+H]$^+$ 406.2.

Example 183 6-(4-(4-cyano-2-methylphenyl)-5-hydroxy-1H-pyrazol-1-yl)-N-((1r,4r)-4-methylcyclohexyl)nicotinamide

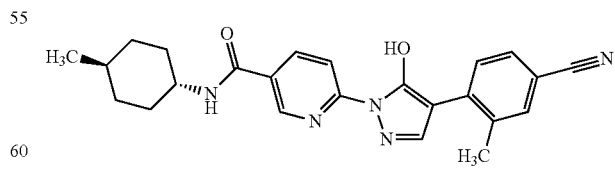

The title compound was prepared in a manner similar to Example 179 using (1r,4r)-4-methylcyclohexanamine. $^1$H NMR (400 MHz, DMSO-d$_6$) δ ppm 0.84-0.92 (m, 3H) 0.95-1.11 (m, 2H) 1.26-1.44 (m, 3H) 1.65-1.94 (m, 4H) 2.41 (s, 3H) 3.66-3.82 (m, 1H) 7.27 (br. s., 2H) 7.43 (d, J=8.34

Hz, 1H) 7.46-7.50 (m, 1H) 7.77 (s, 1H) 8.14-8.34 (m, 3H) 8.54 (d, J=8.84 Hz, 1H) 8.81 (d, J=2.02 Hz, 1H). MS m/z [M+H]⁺ 416.2.

Example 184 4-(5-hydroxy-1-(5-(3-methoxyazetidine-1-carbonyl)pyridin-2-yl)-1H-pyrazol-4-yl)-3-methylbenzonitrile

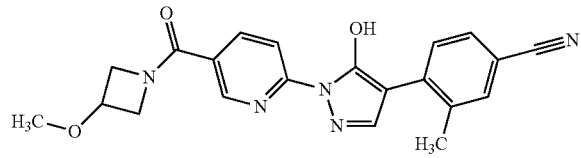 [SMILES: COC1CN(C(=O)c2ccc(-n3ncc(-c4ccc(C#N)cc4C)c3O)nc2)C1]

The title compound was prepared in a manner similar to Example 179 using 3-methoxyazetidine, HCl. ¹H NMR (400 MHz, DMSO-d₆) δ ppm 2.41 (s, 3H) 3.24 (s, 3H) 3.86 (br. s., 1H) 4.26 (br. s., 3H) 4.53 (br. s., 1H) 7.21 (br. s., 3H) 7.38-7.49 (m, 2H) 7.71-7.78 (m, 1H) 7.99 (dd, J=8.72, 2.40 Hz, 1H) 8.35 (d, J=8.34 Hz, 1H) 8.57 (d, J=8.84 Hz, 1H) 8.63 (d, J=2.02 Hz, 1H); MS m/z [M+H]⁺ 390.2.

Example 185 4-(1-(5-(2-oxa-6-azaspiro[3.3]heptane-6-carbonyl)pyridin-2-yl)-5-hydroxy-1H-pyrazol-4-yl)-3-methylbenzonitrile

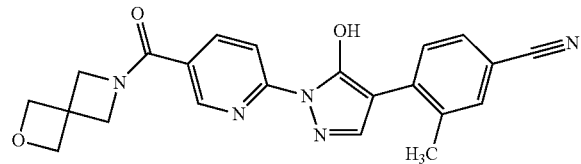 [SMILES: Cc1cc(C#N)ccc1-c1cnn(-c2ccc(C(=O)N3CC4(COC4)C3)cn2)c1O]

Combined 6-(4-(4-cyano-2-methylphenyl)-5-hydroxy-1H-pyrazol-1-yl)nicotinic acid (27 mg, 0.084 mmol) and 2-oxa-6-azaspiro[3.3]heptane (12.53 mg, 0.126 mmol) in acetonitrile (1 mL) and DMF (0.5 mL). Then triethylamine (0.035 mL, 0.253 mmol) and 1-(3-dimethylaminopropyl)-3-ethylcarbodiimide hydrochloride (19.39 mg, 0.101 mmol) were added and the reaction was stirred at room temperature overnight. A few drops of 1N NaOH solution were added to give a clear solution, and then the mixture was diluted in ACN and purified by HPLC (Waters SunFire C18, 5 μm, ID 30×75 mm, 35-65% ACN/water+0.05% TFA) to give the title compound (3.6 mg, 10.64% yield) as a white solid. ¹H NMR (400 MHz, DMSO-d₆) δ ppm 2.43 (s, 3H) 4.23-4.30 (m, 2H) 4.53-4.60 (m, 2H) 4.65-4.74 (m, 3H) 7.61-7.88 (m, 4H) 8.24 (br. s., 2H) 8.49-8.78 (m, 2H) 13.27 (br. s., 2H). MS m/z [M+H]⁺ 402.1.

Example 186 6-(4-(4-cyano-2-methylphenyl)-5-hydroxy-1H-pyrazol-1-yl)-N-(1-methylazetidin-3-yl)nicotinamide

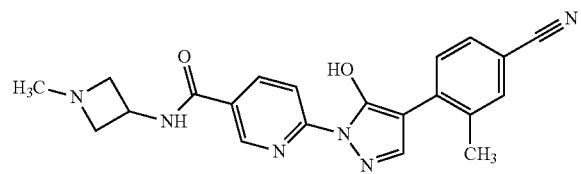 [SMILES: Cc1cc(C#N)ccc1-c1cnn(-c2ccc(C(=O)NC3CN(C)C3)cn2)c1O]

Combined 6-(4-(4-cyano-2-methylphenyl)-5-hydroxy-1H-pyrazol-1-yl)nicotinic acid (27 mg, 0.084 mmol), 1-methylazetidin-3-amine, 2HCl (16.09 mg, 0.101 mmol) and 1-hydroxybenzotriazole (13.67 mg, 0.101 mmol) in acetonitrile (1 mL) and DMF (0.5 mL). Then triethylamine (0.047 mL, 0.337 mmol) and 1-(3-dimethylaminopropyl)-3-ethylcarbodiimide hydrochloride (19.39 mg, 0.101 mmol) were added and the reaction was stirred at room temperature overnight. The reaction mixture was then diluted with acetonitrile and purified by preparatory HPLC (Waters SunFire C18, 5 μm, ID 30×75 mm, 20-50% ACN/water+0.05% TFA) to give the title compound as the TFA salt (12 mg, 28.3% yield) as a white solid. ¹H NMR (400 MHz, DMSO-d₆) δ ppm 2.43 (s, 3H) 2.88-2.97 (m, 3H) 3.99-4.60 (m, 5H) 4.76 (br. s., 1H) 7.57-7.87 (m, 3H) 8.22 (br. s., 1H) 8.36-8.72 (m, 2H) 8.94 (s, 1H) 9.32 (d, J=5.81 Hz, 1H) 9.83 (br. s., 1H) 13.25 (br. s., 1H). MS m/z [M+H]⁺ 389.1.

Example 187 6-(4-(4-cyano-2-methylphenyl)-5-hydroxy-1H-pyrazol-1-yl)-N-(1-(dimethylamino)-2-methylpropan-2-yl)nicotinamide

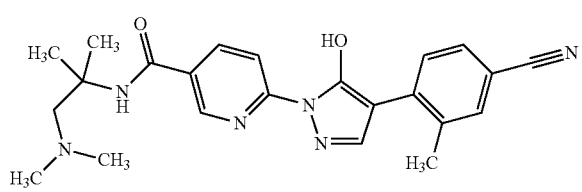 [SMILES: Cc1cc(C#N)ccc1-c1cnn(-c2ccc(C(=O)NC(C)(C)CN(C)C)cn2)c1O]

The title compound was prepared in a manner similar to Example 185 using N1,N1,2-trimethylpropane-1,2-diamine, 2HCl to give the title compound as a TFA salt (36 mg, 40.1% yield) as a white solid. ¹H NMR (400 MHz, DMSO-d₆) δ ppm 1.35-1.64 (m, 6H) 2.44 (s, 3H) 2.74-2.94 (m, 6H) 3.59-3.73 (m, 3H) 7.59-7.91 (m, 3H) 8.04-8.73 (m, 4H) 8.82-8.99 (m, 1H) 9.14 (br. s., 1H) 13.21 (br. s., 1H). MS m/z [M+H]⁺ 419.2.

Example 188 N-benzyl-6-(4-(4-cyano-3-fluorophenyl)-5-hydroxy-1H-pyrazol-1-yl)nicotinamide

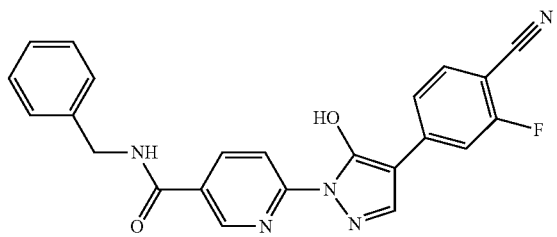 [SMILES: N#Cc1ccc(-c2cnn(-c3ccc(C(=O)NCc4ccccc4)cn3)c2O)cc1F]

Combined N-benzyl-6-hydrazinylnicotinamide (30 mg, 0.124 mmol), methyl 2-(4-cyano-3-fluorophenyl)-3-(dimethylamino)acrylate (40.0 mg, 0.161 mmol) and acetic acid (0.021 mL, 0.371 mmol) in 2-propanol (1.0 mL) and stirred at 20° C. for 28 h. Then Hunig's base (0.130 mL, 0.743 mmol) was added and the reaction mixture was heated at 50° C. for 15 h. The reaction mixture was diluted with DMSO (0.1 mL) and purified by prep HPLC to give the title compound (22 mg, 43.0% yield) as a peach solid. $^1$H NMR (400 MHz, DMSO-d6) δ ppm 4.53 (d, J=5.8 Hz, 2H) 7.21-7.30 (m, 1H) 7.31-7.39 (m, 4H) 7.85 (t, J=7.7 Hz, 1H) 7.99 (d, J=8.3 Hz, 1H) 8.10 (d, J=11.9 Hz, 1H) 8.42-8.58 (m, 2H) 8.74 (br. s., 1H) 8.97 (d, J=1.5 Hz, 1H) 9.27 (t, J=5.9 Hz, 1H) 13.81 (br. s., 1H). MS m/z 414 [M+H]$^+$.

Example 189 6-(4-(4-cyano-3-fluorophenyl)-5-hydroxy-1H-pyrazol-1-yl)-N-((tetrahydro-2H-pyran-4-yl)methyl)nicotinamide

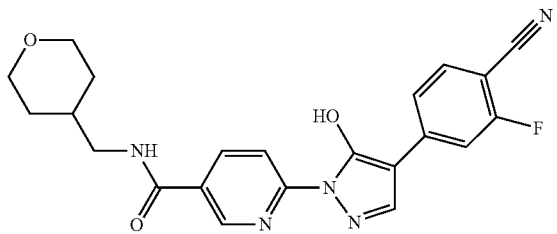 [SMILES: N#Cc1ccc(-c2cnn(-c3ccc(C(=O)NCC4CCOCC4)cn3)c2O)cc1F]

The title compound was prepared in a manner similar to Example 188 using 6-hydrazinyl-N-((tetrahydro-2H-pyran-4-yl)methyl)nicotinamide, HCl. $^1$H NMR (400 MHz, DMSO-d$_6$) δ ppm 1.13-1.30 (m, 2H) 1.62 (d, J=12.9 Hz, 2H) 1.81 (ddd, J=11.1, 7.3, 4.0 Hz, 1H) 3.20 (t, J=6.3 Hz, 2H) 3.27 (td, J=11.6, 1.8 Hz, 2H) 3.86 (dd, J=11.2, 2.7 Hz, 2H) 7.80-7.90 (m, 1H) 7.99 (d, J=8.1 Hz, 1H) 8.10 (d, J=12.1 Hz, 1H) 8.37-8.45 (m, 1H) 8.48 (br. s., 1H) 8.66-8.81 (m, 2H) 8.91 (s, 1H) 13.82 (br. s., 1H). MS m/z 422 [M+H]$^+$.

Example 190 6-(5-hydroxy-4-(4-oxopyridin-1(4H)-yl)-1H-pyrazol-1-yl)-N-((tetrahydro-2H-pyran-4-yl)methyl)nicotinamide

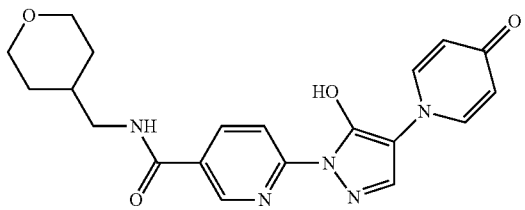 [SMILES: O=C(NCC1CCOCC1)c1ccc(-n2ncc(-n3ccc(=O)cc3)c2O)nc1]

Combined 6-hydrazinyl-N-((tetrahydro-2H-pyran-4-yl)methyl)nicotinamide, 1.0 HCl (30 mg, 0.105 mmol), ethyl 3-(dimethylamino)-2-(4-oxopyridin-1(4H)-yl)acrylate (37.1 mg, 0.157 mmol) and acetic acid (0.018 mL, 0.314 mmol) in 2-propanol (0.8 mL) and stirred at 20° C. for 1 hour and then at 50° C. for 16 hours and then 80° C. for 24 h. The reaction mixture was then diluted with 200 uL DMSO and purified by prep HPLC (ACN/water with formic acid) to give the title compound (11 mg, 26.6% yield) as a yellow solid. $^1$H NMR (400 MHz, DMSO-d$_6$) δ ppm 1.11-1.32 (m, 2H) 1.62 (d, J=13.4 Hz, 2H) 1.73-1.90 (m, 1H) 3.20 (t, J=6.2 Hz, 2H) 3.25 (s, 2H) 3.86 (dd, J=11.4, 2.8 Hz, 2H) 6.56 (br. s., 2H) 8.19 (br. s., 2H) 8.40 (t, J=7.7 Hz, 3H) 8.71 (t, J=5.3 Hz, 1H) 8.91 (s, 1H). MS m/z 396 [M+H]$^+$.

Example 191 N-benzyl-6-(5-hydroxy-4-(4-oxopyridin-1(4H)-yl)-1H-pyrazol-1-yl)nicotinamide

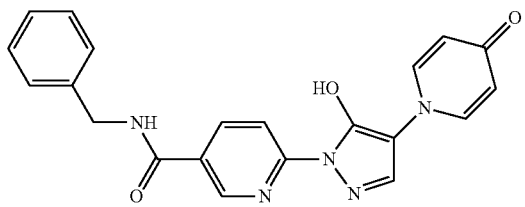 [SMILES: O=C(NCc1ccccc1)c1ccc(-n2ncc(-n3ccc(=O)cc3)c2O)nc1]

The title compound was prepared in a manner similar to Example 188 using N-benzyl-6-hydrazinylnicotinamide and ethyl 3-(dimethylamino)-2-(4-oxopyridin-1(4H)-yl)acrylate. MS m/z 388 [M+H]$^+$. $^1$H NMR (400 MHz, DMSO-d$_6$) δ ppm 4.53 (d, J=5.6 Hz, 2H) 6.68 (br. s., 2H) 7.27 (dq, J=8.5, 4.2 Hz, 1H) 7.30-7.41 (m, 4H) 8.29 (br. s., 2H) 8.37-8.54 (m, 3H) 8.97 (s, 1H) 9.27 (t, J=5.8 Hz, 1H).

Example 192 6-(5-hydroxy-4-(2-oxopyridin-1(2H)-yl)-1H-pyrazol-1-yl)-N-((tetrahydro-2H-pyran-4-yl)methyl)nicotinamide

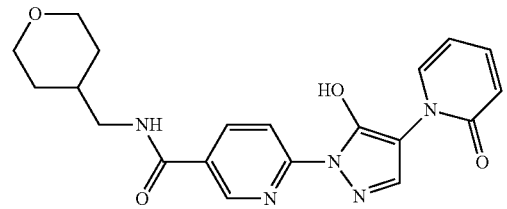 [SMILES: O=C(NCC1CCOCC1)c1ccc(-n2ncc(-n3ccccc3=O)c2O)nc1]

The title compound was prepared in a manner similar to Example 188 using 6-hydrazinyl-N-((tetrahydro-2H-pyran-4-yl)methyl)nicotinamide and ethyl 3-(dimethylamino)-2-(2-oxopyridin-1(2H)-yl)acrylate. $^1$H NMR (400 MHz, DMSO-d$_6$) δ ppm 1.10-1.32 (m, 2H) 1.62 (d, J=12.9 Hz, 2H) 1.81 (ddd, J=11.1, 7.3, 4.0 Hz, 1H) 3.20 (t, J=6.3 Hz, 2H) 3.24-3.31 (m, 2H) 3.86 (dd, J=11.2, 2.7 Hz, 2H) 6.31 (t, J=6.6 Hz, 1H) 6.44-6.59 (m, 1H) 7.48 (t, J=7.8 Hz, 1H) 7.80 (br. s., 1H) 8.27-8.61 (m, 2H) 8.73 (br. s., 1H) 8.92 (s, 1H) 13.12 (br. s., 1H). MS m/z 396 [M+H]$^+$.

Example 193 N-benzyl-6-(5-hydroxy-4-(2-oxopyridin-1(2H)-yl)-1H-pyrazol-1-yl)nicotinamide

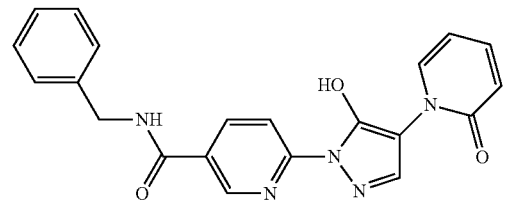 [SMILES: O=C(NCc1ccccc1)c1ccc(-n2ncc(-n3ccccc3=O)c2O)nc1]

The title compound was prepared in a manner similar to Example 188 using ethyl 3-(dimethylamino)-2-(2-oxopyridin-1(2H)-yl)acrylate. $^1$H NMR (400 MHz, DMSO-d$_6$) δ ppm 4.52 (d, J=5.8 Hz, 2H) 6.31 (td, J=6.8, 1.1 Hz, 1H) 6.49 (d, J=9.1 Hz, 1H) 7.19-7.40 (m, 6H) 7.47 (ddd, J=9.2, 6.8, 2.0 Hz, 1H) 7.80 (d, J=6.1 Hz, 1H) 8.28 (br. s., 1H) 8.36-8.56 (m, 1H) 8.93-9.02 (m, 1H) 9.27 (t, J=5.8 Hz, 1H) 13.05 (br. s., 1H). MS m/z 388 [M+H]+.

Example 194 6-(4-(4-cyano-2-methoxyphenyl)-5-hydroxy-1H-pyrazol-1-yl)-N-((tetrahydro-2H-pyran-4-yl)methyl)nicotinamide

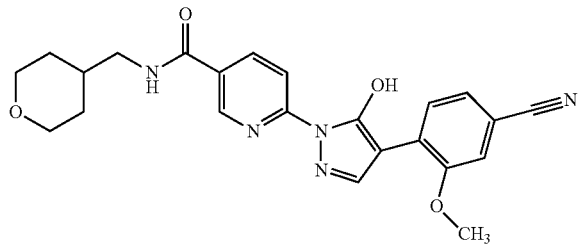 [SMILES: COc1cc(C#N)ccc1-c1cnn(-c2ccc(C(=O)NCC3CCOCC3)cn2)c1O]

The title compound was prepared in a manner similar to Example 188 using ethyl 2-(4-cyano-2-methoxyphenyl)-3-(dimethylamino)acrylate and 6-hydrazinyl-N-((tetrahydro-2H-pyran-4-yl)methyl)nicotinamide to afford the title compound. $^1$H NMR (400 MHz, DMSO-d6) δ ppm 1.09 (t, J=7.1 Hz, 11H) 1.22 (d, J=9.6 Hz, 3H) 1.62 (d, J=12.1 Hz, 2H) 3.19 (dd, J=11.6, 5.6 Hz, 4H) 3.86 (d, J=9.6 Hz, 2H) 3.97 (s, 3H) 7.38-7.57 (m, 2H) 8.43 (br. s., 2H) 8.72 (br. s., 1H) 8.92 (s, 1H). MS m/z [M+H]+ 434.4.

Example 195 N-benzyl-6-(4-(4-cyano-2-methoxyphenyl)-5-hydroxy-1H-pyrazol-1-yl)nicotinamide

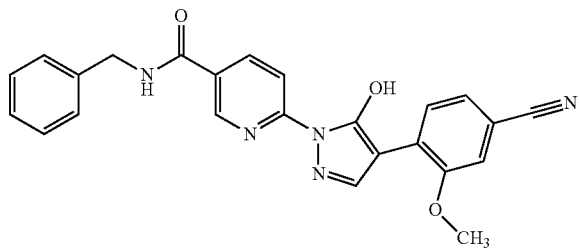 [SMILES: COc1cc(C#N)ccc1-c1cnn(-c2ccc(C(=O)NCc3ccccc3)cn2)c1O]

The title compound was prepared in a manner similar to Example 188 using ethyl 2-(4-cyano-2-methoxyphenyl)-3-(dimethylamino)acrylate and N-benzyl-6-hydrazinylnicotinamide. $^1$H NMR (400 MHz, DMSO-d6) δ ppm 3.97 (s, 3H) 4.53 (d, J=5.6 Hz, 2H) 7.27 (d, J=3.8 Hz, 1H) 7.36 (d, J=4.0 Hz, 5H) 7.42-7.59 (m, 2H) 8.47 (d, J=6.6 Hz, 1H) 8.98 (s, 1H) 9.28 (br. s., 1H). MS m/z [M+H]+ 426.4.

Example 196 N-benzyl-6-(4-(2-chloro-4-cyanophenyl)-5-hydroxy-1H-pyrazol-1-yl)nicotinamide

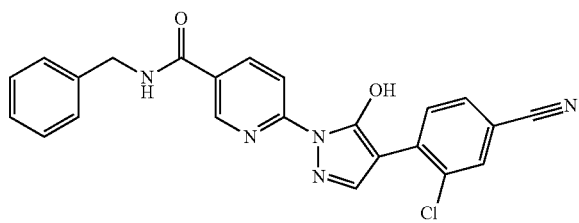 [SMILES: N#Cc1ccc(-c2cnn(-c3ccc(C(=O)NCc4ccccc4)cn3)c2O)c(Cl)c1]

The title compound was prepared in a manner similar to Example 188 using ethyl 2-(2-chloro-4-cyanophenyl)-3-(dimethylamino)acrylate and N-benzyl-6-hydrazinylnicotinamide. $^1$H NMR (400 MHz, DMSO-d6) δ ppm 4.44 (d, J=5.8 Hz, 2H) 7.13-7.22 (m, 2H) 7.27 (d, J=4.3 Hz, 5H) 7.75 (d, J=8.3 Hz, 1H) 8.00 (s, 1H) 8.30-8.47 (m, 2H) 8.90 (s, 1H) 9.20 (t, J=5.3 Hz, 1H). MS m/z [M+H]+ 430.3.

Example 197 6-(4-(2-chloro-4-cyanophenyl)-5-hydroxy-1H-pyrazol-1-yl)-N-((tetrahydro-2H-pyran-4-yl)methyl)nicotinamide

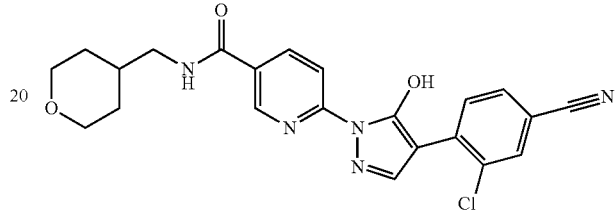

The title compound was prepared in a manner similar to Example 188 using 6-hydrazinyl-N-((tetrahydro-2H-pyran-4-yl)methyl)nicotinamide and ethyl 2-(2-chloro-4-cyanophenyl)-3-(dimethylamino)acrylate. $^1$H NMR (400 MHz, DMSO-d6) δ ppm 1.13-1.39 (m, 4H) 1.68 (d, J=12.9 Hz, 2H) 3.20-3.37 (m, 6H) 3.63 (s, 1H) 3.92 (dd, J=11.2, 2.7 Hz, 2H) 7.90 (d, J=8.1 Hz, 1H) 8.15 (s, 1H) 8.49 (d, J=3.8 Hz, 2H) 8.73-8.87 (m, 1H) 8.98 (s, 1H). MS m/z [M+H]+ 438.4.

Example 198 give 6-(4-(4-cyanophenyl)-5-hydroxy-1H-pyrazol-1-yl)-N-(1-methylcyclopropyl)nicotinamide

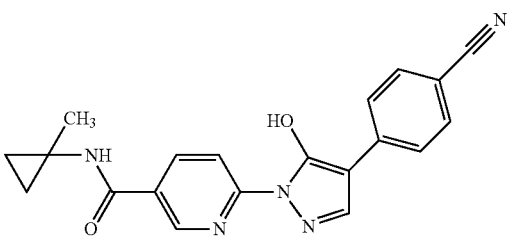 [SMILES: CC1(NC(=O)c2ccc(-n3ncc(-c4ccc(C#N)cc4)c3O)nc2)CC1]

Combined EDC (56.3 mg, 0.294 mmol), HOBT (39.7 mg, 0.294 mmol) and 6-(4-(4-cyanophenyl)-5-hydroxy-1H-pyrazol-1-yl)nicotinic acid (45 mg, 0.147 mmol) in DMF (0.8 mL) then added 1-methylcyclopropanamine hydrochloride (47.4 mg, 0.441 mmol) and Hunig's base (0.180 mL, 1.028 mmol) and stirred at 20° C. for 16 h. The reaction mixture was diluted with 100 uL DMSO and purified by prep HPLC (ACN/water with formic acid) to give the title compound (27 mg, 51.1% yield) as a yellow solid. $^1$H NMR (400 MHz, DMSO-d$_6$) δ ppm 0.60-0.68 (m, 2H) 0.73-0.81 (m, 2H) 1.40 (s, 3H) 7.75 (d, J=8.6 Hz, 2H) 8.06-8.16 (m, 2H) 8.35 (dd, J=8.6, 2.3 Hz, 1H) 8.46 (d, J=8.8 Hz, 1H) 8.54 (s, 1H) 8.82-8.90 (m, 2H) 13.53 (br. s., 1H). MS m/z 360 [M+H]+.

Example 199 6-(4-(4-cyanophenyl)-5-hydroxy-1H-pyrazol-1-yl)-N-(1-(methoxymethyl)cyclobutyl)nicotinamide

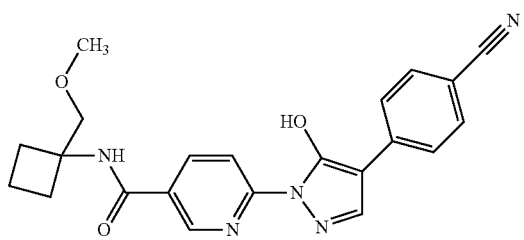 [SMILES: COCC1(NC(=O)c2ccc(-n3ncc(-c4ccc(C#N)cc4)c3O)nc2)CCC1]

Combined 6-(4-(4-cyanophenyl)-5-hydroxy-1H-pyrazol-1-yl)nicotinic acid (48 mg, 0.157 mmol), HATU (119 mg, 0.313 mmol) and 1-(methoxymethyl)cyclobutanamine hydrochloride (47.5 mg, 0.313 mmol) in DMF (0.9 mL) then added Hunig's base (0.137 mL, 0.784 mmol) and the reaction mixture was stirred at 20° C. for 1 h. Water (100 uL) was then added and the mixture was heated at 70° C. for 16 h, then diluted with 100 uL DMSO and purified by prep HPLC (ACN/water with formic acid) to give the title compound (25 mg, 39.5% yield) as a yellow solid. $^1$H NMR (400 MHz, DMSO-$d_6$) δ ppm 1.72-1.95 (m, 2H) 2.10-2.21 (m, 2H) 2.21-2.35 (m, 2H) 3.31 (s, 3H) 3.65 (s, 2H) 7.79 (d, J=8.6 Hz, 2H) 8.14 (d, J=6.1 Hz, 2H) 8.44 (d, J=6.6 Hz, 2H) 8.65 (s, 2H) 8.87-8.95 (m, 1H) 13.55 (br. s., 1H). MS m/z 404 [M+H]$^+$.

Example 200 6-(4-(4-cyanophenyl)-5-hydroxy-1H-pyrazol-1-yl)-N-(1-methoxy-2-methylpropan-2-yl)nicotinamide

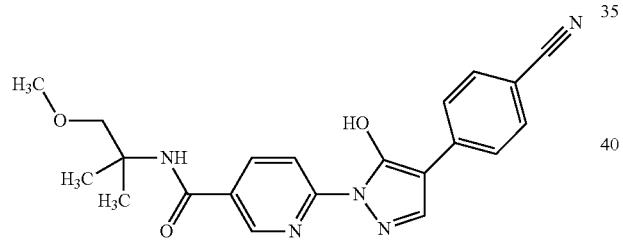

The title compound was prepared in a manner similar to Example 199 using 1-methoxy-2-methylpropan-2-amine. $^1$H NMR (400 MHz, DMSO-$d_6$) δ ppm 1.35 (s, 6H) 3.29 (s, 3H) 3.49-3.59 (m, 2H) 7.80 (d, J=8.6 Hz, 2H) 7.96 (s, 1H) 8.15 (d, J=4.5 Hz, 2H) 8.40 (d, J=7.1 Hz, 2H) 8.66 (br. s., 1H) 8.82-8.89 (m, 1H) 13.57 (br. s., 1H). MS m/z 392 [M+H]$^+$.

Example 201 6-(4-(4-cyanophenyl)-5-hydroxy-1H-pyrazol-1-yl)-N-(1-(methoxymethyl)cyclopropyl)nicotinamide

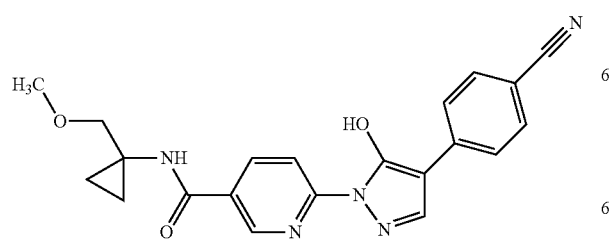

The title compound was prepared in a manner similar to Example 199 using 1-(methoxymethyl)cyclopropanamine hydrochloride. $^1$H NMR (400 MHz, DMSO-$d_6$) δ ppm 0.80 (s, 4H) 3.29 (s, 3H) 3.49 (s, 2H) 7.79 (d, J=8.6 Hz, 2H) 8.15 (d, J=7.6 Hz, 2H) 8.38-8.55 (m, 2H) 8.66 (br. s., 1H) 8.89-8.95 (m, 1H) 8.97 (s, 1H) 13.52 (s, 1H). MS m/z 390 [M+H]$^+$.

Example 202 N-(tert-butyl)-6-(4-(4-cyanophenyl)-5-hydroxy-1H-pyrazol-1-yl)nicotinamide

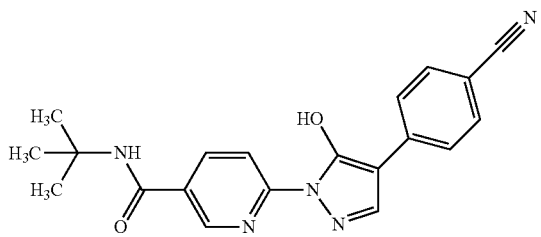 [SMILES: CC(C)(C)NC(=O)c1ccc(-n2ncc(-c3ccc(C#N)cc3)c2O)nc1]

Combined EDC (45.1 mg, 0.235 mmol), HOBT (21.18 mg, 0.157 mmol) and 6-(4-(4-cyanophenyl)-5-hydroxy-1H-pyrazol-1-yl)nicotinic acid (48 mg, 0.157 mmol) in DMF (1 mL) then added tert-butylamine (0.050 mL, 0.470 mmol) and Hunig's base (0.082 mL, 0.470 mmol) and then stirred at 20° C. for 21 h. Addition EDC (45 mg) and tert-butyl amine (100 uL) were then added and stirring continued at 20° C. for 4 h. Then additional HATU (119 mg, 0.313 mmol) was added and stirring continued at 20° C. for 2 h. The reaction mixture was then diluted with EtOAc (50 mL), washed with saturated aqueous ammonium chloride (50 mL) and brine, dried over magnesium sulfate, and concentrated in vacuo to give a residue which was dissolved in DMSO (1 mL) and purified by prep HPLC (ACN/water with formic acid) to give the title compound (9.5 mg, 16.77% yield) as a tan solid. $^1$H NMR (400 MHz, DMSO-$d_6$) δ ppm 1.34 (s, 9H) 7.72 (d, J=8.3 Hz, 2H) 7.98 (s, 1H) 8.07 (br. s., 2H) 8.33 (d, J=7.3 Hz, 2H) 8.58 (br. s., 1H) 8.79 (s, 1H) 13.48 (br. s., 1H). MS m/z 362 [M+H]$^+$.

Example 203 6-(5-hydroxy-4-(2-methoxypyridin-4-yl)-1H-pyrazol-1-yl)-N-(3-methoxypropyl)nicotinamide

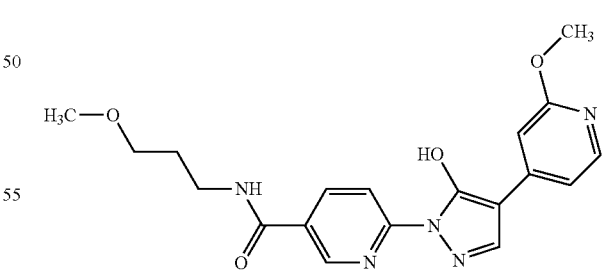

The title compound was prepared in a manner similar to Example 198 using 6-(5-hydroxy-4-(2-methoxypyridin-4-yl)-1H-pyrazol-1-yl)nicotinic acid. $^1$H NMR (400 MHz, DMSO-$d_6$) δ ppm 1.77 (quin, J=6.6 Hz, 2H) 3.24 (s, 3H) 3.28-3.36 (m, 2H) 3.38 (t, J=6.3 Hz, 2H) 3.88 (s, 3H) 7.46 (br. s., 1H) 7.53 (d, J=5.3 Hz, 1H) 8.06 (d, J=5.6 Hz, 1H) 8.36-8.53 (m, 2H) 8.65 (br. s., 1H) 8.70 (t, J=5.6 Hz, 1H) 8.85-8.92 (m, 1H). MS m/z 384 [M+H]$^+$.

Example 204 N-cyclopropyl-6-(5-hydroxy-4-(2-methoxypyridin-4-yl)-1H-pyrazol-1-yl)nicotinamide

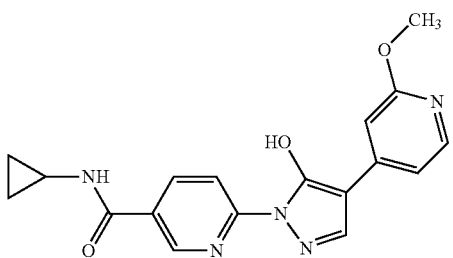 [SMILES: COc1cc(-c2cnn(-c3ccc(C(=O)NC4CC4)cn3)c2O)ccn1]

The title compound was prepared in a manner similar to Example 198 using 6-(5-hydroxy-4-(2-methoxypyridin-4-yl)-1H-pyrazol-1-yl)nicotinic acid and cyclopropanamine. $^1$H NMR (400 MHz, DMSO-$d_6$) δ ppm 0.49-0.57 (m, 2H) 0.63-0.71 (m, 2H) 2.80 (td, J=7.3, 3.8 Hz, 1H) 3.82 (s, 3H) 7.41 (br. s., 1H) 7.48 (d, J=5.6 Hz, 1H) 8.01 (d, J=5.8 Hz, 1H) 8.27-8.35 (m, 1H) 8.38 (br. s., 1H) 8.51-8.68 (m, 2H) 8.76-8.85 (m, 1H). MS m/z 352 [M+H]$^+$.

Example 205 6-(5-hydroxy-4-(2-methoxypyridin-4-yl)-1H-pyrazol-1-yl)-N-(1-(methoxy methyl)cyclopropyl)nicotinamide

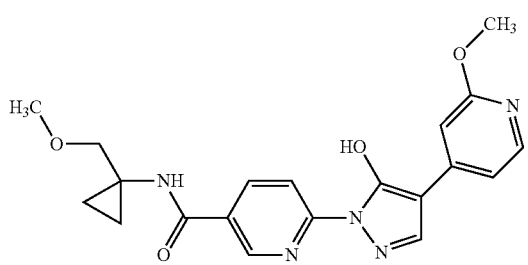 [SMILES: COCC1(NC(=O)c2ccc(-n3ncc(-c4ccnc(OC)c4)c3O)nc2)CC1]

The title compound was prepared in a manner similar to Example 198 using 6-(5-hydroxy-4-(2-methoxypyridin-4-yl)-1H-pyrazol-1-yl)nicotinic acid and 1-(methoxymethyl)cyclopropanamine hydrochloride. $^1$H NMR (400 MHz, DMSO-$d_6$) δ ppm 0.80 (s, 4H) 3.28 (s, 3H) 3.48 (s, 2H) 3.90 (s, 3H) 7.49 (br. s., 1H) 7.57 (d, J=5.3 Hz, 1H) 8.08 (d, J=5.6 Hz, 1H) 8.35-8.50 (m, 2H) 8.68 (br. s., 1H) 8.90 (t, J=1.4 Hz, 1H) 8.98 (s, 1H). MS m/z 396 [M+H]$^+$.

Example 206 6-(4-(4-cyano-2-methylphenyl)-5-hydroxy-1H-pyrazol-1-yl)-N-(2-(tetrahydro-2H-pyran-2-yl)ethyl)nicotinamide

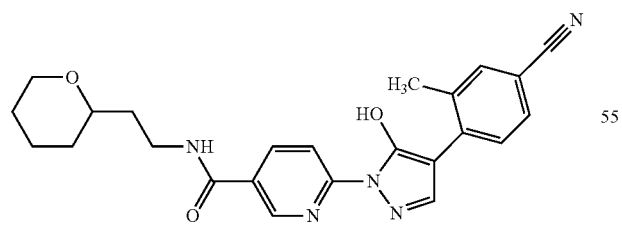

The title compound was prepared in a manner similar to Example 198 using 6-(4-(4-cyano-2-methylphenyl)-5-hydroxy-1H-pyrazol-1-yl)nicotinic acid and 2-(tetrahydro-2H-pyran-2-yl)ethanamine hydrochloride. $^1$H NMR (400 MHz, DMSO-$d_6$) δ ppm 1.13-1.27 (m, 1H) 1.38-1.50 (m, 3H) 1.60 (d, J=12.9 Hz, 1H) 1.62-1.70 (m, 2H) 1.71-1.82 (m, 1H) 2.44 (s, 3H) 3.26-3.33 (m, 2H) 3.35-3.45 (m, 2H) 3.87 (dd, J=11.0, 1.9 Hz, 1H) 7.66 (dd, J=8.0, 1.4 Hz, 1H) 7.72 (s, 1H) 7.80 (d, J=8.1 Hz, 1H) 8.16 (s, 1H) 8.40 (br. s., 2H) 8.67 (t, J=5.6 Hz, 1H) 8.90 (t, J=1.5 Hz, 1H) 13.18 (br. s., 1H). MS m/z 432 [M+H]$^+$.

Example 207 6-(5-hydroxy-4-(2-methoxypyridin-4-yl)-1H-pyrazol-1-yl)-N-(2-(tetrahydro-2H-pyran-2-yl)ethyl)nicotinamide

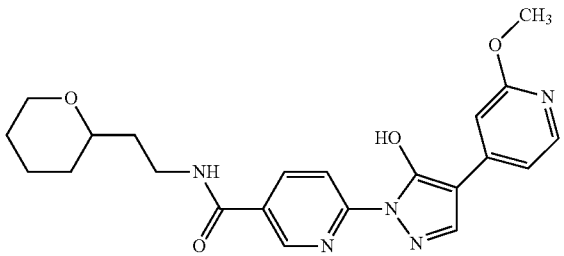 [SMILES: COc1cc(-c2cnn(-c3ccc(C(=O)NCCC4CCCCO4)cn3)c2O)ccn1]

The title compound was prepared in a manner similar to Example 198 using 6-(5-hydroxy-4-(2-methoxypyridin-4-yl)-1H-pyrazol-1-yl)nicotinic acid and 2-(tetrahydro-2H-pyran-2-yl)ethanamine hydrochloride. $^1$H NMR (400 MHz, DMSO-$d_6$) δ ppm 1.06-1.19 (m, 1H) 1.31-1.43 (m, 3H) 1.52 (d, J=12.9 Hz, 1H) 1.58 (q, J=7.1 Hz, 2H) 1.65-1.75 (m, 1H) 3.18-3.25 (m, 2H) 3.29-3.38 (m, 2H) 3.81 (m, J=2.0 Hz, 4H) 7.34 (br. s., 1H) 7.42 (d, J=5.1 Hz, 1H) 7.98 (d, J=5.6 Hz, 1H) 8.26-8.34 (m, 1H) 8.37 (br. s., 1H) 8.52 (br. s., 1H) 8.59 (t, J=5.4 Hz, 1H) 8.82 (s, 1H) 13.45 (br. s., 1H). MS m/z 424 [M+H]$^+$.

Example 208 6-(4-(4-cyanophenyl)-5-hydroxy-1H-pyrazol-1-yl)-N-(1-(2-methoxyethyl)cyclopropyl)nicotinamide

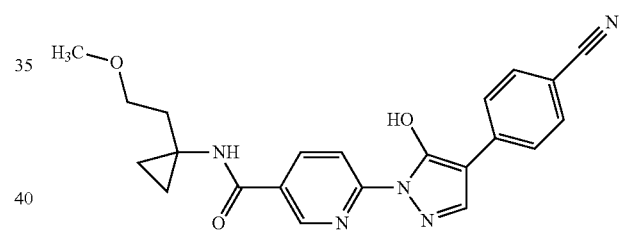

The title compound was prepared in a manner similar to Example 198 using 6-(4-(4-cyanophenyl)-5-hydroxy-1H-pyrazol-1-yl)nicotinic acid and 1-(2-methoxyethyl)cyclopropanamine. $^1$H NMR (400 MHz, DMSO-$d_6$) δ ppm 0.58-0.73 (m, 4H) 1.79 (t, J=6.9 Hz, 2H) 3.14 (s, 3H) 3.39 (t, J=6.9 Hz, 2H) 7.72 (d, J=8.6 Hz, 2H) 8.07 (d, J=7.8 Hz, 2H) 8.27-8.34 (m, 1H) 8.37 (br. s., 1H) 8.57 (br. s., 1H) 8.77 (s, 1H) 8.79-8.83 (m, 1H) 13.46 (br. s., 1H). MS m/z 404 [M+H]$^+$.

Example 209 6-(5-hydroxy-4-(2-methoxypyridin-4-yl)-1H-pyrazol-1-yl)-N-(1-(2-methoxyethyl)cyclopropyl)nicotinamide

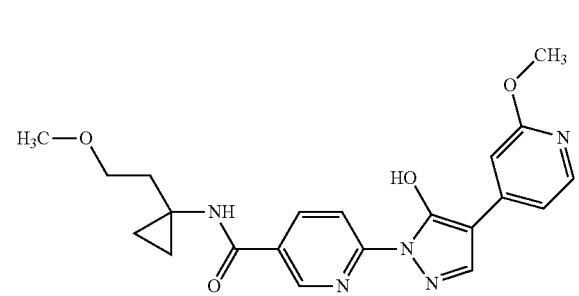 [SMILES: COCCC1(NC(=O)c2ccc(-n3ncc(-c4ccnc(OC)c4)c3O)nc2)CC1]

The title compound was prepared in a manner similar to Example 198 using 6-(5-hydroxy-4-(2-methoxypyridin-4-yl)-1H-pyrazol-1-yl)nicotinic acid and 1-(2-methoxyethyl) cyclopropanamine. ¹H NMR (400 MHz, DMSO-d₆) δ ppm 0.57-0.73 (m, 4H) 1.79 (t, J=7.1 Hz, 2H) 3.14 (s, 3H) 3.39 (t, J=7.1 Hz, 2H) 3.79 (s, 3H) 7.37 (br. s., 1H) 7.44 (br. s., 1H) 7.99 (d, J=5.6 Hz, 1H) 8.31 (d, J=7.8 Hz, 2H) 8.57 (br. s., 1H) 8.77 (s, 1H) 8.79-8.84 (m, 1H) 13.52 (br. s., 1H). MS m/z 410 [M+H]⁺.

Example 210 6-(4-(4-cyano-2-fluorophenyl)-5-hydroxy-1H-pyrazol-1-yl)-N-(1-(2-methoxyethyl)cyclopropyl)nicotinamide

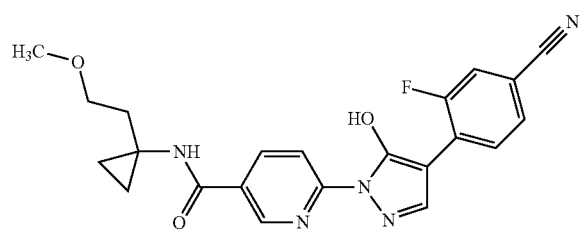 [SMILES: COCCC1(NC(=O)c2ccc(-n3ncc(-c4ccc(C#N)cc4F)c3O)nc2)CC1]

The title compound was prepared in a manner similar to Example 198 using 6-(4-(4-cyano-2-fluorophenyl)-5-hydroxy-1H-pyrazol-1-yl)nicotinic acid and 1-(2-methoxyethyl)cyclopropanamine. ¹H NMR (400 MHz, DMSO-d₆) δ ppm 0.58-0.66 (m, 2H) 0.66-0.73 (m, 2H) 1.80 (t, J=6.9 Hz, 2H) 3.14 (s, 3H) 3.39 (t, J=7.1 Hz, 2H) 7.61 (dd, J=8.2, 1.6 Hz, 1H) 7.75 (dd, J=11.9, 1.5 Hz, 1H) 8.14 (d, J=3.0 Hz, 1H) 8.30 (dd, J=8.7, 2.1 Hz, 1H) 8.40 (d, J=8.6 Hz, 1H) 8.56 (t, J=8.0 Hz, 1H) 8.76 (s, 1H) 8.80 (d, J=1.5 Hz, 1H) 13.69 (br. s., 1H). MS m/z 422 [M+H]⁺.

Example 211 6-(5-hydroxy-4-(1-methyl-2-oxo-1,2-dihydropyridin-4-yl)-1H-pyrazol-1-yl)-N-((tetrahydro-2H-pyran-4-yl)methyl)nicotinamide

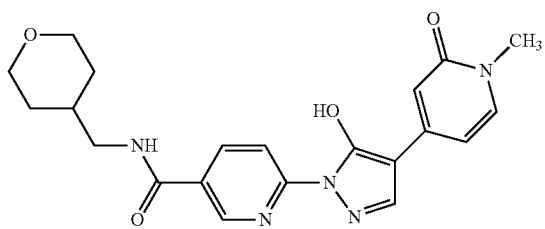 [SMILES: Cn1ccc(-c2cnn(-c3ccc(C(=O)NCC4CCOCC4)cn3)c2O)cc1=O]

Combined 6-(4-bromo-5-methoxy-1H-pyrazol-1-yl)-N-((tetrahydro-2H-pyran-4-yl)methyl)nicotinamide (25 mg, 0.063 mmol), 1-methyl-4-(4,4,5,5-tetramethyl-1,3,2-dioxaborolan-2-yl)pyridin-2(1H)-one (29.7 mg, 0.127 mmol), PdCl₂(dppf)-CH₂Cl₂ adduct (4.13 mg, 5.06 μmol) and sodium bicarbonate (26.6 mg, 0.316 mmol) in dioxane (0.2 mL) and water (0.05 mL) and heated at 110° C. for 1 h in the microwave. More PdCl2(dppf)-CH₂Cl₂ adduct (ca. 3 mg), sodium bicarbonate (10 mg) and water (100 uL) was added and the mixture was heated at 110° C. for 1 h in the microwave. The reaction was concentrated onto Celite® purified on 12 g NH silica gel column eluted with 0 to 5% MeOH in methylene chloride to give 6-(5-methoxy-4-(1-methyl-2-oxo-1,2-dihydropyridin-4-yl)-1H-pyrazol-1-yl)-N-((tetrahydro-2H-pyran-4-yl)methyl)nicotinamide as a brown oil (24 mg). MS m/z 424 [M+H]⁺.

Combined 6-(5-methoxy-4-(1-methyl-2-oxo-1,2-dihydropyridin-4-yl)-1H-pyrazol-1-yl)-N-((tetrahydro-2H-pyran-4-yl)methyl)nicotinamide (24 mg, 0.057 mmol) and lithium chloride (12.01 mg, 0.283 mmol) in DMA (0.5 mL) and heated at 50° C. for 26 h. The reaction mixture was diluted with 0.5 mL DMSO and purified by prep HPLC using acetonitrile/water with ammonium hydroxide to give the title compound (4 mg, 17.24% yield) as a yellow solid. MS m/z 410 [M+H]⁺.

Example 212 6-(4-(2-(dimethylamino)pyridin-4-yl)-5-hydroxy-1H-pyrazol-1-yl)-N-((tetrahydro-2H-pyran-4-yl)methyl)nicotinamide

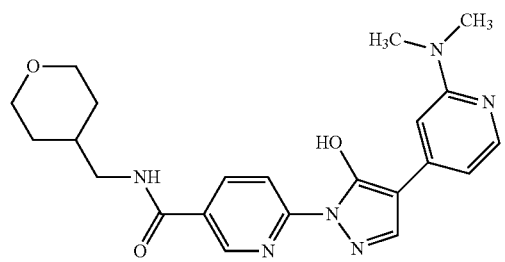 [SMILES: CN(C)c1cc(-c2cnn(-c3ccc(C(=O)NCC4CCOCC4)cn3)c2O)ccn1]

Combined 6-(4-bromo-5-methoxy-1H-pyrazol-1-yl)-N-((tetrahydro-2H-pyran-4-yl)methyl)nicotinamide (80 mg, 0.202 mmol), N,N-dimethyl-4-(4,4,5,5-tetramethyl-1,3,2-dioxaborolan-2-yl)pyridin-2-amine hydrochloride (173 mg, 0.607 mmol), PdCl₂(dppf)-CH₂Cl₂ adduct (16.53 mg, 0.020 mmol) and sodium bicarbonate (136 mg, 1.619 mmol) in dioxane (0.6 mL) and water (0.15 mL) was let stir for 15 min. The mixture was then capped and heated at 110° C. for 1 h in the microwave. Additional PdCl₂(dppf)-CH₂Cl₂ adduct (17 mg) was then added and the heating continued at 110° C. for 1 h in the microwave. The reaction mixture was diluted with EtOAc, concentrated onto Celite® and purified on a 10 g NH silica gel column eluted with 10 to 100% EtOAc in hexanes to give 6-(4-(2-(dimethylamino)pyridin-4-yl)-5-methoxy-1H-pyrazol-1-yl)-N-((tetrahydro-2H-pyran-4-yl)methyl)nicotinamide as a brown oil. MS m/z 437 [M+H]⁺.

Combined 6-(4-(2-(dimethylamino)pyridin-4-yl)-5-methoxy-1H-pyrazol-1-yl)-N-((tetrahydro-2H-pyran-4-yl) methyl)nicotinamide from the above reaction and lithium chloride (42.7 mg, 1.008 mmol) and DMA (1 mL) and heated at 60° C. for 20 h. The reaction mixture was diluted with 0.2 mL DMSO and purified by prep HPLC (ammonium hydroxide conditions) to give the title compound (42 mg, 49.3% yield) as a yellow solid. ¹H NMR (400 MHz, DMSO-d₆) δ ppm 1.12-1.28 (m, 2H) 1.56-1.67 (m, 2H) 1.81 (ddt, J=14.9, 7.5, 3.8, 3.8 Hz, 1H) 3.05 (s, 6H) 3.17 (t, J=6.4 Hz, 2H) 3.28 (td, J=11.6, 1.8 Hz, 2H) 3.86 (dd, J=11.4, 2.5 Hz, 2H) 7.07 (d, J=4.5 Hz, 1H) 7.35 (br. s., 1H) 7.67 (d, J=6.1 Hz, 1H) 7.90 (s, 1H) 8.10-8.19 (m, 1H) 8.47-8.59 (m, 2H) 8.80 (d, J=2.0 Hz, 1H). MS m/z 423 [M+H]⁺.

Example 213 6-(4-(4-cyano-2-fluorophenyl)-5-hydroxy-1H-pyrazol-1-yl)-N-(3-methoxypropyl)nicotinamide

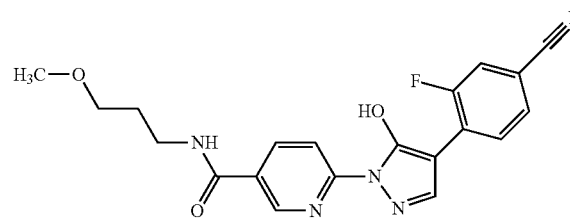

Combined 6-(4-bromo-5-methoxy-1H-pyrazol-1-yl)-N-(3-methoxypropyl)nicotinamide (60 mg, 0.163 mmol), 3-fluoro-4-(4,4,5,5-tetramethyl-1,3,2-dioxaborolan-2-yl)benzonitrile (120 mg, 0.488 mmol), $PdCl_2(dppf)\text{-}CH_2Cl_2$ adduct (19.91 mg, 0.024 mmol) and sodium bicarbonate (68.3 mg, 0.813 mmol) in dioxane (0.6 mL) and water (0.15 mL) and heated at 110° C. for 1 h in the microwave. The reaction mixture was diluted with EtOAc, concentrated onto Celite®, and purified on a 10 g NH silica gel column eluted with 0 to 80% EtOAc in hexanes to give 6-(4-(4-cyano-2-fluorophenyl)-5-methoxy-1H-pyrazol-1-yl)-N-(3-methoxypropyl)nicotinamide as a white solid. MS m/z 410 [M+H]$^+$.

Combined 6-(4-(4-cyano-2-fluorophenyl)-5-methoxy-1H-pyrazol-1-yl)-N-(3-methoxypropyl)nicotinamide and lithium chloride (34.7 mg, 0.818 mmol) and DMA (1 mL) and heated at 50° C. for 15 h. The reaction was diluted with 0.2 mL DMSO and purified by prep HPLC (TFA conditions) to give the title compound as a TFA salt (27 mg, 41.7% yield) as a light green solid. $^1$H NMR (400 MHz, DMSO-d$_6$) δ ppm 1.72-1.85 (m, 2H) 3.25 (s, 3H) 3.31-3.37 (m, 2H) 3.40 (t, J=6.3 Hz, 2H) 7.72 (dd, J=8.2, 1.6 Hz, 1H) 7.87 (dd, J=11.6, 1.5 Hz, 1H) 8.29 (br. s., 1H) 8.39-8.46 (m, 1H) 8.48 (br. s., 1H) 8.60 (br. s., 1H) 8.73 (t, J=5.4 Hz, 1H) 8.89-8.96 (m, 1H) 13.77 (br. s., 1H). MS m/z 396 [M+H]$^+$.

Example 214 6-(5-hydroxy-4-(2-methoxy-6-methylpyridin-4-yl)-1H-pyrazol-1-yl)-N-(3-methoxypropyl)nicotinamide

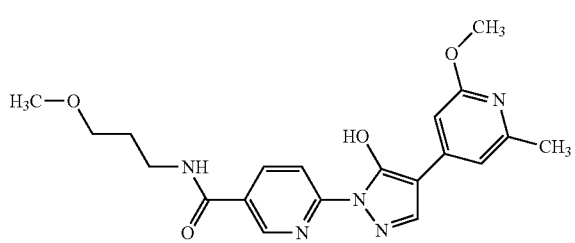

The title compound was prepared in a manner similar to Example 212 using 6-(4-bromo-5-methoxy-1H-pyrazol-1-yl)-N-(3-methoxypropyl)nicotinamide and (2-methoxy-6-methylpyridin-4-yl)boronic acid. $^1$H NMR (400 MHz, DMSO-d$_6$) δ ppm 1.71 (quin, J=6.6 Hz, 2H) 2.30 (s, 3H) 3.18 (s, 3H) 3.22-3.30 (m, 2H) 3.32 (t, J=6.3 Hz, 2H) 3.79 (s, 3H) 7.16 (br. s., 1H) 7.31 (br. s., 1H) 8.31 (br. s., 1H) 8.33-8.53 (m, 2H) 8.61 (br. s., 1H) 8.82 (s, 1H) 13.35 (br. s., 1H). MS m/z 398 [M+H]$^+$.

Example 215 6-(4-(4-cyano-2-methylphenyl)-5-hydroxy-1H-pyrazol-1-yl)-N-(1-(2-methoxyethyl)cyclopropyl)nicotinamide

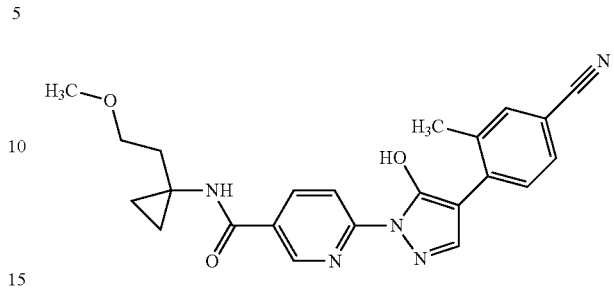

The title compound was prepared in a manner similar to Example 200 using 6-(4-(4-cyano-2-methylphenyl)-5-hydroxy-1H-pyrazol-1-yl)nicotinic acid and 1-(2-methoxyethyl)cyclopropanamine. $^1$H NMR (400 MHz, DMSO-d$_6$) δ ppm 0.65-0.73 (m, 2H) 0.72-0.80 (m, 2H) 1.86 (t, J=7.1 Hz, 2H) 2.43 (s, 3H) 3.21 (s, 3H) 3.46 (t, J=6.9 Hz, 2H) 7.64 (dd, J=8.1, 1.5 Hz, 1H) 7.71 (s, 1H) 7.80 (d, J=8.1 Hz, 1H) 8.14 (s, 1H) 8.38 (br. s., 2H) 8.83 (s, 1H) 8.87 (t, J=1.5 Hz, 1H) 13.17 (br. s., 1H). MS m/z 418 [M+H]$^+$.

Example 216 6-(5-hydroxy-4-(1-methyl-6-oxo-1,6-dihydropyridin-3-yl)-1H-pyrazol-1-yl)-N-(3-methoxy propyl)nicotinamide

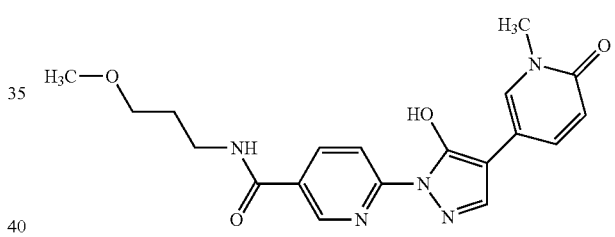

The title compound was prepared in a manner similar to Example 212 using 6-(4-bromo-5-methoxy-1H-pyrazol-1-yl)-N-(3-methoxypropyl)nicotinamide and 1-methyl-5-(4,4,5,5-tetramethyl-1,3,2-dioxaborolan-2-yl)pyridin-2(1H)-one. $^1$H NMR (400 MHz, DMSO-d$_6$) δ ppm 1.70 (quin, J=6.7 Hz, 2H) 3.18 (s, 3H) 3.21-3.29 (m, 2H) 3.32 (t, J=6.3 Hz, 2H) 3.38 (s, 3H) 6.34 (d, J=9.3 Hz, 1H) 7.81 (dd, J=9.5, 2.4 Hz, 1H) 8.03 (s, 1H) 8.20 (d, J=1.8 Hz, 1H) 8.24 (dd, J=8.8, 2.3 Hz, 1H) 8.39 (d, J=8.6 Hz, 1H) 8.56 (t, J=5.4 Hz, 1H) 8.78 (d, J=1.8 Hz, 1H) 12.62 (br. s., 1H). MS m/z 384 [M+H]$^+$.

Example 217 6-(4-(4-(cyanomethyl)phenyl)-5-hydroxy-1H-pyrazol-1-yl)-N-(3-methoxypropyl)nicotinamide

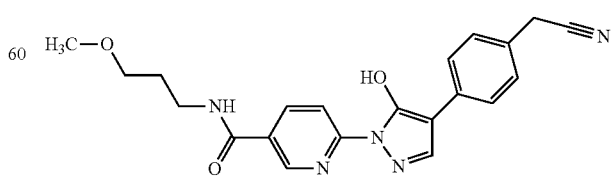

The title compound was prepared in a manner similar to Example 212 using 6-(4-bromo-5-methoxy-1H-pyrazol-1- yl)-N-(3-methoxypropyl)nicotinamide and (4-(cyanomethyl)phenyl)boronic acid. ¹H NMR (400 MHz, DMSO-d₆) δ ppm 1.71 (quin, J=6.7 Hz, 2H) 3.18 (s, 3H) 3.21-3.30 (m, 2H) 3.33 (t, J=6.2 Hz, 2H) 3.94 (s, 2H) 7.25 (d, J=8.3 Hz, 2H) 7.86 (d, J=8.1 Hz, 2H) 8.25-8.34 (m, 2H) 8.36 (br. s., 1H) 8.62 (t, J=5.6 Hz, 1H) 8.79-8.86 (m, 1H) 12.97 (br. s., 1H). MS m/z 392 [M+H]⁺.

Example 218 6-(4-(2-ethoxypyridin-4-yl)-5-hydroxy-1H-pyrazol-1-yl)-N-(3-methoxypropyl)nicotinamide

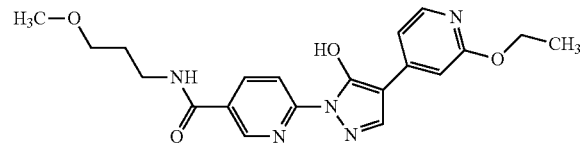 [SMILES: CCOc1cc(-c2cnn(-c3ccc(C(=O)NCCCOC)cn3)c2O)ccn1]

The title compound was prepared in a manner similar to Example 213 using 6-(4-bromo-5-methoxy-1H-pyrazol-1-yl)-N-(3-methoxypropyl)nicotinamide and (2-ethoxypyridin-4-yl)boronic acid. ¹H NMR (400 MHz, DMSO-d₆) δ ppm 1.25 (t, J=7.1 Hz, 3H) 1.71 (quin, J=6.7 Hz, 2H) 3.18 (s, 3H) 3.21-3.29 (m, 2H) 3.32 (t, J=6.3 Hz, 2H) 4.22 (q, J=7.1 Hz, 2H) 7.31 (s, 1H) 7.40 (d, J=5.3 Hz, 1H) 7.94 (d, J=5.6 Hz, 1H) 8.26-8.34 (m, 1H) 8.34-8.42 (m, 1H) 8.47 (br. s., 1H) 8.61 (t, J=5.6 Hz, 1H) 8.82 (d, J=1.5 Hz, 1H) 13.42 (br. s., 1H). MS m/z 398 [M+H]⁺.

Example 219 6-(4-(4-(cyanomethyl)-3-fluorophenyl)-5-hydroxy-1H-pyrazol-1-yl)-N-(3-methoxypropyl)nicotinamide

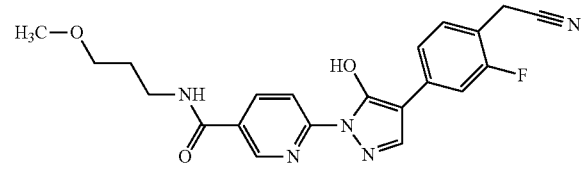 [SMILES: COCCCNC(=O)c1ccc(-n2ncc(-c3ccc(CC#N)c(F)c3)c2O)nc1]

Combined 6-(4-bromo-5-methoxy-1H-pyrazol-1-yl)-N-(3-methoxypropyl)nicotinamide (50 mg, 0.135 mmol), 2-(2-fluoro-4-(4,4,5,5-tetramethyl-1,3,2-dioxaborolan-2-yl)phenyl)acetonitrile (70.7 mg, 0.271 mmol), dichloro[1,1'-bis(di-t-butylphosphino)ferrocene]palladium(II) (8.83 mg, 0.014 mmol) and sodium bicarbonate (56.9 mg, 0.677 mmol) in dioxane (0.60 mL) and water (0.150 mL) was heated at 110° C. in the microwave for 40 min. Additional dichloro[1,1'-bis(di-t-butylphosphino)ferrocene]palladium(II) was added (10 mg) and the reaction heated at 110° C. in the microwave for 1 h. The reaction mixture was diluted with EtOAc, concentrated onto Celite®, and purified on a 10 g NH silica gel column eluted with 0 to 100% EtOAc in hexanes to 6-(4-(4-(cyanomethyl)-3-fluorophenyl)-5-methoxy-1H-pyrazol-1-yl)-N-(3-methoxypropyl)nicotinamide (27 mg, 47.1% yield). MS m/z 424 [M+H]⁺.

Combined 6-(4-(4-(cyanomethyl)-3-fluorophenyl)-5-methoxy-1H-pyrazol-1-yl)-N-(3-methoxypropyl)nicotinamide (27 mg, 0.064 mmol) and lithium chloride (27.0 mg, 0.638 mmol) in DMA (1.0 mL) and heated at 60° C. for 24 h. The reaction mixture was diluted with 0.2 mL DMSO and purified by prep HPLC (formic acid conditions) to give the title compound (15 mg, 57.5% yield) as an off-white solid. ¹H NMR (400 MHz, DMSO-d₆) δ ppm 1.79 (quin, J=6.7 Hz, 2H) 3.25 (s, 3H) 3.30-3.37 (m, 2H) 3.40 (t, J=6.3 Hz, 2H) 4.03 (s, 2H) 7.42 (br. s., 1H) 7.52-8.06 (m, 2H) 8.41 (br. s., 1H) 8.50-8.82 (m, 3H) 8.91 (d, J=1.5 Hz, 1H) 13.28 (br. s., 1H). MS m/z 410 [M+H]⁺.

Example 220 N-benzyl-6-(4-(4-cyano-2-fluorophenyl)-5-hydroxy-1H-pyrazol-1-yl)nicotinamide

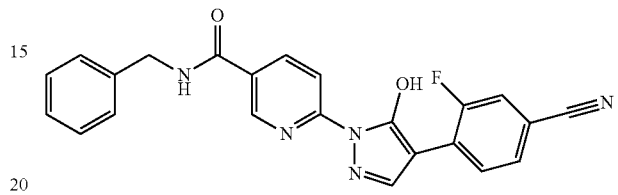

Combined N-benzyl-6-hydrazinylnicotinamide (53.3 mg, 0.220 mmol) and ethyl 2-(4-cyano-2-fluorophenyl)-3-(dimethylamino)acrylate (75 mg, 0.286 mmol) in 2-propanol (1 mL) and added acetic acid (0.038 mL, 0.660 mmol) at 23° C. The reaction mixture was stirred at 23° C. for 18.5 hours, Hunig's base (0.230 mL, 1.320 mmol) was added, and the reaction mixture was stirred at 60° C. for 6 hours. The reaction mixture was cooled to 23° C. and concentrated via rotary evaporation to furnish a brown oil which was dissolved in DMSO (1 mL), filtered through a Hydrophilic PTFE 0.45 µm filter (Millipore Millex™-LCR), rinsed with DMSO (2×0.5 mL), and purified via preparative HPLC (SunFire™ C18, 5 µm, ID 30 mm×75 mm) using a gradient of 50-80% ACN (with 0.035% TFA) in water (with 0.05% TFA). Product containing fractions were combined and concentrated via rotary evaporation to furnish an off-white solid which was collected by filtration, rinsed with water (5×2 mL), and dried in vacuo to give the title compound (9.1 mg, 10.01% yield) as a tan solid. ¹H NMR (400 MHz, DMSO-d₆) δ ppm 4.53 (d, J=5.81 Hz, 2H) 7.21-7.40 (m, 5H) 7.72 (dd, J=8.34, 1.52 Hz, 1H) 7.87 (dd, J=11.75, 1.39 Hz, 1H) 8.29 (br. s., 1H) 8.42-8.54 (m, 2H) 8.60 (br. s., 1H) 8.95-9.03 (m, 1H) 9.29 (t, J=5.94 Hz, 1H) 13.78 (br. s., 1H). MS m/z [M+H]⁺ 414.3.

Example 221 6-(4-(4-cyano-2-fluorophenyl)-5-hydroxy-1H-pyrazol-1-yl)-N-((tetrahydro-2H-pyran-4-yl)methyl)nicotinamide

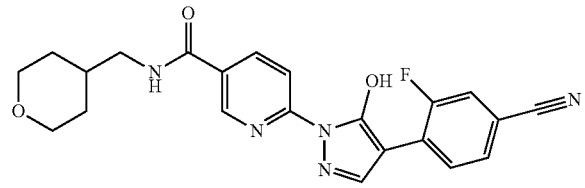 [SMILES: N#Cc1ccc(-c2cnn(-c3ccc(C(=O)NCC4CCOCC4)cn3)c2O)c(F)c1]

The title compound was prepared in a manner similar to Example 220 using 6-hydrazinyl-N-((tetrahydro-2H-pyran-4-yl)methyl)nicotinamide. ¹H NMR (400 MHz, DMSO-d₆) δ ppm 1.22 (qd, J=12.25, 4.42 Hz, 2H) 1.55-1.70 (m, 2H) 1.81 (tdd, J=15.03, 15.03, 6.82, 3.79 Hz, 1H) 3.20 (t, J=6.19 Hz, 2H) 3.24-3.32 (m, 2H) 3.86 (dd, J=11.24, 2.91 Hz, 2H)

7.66-7.77 (m, 1H) 7.87 (dd, J=11.87, 0.76 Hz, 1H) 8.28 (br. s., 1H) 8.35-8.54 (m, 2H) 8.60 (br. s., 1H) 8.73 (t, J=5.81 Hz, 1H) 8.92 (s, 1H) 13.76 (br. s., 1H). MS m/z [M+H]+ 422.4.

Example 222 6-(4-(4-cyano-2-methylphenyl)-5-hydroxy-1H-pyrazol-1-yl)-N-((tetrahydro-2H-pyran-4-yl)methyl)nicotinamide

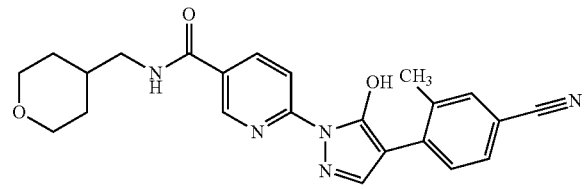 [SMILES: Cc1cc(C#N)ccc1-c1cnn(-c2ccc(C(=O)NCC3CCOCC3)cn2)c1O]

Combined 6-(4-bromo-5-methoxy-1H-pyrazol-1-yl)-N-((tetrahydro-2H-pyran-4-yl)methyl)nicotinamide (25 mg, 0.063 mmol), (4-cyano-2-methylphenyl)boronic acid (30.5 mg, 0.190 mmol), sodium carbonate (26.6 mg, 0.316 mmol), and PdCl$_2$(dppf)-CH$_2$Cl$_2$ adduct (2.58 mg, 3.16 μmot) in dioxane (0.2 mL) and water (0.05 mL) and purged with nitrogen. The reaction mixture was heated in a microwave on high absorbance for 1 hour at 110° C., cooled to 23° C. and diluted with water (1 mL) to give a residue. The residue was extracted with EtOAc (2×1 mL), the organic layers were combined, washed with brine (0.5 mL), dried over Na$_2$SO$_4$, filtered through a Hydrophilic PTFE 0.45 um filter (Millipore Millex™-LCR), rinsed with EtOAc, and dried in vacuo to provide 6-(4-(4-cyano-2-methylphenyl)-5-methoxy-1H-pyrazol-1-yl)-N-((tetrahydro-2H-pyran-4-yl)methyl)nicotinamide (27.3 mg, 100% yield) as a brown oil. MS m/z [M+H]+ 432.5.

Combined 6-(4-(4-cyano-2-methylphenyl)-5-methoxy-1H-pyrazol-1-yl)-N-((tetrahydro-2H-pyran-4-yl)methyl)nicotinamide (27.3 mg, 0.063 mmol) and lithium chloride (13.41 mg, 0.316 mmol) in DMA (0.5 mL) then heated at 50° C. using a heating block for 24 hours. Additional portion of lithium chloride (8.05 mg, 0.190 mmol) was added and the reaction mixture was stirred at 50° C. for an additional 14 hours. The reaction mixture was cooled to 23° C., filtered through a Hydrophilic PTFE 0.45 um filter (Millipore Millex™-LCR), rinsed with DMSO (2×0.5 mL), and purified via preparative HPLC (SunFire™ C18, 5 μm, ID 30 mm×75 mm) using a gradient of 30-60% ACN (with 0.035% TFA) in water (with 0.05% TFA). The product containing fractions were combined and concentrated via rotary evaporation to furnish an off-white solid which was collected by filtration, rinsed with water (5×2 mL), and dried in vacuo to give the title compound (8.2 mg, 31.0% yield) as an off-white solid. $^1$H NMR (400 MHz, DMSO-d$_6$) δ ppm 1.15-1.28 (m, 2H) 1.58-1.67 (m, 2H) 1.75-1.86 (m, 1H) 2.43 (s, 3H) 3.20 (t, J=6.32 Hz, 2H) 3.27 (td, J=11.75, 2.02 Hz, 2H) 3.81-3.90 (m, 2H) 7.60-7.69 (m, 1H) 7.73 (s, 1H) 7.78 (br. s., 1H) 8.05-8.25 (m, 1H) 8.35-8.45 (m, 1H) 8.69-8.80 (m, 1H) 8.89-8.95 (m, 1H) 13.21 (br. s., 1H). MS m/z [M+H]+ 418.5.

Example 223 6-(5-hydroxy-4-(2-methylpyridin-4-yl)-1H-pyrazol-1-yl)-N-((tetrahydro-2H-pyran-4-yl)methyl)nicotinamide

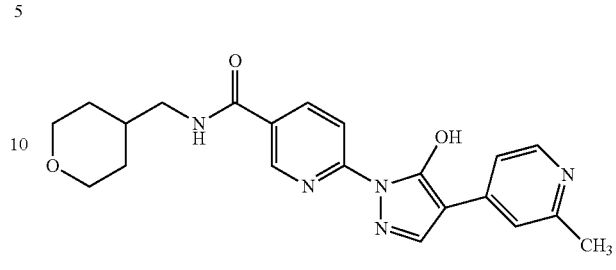

Combined 6-(4-bromo-5-methoxy-1H-pyrazol-1-yl)-N-((tetrahydro-2H-pyran-4-yl)methyl)nicotinamide (25 mg, 0.063 mmol), (2-methylpyridin-4-yl)boronic acid (26.0 mg, 0.190 mmol), sodium bicarbonate (26.6 mg, 0.316 mmol), and PdCl$_2$(dppf)-CH$_2$Cl$_2$ adduct (2.58 mg, 3.16 μmot) in dioxane (0.2 mL) and water (0.05 mL) and purged with nitrogen. The mixture was heated in a microwave reactor on high absorbance for 1 hour at 110° C. Additional portions of (2-methylpyridin-4-yl)boronic acid (26.0 mg, 0.190 mmol), sodium bicarbonate (26.6 mg, 0.316 mmol), PdCl$_2$(dppf)-CH$_2$Cl$_2$ Adduct (2.58 mg, 3.16 μmot), dioxane (0.1 mL), and water (0.025 mL) were added and the reaction mixture was heated again in a microwave reactor on high absorbance for 1 hour at 110° C., then cooled to 23° C. and diluted with water (1 mL) to give a residue which was extracted with EtOAc (2×1 mL), the organic layers were combined, washed with brine (0.5 mL), dried over Na$_2$SO4, filtered through a Hydrophilic PTFE 0.45 um filter (Millipore Millex™-LCR), rinsed with EtOAc, and dried in vacuo to provide crude 6-(5-methoxy-4-(2-methylpyridin-4-yl)-1H-pyrazol-1-yl)-N-((tetrahydro-2H-pyran-4-yl)methyl)nicotinamide (25.8 mg, 100% yield) as a brown oil. MS m/z [M+H]+ 408.5.

Combined 6-(5-methoxy-4-(2-methylpyridin-4-yl)-1H-pyrazol-1-yl)-N-((tetrahydro-2H-pyran-4-yl)methyl)nicotinamide (25.8 mg, 0.063 mmol) and lithium chloride (13.42 mg, 0.317 mmol) in DMA (0.5 mL) and then heated at 50° C. using a heating block for 2 days. Additional portion of lithium chloride (13.42 mg, 0.317 mmol) was added and the reaction mixture was stirred at 100° C. for 17 hours. The reaction mixture was cooled to 23° C., filtered through a Hydrophilic PTFE 0.45 um filter (Millipore Millex™-LCR), rinsed with DMSO (2×0.5 mL), and purified via preparative HPLC (SunFire C18, 5 μm, ID 30 mm×75 mm) using a gradient of 10-40% ACN (with 0.035% TFA) in water (with 0.05% TFA) to give a residue. The residue was dissolved in DMSO, filtered through a Hydrophilic PTFE 0.45 um filter (Millipore Millex™-LCR), rinsed with DMSO, and purified again via preparative HPLC (SunFire™ C18, 5 μm, ID 30 mm×75 mm) using an isocratic method of 17% ACN (with 0.05% TFA) in water (with 0.05% TFA) to give the title compound, as a TFA salt, (6.2 mg, 19.30% yield) as a green oil. $^1$H NMR (400 MHz, DMSO-d$_6$) δ ppm 1.16-1.26 (m, 2H) 1.55-1.67 (m, 2H) 1.77-1.84 (m, 1H) 2.51 (br. s., 3H) 3.17-3.24 (m, 2H) 3.24-3.32 (m, 2H) 3.83-3.88 (m, 2H) 7.77-8.07 (m, 2H) 8.07-8.22 (m, 1H) 8.22-8.30 (m, 1H) 8.36-8.44 (m, 1H) 8.58-8.67 (m, 1H) 8.67-8.81 (m, 1H) 8.81-8.92 (m, 1H) 13.58 (br. s., 1H). MS m/z [M+H]+ 394.5.

Example 224 6-(4-(2,6-dimethylpyridin-4-yl)-5-hydroxy-1H-pyrazol-1-yl)-N-((tetrahydro-2H-pyran-4-yl)methyl)nicotinamide

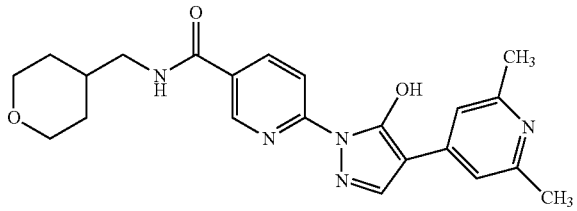 [SMILES: Cc1cc(-c2cnn(-c3ccc(C(=O)NCC4CCOCC4)cn3)c2O)cc(C)n1]

The title compound, as a TFA salt, was prepared in a manner similar to Example 222 using 6-(4-bromo-5-methoxy-1H-pyrazol-1-yl)-N-((tetrahydro-2H-pyran-4-yl)methyl)nicotinamide and (2,6-dimethylpyridin-4-yl)boronic acid. $^1$H NMR (400 MHz, DMSO-d$_6$) δ ppm 1.15-1.27 (m, 2H) 1.57-1.67 (m, 2H) 1.77-1.86 (m, 1H) 2.57 (br. s., 6H) 3.17-3.24 (m, 2H) 3.24-3.32 (m, 2H) 3.79-3.92 (m, 2H) 8.06 (br. s., 2H) 8.42-8.60 (m, 2H) 8.72-8.86 (m, 2H) 8.86-8.97 (m, 1H) 14.03 (br. s., 1H). MS m/z [M+H]$^+$ 408.5.

Example 225 N-benzyl-6-(5-hydroxy-4-(pyridin-4-yl)-1H-pyrazol-1-yl)nicotinamide

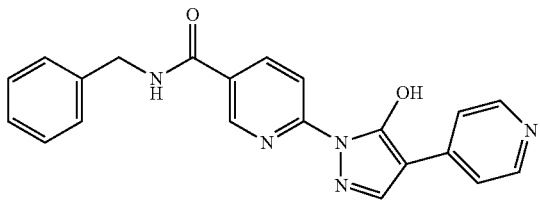 [SMILES: O=C(NCc1ccccc1)c1ccc(-n2ncc(-c3ccncc3)c2O)nc1]

Combined ethyl 3-(dimethylamino)-2-(pyridin-4-yl)acrylate (40.0 mg, 0.182 mmol) and N-benzyl-6-hydrazinylnicotinamide (33.8 mg, 0.140 mmol) in 2-propanol (0.698 mL) and stirred for 18 hours at room temperature. Hunig's base (0.219 mL, 1.257 mmol) was then added and the reaction was stirred for 24 hours at 50° C. The reaction mixture was then purified by preparative HPLC (SunFire™ C18, 5 μm, ID 30 mm×75 mm) eluting with ACN (with 0.035% TFA) in water (with 0.05% TFA) to give the title compound (18.5 mg, 35.7%) as a yellow solid. $^1$H NMR (400 MHz, DMSO-d6) δ ppm 4.58 (d, J=5.8 Hz, 2H) 7.33 (dq, J=8.5, 4.3 Hz, 1H) 7.37-7.45 (m, 4H) 8.28 (d, J=6.3 Hz, 2H) 8.45 (d, J=7.1 Hz, 2H) 8.49-8.58 (m, 2H) 8.63 (s, 1H) 8.99 (s, 1H) 9.33 (t, J=5.9 Hz, 1H). MS m/z [M+H]$^+$ 372.4.

Example 226 6-(5-hydroxy-4-(pyridin-4-yl)-1H-pyrazol-1-yl)-N-((tetrahydro-2H-pyran-4-yl)methyl)nicotinamide

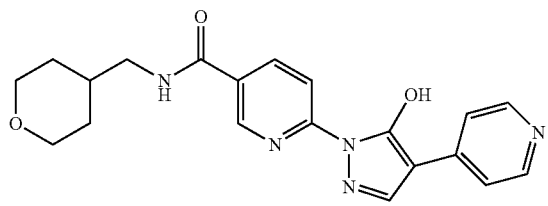 [SMILES: O=C(NCC1CCOCC1)c1ccc(-n2ncc(-c3ccncc3)c2O)nc1]

The title compound was prepared in a manner similar to Example 225 using 6-hydrazinyl-N-((tetrahydro-2H-pyran-4-yl)methyl)nicotinamide. $^1$H NMR (400 MHz, DMSO-d6) δ ppm 1.04-1.36 (m, 3H) 1.62 (d, J=12.4 Hz, 2H) 1.73-1.90 (m, 1H) 3.19 (t, J=6.2 Hz, 2H) 3.86 (dd, J=11.0, 2.4 Hz, 2H) 8.23 (d, J=6.3 Hz, 2H) 8.40-8.53 (m, 4H) 8.62 (s, 1H) 8.74 (t, J=5.7 Hz, 1H) 8.88 (s, 1H). MS m/z [M+H]$^+$ 380.4.

Example 227 6-(4-(4-cyanophenyl)-5-hydroxy-1H-pyrazol-1-yl)-N-((1s,4s)-4-methoxycyclohexyl)nicotinamide

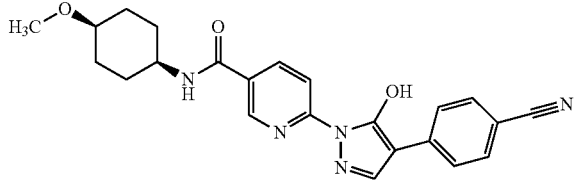 [SMILES: CO[C@H]1CC[C@@H](NC(=O)c2ccc(-n3ncc(-c4ccc(C#N)cc4)c3O)nc2)CC1]

Combined 6-(4-(4-cyanophenyl)-5-hydroxy-1H-pyrazol-1-yl)nicotinic acid (100 mg, 0.327 mmol), (1s,4s)-4-methoxycyclohexanamine, HCl (81 mg, 0.490 mmol), and N1-((ethylimino)methylene)-N3,N3-dimethylpropane-1,3-diamine, HCl (94 mg, 0.490 mmol) in DMF (1.555 mL). Then added 1H-benzo[d][1,2,3]triazol-1-oL, water (75 mg, 0.490 mmol) and Hunig's base (0.171 mL, 0.980 mmol) and stirred for 4 hours at room temperature. The reaction mixture was acidified to a pH of 5 to give a solid. The solid was washed with 50 mL MeOH and 50 mL hexanes, and then dried to afford the title compound (95.3 mg, 66.4%) as light yellow solid. $^1$H NMR (400 MHz, DMSO-d6) δ ppm 1.24 (br. s., 2H) 1.39 (d, J=14.7 Hz, 2H) 1.89 (br. s., 2H) 2.05 (d, J=10.9 Hz, 2H) 3.25 (s, 3H) 3.35 (br.s., 2H) 7.80 (d, J=8.3 Hz, 2H) 8.82-8.96 (m, 1H). MS m/z [M+H]$^+$ 418.4.

Example 228 6-(4-(4-cyanophenyl)-5-hydroxy-1H-pyrazol-1-yl)-N-((1r,4r)-4-methoxycyclohexyl)nicotinamide

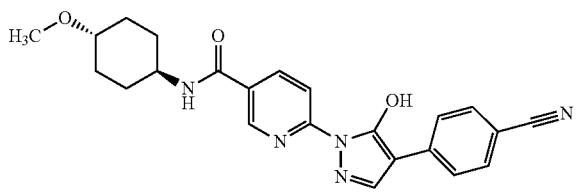 [SMILES: CO[C@H]1CC[C@H](NC(=O)c2ccc(-n3ncc(-c4ccc(C#N)cc4)c3O)nc2)CC1]

The title compound was prepared in a manner similar to Example 227 using 1-(tetrahydro-2H-pyran-4-yl)cyclopropanamine to afford the title compound. $^1$H NMR (400 MHz, DMSO-d6) δ ppm 0.59-0.83 (m, 4H) 1.18-1.45 (m, 2H) 1.54-1.78 (m, 3H) 3.23 (t, J=11.2 Hz, 2H) 3.86 (dd, J=11.0, 3.7 Hz, 2H) 7.79 (d, J=8.6 Hz, 3H) 8.14 (d, J=6.1 Hz, 2H) 8.41 (d, J=6.8 Hz, 1H) 8.83 (s, 1H) 8.89 (s, 1H). MS m/z [M+H]$^+$ 430.5.

Example 229 6-(4-(4-cyanophenyl)-5-hydroxy-1H-pyrazol-1-yl)-N-((1r,4r)-4-methoxycyclohexyl)nicotinamide

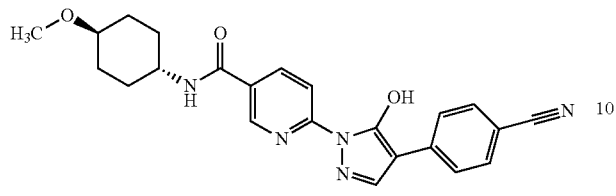

The title compound was prepared in a manner similar to Example 227 using (1r,4r)-4-methoxycyclohexanamine, HCl. $^1$H NMR (400 MHz, DMSO-d6) δ ppm 1.24 (br. s., 2H) 1.39 (d, J=14.7 Hz, 2H) 1.89 (br. s., 2H) 2.05 (d, J=10.9 Hz, 2H) 3.25 (s, 3H) 3.35 (br.s., 2H) 7.80 (d, J=8.3 Hz, 2H) 8.82-8.96 (m, 1H). MS m/z [M+H]$^+$ 418.4.

Example 230 6-(4-(4-cyano-2-methoxyphenyl)-5-hydroxy-1H-pyrazol-1-yl)-N-((1s,4s)-4-methoxycyclohexyl)nicotinamide

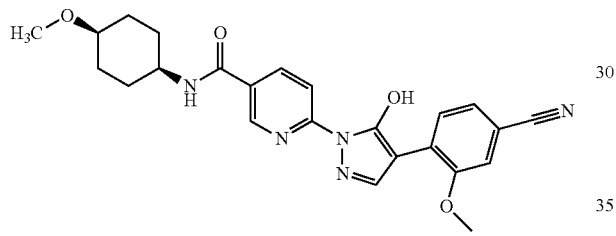

The title compound was prepared in a manner similar to Example 227 using 6-(4-(4-cyano-2-methoxyphenyl)-5-hydroxy-1H-pyrazol-1-yl)nicotinic acid and (1s,4s)-4-methoxycyclohexanamine, HCl. $^1$H NMR (400 MHz, DMSO-d6) δ ppm 1.42-1.54 (m, 2H) 1.55-1.69 (m, 4H) 1.90 (s, 1H) 1.88 (s, 1H) 3.23 (s, 3H) 3.38 (br. s., 1H) 3.87 (br.s., 1H) 3.96 (s, 3H) 7.33-7.59 (m, 2H) 8.44 (t, J=7.1 Hz, 3H) 8.68 (br. s., 1H) 8.91 (s, 1H) 13.40 (br. s., 1H). MS m/z [M+H]$^+$ 448.5.

Example 231 6-(4-(4-cyano-2-methoxy phenyl)-5-hydroxy-1H-pyrazol-1-yl)-N-(3-methoxypropyl)nicotinamide

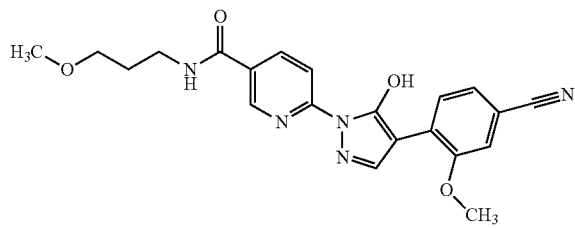 [SMILES: COCCCNC(=O)c1ccc(-n2ncc(-c3ccc(C#N)cc3OC)c2O)nc1]

The title compound was prepared in a manner similar to Example 227 using 6-(4-(4-cyano-2-methoxyphenyl)-5-hydroxy-1H-pyrazol-1-yl)nicotinic acid and 3-methoxypropan-1-amine. $^1$H NMR (400 MHz, DMSO-d6) δ ppm 1.66-1.88 (m, 3H) 3.25 (s, 5H) 3.96 (s, 5H) 7.33-7.56 (m, 3H) 8.31-8.56 (m, 1H) 8.70 (br. s., 1H) 8.91 (s, 1H). MS m/z [M+H]$^+$ 408.4.

Example 232 6-(4-(4-cyano-2-methoxyphenyl)-5-hydroxy-1H-pyrazol-1-yl)-N-cyclopropylnicotinamide

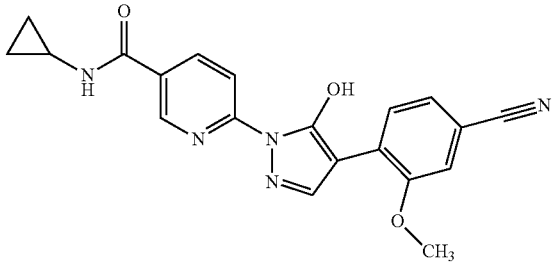 [SMILES: COc1cc(C#N)ccc1-c1cnn(-c2ccc(C(=O)NC3CC3)cn2)c1O]

The title compound was prepared in a manner similar to Example 227 using 6-(4-(4-cyano-2-methoxyphenyl)-5-hydroxy-1H-pyrazol-1-yl)nicotinic acid and cyclopropanamine. $^1$H NMR (400 MHz, DMSO-d6) δ ppm 0.61 (br. s., 2H) 0.67-0.80 (m, 2H) 2.78-2.93 (m, 1H) 3.96 (s, 3H) 7.37-7.55 (m, 2H) 8.38 (d, J=7.6 Hz, 1H) 8.46 (br. s., 1H) 8.59 (br. s., 1H) 8.68 (br. s., 1H) 8.75 (br. s., 1H) 8.89 (s, 1H) 13.40 (br. s., 1H). MS m/z [M+H]$^+$ 376.4.

Example 233 6-(5-hydroxy-4-(2-methoxypyridin-4-yl)-1H-pyrazol-1-yl)-N-(1-(tetrahydro-2H-pyran-4-yl)cyclopropyl)nicotinamide

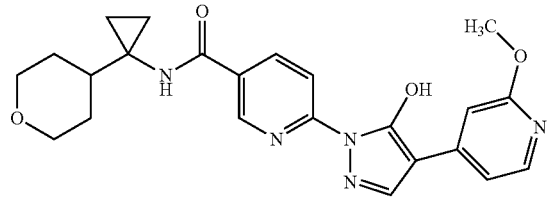 [SMILES: COc1cc(-c2cnn(-c3ccc(C(=O)NC4(C5CCOCC5)CC4)cn3)c2O)ccn1]

The title compound was prepared in a manner similar to Example 227 using 6-(5-hydroxy-4-(2-methoxypyridin-4-yl)-1H-pyrazol-1-yl)nicotinic acid and 1-(tetrahydro-2H-pyran-4-yl)cyclopropanamine. $^1$H NMR (400 MHz, DMSO-d6) δ ppm 0.82-1.03 (m, 5H) 1.25 (s, 1H) 1.45-1.67 (m, 3H) 1.74 (d, J=12.4 Hz, 2H) 3.37 (t, J=11.6 Hz, 2H) 4.03 (dd, J=11.4, 3.5 Hz, 2H) 4.09 (s, 3H) 7.22 (s, 1H) 7.31 (d, J=6.1 Hz, 1H) 7.41 (s, 1H) 7.83 (d, J 8.6 Hz, 1H) 7.90 (s, 1H) 8.13 (d, J=6.1 Hz, 1H) 8.37 (dd, J=8.7, 2.1 Hz, 1H) 8.83 (d, J=1.8 Hz, 1H). MS m/z [M+H]$^+$ 436.4.

Example 234 6-(4-(4-cyanophenyl)-5-hydroxy-1H-pyrazol-1-yl)-N-(3-methoxypropyl)-N-methylnicotinamide

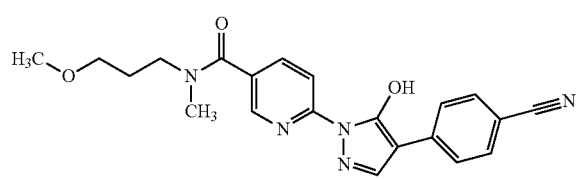 [SMILES: COCCCN(C)C(=O)c1ccc(-n2ncc(-c3ccc(C#N)cc3)c2O)nc1]

The title compound was prepared in a manner similar to Example 227 using 3-methoxy-N-methylpropan-1-amine. ¹H NMR (400 MHz, DMSO-d6) δ ppm 1.66-1.94 (m, 3H) 2.98 (s, 4H) 3.11 (br. s., 2H) 3.22 (br. s., 1H) 3.27 (br. s., 2H) 3.51 (br. s., 1H) 7.80 (d, J=8.3 Hz, 2H) 8.02-8.23 (m, 4H) 8.54 (d, J=9.3 Hz, 2H) 8.68 (br. s., 1H) 13.53 (br. s., 1H). MS m/z [M+H]⁺ 392.4.

Example 235 6-(4-(4-cyanophenyl)-5-hydroxy-1H-pyrazol-1-yl)-N-(4-methoxybutyl)nicotinamide

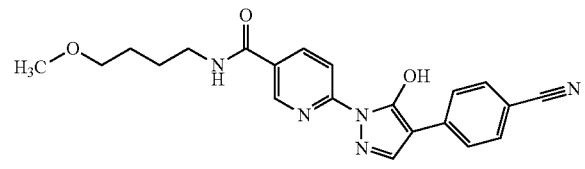 [SMILES: COCCCCNC(=O)c1ccc(-n2ncc(-c3ccc(C#N)cc3)c2O)nc1]

The title compound was prepared in a manner similar to Example 227 using 4-methoxybutan-1-amine. ¹H NMR (400 MHz, DMSO-d6) δ ppm 1.51-1.65 (m, 4H) 3.23 (s, 3H) 3.28-3.40 (m, 8H) 7.80 (d, J=8.3 Hz, 2H) 8.14 (br. s., 2H) 8.42 (d, J=6.8 Hz, 1H) 8.70 (t, J=5.4 Hz, 2H) 8.86-8.97 (m, 1H). MS m/z [M+H]⁺ 392.4.

Example 236 6-(4-(4-cyanophenyl)-5-hydroxy-1H-pyrazol-1-yl)-N-(2-(trifluoromethoxy)ethyl)nicotinamide

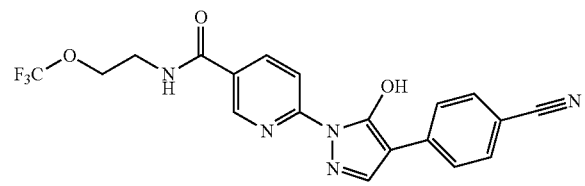 [SMILES: N#Cc1ccc(-c2cnn(-c3ccc(C(=O)NCCOC(F)(F)F)cn3)c2O)cc1]

The title compound was prepared in a manner similar to Example 227 using 2-(trifluoromethoxy)ethanamine, HCl. ¹H NMR (400 MHz, DMSO-d6) δ ppm 3.62 (q, J=5.3 Hz, 2H) 4.24 (t, J=5.3 Hz, 2H) 7.80 (d, J=8.6 Hz, 2H) 8.15 (br. s., 2H) 8.43 (d, J=7.6 Hz, 1H) 8.69 (br. s., 1H) 8.91-8.96 (m, 1H) 9.00 (t, J=5.3 Hz, 1H) 13.54 (br. s., 1H). MS m/z [M+H]⁺ 418.3.

Example 237 6-(4-(4-cyanophenyl)-5-hydroxy-1H-pyrazol-1-yl)-N-(2-oxaspiro[3.3]heptan-6-yl)nicotinamide

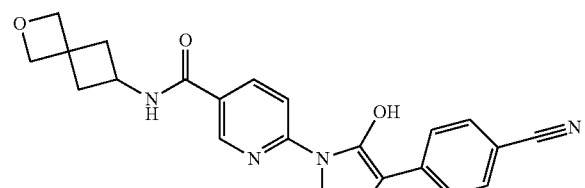

The title compound was prepared in a manner similar to Example 227 using 2-oxaspiro[3.3]heptan-6-amine, HCl.

¹HNMR (400 MHz, DMSO-d6) δ ppm 2.13-2.25 (m, 2H) 2.49-2.59 (m, 2H) 4.08-4.27 (m, 1H) 4.46 (s, 2H) 4.57 (s, 2H) 7.69 (d, J=8.6 Hz, 2H) 8.06 (d, J=8.3 Hz, 2H) 8.30 (dd, J=8.7, 2.1 Hz, 1H) 8.40 (d, J=8.8 Hz, 1H) 8.51 (s, 1H) 8.71 (d, J=7.1 Hz, 1H) 8.81 (d, J=1.8 Hz, 1H) 13.46 (br. s., 1H). MS m/z [M+H]⁺ 402.4.

Example 238 6-(4-(4-cyano-2-methoxyphenyl)-5-hydroxy-1H-pyrazol-1-yl)-N-(4-methoxybutyl)nicotinamide

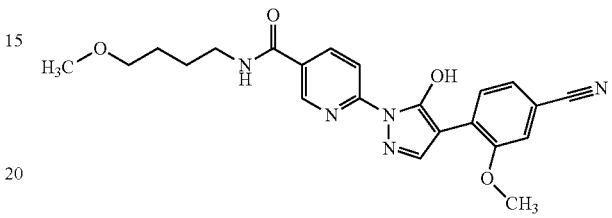

The title compound was prepared in a manner similar to Example 227 using 4-methoxybutan-1-amine. ¹H NMR (400 MHz, DMSO-d6) δ ppm 1.50-1.63 (m, 4H) 3.23 (s, 3H) 3.27-3.41 (m, 8H) 3.91 (br. s., 3H) 7.28 (br. s., 2H) 8.14 (s, 1H) 8.20 (br. s., 1H) 8.26 (d, J=2.3 Hz, 1H) 8.56 (t, J=5.4 Hz, 2H) 8.80 (d, J=6.3 Hz, 1H) 8.86 (br. s., 1H) 12.97 (br. s., 1H). MS m/z [M+H]⁺ 422.4.

Example 239 6-(4-(4-cyanophenyl)-5-hydroxy-1H-pyrazol-1-yl)-N-cyclopropyl-N-methylnicotinamide

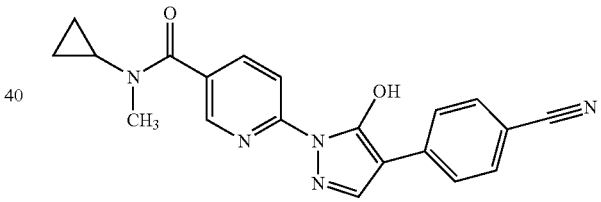

The title compound was prepared in a manner similar to Example 227 using N-methylcyclopropanamine, HCl. ¹H NMR (400 MHz, DMSO-d6) δ ppm 0.47 (br. s., 2H) 0.54-0.74 (m, 2H) 3.02 (s, 4H) 7.80 (d, J=8.6 Hz, 2H) 8.15 (br. s., 2H) 8.21 (d, J=7.1 Hz, 1H) 8.48 (br. s., 1H) 8.65 (br. s., 2H) 13.54 (br. s., 1H). MS m/z [M+H]⁺ 360.3.

Example 240 6-(4-(4-cyano-2-methoxyphenyl)-5-hydroxy-1H-pyrazol-1-yl)-N-(3-methoxypropyl)-N-methylnicotinamide

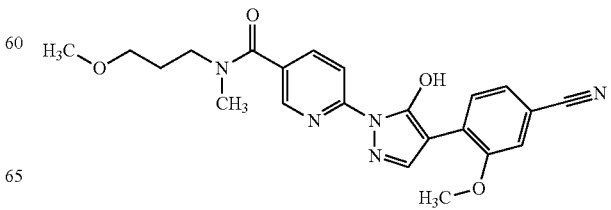

The title compound was prepared in a manner similar to Example 227 using 6-(4-(4-cyano-2-methoxyphenyl)-5-hydroxy-1H-pyrazol-1-yl)nicotinic acid and 3-methoxy-N-methylpropan-1-amine. $^1$H NMR (400 MHz, DMSO-d6) δ ppm 1.76-2.04 (m, 2H) 3.09 (d, J=7.3 Hz, 3H) 3.21 (s, 2H) 3.36 (s, 2H) 3.43-3.56 (m, 2H) 3.65 (t, J=6.9 Hz, 1H) 3.98 (s, 3H) 7.31-7.36 (m, 2H) 8.05 (br. s., 1H) 8.28-8.64 (m, 3H). MS m/z [M+H]$^+$ 422.4.

Example 241 6-(4-(4-cyanophenyl)-5-hydroxy-1H-pyrazol-1-yl)-N-(2-(tetrahydrofuran-2-yl)ethyl)nicotinamide

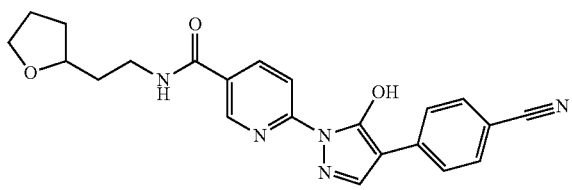 [SMILES: N#Cc1ccc(-c2cnn(-c3ccc(C(=O)NCCC4CCCO4)cn3)c2O)cc1]

The title compound was prepared in a manner similar to Example 227 using 2-(tetrahydrofuran-2-yl)ethanamine. $^1$H NMR (400 MHz, DMSO-d6) δ ppm 1.33-1.51 (m, 1H) 1.65-1.91 (m, 4H) 1.99 (dddd, J=11.8, 8.2, 6.6, 5.2 Hz, 1H) 3.23-3.47 (m, 3H) 3.52-3.68 (m, 1H) 3.71-3.89 (m, 2H) 7.79 (d, J=8.6 Hz, 2H) 8.10-8.18 (m, 2H) 8.41 (d, J=7.1 Hz, 1H) 8.60-8.75 (m, 2H) 8.86-8.95 (m, 1H) 13.54 (br. s., 1H). MS m/z [M+H]$^+$ 404.4.

Example 242 6-(4-(4-cyano-2-methoxyphenyl)-5-hydroxy-1H-pyrazol-1-yl)-N-(2-(tetrahydrofuran-2-yl)ethyl)nicotinamide

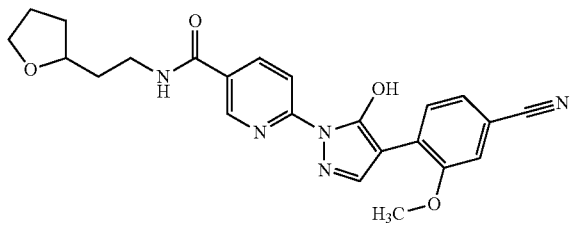 [SMILES: COc1cc(C#N)ccc1-c1cnn(-c2ccc(C(=O)NCCC3CCCO3)cn2)c1O]

The title compound was prepared in a manner similar to Example 227 using 6-(5-hydroxy-4-(2-methoxypyridin-4-yl)-1H-pyrazol-1-yl)nicotinic acid and 2-(tetrahydrofuran-2-yl)ethanamine. $^1$H NMR (400 MHz, DMSO-d6) δ ppm 1.26-1.46 (m, 1H) 1.66 (q, J=6.9 Hz, 2H) 1.70-1.82 (m, 2H) 1.85-2.03 (m, 1H) 3.29-3.39 (m, 2H) 3.47-3.60 (m, 1H) 3.65-3.77 (m, 2H) 3.79 (s, 3H) 7.35 (br. s., 1H) 7.42 (d, J=4.8 Hz, 1H) 7.98 (d, J=5.6 Hz, 1H) 8.28-8.35 (m, 1H) 8.37 (br. s., 1H) 8.53 (br. s., 1H) 8.63 (t, J=5.4 Hz, 1H) 8.77-8.87 (m, 1H) 13.47 (br. s., 1H). MS m/z [M+H]$^+$ 410.3.

Example 243 N-cyclopropyl-6-(5-hydroxy-4-(2-methoxypyridin-4-yl)-1H-pyrazol-1-yl)-N-methylnicotinamide

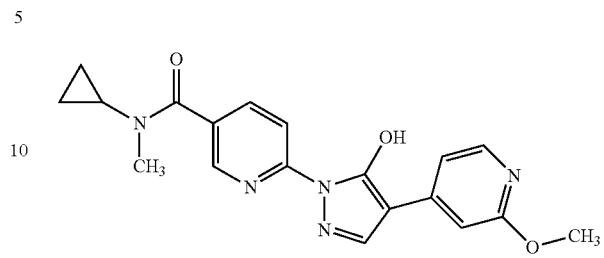

The title compound was prepared in a manner similar to Example 227 using 6-(5-hydroxy-4-(2-methoxypyridin-4-yl)-1H-pyrazol-1-yl)nicotinic acid and N-methylcyclopropanamine, HCl. $^1$H NMR (400 MHz, DMSO-d6) δ ppm 0.40 (br. s., 2H) 0.47-0.60 (m, 2H) 2.95 (s, 5H) 3.81 (s, 3H) 7.39 (br. s., 1H) 7.47 (d, J=4.5 Hz, 1H) 8.01 (d, J=5.6 Hz, 1H) 8.13 (d, J=8.3 Hz, 1H) 8.34 (br. s., 1H) 8.57 (br. s., 2H). MS m/z [M+H]$^+$ 366.3.

Example 244 6-(4-(4-cyano-2-methylphenyl)-5-hydroxy-1H-pyrazol-1-yl)-N-(2-oxaspiro[3.3]heptan-6-yl)nicotinamide

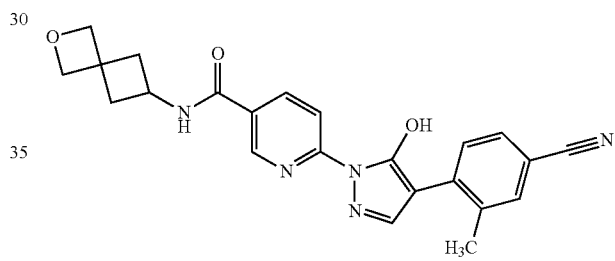

The title compound was prepared in a manner similar to Example 227 using 6-(4-(4-cyano-2-methylphenyl)-5-hydroxy-1H-pyrazol-1-yl)nicotinic acid and 2-oxaspiro[3.3]heptan-6-amine, HCl. $^1$H NMR (400 MHz, DMSO-d6) δ ppm 2.13-2.26 (m, 2H) 2.36 (s, 3H) 2.48-2.60 (m, 2H) 4.18 (sxt, J=8.0 Hz, 1H) 4.46 (s, 2H) 4.57 (s, 2H) 7.55-7.62 (m, 1H) 7.65 (s, 1H) 7.72 (d, J=8.1 Hz, 1H) 8.09 (s, 1H) 8.33 (br. s., 2H) 8.73 (d, J=7.3 Hz, 1H) 8.82 (t, J=1.5 Hz, 1H) 13.10 (br. s., 1H). MS m/z [M+H]$^+$ 416.3.

Example 245 6-(4-(4-cyano-2-methylphenyl)-5-hydroxy-1H-pyrazol-1-yl)-N-(2-(tetrahydrofuran-2-yl)ethyl)nicotinamide

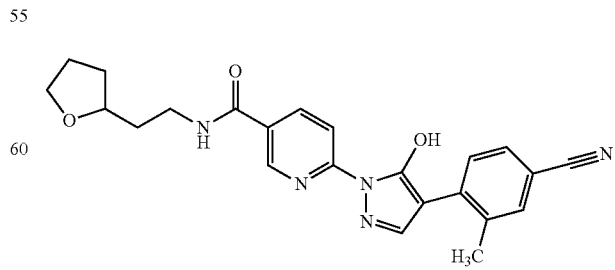

The title compound was prepared in a manner similar to Example 227 using 2-(tetrahydrofuran-2-yl)ethanamine and 6-(4-(4-cyano-2-methylphenyl)-5-hydroxy-1H-pyrazol-1-yl)nicotinic acid. $^1$H NMR (400 MHz, DMSO-d6) δ 1.21-1.29 (m, 1H) 1.37-1.51 (m, 1H) 1.68-1.89 (m, 4H) 1.99 (dddd, J=11.8, 8.2, 6.6, 5.2 Hz, 1H) 2.44 (s, 3H) 3.26-3.47 (m, 3H) 3.61 (td, J=7.9, 6.4 Hz, 1H) 3.70-3.88 (m, 2H) 7.63-7.68 (m, 1H) 7.71-7.81 (m, 2H) 8.18 (br. s., 1H) 8.41 (d, J=6.3 Hz, 1H) 8.72 (t, J=5.4 Hz, 1H) 8.88-8.95 (m, 1H). MS m/z [M+H]$^+$ 418.4.

Example 246 6-(4-(4-cyano-2-methylphenyl)-5-hydroxy-1H-pyrazol-1-yl)-N-cyclopropyl-N-methyl-nicotinamide

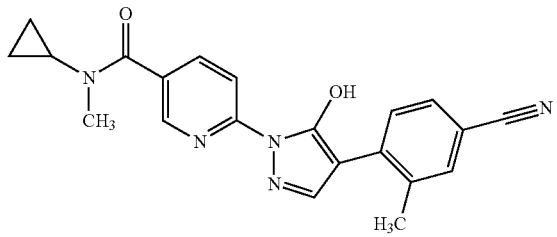 [SMILES: Cc1cc(C#N)ccc1-c1cnn(-c2ccc(C(=O)N(C)C3CC3)cn2)c1O]

The title compound was prepared in a manner similar to Example 227 using 6-(4-(4-cyano-2-methylphenyl)-5-hydroxy-1H-pyrazol-1-yl)nicotinic acid and N-methylcyclopropanamine, HCl. $^1$H NMR (400 MHz, DMSO-d6) δ 0.40 (br. s., 2H) 0.47-0.63 (m, 2H) 2.36 (s, 3H) 2.95 (s, 4H) 7.58 (d, J=8.1 Hz, 1H) 7.65 (s, 1H) 7.73 (d, J=7.8 Hz, 1H) 8.06 (s, 1H) 8.12 (d, J=8.1 Hz, 1H) 8.30 (d, J=8.3 Hz, 1H) 8.58 (br. s., 1H). MS m/z [M+H]$^+$ 374.3.

Example 247 6-(4-(4-cyano-2-methylphenyl)-5-hydroxy-1H-pyrazol-1-yl)-N-((4,4-difluorocyclohexyl)methyl)nicotinamide

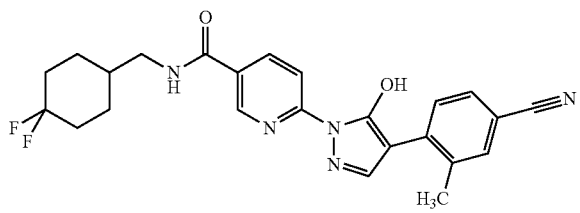 [SMILES: Cc1cc(C#N)ccc1-c1cnn(-c2ccc(C(=O)NCC3CCC(F)(F)CC3)cn2)c1O]

The title compound was prepared in a manner similar to Example 227 using 6-(4-(4-cyano-2-methylphenyl)-5-hydroxy-1H-pyrazol-1-yl)nicotinic acid and (4,4-difluorocyclohexyl)methanamine hydrochloride. $^1$H NMR (400 MHz, DMSO-d6) δ 1.09-1.25 (m, 2H) 1.60-1.82 (m, 5H) 1.95 (d, J=8.1 Hz, 2H) 2.37 (s, 3H) 3.15 (t, J=6.3 Hz, 2H) 7.59 (d, J=7.6 Hz, 1H) 7.67 (s, 1H) 8.36 (br. s., 1H) 8.70 (br. s., 1H) 8.82-8.88 (m, 1H) 13.16 (br. s., 1H). MS m/z [M+H]$^+$ 452.5.

Example 248 4-(5-hydroxy-1-(5-(4-(methoxymethyl)piperidine-1-carbonyl)pyridin-2-yl)-1H-pyrazol-4-yl)-3-methylbenzonitrile

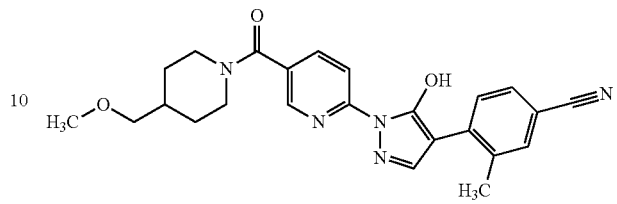

The title compound was prepared in a manner similar to Example 227 using 6-(4-(4-cyano-2-methylphenyl)-5-hydroxy-1H-pyrazol-1-yl)nicotinic acid and 4-(methoxymethyl)piperidine hydrochloride. $^1$H NMR (400 MHz, DMSO-d6) δ 1.10 (qd, J=12.3, 4.0 Hz, 2H) 1.59 (br. s., 1H) 1.67 (br. s., 1H) 1.70-1.85 (m, 1H) 2.36 (s, 3H) 2.74 (br. s., 1H) 3.14 (d, J=6.3 Hz, 2H) 3.17 (s, 3H) 3.57 (br. s., 1H) 4.41 (br. s., 1H) 7.57 (dd, J=8.0, 1.4 Hz, 1H) 7.64 (s, 1H) 7.74 (d, J=8.1 Hz, 1H) 7.96 (dd, J=8.6, 2.3 Hz, 1H) 8.03-8.09 (m, 1H) 8.31 (d, J=8.3 Hz, 1H) 8.42-8.47 (m, 1H) 13.03 (br. s., 1H). MS m/z [M+H]$^+$ 432.5.

Example 249 4-(5-hydroxy-1-(5-(4-methoxypiperidine-1-carbonyl)pyridin-2-yl)-1H-pyrazol-4-yl)-3-methylbenzonitrile

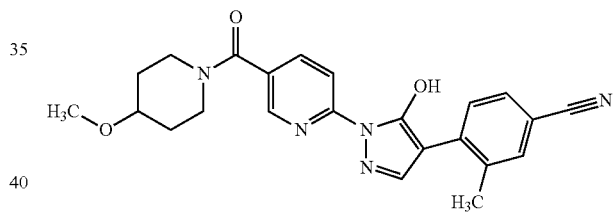

The title compound was prepared in a manner similar to Example 227 using 6-(4-(4-cyano-2-methylphenyl)-5-hydroxy-1H-pyrazol-1-yl)nicotinic acid and 4-methoxypiperidine hydrochloride. $^1$H NMR (400 MHz, DMSO-d6) δ 1.14-1.32 (m, 3H) 1.63-1.93 (m, 5H) 1.96-2.10 (m, 2H) 2.44 (s, 3H) 3.22 (t, J=6.3 Hz, 2H) 7.67 (d, J=7.6 Hz, 1H) 7.74 (s, 1H) 7.81 (br. s., 1H) 8.25 (br. s., 1H) 8.43 (br. s., 1H) 8.57 (br. s., 1H) 8.78 (br. s., 1H) 8.91-8.94 (m, 1H) 13.25 (br. s., 1H). MS m/z [M+H]$^+$ 418.4.

Example 250 6-(4-(4-cyano-2-methylphenyl)-5-hydroxy-1H-pyrazol-1-yl)-N-(2-(trifluoromethoxy)ethyl)nicotinamide

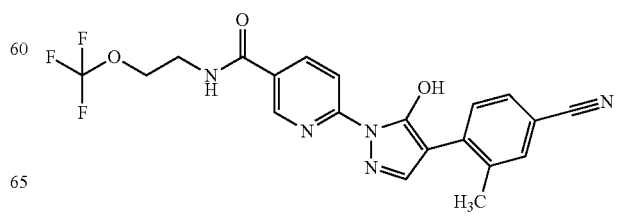

The title compound was prepared in a manner similar to Example 227 using 6-(4-(4-cyano-2-methylphenyl)-5-hydroxy-1H-pyrazol-1-yl)nicotinic acid and 2-(trifluoromethoxy)ethanamine hydrochloride. $^1$H NMR (400 MHz, DMSO-d6) δ 2.36 (s, 3H) 3.55 (q, J=5.3 Hz, 2H) 4.16 (t, J=5.3 Hz, 2H) 7.59 (d, J=7.8 Hz, 1H) 7.66 (s, 1H) 7.71 (br. s., 1H) 8.14 (br. s., 1H) 8.36 (d, J=7.3 Hz, 1H) 8.84-8.88 (m, 1H) 8.93 (t, J=4.4 Hz, 1H) 13.18 (br. s., 1H). MS m/z [M+H]$^+$ 432.4.

Example 251 6-(4-(4-cyano-2-methylphenyl)-5-hydroxy-1H-pyrazol-1-yl)-N-(3-methoxypropyl)-N-methylnicotinamide

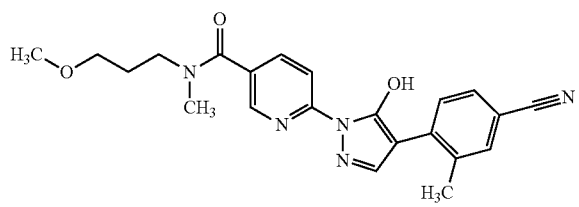 [SMILES: COCCCN(C)C(=O)c1ccc(-n2ncc(-c3ccc(C#N)cc3C)c2O)nc1]

The title compound was prepared in a manner similar to Example 227 using 6-(4-(4-cyano-2-methylphenyl)-5-hydroxy-1H-pyrazol-1-yl)nicotinic acid and 3-methoxy-N-methylpropan-1-amine. $^1$H NMR (400 MHz, DMSO-d6) δ 1.62-1.84 (m, 2H) 2.36 (s, 3H) 2.91 (s, 3H) 3.04 (br. s., 1H) 3.14-3.21 (m, 3H) 7.59 (dd, J=8.1, 1.5 Hz, 1H) 7.65 (s, 1H) 7.72 (d, J=8.1 Hz, 1H) 7.95-8.04 (m, 1H) 8.05-8.09 (m, 1H) 8.30 (d, J=8.3 Hz, 1H) 8.46 (d, J=9.9 Hz, 1H). MS m/z [M+H]$^+$ 406.4.

Example 252 4-(5-hydroxy-1-(5-(3-(methoxymethyl)pyrrolidine-1-carbonyl)pyridin-2-yl)-1H-pyrazol-4-yl)-3-methylbenzonitrile

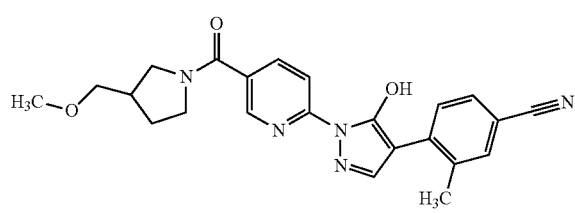 [SMILES: COCC1CCN(C(=O)c2ccc(-n3ncc(-c4ccc(C#N)cc4C)c3O)nc2)C1]

The title compound was prepared in a manner similar to Example 227 using 6-(4-(4-cyano-2-methylphenyl)-5-hydroxy-1H-pyrazol-1-yl)nicotinic acid and 3-(methoxymethyl)pyrrolidine. $^1$H NMR (400 MHz, DMSO-d6) δ 1.51-1.66 (m, 1H) 1.83-1.99 (m, 1H) 2.36 (s, 3H) 3.14 (s, 1H) 3.22 (s, 2H) 3.37-3.62 (m, 4H) 7.56-7.61 (m, 1H) 7.65 (s, 1H) 7.74 (d, J=8.1 Hz, 1H) 8.03-8.15 (m, 2H) 8.31 (d, J=8.3 Hz, 1H) 8.55-8.62 (m, 1H) 13.07 (br. s., 1H). MS m/z [M+H]$^+$ 418.4.

Example 253 6-(4-(4-cyano-3-methoxy phenyl)-5-hydroxy-1H-pyrazol-1-yl)-N-((tetrahydro-2H-pyran-4-yl)methyl)nicotinamide

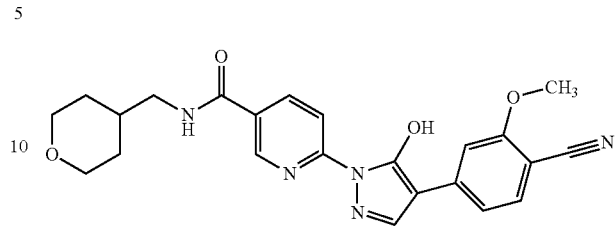

The title compound was prepared in a manner similar to Example 213 using 6-(4-bromo-5-methoxy-1H-pyrazol-1-yl)-N-((tetrahydro-2H-pyran-4-yl)methyl)nicotinamide (50 mg, 0.127 mmol), (4-cyano-3-methoxyphenyl)boronic acid. $^1$H NMR (400 MHz, DMSO-d6) δ 1.14 (d, J=10.6 Hz, 2H) 1.55 (d, J=11.9 Hz, 3H) 3.11 (br. s., 2H) 3.72-3.90 (m, 7H) 6.47 (s, 1H) 7.41 (d, J=15.4 Hz, 3H) 7.77 (br. s., 1H) 8.03-8.23 (m, 3H) 8.41-8.60 (m, 2H) 8.77 (br. s., 1H). MS m/z [M+H]$^+$ 434.4.

Example 254 6-(4-(5-fluoro-2-methoxypyridin-4-yl)-5-hydroxy-1H-pyrazol-1-yl)-N-((tetrahydro-2H-pyran-4-yl)methyl)nicotinamide

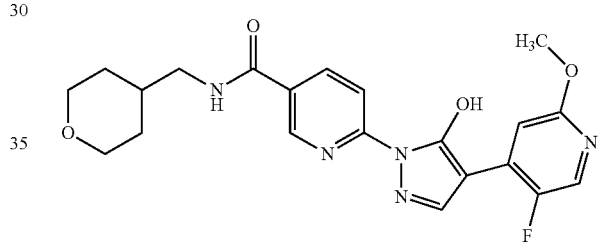

The title compound was prepared in a manner similar to Example 213 using 6-(4-bromo-5-methoxy-1H-pyrazol-1-yl)-N-((tetrahydro-2H-pyran-4-yl)methyl)nicotinamide (60.0 mg, 0.152 mmol), (5-fluoro-2-methoxypyridin-4-yl) boronic acid. $^1$H NMR (400 MHz, DMSO-d6) δ 1.15 (qd, J=12.3, 4.4 Hz, 2H) 1.55 (d, J=12.9 Hz, 2H) 1.74 (ddt, J=11.1, 7.4, 3.9, 3.9 Hz, 1H) 3.13 (t, J=6.3 Hz, 2H) 3.74-3.82 (m, 5H) 7.74 (d, J=4.8 Hz, 1H) 8.03 (d, J=3.0 Hz, 1H) 8.16 (d, J=2.5 Hz, 1H 8.30-8.45 (m, 2H) 8.66 (t, J=5.7 Hz, 1H) 8.84 (d, J=1.3 Hz, 1H). MS m/z [M+H]$^+$ 428.5.

Example 255 6-(4-(2,3-dimethoxypyridin-4-yl)-5-hydroxy-1H-pyrazol-1-yl)-N-((tetrahydro-2H-pyran-4-yl)methyl)nicotinamide

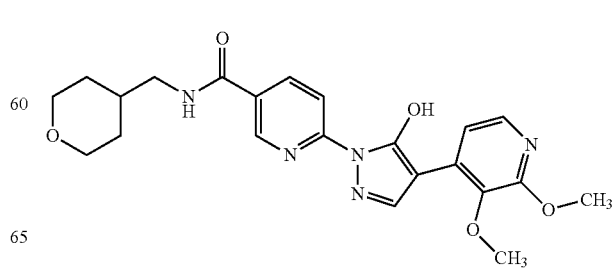

Combined 6-(4-bromo-5-methoxy-1H-pyrazol-1-yl)-N-((tetrahydro-2H-pyran-4-yl)methyl)nicotinamide (60.0 mg, 0.152 mmol), (2,3-dimethoxypyridin-4-yl)boronic acid (41.7 mg, 0.228 mmol), PdCl$_2$(dppf)-CH$_2$Cl$_2$ Adduct (6.20 mg, 7.59 μmol), and sodium bicarbonate (63.8 mg, 0.759 mmol) in dioxane (1139 μl) and water (380 μl) and heated in a microwave reactor for 60 minutes at 110° C. The reaction mixture was diluted with 150 mL EtOAc and washed with 1 N HCl. Organic layers were collected, dried with sodium sulfate, and concentrated to a residue which was purified on a 60 g silica gel column and eluted with hexanes and EtOAc to give 6-(4-(2,3-dimethoxypyridin-4-yl)-5-methoxy-1H-pyrazol-1-yl)-N-((tetrahydro-2H-pyran-4-yl)methyl)nicotinamide (29.4 mg, 42.7%) as a yellow oil. MS m/z [M+H]$^+$ 454.4.

Combined 6-(4-(2,3-dimethoxypyridin-4-yl)-5-methoxy-1H-pyrazol-1-yl)-N-((tetrahydro-2H-pyran-4-yl)methyl)nicotinamide (0.029 g, 0.064 mmol) and lithium chloride (0.014 g, 0.320 mmol) in DMA (0.639 mL) and heated at 50° C. for 16 hours. The reaction mixture was purified by preparative HPLC (SunFire™ C18, 5 μm, ID 30 mm×75 mm) eluting with ACN (with 0.1% ammonium hydroxide) in water (with 0.1% ammonium hydroxide) to give the title compound (7.3 mg, 26.0%). $^1$H NMR (400 MHz, DMSO-d6) δ 1.05-1.23 (m, 2H) 1.49-1.58 (m, 2H) 1.74 (ttt, J=11.1, 11.1, 7.3, 7.3, 3.7, 3.7 Hz, 1H) 2.01 (s, 1H) 3.08-3.13 (m, 3H) 3.63 (s, 3H) 3.77 (d, J=2.8 Hz, 1H) 3.80 (s, 4H) 7.07 (br. s., 1H) 7.63 (d, J=5.3 Hz, 1H) 8.04-8.09 (m, 2H) 8.19 (dd, J=8.8, 2.3 Hz, 1H) 8.45 (d, J=8.8 Hz, 1H) 8.53 (t, J=5.8 Hz, 1H) 8.78 (d, J=2.0 Hz, 1H). MS m/z [M+H]$^+$ 440.5.

Combined 6-(4-(3-cyano-4-fluorophenyl)-5-methoxy-1H-pyrazol-1-yl)-N-((tetrahydro-2H-pyran-4-yl)methyl)nicotinamide (32 mg, 0.073 mmol) and lithium chloride (15.58 mg, 0.367 mmol) in DMA (0.735 mL) and heated at 50° C. for 16 hours. The reaction mixture was purified by preparative HPLC (SunFire™ C18, 5 μm, ID 30 mm×75 mm) eluting with ACN (with 0.1% ammonium hydroxide) in water (with 0.1% ammonium hydroxide) to give the title compound (14.6 mg, 47.1%) as a white solid. $^1$H NMR (400 MHz, DMSO-d6) δ 1.14 (qd, J=12.3, 4.3 Hz, 2H) 1.57 (s, 1H) 1.53 (s, 1H) 1.74 (ddd, J=11.1, 7.3, 3.9 Hz, 1H) 3.09-3.14 (m, 3H) 3.79 (dd, J=11.2, 2.7 Hz, 2H) 7.05 (br. s., 1H) 7.37 (t, J=9.1 Hz, 1H) 8.15-8.28 (m, 3H) 8.33 (dd, J=6.3, 2.3 Hz, 1H) 8.45 (d, J=8.8 Hz, 1H) 8.57 (t, J=5.7 Hz, 1H) 8.80 (d, J=1.8 Hz, 1H). MS m/z [M+H]$^+$ 422.4.

Example 256 6-(4-(4-cyanophenyl)-5-hydroxy-1H-pyrazol-1-yl)-N-(cyclobutylmethyl)nicotinamide

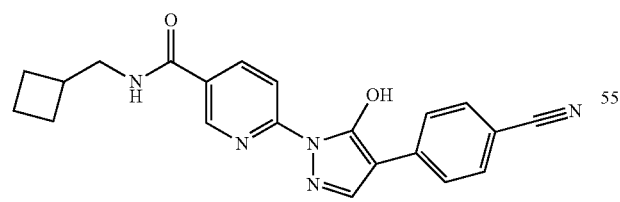

Combined 6-(4-(4-cyanophenyl)-5-hydroxy-1H-pyrazol-1-yl)nicotinic acid (200 mg, 0.654 mmol) and HATU (372 mg, 0.98 mmol) in DMF (3 mL) was added triethylamine (198 mg, 1.961 mmol). Then cyclobutylmethanamine (0.784 mmol) was added and the reaction was stirred at room temperature for 4 h. The reaction mixture was purified by preparative HPLC to give the title compound as a solid. $^1$H NMR (400 MHz, DMSO-d$_6$) δ ppm 8.90 (s, 1H), 8.70-8.65 (m, 2H), 8.45-8.40 (m, 2H), 8.13 (d, J=7.6 Hz, 2H), 7.78 (d, J=7.6 Hz, 2H), 3.31 (m, 2H), 2.56-2.53 (m, 1H), 2.05-2.00 (m, 2H), 1.85-1.82 (m, 2H), 1.75-1.72 (m, 2H). MS m/Z [M+H]$^+$ 374.1.

Example 257 6-(4-(4-cyanophenyl)-5-hydroxy-1H-pyrazol-1-yl)-N-((3-methylcyclobutyl)methyl)nicotinamide

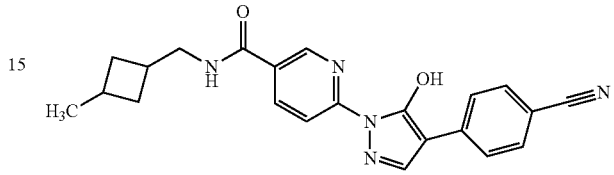

The title compound was prepared in a manner similar to Example 256 using (3-methylcyclobutyl)methanamine. $^1$H NMR (400 MHz, DMSO-d$_6$) δ ppm 8.90 (s, 1H), 8.67-8.61 (m, 2H), 8.44-8.39 (m, 2H), 8.12 (d, J=8.0 Hz, 2H), 7.77 (d, J=8.0 Hz, 2H), 3.39-3.36 (m, 2H), 2.37-2.33 (m, 1H), 2.16-2.14 (m, 2H), 1.90-1.89 (m, 1H), 1.66-1.65 (m, 1H), 1.33-1.29 (m, 1H), 1.09-0.99 (m, 3H). MS m/Z [M+H]$^+$ 388.1.

Example 258 6-(4-(4-cyanophenyl)-5-hydroxy-1H-pyrazol-1-yl)-N-((1s,3r)-3-hydroxycyclopentyl)nicotinamide

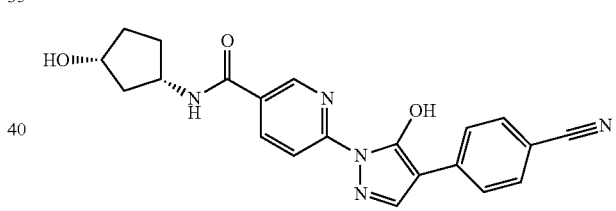

The title compound was prepared in a manner similar to Example 256 using (1r,3s)-3-aminocyclopentanol. $^1$H NMR (400 MHz, DMSO-d$_6$) δ ppm 8.89 (s, 1H), 8.63-8.57 (m, 2H), 8.41 (d, J=6.8 Hz, 2H), 8.11 (d, J=7.6 Hz, 2H), 7.77 (d, J=7.6 Hz, 2H), 4.24-4.18 (m, 1H), 4.14-4.10 (m, 1H), 2.22-2.18 (m, 1H), 1.93-1.88 (m, 1H), 1.76-1.71 (m, 2H), 1.63-1.61 (m, 1H), 1.53-1.50 (m, 1H). MS m/Z [M+H]$^+$ 390.1.

Example 259 6-(4-(4-cyanophenyl)-5-hydroxy-1H-pyrazol-1-yl)-N-((1s,3s)-3-hydroxycyclopentyl)nicotinamide

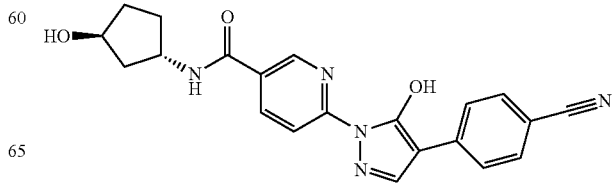

The title compound was prepared in a manner similar to Example 256 using (1s,3s)-3-aminocyclopentanol. ¹H NMR (400 MHz, DMSO-d₆) δ ppm 8.89 (s, 1H), 8.65 (s, 1H), 8.54-8.40 (m, 3H), 8.13 (d, J=8.4 Hz, 2H), 7.78 (d, J=8.4 Hz, 2H), 4.51-4.44 (m, 1H), 4.24-4.22 (m, 1H), 2.10-2.07 (m, 1H), 2.00-1.93 (m, 2H), 1.74-1.70 (m, 1H), 1.52-1.48 (m, 2H). MS m/Z [M+H]⁺ 390.2.

Example 260 (S)-6-(4-(4-cyanophenyl)-5-hydroxy-1H-pyrazol-1-yl)-N-(1-cyclopropylethyl)nicotinamide

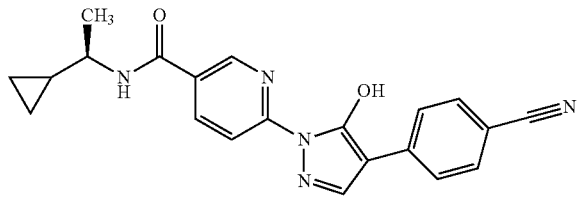 [SMILES: C[C@@H](NC(=O)c1ccc(-n2ncc(-c3ccc(C#N)cc3)c2O)nc1)C1CC1]

The title compound was prepared in a manner similar to Example 256 using (R)-1-cyclopropylethanamine. ¹H NMR (400 MHz, DMSO-d₆) δ ppm 8.90 (s, 1H), 8.65 (s, 1H), 8.61-8.43 (m, 3H), 8.13 (d, J=8.0 Hz, 2H), 7.79 (d, J=8.0 Hz, 2H), 3.52-3.46 (m, 1H), 1.24 (d, J=6.8 Hz, 3H), 1.01-0.99 (m, 1H), 0.54-0.45 (m, 1H), 0.44-0.36 (m, 1H), 0.32-0.30 (m, 1H), 0.24-0.21 (m, 1H). MS m/Z [M+H]⁺ 374.1.

Example 261 6-(4-(4-cyanophenyl)-5-hydroxy-1H-pyrazol-1-yl)-N-((3-methyloxetan-3-yl)methyl)nicotinamide

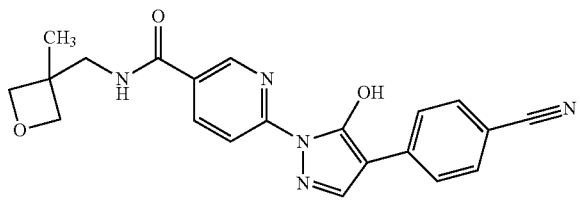 [SMILES: CC1(CNC(=O)c2ccc(-n3ncc(-c4ccc(C#N)cc4)c3O)nc2)COC1]

The title compound was prepared in a manner similar to Example 256 using (3-methyloxetan-3-yl)methanamine. ¹H NMR (400 MHz, DMSO-d₆) δ ppm 8.92 (s, 1H), 8.84 (s, 1H), 8.65 (s, 1H), 8.50-8.42 (m, 2H), 8.13 (d, J=8.0 Hz, 2H), 7.78 (d, J=8.0 Hz, 2H), 4.49 (d, J=6.0 Hz, 2H), 4.22 (d, J=6.0 Hz, 2H), 3.51 (d, J=6.0 Hz, 2H), 1.28 (s, 3H). MS m/Z [M+H]⁺ 390.1.

Example 262 6-(4-(4-cyanophenyl)-5-hydroxy-1H-pyrazol-1-yl)-N-(2-methylcyclopropyl)nicotinamide

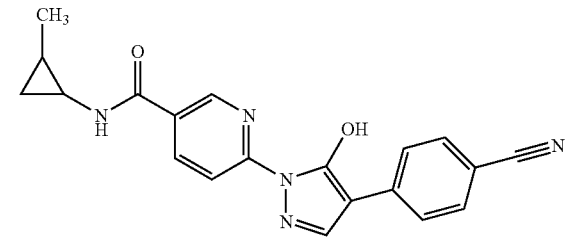 [SMILES: CC1CC1NC(=O)c1ccc(-n2ncc(-c3ccc(C#N)cc3)c2O)nc1]

The title compound was prepared in a manner similar to Example 256 using 2-methylcyclopropanamine. ¹H NMR (400 MHz, DMSO-d₆) δ ppm 8.90 (s, 1H), 8.64-8.61 (m, 2H), 8.45-8.35 (m, 2H), 8.12 (d, J=8.0 Hz, 2H), 7.77 (d, J=8.0 Hz, 2H), 2.58-2.54 (m, 1H), 1.07 (d, J=6.0 Hz, 3H), 0.98-0.95 (m, 1H), 0.78-0.76 (m, 1H), 0.53-0.51 (m, 1H). MS m/Z [M+H]⁺ 360.1.

Example 263 6-(4-(4-cyanophenyl)-5-hydroxy-1H-pyrazol-1-yl)-N-((1-fluorocyclohexyl)methyl)nicotinamide

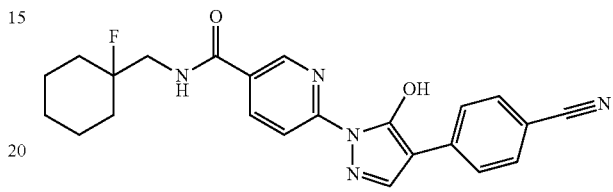

The title compound was prepared in a manner similar to Example 256 using (1-fluorocyclohexyl)methanamine. ¹H NMR (400 MHz, DMSO-d₆) δ ppm 8.95 (s, 1H), 8.83 (t, 1H), 8.67 (s, 1H), 8.53-8.40 (m, 2H), 8.13 (d, J=8.4 Hz, 2H), 7.78 (d, J=8.4 Hz, 2H), 3.55-3.49 (m, 2H), 1.77-1.74 (m, 2H), 1.59-1.46 (m, 7H), 1.29-1.21 (m, 1H). MS m/Z [M+H]⁺ 420.1.

Example 264 6-(4-(4-cyanophenyl)-5-hydroxy-1H-pyrazol-1-yl)-N-((3,3-difluorocyclobutyl)methyl)nicotinamide

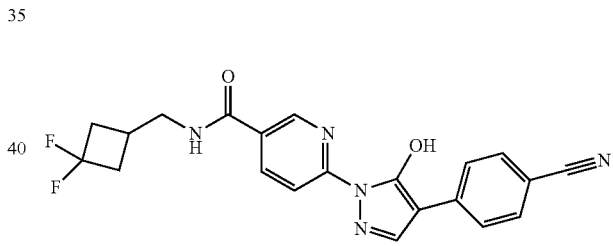

The title compound was prepared in a manner similar to Example 256 using (3,3-difluorocyclobutyl)methanamine. ¹H NMR (400 MHz, DMSO-d₆) δ ppm 8.91 (s, 1H), 8.84-8.81 (m, 1H), 8.64 (s, 1H), 8.46-8.39 (m, 2H), 8.13 (d, J=8.0 Hz, 2H), 7.78 (d, J=8.0 Hz, 2H), 3.44-3.41 (m, 2H), 2.70-2.67 (m, 2H), 2.44-2.38 (m, 3H). MS m/Z [M+H]⁺ 410.1.

Example 265 6-(4-(4-cyanophenyl)-5-hydroxy-1H-pyrazol-1-yl)-N-(3,3-difluorocyclobutyl)nicotinamide

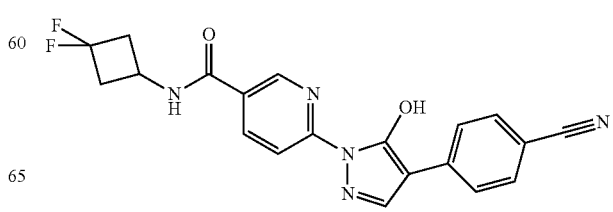

The title compound was prepared in a manner similar to Example 256 using 3,3-difluorocyclobutanamine. ¹H NMR (400 MHz, DMSO-d₆) δ ppm 9.06 (d, J=6.4 Hz, 1H), 8.91 (s, 1H), 8.67 (s, 1H), 8.50-8.40 (m, 2H), 8.14 (d, J=8.0 Hz, 2H), 7.79 (d, J=8.0 Hz, 2H), 4.33-4.26 (m, 1H), 3.01-2.97 (m, 2H), 2.81-2.76 (m, 2H). MS m/Z [M+H]⁺ 396.1.

Example 266 6-(4-(4-cyanophenyl)-5-hydroxy-1H-pyrazol-1-yl)-N-ethylnicotinamide

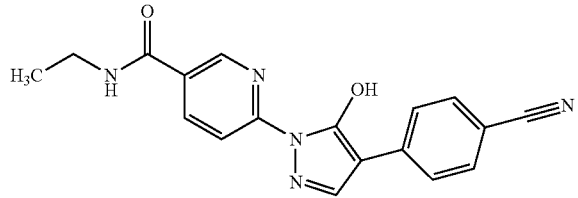 [SMILES: CCNC(=O)c1ccc(-n2ncc(-c3ccc(C#N)cc3)c2O)nc1]

The title compound was prepared in a manner similar to Example 256 using ethanamine. ¹H NMR (400 MHz, DMSO-d₆) δ ppm 8.90 (s, 1H), 8.70-8.78 (m, 2H), 8.50-8.40 (m, 2H), 8.13 (d, J=8.4 Hz, 2H), 7.78 (d, J=8.4 Hz, 2H), 3.34-3.31 (m, 2H), 1.15 (t, J=7.2 Hz, 3H). MS m/Z [M+H]⁺ 334.1.

Example 267 6-(4-(4-cyanophenyl)-5-hydroxy-1H-pyrazol-1-yl)-N-propylnicotinamide

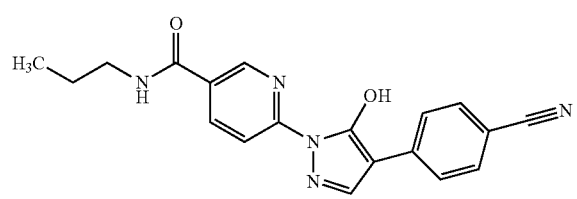 [SMILES: CCCNC(=O)c1ccc(-n2ncc(-c3ccc(C#N)cc3)c2O)nc1]

The title compound was prepared in a manner similar to Example 256 using propan-1-amine. ¹H NMR (400 MHz, DMSO-d₆) δ ppm 8.91 (s, 1H), 8.69-8.62 (m, 2H), 8.42-8.40 (m, 2H), 8.12 (d, J=8.4 Hz, 2H), 7.77 (d, J=8.4 Hz, 2H), 3.25-3.23 (m, 2H), 1.61-1.51 (m, 2H), 0.91 (t, 3H). MS m/Z [M+H]⁺ 348.1.

Example 268 6-(4-(4-cyanophenyl)-5-hydroxy-1H-pyrazol-1-yl)-N-(2-(dimethylamino)ethyl)nicotinamide

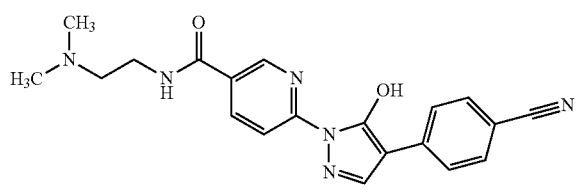 [SMILES: CN(C)CCNC(=O)c1ccc(-n2ncc(-c3ccc(C#N)cc3)c2O)nc1]

The title compound was prepared in a manner similar to Example 256 using N1,N1-dimethylethane-1,2-diamine. ¹H NMR (400 MHz, DMSO-d₆) δ ppm 8.87 (s, 1H), 8.87-8.79 (m, 1H), 8.57-8.55 (d, J=8.4 Hz, 1H), 8.32-8.28 (m, 2H), 8.05 (d, J=8.4 Hz, 2H), 7.65 (d, J=8.4 Hz, 2H), 3.64-3.60 (m, 2H), 3.27-3.24 (m, 2H), 2.84 (s, 6H). MS m/Z [M+H]⁺ 377.1.

Example 269 6-(4-(4-cyanophenyl)-5-hydroxy-1H-pyrazol-1-yl)-N-(3-(dimethylamino)propyl)nicotinamide

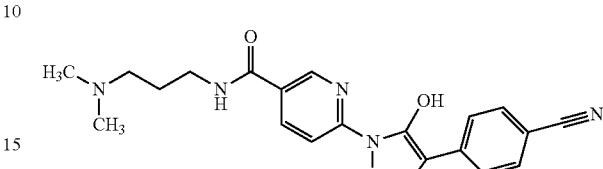

The title compound was prepared in a manner similar to Example 256 using N1,N1-dimethylpropane-1,3-diamine. ¹H NMR (400 MHz, DMSO-d₆) δ ppm 8.91 (s, 1H), 8.83 (t, 1H), 8.62 (s, 1H), 8.49-8.38-8.62 (m, 2H), 8.13 (d, J=8.4 Hz, 2H), 7.77 (d, J=8.4 Hz, 2H), 3.36-3.34 (m, 2H), 3.14-3.10 (m, 2H), 2.79 (s, 6H), 1.93-1.86 (m, 2H). MS m/Z [M+H]⁺ 391.2.

Example 270 6-(4-(4-cyanophenyl)-5-hydroxy-1H-pyrazol-1-yl)-N-(1-methylpiperidin-4-yl)nicotinamide

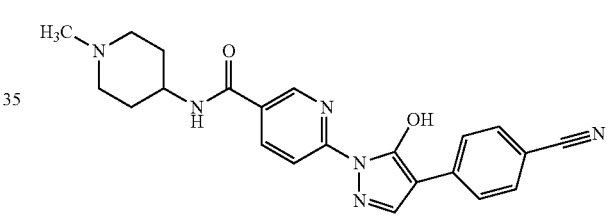

The title compound was prepared in a manner similar to Example 256. The product was purified by preparative HPLC to afford the title compound as an off-white solid. ¹H NMR (400 MHz, DMSO-d₆) δ ppm 13.53 (brs, 1H), 10.15 (br, 1H), 8.97 (s, 1H), 8.95-8.94 (m, 1H), 8.67-8.66 (m, 1H), 8.50-8.46 (m, 1H), 8.13 (d, J=7.6 Hz, 1H), 7.78 (d, J=7.6 Hz, 2H), 4.18-4.04 (m, 1H), 3.46-3.43 (m, 2H), 3.12-3.07 (m, 2H), 2.77 (s, 3H), 2.04-2.02 (m, 2H), 1.92-1.86 (m, 2H). MS m/Z [M+H]⁺ 403.1.

Example 271 6-(4-(4-cyanophenyl)-5-hydroxy-1H-pyrazol-1-yl)-N-((1-methylpiperidin-4-yl)methyl)nicotinamide

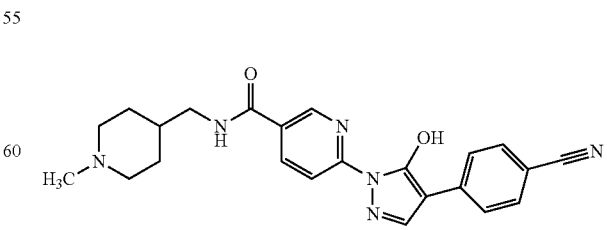

The title compound was prepared in a manner similar to Example 256 using (1-methylpiperidin-4-yl)methanamine. ¹H NMR (400 MHz, DMSO-d₆) δ ppm 8.89 (s, 1H), 8.74 (s, 1H), 8.52-8.49 (m, 2H), 8.37-8.34 (m, 1H), 8.11 (d, J=8.0 Hz, 2H), 7.73 (d, J=8.0 Hz, 2H), 3.45-3.40 (m, 2H), 3.23-3.21 (m, 2H), 2.91-2.89 (m, 2H), 2.76 (s, 3H), 1.91-1.81 (m, 3H), 1.39-1.37 (m, 2H). MS m/Z [M+H]+ 417.1.

Example 272 6-(4-(4-cyanophenyl)-5-hydroxy-1H-pyrazol-1-yl)-N-(3-(methylamino)propyl)nicotinamide hydrochloride

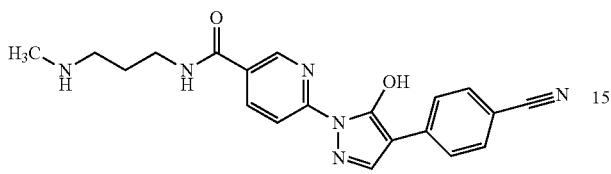

Combined 6-(4-(4-cyanophenyl)-5-hydroxy-1H-pyrazol-1-yl)nicotinic acid (200 mg, 0.65 mmol) HATU (372 mg, 0.98 mmol), and Et3N (198 mg, 1.96 mmol) in DMF (3.0 mL). The mixture was stirred at room temperature for 0.5 hour, then tert-butyl (3-aminopropyl)(methyl)carbamate (147.39 mg, 0.79 mmol) was added. The mixture was stirred overnight at room temperature. The reaction mixture was purified by preparative HPLC to give tert-butyl (3-(6-(4-(4-cyanophenyl)-5-hydroxy-1H-pyrazol-1-yl)nicotinamido) propyl)(methyl)carbamate (150 mg, 48%).

Combined tert-butyl (3-(6-(4-(4-cyanophenyl)-5-hydroxy-1H-pyrazol-1-yl)nicotinamido)propyl)(methyl)carbamate and EtOAc (5 mL) and added HCl-EtOAc (5 mL) and stir at room temperature for 5 h. The reaction mixture was evaporated in vacuo to give the title compound as a yellow green solid. 1H NMR (400 MHz, DMSO-d6) δ ppm 9.09-9.04 (m, 1H), 9.00 (s, 1H), 8.89 (br. s., 2H), 8.67 (s, 1H), 8.48 (br. s., 2H), 8.15 (d, J=8.2 Hz, 2H), 7.79 (d, J=8.4 Hz, 2H), 3.38 (d, J=6.0 Hz, 2H), 2.95 (br. s., 2H), 2.54 (t, J=5.3 Hz, 3H), 1.96-1.85 (m, 2H). MS m/Z [M+H]+ 377.1.

Example 273 6-(4-(4-cyanophenyl)-5-hydroxy-1H-pyrazol-1-yl)-N,4-dimethylnicotinamide

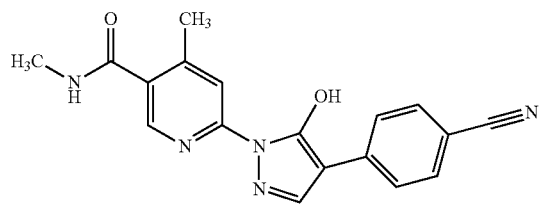 [SMILES: CNC(=O)c1cnc(-n2ncc(-c3ccc(C#N)cc3)c2O)cc1C]

Combined 6-(4-(4-cyanophenyl)-5-hydroxy-1H-pyrazol-1-yl)-4-methylnicotinic acid (200 mg, 0.625 mmol), HATU (356.25 mg, 0.938 mmol) and triethylamine (315.63 mg, 3.125 mmol) and stirred at room temperature for 0.5 h. Then methanamine (108.75 mg, 1.25 mmol) was added and the reaction was stirred at room temperature overnight. The reaction mixture was purified by preparative HPLC to afford the title compound as a light yellow solid (88.38 mg, 42.46%). 1H NMR (400 MHz, DMSO-d6) δ ppm 8.59 (brs, 1H), 8.49-8.48 (m, 1H), 8.43 (s, 1H), 8.27 (s, 1H), 8.11 (m, 2H), 7.77 (d, J=8.0 Hz, 2H), 2.79 (d, J=4.4 Hz, 2H), 2.48 (s, 3H). MS m/Z [M+H]+ 334.1.

Example 274 6-(4-(4-cyanophenyl)-5-hydroxy-1H-pyrazol-1-yl)-N-ethyl-4-methylnicotinamide

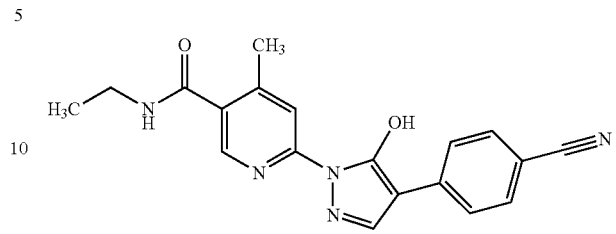

The title compound was prepared in a manner similar to Example 273 using ethanamine. 1H NMR (400 MHz, DMSO-d6) δ ppm 8.57-8.52 (m, 2H), 8.41 (s, 1H), 8.31-8.26 (m, 1H), 8.10 (m., 2H), 7.79 (d, J=8.4 Hz, 2H), 3.27 (q, J=7.2 Hz, 2H), 2.47 (s, 3H), 1.14 (t, J=7.2 Hz, 3H). MS m/Z [M+H]+ 348.1.

Example 275 6-(4-(4-cyanophenyl)-5-hydroxy-1H-pyrazol-1-yl)-N-cyclopropyl-4-methylnicotinamide

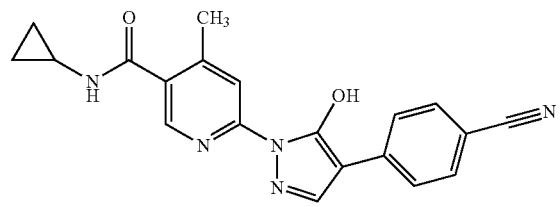 [SMILES: Cc1cc(-n2ncc(-c3ccc(C#N)cc3)c2O)ncc1C(=O)NC1CC1]

The title compound was prepared in a manner similar to Example 273 using cyclopropanamine. 1H NMR (400 MHz, DMSO-d6) δ ppm 8.58 (m, 2H), 8.38 (s, 1H), 8.24 (s, 1H), 8.10 (d, J=8.0 Hz, 2H), 7.78 (d, J=8.0 Hz, 2H), 2.86-2.83 (m, 1H), 2.46 (s, 3H), 0.74-0.70 (m, 2H), 0.58-0.54 (m, 2H). MS m/Z [M+H]+ 360.1.

Example 276 6-(4-(4-cyanophenyl)-5-hydroxy-1H-pyrazol-1-yl)-N-(2-methoxyethyl)-4-methylnicotinamide

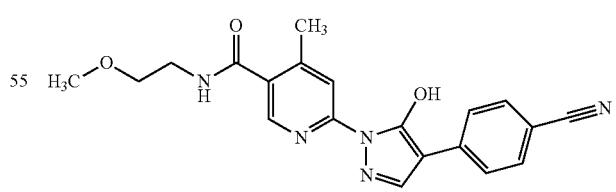

The title compound was prepared in a manner similar to Example 273 using 2-methoxyethanamine. 1H NMR (400 MHz, DMSO-d6) δ ppm 8.56-8.54 (m, 2H), 8.53 (s, 1H), 8.41-8.40 (brs, 1H), 8.11-8.10 (m, 2H), 7.79 (d, J=8.0 Hz, 2H), 3.42-3.39 (m, 2H), 3.30-3.26 (m, 2H), 3.25 (s, 3H), 2.47 (s, 3H)), 1.79-1.73 (m, 2H). MS m/Z [M+H]+ 392.1.

Example 277 (S)-6-(4-(4-cyanophenyl)-5-hydroxy-1H-pyrazol-1-yl)-4-methyl-N-(tetrahydrofuran-3-yl)nicotinamide

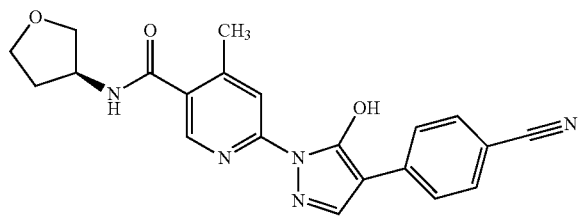 [SMILES: Cc1cc(-n2ncc(-c3ccc(C#N)cc3)c2O)ncc1C(=O)N[C@H]1CCOC1]

The title compound was prepared in a manner similar to Example 273 using (S)-tetrahydrofuran-3-amine. $^1$H NMR (400 MHz, DMSO-d$_6$) δ ppm 8.76 (d, J=6.4 Hz, 1H), 8.54 (s, 1H), 8.41 (s, 1H), 8.26 (brs., 1H), 8.09 (d, J=8.0 Hz, 2H), 7.78 (d, J=8.0 Hz, 2H), 4.45 (s, 1H), 3.88-3.82 (m, 2H), 3.73-3.70 (m, 1H), 3.63-3.62 (m, 1H), 2.46 (s, 3H), 2.21-2.11 (m, 1H), 1.88-1.87 (m, 1H). MS m/Z [M+H]$^+$ 390.1.

Example 278 6-(4-(4-cyanophenyl)-5-hydroxy-1H-pyrazol-1-yl)-N-((1s,4s)-4-hydroxycyclohexyl)-4-methylnicotinamide

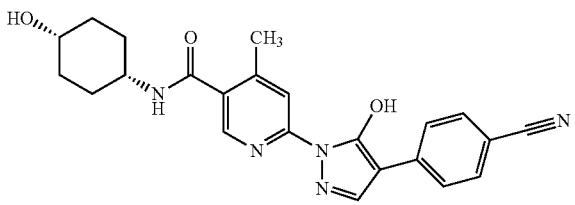 [SMILES: Cc1cc(-n2ncc(-c3ccc(C#N)cc3)c2O)ncc1C(=O)N[C@H]1CC[C@@H](O)CC1]

The title compound was prepared in a manner similar to Example 273 using (1s,4s)-4-aminocyclohexanol. $^1$H NMR (400 MHz, DMSO-d$_6$) δ ppm 8.57 (brs, 1H), 8.41 (d, J=7.6 Hz, 1H), 8.37 (s, 1H), 8.24 (s, 1H), 8.10 (m, 2H), 7.79 (d, J=8.4 Hz, 2H), 4.40 (brs, 1H), 3.80-3.73 (m, 2H), 2.46 (s, 3H), 1.73-1.51 (m, 8H). MS m/Z [M+H]$^+$ 418.2.

Example 279 6-(4-(4-cyanophenyl)-5-hydroxy-1H-pyrazol-1-yl)-4-methyl-N-(2-(tetrahydro-2H-pyran-3-yl)ethyl)nicotinamide

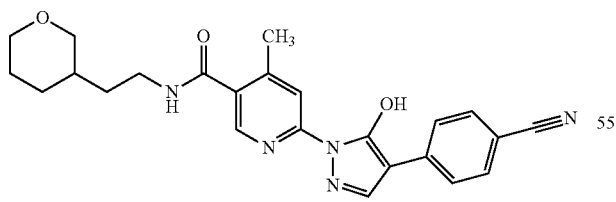

The title compound was prepared in a manner similar to Example 273 using 2-(tetrahydro-2H-pyran-3-yl)ethanamine. $^1$H NMR (400 MHz, DMSO-d$_6$) δ ppm 8.57-8.54 (m, 2H), 8.40 (s, 1H), 8.25 (s, 1H), 8.11 (d, J=8.0 Hz, 2H), 7.79 (d, J=8.0 Hz, 2H), 3.80-3.74 (m, 2H), 3.30-3.25 (m, 3H), 3.01 (t, J=10.4 Hz, 1H), 2.47 (s, 3H), 1.85-1.84 (m, 1H), 1.58-1.35 (m, 5H), 1.16-1.11 (m, 1H). MS m/Z [M+H]$^+$ 432.2

Example 280 N-benzyl-4-(5-hydroxy-4-(pyridin-2-yl)-1H-pyrazol-1-yl)benzamide

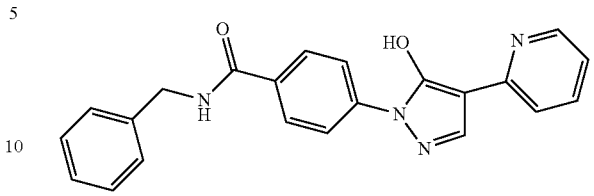

Combined methyl 3-(2-(5-(benzylcarbamoyl)pyridin-2-yl)hydrazinyl)-2-(pyridin-2-yl)acrylate (110 mg, 0.273 mmol) and potassium carbonate (56.5 mg, 0.409 mmol) in ethanol (10 mL) and heated at 60° C. for 1 hour. The precipitate was filtered and washed with ethanol to give an off-white solid. This solid was then dissolved in ethyl acetate. The organic layer was washed with water, dried and concentrated to give the title compound as a yellow solid. (60 mg, 59%). $^1$H NMR (400 MHz, DMSO-d$_6$) δ ppm 4.50 (d, J=6.06 Hz, 2H), 6.69 (ddd, J=7.07, 4.80, 1.26 Hz, 1H), 7.19-7.30 (m, 1H), 7.34 (d, J=4.55 Hz, 4H), 7.44 (ddd, J=8.21, 7.20, 2.02 Hz, 1H), 7.85 (s, 1H), 8.10-8.19 (m, 2H), 8.19-8.25 (m, 1H), 8.64 (dd, J=8.84, 0.76 Hz, 1H), 8.84 (dd, J=2.53, 0.76 Hz, 1H), 9.04 (t, J=5.81 Hz, 1H). MS m/z [M+H]$^+$ 372.4

Example of 281 N-benzyl-6-(4-(4-cyanophenyl)-5-hydroxy-1H-pyrazol-1-yl)nicotinamide

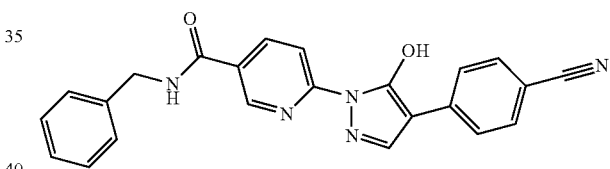

Combined ethyl 3-(2-(5-(benzylcarbamoyl)pyridin-2-yl)hydrazono)-2-(4-cyanophenyl)propanoate (90 mg, 0.204 mmol) and potassium carbonate (42.3 mg, 0.306 mmol) in ethanol (2 mL) and heated for 1 hour at 60° C. The reaction mixture was evaporated to give a residue which was purified by HPLC (ZQ9, Prep-TFA-50-55, Rt 4.54 min) to give the title compound (5 mg, 6%) as an off-white solid. $^1$H NMR (400 MHz, chloroform-d) δ ppm 4.69 (d, J=5.56 Hz, 2H), 6.37 (br. s., 1H), 7.30-7.42 (m, 5H), 7.62-7.69 (m, 2H), 7.77-7.83 (m, 2H), 7.91 (s, 1H), 8.02 (d, J=8.08 Hz, 1H), 8.32 (dd, J=8.84, 2.27 Hz, 1H), 8.80 (d, J=1.77 Hz, 1H). MS m/z [M+H]$^+$ 396.3.

Example 282 4-(1-(5-(4-ethylpiperazine-1-carbonyl)pyridin-2-yl)-5-hydroxy-1H-pyrazol-4-yl)-3-methyl-benzonitrile

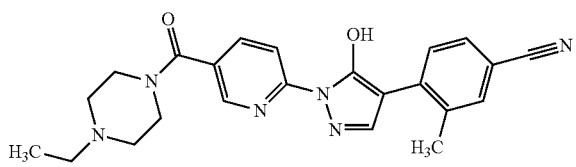 [SMILES: CCN1CCN(C(=O)c2ccc(-n3ncc(-c4ccc(C#N)cc4C)c3O)nc2)CC1]

Combined 6-(4-(4-cyano-2-methylphenyl)-5-hydroxy-1H-pyrazol-1-yl)nicotinic acid (0.524 g, 1.636 mmol) in THF (3 mL) and added DMSO (1 mL) and DMAP (3.00 mg, 0.025 mmol) followed by a dropwise addition of a solution of CDI (0.292 g, 1.80 mmol) in DMSO (1 mL). The resulting clear solution was stirred at ambient temperature for 45 minutes and an additional portion of CDI (73.0 mg, 0.450 mmol) was added. The mixture was stirred for a total of 2 hours and 1-ethylpiperazine (0.270 mL, 2.127 mmol) was added. The resulting mixture was stirred for 4.5 hours and then diluted with water (6 mL, dropwise), acidified to pH=7 with 6N aqueous hydrochloric acid, and then further diluted with water (4 mL) to give a solid. The solid was filtered and dried in vacuum to give the title compound (0.613 g, 90%). $^1$H NMR (400 MHz, DMSO-$d_6$) δ ppm 1.06 (t, J=7.07 Hz, 3H) 2.43 (s, 3H) 2.53-2.63 (m, 4H) 3.57 (br. s., 6H) 7.61 (d, J=8.08 Hz, 1H) 7.67 (s, 1H) 7.90 (d, J=8.08 Hz, 1H) 8.02 (dd, J=8.59, 2.27 Hz, 1H) 8.06 (s, 1H) 8.42 (d, J=8.59 Hz, 1H) 8.52 (d, J=1.77 Hz, 1H); MS (M+H)+417.

Example 283 4-(5-hydroxy-1-(5-(4-propylpiperazine-1-carbonyl)pyridin-2-yl)-1H-pyrazol-4-yl)-3-methylbenzonitrile

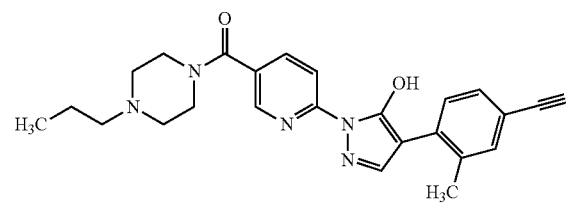

Combined 6-(4-(4-cyano-2-methylphenyl)-5-hydroxy-1H-pyrazol-1-yl)nicotinic acid (0.5 g, 1.561 mmol), N1-((ethylimino)methylene)-N3,N3-dimethylpropane-1,3-diamine hydrochloride (0.449 g, 2.342 mmol), HOBT (0.359 g, 2.342 mmol) and 1-propylpiperazine dihydrobromide (0.543 g, 1.873 mmol) in DMF (1.56 mL) and added DIPEA (1.09 mL, 6.24 mmol) to give an orange solution. After stirring for 20 minutes the reaction mixture was heated to 60° C. for 3 hours, then was diluted with water (5 mL) and acidified with 6N aqueous hydrochloric acid to pH 6 and stirred at ambient temperature for 30 minutes to give a solid. The solid was collected by filtration, washed with water (3 mL) and suspended in ACN (10 mL). The suspension was treated with 1N aqueous hydrochloric acid (2 mL) and heated to 40° C. Ethyl ether was then added until the mixture became slightly cloudy (~8 mL) and then allowed to cool to ambient temperature to give a solid, and then cooled in an ice bath for 30 minutes. The solid was collected by filtration and dried in vacuum at 80° C. for 1.5 hour to give the title compound as a hydrochloride salt (81.3 mg, 0.174 mmol, 11.15%). $^1$H NMR (400 MHz, DMSO-d6) δ ppm 0.92 (t, J=7.45 Hz, 3H) 1.64-1.79 (m, 2H) 2.43 (s, 3H) 2.81-3.20 (m, 4H) 3.21-4.90 (m, 6H) 7.67 (d, J=7.58 Hz, 1H) 7.71-7.91 (m, 2H) 7.93-8.74 (m, 4H) 10.75 (br. s., 1H) 13.23 (br. s., 1H); [M+H]+ 431.

Example 284 6-(4-(4-cyano-2-fluorophenyl)-5-hydroxy-1H-pyrazol-1-yl)-N-((1s,4s)-4-methoxycyclohexyl)nicotinamide

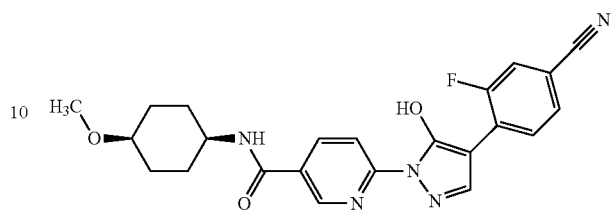

Combined EDC (115 mg, 0.601 mmol), HOBT (27.1 mg, 0.200 mmol), (cis)-4-methoxycyclohexanamine hydrochloride (66.4 mg, 0.401 mmol) and 6-(4-(4-cyano-2-fluorophenyl)-5-hydroxy-1H-pyrazol-1-yl)nicotinic acid (65 mg, 0.200 mmol) in DMF (0.8 mL) and then added DIPEA (0.175 mL, 1.002 mmol). After 24 hours, the reaction mixture was purified by preparative HPLC (ACN/water with formic acid) to give the title compound (23 mg, 0.053 mmol, 26.3%) as a tan solid. MS: 436 (M+H). $^1$H NMR (400 MHz, DMSO-$d_6$) δ ppm 1.34-1.48 (m, 2H) 1.49-1.65 (m, 4H) 1.76-1.88 (m, 2H) 3.17 (s, 3H) 3.31 (br. s., 1H) 3.73-3.87 (m, 1H) 7.62 (dd, J=8.2, 1.6 Hz, 1H) 7.77 (dd, J=11.7, 1.6 Hz, 1H) 8.16 (d, J=3.0 Hz, 1H) 8.31-8.44 (m, 3H) 8.55 (t, J=8.0 Hz, 1H) 8.84 (dd, J=2.0, 1.0 Hz, 1H) 13.71 (br. s., 1H).

Example 285 6-(4-(4-cyano-2-fluorophenyl)-5-hydroxy-1H-pyrazol-1-yl)-N-(4-methoxybutyl)nicotinamide

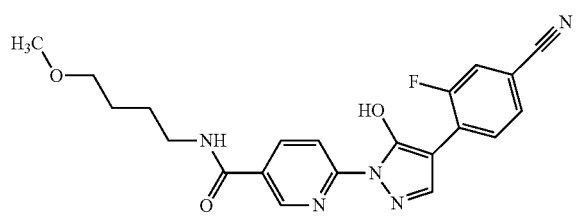 [SMILES: COCCCCNC(=O)c1ccc(-n2ncc(-c3ccc(C#N)cc3F)c2O)nc1]

The title compound was prepared in a manner similar to Example 284 using 4-methoxybutan-1-amine. MS: 410 (M+H). $^1$H NMR (400 MHz, DMSO-d6) δ ppm 1.42-1.57 (m, 4H) 3.16 (s, 3H) 3.19-3.32 (m, 4H) 7.61 (d, J=8.1 Hz, 1H) 7.75 (d, J=11.6 Hz, 1H) 8.16 (d, J=2.5 Hz, 1H) 8.28-8.36 (m, 1H) 8.37-8.46 (m, 1H) 8.56 (t, J=8.0 Hz, 1H) 8.61 (t, J=5.6 Hz, 1H) 8.83 (s, 1H) 13.72 (br. s., 1H).

Example 286 6-(4-(4-cyano-2-methylphenyl)-5-hydroxy-1H-pyrazol-1-yl)-N-(2-(dimethylamino)ethyl)-N-methylnicotinamide

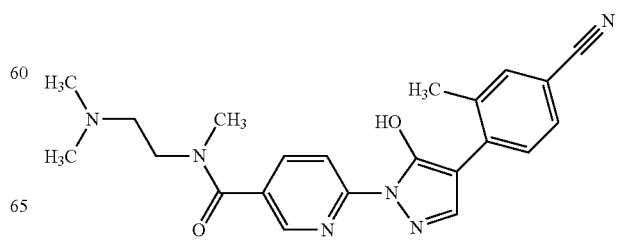

The title compound was prepared in a manner similar to Example 284 using N1,N1,N2-trimethylethane-1,2-diamine and 6-(4-(4-cyano-2-methylphenyl)-5-hydroxy-1H-pyrazol-1-yl)nicotinic acid to give a formic acid salt (61 mg, 0.135 mmol, 72.3%) as an off-white solid. MS: 405 (M+H). $^1$H NMR (400 MHz, DMSO-d6) δ ppm 2.42 (s, 3H) 2.53-2.70 (m, 4H) 3.02 (s, 3H) 3.11-3.80 (m, 6H) 7.53 (d, J=8.3 Hz, 1H) 7.58 (s, 1H) 7.89-7.99 (m, 2H) 8.10 (br. s., 1H) 8.50 (m, 2H).

Example 287 4-(5-hydroxy-1-(5-(4-methyl-1,4-diazepane-1-carbonyl)pyridin-2-yl)-1H-pyrazol-4-yl)-3-methylbenzonitrile

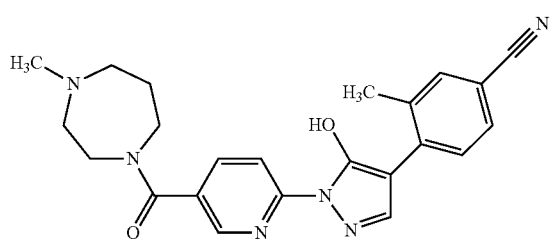 [SMILES: Cc1cc(C#N)ccc1-c1cnn(-c2ccc(C(=O)N3CCCN(C)CC3)cn2)c1O]

The title compound was prepared in a manner similar to Example 284 using 1-methyl-1,4-diazepane and 6-(4-(4-cyano-2-methylphenyl)-5-hydroxy-1H-pyrazol-1-yl)nicotinic acid to give a formic acid salt (67 mg, 0.145 mmol, 77%) as an off-white solid. MS: 417 (M+H). $^1$H NMR (400 MHz, DMSO-d6) δ ppm 1.88 (br. s., 2H) 2.35 (s, 3H) 2.54 (br. s., 2H) 2.86 (d, J=17.7 Hz, 3H) 3.01 (br. s., 1H) 3.39-3.76 (m, 5H) 7.45 (d, J=8.1 Hz, 1H) 7.50 (s, 1H) 7.78-7.91 (m, 2H) 8.04 (d, J=7.6 Hz, 1H) 8.42 (br. s., 2H) 11.65 (br. s., 1H)

Example 288 (+/−)-4-(5-hydroxy-1-(5-(octahydropyrrolo[1,2-a]pyrazine-2-carbonyl)pyridin-2-yl)-1H-pyrazol-4-yl)-3-methylbenzonitrile

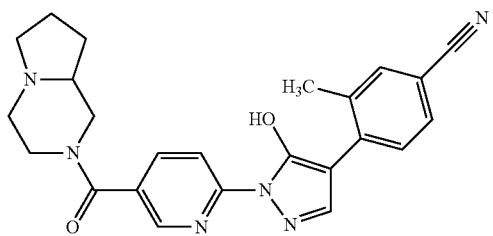 [SMILES: Cc1cc(C#N)ccc1-c1cnn(-c2ccc(C(=O)N3CCN4CCCC4C3)cn2)c1O]

The title compound was prepared in a manner similar to Example 284 using octahydropyrrolo[1,2-a]pyrazine and 6-(4-(4-cyano-2-methylphenyl)-5-hydroxy-1H-pyrazol-1-yl)nicotinic acid to give a formic acid salt (47 mg, 0.099 mmol, 79%) as a white solid. MS: 429 (M+H). $^1$H NMR (400 MHz, DMSO-d6) δ ppm 1.15-1.52 (m, 1H) 1.72 (br. s., 3H) 2.09 (br. s., 1H) 2.21 (d, J=8.8 Hz, 2H) 2.43 (s, 3H) 2.54-2.61 (m, 1H) 2.87-3.15 (m, 3H) 3.50-3.88 (m, 1H) 4.30-4.68 (m, 1H) 7.63 (d, J=8.1 Hz, 1H) 7.69 (s, 1H) 7.88 (d, J=8.1 Hz, 1H) 8.03 (dd, J=8.6, 2.0 Hz, 1H) 8.09 (s, 1H) 8.42 (d, J=8.3 Hz, 1H) 8.52 (d, J=2.0 Hz, 1H) 12.77 (br. s., 1H).

Example 289 6-(4-(4-cyano-2-methylphenyl)-5-hydroxy-1H-pyrazol-1-yl)-N-methyl-N-(1-methylpiperidin-4-yl)nicotinamide

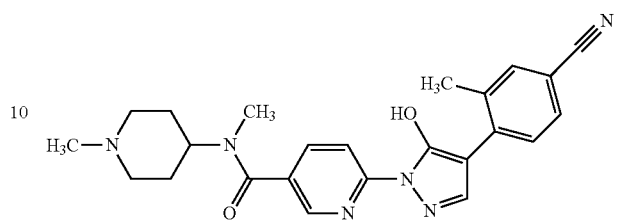

The title compound was prepared in a manner similar to Example 284 using N,1-dimethylpiperidin-4-amine and 6-(4-(4-cyano-2-methylphenyl)-5-hydroxy-1H-pyrazol-1-yl)nicotinic acid to give a formic acid salt (42 mg, 0.088 mmol, 70.6%) as a white solid. MS: 431 (M+H). $^1$H NMR (400 MHz, DMSO-d6) δ ppm 1.71 (d, J=11.6 Hz, 2H) 1.78-1.95 (m, 2H) 2.35 (s, 3H) 2.78 (s, 3H) 2.92-3.83 (m, 7H) 4.34 (br. s., 1H) 7.43 (d, J=8.3 Hz, 1H) 7.48 (s, 1H) 7.76-7.88 (m, 2H) 8.06-8.11 (m, 1H) 8.38 (br. s., 1H) 8.43 (d, J=8.8 Hz, 1H).

Example 290 4-(5-hydroxy-1-(5-(4-methylpiperazine-1-carbonyl)pyridin-2-yl)-1H-pyrazol-4-yl)-3-methylbenzonitrile

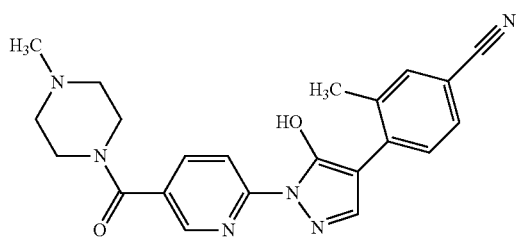 [SMILES: Cc1cc(C#N)ccc1-c1cnn(-c2ccc(C(=O)N3CCN(C)CC3)cn2)c1O]

The title compound was prepared in a manner similar to Example 284 using 1-methylpiperazine and 6-(4-(4-cyano-2-methylphenyl)-5-hydroxy-1H-pyrazol-1-yl)nicotinic acid to give a formic acid salt (22 mg, 0.055 mmol, 43.8%) as a white solid. MS: 403 (M+H). $^1$H NMR (400 MHz, DMSO-d6) δ ppm 2.32 (s, 3H) 2.43 (s, 3H) 3.28-3.70 (m, 8H) 7.62 (d, J=8.1 Hz, 1H) 7.68 (s, 1H) 7.90 (d, J=8.1 Hz, 1H) 8.02 (dd, J=8.6, 2.3 Hz, 1H) 8.08 (s, 1H) 8.43 (d, J=8.6 Hz, 1H) 8.52 (d, J=2.0 Hz, 1H) 12.74 (br. s., 1H).

Example 291 4-(1-(5-(4-(tert-butyl)piperazine-1-carbonyl)pyridin-2-yl)-5-hydroxy-1H-pyrazol-4-yl)-3-methylbenzonitrile

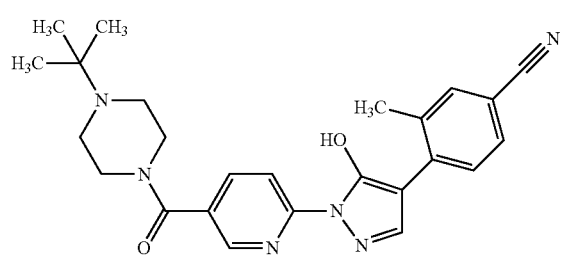 [SMILES: Cc1cc(C#N)ccc1-c1cnn(-c2ccc(C(=O)N3CCN(C(C)(C)C)CC3)cn2)c1O]

The title compound was prepared in a manner similar to Example 284 using 1-t-butyl piperazine and 6-(4-(4-cyano-2-methylphenyl)-5-hydroxy-1H-pyrazol-1-yl)nicotinic acid to give a formic acid salt (53 mg, 0.119 mmol, 76%) as a white solid. MS: 445 (M+H). ¹H NMR (400 MHz, DMSO-d6) δ ppm 1.10 (s, 9H) 2.43 (s, 3H) 2.71 (br. s., 4H) 3.57 (br. s., 4H) 7.56-7.62 (m, 1H) 7.65 (s, 1H) 7.94 (d, J=8.1 Hz, 1H) 7.98-8.07 (m, 2H) 8.42 (d, J=8.6 Hz, 1H) 8.52 (d, J=1.5 Hz, 1H) 12.42 (br. s., 1H).

Example 292 4-(5-hydroxy-1-(5-((3aR,6aS)-5-methyloctahydropyrrolo[3,4-c]pyrrole-2-carbonyl)pyridin-2-yl)-1H-pyrazol-4-yl)-3-methylbenzonitrile

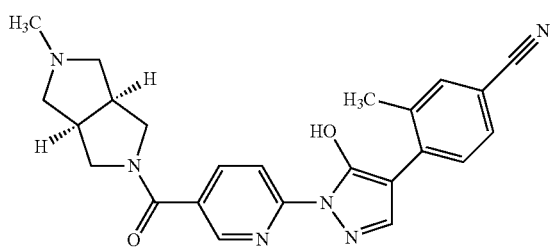 [SMILES: Cc1cc(C#N)ccc1-c1cnn(-c2ccc(C(=O)N3C[C@H]4CN(C)C[C@H]4C3)cn2)c1O]

Combined 6-(4-(4-cyano-2-methylphenyl)-5-hydroxy-1H-pyrazol-1-yl)nicotinic acid (50 mg, 0.156 mmol), N1-((ethylimino)methylene)-N3,N3-dimethylpropane-1,3-diamine hydrochloride (90 mg, 0.468 mmol) and HOBT (21.09 mg, 0.156 mmol) in DMF (0.8 mL) and added N-ethyl-N-isopropylpropan-2-amine (0.056 mL, 0.468 mmol) and (3aR,6aS)-2-methyloctahydropyrrolo[3,4-c]pyrrole (79 mg, 0.624 mmol). After 17 hours, the reaction mixture was diluted with DMSO (100 uL) and purified by preparative HPLC (ACN/water with formic acid) to give the title compound as a 0.63 formic acid salt (60 mg, 0.131 mmol, 84%) as a tan solid. MS: 429 (M+H). ¹H NMR (400 MHz, DMSO-d6) δ ppm 2.35 (s, 3H) 2.48 (s, 3H) 2.77 (br. s., 2H) 2.91 (br. s., 4H) 3.43 (br. s., 2H) 3.67 (dd, J=11.5, 6.4 Hz, 2H) 7.43-7.49 (m, 1H) 7.51 (s, 1H) 7.87 (s, 1H) 7.94 (dd, J=8.7, 2.4 Hz, 1H) 8.02 (d, J=8.1 Hz, 1H) 8.41 (d, J=8.6 Hz, 1H) 8.49 (d, J=1.8 Hz, 1H) 11.91 (br. s., 1H).

Example 293 4-(5-hydroxy-1-(5-(2-methyl-2,6-diazaspiro[3.4]octane-6-carbonyl)pyridin-2-yl)-1H-pyrazol-4-yl)-3-methylbenzonitrile

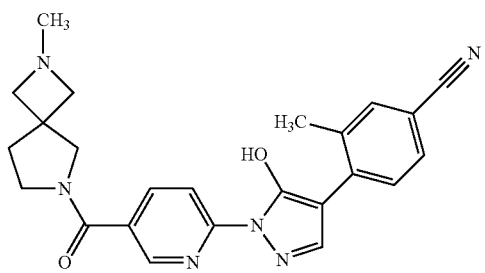 [SMILES: Cc1cc(C#N)ccc1-c1cnn(-c2ccc(C(=O)N3CCC4(CN(C)C4)C3)cn2)c1O]

The title compound was prepared in a manner similar to Example 292 using 2-methyl-2,6-diazaspiro[3.4]octane to a 0.56 formic acid salt (48 mg, 0.106 mmol, 67.7%) as a tan solid. MS: 429 (M+H). ¹H NMR (400 MHz, DMSO-d6) δ ppm 2.08 (d, J=4.3 Hz, 2H) 2.35 (s, 3H) 2.54-2.72 (m, 3H) 3.45 (t, J=6.8 Hz, 1H) 3.50 (d, J=6.6 Hz, 1H) 3.60-3.71 (m, 2H) 3.71-3.81 (m, 2H) 3.81-3.93 (m, 2H) 7.38 (d, J=8.1 Hz, 1H) 7.42 (s, 1H) 7.74 (s, 1H) 7.88 (d, J=8.1 Hz, 1H) 8.22 (dd, J=13.9, 8.3 Hz, 1H) 8.48 (d, J=8.6 Hz, 2H) 10.87-12.25 (m, 1H).

Example 294 6-(4-(4-cyano-2-methylphenyl)-5-hydroxy-1H-pyrazol-1-yl)-N-methyl-N-(1-propylpiperidin-4-yl)nicotinamide

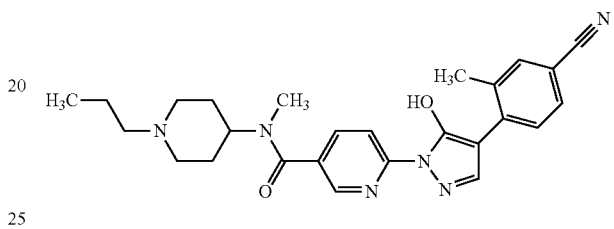

The title compound was prepared in a manner similar to Example 292 using N-methyl-1-propylpiperidin-4-amine and purified by preparative HPLC (ACN/water with TFA) to give a TFA salt (129 mg, 0.225 mmol, 72.2%) as a white solid. MS: 459 (M+H). ¹H NMR (400 MHz, DMSO-d6) δ ppm 0.90 (br. s., 3H) 1.65 (br. s., 2H) 1.93 (d, J=11.9 Hz, 2H) 2.07 (q, J=11.8 Hz, 2H) 2.43 (s, 3H) 2.87 (s, 3H) 2.98-3.27 (m, 2H) 3.42-3.85 (m, 5H) 7.67 (d, J=7.3 Hz, 1H) 7.74 (br. s., 1H) 7.80 (br. s., 1H) 8.09 (br. s., 1H) 8.24 (br. s., 1H) 8.56 (br. s., 1H) 9.15 (br. s., 1H) 13.23 (br. s., 1H).

Example 295 (+/−)-4-(1-(5-(3-((ethyl(methyl)amino)methyl)pyrrolidine-1-carbonyl)pyridin-2-yl)-5-hydroxy-1H-pyrazol-4-yl)-3-methylbenzonitrile

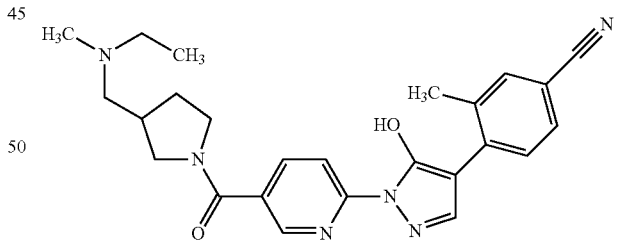

The title compound was prepared in a manner similar to Example 292 using N-methyl-N-(pyrrolidin-3-ylmethyl)ethanamine and purified by preparative HPLC (ACN/water with TFA) to give a TFA salt (73 mg, 0.131 mmol, 84%) as a white solid. MS: 445 (M+H). ¹H NMR (400 MHz, DMSO-d6) δ ppm 1.11-1.30 (m, 3H) 1.69 (t, J=9.2 Hz, 1H) 2.13 (br. s., 1H) 2.43 (s, 3H) 2.56-2.70 (m, 1H) 2.70-2.85 (m, 3H) 3.24-3.36 (m, 2H) 3.46-3.69 (m, 5H) 3.69-3.88 (m, 1H) 7.67 (d, J=7.6 Hz, 1H) 7.74 (s, 1H) 7.81 (br. s., 1H) 8.11-8.62 (m, 2H) 8.66 (s, 1H) 8.90-9.27 (m, 1H) 13.22 (br. s., 1H).

Example 296 6-(4-(4-cyano-2-methylphenyl)-5-hydroxy-1H-pyrazol-1-yl)-N-(1-cyclopropylpiperidin-4-yl)-N-methylnicotinamide

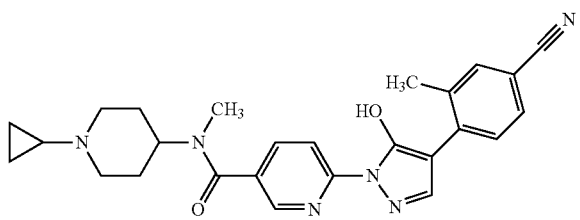 [SMILES: Cc1cc(C#N)ccc1-c1cnn(-c2ccc(C(=O)N(C)C3CCN(C4CC4)CC3)cn2)c1O]

The title compound was prepared in a manner similar to Example 292 using 1-cyclopropyl-N-methylpiperidin-4-amine (62.6 mg, 0.406 mmol) and purified by preparative HPLC (ACN/water with TFA) to give a TFA salt (53 mg, 0.093 mmol, 59.5%) as a white solid. MS: 457 (M+H). $^1$H NMR (400 MHz, DMSO-d6) δ ppm 0.71-1.00 (m, 4H) 1.85-2.09 (m, 4H) 2.43 (s, 3H) 2.86 (s, 3H) 3.14 (br. s., 1H) 3.50-3.78 (m, 4H) 4.57 (br. s., 1H) 7.67 (d, J=7.3 Hz, 1H) 7.74 (s, 1H) 7.80 (br. s., 1H) 8.10 (br. s., 1H) 8.24 (br. s., 1H) 8.57 (br. s., 1H) 8.93 (br. s., 1H) 13.24 (br. s., 1H).

Example 297 4-(1-(5-(3-(cyclobutyl(methyl)amino)azetidine-1-carbonyl)pyridin-2-yl)-5-hydroxy-1H-pyrazol-4-yl)-3-methylbenzonitrile

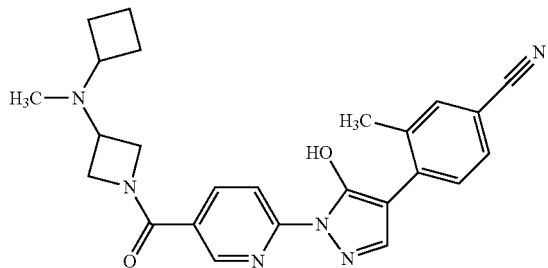 [SMILES: Cc1cc(C#N)ccc1-c1cnn(-c2ccc(C(=O)N3CC(N(C)C4CCC4)C3)cn2)c1O]

The title compound was prepared in a manner similar to Example 292 using N-cyclobutyl-N-methylazetidin-3-amine dihydrochloride and purified by preparative HPLC (ACN/water with trifluoroacetic acid) to give a TFA salt (48 mg, 0.086 mmol, 69.1%) as a white solid. MS: 443 (M+H). $^1$H NMR (400 MHz, DMSO-d6) δ ppm 1.55-1.82 (m, 2H) 2.00-2.27 (m, 4H) 2.43 (s, 3H) 2.68 (br. s., 3H) 3.71 (d, J=8.1 Hz, 1H) 4.19 (d, J=5.3 Hz, 1H) 4.31 (br. s., 2H) 4.62 (br. s., 2H) 7.67 (d, J=7.8 Hz, 1H) 7.74 (s, 2H) 8.26 (d, J=8.3 Hz, 2H) 8.53 (br. s., 1H) 8.74 (d, J=1.5 Hz, 1H) 13.23 (br. s., 1H).

Example 298 4-(1-(5-(3-(cyclopropyl(methyl)amino)azetidine-1-carbonyl)pyridin-2-yl)-5-hydroxy-1H-pyrazol-4-yl)-3-methylbenzonitrile

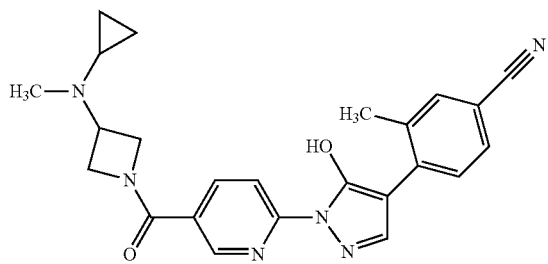 [SMILES: Cc1cc(C#N)ccc1-c1cnn(-c2ccc(C(=O)N3CC(N(C)C4CC4)C3)cn2)c1O]

The title compound was prepared in a manner similar to Example 292 using N-cyclopropyl-N-methylazetidin-3-amine dihydrochloride and purified by preparative HPLC (ACN/water with trifluoroacetic acid) to give a TFA salt (35 mg, 0.065 mmol, 51.7%) as a white solid. MS: 429 (M+H). $^1$H NMR (400 MHz, DMSO-d6) δ ppm 0.42-1.05 (m, 4H) 2.43 (s, 3H) 2.66 (br. s, 3H) 4.28 (br. s., 4H) 4.58 (br. s., 2H) 7.67 (d, J=7.6 Hz, 1H) 7.74 (s, 1H) 7.76-7.89 (m, 1H) 8.28 (br. s., 2H) 8.60 (br. s., 1H) 8.75 (s, 1H) 13.23 (br. s., 1H).

Example 299 4-(1-(5-(6,6-difluoro-4-methyl-1,4-diazepane-1-carbonyl)pyridin-2-yl)-5-hydroxy-1H-pyrazol-4-yl)-3-methylbenzonitrile

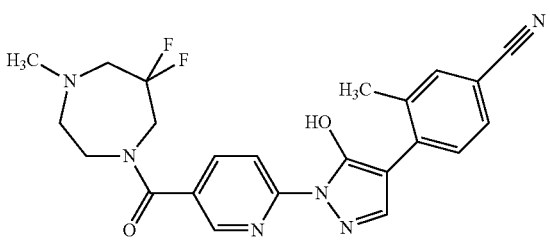 [SMILES: Cc1cc(C#N)ccc1-c1cnn(-c2ccc(C(=O)N3CCN(C)CC(F)(F)C3)cn2)c1O]

The title compound was prepared in a manner similar to Example 292 using 6,6-difluoro-1-methyl-1,4-diazepane hydrochloride and purified by preparative HPLC (ACN/water with trifluoroacetic acid) to give a TFA salt (40 mg, 0.071 mmol, 45.2%) as a white solid. MS: 453 (M+H). $^1$H NMR (400 MHz, DMSO-d6) δ ppm 2.43 (s, 3H) 2.54-2.78 (m, 2H) 2.85-3.26 (m, 2H) 3.27-3.70 (m, 3H) 3.71-4.30 (m, 4H) 7.67 (d, J=8.1 Hz, 1H) 7.74 (s, 1H) 7.77 (br. s., 1H) 8.12 (br. s., 2H) 8.29-8.53 (m, 1H) 8.58 (br. s., 1H) 13.22 (br. s., 1H).

Example 300 6-(4-(4-cyano-2-cyclopropylphenyl)-5-hydroxy-1H-pyrazol-1-yl)-N-(3-methoxypropyl)nicotinamide

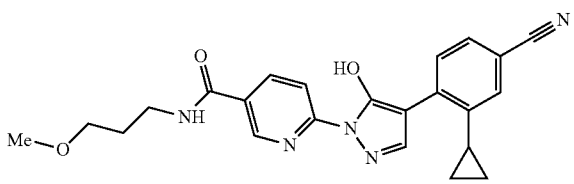 [SMILES: COCCCNC(=O)c1ccc(-n2ncc(-c3ccc(C#N)cc3C3CC3)c2O)nc1]

Combined 6-(4-bromo-5-methoxy-1H-pyrazol-1-yl)-N-(3-methoxypropyl)nicotinamide (150 mg, 0.406 mmol), 3-cyclopropyl-4-(4,4,5,5-tetramethyl-1,3,2-dioxaborolan-2-yl)benzonitrile (219 mg, 0.813 mmol), and THF (3047 µl) water (1016 µl) in a microwave vial. The reaction mixture was degassed by bubbling nitrogen through the mixture. After a few minutes of degassing, Pd(PPh$_3$)$_4$ (23.47 mg, 0.020 mmol) and sodium carbonate (172 mg, 1.625 mmol) were added. The reaction was degassed 2 minutes more, then capped, and subjected to microwave irradiation to 110° C. for 1 hour. The reaction mixture was then diluted with ethyl acetate (20 mL) and washed with water (2×10 mL) followed by brine (20 mL). The organic layer was collected, dried with sodium sulfate, and concentrated to residue which was purified by column (30 g, 60 mesh silica, 10% to 100% EtOAc in heptane gradient) to give 6-(4-(4-cyano-3-cyclopropylphenyl)-5-methoxy-1H-pyrazol-1-yl)-N-(3-methoxypropyl)nicotinamide (134 mg, 76%) as a white solid.

Combined 6-(4-(4-cyano-3-cyclopropylphenyl)-5-methoxy-1H-pyrazol-1-yl)-N-(3-methoxypropyl)nicotinamide (134 mg, 0.311 mmol) and lithium chloride (132 mg, 3.11 mmol) in DMA (3.1 mL) and heated at 70° C. for 2 days. The reaction mixture was cooled to ambient temperature, diluted with DMSO (0.3 mL), and purified via preparative HPLC to give the title compound (44.6 mg, 0.107 mmol, 26%) as a white solid. $^1$H NMR (400 MHz, DMSO-$d_6$) δ ppm 0.60-0.75 (m, 2H) 0.83-0.95 (m, 2H) 1.72 (quin, J=6.69 Hz, 2H) 2.10 (d, J=5.05 Hz, 1H) 3.18 (s, 3H) 3.22-3.36 (m, 4H) 7.41 (d, J=1.26 Hz, 1H) 7.57 (dd, J=8.08, 1.77 Hz, 1H) 7.63-8.55 (m, 4H) 8.64 (br. s., 1H) 8.77-8.90 (m, 1H); ESI-MS m/z [M+H]$^+$ 418.4.

Example 301 6-(4-(4-cyano-2-methylphenyl)-5-hydroxy-1H-pyrazol-1-yl)-N,N-dimethylnicotinamide

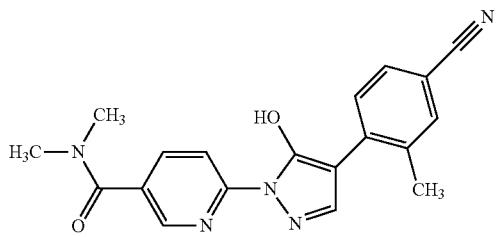 [SMILES: Cc1cc(C#N)ccc1-c1cnn(-c2ccc(C(=O)N(C)C)cn2)c1O]

Combined 6-(4-(4-cyano-2-methylphenyl)-5-hydroxy-1H-pyrazol-1-yl)nicotinic acid (107 mg, 0.334 mmol), HOBT hydrate (77 mg, 0.501 mmol), N1-((ethylimino)methylene)-N3,N3-dimethylpropane-1,3-diamine hydrochloride (96 mg, 0.501 mmol) in DMF (2 mL), and added triethylamine (0.188 mL, 1.336 mmol), stirred at ambient temperature for 5 minutes and dimethylamine hydrochloride (54.5 mg, 0.668 mmol) was added. The reaction was stirred at 50° C. for 3 hours, then cooled to ambient temperature and diluted with MeOH (5 mL), water (5 mL), and acidified to pH 5 using 1N aqueous hydrochloric acid, to give a solid which was filtered, washed with water, and dried under vacuum to give the title compound (76.2 mg, 0.219 mmol, 66%) as a white solid. $^1$H NMR (400 MHz, DMSO-$d_6$) δ ppm 2.43 (s, 3H) 3.01 (br. s., 6H) 7.65 (dd, J=8.08, 1.52 Hz, 1H) 7.70-7.82 (m, 2H) 8.02-8.20 (m, 2H) 8.37 (br. s., 1H) 8.56 (dd, J=2.27, 0.76 Hz, 1H) 13.11 (br. s., 1H). ESI-MS m/z [M+H]$^+$ 348.3.

Example 302 6-(4-(4-cyano-2-methylphenyl)-5-hydroxy-1H-pyrazol-1-yl)-N-(1-(2,2,2-trifluoroethyl)piperidin-4-yl)nicotinamide

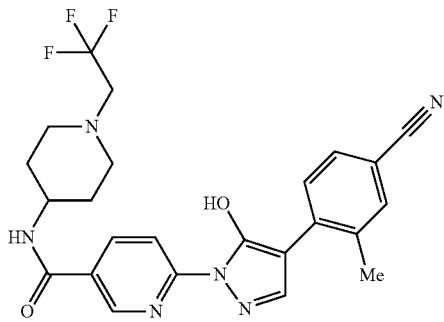 [SMILES: Cc1cc(C#N)ccc1-c1cnn(-c2ccc(C(=O)NC3CCN(CC(F)(F)F)CC3)cn2)c1O]

The title compound was prepared in a manner similar to Example example 301 using 1-(2,2,2-trifluoroethyl)piperidin-4-amine. $^1$H NMR (400 MHz, DMSO-$d_6$) δ ppm 1.60 (qd, J=11.92, 3.66 Hz, 2H) 1.81 (d, J=9.60 Hz, 2H) 2.35-2.48 (m, 5H) 2.87-3.00 (m, 2H) 3.18 (q, J=10.11 Hz, 2H) 3.71-3.89 (m, 1H) 7.59-7.81 (m, 3H) 8.15 (br. s., 1H) 8.23-8.53 (m, 3H) 8.82-8.96 (m, 1H) 13.14 (br. s., 1H). ESI-MS m/z [M+H]$^+$ 485.2.

Example 303 6-(4-(4-cyano-2-methylphenyl)-5-hydroxy-1H-pyrazol-1-yl)-N-methyl-N-(3-(piperidin-1-yl)propyl)nicotinamide

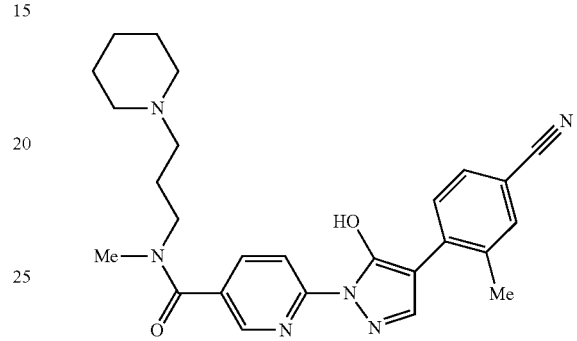

Combined 6-(4-(4-cyano-2-methylphenyl)-5-hydroxy-1H-pyrazol-1-yl)nicotinic acid (70 mg, 0.219 mmol), HOBT hydrate (50.2 mg, 0.328 mmol), N1-((ethylimino)methylene)-N3,N3-dimethylpropane-1,3-diamine hydrochloride (62.8 mg, 0.328 mmol) in DMF (1 mL), and added triethylamine (0.092 mL, 0.656 mmol), then stirred at ambient temperature for 5 minutes and N-methyl-3-(piperidin-1-yl)propan-1-amine (0.085 mL, 0.437 mmol) was added. The reaction was stirred at 50° C. for 3 hours. The crude reaction was then cooled to ambient temperature and diluted with DMSO (1 mL) and purified via preparative HPLC (25-45% acetonitrile in water, with trifluoroacetic acid) to give the title compound (61.5 mg, 0.134 mmol, 61.4%) as a tan solid. $^1$H NMR (400 MHz, DMSO-$d_6$) δ ppm 1.30-1.49 (m, 1H) 1.68 (br. s., 3H) 1.82 (br. s., 2H) 1.93-2.07 (m, 2H) 2.43 (s, 3H) 2.88-3.15 (m, 7H) 3.31-3.43 (m, 1H) 3.45-3.58 (m, 3H) 7.65-7.87 (m, 3H) 8.04-8.67 (m, 4H) 9.35 (br. s., 1H). ESI-MS m/z [M+H]$^+$ 459.3.

Example 304 6-(4-(4-cyanophenyl)-5-hydroxy-1H-pyrazol-1-yl)-N-methyl-N-(3-(piperidin-1-yl)propyl)nicotinamide

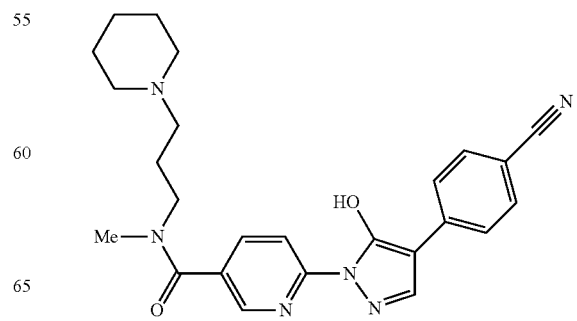

The title compound was prepared in a manner similar to Example 303 using 6-(4-(4-cyanophenyl)-5-hydroxy-1H-pyrazol-1-yl)nicotinic acid and N-methyl-3-(piperidin-1-yl)propyl amine. ¹H NMR (400 MHz, DMSO-d₆) δ ppm 1.39 (d, J=9.60 Hz, 1H) 1.66 (d, J=13.89 Hz, 3H) 1.82 (br. s., 2H) 2.01 (br. s., 2H) 2.83-3.13 (m, 7H) 3.32-3.58 (m, 4H) 7.79 (d, J=8.34 Hz, 2H) 8.13 (br. s., 3H) 8.58 (br. s., 3H) 9.05-9.50 (m, 1H) 12.43-14.49 (m, 1H). ESI-MS m/z [M+H]⁺ 445.2.

Example 305 4-(1-(5-(4-ethylpiperazine-1-carbonyl)pyridin-2-yl)-5-hydroxy-1H-pyrazol-4-yl)-2-fluoro-3-methylbenzonitrile

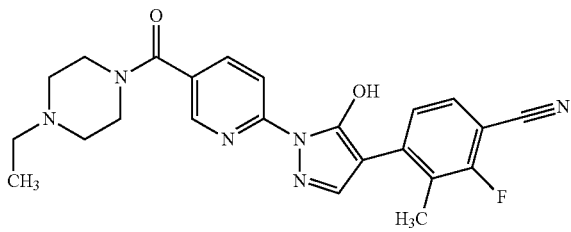 [SMILES: CCN1CCN(C(=O)c2ccc(-n3ncc(-c4ccc(C#N)c(F)c4C)c3O)nc2)CC1]

Combined 6-(4-bromo-5-methoxy-1H-pyrazol-1-yl)nicotinic acid (500 mg, 1.677 mmol), 2-fluoro-3-methyl-4-(4,4,5,5-tetramethyl-1,3,2-dioxaborolan-2-yl)benzonitrile (876 mg, 3.35 mmol), THF (10.500 mL), and water (3.50 mL) in a microwave vial. Degassed with nitrogen then added [1,1'-bis(di-tert-butylphosphino)ferrocene]dichloropalladium(II) (1093 mg, 1.677 mmol) and sodium carbonate (711 mg, 6.71 mmol). The reaction was degassed 2 minutes more, then capped and subjected to microwave irradiation at 110° C. for 1 hour. The reaction mixture was then diluted with EA (20 mL) and washed with water (20 mL). A precipitate was observed in the aqueous layer which was filtered and the solids collected to give 6-(4-(4-cyano-3-fluoro-2-methylphenyl)-5-methoxy-1H-pyrazol-1-yl)nicotinic acid (275 mg, 0.781 mmol, 46.5%) which was dried under vacuum and used in the next step without further purification. ESI-MS m/z [M+H]⁺ 353.2.

Combined 6-(4-(4-cyano-3-fluoro-2-methylphenyl)-5-methoxy-1H-pyrazol-1-yl)nicotinic acid (106 mg, 0.300 mmol), HOBT hydrate (68.9 mg, 0.450 mmol), N1-((ethylimino)methylene)-N3,N3-dimethylpropane-1,3-diamine hydrochloride (86 mg, 0.450 mmol), and N-ethyl-N-isopropylpropan-2-amine (0.157 mL) in DMF (1 mL) and stirred for 5 min. The mixture was then added to 1-ethylpiperazine (68.5, 0.600 mmol). After 18 hours the reaction mixture was purified via preparative HPLC (20-40% acetonitrile in water, with TFA) to give 4-(1-(5-(4-ethylpiperazine-1-carbonyl)pyridin-2-yl)-5-methoxy-1H-pyrazol-4-yl)-2-fluoro-3-methylbenzonitrile (70 mg, 0.156 mmol, 52%). ESI-MS m/z [M+H]⁺ 449.3.

Combined 4-(1-(5-(4-ethylpiperazine-1-carbonyl)pyridin-2-yl)-5-methoxy-1H-pyrazol-4-yl)-2-fluoro-3-methylbenzonitrile (70 mg, 0.156 mmol) and DMA (1561 µl) then added lithium chloride (66.2 mg, 1.561 mmol) and heated at 70° C. overnight. The crude reaction was then diluted with DMSO (500 uL) and purified via preparative HPLC (acetonitrile-water, with TFA) to give the title compound (24.6 mg, 0.057 mmol, 36.3%) as a white solid. ¹H NMR (400 MHz, DMSO-d₆) δ ppm 1.23 (t, J=7.33 Hz, 3H) 2.33 (d, J=2.27 Hz, 3H) 3.16 (t, J=7.20 Hz, 2H) 3.24-4.06 (m, 8H) 7.49-7.84 (m, 2H) 8.04-8.30 (m, 2H) 8.43 (br. s., 1H) 8.60 (dd, J=2.15, 0.63 Hz, 1H). ESI-MS m/z [M+H]⁺ 435.3.

Example 306 4-(1-(5-(4-ethylpiperazine-1-carbonyl)pyridin-2-yl)-5-hydroxy-1H-pyrazol-4-yl)-2-fluoro-5-methylbenzonitrile

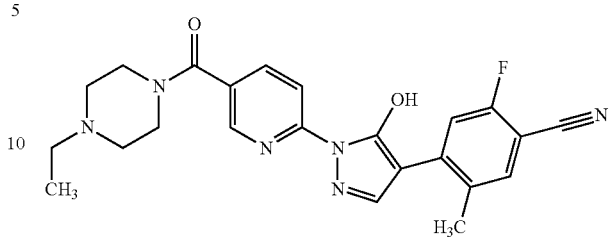

The title compound was prepared in a manner similar to Example 305 using 2-fluoro-5-methyl-4-(4,4,5,5-tetramethyl-1,3,2-dioxaborolan-2-yl)benzonitrile. ¹H NMR (400 MHz, DMSO-d₆) δ ppm 1.24 (t, J=7.33 Hz, 3H) 2.42 (s, 3H) 3.17 (q, J=7.24 Hz, 2H) 3.26-4.82 (m, 8H) 7.79 (d, J=7.07 Hz, 1H) 7.88 (d, J=11.37 Hz, 1H) 8.13 (dd, J=8.72, 2.15 Hz, 1H) 8.29 (br. s., 1H) 8.47 (br. s., 1H) 8.60 (d, J=2.27 Hz, 1H). ESI-MS m/z [M+H]⁺ 435.3.

Example 307 4-(1-(5-(4-cyclopropylpiperazine-1-carbonyl)pyridin-2-yl)-5-hydroxy-1H-pyrazol-4-yl)-2-fluoro-3-methylbenzonitrile

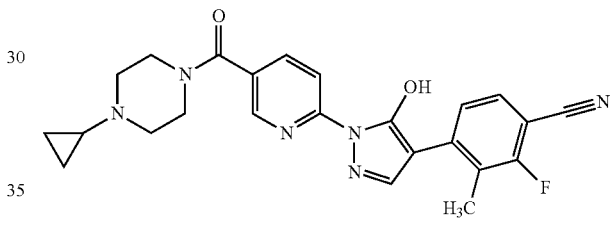

The title compound was prepared in a manner similar to Example 305 using 1-cyclopropylpiperazine. ¹H NMR (400 MHz, DMSO-d₆) δ ppm 0.68 (br. s., 4H) 2.33 (d, J=2.27 Hz, 3H) 3.06 (br. s., 4H) 3.55 (br. s., 4H) 7.63 (d, J=8.08 Hz, 1H) 7.70-7.85 (m, 1H) 8.11 (dd, J=8.59, 2.02 Hz, 1H) 8.23 (br. s., 1H) 8.42 (br. s., 1H) 8.58 (d, J=1.52 Hz, 1H). ESI-MS m/z [M+H]⁺ 447.3.

Example 308 4-(1-(5-(4-cyclopropylpiperazine-1-carbonyl)pyridin-2-yl)-5-hydroxy-1H-pyrazol-4-yl)-2-fluoro-5-methylbenzonitrile

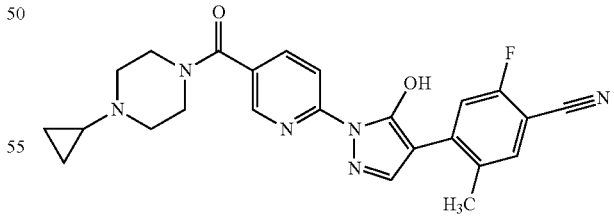

The title compound was prepared in a manner similar to Example 305 using 1-cyclopropylpiperazine and 2-fluoro-5-methyl-4-(4,4,5,5-tetramethyl-1,3,2-dioxaborolan-2-yl)benzonitrile. ¹H NMR (400 MHz, DMSO-d6) δ ppm 0.64-1.07 (m, 4H) 2.42 (s, 3H) 2.60-2.85 (m, 1H) 3.30 (br. s., 4H) 3.47-4.15 (m, 4H) 7.79 (d, J=7.07 Hz, 1H) 7.88 (d, J=10.86 Hz, 1H) 8.13 (dd, J=8.72, 2.15 Hz, 1H) 8.29 (br. s., 1H) 8.47 (br. s., 1H) 8.60 (dd, J=2.27, 0.51 Hz, 1H). ESI-MS m/z [M+H]⁺ 447.3.

Example 309 4-(1-(5-(4-ethylpiperazine-1-carbonyl)pyridin-2-yl)-5-hydroxy-1H-pyrazol-4-yl)-2,3-dimethylbenzonitrile

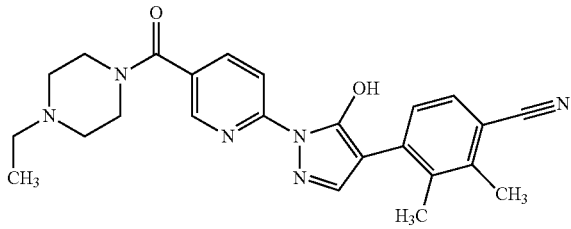 [SMILES: CCN1CCN(C(=O)c2ccc(-n3ncc(-c4ccc(C#N)c(C)c4C)c3O)nc2)CC1]

The title compound was prepared in a manner similar to Example 305 using 2,3-dimethyl-4-(4,4,5,5-tetramethyl-1,3,2-dioxaborolan-2-yl)benzonitrile. $^1$H NMR (400 MHz, DMSO-$d_6$) δ ppm 1.23 (t, J=7.20 Hz, 3H) 2.30 (s, 3H) 2.49-2.49 (m, 2H) 3.16 (d, J=7.33 Hz, 3H) 3.41 (br. s., 8H) 7.44 (d, J=7.83 Hz, 1H) 7.60 (s, 1H) 7.78-7.80 (m, 1H) 8.12 (d, J=7.33 Hz, 2H) 8.47-8.63 (m, 1H). ESI-MS m/z [M+H]$^+$ 431.3.

Example 310 4-(1-(5-(4-cyclopropylpiperazine-1-carbonyl)pyridin-2-yl)-5-hydroxy-1H-pyrazol-4-yl)-2,3-dimethylbenzonitrile

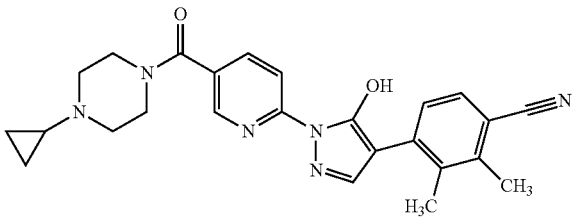 [SMILES: Cc1c(C#N)ccc(-c2cnn(-c3ccc(C(=O)N4CCN(C5CC5)CC4)cn3)c2O)c1C]

The title compound was prepared in a manner similar to Example 305 using 1-cyclopropylpiperazine and 2,3-dimethyl-4-(4,4,5,5-tetramethyl-1,3,2-dioxaborolan-2-yl)benzonitrile. $^1$H NMR (400 MHz, DMSO-$d_6$) δ ppm 0.80 (br. s., 4H) 2.30 (s, 3H) 2.49 (br. s., 3H) 3.32-5.12 (m, 8H) 7.44 (d, J=7.58 Hz, 1H) 7.61 (d, J=8.08 Hz, 1H) 7.76-8.73 (m, 4H). ESI-MS m/z [M+H]$^+$ 443.3.

Example 311 4-(1-(5-(4-(2,2-difluoroethyl)piperazine-1-carbonyl)pyridin-2-yl)-5-hydroxy-1H-pyrazol-4-yl)-3-methylbenzonitrile

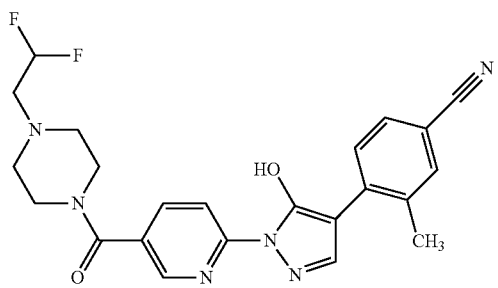 [SMILES: Cc1cc(C#N)ccc1-c1cnn(-c2ccc(C(=O)N3CCN(CC(F)F)CC3)cn2)c1O]

The title compound was prepared in a manner similar to Example 301 using 1-(2,2-difluoroethyl)piperazine hydrochloride. $^1$H NMR (400 MHz, DMSO-$d_6$) δ ppm 2.42 (s, 3H) 2.58 (br. s., 4H) 2.79 (td, J=15.66, 4.29 Hz, 2H) 3.39-3.68 (m, 4H) 5.95-6.35 (m, 1H) 7.67 (d, J=8.26 Hz, 1H) 7.71-7.80 (m, 2H) 8.03-8.21 (m, 2H) 8.53 (m, J=2.10, 0.90 Hz, 2H) 13.13 (br. s., 1H). ESI-MS m/z [M+H]$^+$ 453.3 minutes.

Example 312 4-(5-hydroxy-1-(5-(4-(2,2,2-trifluoroethyl)piperazine-1-carbonyl)pyridin-2-yl)-1H-pyrazol-4-yl)-3-methylbenzonitrile

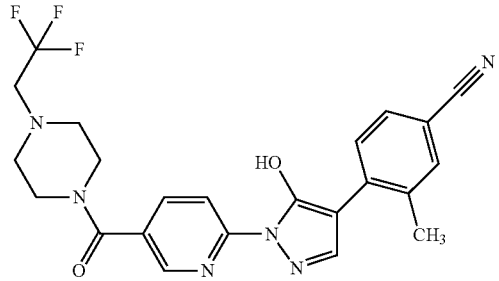 [SMILES: Cc1cc(C#N)ccc1-c1cnn(-c2ccc(C(=O)N3CCN(CC(F)(F)F)CC3)cn2)c1O]

The title compound was prepared in a manner similar to Example 301 using 1-(2,2,2-trifluoroethyl)piperazine dihydrochloride. $^1$H NMR (400 MHz, DMSO-$d_6$) δ ppm 2.42 (s, 3H) 2.59-2.74 (m, 4H) 3.25 (q, J=10.11 Hz, 2H) 3.39-3.71 (m, 4H) 7.65 (dd, J=8.08, 1.52 Hz, 1H) 7.72 (s, 1H) 7.78 (d, J=8.08 Hz, 1H) 8.06 (dd, J=8.72, 2.15 Hz, 1H) 8.15 (s, 1H) 8.39 (d, J=8.34 Hz, 1H) 8.53 (dd, J=2.27, 0.76 Hz, 1H) 12.45-13.65 (m, 1H). ESI-MS m/z [M+H]$^+$ 471.2.

Example 313 6-(4-(4-cyano-2-methylphenyl)-5-hydroxy-1H-pyrazol-1-yl)-N-(3-(dimethylamino)propyl)-N-methylnicotinamide

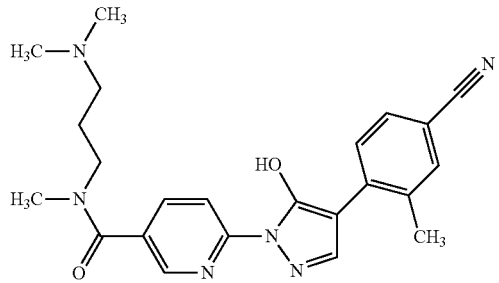 [SMILES: Cc1cc(C#N)ccc1-c1cnn(-c2ccc(C(=O)N(C)CCCN(C)C)cn2)c1O]

The title compound was prepared in a manner similar to Example 303 using 6-(4-(4-cyano-2-methylphenyl)-5-hydroxy-1H-pyrazol-1-yl)nicotinic acid and N1,N1,N3-trimethylpropane-1,3-diamine. $^1$H NMR (400 MHz, DMSO-$d_6$) δ ppm 1.98 (br. s., 2H) 2.43 (s, 3H) 2.68-2.95 (m, 7H) 3.00 (s, 3H) 3.13 (br. s., 1H) 3.23-3.61 (m, 2H) 7.60-7.89 (m, 3H) 7.99-8.82 (m, 4H) 9.53 (br. s., 1H) 12.69-13.62 (m, 1H). ESI-MS m/z [M+H]$^+$ 419.3.

Example 314 4-(1-(5-([1,3'-bipiperidine]-r-carbonyl)pyridin-2-yl)-5-hydroxy-1H-pyrazol-4-yl)-3-methylbenzonitrile

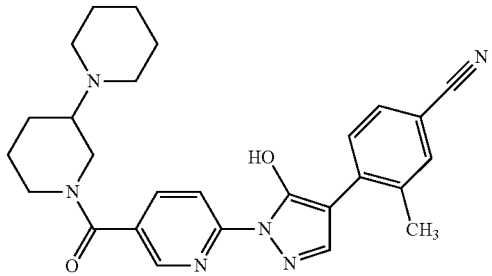 [SMILES: Cc1cc(C#N)ccc1-c1cnn(-c2ccc(C(=O)N3CCCC(N4CCCCC4)C3)cn2)c1O]

The title compound was prepared in a manner similar to Example 303 using 6-(4-(4-cyano-2-methylphenyl)-5-hydroxy-1H-pyrazol-1-yl)nicotinic acid and 1,3'-bipiperidine dihydrochloride. ¹H NMR (400 MHz, DMSO-d₆) δ ppm 1.54 (d, J=12.88 Hz, 2H) 1.62-1.89 (m, 7H) 2.17 (d, J=10.86 Hz, 1H) 2.43 (s, 3H) 2.97-3.51 (m, 6H) 3.56-4.15 (m, 1H) 4.32-4.88 (m, 1H) 7.62-7.85 (m, 3H) 7.82-7.83 (m, 1H) 7.95-8.64 (m, 4H) 9.40 (br. s., 1H) 12.56-13.62 (m, 1H). ESI-MS m/z [M+H]⁺ 471.3.

Example 315 (R)-4-(1-(5-(3-(dimethylamino)piperidine-1-carbonyl)pyridin-2-yl)-5-hydroxy-1H-pyrazol-4-yl)-3-methylbenzonitrile

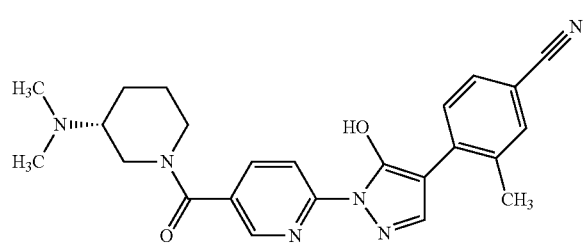 [SMILES: Cc1cc(C#N)ccc1-c1cnn(-c2ccc(C(=O)N3CCC[C@@H](N(C)C)C3)cn2)c1O]

The title compound was prepared in a manner similar to Example 301 using (R)—N,N-dimethylpiperidin-3-amine dihydrochloride. ¹H NMR (500 MHz, DMSO-d6) δ ppm 1.32-1.97 (m, 3H) 2.15 (br. s., 1H) 2.39-2.46 (m, 3H) 2.54-3.71 (m, 10H) 3.87-4.56 (m, 1H) 7.65 (dd, J=8.05, 1.71 Hz, 1H) 7.68-7.74 (m, 1H) 7.80 (d, J=7.81 Hz, 1H) 8.04-8.18 (m, 2H) 8.40 (d, J=8.79 Hz, 1H) 8.59 (br. s., 1H) 12.04 (br. s., 1H). ESI-MS m/z [M+H]⁺ 431.3.

Example 316 2-fluoro-4-(5-hydroxy-1-(5-(4-methoxypiperidine-1-carbonyl)pyridin-2-yl)-1H-pyrazol-4-yl)-3-methylbenzonitrile

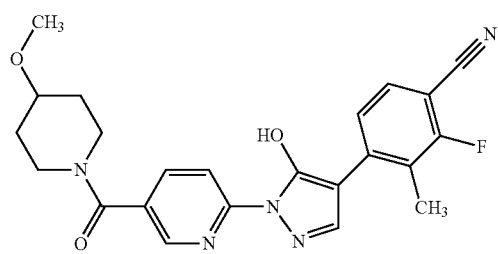 [SMILES: COC1CCN(C(=O)c2ccc(-n3ncc(-c4ccc(C#N)c(F)c4C)c3O)nc2)CC1]

The title compound was prepared in a manner similar to Example 303 using 6-(4-(4-cyano-3-fluoro-2-methylphenyl)-5-hydroxy-1H-pyrazol-1-yl)nicotinic acid and 4-methoxypiperidine. ¹H NMR (500 MHz, DMSO-d₆) δ ppm 1.49 (br. s., 2H) 1.75-1.97 (m, 2H) 2.33 (d, J=1.95 Hz, 3H) 3.11-3.68 (m, 7H) 3.92 (br. s., 1H) 7.64 (br. s., 1H) 7.70-7.79 (m, 1H) 8.07 (d, J=7.81 Hz, 1H) 8.12-8.65 (m, 3H). ESI-MS m/z [M+H]⁺ 436.3.

Example 317 (R)-4-(1-(5-(3-(dimethylamino)pyrrolidine-1-carbonyl)pyridin-2-yl)-5-hydroxy-1H-pyrazol-4-yl)-2-fluoro-3-methylbenzonitrile

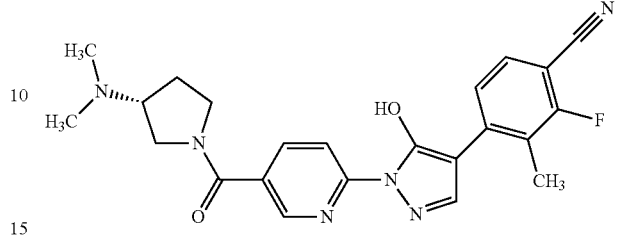

The title compound was prepared in a manner similar to Example 301 using 6-(4-(4-cyano-3-fluoro-2-methylphenyl)-5-hydroxy-1H-pyrazol-1-yl)nicotinic acid and (R)—N,N-dimethylpyrrolidin-3-amine. ¹H NMR (400 MHz, DMSO-d₆) δ ppm 2.07-2.22 (m, 1H) 2.33 (s, 4H) 2.70-2.95 (m, 6H) 3.71 (d, J=5.05 Hz, 3H) 3.83-4.01 (m, 2H) 7.64 (br. s., 1H) 7.68-7.80 (m, 1H) 8.05-8.61 (m, 3H) 8.67 (s, 1H). ESI-MS m/z [M+H]⁺ 435.3.

Example 318 (S)-4-(1-(5-(3-(dimethylamino)pyrrolidine-1-carbonyl)pyridin-2-yl)-5-hydroxy-1H-pyrazol-4-yl)-2-fluoro-3-methylbenzonitrile

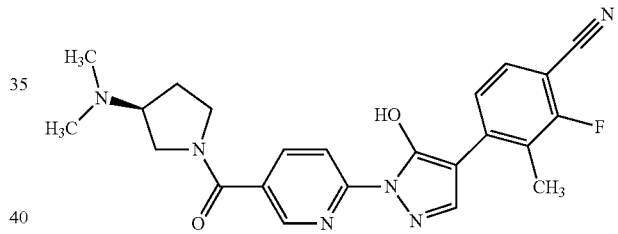

The title compound was prepared in a manner similar to Example 301 using 6-(4-(4-cyano-3-fluoro-2-methylphenyl)-5-hydroxy-1H-pyrazol-1-yl)nicotinic acid and (S)—N,N-dimethylpyrrolidin-3-amine. ¹H NMR (400 MHz, DMSO-d₆) δ ppm 2.09-2.30 (m, 1H) 2.33 (d, J=2.27 Hz, 4H) 2.76-2.93 (m, 6H) 3.52-3.78 (m, 3H) 3.83-4.00 (m, 2H) 7.63 (d, J=7.83 Hz, 1H) 7.74 (t, J=7.58 Hz, 1H) 8.21 (d, J=7.58 Hz, 3H) 8.67 (s, 1H).). ESI-MS m/z [M+H]⁺ 435.3.

Example 319 (R)-4-(1-(5-(3-(dimethylamino)piperidine-1-carbonyl)pyridin-2-yl)-5-hydroxy-1H-pyrazol-4-yl)-2-fluoro-3-methylbenzonitrile

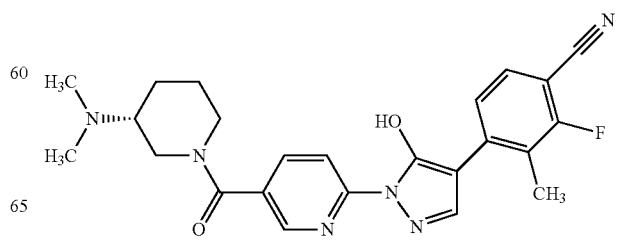

The title compound was prepared in a manner similar to Example 301 using 6-(4-(4-cyano-3-fluoro-2-methylphenyl)-5-hydroxy-1H-pyrazol-1-yl)nicotinic acid and (R)—N,N-dimethylpiperidin-3-amine. ¹H NMR (500 MHz, DMSO-d₆) δ ppm 1.53 (d, J=13.18 Hz, 1H) 1.77 (m, J=16.10 Hz, 2H) 2.10 (br. s., 1H) 2.33 (s, 3H) 2.57-2.89 (m, 6H) 2.90-4.77 (m, 5H) 7.63 (br. s., 1H) 7.74 (t, J=7.54 Hz, 1H) 8.09 (d, J=7.81 Hz, 1H) 8.24 (br. s., 1H) 8.35-8.66 (m, 2H) 9.86 (br. s., 1H). ESI-MS m/z [M+H]⁺ 449.3.

Example 320 (S)-4-(1-(5-(3-(dimethylamino)piperidine-1-carbonyl)pyridin-2-yl)-5-hydroxy-1H-pyrazol-4-yl)-2-fluoro-3-methylbenzonitrile

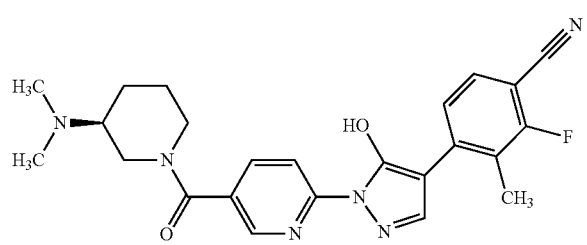 [SMILES: Cc1c(-c2cnn(-c3ccc(C(=O)N4CCC[C@H](N(C)C)C4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and (S)—N,N-dimethylpiperidin-3-amine. ¹H NMR (400 MHz, DMSO-d₆) δ ppm 1.54 (d, J=11.12 Hz, 1H) 1.78 (m, J=16.20 Hz, 2H) 2.12 (d, J=10.86 Hz, 1H) 2.33 (d, J=2.27 Hz, 3H) 2.67-2.94 (m, 6H) 3.13-4.79 (m, 5H) 7.48-7.70 (m, 1H) 7.70-7.80 (m, 1H) 7.98-8.34 (m, 2H) 8.57 (m, J=1.50 Hz, 2H) 9.44-10.31 (m, 1H). ESI-MS m/z [M+H]⁺ 449.3.

Example 321 4-(1-(5-(3-(dimethylamino)azetidine-1-carbonyl)pyridin-2-yl)-5-hydroxy-1H-pyrazol-4-yl)-2-fluoro-3-methylbenzonitrile

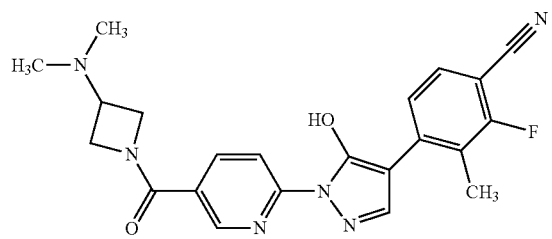 [SMILES: Cc1c(-c2cnn(-c3ccc(C(=O)N4CC(N(C)C)C4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and N,N-dimethylazetidin-3-amine. ¹H NMR (500 MHz, DMSO-d₆) δ ppm 2.33 (d, J=1.95 Hz, 3H) 2.81 (s, 6H) 4.07-4.21 (m, 1H) 4.29 (br. s., 2H) 4.47-4.59 (m, 1H) 4.66 (m, J=7.80 Hz, 1H) 7.63 (br. s., 1H) 7.71-7.78 (m, 1H) 7.91-8.81 (m, 4H). ESI-MS m/z [M+H]⁺ 421.3.

Example 322 2-fluoro-4-(5-hydroxy-1-(5-(4-methylpiperazine-1-carbonyl)pyridin-2-yl)-1H-pyrazol-4-yl)-3-methylbenzonitrile

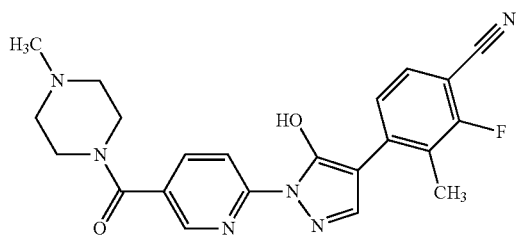 [SMILES: Cc1c(-c2cnn(-c3ccc(C(=O)N4CCN(C)CC4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and 1-methylpiperazine. ¹H NMR (400 MHz, DMSO-d₆) δ ppm 2.33 (d, J=2.53 Hz, 3H) 2.84 (s, 3H) 3.17 (s, 8H) 7.63 (d, J=7.58 Hz, 1H) 7.70-7.79 (m, 1H) 8.04-8.57 (m, 3H) 8.59 (d, J=1.52 Hz, 1H). ESI-MS m/z [M+H]⁺ 421.3.

Example 323 4-(1-(5-(4-cyclopropyl-1,4-diazepane-1-carbonyl)pyridin-2-yl)-5-hydroxy-1H-pyrazol-4-yl)-2-fluoro-3-methylbenzonitrile

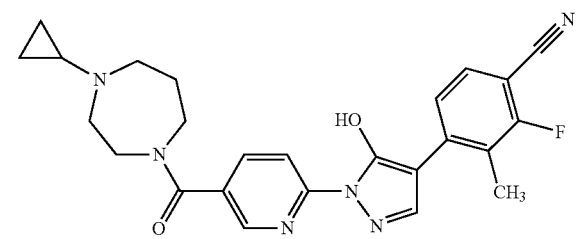 [SMILES: Cc1c(-c2cnn(-c3ccc(C(=O)N4CCCN(C5CC5)CC4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and 1-cyclopropyl-1,4-diazepane. ¹H NMR (400 MHz, DMSO-d₆) δ ppm 0.66-1.06 (m, 4H) 1.94-2.23 (m, 2H) 2.33 (d, J=2.02 Hz, 3H) 2.81-3.07 (m, 1H) 3.41-4.30 (m, 8H) 7.54-7.70 (m, 1H) 7.75 (t, J=7.45 Hz, 1H) 7.98-8.65 (m, 4H). ESI-MS m/z [M+H]⁺ 461.3.

Example 324 2-fluoro-4-(5-hydroxy-1-(5-(4-methyl-4,7-diazaspiro[2.5]octane-7-carbonyl)pyridin-2-yl)-1H-pyrazol-4-yl)-3-methylbenzonitrile

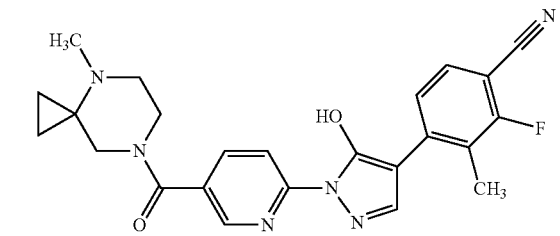 [SMILES: Cc1c(-c2cnn(-c3ccc(C(=O)N4CCN(C)C5(CC5)C4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and 4-methyl-4,7-diazaspiro[2.5]octane. ¹H NMR (400 MHz, DMSO-d₆) δ ppm 0.58-1.34 (m, 4H) 2.33 (d, J=2.27 Hz, 3H) 2.91 (s, 3H) 3.31-3.85 (m, 6H) 7.62 (d, J=7.83 Hz, 1H) 7.70-7.78 (m, 1H) 7.82-8.75 (m, 4H). ESI-MS m/z [M+H]⁺ 447.3.

Example 325 2-fluoro-4-(5-hydroxy-1-(5-(pyrrolidine-1-carbonyl)pyridin-2-yl)-1H-pyrazol-4-yl)-3-methylbenzonitrile

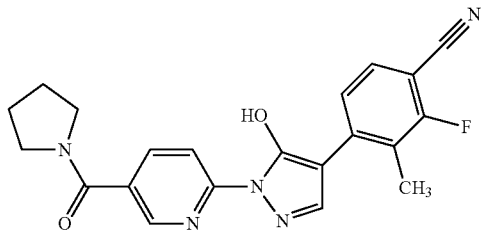 [SMILES: Cc1c(-c2cnn(-c3ccc(C(=O)N4CCCC4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and pyrrolidine. ¹H NMR (500 MHz, DMSO-d₆) δ ppm 1.79-1.95 (m, 4H) 2.33 (d, J=2.44 Hz, 3H) 3.49 (t, J=5.61 Hz, 4H) 7.42-7.82 (m, 2H) 7.84-8.76 (m, 4H). ESI-MS m/z [M+H]⁺ 392.3.

Example 326 6-(4-(4-cyano-3-fluoro-2-methylphenyl)-5-hydroxy-1H-pyrazol-1-yl)-N-(3-methoxypropyl)-N-methylnicotinamide

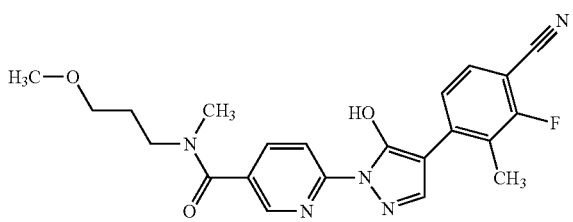 [SMILES: COCCCN(C)C(=O)c1ccc(-n2ncc(-c3ccc(C#N)c(F)c3C)c2O)nc1]

The title compound was prepared in a manner similar to Example 301 using 6-(4-(4-cyano-3-fluoro-2-methylphenyl)-5-hydroxy-1H-pyrazol-1-yl)nicotinic acid and 3-methoxy-N-methylpropan-1-amine. ¹H NMR (400 MHz, DMSO-d₆) δ ppm 1.66-1.93 (m, 2H) 2.34 (d, J=2.27 Hz, 3H) 2.98 (s, 3H) 3.07-3.67 (m, 7H) 7.64 (br. s., 1H) 7.70-7.81 (m, 1H) 7.84-8.64 (m, 4H). ESI-MS m/z [M+H]⁺ 424.3.

Example 327 2-fluoro-4-(5-hydroxy-1-(5-(morpholine-4-carbonyl)pyridin-2-yl)-1H-pyrazol-4-yl)-3-methylbenzonitrile

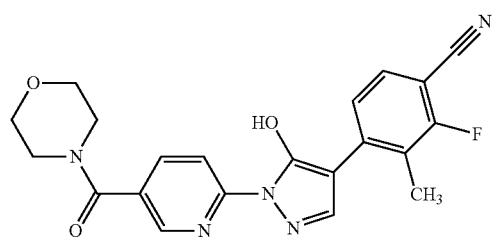 [SMILES: Cc1c(-c2cnn(-c3ccc(C(=O)N4CCOCC4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and morpholine. ¹H NMR (500 MHz, DMSO-d₆) δ ppm 2.33 (d, J=1.95 Hz, 3H) 3.34 (br. s., 2H) 3.64 (br. s., 6H) 7.64 (br. s., 1H) 7.74 (t, J=7.32 Hz, 1H) 7.90-8.63 (m, 4H). ESI-MS m/z [M+H]⁺ 408.3.

Example 328 (S)-4-(1-(5-(4-ethyl-3-methylpiperazine-1-carbonyl)pyridin-2-yl)-5-hydroxy-1H-pyrazol-4-yl)-2-fluoro-3-methylbenzonitrile

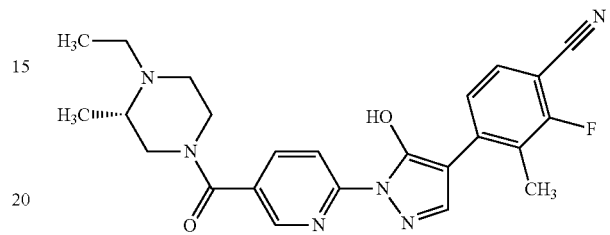

The title compound was prepared in a manner similar to Example 303 using 6-(4-(4-cyano-3-fluoro-2-methylphenyl)-5-hydroxy-1H-pyrazol-1-yl)nicotinic acid and (S)-1-ethyl-2-methylpiperazine. ¹H NMR (400 MHz, DMSO-d₆) δ ppm 1.22 (t, J=7.20 Hz, 6H) 2.33 (d, J=2.27 Hz, 3H) 3.08-3.36 (m, 4H) 3.42 (br. s., 2H) 4.11-4.93 (m, 3H) 7.64 (br. s., 1H) 7.71-7.80 (m, 1H) 7.87-8.79 (m, 4H) 9.53-10.44 (m, 1H) 12.23-14.36 (m, 1H). ESI-MS m/z [M+H]⁺ 449.3.

Example 329 (S)-4-(1-(5-(3,4-dimethylpiperazine-1-carbonyl)pyridin-2-yl)-5-hydroxy-1H-pyrazol-4-yl)-2-fluoro-3-methylbenzonitrile

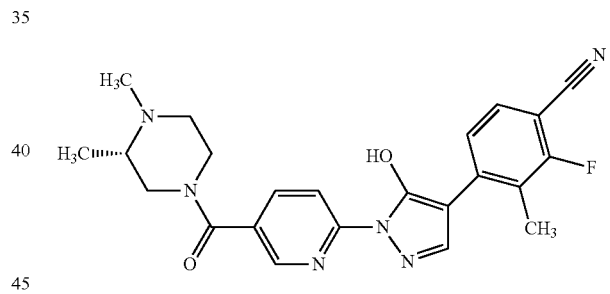

The title compound was prepared in a manner similar to Example 303 using 6-(4-(4-cyano-3-fluoro-2-methylphenyl)-5-hydroxy-1H-pyrazol-1-yl)nicotinic acid and (S)-1,2-dimethylpiperazine. ¹H NMR (400 MHz, DMSO-d₆) δ ppm 1.28 (br. s., 3H) 2.33 (d, J=2.27 Hz, 3H) 2.84 (s, 3H) 3.13-3.74 (m, 7H) 7.63 (d, J=6.82 Hz, 1H) 7.71-7.78 (m, 1H) 7.90-8.67 (m, 4H). ESI-MS m/z [M+H]⁺ 435.3.

Example 330 (R)-4-(1-(5-(4-ethyl-2-methylpiperazine-1-carbonyl)pyridin-2-yl)-5-hydroxy-1H-pyrazol-4-yl)-2-fluoro-3-methylbenzonitrile

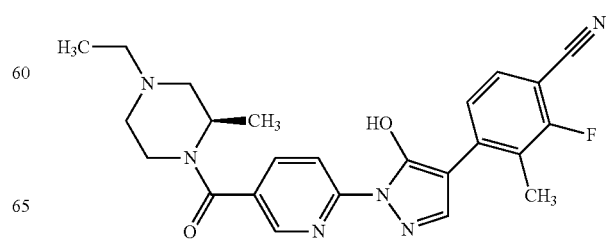

The title compound was prepared in a manner similar to Example 303 using 6-(4-(4-cyano-3-fluoro-2-methylphenyl)-5-hydroxy-1H-pyrazol-1-yl)nicotinic acid and (R)-1-ethyl-3-methylpiperazine and 6-(4-(4-cyano-2-methylphenyl)-5-hydroxy-1H-pyrazol-1-yl)nicotinic acid. ¹H NMR (400 MHz, DMSO-d₆) δ ppm 1.24 (t, J=7.33 Hz, 3H) 1.38 (d, J=7.07 Hz, 3H) 2.33 (d, J=2.53 Hz, 3H) 2.95-3.26 (m, 4H) 3.34-3.55 (m, 2H) 3.73-4.28 (m, 3H) 7.64 (br. s., 1H) 7.71-7.78 (m, 1H) 7.93-8.68 (m, 4H). ESI-MS m/z [M+H]⁺ 449.3.

Example 331 (R)-4-(1-(5-(3-(cyclopropyl(methyl)amino)piperidine-1-carbonyl)pyridin-2-yl)-5-hydroxy-1H-pyrazol-4-yl)-2-fluoro-3-methylbenzonitrile

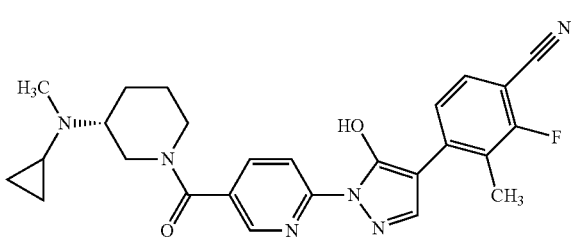 [SMILES: Cc1c(-c2cnn(-c3ccc(C(=O)N4CCC[C@@H](N(C)C5CC5)C4)cn3)c2O)ccc(C#N)c1F]

The title compound was prepared in a manner similar to Example 303 using 6-(4-(4-cyano-3-fluoro-2-methylphenyl)-5-hydroxy-1H-pyrazol-1-yl)nicotinic acid and (R)-1-ethyl-3-methylpiperazine. ¹H NMR (400 MHz, DMSO-d₆) δ ppm 0.61-1.18 (m, 4H) 1.50-1.66 (m, 1H) 1.71-2.01 (m, 2H) 2.16-2.28 (m, 1H) 2.33 (d, J=2.53 Hz, 3H) 2.77-3.04 (m, 4H) 3.09-3.23 (m, 1H) 3.70-4.02 (m, 4H) 7.64 (br. s., 1H) 7.70-7.79 (m, 1H) 7.86-8.78 (m, 4H) 8.91-9.92 (m, 1H). ESI-MS m/z [M+H]⁺ 475.3.

Example 332 (S)-2-fluoro-4-(5-hydroxy-1-(5-(3-(methyl(2,2,2-trifluoroethyl)amino)piperidine-1-carbonyl)pyridin-2-yl)-1H-pyrazol-4-yl)-3-methylbenzonitrile

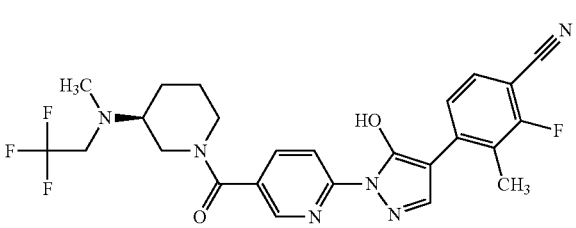 [SMILES: Cc1c(-c2cnn(-c3ccc(C(=O)N4CCC[C@H](N(C)CC(F)(F)F)C4)cn3)c2O)ccc(C#N)c1F]

The title compound was prepared in a manner similar to Example 303 using 6-(4-(4-cyano-3-fluoro-2-methylphenyl)-5-hydroxy-1H-pyrazol-1-yl)nicotinic acid and (S)—N-methyl-N-(2,2,2-trifluoroethyl)piperidin-3-amine. ¹H NMR (400 MHz, DMSO-d₆) δ ppm 1.34-1.92 (m, 4H) 2.26-2.41 (m, 4H) 2.59-2.80 (m, 2H) 2.93-3.36 (m, 3H) 3.55 (br. s., 1H) 3.75-4.19 (m, 2H) 4.36-4.54 (m, 1H) 7.55-7.68 (m, 1H) 7.71-7.78 (m, 1H) 8.53 (s, 4H). ESI-MS m/z [M+H]⁺ 517.3.

Example 333 (S)-4-(1-(5-(3-((2,2-difluoroethyl)(methyl)amino)piperidine-1-carbonyl)pyridin-2-yl)-5-hydroxy-1H-pyrazol-4-yl)-2-fluoro-3-methylbenzonitrile

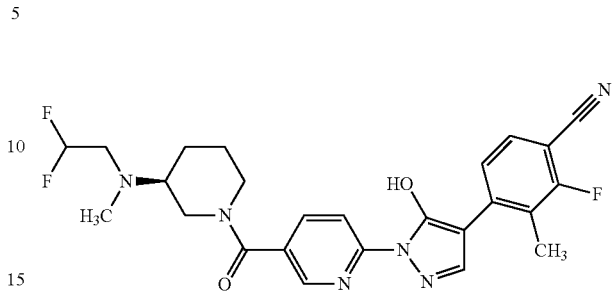

The title compound was prepared in a manner similar to Example 303 using 6-(4-(4-cyano-3-fluoro-2-methylphenyl)-5-hydroxy-1H-pyrazol-1-yl)nicotinic acid and (S)—N-(2,2-difluoroethyl)-N-methylpiperidin-3-amine. ¹H NMR (400 MHz, DMSO-d₆) δ ppm 1.41-1.93 (m, 3H) 1.98-2.06 (m, 1H) 2.33 (d, J=2.27 Hz, 3H) 2.52-3.90 (m, 9H) 4.26-4.73 (m, 1H) 5.99-6.62 (m, 1H) 7.63 (d, J=7.33 Hz, 1H) 7.74 (t, J=7.58 Hz, 1H) 8.08 (d, J=8.34 Hz, 1H) 8.13-8.51 (m, 2H) 8.54 (d, J=1.77 Hz, 1H). ESI-MS m/z [M+H]⁺ 499.3.

Example 334 (R)-2-fluoro-4-(5-hydroxy-1-(5-(octahydropyrrolo[1,2-a]pyrazine-2-carbonyl)pyridin-2-yl)-1H-pyrazol-4-yl)-3-methylbenzonitrile

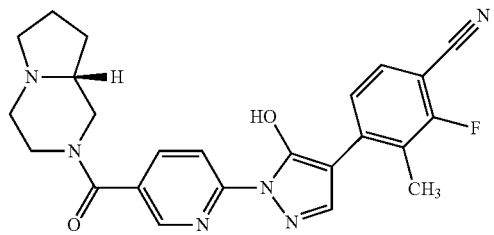 [SMILES: Cc1c(-c2cnn(-c3ccc(C(=O)N4CCN5CCC[C@@H]5C4)cn3)c2O)ccc(C#N)c1F]

The title compound was prepared in a manner similar to Example 303 using 6-(4-(4-cyano-3-fluoro-2-methylphenyl)-5-hydroxy-1H-pyrazol-1-yl)nicotinic acid and (R)-octahydropyrrolo[1,2-a]pyrazine. ¹H NMR (400 MHz, DMSO-d₆) δ ppm 2.08 (s, 4H) 2.33 (d, J=2.53 Hz, 3H) 2.81-4.24 (m, 9H) 7.64 (br. s., 1H) 7.75 (t, J=7.45 Hz, 1H) 7.95-8.83 (m, 4H). ESI-MS m/z [M+H]⁺ 447.3.

Example 335 2-fluoro-4-(5-hydroxy-1-(5-(3-(piperidin-1-yl)azetidine-1-carbonyl)pyridin-2-yl)-1H-pyrazol-4-yl)-3-methylbenzonitrile

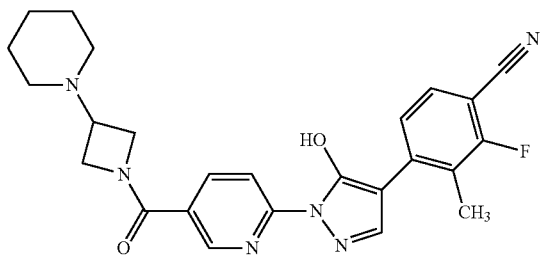 [SMILES: Cc1c(-c2cnn(-c3ccc(C(=O)N4CC(N5CCCCC5)C4)cn3)c2O)ccc(C#N)c1F]

The title compound was prepared in a manner similar to Example 303 using 6-(4-(4-cyano-3-fluoro-2-methylphenyl)-5-hydroxy-1H-pyrazol-1-yl)nicotinic acid and 1-(azetidin-3-yl)piperidine. $^1$H NMR (400 MHz, DMSO-d$_6$) δ ppm 1.22-2.00 (m, 6H) 2.33 (d, J=2.27 Hz, 3H) 2.84 (br. s., 2H) 3.23-3.70 (m, 2H) 4.06-4.19 (m, 1H) 4.33 (br. s., 2H) 4.61 (br. s., 1H) 4.66-4.77 (m, 1H) 7.63 (d, J=7.07 Hz, 1H) 7.75 (t, J=7.45 Hz, 1H) 7.98-8.89 (m, 4H). ESI-MS m/z [M+H]$^+$ 461.3.

Example 336 (R)-4-(1-(5-(3-((2,2-difluoroethyl)(methyl)amino)piperidine-1-carbonyl)pyridin-2-yl)-5-hydroxy-1H-pyrazol-4-yl)-2-fluoro-3-methylbenzonitrile

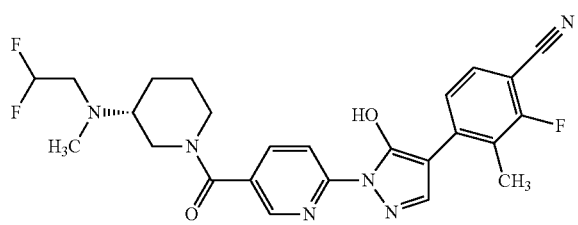 [SMILES: Cc1c(-c2cnn(-c3ccc(C(=O)N4CCC[C@@H](N(C)CC(F)F)C4)cn3)c2O)ccc(C#N)c1F]

The title compound was prepared in a manner similar to Example 303 using 6-(4-(4-cyano-3-fluoro-2-methylphenyl)-5-hydroxy-1H-pyrazol-1-yl)nicotinic acid and (R)—N-(2,2-difluoroethyl)-N-methylpiperidin-3-amine. $^1$H NMR (400 MHz, DMSO-d$_6$) δ ppm 1.41-1.58 (m, 1H) 1.61-1.94 (m, 2H) 1.97-2.07 (m, 1H) 2.33 (d, J=2.27 Hz, 3H) 2.54-2.87 (m, 3H) 3.11 (br. s., 3H) 3.40-3.97 (m, 2H) 4.20-4.76 (m, 1H) 6.03-6.58 (m, 1H) 7.64 (br. s., 1H) 7.68-7.80 (m, 1H) 7.94-8.62 (m, 4H). ESI-MS m/z [M+H]$^+$ 499.3.

Example 337 (R)-2-fluoro-4-(5-hydroxy-1-(5-(4-isopropyl-3-methylpiperazine-1-carbonyl)pyridin-2-yl)-1H-pyrazol-4-yl)-3-methylbenzonitrile

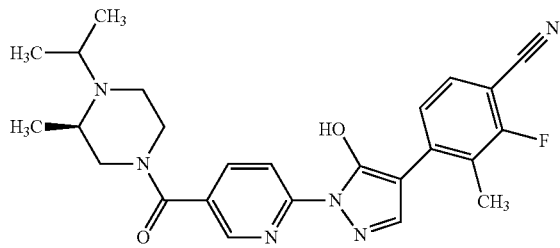 [SMILES: Cc1c(-c2cnn(-c3ccc(C(=O)N4CCN(C(C)C)[C@H](C)C4)cn3)c2O)ccc(C#N)c1F]

The title compound was prepared in a manner similar to Example 303 using 6-(4-(4-cyano-3-fluoro-2-methylphenyl)-5-hydroxy-1H-pyrazol-1-yl)nicotinic acid and (R)-1-isopropyl-2-methylpiperazine. $^1$H NMR (400 MHz, DMSO-d$_6$) δ ppm 1.18 (d, J=5.81 Hz, 4H) 1.30 (d, J=6.32 Hz, 5H) 2.33 (d, J=2.27 Hz, 3H) 2.85-3.65 (m, 5H) 3.89 (br. s., 2H) 4.20-4.83 (m, 1H) 7.64 (br. s., 1H) 7.70-7.79 (m, 1H) 7.93-8.77 (m, 4H) 9.36-10.10 (m, 1H). ESI-MS m/z [M+H]$^+$ 463.3.

Example 338 (R)-4-(1-(5-(4-ethyl-3-methylpiperazine-1-carbonyl)pyridin-2-yl)-5-hydroxy-1H-pyrazol-4-yl)-2-fluoro-3-methylbenzonitrile

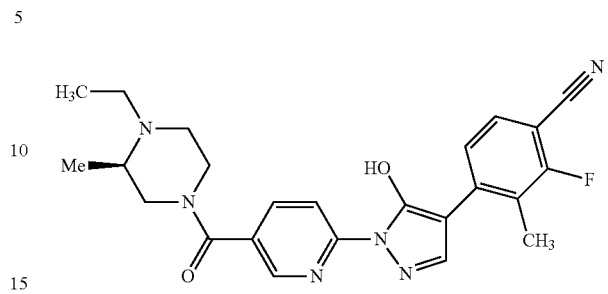

The title compound was prepared in a manner similar to Example 303 using 6-(4-(4-cyano-3-fluoro-2-methylphenyl)-5-hydroxy-1H-pyrazol-1-yl)nicotinic acid and (R)-1-ethyl-2-methylpiperazine. $^1$H NMR (400 MHz, DMSO-d$_6$) δ ppm 1.22 (m, J=7.20, 7.20 Hz, 6H) 2.33 (d, J=2.27 Hz, 3H) 2.91-4.72 (m, 9H) 7.63 (br. s., 1H) 7.71-7.79 (m, 1H) 7.94-8.81 (m, 4H) 9.52-10.21 (m, 1H). ESI-MS m/z [M+H]$^+$ 449.3.

Example 339 (S)-2-fluoro-4-(5-hydroxy-1-(5-(4-isopropyl-3-methylpiperazine-1-carbonyl)pyridin-2-yl)-1H-pyrazol-4-yl)-3-methylbenzonitrile

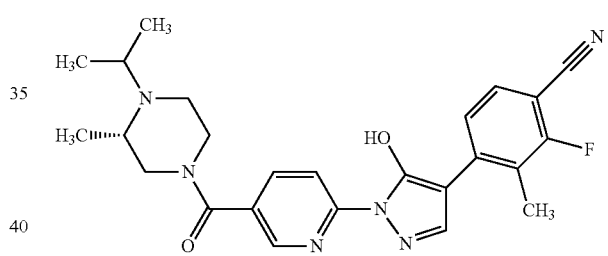

The title compound was prepared in a manner similar to Example 303 using 6-(4-(4-cyano-3-fluoro-2-methylphenyl)-5-hydroxy-1H-pyrazol-1-yl)nicotinic acid and (S)-1-isopropyl-2-methylpiperazine. $^1$H NMR (400 MHz, DMSO-d$_6$) δ ppm 1.02-1.50 (m, 9H) 2.33 (d, J=2.53 Hz, 3H) 2.88-3.64 (m, 5H) 3.89 (br. s., 2H) 4.22-4.92 (m, 1H) 7.53-7.69 (m, 1H) 7.70-7.79 (m, 1H) 7.84-8.79 (m, 4H) 9.49-10.25 (m, 1H). ESI-MS m/z [M+H]$^+$ 463.3.

Example 340 (R)-4-(1-(5-(3,4-dimethylpiperazine-1-carbonyl)pyridin-2-yl)-5-hydroxy-1H-pyrazol-4-yl)-2-fluoro-3-methylbenzonitrile

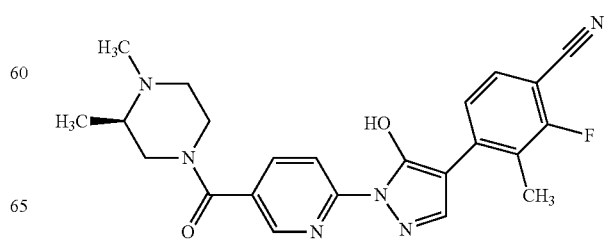

The title compound was prepared in a manner similar to Example 303 using 6-(4-(4-cyano-3-fluoro-2-methylphenyl)-5-hydroxy-1H-pyrazol-1-yl)nicotinic acid and (R)-1,2-dimethylpiperazine. ¹H NMR (400 MHz, DMSO-d₆) δ ppm 1.01-1.53 (m, 3H) 2.33 (d, J=2.27 Hz, 3H) 2.84 (br. s., 3H) 2.93-4.70 (m, 7H) 7.63 (d, J=7.07 Hz, 1H) 7.71-7.80 (m, 1H) 7.88-8.77 (m, 4H). ESI-MS m/z [M+H]⁺ 435.3.

Example 341 (S)-4-(1-(5-(4-ethyl-2-methylpiperazine-1-carbonyl)pyridin-2-yl)-5-hydroxy-1H-pyrazol-4-yl)-2-fluoro-3-methylbenzonitrile

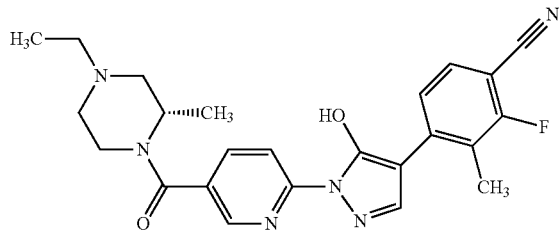 [SMILES: CCN1CCN(C(=O)c2ccc(-n3ncc(-c4ccc(C#N)c(F)c4C)c3O)nc2)[C@@H](C)C1]

The title compound was prepared in a manner similar to Example 303 using 6-(4-(4-cyano-3-fluoro-2-methylphenyl)-5-hydroxy-1H-pyrazol-1-yl)nicotinic acid and (S)-1-ethyl-3-methylpiperazine. ¹H NMR (400 MHz, DMSO-d₆) δ ppm 1.24 (t, J=7.20 Hz, 3H) 1.38 (d, J=7.07 Hz, 3H) 2.33 (d, J=2.27 Hz, 3H) 2.68-5.32 (m, 9H) 7.63 (d, J=7.33 Hz, 1H) 7.70-7.80 (m, 1H) 7.94-8.73 (m, 4H) 8.97-10.49 (m, 1H). ESI-MS m/z [M+H]⁺ 449.3.

Example 342 2-fluoro-4-(5-hydroxy-1-(5-(6-methyl-2,6-diazaspiro[3.3]heptane-2-carbonyl)pyridin-2-yl)-1H-pyrazol-4-yl)-3-methylbenzonitrile

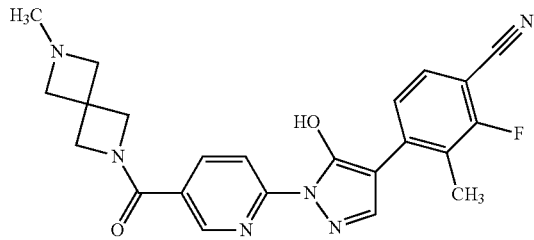 [SMILES: Cc1c(-c2cnn(-c3ccc(C(=O)N4CC5(CN(C)C5)C4)cn3)c2O)ccc(C#N)c1F]

The title compound was prepared in a manner similar to Example 301 using 6-(4-(4-cyano-3-fluoro-2-methylphenyl)-5-hydroxy-1H-pyrazol-1-yl)nicotinic acid and 2-methyl-2,6-diazaspiro[3.3]heptane dihydrochloride. ¹H NMR (400 MHz, DMSO-d₆) δ ppm 2.33 (d, J=2.27 Hz, 3H) 2.80 (d, J=4.55 Hz, 3H) 3.94-4.67 (m, 8H) 7.61 (d, J=8.08 Hz, 1H) 7.69-7.78 (m, 1H) 8.16-8.29 (m, 2H) 8.42 (d, J=8.59 Hz, 1H) 8.69 (br. s., 1H). ESI-MS m/z [M+H]⁺ 433.3.

Example 343 2-fluoro-4-(5-hydroxy-1-(5-(6-methyl-2,6-diazaspiro[3.3]heptane-2-carbonyl)pyridin-2-yl)-1H-pyrazol-4-yl)-5-methylbenzonitrile

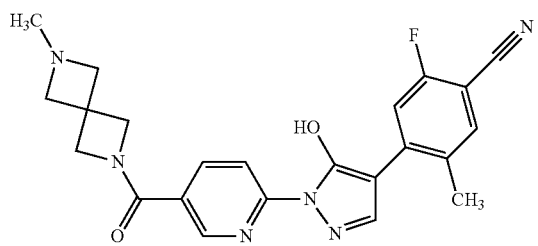 [SMILES: Cc1cc(C#N)c(F)cc1-c1cnn(-c2ccc(C(=O)N3CC4(CN(C)C4)C3)cn2)c1O]

The title compound was prepared in a manner similar to Example 303 using 6-(4-(4-cyano-3-fluoro-2-methylphenyl)-5-hydroxy-1H-pyrazol-1-yl)nicotinic acid and 2-methyl-2,6-diazaspiro[3.3]heptane dihydrochloride. ¹H NMR (400 MHz, DMSO-d₆) δ ppm 2.42 (s, 3H) 2.80 (br. s., 3H) 4.05-4.44 (m, 6H) 4.50-4.64 (m, 2H) 7.79 (d, J=7.07 Hz, 1H) 7.87 (d, J=8.59 Hz, 1H) 8.13-8.79 (m, 4H) 9.63-10.00 (m, 1H). ESI-MS m/z [M+H]⁺ 433.3.

Example 344 4-(5-hydroxy-1-(5-(3-(piperidin-1-yl)azetidine-1-carbonyl)pyridin-2-yl)-1H-pyrazol-4-yl)-3-methylbenzonitrile

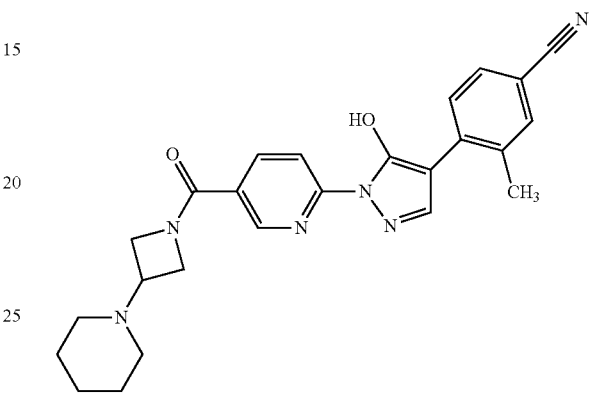

The title compound was prepared in a manner similar to Example 112 using 6-(4-(4-cyano-2-methylphenyl)-5-hydroxy-1H-pyrazol-1-yl)nicotinic acid and 1-(azetidin-3-yl)piperidine dihydrochloride. ¹H NMR (400 MHz, DMSO-d₆) δ ppm 1.36 (d, J=4.80 Hz, 2H) 1.41-1.54 (m, 4H) 2.23-2.34 (m, 3H) 2.36 (s, 3H) 3.13-3.21 (m, 1H) 3.86 (dd, J=9.47, 4.67 Hz, 1H) 4.05 (t, J=8.46 Hz, 1H) 4.20 (d, J=4.80 Hz, 1H) 4.28-4.43 (m, 1H) 7.55 (dd, J=8.08, 1.52 Hz, 1H) 7.62 (s, 1H) 7.78 (d, J=8.08 Hz, 1H) 8.03 (s, 1H) 8.15 (dd, J=8.72, 2.40 Hz, 1H) 8.35 (d, J=8.84 Hz, 1H) 8.65 (dd, J=2.27, 0.76 Hz, 1H) 12.19-13.21 (m, 1H); ESI-MS m/z [M+H]⁺ 443.3

Example 345 4-(1-(5-(3-(dimethylamino)azetidine-1-carbonyl)pyridin-2-yl)-5-hydroxy-1H-pyrazol-4-yl)-3-methylbenzonitrile

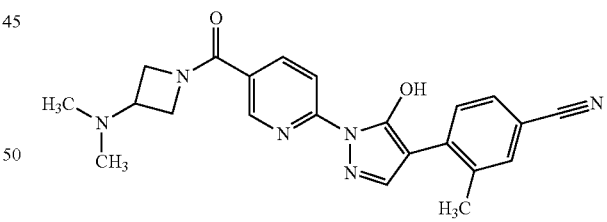

Combined 6-(4-(4-cyano-2-methylphenyl)-5-hydroxy-1H-pyrazol-1-yl)nicotinic acid (105 mg, 0.328 mmol), N1-((ethylimino)methylene)-N3,N3-dimethylpropane-1,3-diamine hydrochloride (94.0 mg, 0.490 mmol), HOBT (66.4 mg, 0.492 mmol) in DMF (1.0 mL) and added N,N-diisopropylethylamine (0.285 mL, 1.639 mmol). Then added N,N-dimethylazetidin-3-amine hydrochloride (67.2 mg, 0.492 mmol) and the reaction was allowed to stir at room temperature for 16 hours. The reaction mixture was diluted with water (3.5 mL) and acidified to pH 4 with 10% citric acid to give a solid, which was collected by filtration, washed with water, methanol, and diethyl ether and dried to give the title compound as a citrate salt. ¹H NMR (400 MHz, DMSO-d$_6$) δ ppm 2.17 (s, 6H) 2.36 (s, 3H) 2.52-2.58 (m, 1H) 2.61-2.68 (m, 1H) 3.24 (ddd, J=12.25, 7.07, 5.18 Hz, 1H) 3.87 (d, J=5.05 Hz, 1H) 4.07 (t, J=8.34 Hz, 1H) 4.20 (br. s., 1H) 4.37 (t, J=7.83 Hz, 1H) 7.57 (dd, J=7.96, 1.39 Hz, 1H) 7.63 (s, 1H) 7.75 (d, J=8.08 Hz, 1H) 8.06 (s, 1H) 8.17 (dd, J=8.59, 2.27 Hz, 1H) 8.34 (d, J=8.84 Hz, 1H) 8.66 (dd, J=2.27, 0.76 Hz, 1H); ESI-MS m/z [M+H]$^+$ 403.1.

Example 346 4-(5-hydroxy-1-(5-(7-methyl-2,7-diazaspiro[4.4]nonane-2-carbonyl)pyridin-2-yl)-1H-pyrazol-4-yl)-3-methylbenzonitrile

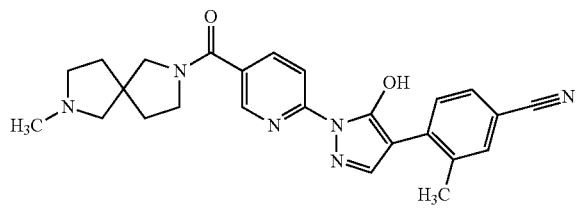 [SMILES: Cc1cc(C#N)ccc1-c1cnn(-c2ccc(C(=O)N3CCC4(CCN(C)C4)C3)cn2)c1O]

The title compound was prepared in a manner similar to Example 74 using 6-(4-(4-cyano-2-methylphenyl)-5-hydroxy-1H-pyrazol-1-yl)nicotinic acid and 2-methyl-2,7-diazaspiro[4.4]nonane to give the title compound as a TFA salt. $^1$H NMR (400 MHz, DMSO-d$_6$) δ ppm 1.81-1.98 (m, 1H) 2.07 (d, J=7.83 Hz, 3H) 2.43 (s, 3H) 2.77-2.86 (m, 2H) 2.89 (br. s., 1H) 2.97-3.14 (m, 1H) 3.14-3.29 (m, 1H) 3.49 (d, J=11.62 Hz, 1H) 3.60 (d, J=7.83 Hz, 4H) 3.67 (d, J=8.34 Hz, 1H) 7.67 (d, J=7.83 Hz, 1H) 7.74 (s, 1H) 7.78 (br. s., 1H) 8.04-8.28 (m, 2H) 8.43 (br. s., 1H) 8.67 (d, J=8.34 Hz, 1H) 9.73-10.22 (m, 1H); ESI-MS m/z [M+H]$^+$ 443.2.

Example 347 4-(5-hydroxy-1-(5-(3-morpholinopyrrolidine-1-carbonyl)pyridin-2-yl)-1H-pyrazol-4-yl)-3-methylbenzonitrile

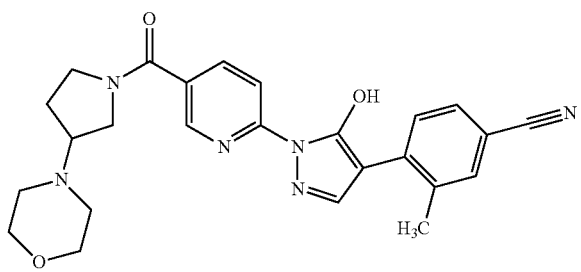 [SMILES: Cc1cc(C#N)ccc1-c1cnn(-c2ccc(C(=O)N3CCC(N4CCOCC4)C3)cn2)c1O]

The title compound was prepared in a manner similar to Example 112 using 6-(4-(4-cyano-2-methylphenyl)-5-hydroxy-1H-pyrazol-1-yl)nicotinic acid and 4-(pyrrolidin-3-yl)morpholine to give the title compound. $^1$H NMR (400 MHz, DMSO-d$_6$) δ ppm 1.68-1.84 (m, 1H) 2.04-2.20 (m, 1H) 2.29-2.39 (m, 1H) 2.39-2.48 (m, 5H) 2.77-2.97 (m, 1H) 3.24-3.35 (m, 1H) 3.37-3.84 (m, 8H) 7.65 (dd, J=8.08, 1.52 Hz, 1H) 7.72 (s, 1H) 7.78 (d, J=7.83 Hz, 1H) 8.13 (s, 1H) 8.19 (td, J=5.49, 2.40 Hz, 1H) 8.36 (br. s., 1H) 8.65 (s, 1H) 13.03 (br. s., 1H); ESI-MS m/z [M+H]$^+$ 459.2.

Example 348 (S)-4-(5-hydroxy-1-(5-(2-(pyrrolidin-1-ylmethyl)pyrrolidine-1-carbonyl)pyridin-2-yl)-1H-pyrazol-4-yl)-3-methylbenzonitrile

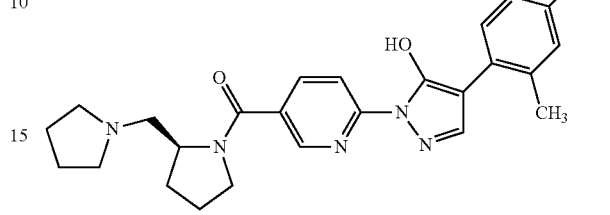

The title compound was prepared in a manner similar to Example 74 using 6-(4-(4-cyano-2-methylphenyl)-5-hydroxy-1H-pyrazol-1-yl)nicotinic acid and (S)-1-(pyrrolidin-2-ylmethyl)pyrrolidine to give the title compound as a TFA salt. $^1$H NMR (400 MHz, DMSO-d$_6$) δ ppm 1.71-1.88 (m, 2H) 1.88-1.99 (m, 3H) 1.99-2.10 (m, 3H) 2.11-2.22 (m, 1H) 2.44 (s, 3H) 3.12 (br. s., 1H) 3.21 (br. s., 1H) 3.26-3.36 (m, 1H) 3.45-3.56 (m, 2H) 3.59-3.75 (m, 2H) 3.83 (br. s., 1H) 4.44-4.63 (m, 1H) 7.66 (dd, J=8.08, 1.52 Hz, 1H) 7.73 (s, 1H) 7.77 (d, J=7.83 Hz, 1H) 8.18 (d, J=5.81 Hz, 1H) 8.19-8.27 (m, 1H) 8.42 (br. s., 1H) 8.63-8.75 (m, 1H) 9.46 (br. s., 1H); ESI-MS m/z [M+H]$^+$ 457.2.

Example 349 4-(1-(5-(3-((dimethylamino)methyl)pyrrolidine-1-carbonyl)pyridin-2-yl)-5-hydroxy-1H-pyrazol-4-yl)-3-methylbenzonitrile

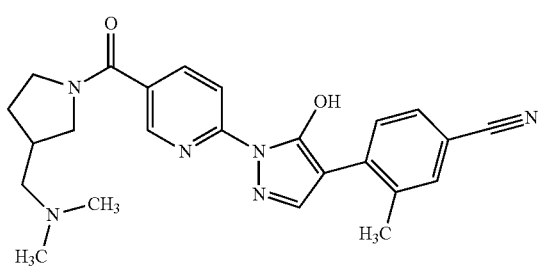 [SMILES: Cc1cc(C#N)ccc1-c1cnn(-c2ccc(C(=O)N3CCC(CN(C)C)C3)cn2)c1O]

The title compound was prepared in a manner similar to Example 74 using 6-(4-(4-cyano-2-methylphenyl)-5-hydroxy-1H-pyrazol-1-yl)nicotinic acid and N,N-dimethyl-1-(pyrrolidin-3-yl)methanamine to give the title compound as a TFA salt. $^1$H NMR (400 MHz, DMSO-d$_6$) δ ppm 1.63-1.76 (m, 1H) 2.05-2.20 (m, 1H) 2.43 (s, 3H) 2.57-2.73 (m, 1H) 2.77 (s, 3H) 2.85 (s, 3H) 3.08-3.21 (m, 1H) 3.21-3.37 (m, 2H) 3.47-3.69 (m, 2H) 3.69-3.86 (m, 1H) 7.67 (d, J=7.83 Hz, 1H) 7.74 (s, 1H) 7.77 (br. s., 1H) 8.19 (d, J=5.31 Hz, 2H) 8.43 (br. s., 1H) 8.66 (s, 1H) 9.35-9.67 (m, 1H); ESI-MS m/z [M+H]$^+$ 431.2.

Example 350 4-(5-hydroxy-1-(5-(7-methyl-2,7-diazaspiro[4.4]nonane-2-carbonyl)pyridin-2-yl)-1H-pyrazol-4-yl)benzonitrile

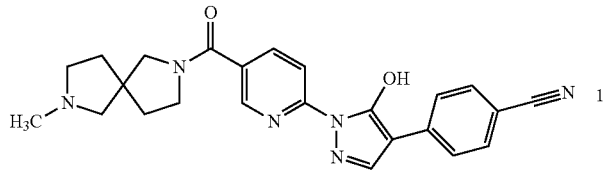

The title compound was prepared in a manner similar to Example 74 using 6-(4-(4-cyanophenyl)-5-hydroxy-1H-pyrazol-1-yl)nicotinic acid and 2-methyl-2,7-diazaspiro[4.4]nonane to give a TFA salt. $^1$H NMR (400 MHz, DMSO-d$_6$) δ ppm 1.81-2.01 (m, 2H) 2.07 (d, J=8.08 Hz, 2H) 2.81 (br. s., 2H) 2.89 (br. s., 1H) 2.98-3.14 (m, 1H) 3.18 (dd, J=13.01, 7.45 Hz, 1H) 3.44-3.76 (m, 6H) 7.80 (d, J=8.34 Hz, 2H) 8.06-8.28 (m, 3H) 8.54 (d, J=17.68 Hz, 1H) 8.67 (d, J=7.07 Hz, 2H); ESI-MS m/z [M+H]$^+$ 429.2.

Example 351 4-(5-hydroxy-1-(5-(3-morpholinopyrrolidine-1-carbonyl)pyridin-2-yl)-1H-pyrazol-4-yl)benzonitrile

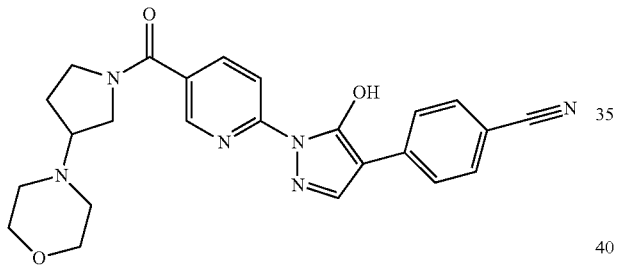

The title compound was prepared in a manner similar to Example 74 using 6-(4-(4-cyanophenyl)-5-hydroxy-1H-pyrazol-1-yl)nicotinic acid and 4-(pyrrolidin-3-yl)morpholine to give a TFA salt. $^1$H NMR (400 MHz, DMSO-d$_6$) δ ppm 2.09-2.22 (m, 1H) 2.28-2.44 (m, 1H) 3.32 (br. s., 4H) 3.49-3.70 (m, 2H) 3.75 (d, J=4.29 Hz, 3H) 3.87 (br. s., 2H) 3.97 (br. s., 2H) 7.80 (d, J=8.59 Hz, 2H) 8.15 (d, J=6.82 Hz, 2H) 8.21 (br. s., 1H) 8.37-8.58 (m, 1H) 8.67 (br. s., 2H); ESI-MS m/z [M+H]$^+$ 445.2.

Example 352 (S)-4-(5-hydroxy-1-(5-(2-(pyrrolidin-1-ylmethyl)pyrrolidine-1-carbonyl)pyridin-2-yl)-1H-pyrazol-4-yl)benzonitrile

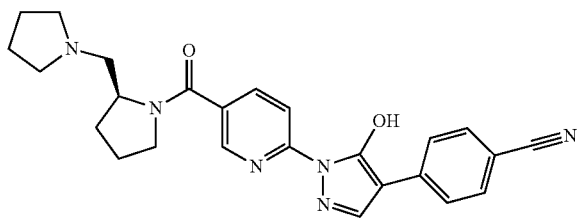 [SMILES: N#Cc1ccc(-c2cnn(-c3ccc(C(=O)N4CCC[C@H]4CN4CCCC4)cn3)c2O)cc1]

The title compound was prepared in a manner similar to Example 74 using (S)-1-(pyrrolidin-2-ylmethyl)pyrrolidine to give a TFA salt. $^1$H NMR (400 MHz, DMSO-d$_6$) δ ppm 1.71-1.87 (m, 2H) 1.87-1.99 (m, 3H) 1.99-2.11 (m, 2H) 2.11-2.23 (m, 1H) 3.03-3.17 (m, 1H) 3.21 (br. s., 1H) 3.26-3.36 (m, 1H) 3.44-3.57 (m, 2H) 3.65 (dt, J=10.04, 6.98 Hz, 2H) 3.82 (br. s., 1H) 4.48-4.61 (m, 1H) 7.80 (d, J=8.34 Hz, 2H) 8.06-8.20 (m, 2H) 8.20-8.31 (m, 1H) 8.40-8.59 (m, 1H) 8.59-8.79 (m, 2H) 9.33 (br. s., 1H); ESI-MS m/z [M+H]$^+$ 443.2.

Example 353 4-(1-(5-(3-((dimethylamino)methyl)pyrrolidine-1-carbonyl)pyridin-2-yl)-5-hydroxy-1H-pyrazol-4-yl)benzonitrile

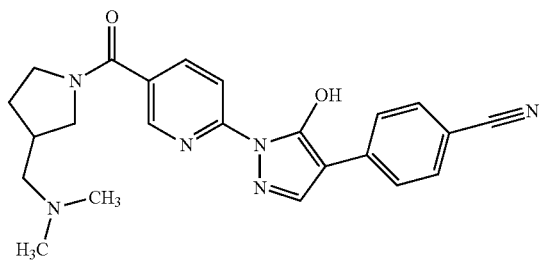 [SMILES: CN(C)CC1CCN(C(=O)c2ccc(-n3ncc(-c4ccc(C#N)cc4)c3O)nc2)C1]

The title compound was prepared in a manner similar to Example 74 using N,N-dimethyl-1-(pyrrolidin-3-yl)methanamine to give a TFA salt. $^1$H NMR (400 MHz, DMSO-d$_6$) δ ppm 1.62-1.77 (m, 1H) 2.05-2.19 (m, 1H) 2.58-2.73 (m, 1H) 2.77 (s, 3H) 2.85 (s, 3H) 3.11-3.21 (m, 1H) 3.25 (d, J=6.82 Hz, 1H) 3.27-3.37 (m, 1H) 3.46-3.69 (m, 2H) 3.69-3.86 (m, 1H) 7.80 (d, J=8.59 Hz, 2H) 8.06-8.26 (m, 3H) 8.36-8.61 (m, 1H) 8.61-8.79 (m, 2H) 9.37-9.67 (m, 1H) 13.49 (br. s., 1H); ESI-MS m/z [M+H]$^+$ 417.2.

Example 354 6-(4-(4-cyanophenyl)-5-hydroxy-1H-pyrazol-1-yl)-N-(1-(2-methoxyethyl)cyclopentyl)nicotinamide

The title compound was prepared in a manner similar to Example 112 using 1-(2-methoxyethyl)cyclopentanamine. $^1$H NMR (400 MHz, DMSO-d$_6$) δ ppm 1.55-1.75 (m, 6H) 2.07-2.16 (m, 2H) 2.16-2.27 (m, 2H) 3.16-3.22 (m, 3H) 3.38 (t, J=6.95 Hz, 2H) 7.79 (d, J=8.59 Hz, 2H) 7.99 (s, 1H) 8.13 (d, J=7.07 Hz, 2H) 8.37 (d, J=6.57 Hz, 2H) 8.62 (br. s., 1H) 8.79-8.88 (m, 1H) 13.50 (br. s., 1H); ESI-MS m/z [M+H]$^+$ 432.2.

Example 355 6-(4-(4-cyano-2-methylphenyl)-5-hydroxy-1H-pyrazol-1-yl)-N-((1-ethylpyrrolidin-2-yl)methyl)-N-methylnicotinamide

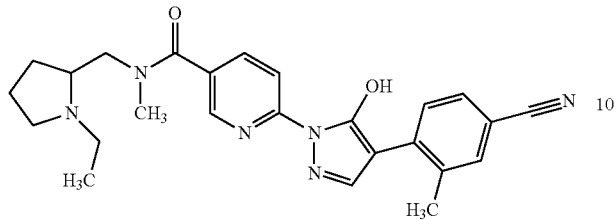

The title compound was prepared in a manner similar to Example 112 using 6-(4-(4-cyano-2-methylphenyl)-5-hydroxy-1H-pyrazol-1-yl)nicotinic acid and 1-(1-ethylpyrrolidin-2-yl)-N-methylmethanamine. $^1$H NMR (400 MHz, DMSO-$d_6$) δ ppm 0.92-1.36 (m, 3H) 1.60-1.96 (m, 2H) 2.11 (br. s., 1H) 2.43 (s, 3H) 2.60-2.95 (m, 2H) 3.06 (br. s., 3H) 3.12-3.58 (m, 5H) 3.58-3.84 (m, 1H) 7.54 (d, J=8.08 Hz, 1H) 7.59 (s, 1H) 7.93 (s, 1H) 7.98 (dd, J=8.72, 2.15 Hz, 1H) 8.07 (br. s., 1H) 8.48 (d, J=8.08 Hz, 1H) 8.50-8.54 (m, 1H); ESI-MS m/z [M+H]$^+$ 445.2.

Example 356 6-(4-(4-cyano-2-methylphenyl)-5-hydroxy-1H-pyrazol-1-yl)-N-(1-cyclopropylpiperidin-4-yl)nicotinamide

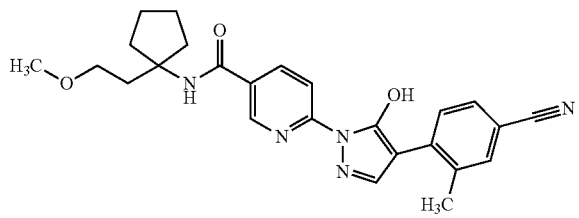 [SMILES: COCCC1(NC(=O)c2ccc(-n3ncc(-c4ccc(C#N)cc4C)c3O)nc2)CCCC1]

The title compound was prepared in a manner similar to Example 112 using 6-(4-(4-cyano-2-methylphenyl)-5-hydroxy-1H-pyrazol-1-yl)nicotinic acid and 1-(2-methoxyethyl)cyclopentanamine. $^1$H NMR (400 MHz, DMSO-$d_6$) δ ppm 1.54-1.75 (m, 6H) 2.12 (t, J=6.95 Hz, 2H) 2.15-2.25 (m, 2H) 2.43 (s, 3H) 3.19 (s, 3H) 3.38 (t, J=6.95 Hz, 2H) 7.66 (dd, J=7.96, 1.39 Hz, 1H) 7.73 (s, 1H) 7.76 (br. s., 1H) 8.00 (s, 1H) 8.14 (br. s., 1H) 8.37 (d, J=6.57 Hz, 2H) 8.81-8.88 (m, 1H) 13.14 (br. s., 1H); ESI-MS m/z [M+H]$^+$ 446.3

Example 357 (R)-6-(4-(4-cyanophenyl)-5-hydroxy-1H-pyrazol-1-yl)-N-(4-methoxybutan-2-yl)nicotinamide

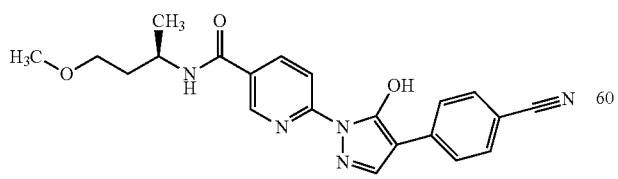

The title compound was prepared in a manner similar to Example 112 using (R)-4-methoxybutan-2-amine to give the title compound. $^1$H NMR (400 MHz, DMSO-$d_6$) δ ppm 1.11 (d, J=6.82 Hz, 3H) 1.59-1.70 (m, 1H) 1.70-1.81 (m, 1H) 3.16 (s, 3H) 3.31 (t, J=6.57 Hz, 2H) 3.99-4.11 (m, 1H) 7.72 (d, J=8.59 Hz, 2H) 8.07 (d, J=6.82 Hz, 2H) 8.35 (d, J=8.08 Hz, 3H) 8.56 (br. s., 1H) 8.74-8.93 (m, 1H) 13.42 (br. s., 1H); ESI-MS m/z [M+H]$^+$ 392.2.

Example 358 (S)-6-(4-(4-cyanophenyl)-5-hydroxy-1H-pyrazol-1-yl)-N-(4-methoxybutan-2-yl)nicotinamide

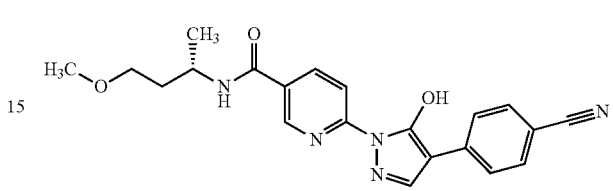

The title compound was prepared in a manner similar to Example 112 using (S)-4-methoxybutan-2-amine. $^1$H NMR (400 MHz, DMSO-$d_6$) δ ppm 1.19 (d, J=6.82 Hz, 3H) 1.68-1.77 (m, 1H) 1.77-1.87 (m, 1H) 3.23 (s, 3H) 3.39 (t, J=6.57 Hz, 2H) 4.08-4.18 (m, 1H) 7.79 (d, J=8.59 Hz, 2H) 8.14 (d, J=6.57 Hz, 2H) 8.42 (d, J=7.83 Hz, 3H) 8.64 (br. s., 1H) 8.87-8.93 (m, 1H); ESI-MS m/z [M+H]$^+$ 392.2.

Example 359 (R)-6-(4-(4-cyano-2-methylphenyl)-5-hydroxy-1H-pyrazol-1-yl)-N-(4-methoxybutan-2-yl)nicotinamide

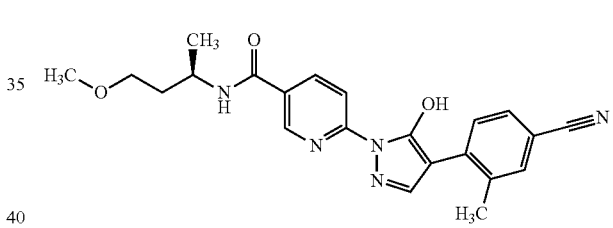

The title compound was prepared in a manner similar to Example 112 using 6-(4-(4-cyano-2-methylphenyl)-5-hydroxy-1H-pyrazol-1-yl)nicotinic acid and (R)-4-methoxybutan-2-amine. $^1$H NMR (400 MHz, DMSO-$d_6$) δ ppm 1.19 (d, J=6.82 Hz, 3H) 1.67-1.77 (m, 1H) 1.77-1.89 (m, 1H) 2.44 (s, 3H) 3.39 (t, J=6.57 Hz, 2H) 4.05-4.20 (m, 1H) 7.67 (d, J=8.08 Hz, 1H) 7.74 (s, 1H) 7.78 (br. s., 1H) 8.17 (br. s., 1H) 8.43 (d, J=7.07 Hz, 3H) 8.87-8.95 (m, 1H) 12.98-13.34 (m, 1H); ESI-MS m/z [M+H]$^+$ 406.2.

Example 360 (S)-6-(4-(4-cyano-2-methylphenyl)-5-hydroxy-1H-pyrazol-1-yl)-N-(4-methoxybutan-2-yl)nicotinamide

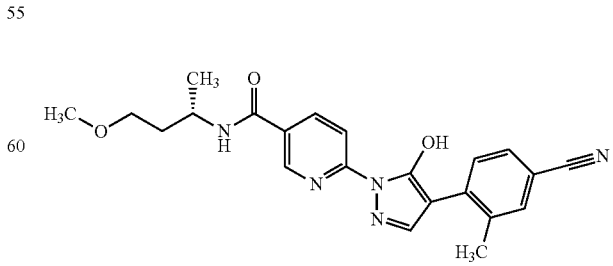

The title compound was prepared in a manner similar to Example 112 using 6-(4-(4-cyano-2-methylphenyl)-5-hydroxy-1H-pyrazol-1-yl)nicotinic acid and (S)-4-methoxybutan-2-amine. ¹H NMR (400 MHz, DMSO-d₆) δ ppm 1.19 (d, J=6.82 Hz, 3H) 1.67-1.77 (m, 1H) 1.77-1.88 (m, 1H) 2.44 (s, 3H) 3.23 (s, 3H) 3.39 (t, J=6.57 Hz, 2H) 4.06-4.20 (m, 1H) 7.67 (d, J=8.08 Hz, 1H) 7.73 (s, 1H) 7.78 (br. s., 1H) 8.17 (br. s., 1H) 8.43 (d, J=7.33 Hz, 3H) 8.89-8.95 (m, 1H) 13.16 (br. s., 1H); ESI-MS m/z [M+H]⁺ 406.2.

Example 361 6-(4-(4-cyano-2-methylphenyl)-5-hydroxy-1H-pyrazol-1-yl)-N-methyl-N-((1-methylpiperidin-3-yl)methyl)nicotinamide

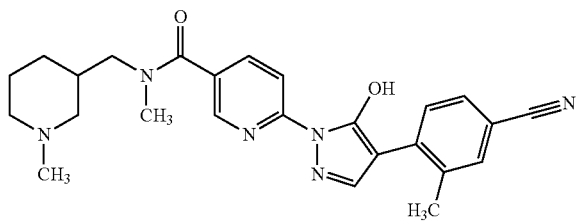 [SMILES: Cc1cc(C#N)ccc1-c1cnn(-c2ccc(C(=O)N(C)CC3CCCN(C)C3)cn2)c1O]

The title compound was prepared in a manner similar to Example 112 using 6-(4-(4-cyano-2-methylphenyl)-5-hydroxy-1H-pyrazol-1-yl)nicotinic acid and N-methyl-1-(1-methylpiperidin-3-yl)methanamine. ¹H NMR (400 MHz, DMSO-d₆) δ ppm 1.09-1.27 (m, 1H) 1.45-1.92 (m, 3H) 2.15 (br. s., 2H) 2.37-2.47 (m, 4H) 2.57-2.75 (m, 3H) 2.96 (s, 4H) 3.28 (dd, J=12.88, 5.81 Hz, 3H) 3.49 (d, J=15.41 Hz, 1H) 7.47 (d, J=8.53 Hz, 1H) 7.52 (s, 1H) 7.84 (s, 1H) 7.89 (br. s., 1H) 8.20 (d, J=8.34 Hz, 1H) 8.49 (br. s., 1H) 8.52 (d, J=8.84 Hz, 1H); ESI-MS m/z [M+H]⁺ 445.2.

Example 362 6-(4-(4-cyano-2-methylphenyl)-5-hydroxy-1H-pyrazol-1-yl)-N-((1-isopropylpyrrolidin-3-yl)methyl)-N-methylnicotinamide

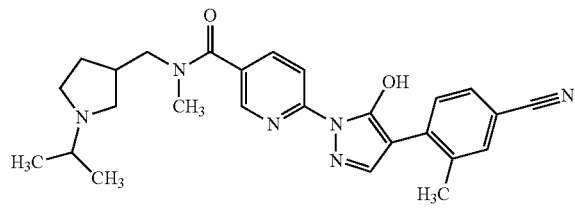 [SMILES: Cc1cc(C#N)ccc1-c1cnn(-c2ccc(C(=O)N(C)CC3CCN(C(C)C)C3)cn2)c1O]

The title compound was prepared in a manner similar to Example 112 using 6-(4-(4-cyano-2-methylphenyl)-5-hydroxy-1H-pyrazol-1-yl)nicotinic acid and 1-(1-isopropylpyrrolidin-3-yl)-N-methylmethanamine. ¹H NMR (400 MHz, DMSO-d₆) δ ppm 1.21 (br. s., 5H) 2.09 (br. s., 1H) 2.42 (s, 3H) 2.60-2.78 (m, 1H) 2.90-3.09 (m, 4H) 3.09-3.44 (m, 5H) 7.44 (d, J=8.49 Hz, 1H) 7.47 (s, 1H) 7.76-7.80 (m, 1H) 7.85 (d, J=7.33 Hz, 1H) 8.30 (d, J=8.34 Hz, 1H) 8.45 (br. s., 1H) 8.55 (d, J=8.59 Hz, 1H); ESI-MS m/z [M+H]⁺ 459.2.

Example 363 6-(4-(4-cyanophenyl)-5-hydroxy-1H-pyrazol-1-yl)-N-((1-ethylpyrrolidin-2-yl)methyl)-N-methylnicotinamide

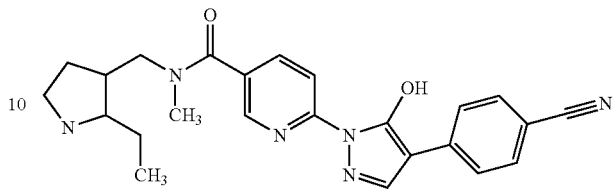

The title compound was prepared in a manner similar to Example 74 using 1-(1-ethylpyrrolidin-2-yl)-N-methylmethanamine to give a TFA salt. ¹H NMR (400 MHz, DMSO-d₆) δ ppm 1.14-1.40 (m, 3H) 1.76-1.91 (m, 1H) 1.99 (d, J=5.56 Hz, 2H) 2.21-2.36 (m, 1H) 3.04 (s, 3H) 3.19 (br. s., 2H) 3.43 (br. s., 1H) 3.64 (br. s., 1H) 3.76 (br. s., 1H) 3.85 (br. s., 2H) 7.79 (d, J=8.59 Hz, 2H) 8.14 (br. s., 3H) 8.33-8.63 (m, 2H) 8.63-8.79 (m, 1H) 9.39 (br. s., 1H); ESI-MS m/z [M+H]⁺ 431.2.

Example 364 (R)-4-(5-hydroxy-1-(5-(2-(pyrrolidin-1-ylmethyl)pyrrolidine-1-carbonyl)pyridin-2-yl)-1H-pyrazol-4-yl)benzonitrile

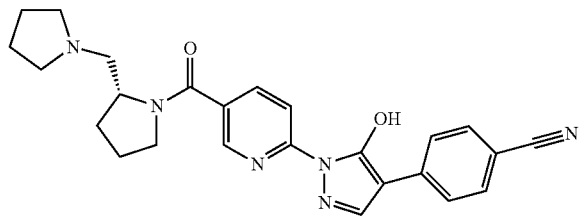 [SMILES: N#Cc1ccc(-c2cnn(-c3ccc(C(=O)N4CCC[C@@H]4CN4CCCC4)cn3)c2O)cc1]

The title compound was prepared in a manner similar to Example 74 using (R)-1-(pyrrolidin-2-ylmethyl)pyrrolidine to give a TFA salt. ¹H NMR (400 MHz, DMSO-d₆) δ ppm 1.68-1.87 (m, 2H) 1.87-1.99 (m, 3H) 2.06 (d, J=10.86 Hz, 2H) 2.11-2.23 (m, 1H) 3.01-3.26 (m, 2H) 3.26-3.37 (m, 1H) 3.44-3.57 (m, 2H) 3.59-3.73 (m, 2H) 3.82 (br. s., 1H) 4.48-4.62 (m, 1H) 7.79 (d, J=8.59 Hz, 2H) 8.15 (d, J=7.33 Hz, 2H) 8.22 (dd, J=8.59, 2.02 Hz, 1H) 8.49 (br. s., 1H) 8.68 (d, J=1.52 Hz, 2H) 9.43 (br. s., 1H); ESI-MS m/z [M+H]⁺ 443.3.

Example 365 (R)-4-(5-hydroxy-1-(5-(2-(pyrrolidin-1-ylmethyl)pyrrolidine-1-carbonyl)pyridin-2-yl)-1H-pyrazol-4-yl)-3-methylbenzonitrile

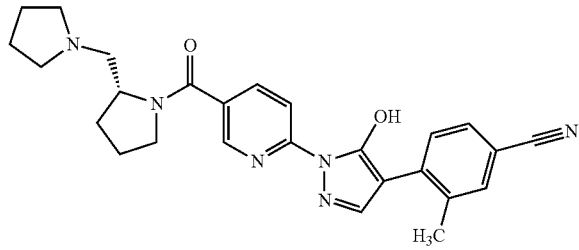 [SMILES: Cc1cc(C#N)ccc1-c1cnn(-c2ccc(C(=O)N3CCC[C@@H]3CN3CCCC3)cn2)c1O]

The title compound was prepared in a manner similar to Example 74 using 6-(4-(4-cyano-2-methylphenyl)-5-hydroxy-1H-pyrazol-1-yl)nicotinic acid and (R)-1-(pyrrolidin-2-ylmethyl)pyrrolidine to give a TFA salt. ¹H NMR (400 MHz, DMSO-d₆) δ ppm 1.69-1.87 (m, 2H) 1.87-1.99 (m, 3H) 2.06 (d, J=10.61 Hz, 2H) 2.11-2.24 (m, 1H) 2.44 (s, 3H) 3.12 (br. s., 1H) 3.21 (br. s., 1H) 3.26-3.37 (m, 1H) 3.44-3.57 (m, 2H) 3.60-3.73 (m, 2H) 3.83 (br. s., 1H) 4.47-4.61 (m, 1H) 7.62-7.70 (m, 1H) 7.74 (s, 1H) 7.76 (br. s., 1H) 8.18 (br. s., 1H) 8.22 (dd, J=8.59, 1.52 Hz, 1H) 8.45 (br. s., 1H) 8.64-8.73 (m, 1H) 9.37 (br. s., 1H); ESI-MS m/z [M+H]⁺ 457.3.

Example 366 6-(4-(4-cyanophenyl)-5-hydroxy-1H-pyrazol-1-yl)-N-((1-ethylpyrrolidin-3-yl)methyl)-N-methylnicotinamide

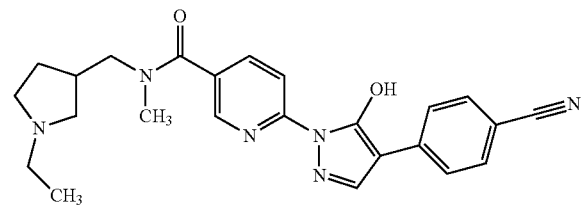 [SMILES: CCN1CCC(CN(C)C(=O)c2ccc(-n3ncc(-c4ccc(C#N)cc4)c3O)nc2)C1]

The title compound was prepared in a manner similar to Example 74 using 1-(1-ethylpyrrolidin-3-yl)-N-methylmethanamine. ¹H NMR (400 MHz, DMSO-d₆) δ ppm 1.23 (br. s., 3H) 1.61-1.94 (m, 1H) 2.02-2.32 (m, 1H) 2.64-2.96 (m, 2H) 3.02 (s, 4H) 3.19 (br. s., 3H) 3.33-3.86 (m, 5H) 7.80 (d, J=8.34 Hz, 2H) 8.14 (br. s., 3H) 8.35-8.76 (m, 3H) 9.72 (br. s., 1H); ESI-MS m/z [M+H]⁺ 445.3.

Example 367 6-(4-(4-cyanophenyl)-5-hydroxy-1H-pyrazol-1-yl)-N-methyl-N-((1-methylpiperidin-2-yl)methyl)nicotinamide

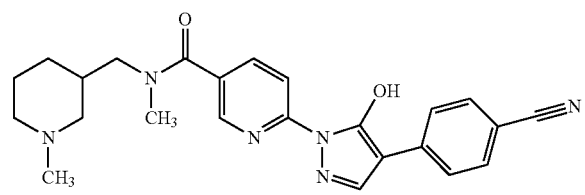 [SMILES: CN1CCCC(CN(C)C(=O)c2ccc(-n3ncc(-c4ccc(C#N)cc4)c3O)nc2)C1]

The title compound was prepared in a manner similar to Example 112 using N-methyl-1-(1-methylpiperidin-2-yl)methanamine to give a hydrochloride salt. ¹H NMR (400 MHz, DMSO-d₆) δ ppm 1.42 (d, J=12.38 Hz, 1H) 1.55-2.02 (m, 4H) 2.67-2.87 (m, 2H) 3.00 (s, 3H) 3.06-3.20 (m, 1H) 3.36 (br. s., 1H) 3.46-4.14 (m, 5H) 7.72 (d, J=8.34 Hz, 2H) 8.08 (br. s., 3H) 8.58 (br. s., 3H) 10.42-11.10 (m, 1H); ESI-MS m/z [M+H]⁺ 431.3.

Example 368 6-(4-(4-cyano-2-methylphenyl)-5-hydroxy-1H-pyrazol-1-yl)-N-methyl-N-(1-methylpyrrolidin-3-yl)nicotinamide

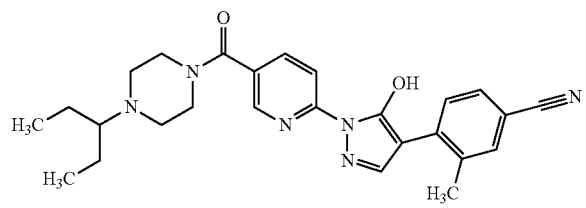 [SMILES: CCC(CC)N1CCN(C(=O)c2ccc(-n3ncc(-c4ccc(C#N)cc4C)c3O)nc2)CC1]

The title compound was prepared in a manner similar to Example 74 using 6-(4-(4-cyano-2-methylphenyl)-5-hydroxy-1H-pyrazol-1-yl)nicotinic acid and N,1-dimethylpyrrolidin-3-amine to give a TFA salt. ¹H NMR (400 MHz, DMSO-d₆) δ ppm 2.09-2.32 (m, 2H) 2.43 (s, 3H) 2.76-2.94 (m, 3H) 2.98 (s, 3H) 3.13-3.45 (m, 2H) 3.72 (br. s., 2H) 4.94 (br. s., 1H) 7.61-7.84 (m, 3H) 8.01-8.26 (m, 2H) 8.42 (br. s., 1H) 8.58 (br. s., 1H); ESI-MS m/z [M+H]⁺ 417.2.

Example 369 4-(5-hydroxy-1-(5-(4-(pentan-3-yl)piperazine-1-carbonyl)pyridin-2-yl)-1H-pyrazol-4-yl)-3-methylbenzonitrile

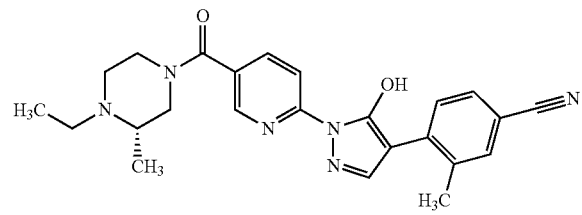 [SMILES: CCN1CCN(C(=O)c2ccc(-n3ncc(-c4ccc(C#N)cc4C)c3O)nc2)C[C@@H]1C]

The title compound was prepared in a manner similar to Example 112 using 6-(4-(4-cyano-2-methylphenyl)-5-hydroxy-1H-pyrazol-1-yl)nicotinic acid and 1-(pentan-3-yl)piperazine. ¹H NMR (400 MHz, DMSO-d₆) δ ppm 0.88 (t, J=7.33 Hz, 6H) 1.29 (dt, J=14.08, 6.98 Hz, 2H) 1.47 (dt, J=14.08, 6.98 Hz, 2H) 2.26 (t, J=6.57 Hz, 1H) 2.43 (s, 3H) 2.56 (br. s., 4H) 3.37-3.48 (m, 2H) 3.62 (br. s., 2H) 7.64 (dd, J=8.08, 1.52 Hz, 1H) 7.71 (s, 1H) 7.82 (d, J=8.08 Hz, 1H) 8.05 (dd, J=8.59, 2.27 Hz, 1H) 8.12 (s, 1H) 8.39 (d, J=8.59 Hz, 1H) 8.53 (d, J=2.27 Hz, 1H) 12.82 (br. s., 1H); ESI-MS m/z [M+H]⁺ 459.3.

Example 370 (S)-4-(1-(5-(4-ethyl-3-methylpiperazine-1-carbonyl)pyridin-2-yl)-5-hydroxy-1H-pyrazol-4-yl)-3-methylbenzonitrile The title compound was prepared in a manner similar to Example 112 using 6-(4-(4-cyano-2-methylphenyl)-5-hydroxy-1H-pyrazol-1-yl)nicotinic acid and (S)-1-ethyl-2-methylpiperazine. ¹H NMR (400 MHz, DMSO-d₆) δ ppm 0.87-1.19 (m, 6H) 2.42 (s, 3H) 2.47 (br. s., 1H) 2.52-2.59 (m, 1H) 2.62-2.76 (m, 1H) 2.77-2.98 (m, 2H) 3.06 (d, J=10.61 Hz, 1H) 3.35 (br. s., 1H) 3.46-3.75 (m, 1H) 4.05 (br. s., 1H) 7.60 (dd, J=7.96, 1.64 Hz, 1H) 7.66 (d, J=1.26 Hz, 1H) 7.90 (d, J=8.34 Hz, 1H) 8.01 (dd, J=8.72, 2.15 Hz, 1H) 8.06 (s, 1H) 8.43 (d, J=8.59 Hz, 1H) 8.51 (d, J=1.77 Hz, 1H) 11.83-12.92 (m, 1H); ESI-MS m/z [M+H]⁺ 431.3.

Example 371 (R)-6-(4-(4-cyano-2-methylphenyl)-5-hydroxy-1H-pyrazol-1-yl)-N-(3-methoxybutyl)nicotinamide

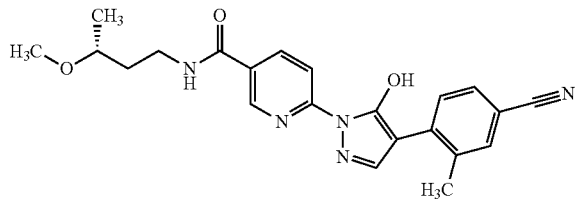 [SMILES: CO[C@H](C)CCNC(=O)c1ccc(-n2ncc(-c3ccc(C#N)cc3C)c2O)nc1]

The title compound was prepared in a manner similar to Example 112 using 6-(4-(4-cyano-2-methylphenyl)-5-hydroxy-1H-pyrazol-1-yl)nicotinic acid and (R)-3-methoxybutan-1-amine hydrochloride. ¹H NMR (400 MHz, DMSO-d₆) δ ppm 1.11 (d, J=6.32 Hz, 3H) 1.58-1.79 (m, 2H) 2.43 (s, 3H) 3.24 (s, 3H) 3.30-3.42 (m, 3H) 7.66 (dd, J=7.83, 1.26 Hz, 1H) 7.73 (s, 1H) 7.77 (br. s., 1H) 8.18 (br. s., 1H) 8.29-8.59 (m, 2H) 8.68 (t, J=5.31 Hz, 1H) 8.87-8.94 (m, 1H) 13.17 (br. s., 1H); ESI-MS m/z [M+H]⁺ 406.2.

Example 372 (S)-4-(1-(5-(3,4-dimethylpiperazine-1-carbonyl)pyridin-2-yl)-5-hydroxy-1H-pyrazol-4-yl)-3-methylbenzonitrile

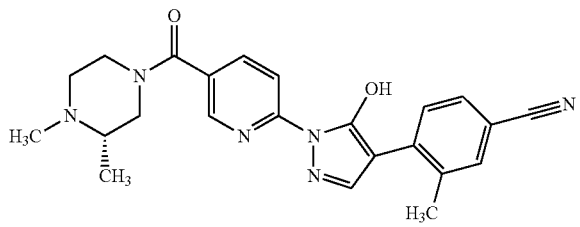 [SMILES: Cc1cc(C#N)ccc1-c1cnn(-c2ccc(C(=O)N3CCN(C)[C@@H](C)C3)cn2)c1O]

The title compound was prepared in a manner similar to Example 112 using 6-(4-(4-cyano-2-methylphenyl)-5-hydroxy-1H-pyrazol-1-yl)nicotinic acid and (S)-1,2-dimethylpiperazine dihydrochloride. ¹H NMR (400 MHz, DMSO-d₆) δ ppm 1.16 (br. s., 3H) 2.36 (s, 3H) 2.60 (s, 3H) 2.90 (br. s., 1H) 3.04 (br. s., 1H) 3.26 (br. s., 2H) 3.41-3.57 (m, 1H) 3.73 (d, J=17.68 Hz, 1H) 4.29 (br. s., 1H) 7.59 (dd, J=8.08, 1.52 Hz, 1H) 7.66 (s, 1H) 7.72 (d, J=8.08 Hz, 1H) 8.03 (dd, J=8.59, 2.02 Hz, 1H) 8.10 (s, 1H) 8.35 (d, J=7.83 Hz, 1H) 8.51 (d, J=1.52 Hz, 1H) 12.09 (br. s., 1H); ESI-MS m/z [M+H]⁺ 417.3.

Example 373 4-(1-(5-(4-cyclobutylpiperazine-1-carbonyl)pyridin-2-yl)-5-hydroxy-1H-pyrazol-4-yl)-3-methylbenzonitrile

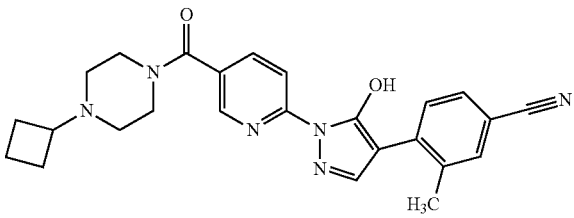 [SMILES: Cc1cc(C#N)ccc1-c1cnn(-c2ccc(C(=O)N3CCN(C4CCC4)CC3)cn2)c1O]

The title compound was prepared in a manner similar to Example 112 using 6-(4-(4-cyano-2-methylphenyl)-5-hydroxy-1H-pyrazol-1-yl)nicotinic acid and 1-cyclobutylpiperazine. ¹H NMR (400 MHz, DMSO-d₆) δ ppm 1.58-1.71 (m, 2H) 1.76-1.90 (m, 2H) 1.90-2.07 (m, 2H) 2.37 (br. s., 4H) 2.42 (s, 3H) 2.83 (quin, J=7.71 Hz, 1H) 3.44 (d, J=7.07 Hz, 2H) 3.64 (br. s., 2H) 7.63 (dd, J=7.96, 1.64 Hz, 1H) 7.69 (s, 1H) 7.84 (d, J=8.08 Hz, 1H) 8.03 (dd, J=8.59, 2.27 Hz, 1H) 8.11 (s, 1H) 8.40 (d, J=8.59 Hz, 1H) 8.52 (dd, J=2.27, 0.76 Hz, 1H); ESI-MS m/z [M+H]⁺ 443.3.

Example 374 (S)-4-(5-hydroxy-1-(5-(3-methyl-4-propylpiperazine-1-carbonyl)pyridin-2-yl)-1H-pyrazol-4-yl)-3-methylbenzonitrile

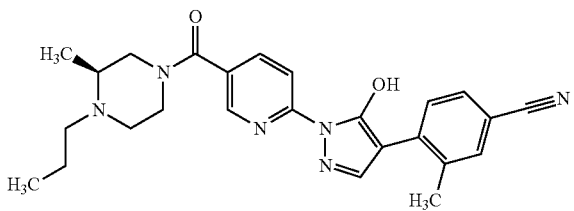 [SMILES: CCCN1CCN(C(=O)c2ccc(-n3ncc(-c4ccc(C#N)cc4C)c3O)nc2)C[C@@H]1C]

The title compound was prepared in a manner similar to Example 112 using 6-(4-(4-cyano-2-methylphenyl)-5-hydroxy-1H-pyrazol-1-yl)nicotinic acid and (S)-2-methyl-1-propylpiperazine dihydrochloride. ¹H NMR (500 MHz, DMSO-d₆) δ ppm 0.86 (t, J=7.32 Hz, 3H) 0.90-1.15 (m, 3H) 1.35-1.56 (m, 2H) 2.31-2.41 (m, 2H) 2.43 (s, 3H) 2.58-2.73 (m, 2H) 2.81-3.01 (m, 1H) 3.02-3.17 (m, 2H) 3.44-3.65 (m, 1H) 4.02 (br. s., 1H) 7.62 (dd, J=8.05, 1.71 Hz, 1H) 7.69 (d, J=0.98 Hz, 1H) 7.86 (d, J=7.81 Hz, 1H) 8.03 (dd, J=8.54, 2.20 Hz, 1H) 8.08 (s, 1H) 8.41 (d, J=8.30 Hz, 1H) 8.52 (d, J=1.95 Hz, 1H); ESI-MS m/z [M+H]⁺ 445.3.

Example 375 (R)-4-(1-(5-(4-cyclopropyl-3-methylpiperazine-1-carbonyl)pyridin-2-yl)-5-hydroxy-1H-pyrazol-4-yl)-3-methylbenzonitrile

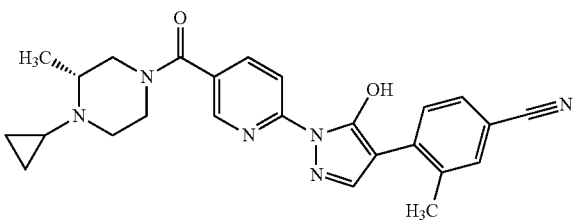 [SMILES: Cc1cc(C#N)ccc1-c1cnn(-c2ccc(C(=O)N3CCN(C4CC4)[C@H](C)C3)cn2)c1O]

The title compound was prepared in a manner similar to Example 112 using 6-(4-(4-cyano-2-methylphenyl)-5-hydroxy-1H-pyrazol-1-yl)nicotinic acid and (R)-1-cyclopropyl-2-methylpiperazine dihydrochloride. ¹H NMR (400 MHz, DMSO-d₆) δ ppm 0.26 (br. s., 1H) 0.36-0.51 (m, 2H) 0.61 (d, J=5.56 Hz, 1H) 0.93-1.29 (m, 3H) 1.65 (br. s., 1H) 2.16-2.40 (m, 1H) 2.43 (s, 3H) 2.58 (br. s., 1H) 2.75-3.03 (m, 2H) 3.15 (br. s., 1H) 3.43-3.59 (m, 1H) 4.09 (br. s., 1H) 7.66 (d, J=8.32 Hz, 1H) 7.73 (s, 1H) 7.78 (d, J=8.08 Hz, 1H) 8.06 (dd, J=8.59, 2.02 Hz, 1H) 8.15 (s, 1H) 8.38 (br. s., 1H) 8.53 (d, J=1.77 Hz, 1H); ESI-MS m/z [M+H]⁺ 443.3.

Example 376 (S)-4-(1-(5-(3-(dimethylamino)piperidine-1-carbonyl)pyridin-2-yl)-5-hydroxy-1H-pyrazol-4-yl)-3-methylbenzonitrile

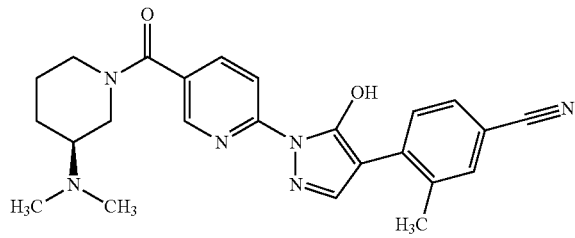 [SMILES: Cc1cc(C#N)ccc1-c1cnn(-c2ccc(C(=O)N3CCC[C@H](N(C)C)C3)cn2)c1O]

The title compound was prepared in a manner similar to Example 112 using 6-(4-(4-cyano-2-methylphenyl)-5-hydroxy-1H-pyrazol-1-yl)nicotinic acid and (S)—N,N-dimethylpiperidin-3-amine dihydrochloride. ¹H NMR (400 MHz, DMSO-d₆) δ ppm 1.53 (d, J=13.39 Hz, 1H) 1.83 (br. s., 2H) 2.06-2.23 (m, 1H) 2.43 (s, 3H) 2.81 (br. s., 7H) 3.04-3.25 (m, 1H) 3.35-3.42 (m, 1H) 3.54 (br. s., 1H) 4.02 (br. s., 1H) 4.44 (br. s., 1H) 7.67 (d, J=8.22 Hz, 1H) 7.74 (s, 1H) 7.78 (d, J=7.83 Hz, 1H) 8.11 (dd, J=8.59, 1.77 Hz, 1H) 8.17 (br. s., 1H) 8.42 (br. s., 1H) 8.58 (d, J=1.52 Hz, 1H); ESI-MS m/z [M+H]⁺ 431.3.

Example 377 4-(5-hydroxy-1-(5-(3,3,4-trimethylpiperazine-1-carbonyl)pyridin-2-yl)-1H-pyrazol-4-yl)-3-methylbenzonitrile

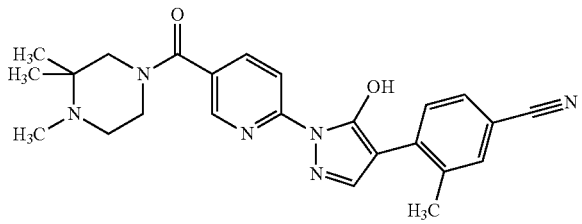 [SMILES: Cc1cc(C#N)ccc1-c1cnn(-c2ccc(C(=O)N3CCN(C)C(C)(C)C3)cn2)c1O]

The title compound was prepared in a manner similar to Example 112 using 6-(4-(4-cyano-2-methylphenyl)-5-hydroxy-1H-pyrazol-1-yl)nicotinic acid and 1,2,2-trimethylpiperazine. ¹H NMR (400 MHz, DMSO-d₆) δ ppm 0.95 (br. s., 6H) 2.20 (s, 3H) 2.35 (s, 3H) 2.60 (t, J=5.05 Hz, 2H) 2.97-3.72 (m, 4H) 7.53 (dd, J=8.08, 1.52 Hz, 1H) 7.59 (d, J=1.01 Hz, 1H) 7.85 (d, J=8.08 Hz, 1H) 7.93 (d, J=7.33 Hz, 1H) 7.98 (s, 1H) 8.36 (d, J=8.59 Hz, 1H) 8.43 (br. s., 1H); ESI-MS m/z [M+H]⁺ 431.3.

Example 378 4-(1-(5-(4-ethyl-3,3-dimethylpiperazine-1-carbonyl)pyridin-2-yl)-5-hydroxy-1H-pyrazol-4-yl)-3-methylbenzonitrile

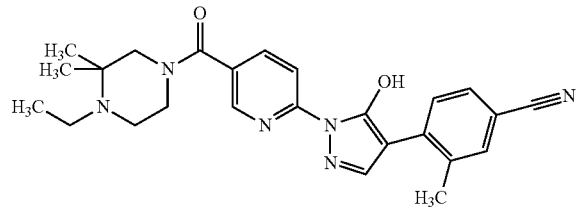 [SMILES: CCN1CCN(C(=O)c2ccc(-n3ncc(-c4ccc(C#N)cc4C)c3O)nc2)CC1(C)C]

The title compound was prepared in a manner similar to Example 112 using 6-(4-(4-cyano-2-methylphenyl)-5-hydroxy-1H-pyrazol-1-yl)nicotinic acid and 1-ethyl,2,2-dimethylpiperazine. ¹H NMR (400 MHz, ACETONITRILE-d₃) δ ppm 0.79-1.20 (m, 9H) 2.36-2.48 (m, 5H) 2.59 (d, J=6.06 Hz, 2H) 3.15 (br. s., 1H) 3.44 (br. s., 2H) 3.69 (br. s., 1H) 7.53-7.59 (m, 1H) 7.60-7.63 (m, 1H) 7.63-7.66 (m, 1H) 7.75 (s, 1H) 8.01 (br. s., 2H) 8.42 (br. s., 1H); ESI-MS m/z [M+H]⁺ 445.3.

Example 379 (R)-4-(5-hydroxy-1-(5-(4-isopropyl-3-methylpiperazine-1-carbonyl)pyridin-2-yl)-1H-pyrazol-4-yl)-3-methylbenzonitrile

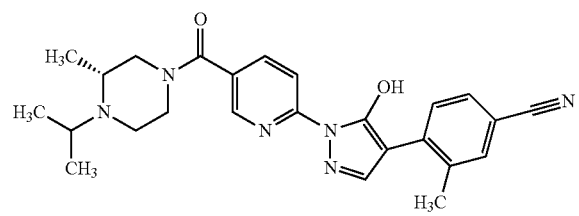 [SMILES: Cc1cc(C#N)ccc1-c1cnn(-c2ccc(C(=O)N3CCN(C(C)C)[C@H](C)C3)cn2)c1O]

The title compound was prepared in a manner similar to Example 112 using 6-(4-(4-cyano-2-methylphenyl)-5-hydroxy-1H-pyrazol-1-yl)nicotinic acid and (R)-1-isopropyl-2-methylpiperazine. ¹H NMR (500 MHz, CHLOROFORM-d) δ ppm 0.93 (br. s., 3H) 1.01 (br. s., 2H) 1.16 (br. s., 5H) 2.43 (s, 1H) 2.47 (s, 3H) 2.61 (d, J=12.20 Hz, 1H) 2.75-2.98 (m, 1H) 3.07 (br. s., 1H) 3.29 (br. s., 2H) 4.39 (br. s., 1H) 7.47-7.62 (m, 3H) 7.68 (s, 1H) 7.95-8.11 (m, 2H) 8.44 (s, 1H); ESI-MS m/z [M+H]⁺ 445.3.

Example 380 4-(1-(5-(3-(diethylamino)piperidine-1-carbonyl)pyridin-2-yl)-5-hydroxy-1H-pyrazol-4-yl)-3-methylbenzonitrile

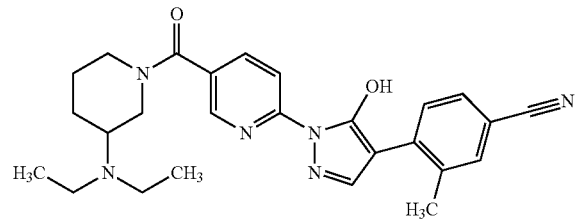 [SMILES: CCN(CC)C1CCCN(C(=O)c2ccc(-n3ncc(-c4ccc(C#N)cc4C)c3O)nc2)C1]

The title compound was prepared in a manner similar to Example 112 using 6-(4-(4-cyano-2-methylphenyl)-5-hydroxy-1H-pyrazol-1-yl)nicotinic acid and N,N-diethylpiperidin-3-amine dihydrochloride. ¹H NMR (500 MHz, CHLOROFORM-d) δ ppm 1.26 (br. s., 6H) 1.57 (br. s., 2H) 1.76-2.17 (m, 2H) 2.36-2.90 (m, 9H) 3.02 (br. s., 1H) 3.70 (br. s., 1H) 4.52-4.92 (m, 1H) 7.48-7.60 (m, 3H) 7.63-7.73 (m, 1H) 7.95-8.10 (m, 2H) 8.43 (s, 1H); ESI-MS m/z [M+H]⁺ 459.3.

Example 381 (S)-4-(5-hydroxy-1-(5-(3-(pyrrolidin-1-yl)piperidine-1-carbonyl)pyridin-2-yl)-1H-pyrazol-4-yl)-3-methylbenzonitrile

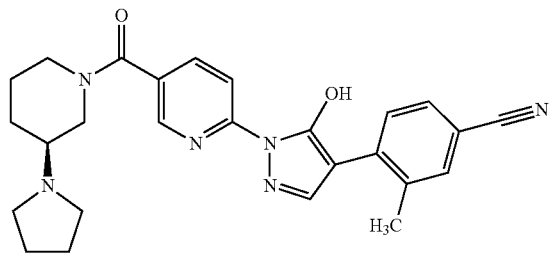 [SMILES: Cc1cc(C#N)ccc1-c1cnn(-c2ccc(C(=O)N3CCC[C@H](N4CCCC4)C3)cn2)c1O]

The title compound was prepared in a manner similar to Example 112 using 6-(4-(4-cyano-2-methylphenyl)-5-hydroxy-1H-pyrazol-1-yl)nicotinic acid and (S)-3-(pyrrolidin-1-yl)piperidine dihydrochloride. ¹H NMR (500 MHz, DMSO-d₆) δ ppm 1.42-1.55 (m, 1H) 1.61 (d, J=9.76 Hz, 1H) 1.77 (br. s., 5H) 2.06 (d, J=8.79 Hz, 1H) 2.42 (s, 3H) 2.77 (br. s., 2H) 2.87-3.09 (m, 2H) 3.12-3.24 (m, 2H) 3.33 (br. s., 1H) 3.47-3.92 (m, 1H) 3.93-4.48 (m, 1H) 7.53 (dd, J=8.30, 1.95 Hz, 1H) 7.58 (s, 1H) 7.90-7.95 (m, 2H) 8.08 (d, J=7.81 Hz, 1H) 8.46-8.51 (m, 2H); ESI-MS m/z [M+H]⁺ 457.3.

Example 382 (R)-4-(1-(5-(3-(ethyl(methyl)amino)piperidine-1-carbonyl)pyridin-2-yl)-5-hydroxy-1H-pyrazol-4-yl)-3-methylbenzonitrile

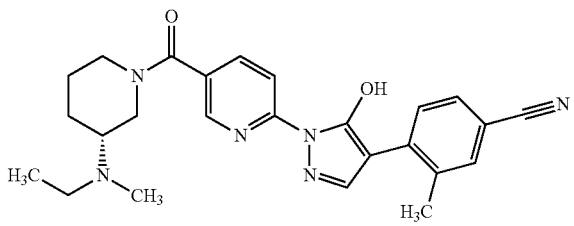 [SMILES: CCN(C)[C@@H]1CCCN(C(=O)c2ccc(-n3ncc(-c4ccc(C#N)cc4C)c3O)nc2)C1]

The title compound was prepared in a manner similar to Example 74 using 6-(4-(4-cyano-2-methylphenyl)-5-hydroxy-1H-pyrazol-1-yl)nicotinic acid and (R)-N-ethyl-N-methylpiperidin-3-amine dihydrochloride to give a TFA salt. ¹H NMR (400 MHz, DMSO-d₆) δ ppm 1.15-1.33 (m, 3H) 1.57 (d, J=12.63 Hz, 1H) 1.77 (d, J=11.62 Hz, 2H) 2.11 (d, J=10.36 Hz, 1H) 2.43 (s, 3H) 2.80 (br. s., 3H) 3.08-3.36 (m, 3H) 3.38-3.52 (m, 2H) 3.52-3.69 (m, 1H) 4.60 (br. s., 1H) 7.67 (d, J=7.83 Hz, 1H) 7.71-7.81 (m, 2H) 8.10 (d, J=7.07 Hz, 2H) 8.40-8.64 (m, 2H) 9.66 (br. s., 1H); ESI-MS m/z [M+H]⁺ 445.3.

Example 383 (R)-4-(1-(5-(3-(cyclopropyl(methyl)amino)piperidine-1-carbonyl)pyridin-2-yl)-5-hydroxy-1H-pyrazol-4-yl)-3-methylbenzonitrile

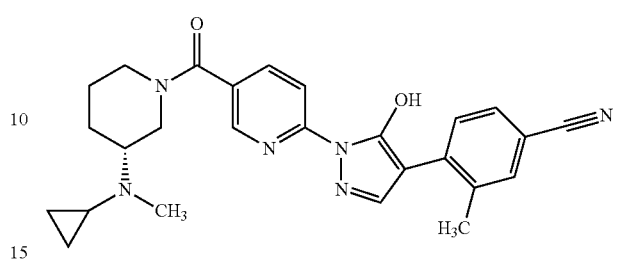

The title compound was prepared in a manner similar to Example 112 using 6-(4-(4-cyano-2-methylphenyl)-5-hydroxy-1H-pyrazol-1-yl)nicotinic acid and (R)—N-cyclopropyl-N-methylpiperidin-3-amine dihydrochloride. ¹H NMR (400 MHz, DMSO-d₆) δ ppm 0.13-0.61 (m, 4H) 1.38-1.64 (m, 2H) 1.64-2.09 (m, 3H) 2.15-2.41 (m, 3H) 2.43 (s, 3H) 2.55-2.86 (m, 2H) 3.04 (br. s., 1H) 3.49-3.87 (m, 1H) 4.33-4.77 (m, 1H) 7.65 (dd, J=8.08, 1.52 Hz, 1H) 7.72 (s, 1H) 7.81 (d, J=8.08 Hz, 1H) 8.05 (dd, J=8.59, 2.02 Hz, 1H) 8.13 (s, 1H) 8.40 (d, J=7.33 Hz, 1H) 8.53 (d, J=1.77 Hz, 1H); ESI-MS m/z [M+H]⁺ 457.3.

Example 384 (S)-4-(1-(5-(3-(ethyl(methyl)amino)piperidine-1-carbonyl)pyridin-2-yl)-5-hydroxy-1H-pyrazol-4-yl)-3-methylbenzonitrile

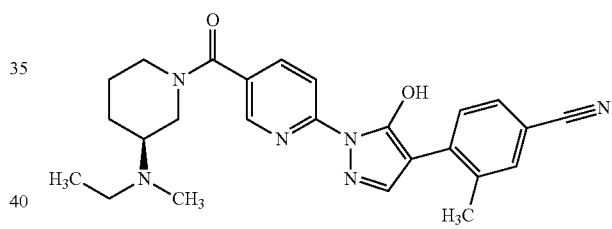

The title compound was prepared in a manner similar to Example 74 using 6-(4-(4-cyano-2-methylphenyl)-5-hydroxy-1H-pyrazol-1-yl)nicotinic acid and (S)—N-ethyl-N-methylpiperidin-3-amine dihydrochloride to give a TFA salt. ¹H NMR (400 MHz, DMSO-d₆) δ ppm 1.09-1.34 (m, 3H) 1.57 (d, J=12.13 Hz, 1H) 1.77 (d, J=10.86 Hz, 2H) 2.11 (d, J=11.12 Hz, 1H) 2.43 (s, 3H) 2.64-2.90 (m, 3H) 3.23 (br. s., 3H) 3.39-3.69 (m, 2H) 3.80-4.77 (m, 2H) 7.63-7.71 (m, 1H) 7.74 (s, 1H) 7.77 (br. s., 1H) 7.99-8.28 (m, 2H) 8.34-8.68 (m, 2H) 9.67 (br. s., 1H); ESI-MS m/z [M+H]⁺ 445.3.

Example 385 (R)-4-(1-(5-(2,4-dimethylpiperazine-1-carbonyl)pyridin-2-yl)-5-hydroxy-1H-pyrazol-4-yl)-3-methylbenzonitrile

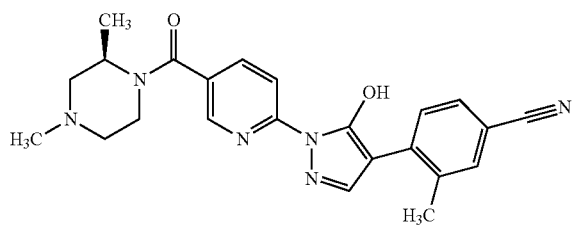

The title compound was prepared in a manner similar to Example 74 using 6-(4-(4-cyano-2-methylphenyl)-5-hydroxy-1H-pyrazol-1-yl)nicotinic acid and (R)-1,3-dimethylpiperazine dihydrochloride to give a TFA salt. ¹H NMR (400 MHz, DMSO-d₆) δ ppm 1.37 (d, J=7.07 Hz, 3H) 2.43 (s, 3H) 3.09 (br. s., 1H) 3.23 (d, J=9.09 Hz, 1H) 3.41 (br. s., 3H) 3.67-4.42 (m, 1H) 4.42-5.15 (m, 1H) 7.67 (d, J=8.30 Hz, 1H) 7.72-7.81 (m, 2H) 8.10 (d, J=8.08 Hz, 1H) 8.19 (br. s., 1H) 8.33-8.62 (m, 2H) 9.98 (br. s., 1H) 13.20 (br. s., 1H); ESI-MS m/z [M+H]⁺ 417.3.

Example 386 (S)-4-(1-(5-(3-(cyclopropyl(methyl) amino)piperidine-1-carbonyl)pyridin-2-yl)-5-hydroxy-1H-pyrazol-4-yl)-3-methylbenzonitrile

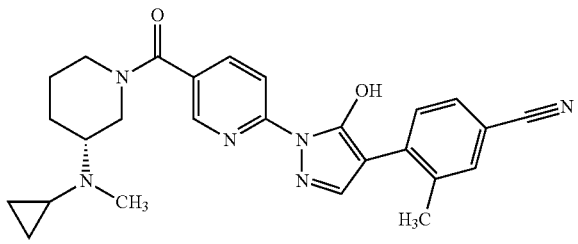 [SMILES: Cc1cc(C#N)ccc1-c1cnn(-c2ccc(C(=O)N3CCC[C@@H](N(C)C4CC4)C3)cn2)c1O]

The title compound was prepared in a manner similar to Example 112 using 6-(4-(4-cyano-2-methylphenyl)-5-hydroxy-1H-pyrazol-1-yl)nicotinic acid and (S)—N-cyclopropyl-N-methylpiperidin-3-amine dihydrochloride. ¹H NMR (400 MHz, DMSO-d₆) δ ppm 0.68-1.16 (m, 4H) 1.49-1.68 (m, 1H) 1.71-2.00 (m, 2H) 2.17-2.30 (m, 1H) 2.43 (s, 3H) 2.91 (d, J=12.38 Hz, 4H) 3.18 (br. s., 1H) 3.56 (br. s., 2H) 3.91-4.58 (m, 1H) 4.79 (br. s., 1H) 7.67 (d, J=7.83 Hz, 1H) 7.71-7.86 (m, 2H) 8.00-8.28 (m, 2H) 8.57 (s, 2H) 9.53 (br. s., 1H); ESI-MS m/z [M+H]⁺ 457.3.

Example 387 (R)-4-(5-hydroxy-1-(5-(3-(pyrrolidin-1-yl)piperidine-1-carbonyl)pyridin-2-yl)-1H-pyrazol-4-yl)-3-methylbenzonitrile

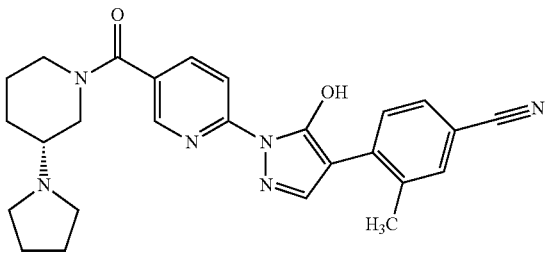 [SMILES: Cc1cc(C#N)ccc1-c1cnn(-c2ccc(C(=O)N3CCC[C@@H](N4CCCC4)C3)cn2)c1O]

The title compound was prepared in a manner similar to Example 74 using 6-(4-(4-cyano-2-methylphenyl)-5-hydroxy-1H-pyrazol-1-yl)nicotinic acid and (R)-3-(pyrrolidin-1-yl)piperidine dihydrochloride. ¹H NMR (400 MHz, DMSO-d₆) δ ppm 1.54 (d, J=9.09 Hz, 1H) 1.72-1.96 (m, 4H) 1.96-2.11 (m, 2H) 2.16 (br. s., 1H) 2.43 (s, 3H) 2.82-3.35 (m, 3H) 3.35-3.87 (m, 5H) 4.26 (br. s., 1H) 7.67 (d, J=8.08 Hz, 1H) 7.74 (s, 2H) 8.11 (d, J=8.08 Hz, 2H) 8.57 (d, J=2.02 Hz, 2H) 9.83 (br. s., 1H); ESI-MS m/z [M+H]⁺ 457.3.

Example 388 (R)-4-(1-(5-(4-ethyl-3-methylpiperazine-1-carbonyl)pyridin-2-yl)-5-hydroxy-1H-pyrazol-4-yl)-3-methylbenzonitrile

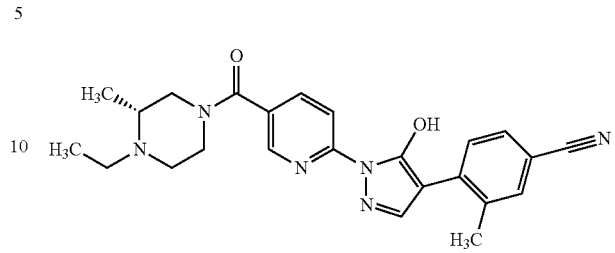

The title compound was prepared in a manner similar to Example 112 using 6-(4-(4-cyano-2-methylphenyl)-5-hydroxy-1H-pyrazol-1-yl)nicotinic acid and (R)-1-ethyl-2-methylpiperazine. ¹H NMR (400 MHz, DMSO-d₆) δ ppm 0.96 (m, J=7.20, 7.20 Hz, 6H) 2.36 (s, 3H) 2.39 (br. s., 1H) 2.45-2.52 (m, 1H) 2.53-2.68 (m, 1H) 2.71-2.90 (m, 2H) 2.99 (br. s., 1H) 3.41-3.66 (m, 1H) 3.97 (br. s., 1H) 7.53 (d, J=7.83 Hz, 1H) 7.60 (s, 1H) 7.84 (d, J=8.08 Hz, 1H) 7.94 (d, J=7.79 Hz, 1H) 7.99 (s, 1H) 8.36 (d, J=8.59 Hz, 1H) 8.44 (d, J=1.77 Hz, 1H); ESI-MS m/z [M+H]⁺ 431.3.

Example 389 (S)-4-(1-(5-(4-cyclopropyl-3-methylpiperazine-1-carbonyl)pyridin-2-yl)-5-hydroxy-1H-pyrazol-4-yl)-3-methylbenzonitrile

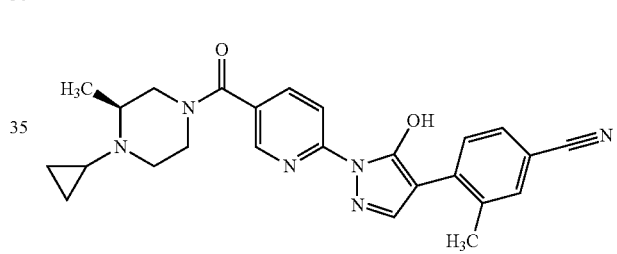

The title compound was prepared in a manner similar to Example 112 using 6-(4-(4-cyano-2-methylphenyl)-5-hydroxy-1H-pyrazol-1-yl)nicotinic acid and (S)-1-cyclopropyl-2-methylpiperazine dihydrochloride. ¹H NMR (400 MHz, DMSO-d₆) δ ppm 0.09-0.71 (m, 4H) 0.87-1.23 (m, 3H) 3.43 (br. s., 1H) 2.36 (s, 3H) 2.48-2.65 (m, 1H) 2.72-3.14 (m, 3H) 3.43 (br. s., 2H) 4.05 (br. s., 1H) 7.59 (d, J=7.64 Hz, 1H) 7.66 (s, 1H) 7.70 (br. s., 1H) 8.00 (d, J=8.08 Hz, 1H) 8.09 (br. s., 1H) 8.34 (br. s., 1H) 8.44-8.50 (m, 1H); ESI-MS m/z [M+H]⁺ 443.3.

Example 390 4-(5-hydroxy-1-(5-(4-methyl-4,7-diazaspiro[2.5]octane-7-carbonyl)pyridin-2-yl)-1H-pyrazol-4-yl)-3-methylbenzonitrile

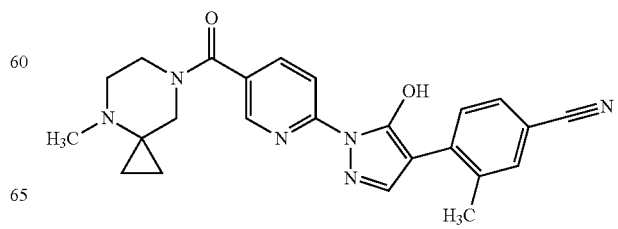

The title compound was prepared in a manner similar to Example 112 using 6-(4-(4-cyano-2-methylphenyl)-5-hydroxy-1H-pyrazol-1-yl)nicotinic acid and 4-methyl-4,7-diazaspiro[2.5]octane dihydrochloride. ¹H NMR (400 MHz, DMSO-d₆) δ ppm 0.32 (br. s., 1H) 0.50-0.78 (m, 3H) 2.39 (s, 3H) 2.42 (s, 3H) 2.86 (br. s., 2H) 3.31 (br. s., 1H) 3.41-3.62 (m, 2H) 3.73 (br. s., 1H) 7.63-7.68 (m, 1H) 7.72 (s, 1H) 7.77 (d, J=7.83 Hz, 1H) 8.04 (br. s., 1H) 8.14 (s, 1H) 8.38 (d, J=8.08 Hz, 1H) 8.50 (br. s., 1H) 12.85 (br. s., 1H); ESI-MS m/z [M+H]⁺ 429.3.

Example 391 (S)-4-(1-(5-(2,4-dimethylpiperazine-1-carbonyl)pyridin-2-yl)-5-hydroxy-1H-pyrazol-4-yl)-3-methylbenzonitrile

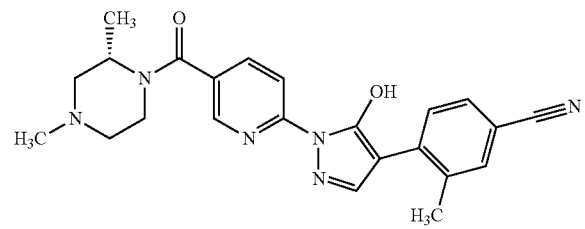 [SMILES: Cc1cc(C#N)ccc1-c1cnn(-c2ccc(C(=O)N3CCN(C)C[C@@H]3C)cn2)c1O]

The title compound was prepared in a manner similar to Example 74 using 6-(4-(4-cyano-2-methylphenyl)-5-hydroxy-1H-pyrazol-1-yl)nicotinic acid and (S)-1,3-dimethylpiperazine to give a TFA salt. ¹H NMR (400 MHz, DMSO-d₆) δ ppm 1.36 (d, J=7.33 Hz, 3H) 2.43 (s, 3H) 2.84 (s, 3H) 3.09 (br. s., 1H) 3.22 (d, J=9.85 Hz, 1H) 3.28-3.93 (m, 3H) 3.93-5.17 (m, 2H) 7.67 (d, J=8.08 Hz, 1H) 7.71-7.86 (m, 2H) 8.02-8.30 (m, 2H) 8.57 (d, J=2.02 Hz, 2H) 9.78 (br. s., 1H); ESI-MS m/z [M+H]⁺ 417.3.

Example 392 (R)-4-(1-(5-(3,4-dimethylpiperazine-1-carbonyl)pyridin-2-yl)-5-hydroxy-1H-pyrazol-4-yl)-3-methylbenzonitrile

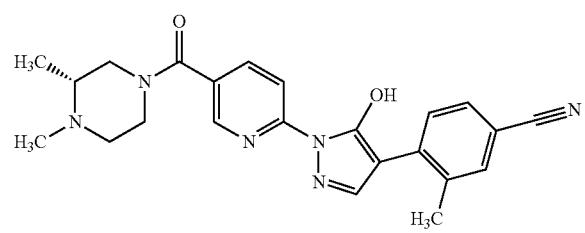 [SMILES: Cc1cc(C#N)ccc1-c1cnn(-c2ccc(C(=O)N3CCN(C)[C@H](C)C3)cn2)c1O]

The title compound was prepared in a manner similar to Example 74 using 6-(4-(4-cyano-2-methylphenyl)-5-hydroxy-1H-pyrazol-1-yl)nicotinic acid and (R)-1,2-dimethylpiperazine dihydrochloride to give a TFA salt. ¹H NMR (400 MHz, DMSO-d₆) δ ppm 1.28 (br. s., 3H) 2.43 (s, 3H) 2.85 (br. s., 3H) 2.91-3.11 (m, 1H) 3.12-3.63 (m, 4H) 3.63-4.81 (m, 2H) 7.67 (dd, J=8.08, 1.26 Hz, 1H) 7.71-7.87 (m, 2H) 8.02-8.30 (m, 2H) 8.32-8.64 (m, 2H) 9.92-10.48 (m, 1H); ESI-MS m/z [M+H]⁺ 417.3.

Example 393 (S)-4-(5-hydroxy-1-(5-(4-isopropyl-3-methylpiperazine-1-carbonyl)pyridin-2-yl)-1H-pyrazol-4-yl)-3-methylbenzonitrile

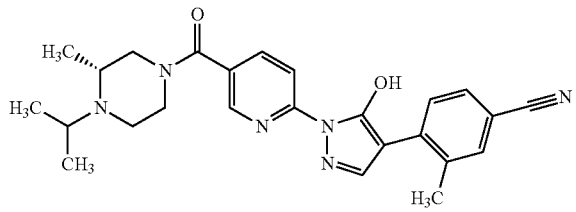 [SMILES: Cc1cc(C#N)ccc1-c1cnn(-c2ccc(C(=O)N3CCN(C(C)C)[C@H](C)C3)cn2)c1O]

The title compound was prepared in a manner similar to Example 112 using 6-(4-(4-cyano-2-methylphenyl)-5-hydroxy-1H-pyrazol-1-yl)nicotinic acid and (S)-1-isopropyl-2-methylpiperazine to give a TFA salt. ¹H NMR (400 MHz, DMSO-d₆) δ ppm 0.98-1.51 (m, 9H) 2.43 (s, 3H) 2.88-3.28 (m, 2H) 3.28-3.66 (m, 2H) 3.90 (br. s., 2H) 4.61 (br. s., 1H) 7.64-7.71 (m, 1H) 7.71-7.82 (m, 2H) 8.08-8.39 (m, 2H) 8.63 (s, 2H) 9.80 (br. s., 1H); ESI-MS m/z [M+H]⁺ 445.3.

Example 394 4-(1-(5-(3-(dimethylamino)azetidine-1-carbonyl)pyridin-2-yl)-5-hydroxy-1H-pyrazol-4-yl)-2-fluoro-5-methylbenzonitrile

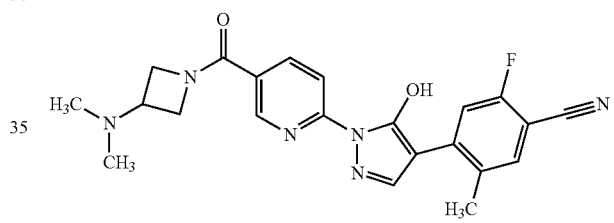

The title compound was prepared in a manner similar to Example 112 using 6-(4-(4-cyano-5-fluoro-2-methylphenyl)-5-hydroxy-1H-pyrazol-1-yl)nicotinic acid and N,N-dimethylazetidin-3-amine dihydrochloride. ¹H NMR (400 MHz, DMSO-d₆) δ ppm 2.37 (s, 3H) 2.77 (br. s., 6H) 4.07-4.18 (m, 1H) 4.26 (br. s., 2H) 4.52 (br. s., 1H) 4.63 (br. s., 1H) 7.70 (d, J=6.82 Hz, 1H) 7.79 (d, J=11.37 Hz, 1H) 8.19-8.26 (m, 2H) 8.43 (d, J=8.84 Hz, 1H) 8.69 (d, J=2.27 Hz, 1H); ESI-MS m/z [M+H]⁺ 421.3.

Example 395 (R)-4-(1-(5-(4-ethyl-3-methylpiperazine-1-carbonyl)pyridin-2-yl)-5-hydroxy-1H-pyrazol-4-yl)-2-fluoro-5-methylbenzonitrile

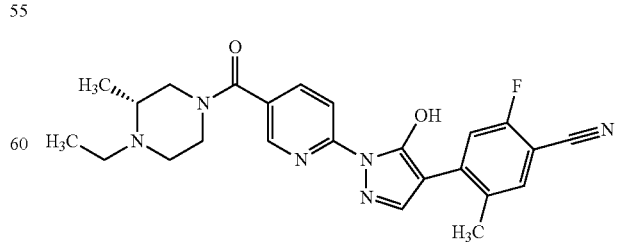

The title compound was prepared in a manner similar to Example 112 using 6-(4-(4-cyano-5-fluoro-2-methylphenyl)-5-hydroxy-1H-pyrazol-1-yl)nicotinic acid and (R)-1-ethyl-2-methylpiperazine. $^1$H NMR (400 MHz, DMSO-d$_6$) δ ppm 1.03 (t, J=7.20 Hz, 6H) 2.33 (s, 3H) 2.65-2.79 (m, 2H) 2.88-3.02 (m, 2H) 3.06 (d, J=10.86 Hz, 1H) 3.10-3.21 (m, 1H) 3.39 (br. s., 1H) 3.57-4.21 (m, 2H) 7.52 (d, J=7.07 Hz, 1H) 7.84-7.92 (m, 1H) 7.95 (s, 1H) 8.23 (d, J=13.14 Hz, 1H) 8.37-8.50 (m, 2H); ESI-MS m/z [M+H]$^+$ 449.3.

Example 396 2-fluoro-4-(5-hydroxy-1-(5-(4-methylpiperazine-1-carbonyl)pyridin-2-yl)-1H-pyrazol-4-yl)-5-methylbenzonitrile

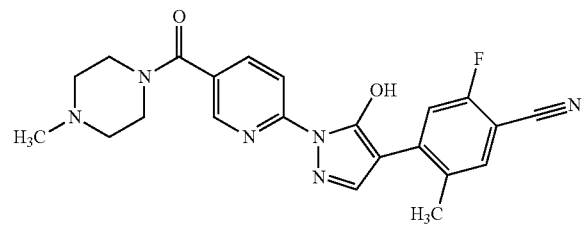 [SMILES: Cc1cc(C#N)c(F)cc1-c1cnn(-c2ccc(C(=O)N3CCN(C)CC3)cn2)c1O]

The title compound was prepared in a manner similar to Example 74 using 6-(4-(4-cyano-5-fluoro-2-methylphenyl)-5-hydroxy-1H-pyrazol-1-yl)nicotinic acid and 1-methylpiperazine to give a TFA salt. $^1$H NMR (400 MHz, DMSO-d$_6$) δ ppm 1.26 (d, J=17.18 Hz, 3H) 2.42 (s, 3H) 2.85 (br. s., 3H) 3.21 (br. s., 1H) 3.34 (br. s., 1H) 3.40-3.74 (m, 2H) 7.80 (d, J=7.07 Hz, 1H) 7.87 (br. s., 1H) 8.13 (d, J=8.59 Hz, 1H) 8.30 (br. s., 1H) 8.49 (br. s., 1H) 8.56-8.65 (m, 1H) 9.85-10.51 (m, 1H); ESI-MS m/z [M+H]$^+$ 421.3.

Example 397 (S)-4-(1-(5-(4-ethyl-3-methylpiperazine-1-carbonyl)pyridin-2-yl)-5-hydroxy-1H-pyrazol-4-yl)-2-fluoro-5-methylbenzonitrile

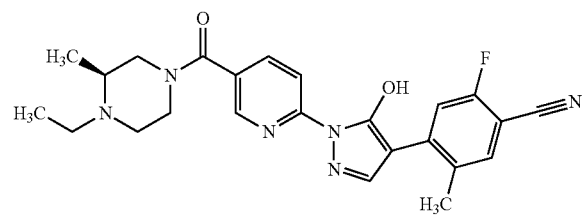 [SMILES: CCN1CCN(C(=O)c2ccc(-n3ncc(-c4cc(F)c(C#N)cc4C)c3O)nc2)C[C@@H]1C]

The title compound was prepared in a manner similar to Example 112 using 6-(4-(4-cyano-5-fluoro-2-methylphenyl)-5-hydroxy-1H-pyrazol-1-yl)nicotinic acid and (S)-1-ethyl-2-methylpiperazine. $^1$H NMR (400 MHz, DMSO-d$_6$) δ ppm 0.95-1.30 (m, 6H) 2.41 (s, 3H) 2.79 (dt, J=12.95, 6.54 Hz, 2H) 2.94-3.10 (m, 2H) 3.13 (d, J=11.37 Hz, 1H) 3.23 (dd, J=13.14, 8.34 Hz, 1H) 3.46 (br. s., 1H) 3.61-4.25 (m, 2H) 7.59 (d, J=7.33 Hz, 1H) 7.91-8.00 (m, 1H) 8.03 (s, 1H) 8.30 (d, J=13.14 Hz, 1H) 8.45-8.57 (m, 2H); ESI-MS m/z [M+H]$^+$ 449.3.

Example 398 2-fluoro-4-(5-hydroxy-1-(5-(morpholine-4-carbonyl)pyridin-2-yl)-1H-pyrazol-4-yl)-5-methylbenzonitrile

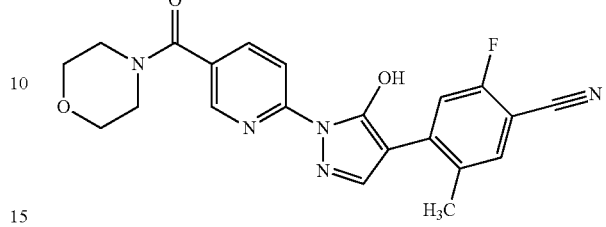

The title compound was prepared in a manner similar to Example 112 using 6-(4-(4-cyano-5-fluoro-2-methylphenyl)-5-hydroxy-1H-pyrazol-1-yl)nicotinic acid and morpholine. $^1$H NMR (400 MHz, DMSO-d$_6$) δ ppm 2.42 (s, 3H) 3.40-3.87 (m, 8H) 7.79 (d, J=7.07 Hz, 1H) 7.88 (d, J=10.86 Hz, 1H) 8.10 (dd, J=8.59, 2.02 Hz, 1H) 8.27 (br. s., 1H) 8.44 (br. s., 1H) 8.57 (dd, J=2.27, 0.76 Hz, 1H) 13.47 (br. s., 1H); ESI-MS m/z [M+H]$^+$ 408.3.

Example 399 2-fluoro-4-(5-hydroxy-1-(5-(4-methyl-4,7-diazaspiro[2.5]octane-7-carbonyl)pyridin-2-yl)-1H-pyrazol-4-yl)-5-methylbenzonitrile

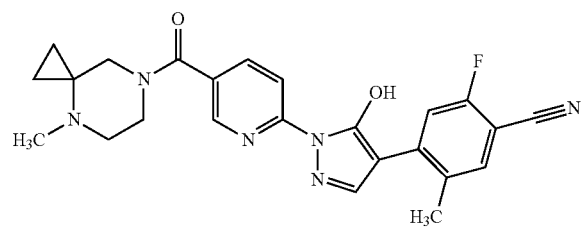 [SMILES: Cc1cc(C#N)c(F)cc1-c1cnn(-c2ccc(C(=O)N3CCN(C)C4(CC4)C3)cn2)c1O]

The title compound was prepared in a manner similar to Example 112 using 6-(4-(4-cyano-5-fluoro-2-methylphenyl)-5-hydroxy-1H-pyrazol-1-yl)nicotinic acid and 4-methyl-4,7-diazaspiro[2.5]octane dihydrochloride. $^1$H NMR (400 MHz, DMSO-d$_6$) δ ppm 0.26-0.83 (m, 4H) 2.41 (d, J=3.79 Hz, 6H) 2.89 (br. s., 2H) 3.40-3.91 (m, 4H) 7.73 (d, J=7.07 Hz, 1H) 7.98 (d, J=11.87 Hz, 2H) 8.20 (s, 1H) 8.35-8.63 (m, 2H); ESI-MS m/z [M+H]$^+$ 447.3.

Example 400 (S)-4-(1-(5-(3,4-dimethylpiperazine-1-carbonyl)pyridin-2-yl)-5-hydroxy-1H-pyrazol-4-yl)-2-fluoro-5-methylbenzonitrile

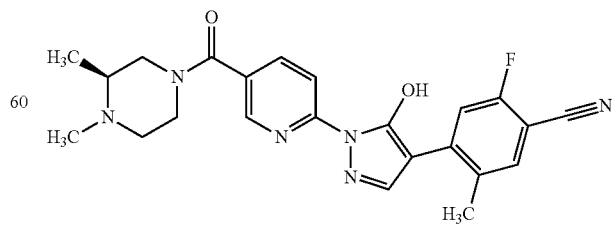

The title compound was prepared in a manner similar to Example 74 using 6-(4-(4-cyano-5-fluoro-2-methylphenyl)-

5-hydroxy-1H-pyrazol-1-yl)nicotinic acid and (S)-1,2-methylpiperazine to give a TFA salt. $^1$H NMR (400 MHz, DMSO-d$_6$) δ ppm 1.07-1.47 (m, 3H) 2.42 (s, 3H) 2.85 (br. s., 3H) 3.07-3.71 (m, 5H) 3.74-4.10 (m, 1H) 4.57 (br. s., 1H) 7.80 (d, J=7.07 Hz, 1H) 7.87 (br. s., 1H) 8.13 (d, J=8.34 Hz, 1H) 8.30 (br. s., 1H) 8.49 (br. s., 1H) 8.60 (d, J=1.52 Hz, 1H) 9.87-10.44 (m, 1H); ESI-MS m/z [M+H]$^+$ 435.3.

Example 401 (R)-4-(1-(5-(3,4-dimethylpiperazine-1-carbonyl)pyridin-2-yl)-5-hydroxy-1H-pyrazol-4-yl)-2-fluoro-5-methylbenzonitrile

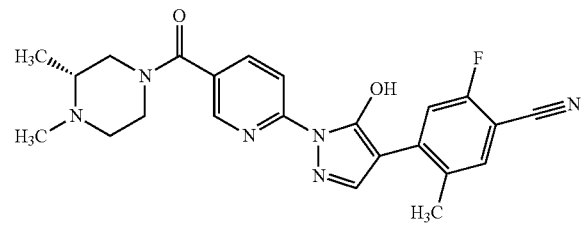 [SMILES: Cc1cc(C#N)c(F)cc1-c1cnn(-c2ccc(C(=O)N3CCN(C)[C@H](C)C3)cn2)c1O]

The title compound was prepared in a manner similar to Example 74 using 6-(4-(4-cyano-5-fluoro-2-methylphenyl)-5-hydroxy-1H-pyrazol-1-yl)nicotinic acid and (R)-1,2-methylpiperazine to give a TFA salt. $^1$H NMR (400 MHz, DMSO-d$_6$) δ ppm 1.05-1.53 (m, 3H) 2.42 (s, 3H) 2.85 (br. s., 3H) 3.09-3.41 (m, 3H) 3.42-3.73 (m, 2H) 3.75-4.09 (m, 1H) 4.55 (br. s., 1H) 7.80 (d, J=7.07 Hz, 1H) 7.87 (br. s., 1H) 8.13 (d, J=8.08 Hz, 1H) 8.30 (br. s., 1H) 8.49 (br. s., 1H) 8.60 (d, J=1.52 Hz, 1H) 9.83-10.45 (m, 1H); ESI-MS m/z [M+H]$^+$ 435.3.

Example 402 6-(4-(4-cyano-3-methylphenyl)-5-hydroxy-1H-pyrazol-1-yl)-N-(3-methoxypropyl)nicotinamide

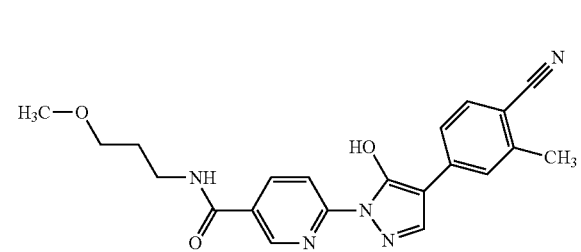 [SMILES: COCCCNC(=O)c1ccc(-n2ncc(-c3ccc(C#N)c(C)c3)c2O)nc1]

Combined 6-(4-bromo-5-methoxy-1H-pyrazol-1-yl)-N-(3-methoxypropyl)nicotinamide (50 mg, 0.135 mmol), 2-methyl-4-(4,4,5,5-tetramethyl-1,3,2-dioxaborolan-2-yl)benzonitrile (65.8 mg, 0.271 mmol), [1,1'-bis(di-tert-butylphosphino) ferrocene]dichloropalladium(II) (13.86 mg, 0.021 mmol) and sodium bicarbonate (56.9 mg, 0.677 mmol) in dioxane (599 µl) and water (150 µl) was heated at 110° C. in the microwave for 40 minutes. The reaction mixture was filtered through Celite® and concentrated in vacuo to give 6-(4-(4-cyano-3-methylphenyl)-5-methoxy-1H-pyrazol-1-yl)-N-(3-methoxypropyl)nicotinamide which was used in next step without further purification.

Combined 6-(4-(4-cyano-3-methylphenyl)-5-methoxy-1H-pyrazol-1-yl)-N-(3-methoxypropyl)nicotinamide (54.7 mg, 0.135 mmol) and lithium chloride (57.2 mg, 1.350 mmol) in DMA (2109 µl) and heated at 60° C. for 24 hours. The reaction mixture was then diluted with 0.6 mL DMSO and purified by preparative HPLC (35-60% acetonitrile in water under TFA conditions) and then again (15-40% acetonitrile in water under basic conditions) to give the title compound (14 mg, 0.036 mmol, 26.5%) as an off-white solid. $^1$H NMR (400 MHz, DMSO-d$_6$) δ ppm 1.77 (quin, J=6.63 Hz, 2H) 2.43 (s, 3H) 3.25 (s, 3H) 3.38-3.41 (m, 4H) 7.08 (br. s., 2H) 7.58 (d, J=8.08 Hz, 1H) 7.88 (d, J=9.35 Hz, 1H) 7.97 (s, 1H) 8.29 (dd, J=8.46, 2.40 Hz, 1H) 8.50 (d, J=8.34 Hz, 1H) 8.61 (t, J=6.06 Hz, 1H) 8.85 (d, J=1.77 Hz, 1H); MS (M+H)$^+$ 392.

Example 403 6-(4-(4-cyano-2,5-dimethylphenyl)-5-hydroxy-1H-pyrazol-1-yl)-N-(3-methoxypropyl)nicotinamide

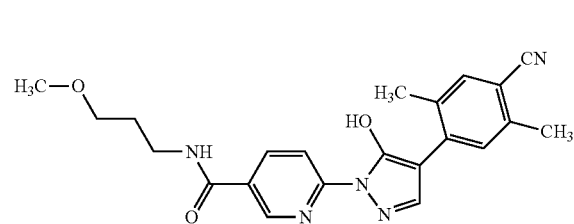

The title compound was prepared in a manner similar to Example 402 using 2,5-dimethyl-4-(4,4,5,5-tetramethyl-1,3,2-dioxaborolan-2-yl)benzonitrile. $^1$H NMR (400 MHz, DMSO-d$_6$) δ ppm 1.77 (quin, J=6.63 Hz, 2H) 2.36 (s, 3H) 2.39 (s, 3H) 3.25 (s, 3H) 3.38-3.41 (m, 4H) 7.15 (br. s., 1H) 7.45 (s, 1H) 7.84 (s, 1H) 8.06 (s, 1H) 8.22 (dd, J=8.72, 2.40 Hz, 1H) 8.50-8.61 (m, 2H) 8.83 (d, J=1.77 Hz, 1H); ESI-MS m/z (M+H)$^+$ calc'd for C$_{22}$H$_{23}$N$_5$O$_3$, 406.18. found 406.4.

Example 404 6-(4-(4-cyano-2-fluoro-6-methylphenyl)-5-hydroxy-1H-pyrazol-1-yl)-N-(3-methoxypropyl)nicotinamide

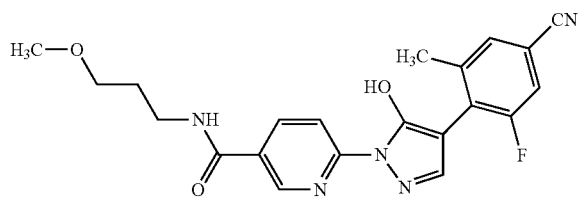 [SMILES: COCCCNC(=O)c1ccc(-n2ncc(-c3c(C)cc(C#N)cc3F)c2O)nc1]

The title compound was prepared in a manner similar to Example 402 using 3-fluoro-5-methyl-4-(4,4,5,5-tetramethyl-1,3,2-dioxaborolan-2-yl)benzonitrile. ESI-MS m/z (M+H)$^+$ calc'd for C$_{21}$H$_{20}$FN$_5$O$_3$, 410.16. found 410.4.

Example 405 6-(4-(4-cyano-5-fluoro-2-methylphenyl)-5-hydroxy-1H-pyrazol-1-yl)-N-(3-methoxypropyl)nicotinamide

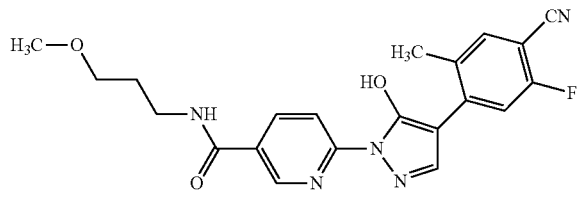 [SMILES: COCCCNC(=O)c1ccc(-n2ncc(-c3cc(F)c(C#N)cc3C)c2O)nc1]

The title compound was prepared in a manner similar to Example 402 using 2-fluoro-5-methyl-4-(4,4,5,5-tetramethyl-1,3,2-dioxaborolan-2-yl)benzonitrile. $^1$H NMR (400 MHz, DMSO-$d_6$) δ ppm 1.74-1.82 (m, 2H) 2.42 (s, 3H) 3.25 (s, 3H) 3.38-3.44 (m, 4H) 6.54 (br. s., 1H) 7.79 (d, J=7.07 Hz, 1H) 7.89 (br. s., 1H) 8.28 (br. s., 1H) 8.41 (d, J=6.32 Hz, 1H) 8.71 (t, J=5.68 Hz, 1H) 8.91 (s, 1H) 13.61 (br. s., 1H); ESI-MS m/z (M+H)$^+$ calc'd for $C_{21}H_{20}FN_5O_3$, 410.16. found 410.5.

Example 406 6-(4-(4-cyano-3-fluoro-2-methylphenyl)-5-hydroxy-1H-pyrazol-1-yl)-N-(3-methoxypropyl)nicotinamide

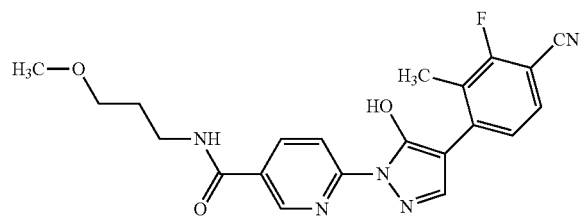 [SMILES: COCCCNC(=O)c1ccc(-n2ncc(-c3ccc(C#N)c(F)c3C)c2O)nc1]

The title compound was prepared in a manner similar to Example 402 using 2-fluoro-3-methyl-4-(4,4,5,5-tetramethyl-1,3,2-dioxaborolan-2-yl)benzonitrile. $^1$H NMR (400 MHz, DMSO-$d_6$) δ ppm 1.70-1.82 (m, 2H) 2.33 (d, J=2.27 Hz, 3H) 3.25 (s, 3H) 3.38-3.43 (m, 4H) 6.54 (br. s., 1H) 7.64 (br. s., 1H) 7.72-7.80 (m, 1H) 8.25 (br. s., 1H) 8.41 (d, J=6.57 Hz, 1H) 8.71 (t, J=5.56 Hz, 1H) 8.91 (d, J=1.01 Hz, 1H) 13.48 (br. s., 1H); ESI-MS m/z (M+H)$^+$ calc'd for $C_{21}H_{20}FN_5O_3$, 410.16. found 410.4.

Example 407 4-(5-hydroxy-1-(5-(octahydropyrrolo[1,2-a]pyrazine-2-carbonyl)pyridin-2-yl)-1H-pyrazol-4-yl)-3-methylbenzonitrile

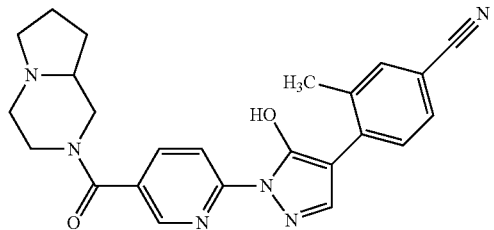 [SMILES: Cc1cc(C#N)ccc1-c1cnn(-c2ccc(C(=O)N3CCN4CCCC4C3)cn2)c1O]

Combined 6-(4-(4-cyano-2-methylphenyl)-5-hydroxy-1H-pyrazol-1-yl)nicotinic acid (500 mg, 1.561 mmol), EDC (449 mg, 2.342 mmol) and HOBT (316 mg, 2.342 mmol) in DMF (3122 µl) and treated with DIPEA (818 µl, 4.68 mmol). Octahydropyrrolo[1,2-a]pyrazine (296 mg, 2.342 mmol) was then added. The reaction was allowed to stir for 8 hours and filtered and the filtrate was purified by preparative HPLC (15-40% ACN/water under basic conditions) to give a solid which was recrystallized from MeOH, filtered, and dried in vacuum to give the title compound (286 mg, 0.603 mmol, 38.6%) as a white solid. $^1$H NMR (400 MHz, DMSO-$d_6$) δ ppm 1.34 (br. s., 1H) 1.72 (br. s., 1H) 2.12 (br. s., 1H) 2.23 (d, J=7.07 Hz, 2H) 2.42 (s, 3H) 2.51-2.53 (m, 1H) 3.06 (t, J=8.08 Hz, 3H) 3.72 (br. s., 1H) 4.44-4.56 (m, 1H) 7.63 (dd, J=8.08, 1.77 Hz, 1H) 7.69 (d, J=1.26 Hz, 1H) 7.84 (d, J=8.08 Hz, 1H) 8.04 (dd, J=8.59, 2.27 Hz, 1H) 8.09 (s, 1H) 8.40 (d, J=7.58 Hz, 1H) 8.52 (d, J=2.27 Hz, 1H); ESI-MS m/z (M+H)$^+$ calc'd for $C_{24}H_{24}N_6O_2$, 429.20. found 429.3.

Example 408 4-(5-hydroxy-1-(5-(4-methylpiperazine-1-carbonyl)pyridin-2-yl)-1H-pyrazol-4-yl)-3-methylbenzonitrile

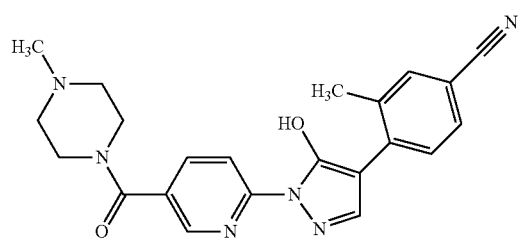 [SMILES: Cc1cc(C#N)ccc1-c1cnn(-c2ccc(C(=O)N3CCN(C)CC3)cn2)c1O]

Combined EDC (599 mg, 3.12 mmol), HOBT (211 mg, 1.561 mmol) and 6-(4-(4-cyano-2-methylphenyl)-5-hydroxy-1H-pyrazol-1-yl)nicotinic acid (500 mg, 1.561 mmol) in DMF (10 ml) and added 1-methylpiperazine (519 µl, 4.68 mmol) and DIPEA (818 µl, 4.68 mmol) and the solution was stirred at 20° C. overnight. The reaction mixture was then purified by preparative HPLC (15-40% ACN in water under basic conditions) to give the free base, which was suspended in acetonitrile (28 mL) and treated with 1N aqueous hydrochloric acid (2.341 mL, 2.341 mmol). The resulting cloudy mixture was heated until cleared and allowed to cool to ambient temperature. The mixture was filtered and the filtrate was cooled to 0° C. and filtered again. The filtrate was diluted with ethyl ether (10 mL) to give a solid and the mixture was heated until all solids dissolved, and then cooled to ambient temperature to give a solid. The mixture was cooled to 0° C. and filtered, and the solid was dried in vacuum at 80° C. for 1 hour to give the title compound as a hydrochloride salt (94 mg, 13.7%) as a light pink solid. $^1$H NMR (400 MHz, DMSO-$d_6$) δ ppm 2.43 (s, 3H) 2.79 (s, 3H) 3.16 (br. s., 4H) 3.64-4.57 (m, 4H) 7.67 (d, J=7.83 Hz, 1H) 7.74 (s, 1H) 7.78 (br. s., 1H) 8.12 (d, J=7.33 Hz, 1H) 8.21 (br. s., 1H) 8.51 (br. s., 1H) 8.57-8.61 (m, 1H); ESI-MS m/z (M+H)$^+$ calc'd for $C_{22}H_{22}N_6O_2$, 403.18. found 403.2.

Example 409 6-(4-(4-cyano-2,3-dimethylphenyl)-5-hydroxy-1H-pyrazol-1-yl)-N-(3-methoxypropyl)nicotinamide

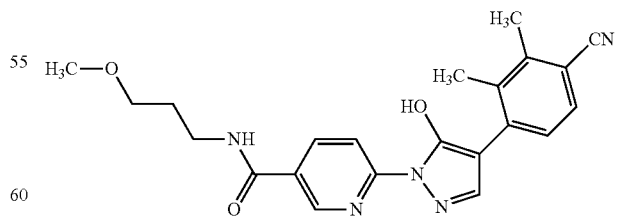

The title compound was prepared in a manner similar to Example 402 using 2,3-dimethyl-4-(4,4,5,5-tetramethyl-1,3,2-dioxaborolan-2-yl)benzonitrile. $^1$H NMR (400 MHz, DMSO-$d_6$) δ ppm 1.78 (quin, J=6.69 Hz, 2H) 2.32 (s, 3H) 2.44 (s, 3H) 3.25 (s, 3H) 3.33-3.43 (m, 4H) 7.13 (br. s., 1H)

7.43 (d, J=8.34 Hz, 1H) 7.69-7.76 (m, 2H) 8.21 (dd, J=8.84, 2.27 Hz, 1H) 8.48-8.56 (m, 2H) 8.83 (d, J=1.77 Hz, 1H); ESI-MS m/z (M+H)+ calc'd for C22H23N5O3, 406.18. found 406.4.

Example 410 6-(4-(4-cyano-2-(methoxymethyl)phenyl)-5-hydroxy-1H-pyrazol-1-yl)-N-(3-methoxypropyl)nicotinamide

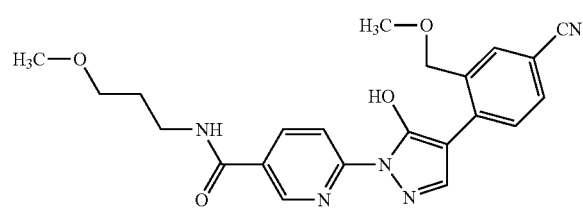 [SMILES: COCCCNC(=O)c1ccc(-n2ncc(-c3ccc(C#N)cc3COC)c2O)nc1]

The title compound was prepared in a manner similar to Example 402 using 3-(methoxymethyl)-4-(4,4,5,5-tetramethyl-1,3,2-dioxaborolan-2-yl)benzonitrile. $^1$H NMR (400 MHz, DMSO-d$_6$) δ ppm 1.73-1.83 (m, 2H) 3.25 (s, 3H) 3.34-3.43 (m, 4H) 4.52 (s, 2H) 7.75 (dd, J=8.21, 1.39 Hz, 1H) 7.83 (d, J=1.77 Hz, 1H) 7.96-8.10 (m, 2H) 8.37 (dd, J=8.59, 2.78 Hz, 1H) 8.45 (br. s., 1H) 8.66 (t, J=5.43 Hz, 1H) 8.89 (d, J=3.03 Hz, 1H); ESI-MS m/z (M+H)+ calc'd for C22H23N5O4, 422.18. found 422.5.

Example 411 6-(4-(4-cyano-3-methoxy-2-methylphenyl)-5-hydroxy-1H-pyrazol-1-yl)-N-(3-methoxypropyl)nicotinamide

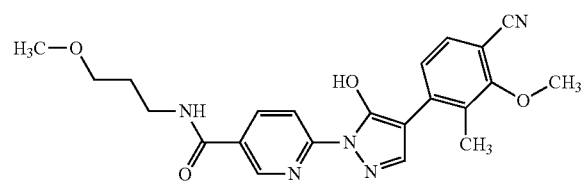

The title compound was prepared in a manner similar to Example 402 using 2-methoxy-3-methyl-4-(4,4,5,5-tetramethyl-1,3,2-dioxaborolan-2-yl)benzonitrile. $^1$H NMR (400 MHz, DMSO-d$_6$) δ ppm 1.73-1.83 (m, 2H) 2.31 (s, 3H) 3.25 (s, 3H) 3.33-3.44 (m, 4H) 3.89 (s, 3H) 7.52-7.61 (m, 2H) 8.06 (br. s., 1H) 8.33-8.47 (m, 2H) 8.65 (t, J=5.31 Hz, 1H) 8.86-8.92 (m, 1H); ESI-MS m/z (M+H)+ calc'd for C22H23N5O4, 422.18. found 422.5.

Example 412 (S)-4-(1-(5-(3-(dimethylamino)pyrrolidine-1-carbonyl)pyridin-2-yl)-5-hydroxy-1H-pyrazol-4-yl)-3-methylbenzonitrile

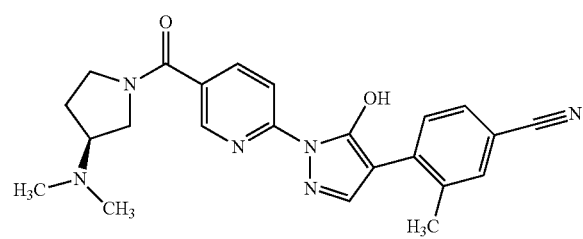 [SMILES: Cc1cc(C#N)ccc1-c1cnn(-c2ccc(C(=O)N3CC[C@H](N(C)C)C3)cn2)c1O]

Combined 6-(4-(4-cyano-2-methylphenyl)-5-hydroxy-1H-pyrazol-1-yl)nicotinic acid (50.0 mg, 0.156 mmol), (S)—N,N-dimethylpyrrolidin-3-amine (26.7 mg, 0.234 mmol), and N1-((ethylimino)methylene)-N3,N3-dimethylpropane-1,3-diamine hydrochloride (44.9 mg, 0.234 mmol) in DMF (1561 μl). HOBT (35.9 mg, 0.234 mmol) and DIPEA (136 μl, 0.781 mmol) were added. The reaction was allowed to stir overnight. Then 1N aqueous hydrochloric acid (21 ML) was added and reaction mixture was then purified using preparative HPLC eluting with 0.1% formic acid in water and 5-30% acetonitrile to give the title compound (30 mg, 0.072 mmol, 46.1%) as an off-white solid. $^1$H NMR (400 MHz, DMSO-d$_6$) δ ppm 1.78-1.88 (m, 1H) 2.24 (br. s., 3H) 2.36 (br. s., 3H) 2.42 (s, 3H) 2.88-3.05 (m, 2H) 3.59-3.81 (m, 4H) 7.58 (d, J=7.83 Hz, 1H) 7.64 (s, 1H) 7.95 (d, J=7.83 Hz, 1H) 8.01 (s, 1H) 8.11 (d, J=9.09 Hz, 1H) 8.43 (d, J=8.84 Hz, 1H) 8.62 (s, 1H); ESI-MS m/z (M+H)+ calc'd for C23H24N6O2, 417.20. found 417.5.

Example 413 (R)-4-(1-(5-(3-(dimethylamino)pyrrolidine-1-carbonyl)pyridin-2-yl)-5-hydroxy-1H-pyrazol-4-yl)-3-methylbenzonitrile

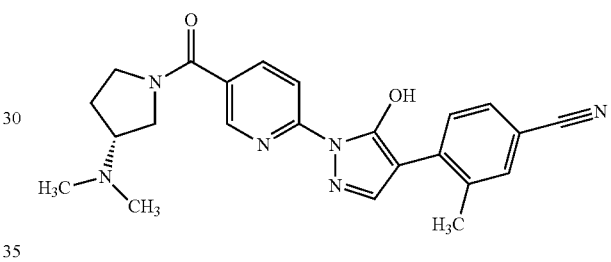

The title compound was prepared in a manner similar to Example 412 using (R)—N,N-dimethylpyrrolidin-3-amine. $^1$H NMR (400 MHz, DMSO-d$_6$) δ ppm 1.80-1.91 (m, 1H) 2.27 (br. s., 3H) 2.40 (br. s., 3H) 2.42 (s, 3H) 2.90-3.16 (m, 2H) 3.38-3.51 (m, 2H) 3.69-3.81 (m, 2H) 7.58 (d, J=8.08 Hz, 1H) 7.64 (s, 1H) 7.94 (d, J=8.08 Hz, 1H) 8.02 (s, 1H) 8.11 (dd, J=8.84, 2.02 Hz, 1H) 8.42 (d, J=8.84 Hz, 1H) 8.62 (s, 1H); ESI-MS m/z (M+H)+ calc'd for C23H24N6O2, 417.20. found 417.5.

Example 414 4-(1-(5-(4-cyclopropylpiperazine-1-carbonyl)pyridin-2-yl)-5-hydroxy-1H-pyrazol-4-yl)-3-methylbenzonitrile

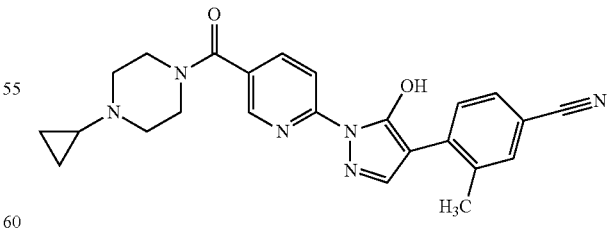

The title compound was prepared in a manner similar to Example 412 using 1-cyclopropylpiperazine. $^1$H NMR (400 MHz, DMSO-d$_6$) δ ppm 0.30-0.38 (m, 2H) 0.39-0.48 (m, 2H) 1.64-1.72 (m, 1H) 2.43 (s, 3H) 2.52-2.69 (m, 4H) 3.58 (br. s., 4H) 7.61-7.68 (m, 1H) 7.70 (s, 1H) 7.82 (d, J=8.08 Hz, 1H) 8.04 (dd, J=8.59, 2.27 Hz, 1H) 8.11 (s, 1H) 8.39 (d, J=8.34 Hz, 1H) 8.52 (d, J=2.27 Hz, 1H); ESI-MS m/z (M+H)+ calc'd for $C_{24}H_{24}N_6O_2$, 429.20. found 429.5.

Example 415 4-(5-hydroxy-1-(5-(4-propylpiperazine-1-carbonyl)pyridin-2-yl)-1H-pyrazol-4-yl)-3-methylbenzonitrile

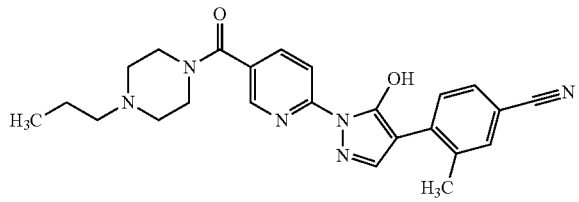 [SMILES: CCCN1CCN(C(=O)c2ccc(-n3ncc(-c4ccc(C#N)cc4C)c3O)nc2)CC1]

The title compound was prepared in a manner similar to Example 412 using 1-propylpiperazine dihydrobromide. $^1$H NMR (400 MHz, DMSO-$d_6$) δ ppm 0.87 (t, J=7.33 Hz, 3H) 1.53 (dq, J=15.09, 7.43 Hz, 2H) 2.42 (s, 3H) 2.53-2.60 (m, 2H) 2.74 (br. s., 4H) 3.63 (br. s., 4H) 7.60-7.65 (m, 1H) 7.68 (s, 1H) 7.83 (d, J=8.08 Hz, 1H) 8.05 (dd, J=8.59, 2.27 Hz, 1H) 8.09 (s, 1H) 8.14 (s, 1H) 8.39 (d, J=8.59 Hz, 1H) 8.54 (d, J=1.52 Hz, 1H); ESI-MS m/z (M+H)+ calc'd for $C_{24}H_{26}N_6O_2$, 431.21. found 431.5.

Example 416 4-(1-(5-(4-(dimethylamino)piperidine-1-carbonyl)pyridin-2-yl)-5-hydroxy-1H-pyrazol-4-yl)-3-methylbenzonitrile

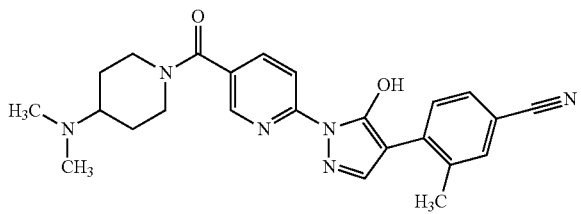 [SMILES: Cc1cc(C#N)ccc1-c1cnn(-c2ccc(C(=O)N3CCC(N(C)C)CC3)cn2)c1O]

The title compound was prepared in a manner similar to Example 412 using N,N-dimethylpiperidin-4-amine. $^1$H NMR (400 MHz, DMSO-$d_6$) δ ppm 1.55-1.72 (m, 2H) 2.01 (br. s., 2H) 2.42 (s, 3H) 2.68 (s, 6H) 3.33 (t, J=11.49 Hz, 1H) 4.21 (br. s., 4H) 7.52 (d, J=8.08 Hz, 1H) 7.56 (s, 1H) 7.88-7.96 (m, 2H) 8.09 (d, J=8.08 Hz, 1H) 8.45-8.56 (m, 2H); ESI-MS m/z (M+H)+ calc'd for $C_{24}H_{26}N_6O_2$, 431.21. found 431.5.

Example 417 4-(5-hydroxy-1-(5-((3aR,7aS)-2-methyloctahydro-1H-pyrrolo[3,4-c]pyridine-5-carbonyl)pyridin-2-yl)-1H-pyrazol-4-yl)-3-methylbenzonitrile

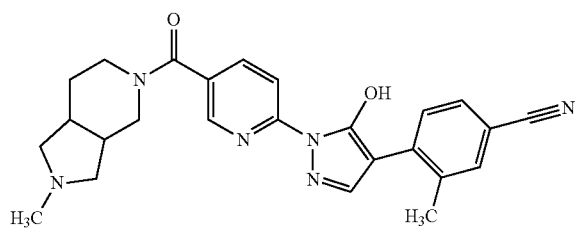 [SMILES: Cc1cc(C#N)ccc1-c1cnn(-c2ccc(C(=O)N3CCC4CN(C)CC4C3)cn2)c1O]

The title compound was prepared in a manner similar to Example 412 using 2-methyloctahydro-1H-pyrrolo[3,4-c]pyridine. $^1$H NMR (400 MHz, DMSO-$d_6$) δ ppm 1.61-1.86 (m, 2H) 2.43 (s, 3H) 2.55 (br. s., 2H) 2.72 (br. s., 3H) 3.08 (br. s., 1H) 3.15 (d, J=9.60 Hz, 1H) 3.24-3.30 (m, 2H) 3.59 (d, J=11.37 Hz, 2H) 3.80 (br. s., 2H) 7.44-7.50 (m, 1H) 7.51 (s, 1H) 7.80-7.88 (m, 2H) 8.16 (s, 1H) 8.20 (d, J=8.08 Hz, 1H) 8.41 (br. s., 1H) 8.57 (br. s., 1H); ESI-MS m/z (M+H)+ calc'd for $C_{25}H_{26}N_6O_2$, 443.21. found 443.5.

Example 418 4-(1-(5-(4-(cyclopropylmethyl)piperazine-1-carbonyl)pyridin-2-yl)-5-hydroxy-1H-pyrazol-4-yl)-3-methylbenzonitrile

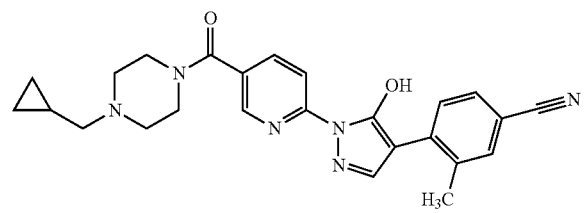 [SMILES: Cc1cc(C#N)ccc1-c1cnn(-c2ccc(C(=O)N3CCN(CC4CC4)CC3)cn2)c1O]

The title compound was prepared in a manner similar to Example 412 using 1-(cyclopropylmethyl)piperazine. $^1$H NMR (400 MHz, DMSO-$d_6$) δ ppm 0.09-0.15 (m, 2H) 0.46-0.53 (m, 2H) 0.84-0.91 (m, 1H) 2.32-2.37 (m, 2H) 2.42 (s, 3H) 2.60 (br. s., 4H) 3.58 (br. s., 4H) 7.60 (d, J=8.34 Hz, 1H) 7.67 (s, 1H) 7.90 (d, J=8.08 Hz, 1H) 8.01 (dd, J=8.72, 2.15 Hz, 1H) 8.05 (s, 1H) 8.41 (d, J=8.59 Hz, 1H) 8.51 (d, J=1.77 Hz, 1H); ESI-MS m/z (M+H)+ calc'd for $C_{25}H_{26}N_6O_2$, 443.21. found 443.5.

Example 419 4-(1-(5-(4-((dimethylamino)methyl)piperidine-1-carbonyl)pyridin-2-yl)-5-hydroxy-1H-pyrazol-4-yl)-3-methylbenzonitrile

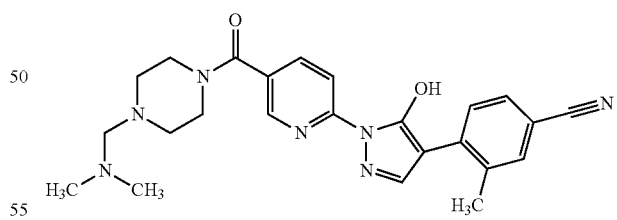

The title compound was prepared in a manner similar to Example 412 using N,N-dimethyl-1-(piperidin-4-yl)methanamine. $^1$H NMR (400 MHz, DMSO-$d_6$) δ ppm 1.07-1.22 (m, 2H) 1.75 (d, J=9.60 Hz, 2H) 1.93-2.02 (m, 1H) 2.42 (s, 3H) 2.55 (s, 6H) 2.68 (d, J=6.82 Hz, 2H) 2.85-3.14 (m, 2H) 4.40 (br. s., 2H) 7.46-7.51 (m, 1H) 7.54 (s, 1H) 7.82-7.90 (m, 2H) 8.14-8.16 (m, 1H) 8.43 (d, J=1.77 Hz, 1H) 8.50 (d, J=8.59 Hz, 1H); ESI-MS m/z (M+H)+ calc'd for $C_{25}H_{28}N_6O_2$, 445.23. found 445.5.

Example 420 6-(4-(4-cyano-2-methylphenyl)-5-hydroxy-1H-pyrazol-1-yl)-N-cyclopropyl-N-(1-methylpiperidin-4-yl)nicotinamide

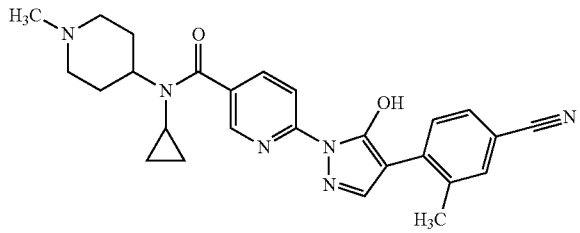 [SMILES: Cc1cc(C#N)ccc1-c1cnn(-c2ccc(C(=O)N(C3CC3)C3CCN(C)CC3)cn2)c1O]

The title compound was prepared in a manner similar to Example 412 using N-cyclopropyl-1-methylpiperidin-4-amine. $^1$H NMR (400 MHz, DMSO-d$_6$) δ ppm 0.40-0.46 (m, 2H) 0.59-0.65 (m, 2H) 1.98 (d, J=12.38 Hz, 2H) 2.22 (td, J=12.69, 9.22 Hz, 2H) 2.42 (s, 3H) 2.56 (s, 3H) 2.67-2.75 (m, 2H) 2.88 (dt, J=6.88, 3.25 Hz, 1H) 3.26-3.28 (m, 2H) 4.05 (ddd, J=12.00, 8.08, 3.92 Hz, 1H) 7.47-7.52 (m, 1H) 7.54 (s, 1H) 7.87 (s, 1H) 8.00 (dd, J=8.72, 2.40 Hz, 1H) 8.12-8.16 (m, 1H) 8.48 (d, J=8.59 Hz, 1H) 8.55 (d, J=1.52 Hz, 1H); ESI-MS m/z (M+H)$^+$ calc'd for C$_{26}$H$_{28}$N$_6$O$_2$, 457.23. found 457.5.

Example 421 4-(5-hydroxy-1-(5-(4-morpholinopiperidine-1-carbonyl)pyridin-2-yl)-1H-pyrazol-4-yl)-3-methylbenzonitrile

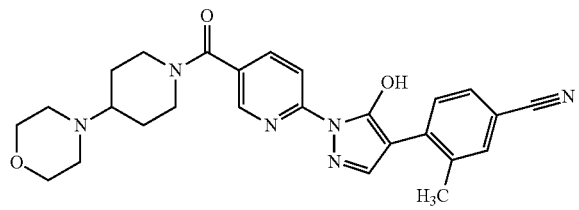 [SMILES: Cc1cc(C#N)ccc1-c1cnn(-c2ccc(C(=O)N3CCC(N4CCOCC4)CC3)cn2)c1O]

The title compound was prepared in a manner similar to Example 412 using 4-(piperidin-4-yl)morpholine. $^1$H NMR (400 MHz, DMSO-d$_6$) δ ppm 1.44 (qd, J=11.87, 4.04 Hz, 2H) 1.86 (br. s., 2H) 2.43 (s, 3H) 2.58 (br. s., 4H) 2.86 (br. s., 2H) 3.52-3.76 (m, 6H) 4.46 (br. s., 1H) 7.63 (dd, J=8.08, 1.52 Hz, 1H) 7.70 (s, 1H) 7.82 (d, J=8.08 Hz, 1H) 8.04 (dd, J=8.59, 2.27 Hz, 1H) 8.10 (s, 1H) 8.38 (d, J=8.59 Hz, 1H) 8.52 (d, J=1.52 Hz, 1H); ESI-MS m/z (M+H)$^+$ calc'd for C$_{26}$H$_{28}$N$_6$O$_3$, 473.22. found 473.5.

Example 422 6-(4-(4-cyano-2-methylphenyl)-5-hydroxy-1H-pyrazol-1-yl)-N-(2-methoxyethyl)-N-(1-methylpiperidin-4-yl)nicotinamide

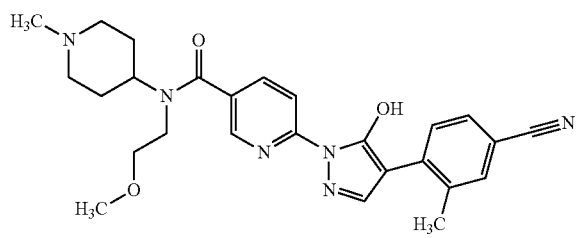 [SMILES: COCCN(C(=O)c1ccc(-n2ncc(-c3ccc(C#N)cc3C)c2O)nc1)C1CCN(C)CC1]

The title compound was prepared in a manner similar to Example 412 using N-(2-methoxyethyl)-1-methylpiperidin-4-amine. $^1$H NMR (400 MHz, DMSO-d$_6$) δ ppm 1.85 (d, J=12.13 Hz, 2H) 2.11 (br. s., 2H) 2.42 (s, 3H) 2.57 (br. s., 2H) 2.74 (br. s., 2H) 3.25 (br. s., 3H) 3.45 (br. s., 3H) 3.70 (br. s., 5H) 7.55 (dd, J=8.08, 1.77 Hz, 1H) 7.60 (s, 1H) 7.92 (dd, J=8.59, 2.53 Hz, 1H) 7.96 (s, 1H) 8.02 (d, J=8.08 Hz, 1H) 8.41-8.52 (m, 2H); ESI-MS m/z (M+H)$^+$ calc'd for C$_{26}$H$_{30}$N$_6$O$_3$, 475.24. found 475.6.

Example 423 4-(1-(5-(4-(2-(dimethylamino)ethyl)piperazine-1-carbonyl)pyridin-2-yl)-5-hydroxy-1H-pyrazol-4-yl)-3-methylbenzonitrile

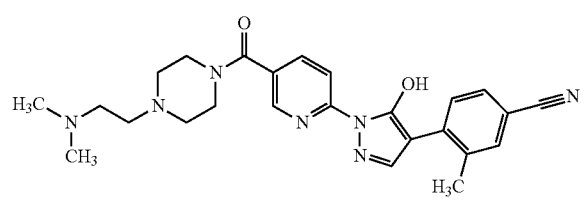 [SMILES: Cc1cc(C#N)ccc1-c1cnn(-c2ccc(C(=O)N3CCN(CCN(C)C)CC3)cn2)c1O]

The title compound was prepared in a manner similar to Example 412 using N,N-dimethyl-2-(piperazin-1-yl)ethanamine. $^1$H NMR (400 MHz, DMSO-d$_6$) δ ppm 2.41 (s, 3H) 2.60 (s, 2H) 2.61-2.70 (m, 6H) 3.02 (t, J=6.44 Hz, 2H) 3.54 (br. s., 8H) 7.42-7.47 (m, 1H) 7.48 (s, 1H) 7.79 (s, 1H) 7.83 (dd, J=8.46, 2.40 Hz, 1H) 8.27 (d, J=8.34 Hz, 1H) 8.43 (d, J=1.77 Hz, 1H) 8.55 (d, J=8.59 Hz, 1H); ESI-MS m/z (M+H)$^+$ calc'd for C$_{25}$H$_{29}$N$_7$O$_2$, 460.24. found 460.5.

Example 424 4-(5-hydroxy-1-(5-(4-propyl-1,4-diazepane-1-carbonyl)pyridin-2-yl)-1H-pyrazol-4-yl)-3-methylbenzonitrile

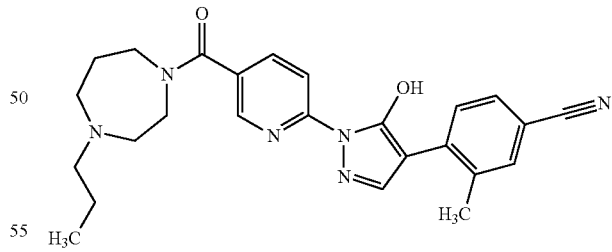

The title compound was prepared in a manner similar to Example 412 using 1-propyl-1,4-diazepane. $^1$H NMR (400 MHz, DMSO-d$_6$) δ ppm 0.77-0.94 (m, 3H) 1.42-1.59 (m, 2H) 1.89 (br. s., 2H) 2.42 (s, 3H) 2.56 (br. s., 1H) 2.72 (br. s., 1H) 2.78-2.97 (m, 3H) 3.04 (br. s., 1H) 3.50 (br. s., 2H) 3.65 (br. s., 1H) 3.73 (br. s., 1H) 7.52-7.59 (m, 1H) 7.61 (s, 1H) 7.89-8.06 (m, 3H) 8.45 (d, J=8.08 Hz, 1H) 8.49 (d, J=1.01 Hz, 1H); ESI-MS m/z (M+H)$^+$ calc'd for C$_{25}$H$_{28}$N$_6$O$_2$, 445.23. found 445.5.

Example 425 6-(4-(4-cyano-2-methylphenyl)-5-hydroxy-1H-pyrazol-1-yl)-N-(1-ethylpiperidin-4-yl)-N-methylnicotinamide

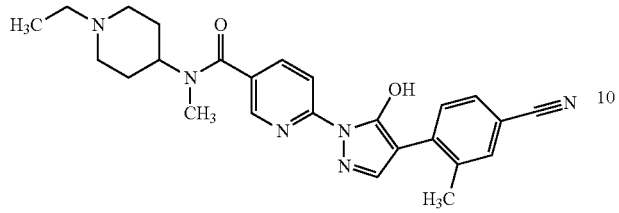

The title compound was prepared in a manner similar to Example 412 using 1-ethyl-N-methylpiperidin-4-amine. $^1$H NMR (400 MHz, DMSO-$d_6$) δ ppm 1.11 (br. s., 3H) 1.82 (d, J=12.13 Hz, 2H) 1.91-2.01 (m, 2H) 2.07 (s, 2H) 2.42 (s, 3H) 2.87 (s, 3H) 7.51 (dd, J=8.08, 1.77 Hz, 1H) 7.56 (d, J=1.26 Hz, 1H) 7.87-7.97 (m, 2H) 8.11 (d, J=8.08 Hz, 1H) 8.42-8.54 (m, 2H); ESI-MS m/z (M+H)$^+$ calc'd for $C_{25}H_{28}N_6O_2$, 445.23. found 445.5.

Example 426 6-(4-(4-cyano-5-methoxy-2-methylphenyl)-5-hydroxy-1H-pyrazol-1-yl)-N-(3-methoxypropyl)nicotinamide

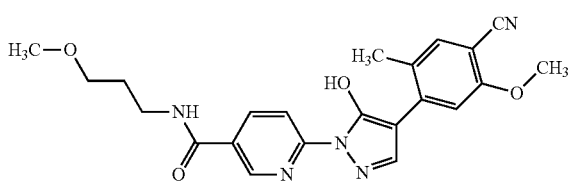

The title compound was prepared in a manner similar to Example 402 using 2-methoxy-5-methyl-4-(4,4,5,5-tetramethyl-1,3,2-dioxaborolan-2-yl)benzonitrile. $^1$H NMR (400 MHz, DMSO-$d_6$) δ ppm 1.78 (dt, J=13.20, 6.41 Hz, 2H) 2.34 (br. s., 3H) 3.25 (s, 3H) 3.36-3.44 (m, 4H) 3.89 (s, 3H) 7.56 (br. s., 2H) 8.15 (br. s., 1H) 8.39 (d, J=7.33 Hz, 1H) 8.68 (br. s., 1H) 8.90 (br. s., 1H); ESI-MS m/z (M+H)$^+$ calc'd for $C_{22}H_{23}N_5O_4$, 422.18. found 422.5.

Example 427 6-(4-(4-cyano-2-methylphenyl)-5-hydroxy-1H-pyrazol-1-yl)-N-(1-(2-methoxyethyl)piperidin-4-yl)-N-methylnicotinamide

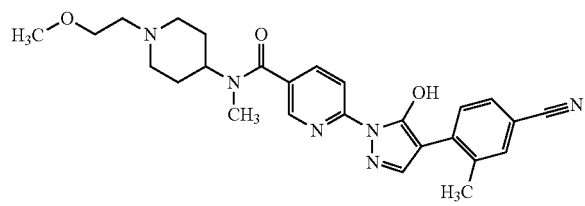 [SMILES: COCCN1CCC(N(C)C(=O)c2ccc(-n3ncc(-c4ccc(C#N)cc4C)c3O)nc2)CC1]

The title compound was prepared in a manner similar to Example 412 using 1-(2-methoxyethyl)-N-methylpiperidin-4-amine. $^1$H NMR (400 MHz, DMSO-$d_6$) δ ppm 1.69 (d, J=11.37 Hz, 2H) 1.84-1.96 (m, 2H) 2.42 (s, 3H) 2.69 (br. s., 2H) 2.86 (s, 3H) 3.10 (br. s., 2H) 3.24 (br. s., 3H) 3.46 (br. s., 4H) 4.34 (br. s., 1H) 6.51 (br. s., 1H) 7.52 (d, J=8.08 Hz, 1H) 7.57 (s, 1H) 7.91 (s, 2H) 8.09 (d, J=8.08 Hz, 1H) 8.40-8.51 (m, 2H); ESI-MS m/z (M+H)$^+$ calc'd for $C_{26}H_{30}N_6O_3$, 475.24. found 475.6.

Example 428 (S)-4-(1-(5-(1,4-diazabicyclo[3.2.2]nonane-4-carbonyl)pyridin-2-yl)-5-hydroxy-1H-pyrazol-4-yl)-3-methylbenzonitrile

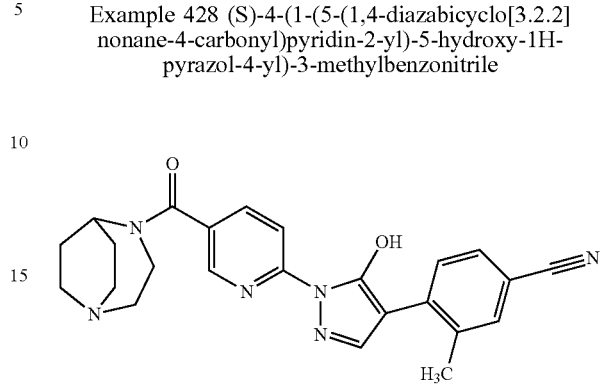

The title compound was prepared in a manner similar to Example 412 using 1,4-diazabicyclo[3.2.2]nonane dihydrochloride. $^1$H NMR (400 MHz, DMSO-$d_6$) δ ppm 1.97 (br. s., 2H) 2.16 (br. s., 2H) 2.43 (s, 3H) 3.24 (d, J=5.31 Hz, 6H) 3.71 (br. s., 2H) 4.75 (br. s., 1H) 6.50 (br. s., 1H) 7.51 (d, J=8.08 Hz, 1H) 7.56 (s, 1H) 7.88-7.99 (m, 2H) 8.12-8.14 (m, 1H) 8.56 (br. s., 2H); ESI-MS m/z (M+H)$^+$ calc'd for $C_{24}H_{24}N_6O_2$, 429.20. found 429.5.

Example 429 6-(4-(4-cyano-2-methylphenyl)-5-hydroxy-1H-pyrazol-1-yl)-N-ethyl-N-(1-methylpiperidin-4-yl)nicotinamide

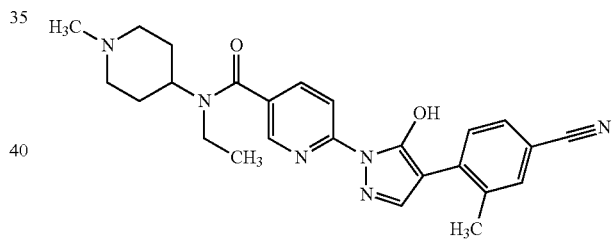

The title compound was prepared in a manner similar to Example 412 using N-ethyl-1-methylpiperidin-4-amine. $^1$H NMR (400 MHz, DMSO-$d_6$) δ ppm 1.11 (br. s., 3H) 1.81 (d, J=11.12 Hz, 2H) 2.01 (br. s., 2H) 2.42 (s, 3H) 2.45 (br. s., 2H) 3.14 (br. s., 3H) 3.64-4.56 (m, 5H) 7.47-7.52 (m, 1H) 7.54 (s, 1H) 7.83-7.89 (m, 2H) 8.14 (d, J=8.08 Hz, 1H) 8.41 (d, J=2.02 Hz, 1H) 8.49 (d, J=8.59 Hz, 1H); ESI-MS m/z (M+H)$^+$ calc'd for $C_{25}H_{28}N_6O_2$, 445.23. found 445.5.

Example 430 4-(5-hydroxy-1-(4-methyl-5-(4-methylpiperazine-1-carbonyl)pyridin-2-yl)-1H-pyrazol-4-yl)benzonitrile

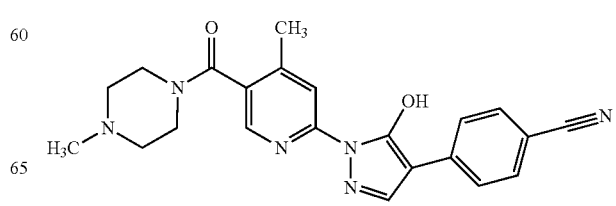

The title compound was prepared in a manner similar to Example 412 using 6-(4-(4-cyanophenyl)-5-hydroxy-1H-pyrazol-1-yl)-4-methylnicotinic acid and 1-methylpiperazine. $^1$H NMR (400 MHz, DMSO-d$_6$) δ ppm 2.39 (s, 3H) 2.82 (s, 3H) 4.02 (br. s., 4H) 4.56 (br. s., 4H) 7.79 (d, J=8.59 Hz, 2H) 8.12 (br. s., 2H) 8.37 (s, 1H) 8.59 (br. s., 2H); ESI-MS m/z (M+H)$^+$ calc'd for C$_{22}$H$_{22}$N$_6$O$_2$, 403.18. found 403.3.

Example 431 6-(4-(4-cyanophenyl)-5-hydroxy-1H-pyrazol-1-yl)-N,4-dimethyl-N-(1-methylpiperidin-4-yl)nicotinamide

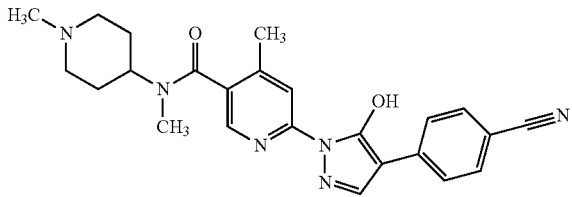 [SMILES: Cc1cc(-n2ncc(-c3ccc(C#N)cc3)c2O)ncc1C(=O)N(C)C1CCN(C)CC1]

The title compound was prepared in a manner similar to Example 412 using 6-(4-(4-cyanophenyl)-5-hydroxy-1H-pyrazol-1-yl)-4-methylnicotinic acid and N,1-dimethylpiperidin-4-amine. ESI-MS m/z (M+H)$^+$ calc'd for C$_{24}$H$_{26}$N$_6$O$_2$, 431.21. found 431.5.

Example 432 6-(4-(4-cyano-2-methylphenyl)-5-hydroxy-1H-pyrazol-1-yl)-N-methyl-N-(1-methyl-azetidin-3-yl)nicotinamide

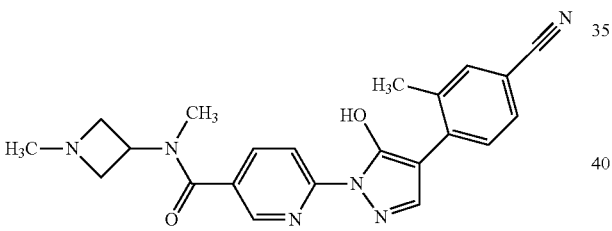

The title compound was prepared in a manner similar to Example 412 using N,1-dimethylazetidin-3-amine hydrochloride. $^1$H NMR (400 MHz, DMSO-d$_6$) δ ppm 2.43 (s, 3H) 2.90 (br. s., 3H) 3.06 (br. s., 3H) 3.99-5.12 (m, 5H) 7.67 (d, J=7.83 Hz, 1H) 7.69-7.89 (m, 2H) 8.10 (br. s., 1H) 8.22 (br. s., 1H) 8.58 (br. s., 2H) 9.80 (br. s., 1H); ESI-MS m/z (M+H)$^+$ calc'd for C$_{22}$H$_{22}$N$_6$O$_2$, 403.18. found 403.3.

Example 433 (S)-4-(1-(5-(4-ethyl-2-methylpiperazine-1-carbonyl)pyridin-2-yl)-5-hydroxy-1H-pyrazol-4-yl)-2-fluoro-5-methylbenzonitrile

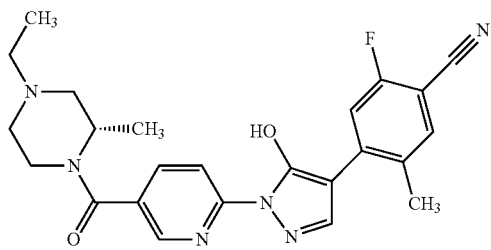 [SMILES: CCN1CCN(C(=O)c2ccc(-n3ncc(-c4cc(F)c(C#N)cc4C)c3O)nc2)[C@@H](C)C1]

Combined 6-(4-(4-cyano-5-fluoro-2-methylphenyl)-5-hydroxy-1H-pyrazol-1-yl)nicotinic acid (100 mg, 0.296 mmol), 1H-benzo[d][1,2,3]triazol-1-ol (47.9 mg, 0.355 mmol), N1-((ethylimino)methylene)-N3,N3-dimethylpropane-1,3-diamine hydrochloride (68.0 mg, 0.355 mmol), DMF (Volume: 591 µl), and N-ethyl-N-isopropylpropan-2-amine (258 µl, 1.478 mmol). The orange solution was stirred at ambient temperature for 5 minutes then (S)-1-ethyl-3-methylpiperazine dihydrochloride (65.4 mg, 0.325 mmol) was added and the reaction was stirred at ambient temperature for 12 h. The reaction mixture was diluted with a pre-made solution of water:ethanol (1:1, 5 mL). The reaction was acidified to pH 5 using 1N HCl. The solution was left to stir slowly at ambient temperature overnight. The precipitate was filtered and the solids were washed with water: ethanol (1:1, 2 mL), then dried on the filter paper. The white solids were collected and dried further under vacuum. The dried solids were taken up in 10 volumes of water:ethanol (1:1) and stirred at reflux until the solution was almost completely translucent. The hot solution was filtered and then slowly cooled to ambient temperature and stirred slowly at ambient temperature overnight to give solids. The solids were filtered and washed with water:ethanol (1:1, 2 mL), partially dried on filter paper, then dried under vacuum to give the title compound (57.9 mg, 0.129 mmol, 43.7% yield) as a white solid. $^1$H NMR (400 MHz, DMSO-d$_6$) δ ppm 1.06 (t, J=7.20 Hz, 3H) 1.30 (d, J=6.82 Hz, 3H) 2.14-2.28 (m, 1H) 2.31-2.45 (m, 4H) 2.53-2.60 (m, 2H) 2.81-3.06 (m, 2H) 3.13-3.43 (m, 2H) 4.08-4.62 (m, 1H) 7.64 (d, J=7.33 Hz, 1H) 7.96 (dd, J=8.84, 2.27 Hz, 1H) 8.08 (s, 1H) 8.19 (d, J=12.63 Hz, 1H) 8.43-8.52 (m, 2H). ESI-MS m/z [M+H]$^+$ 449.3, ret time: 0.79 minutes.

Example 434 (R)-4-(1-(5-(4-ethyl-2-methylpiperazine-1-carbonyl)pyridin-2-yl)-5-hydroxy-1H-pyrazol-4-yl)-3-methylbenzonitrile

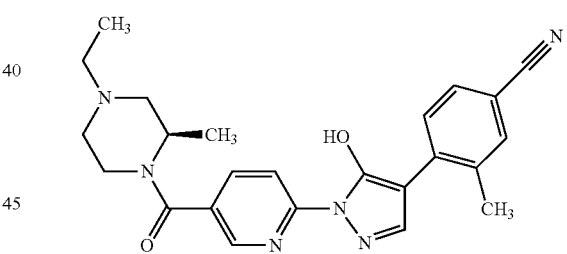

Combined 6-(4-(4-cyano-2-methylphenyl)-5-hydroxy-1H-pyrazol-1-yl)nicotinic acid (100 mg, 0.312 mmol), 1H-benzo[d][1,2,3]triazol-1-ol (50.6 mg, 0.375 mmol), N1-((ethylimino)methylene)-N3,N3-dimethylpropane-1,3-diamine hydrochloride (71.8 mg, 0.375 mmol), DMF (Volume: 624 µl), and N-ethyl-N-isopropylpropan-2-amine (273 µl, 1.561 mmol). The solution was stirred at ambient temperature for 5 minutes then (R)-1-ethyl-3-methylpiperazine dihydrochloride (69.1 mg, 0.343 mmol) was added. The reaction was stirred at ambient temperature for 12 h. The reaction was diluted with a pre-made solution of water:ethanol (1:1, 10 mL). The reaction was acidified to pH 5 using 1N HCl and left to stir slowly at ambient temperature overnight. The precipitate was filtered and the solids were washed with water:ethanol (1:1, 2 mL), then dried on the filter paper. The white solids were collected and dried further under vacuum. The dried solids were taken up in 10 volumes of water:ethanol (1:1) and stirred at reflux until the solution was almost completely translucent. The hot solution was filtered and then slowly cooled to ambient temperature and stirred slowly at ambient temperature overnight to give solids. The solids were filtered and washed with water:ethanol (1:1, 2 mL), partially dried on filter paper, then collected and dried under vacuum to give the title compound (67.7 mg, 0.157 mmol, 50.4% yield) as a white solid. $^1$H NMR (400 MHz, DMSO-d6) δ ppm 1.01 (s, 3H) 1.21-1.37 (m, 3H) 1.92-2.06 (m, 1H) 2.09-2.21 (m, 1H) 2.42 (s, 5H) 2.67-2.99 (m, 2H) 3.05-4.61 (m, 3H) 7.61 (dd, J=8.08, 1.52 Hz, 1H) 7.68 (s, 1H) 7.86 (d, J=8.08 Hz, 1H) 8.00 (dd, J=8.59, 2.27 Hz, 1H) 8.08 (s, 1H) 8.40 (d, J=8.59 Hz, 1H) 8.49 (d, J=2.27 Hz, 1H). ESI-MS m/z [M+H]$^+$ 431.3, ret time: 0.80 minutes.

Example R1 N-tert-butyl-6-(5-oxo-4-pyridin-3-yl-2,5-dihydro-1H-pyrazol-1-yl)pyridine-3-carboxamide

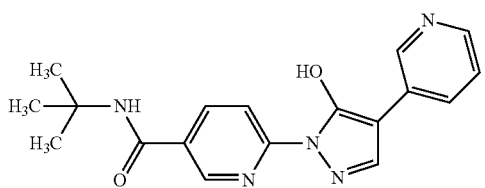 [SMILES: CC(C)(C)NC(=O)c1ccc(-n2ncc(-c3cccnc3)c2O)nc1]

The free base of compound of US 2010/0093803 Example 18 was prepared. $^1$H NMR (400 MHz, DMSO-d$_6$) δ ppm 1.42 (s, 9H) 1.40-1.44 (m, 1H) 7.40 (dd, J=7.83, 4.80 Hz, 1H) 8.06 (s, 1H) 8.30 (d, J=6.82 Hz, 1H) 8.35-8.44 (m, 2H) 8.55 (br. s., 1H) 8.78-8.93 (m, 1H) 9.13 (br. s., 1H) 13.29 (br. s., 1H), ESI-MS m/z [M+H]$^+$ 337.4.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage, typically on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

Compounds of the present invention are inhibitors of one or more PHD isoforms, and as such are useful in the treatment and prevention of conditions associated with HIF.

In another embodiment, the invention provides methods of treating conditions associated with HIF, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat the conditions associated with HIF described herein. The compounds of the present invention are useful as PHD inhibitors for a variety of subjects (e.g., humans, non-human mammals and non-mammals).

As used herein terms "condition," "disorder," and "disease" relate to any unhealthy or abnormal state. The term "conditions associated with HIF" includes conditions, disorders, and diseases in which the inhibition of PHD provides a therapeutic benefit, such as hypoxic conditions, including cardiovascular disorders, hematological disorders, pulmonary disorders, kidney disorders, brain disorders, and cancer.

The terms "hypoxia" and "hypoxic" refer to levels of oxygen below normal and can lead to cellular dysfunction and even cell death. Hypoxia can result from decreased blood flow, insufficient oxygen in the blood, decreased capacity of the blood to carry oxygen, and various other causes. The term "hypoxic condition" includes, but is not limited to, ischemic conditions (ischemic hypoxia). The term "ischemia" refers to a deficient supply of blood to a cell, tissue, or organ and is associated with a reduction in oxygen delivered to tissues.

Since the heart, brain, and kidney are especially sensitive to hypoxic stress inhibitors of PHD are useful in treating cardiovascular disorders, such as ischemic events, hematological disorders, such as anemia, and kidney disorders.

Ischemia may arise due to reduced circulation such as stroke, myocardial infarction, congestive heart failure, atherosclerosis, and formation of a thrombus in an artery or vein, blockage of an artery or vein by an embolus, vascular closure due to other causes. Such conditions may reduce blood flow, producing a state of hypoperfusion to an organ or tissue, or block blood flow completely.

Other conditions that can lead to ischemia include tissue damage due to trauma or injury, such as, e.g., spinal cord injury; viral infection. The term "conditions associated with HIF" includes the term "ischemic conditions" which refers to conditions or events that are associated with or result in ischemia. Thus, the term "conditions associated with HIF" includes conditions associated or resulting in ischemia including, but are not limited to, an event selected from the group consisting of pulmonary embolism, perinatal hypoxia, circulatory shock including, e.g., hemorrhagic, septic, cardiogenic, etc.; mountain sickness, acute respiratory failure, intestinal infarction, acute kidney failure, renal ischemia reperfusion injury, atherosclerosis, chronic venous insufficiency, congestive heart failure, cardiac cirrhosis, diabetes, macular degeneration, sleep apnea, Raynaud's disease, systemic sclerosis, occlusive artery disease, transient ischemic attacks, chronic alcoholic liver disease, chronic kidney failure, peripheral vascular disorders, ulcers, burns, chronic wounds, and the like. Ischemia can also result when individuals are placed under general anesthesia, and can cause tissue damage in organs prepared for transplant.

Another embodiment is a method of treating ischemic conditions. In particular the present invention provides a method of treating myocardial infarctions, including acute myocardial infarction. The present invention provides a method of treating acute heart failure. The present invention provides a method of treating congestive heart failure. The present invention provides a method of treating the exacerbation of congestive heart failure with and without acute myocardial infarction. The present invention also provides a method of treating stroke. The present invention also provides a method of treating acute kidney injury of ischemic and non-ischemic etiology.

Hypoxia results from reduced oxygen content in the blood due to pulmonary disorders (hypoxic hypoxia) such as COPD, severe pneumonia, pulmonary edema, pulmonary hypertension, and the like. Hypoxia also results from anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, decreased concentration of hemoglobin or red blood cells, and altitude sickness, and the like.

The term "conditions associated with HIF" includes specifically, but is not limited to, COPD. The term "conditions associated with HIF" includes pulmonary disorders specifically, but is not limited to, diffuse parenchymal lung diseases such as idiopathic interstitial pneumonias, idiopathic pulmonary fibrosis, usual interstitial pneumonia, desquamative pulmonary fibrosis, cryptogenic organizing pneumonia, acute interstitial pneumonia, non-specific interstitial pneumonia, respiratory bronchiolitis associated with instial lung disease, cryptogenic organizing pneumonia, lymphocytic interstitial pneumonia, hypersensitivity pneumonitis, and decreased pulmonary function due to lupus, sarcoidosis, Wegner's granulomatosis, radiation of the chest, and certain medications, for example, amiodarone, bleomycin, busulfan, methotrexate, and nitrofurantoin.

The term "anemia" refers to any reduction in the number of red blood cells and/or in the level of hemoglobin in blood relative to normal blood levels.

The term "conditions associated with HIF" includes anemia, and specifically includes, but is not limited to, chemotherapy-induced anemia (such as treatment with antiviral drug regimens for HIV and hepatitis), anemia of chronic disease, anemia associated with cancer conditions, anemia resulting from treatment for cancer, anemias of chronic immune disorders such as rheumatoid arthritis, inflammatory bowel disease, lupus, menstruation, iron processing deficiencies, acute or chronic kidney disease, infections, inflammation, irradiation, toxins, diabetes, infection due to, e.g., virus, bacteria, and/or parasites, anemia can be associated with blood loss due to, e.g., trauma, stomach ulcers, duodenal ulcers, hemorrhoids, cancer of the stomach or large intestine, injury, surgical procedures; diseases associated with bone marrow failure or decreased bone marrow function; microcytic anemia, hypochromic anemia, sideroblastic anemia, and the like.

The term "conditions associated with HIF" includes cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 200 mg. Specific amounts can be determined by the skilled person. Although these dosages are based on an average human subject having a mass of about 60 kg to about 70 kg, the physician will be able to determine the appropriate dose for a patient (e.g., an infant) whose mass falls outside of this weight range.

The compounds of the invention may be combined with one or more other pharmacologically active compounds or therapies for the treatment of one or more disorders, diseases or conditions for which HIF is indicated may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

The activity of compounds as PHD inhibitors may be determined by a variety of methods, including in vitro and in vivo methods.

Example A Inhibition of PHD Enzyme

The $IC_{50}$ values for the PHD2 enzyme (residues 181-417) were determined by mixing increasing amounts of inhibitor with a fixed amount of enzyme (5 nM, final concentration) and Biotin labeled peptide (Biotin-Asp-Leu-Glu-Met-Leu-Ala-Pro-Tyr-Ile-Pro-Met-Asp-Asp-Asp-Phe-Gln-Leu, 1 uM final concentration) and 2-Oxyglutarate (2 uM final concentration) in 50 mM HEPES, 50 mM KCl, 0.5 mM TCEP, 2 uM FeCl2, 0.1 mg/ml BSA, at pH 7.3. The reaction was conducted by pre-incubating the enzyme in the presence of inhibitor for 60 min at room temperature. The activity of the free enzyme was measured by adding the peptide, the 2-Oxoglutarate (see above for final concentrations), and Ascorbic Acid (1 mM final concentration). The enzymatic activity was quenched after 60 min by adding an excess of a tight binding inhibitor to the assay mixture. The amount of product released was measured by using a LC/MS system (Agilent HPLC with Applied Biosystems API3000 Mass Spectrometer). Data were analyzed using the classical isotherm equation for the determination of $IC_{50}$ values and are $pIC_{50}$, i.e., $-\log(IC_{50})$, where $IC_{50}$ is molar concentration and are reported as $pIC_{50}$, i.e., $-\log(IC_{50})$, where $IC_{50}$ is molar concentration.

Table A provides results for exemplified compounds in Example A.

TABLE A

PHD Inhibition ($pIC_{50}$) for Example (Ex) Compounds

| Ex | $pIC_{50}$ |
|---|---|
| 1 | 7.1 |
| 2 | 7.03 |
| 3 | 7.3 |
| 4 | 6.92 |
| 5 | 7.01 |
| 6 | 7.02 |
| 7 | 7.03 |
| 8 | 7.03 |
| 9 | 7.5 |
| 10 | 7.09 |
| 12 | 7.44 |
| 11 | NT |
| 13 | 7.15 |
| 14 | 7.27 |
| 15 | 7.21 |
| 16 | 7.38 |
| 17 | 7.03 |
| 18 | 7.06 |
| 19 | 7.01 |
| 20 | 7.29 |
| 21 | 7.43 |
| 22 | 7.11 |
| 23 | 6.9 |
| 24 | 7.04 |
| 25 | 7.1 |
| 26 | 7.01 |
| 27 | 6.99 |
| 28 | 7.01 |
| 29 | NT |
| 30 | 7.5 |
| 31 | 7.5 |
| 32 | 7.8 |
| 33 | 7.4 |
| 34 | 8 |
| 35 | 7.8 |
| 36 | 7.4 |
| 37 | 7.4 |
| 38 | 7.5 |
| 39 | 7.3 |
| 40 | 7.9 |
| 41 | 8 |
| 42 | 7.5 |
| 43 | 8.2 |
| 44 | 7.3 |
| 45 | 8 |
| 46 | 7.8 |
| 47 | 8.4 |
| 48 | 8 |
| 49 | 7.9 |
| 50 | 8.1 |
| 51 | 7.3 |
| 52 | 8.3 |
| 53 | 7.03 |
| 54 | 7.22 |
| 55 | 7.2 |
| 56 | 7.12 |
| 57 | 6.98 |
| 58 | 7.16 |
| 59 | 7.33 |
| 60 | 7.14 |
| 61 | 7.19 |
| 62 | 7.14 |
| 63 | 7.25 |
| 64 | 7.25 |
| 65 | 7.08 |
| 66 | 7.22 |
| 67 | 7.11 |

TABLE A-continued

PHD Inhibition (pIC$_{50}$) for Example (Ex) Compounds

| Ex | pIC$_{50}$ |
|---|---|
| 68 | 7.44 |
| 69 | 7.22 |
| 70 | 7.17 |
| 71 | 7.24 |
| 72 | 7.8 |
| 73 | 7.2 |
| 74 | 7.05 |
| 75 | 7.28 |
| 76 | 6.68 |
| 77 | 7.03 |
| 78 | 7.07 |
| 79 | NT |
| 80 | 7.23 |
| 81 | 7.2 |
| 82 | 6.89 |
| 83 | NT |
| 84 | 6.91 |
| 85 | 6.94 |
| 86 | 7.39 |
| 87 | 7.66 |
| 88 | NT |
| 89 | 7.24 |
| 90 | 6.95 |
| 91 | 7.18 |
| 92 | 6.87 |
| 93 | 7.08 |
| 94 | 7.9 |
| 95 | 7.9 |
| 96 | 8 |
| 97 | 8 |
| 98 | 7.9 |
| 99 | 7.9 |
| 100 | 8.1 |
| 101 | 8.1 |
| 102 | 7.9 |
| 103 | 8.1 |
| 104 | 8.2 |
| 105 | 8 |
| 106 | 8 |
| 107 | 8.4 |
| 108 | 8.3 |
| 109 | 7.7 |
| 110 | 8.1 |
| 111 | 7.8 |
| 112 | 7.32 |
| 113 | 7.22 |
| 114 | 6.55 |
| 115 | 6.91 |
| 117 | 7.44 |
| 116 | 7.42 |
| 118 | 7.36 |
| 118A | NT |
| 119 | 7.11 |
| 120 | 7.2 |
| 121 | 7.17 |
| 122 | 7.06 |
| 123 | 7.16 |
| 125 | 7.19 |
| 126 | 7.24 |
| 127 | 7.18 |
| 128 | 7.04 |
| 129 | 7.14 |
| 130 | 7.27 |
| 131 | 7.21 |
| 132 | 7.26 |
| 133 | 7.17 |
| 134 | 7.21 |
| 135 | 7.15 |
| 136 | 7.13 |
| 137 | 7.21 |
| 138A | 6.95 |
| 139 | 7.36 |
| 140 | 8.1 |
| 141 | 8.3 |
| 142 | 8.3 |
| 143 | 7.9 |
| 144 | 8.1 |
| 145 | 8.3 |
| 146 | 8.3 |
| 147 | 7.9 |
| 148 | 7.57 |
| 149 | 7.28 |
| 150 | 7.58 |
| 151 | 7.12 |
| 152 | 7.6 |
| 153 | 7.57 |
| 154 | 7.68 |
| 155 | 7.62 |
| 156 | 7.47 |
| 157 | 6.97 |
| 158 | 6.71 |
| 159 | 7.15 |
| 160 | 6.9 |
| 161 | 7.18 |
| 162 | 7.23 |
| 163 | 7.28 |
| 164 | 7.5 |
| 165 | 7.68 |
| 166 | 7.28 |
| 167 | 7.46 |
| 168 | 8.1 |
| 169 | 7.22 |
| 170 | 7.29 |
| 171 | 7.18 |
| 172 | 7.33 |
| 173 | 7.21 |
| 174 | 7.31 |
| 175 | 7.37 |
| 176 | 7.53 |
| 177 | 7.64 |
| 178 | 7.63 |
| 179 | 8.3 |
| 180 | 8.2 |
| 181 | 8.2 |
| 182 | 8.1 |
| 183 | 7.9 |
| 184 | 8.1 |
| 185 | 8 |
| 186 | 7.8 |
| 187 | 7.8 |
| 188 | 7.3 |
| 189 | 7.49 |
| 190 | 7 |
| 191 | 7.19 |
| 192 | 6.84 |
| 193 | 7.57 |
| 194 | 7.3 |
| 195 | 7.01 |
| 196 | 6.84 |
| 197 | 6.83 |
| 198 | 7.35 |
| 199 | 6.89 |
| 200 | 7.09 |
| 201 | 7.29 |
| 202 | 7.23 |
| 203 | 7.1 |
| 204 | 7.08 |
| 205 | 6.89 |
| 206 | 8.2 |
| 207 | 8.3 |
| 208 | 7.38 |
| 209 | 6.98 |
| 210 | 8.3 |
| 211 | 6.47 |
| 212 | 6.21 |
| 213 | 7.45 |
| 214 | 6.76 |
| 215 | 7.21 |
| 216 | 7.1 |
| 217 | 8.1 |
| 218 | 7.9 |
| 219 | 8.2 |

TABLE A-continued

PHD Inhibition (pIC$_{50}$) for Example (Ex) Compounds

| Ex | pIC$_{50}$ |
|---|---|
| 220 | 7.13 |
| 221 | 7.11 |
| 222 | 7.25 |
| 223 | 5.43 |
| 224 | 5.83 |
| 225 | 7.56 |
| 226 | 6.6 |
| 227 | 7.38 |
| 228 | 7.48 |
| 229 | 7.62 |
| 230 | 6.83 |
| 231 | 6.95 |
| 232 | 7.01 |
| 233 | 6.7 |
| 234 | 7.12 |
| 235 | 7.43 |
| 236 | 7.51 |
| 237 | 7.54 |
| 238 | 6.85 |
| 239 | 7.12 |
| 240 | 6.63 |
| 241 | 7.51 |
| 242 | 7.18 |
| 243 | 6.9 |
| 244 | 8.4 |
| 245 | 8.4 |
| 246 | 7.8 |
| 247 | 8.2 |
| 248 | 8.3 |
| 249 | 8.3 |
| 250 | 8 |
| 251 | 8.2 |
| 252 | 8.3 |
| 253 | 8.3 |
| 254 | 8 |
| 255 | 7.6 |
| 256 | 6.72 |
| 257 | 7.24 |
| 258 | 7.44 |
| 259 | 7.39 |
| 260 | 7.17 |
| 261 | 7.39 |
| 262 | 7.38 |
| 263 | 7.22 |
| 264 | 6.99 |
| 265 | 6.77 |
| 266 | 7.23 |
| 267 | 7.36 |
| 268 | 6.32 |
| 269 | 6.82 |
| 270 | 7.34 |
| 271 | 6.98 |
| 272 | 7.03 |
| 273 | 7.06 |
| 274 | 7.03 |
| 275 | 7.03 |
| 276 | 7.01 |
| 277 | 6.89 |
| 278 | 7.05 |
| 279 | 7.1 |
| 280 | 5.69 |
| 281 | 7.37 |
| 282 | 8.00 |
| 283 | 8.60 |
| 284 | 8.21 |
| 285 | 8.48 |
| 286 | 7.94 |
| 287 | 8.10 |
| 288 | 8.48 |
| 289 | 8.03 |
| 290 | 8.33 |
| 291 | 8.15 |
| 292 | 8.04 |
| 293 | 8.05 |
| 294 | 8.22 |
| 295 | 7.85 |

TABLE A-continued

PHD Inhibition (pIC$_{50}$) for Example (Ex) Compounds

| Ex | pIC$_{50}$ |
|---|---|
| 296 | 8.23 |
| 297 | 8.39 |
| 298 | 8.18 |
| 299 | 8.46 |
| 300 | 7.99 |
| 301 | 8.67 |
| 302 | 8.41 |
| 303 | 7.88 |
| 304 | 7.23 |
| 305 | 8.27 |
| 306 | 8.29 |
| 307 | 8.39 |
| 308 | 8.28 |
| 309 | 7.97 |
| 310 | 8.13 |
| 311 | 8.51 |
| 312 | 8.50 |
| 313 | 7.59 |
| 314 | 7.90 |
| 315 | 8.09 |
| 316 | 8.31 |
| 317 | 8.31 |
| 318 | 8.35 |
| 319 | 8.17 |
| 320 | 8.17 |
| 321 | 8.40 |
| 322 | 8.26 |
| 323 | 8.33 |
| 324 | 8.54 |
| 325 | 8.44 |
| 326 | 8.33 |
| 327 | 8.47 |
| 328 | 8.39 |
| 329 | 8.50 |
| 330 | 8.34 |
| 331 | 8.33 |
| 332 | 8.47 |
| 333 | 8.55 |
| 334 | 8.50 |
| 335 | 8.43 |
| 336 | 8.53 |
| 337 | 8.36 |
| 338 | 8.40 |
| 339 | 8.29 |
| 340 | 8.39 |
| 341 | 8.47 |
| 342 | 7.60 |
| 343 | 8.07 |
| 344 | 8.17 |
| 345 | 8.35 |
| 346 | 7.75 |
| 347 | 8.29 |
| 348 | 7.72 |
| 349 | 7.77 |
| 350 | 7.26 |
| 351 | 7.67 |
| 352 | 7.47 |
| 353 | 7.25 |
| 354 | 8.36 |
| 355 | 7.94 |
| 356 | 8.16 |
| 357 | 8.46 |
| 358 | 8.75 |
| 359 | 8.45 |
| 360 | 8.60 |
| 361 | 7.76 |
| 362 | 7.80 |
| 363 | 7.28 |
| 364 | 6.73 |
| 365 | 7.80 |
| 366 | 7.25 |
| 367 | 7.38 |
| 368 | 7.89 |
| 369 | 7.701 |
| 370 | 8.287 |
| 371 | 8.20 |

TABLE A-continued

PHD Inhibition (pIC$_{50}$) for Example (Ex) Compounds

| Ex | pIC$_{50}$ |
|---|---|
| 372 | 8.26 |
| 373 | 8.00 |
| 374 | NT |
| 375 | 8.06 |
| 376 | 7.61 |
| 377 | 8.44 |
| 378 | 8.21 |
| 379 | 8.20 |
| 380 | 8.17 |
| 381 | 7.94 |
| 382 | 8.00 |
| 383 | 8.28 |
| 384 | 7.93 |
| 385 | 8.18 |
| 386 | 8.23 |
| 387 | 7.91 |
| 388 | 8.25 |
| 389 | 8.20 |
| 390 | 8.29 |
| 391 | NT |
| 392 | 8.20 |
| 393 | 7.86 |
| 394 | 7.88 |
| 395 | 8.48 |
| 396 | 8.59 |
| 397 | 8.52 |
| 398 | 8.65 |
| 399 | 8.63 |
| 400 | 8.50 |
| 401 | 8.44 |
| 402 | 7.99 |
| 403 | 7.78 |
| 404 | 8.01 |
| 405 | 8.48 |
| 406 | 8.49 |
| 407 | 8.23 |
| 408 | NT |
| 409 | 8.24 |
| 410 | 8.07 |
| 411 | 8.20 |
| 412 | 8.11 |
| 413 | 8.10 |
| 414 | 8.39 |
| 415 | 8.41 |
| 416 | 7.78 |
| 417 | 7.87 |
| 418 | 8.17 |
| 419 | 7.98 |
| 420 | 7.87 |
| 421 | 8.31 |
| 422 | 7.87 |
| 423 | 7.99 |
| 424 | 7.70 |
| 425 | 7.74 |
| 426 | 8.18 |
| 427 | 7.83 |
| 428 | 7.88 |
| 429 | 7.95 |
| 430 | 7.44 |
| 431 | 7.31 |
| 432 | 8.02 |
| 433 | 8.20 |
| 434 | 8.20 |
| R1 | 8.00 |

Example B Inhibition of PHD in Cells

PHD Inhibition is Determined Using (Secondary Assay) Cell-Based HIF-Alpha Stabilization Assay:

H9c2 rat cardiomyocytes (ATCC) were seeded in 96-well tissue culture microplates and cultured for 24 hours prior to addition of compounds (11 point range of serial dilutions) or dimethylsulfoxide vehicle. After 24 hrs of compound incubation, whole cell extracts were prepared by lysing cells in cell extraction buffer containing protease and phosphatase inhibitors (Meso-Scale Discovery). HIF1a protein content was assessed by ELISA (Meso-Scale Discovery) and expressed as a % relative to the maximum response obtained from the positive control, desferrioxamine (Sigma-Aldrich). Compound EC$_{50}$s were obtained by curve-fitting using XLfit4 MicroSoft Excel curve-fitting software. Compound EC$_{50pos}$ were obtained using XLfit4 to calculate the compound concentration that results in 50% of the desferrioxamine maximum response.

Table B provides results for exemplified compounds in Example B.

TABLE B

Inhibition of PHD in cells (pEC$_{50}$) for Example (Ex) Compounds

| Ex | pEC$_{50}$ |
|---|---|
| 1 | 6.27 |
| 2 | 5.9 |
| 3 | 6.14 |
| 4 | 6.28 |
| 5 | 6.25 |
| 6 | 6.02 |
| 7 | 6 |
| 8 | 6.22 |
| 9 | 6.28 |
| 10 | 6.17 |
| 12 | 6.18 |
| 11 | 6.27 |
| 13 | 6.38 |
| 14 | 6.06 |
| 15 | 6.19 |
| 16 | 6.7 |
| 17 | 6.46 |
| 18 | 6.03 |
| 19 | 5.86 |
| 20 | NT |
| 21 | 6.46 |
| 22 | NT |
| 23 | 6.00 |
| 24 | 4.97 |
| 25 | 5.35 |
| 26 | 5.44 |
| 27 | NT |
| 28 | NT |
| 29 | 6.06 |
| 30 | 5.70 |
| 31 | 6.00 |
| 32 | 6.09 |
| 33 | 5.93 |
| 34 | 6.29 |
| 35 | 5.50 |
| 36 | 5.83 |
| 37 | NT |
| 38 | 6.02 |
| 39 | 5.58 |
| 40 | 6.01 |
| 41 | 6.26 |
| 42 | 5.47 |
| 43 | 6.46 |
| 44 | NT |
| 45 | 6.25 |
| 46 | 5.87 |
| 47 | 6.45 |
| 48 | 6.19 |
| 49 | 6.06 |
| 50 | 6.06 |
| 51 | 5.74 |
| 52 | 6.03 |
| 53 | 6.28 |
| 54 | 6.48 |
| 55 | 5.73 |
| 56 | 5.84 |
| 57 | 5.70 |
| 58 | 6.8 |

TABLE B-continued

Inhibition of PHD in cells (pEC$_{50}$) for Example (Ex) Compounds

| Ex | pEC$_{50}$ |
|---|---|
| 59 | 7.15 |
| 60 | 6.7 |
| 61 | 7.1 |
| 62 | 6.74 |
| 63 | 6.8 |
| 64 | 6.8 |
| 65 | 6.74 |
| 66 | 6.92 |
| 67 | 6.66 |
| 68 | 7.3 |
| 69 | 7.05 |
| 70 | 6.64 |
| 71 | 6.57 |
| 72 | 5.54 |
| 73 | NT |
| 74 | 5.5 |
| 75 | 5.77 |
| 76 | 5.51 |
| 77 | 5.9 |
| 78 | 5.81 |
| 79 | 5.88 |
| 80 | 5.97 |
| 81 | 5.32 |
| 82 | 5.32 |
| 83 | 5.75 |
| 84 | 5.65 |
| 85 | 5.65 |
| 86 | 5.94 |
| 87 | 6.22 |
| 88 | 5.50 |
| 89 | 6.15 |
| 90 | NT |
| 91 | 6.03 |
| 92 | NT |
| 93 | 6.06 |
| 94 | 7.03 |
| 95 | 7.08 |
| 96 | 7.25 |
| 97 | 7.25 |
| 98 | 6.92 |
| 99 | 7.27 |
| 100 | 7.12 |
| 101 | 6.80 |
| 102 | 7.23 |
| 103 | 6.75 |
| 104 | 7.02 |
| 105 | 7.21 |
| 106 | 6.45 |
| 107 | 6.89 |
| 108 | 6.96 |
| 109 | 5.92 |
| 110 | 5.91 |
| 111 | 5.67 |
| 112 | 5.86 |
| 113 | 5.86 |
| 114 | 6.59 |
| 115 | 5.74 |
| 116 | 6.13 |
| 117 | 6.19 |
| 118 | 6.50 |
| 118A | 7.10 |
| 119 | 6.90 |
| 120 | 6.99 |
| 121 | 6.72 |
| 122 | 7.02 |
| 123 | 5.32 |
| 125 | 6.43 |
| 126 | 6.42 |
| 127 | 7.03 |
| 128 | 6.84 |
| 129 | 6.73 |
| 130 | 6.38 |
| 131 | 6.59 |
| 132 | 6.59 |
| 133 | 6.71 |
| 134 | 6.47 |
| 135 | 6.83 |
| 136 | 6.95 |
| 137 | 6.61 |
| 138A | 6.52 |
| 139 | 7.09 |
| 140 | 6.92 |
| 141 | 6.39 |
| 142 | 7.07 |
| 143 | 6.05 |
| 144 | 5.77 |
| 145 | 6.30 |
| 146 | 6.16 |
| 147 | 5.49 |
| 148 | 6.20 |
| 149 | 6.11 |
| 150 | 5.6 |
| 151 | 5.44 |
| 152 | 5.69 |
| 153 | 5.86 |
| 154 | 5.83 |
| 155 | 5.81 |
| 156 | 6.05 |
| 157 | 5.77 |
| 158 | 5.02 |
| 159 | 6.04 |
| 160 | 6.12 |
| 161 | 6.35 |
| 162 | 5.94 |
| 163 | 5.83 |
| 164 | 6.28 |
| 165 | 6.6 |
| 166 | 6.36 |
| 167 | 6.55 |
| 168 | 6.36 |
| 169 | 6.05 |
| 170 | 5.56 |
| 171 | 5.84 |
| 172 | 5.9 |
| 173 | 5.96 |
| 174 | 6.12 |
| 175 | 6.31 |
| 176 | 6.4 |
| 177 | 6.51 |
| 178 | 6.55 |
| 179 | 6.91 |
| 180 | 6.40 |
| 181 | 6.49 |
| 182 | 6.51 |
| 183 | 6.19 |
| 184 | 6.67 |
| 185 | 6.25 |
| 186 | 6.53 |
| 187 | 6.45 |
| 188 | 5.28 |
| 189 | 5.33 |
| 190 | 4.8 |
| 191 | 5.17 |
| 192 | 4.3 |
| 193 | 5.57 |
| 194 | 6.29 |
| 195 | 5.6 |
| 196 | 5.45 |
| 197 | 5.8 |
| 198 | 6.13 |
| 199 | 5.63 |
| 200 | 5.96 |
| 201 | 6.11 |
| 202 | 6.14 |
| 203 | 6.22 |
| 204 | 6.33 |
| 205 | 6.2 |
| 206 | 6.96 |
| 207 | 6.91 |
| 208 | 6.57 |
| 209 | 6.4 |
| 210 | NT |

TABLE B-continued

Inhibition of PHD in cells (pEC$_{50}$) for Example (Ex) Compounds

| Ex | pEC$_{50}$ |
|---|---|
| 211 | 4.3 |
| 212 | NT |
| 213 | 6.42 |
| 214 | 5.55 |
| 215 | 6.59 |
| 216 | 5.28 |
| 217 | 5.91 |
| 218 | 5.33 |
| 219 | 5.91 |
| 220 | 5.97 |
| 221 | 6.03 |
| 222 | 7 |
| 223 | 4.3 |
| 224 | NT |
| 225 | 5.63 |
| 226 | NT |
| 227 | 6.26 |
| 228 | 6.59 |
| 229 | 5.98 |
| 230 | 6.39 |
| 231 | 6.43 |
| 232 | 6.47 |
| 233 | 6.23 |
| 234 | 5.65 |
| 235 | 6.57 |
| 236 | 6.23 |
| 237 | 6.35 |
| 238 | 6.33 |
| 239 | 5.77 |
| 240 | NT |
| 241 | 6.36 |
| 242 | NT |
| 243 | 5.38 |
| 244 | 6.62 |
| 245 | 6.62 |
| 246 | 6.39 |
| 247 | 6.09 |
| 248 | 6.60 |
| 249 | 6.56 |
| 250 | 6.34 |
| 251 | 6.49 |
| 252 | 6.58 |
| 253 | 5.25 |
| 254 | 5.56 |
| 255 | 5.84 |
| 256 | NT |
| 257 | NT |
| 258 | 6.09 |
| 259 | 6 |
| 260 | 6.23 |
| 261 | 5.95 |
| 262 | 6.28 |
| 263 | 5.91 |
| 264 | 5.79 |
| 265 | 5.18 |
| 266 | 5.72 |
| 267 | 6.15 |
| 268 | 5.71 |
| 269 | 5.71 |
| 270 | 6 |
| 271 | 5.81 |
| 272 | NT |
| 273 | 5.03 |
| 274 | 5.19 |
| 275 | 5.42 |
| 276 | 5.44 |
| 277 | 5.15 |
| 278 | 5.49 |
| 279 | 5.58 |
| 280 | 4.3 |
| 281 | 6.59 |
| 282 | 6.24 |
| 283 | 5.72 |
| 284 | 5.89 |
| 285 | 6.03 |
| 286 | 6.22 |
| 287 | 5.45 |
| 288 | 6.24 |
| 289 | 5.91 |
| 290 | 6.04 |
| 291 | 6.01 |
| 292 | 6.39 |
| 293 | 6.49 |
| 294 | 5.95 |
| 295 | 6.47 |
| 296 | 6.00 |
| 297 | 6.28 |
| 298 | 6.01 |
| 299 | 5.98 |
| 300 | 7.76 |
| 301 | 6.60 |
| 302 | 6.54 |
| 303 | 6.55 |
| 304 | 5.55 |
| 305 | 5.88 |
| 306 | 5.34 |
| 307 | 5.63 |
| 308 | 5.18 |
| 309 | 5.58 |
| 310 | 5.50 |
| 311 | 5.83 |
| 312 | 5.74 |
| 313 | 5.95 |
| 314 | 6.26 |
| 315 | 6.25 |
| 316 | 5.89 |
| 317 | 6.17 |
| 318 | 6.15 |
| 319 | 6.27 |
| 320 | 6.13 |
| 321 | 6.23 |
| 322 | 6.03 |
| 323 | 5.74 |
| 324 | 6.08 |
| 325 | 6.01 |
| 326 | 6.31 |
| 327 | 6.23 |
| 328 | 6.51 |
| 329 | 6.48 |
| 330 | 6.39 |
| 331 | 6.09 |
| 332 | 6.12 |
| 333 | 6.13 |
| 334 | 5.86 |
| 335 | 5.88 |
| 336 | 6.01 |
| 337 | 5.87 |
| 338 | 6.03 |
| 339 | 5.69 |
| 340 | 6.12 |
| 341 | 6.23 |
| 342 | 6.37 |
| 343 | 5.94 |
| 344 | 6.33 |
| 345 | 6.44 |
| 346 | 6.43 |
| 347 | 6.20 |
| 348 | 6.13 |
| 349 | 6.32 |
| 350 | 5.48 |
| 351 | 5.27 |
| 352 | 5.46 |
| 353 | 5.45 |
| 354 | 5.80 |
| 355 | 6.14 |
| 356 | 6.01 |
| 357 | 5.62 |
| 358 | 5.94 |
| 359 | 6.27 |
| 360 | 6.39 |
| 361 | 6.34 |
| 362 | 6.28 |

TABLE B-continued

Inhibition of PHD in cells (pEC$_{50}$) for Example (Ex) Compounds

| Ex | pEC$_{50}$ |
|---|---|
| 363 | 5.68 |
| 364 | 5.11 |
| 365 | 6.38 |
| 366 | 5.42 |
| 367 | 5.55 |
| 368 | 6.24 |
| 369 | 5.92 |
| 370 | 6.25 |
| 371 | 6.08 |
| 372 | 6.08 |
| 373 | 5.92 |
| 374 | 7.0 |
| 375 | 6.00 |
| 376 | 6.05 |
| 377 | 6.09 |
| 378 | 5.89 |
| 379 | 6.10 |
| 380 | 6.24 |
| 381 | 5.97 |
| 382 | 6.01 |
| 383 | 5.96 |
| 384 | 5.82 |
| 385 | 6.02 |
| 386 | 6.15 |
| 387 | 6.06 |
| 388 | 6.29 |
| 389 | 5.94 |
| 390 | 6.02 |
| 391 | 5.81 |
| 392 | 6.45 |
| 393 | 5.84 |
| 394 | 5.55 |
| 395 | 5.58 |
| 396 | 5.68 |
| 397 | 5.79 |
| 398 | 5.71 |
| 399 | 5.77 |
| 400 | 5.78 |
| 401 | 5.80 |
| 402 | 5.36 |
| 403 | 5.73 |
| 404 | 6.20 |
| 405 | 6.49 |
| 406 | 6.72 |
| 407 | NT |
| 408 | NT |
| 409 | 6.59 |
| 410 | 6.29 |
| 411 | 6.17 |
| 412 | 6.55 |
| 413 | 5.68 |
| 414 | 6.08 |
| 415 | 6.20 |
| 416 | 5.85 |
| 417 | 6.24 |
| 418 | 5.93 |
| 419 | 6.20 |
| 420 | 6.27 |
| 421 | 6.18 |
| 422 | 6.30 |
| 423 | 6.15 |
| 424 | NT |
| 425 | 6.11 |
| 426 | 5.67 |
| 427 | 6.19 |
| 428 | 6.30 |
| 429 | 6.23 |
| 430 | 5.07 |
| 431 | 5.56 |
| 432 | 6.13 |
| 433 | 6.44 |
| 434 | 5.89 |
| R1 | 6.02 |

Example C In Vivo Cardioprotection Assay

PHD inhibitor or vehicle was administered orally to 8-week old male C57 mice or Sprague Dawley rats. Four hours after dosing, hearts were removed quickly and perfused in a retrograde manner with modified Krebs-Henseleit buffer in a Langendorff apparatus at constant pressure (80 mmHg). To measure infarct size, hearts were first perfused for 20 min to reach equilibrium and then subjected to a 30-minute global ischemia (no-flow) period followed by a 60-min reperfusion period in mice or 90-min reperfusion in rats. The ventricles were cut transversely into 5 sections. The slices were stained 1% 2,3,5-triphenyl tetrazolium chloride (TTC) and scanned to measure the infarct area and the total area. Cardiac injury was assessed by measuring lactate dehydrogenase (LDH) release to coronary effluent during the 60-min reperfusion period (in mice only). The amount of LDH release was determined using an LDH activity assay kit (MBL International Corp.) as expressed as % of vehicle treated hearts.

The compound of Example 282 reduced area of the infarct in mice by 59% at 30 mg/kg and by 50% at 10 mg/kg as compared to the vehicle control values. Corresponding reduction of LDH released to the coronary effluent was 56% and 51% at 30 and 10 mg/kg, respectively. The compound of Example 282 reduced area of the infarct in rats by 30% at a dose of 5 mg/kg.

Example D Determination of Heart Gene Changes for Vascular Endothelial Growth Factor (VEGF)

PHD inhibitor or vehicle were administered orally to male C57BL/6 in groups of four. The compounds were formulated in 30% hydroxypropyl beta-cyclodextrin in 50 mM Sodium Phosphate pH7.4 at doses of 30 mg/kg and 60 mg/kg. Two hours after dosing the mice were euthanized by $CO_2$ and the hearts were removed quickly, sectioned into 2 pieces; the lower (apical) section was snap frozen and stored at −80° C. and analyzed for VEGF gene changes applying qRT-PCR and using Life Technologies #4392938 and an RNA extraction protocol using Qiagen #74881 RNeasy 96 Universal Tissue Kit. Standards are made from RNA from combined vehicle treated animals at a concentration of 100 μg/mL, a 7 point curve is made with 1:4 dilutions and a blank. Samples are run on using RNA-to-C$_T$ 1-Step method using a StepOnePlus Real-Time PCR System from Applied Biosystems Relative quantitation is expressed by dividing the quantity of VEGF by the quantity of the reference gene. Treatment groups and vehicle control were combined and averaged.

Table D provides results for selected exemplified compounds in Example D.

| Ex | Dose (mg/kg) | % Increase Compared to Control | S.E.M. |
|---|---|---|---|
| Vehicle |  | 0.0 | 6.7 |
| 282 | 60 | 203.1 | 12.4 |
| R1 | 60 | 95.2 | 26.7 |

It is well-known that and increase in VEGF and other angiogenic factors provides protection against ischemic injury. Nature Med. 9, 653-660 (2003). PHD is an important regulator involved in gene expression. Biochem J. 2004, 381 (Pt 3): 761-767. At a dose of 60 mg/kg, the compound of Example 282 provides a 2 fold greater VEGF mRNA production compared to the compound of Example R1. It is also well-known that neovascularization stimulated by VEGF is beneficial in several important clinical contexts, including myocardial ischemia. Mol. Cell Bio. 1996 September; 16(9): 4604-4613.

What is claimed is:

1. A compound of formula 5,

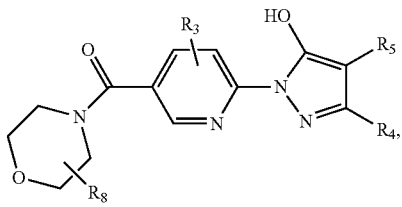

or a pharmaceutically acceptable salt thereof, wherein:

$R_3$, each time taken, is independently selected from the group consisting of hydrogen, hydroxyl, amino, $C_{1-8}$ alkylamino, cyano, halo, $C_{1-6}$ alkyl, and $C_{1-4}$ alkoxy;

$R_4$ is selected from the group consisting of hydrogen, cyano, halo, methyl, ethyl, methoxy, and trifluoromethyl;

$R_5$ is selected from the group consisting of

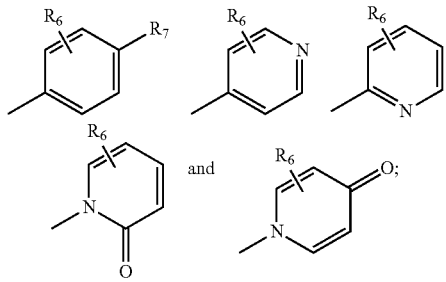

$R_6$, each time taken, is independently selected from the group consisting of hydrogen, cyano, halo, $C_{3-8}$ cycloalkyl, $C_{1-6}$ alkyl, $C_{1-4}$ alkoxy, and trifluoromethyl;

$R_7$ is selected from the group consisting of cyano and cyanomethyl; and $R_8$, each time taken, is independently selected from the group consisting of hydrogen, cyano, halo, $C_{1-4}$ alkyl, $C_{1-4}$ alkoxy, and trifluoromethyl.

2. The compound or pharmaceutically acceptable salt according to claim 1, wherein $R_5$ is

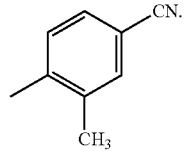

3. The compound or pharmaceutically acceptable salt according to claim 1, wherein $R_6$ is $C_{1-6}$ alkyl.

4. The compound or pharmaceutically acceptable salt according to claim 1, wherein each $R_8$ is hydrogen.

5. The compound or pharmaceutically acceptable salt according to claim 1, wherein each $R_3$ is hydrogen and $R_4$ is hydrogen.

6. The compound according to claim 1, which is selected from the group consisting of:
   4-(5-hydroxy-1-(5-(morpholine-4-carbonyl)pyridin-2-yl)-1H-pyrazol-4-yl)benzonitrile;
   2-fluoro-4-(5-hydroxy-1-(5-(morpholine-4-carbonyl)pyridin-2-yl)-1H-pyrazol-4-yl)-3-methylbenzonitrile;
   2-fluoro-4-(5-hydroxy-1-(5-(morpholine-4-carbonyl)pyridin-2-yl)-1H-pyrazol-4-yl)-5-methylbenzonitrile; and
   a pharmaceutically acceptable salt of any one of the above-mentioned compounds.

7. A pharmaceutical composition comprising a compound or pharmaceutically acceptable salt as defined in claim 1; and a pharmaceutically acceptable excipient.

* * * * *